(12) United States Patent
Miller et al.

(10) Patent No.: US 11,793,885 B2
(45) Date of Patent: Oct. 24, 2023

(54) SUBSTITUTED BENZO[5,6][1,4]DIAZEPINO[1,2-A]INDOLES FOR THE TREATMENT OF PROLIFERATIVE DISORDERS

(71) Applicant: IMMUNOGEN, INC., Waltham, MA (US)

(72) Inventors: Michael Louis Miller, Framingham, MA (US); Manami Shizuka, Belmont, MA (US); Ravi V. J. Chari, Newton, MA (US)

(73) Assignee: IMMUNOGEN, INC., Waltham, MA (US)

( * ) Notice: Subject to any disclaimer, the term of this patent is extended or adjusted under 35 U.S.C. 154(b) by 256 days.

(21) Appl. No.: 16/954,878

(22) PCT Filed: Dec. 27, 2018

(86) PCT No.: PCT/US2018/067589
§ 371 (c)(1),
(2) Date: Jun. 17, 2020

(87) PCT Pub. No.: WO2019/133652
PCT Pub. Date: Jul. 4, 2019

(65) Prior Publication Data
US 2020/0397914 A1    Dec. 24, 2020

Related U.S. Application Data

(60) Provisional application No. 62/655,523, filed on Apr. 10, 2018, provisional application No. 62/611,056, filed on Dec. 28, 2017.

(51) Int. Cl.
| C07D 243/10 | (2006.01) |
| A61K 47/68 | (2017.01) |
| A61P 35/00 | (2006.01) |

(52) U.S. Cl.
CPC ...... *A61K 47/6803* (2017.08); *A61K 47/6869* (2017.08); *A61P 35/00* (2018.01)

(58) Field of Classification Search
CPC .................................................. C07D 243/10

USPC ......................................................... 540/555
See application file for complete search history.

(56) References Cited

FOREIGN PATENT DOCUMENTS

| EP | 3100745 A1 | 12/2016 |
| JP | 2009-532491 A | 9/2009 |
| JP | 2012-516896 A | 7/2012 |
| TW | 201811793 A | 4/2018 |
| WO | 2010/091150 A1 | 8/2010 |
| WO | 2017/201132 A2 | 11/2017 |
| WO | 2017/223275 A1 | 12/2017 |
| WO | 2018/075842 A1 | 4/2018 |

OTHER PUBLICATIONS

International Search Report and Written Opinion for Application No. PCT/US2018/067589, dated May 31, 2019, 14 pages.

*Primary Examiner* — Douglas M Willis
(74) *Attorney, Agent, or Firm* — McCarter & English, LLP; Xin Zhang; Daniel R. Jones

(57) ABSTRACT

The invention relates to novel benzodiazepine derivatives with antiproliferative activity and more specifically to novel benzodiazepine compounds of formulae (I), (II) and (III). The invention also provides conjugates of the benzodiazepine compounds linked to a cell-binding agent. The invention further provides compositions and methods useful for inhibiting abnormal cell growth or treating a proliferative disorder in a mammal using the compounds or conjugates of the invention.

(I)

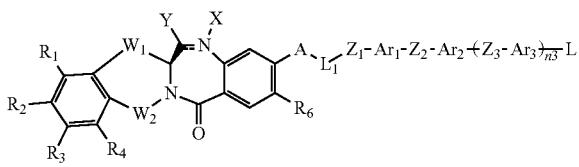

12 Claims, 9 Drawing Sheets
Specification includes a Sequence Listing.

| ADC | IGN Dose (µg/kg) | Ab Dose (mg/kg) | T/C (%) Day 22 | PR | CR | Result |
|---|---|---|---|---|---|---|
| M9346A-sSPDB-16 Ag (+) | 50 | 2.5 | 2 | 8/8 | 4/8 | Highly Active |
|  | 100 | 5 | 2 | 8/8 | 3/8 | Highly Active |
| chKTI-sSPDB-16 Ag (−) | 100 | 5 | 61 | 0/8 | 0/8 | Inactive |

SUBSTITUTED BENZO[5,6][1,4]DIAZEPINO[1,2-A]INDOLES FOR THE TREATMENT OF PROLIFERATIVE DISORDERS

RELATED APPLICATIONS

This application is a 35 U.S.C. § 371 national stage filing of International Application No. PCT/US2018/067589, filed on Dec. 27, 2018, which claims the benefit of the filing date, under 35 U.S.C. § 119(e), of U.S. Provisional Patent Application No. 62/611,056, filed on Dec. 28, 2017, and U.S. Provisional Patent Application No. 62/655,523, filed on Apr. 10, 2018. The entire content of each of the foregoing applications is hereby incorporated by reference.

FIELD OF THE INVENTION

The present invention relates to novel cytotoxic compounds, and cytotoxic conjugates comprising these cytotoxic compounds and cell-binding agents. More specifically, this invention relates to novel benzodiazepine compounds, derivatives thereof, intermediates thereof, conjugates thereof, and pharmaceutically acceptable salts thereof, which are useful as medicaments, in particular as anti-proliferative agents.

BACKGROUND OF THE INVENTION

Benzodiazepine derivatives are useful compounds for treating various disorders, and include medicaments such as, antiepileptics (imidazo[2,1-b][1,3,5]benzothiadiazepines, U.S. Pat. Nos. 4,444,688; 4,062,852), antibacterials (pyrimido[1,2-c][1,3,5]benzothiadiazepines, GB 1476684), diuretics and hypotensives (pyrrolo(1,2-b)[1,2,5]benzothiadiazepine 5,5 dioxide, U.S. Pat. No. 3,506,646), hypolipidemics (WO 03091232), anti-depressants (U.S. Pat. No. 3,453,266); osteoporosis (JP 2138272).

It has been shown in animal tumor models that benzodiazepine derivatives, such as pyrrolobenzodiazepines (PBDs), act as anti-tumor agents (N-2-imidazolyl alkyl substituted 1,2,5-benzothiadiazepine-1,1-dioxide, U.S. Pat. No. 6,156,746), benzo-pyrido or dipyrido thiadiazepine (WO 2004/069843), pyrrolo[1,2-b] [1,2,5] benzothiadiazepines and pyrrolo[1,2-b][1,2,5] benzodiazepine derivatives (WO2007/015280), tomaymycin derivatives (e.g., pyrrolo [1,4]benzodiazepines), such as those described in WO 00/12508, WO2005/085260, WO2007/085930, and EP 2019104. Benzodiazepines are also known to affect cell growth and differentiation (Kamal A., et al., Bioorg. Med. Chem., 2008 Aug. 15; 16(16):7804-10 (and references cited therein); Kumar R, Mini Rev Med Chem. 2003 June; 3(4):323-39 (and references cited therein); Bednarski J. J., et al., 2004; Sutter A. P, et al., 2002; Blatt N B, et al., 2002), Kamal A. et al., Current Med. Chem., 2002; 2; 215-254, Wang J-J., J. Med. Chem., 2206; 49:1442-1449, Alley M. C. et al., Cancer Res. 2004; 64:6700-6706, Pepper C. J., Cancer Res 2004; 74:6750-6755, Thurston D. E. and Bose D. S., Chem. Rev., 1994; 94:433-465; and Tozuka, Z., et al., Journal of Antibiotics, (1983) 36; 1699-1708. The general structure of PBDs is described in US Publication Number 20070072846. The PBDs differ in the number, type and position of substituents, in both their aromatic A rings and pyrrolo C rings, and in the degree of saturation of the C ring. Their ability to form an adduct in the minor groove and crosslink DNA enables them to interfere with DNA processing, hence their potential for use as antiproliferative agents.

The first pyrrolobenzodiazepine to enter the clinic, SJG-136 (NSC 694501) is a potent cytotoxic agent that causes DNA inter-strand crosslinks (S. G Gregson et al., 2001, *J. Med. Chem.*, 44: 737-748; M. C. Alley et al., 2004, *Cancer Res.*, 64: 6700-6706; J. A. Hartley et al., 2004, *Cancer Res.*, 64: 6693-6699; C. Martin et al., 2005, *Biochemistry.*, 44: 4135-4147; S. Arnould et al., 2006, *Mol. Cancer Ther.*, 5: 1602-1509). Results from a Phase I clinical evaluation of SJG-136 revealed that this drug was toxic at extremely low doses (maximum tolerated dose of 45 μg/m², and several adverse effects were noted, including vascular leak syndrome, peripheral edema, liver toxicity and fatigue. DNA damage was noted at all doses in circulating lymphocytes (D. Hochhauser et al., 2009, *Clin. Cancer Res.*, 15: 2140-2147).

Thus, there exists a need for improved benzodiazepine derivatives that are less toxic and still therapeutically active for treating a variety of proliferative diseases, such as cancer.

SUMMARY OF THE INVENTION

The present invention provides novel benzodiazepine cytotoxic compounds and cell-binding agent conjugates thereof. In some embodiments, the cytotoxic compounds comprise a bis/bi-aryl DNA binding motif, which can lead to improved metabolism, potency, tolerability and/or solubility of the corresponding cell-binding agent conjugates.

In a first aspect, the present invention is directed to a cytotoxic compound represented by the following formula:

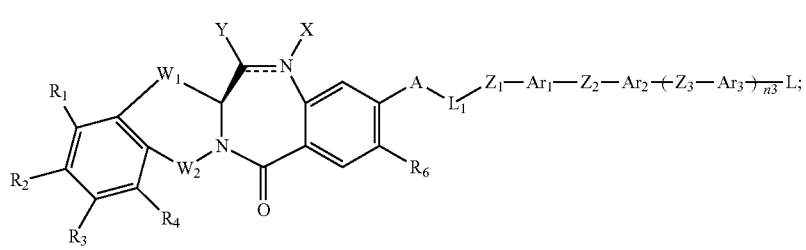

(I)

-continued

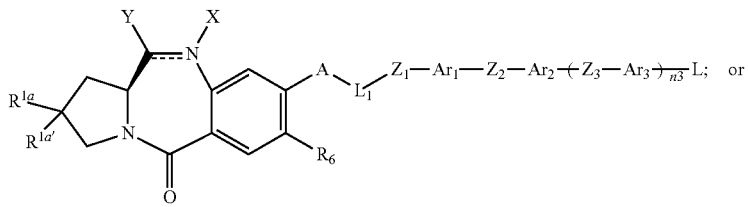

(II)

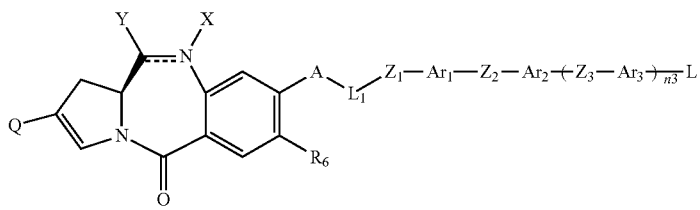

(III)

or a pharmaceutically acceptable salt thereof, wherein:
$W_1$ is —$(CH_2)_{n1}$—;
$W_2$ is —$(CH_2)_{n2}$—
n1 is 1, 2 or 3;
n2 is 0, 1 or 2;
n3 is 0 or 1;
$R^{1a}$ and $R^{1a'}$ are each independently H, halide, —OH, or $(C_1-C_6)$alkyl; or $R^{1a}$ and $R^{1a'}$ together form a double bond containing group =B;
=B is selected from a $(C_2-C_6)$alkenyl or a carbonyl group, wherein the $(C_2-C_6)$alkenyl is optionally substituted with a halogen, —OH, $(C_1-C_3)$alkoxy or phenyl;
Q is $Q_1$-Ar-$Q_2$;
$Q_1$ is absent, $(C_1-C_6)$alkyl, or —CH=CH—;
Ar is absent or an aryl group;
$Q_2$ is —H, a $(C_1-C_6)$alkyl, a $(C_1-C_6)$alkenyl, a polyethylene glycol unit —$R^{c'}$—$(OCH_2CH_2)_n$—$R^c$, or a substituent selected from a halogen, guanidinium [—NH(C=NH)NH$_2$], —R, —OR, —NR'R", —NO$_2$, —NCO, —NR'COR", NR'(C=O)OR"— SR, —SOR', —SO$_2$R', —SO$_3$H, —OSO$_3$H, —SO$_2$NR'R", cyano, an azido, —COR', —OCOR' and —OCONR'R";
n is an integer from 1 to 10;
$R^{c'}$ is a $(C_1-C_4)$alkyl,
$R^c$ is H, or a $(C_1-C_4)$alkyl,
the double line ⚌ between N and C represents a single bond or a double bond, provided that when it is a double bond X is absent and Y is —H, or a $(C_1-C_4)$ alkyl, and when it is a single bond, X is —H, an amine protecting moiety or $R^L$; and
Y is H of a leaving group selected from —$OR^Y$, —$OCOR^{Y1}$, —$OCOOR^{Y1}$, —$OCONR^{Y1}R^{Y2}$, —$NR^{Y1}R^{Y2}$, —$NR^{Y1}COR^{Y2}$, —$NR^{Y1}NR^{Y1}R^{Y2}$, an optionally substituted 5- or 6-membered nitrogen-containing heterocycle (e.g., piperidine, tetrahydropyrrole, pyrazole, morpholine, etc. attached through the nitrogen atom), a guanidinum represented by —$NR^{Y1}$(C=NH)$NR^{Y1}R^{Y2}$, an amino acid residue, or a peptide represented by —NRCOP', —$SR^Y$, —$SOR^{Y1}$, halogen, cyano, azido, —OSO$_3$H, sulfite (—SO$_3$H or —SO$_2$H), metabisulfite (H$_2$S$_2$O$_5$), mono-, di-, tri-, and tetra-thiophosphate (PO$_3$SH$_3$, PO$_2$S$_2$H$_2$, POS$_3$H$_2$, PS$_4$H$_2$), thio phosphate ester ($R^iO)_2$PS($OR^i$), $R^iS$—, $R^iSO$, $RSO_2$, $R^iSO_3$, thiosulfate (HS$_2$O$_3$), dithionite (HS$_2$O$_4$), phosphorodithioate (P(=S)($OR^{k'}$)(S)(OH)), hydroxamic acid ($R^{k'}$C(=O)NOH), and formaldehyde sulfoxylate (HOCH$_2$SO$_2$—) or a mixture thereof, wherein $R^i$ is a linear or branched alkyl having 1 to 10 carbon atoms and is substituted with at least one substituent selected from —N($R^j$)$_2$, —CO$_2$H, —SO$_3$H, and —PO$_3$H;
$R^i$ can be further optionally substituted with a substituent for an alkyl described herein;
$R^j$ is a linear or branched alkyl having 1 to 6 carbon atoms;
$R^{k'}$ is a linear, branched or cyclic alkyl, alkenyl or alkynyl having 1 to 10 carbon atoms, aryl, heterocyclyl or heteroaryl;
P' is an amino acid residue or a polypeptide containing between 2 to 20 amino acid residues,
$R^Y$, for each occurrence, is independently selected from the group consisting of —H, an optionally substituted linear, branched or cyclic alkyl, alkenyl or alkynyl having from 1 to 10 carbon atoms, a polyethylene glycol unit —$(CH_2CH_2O)_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;
$R^{Y1}$ and $R^{Y2}$ are each independently selected from —H, —OH, —$OR^Y$, —$NHR^Y$, —$NR^Y_2$, —$COR^Y$, an optionally substituted linear, branched or cyclic alkyl, alkenyl or alkynyl having from 1 to 10 carbon atoms, a polyethylene glycol unit;
$R^L$ is self-immolative linker bearing a reactive group that is capable of covalently linking the cytotoxic compound to a cell-binding agent (CBA);
$R_1$, $R_2$, $R_3$ and $R_4$ are each independently selected from —H, a $(C_1-C_6)$alkyl, halogen, —OR, —NR'R", —NO$_2$, —NR'COR", —SR, —SOR', —SO$_2$R', —SO$_3$H, —OSO$_3$H, —SO$_2$NR'R", cyano, —COR', —OCOR', and —OCONR'R";
R, for each occurrence, is —H or a $(C_1-C_6)$alkyl;
R' and R" are each independently selected from —H, —OH, —OR, —NHR, —NR$_2$, —COR, or a $(C_1-C_6)$alkyl;

$R_6$ is —H, —R, —OR, —SR, —NR'R", —NO$_2$, or halogen;

A is absent or is selected from —O—, —C(=O)—, —CRR'O—, —CRR'—, —S—, —CRR'S—, —NR$_5$ and —CRR'N(R$_5$)—;

L$_1$ is a spacer;

Z$_1$ is a bond,

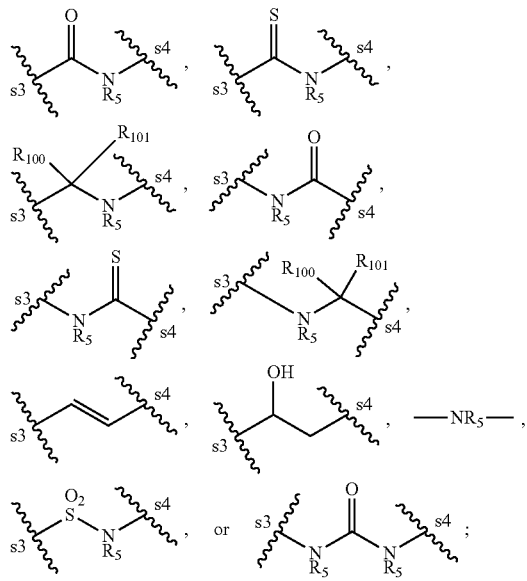

s3 is the site connected L$_1$ and s4 is the site connected to Ar$_1$;

R$_5$ is —H or a (C$_1$-C$_4$)alkyl;

R$_{100}$ and R$_{101}$, for each occurrence, are each independently —H, halogen, (C$_1$-C$_4$)alkyl, or (C$_1$-C$_4$)haloalkyl;

Ar$_1$ is a 6- to 18-membered aromatic ring, a 5- to 18-membered heteroaromatic ring, or -Ar$_1$'-Ar$_1$"-, wherein Ar$_1$' and Ar$_1$" are each independently a 6- to 18-membered aromatic ring or a 5- to 18-membered heteroaromatic ring;

Z$_2$ is absent,

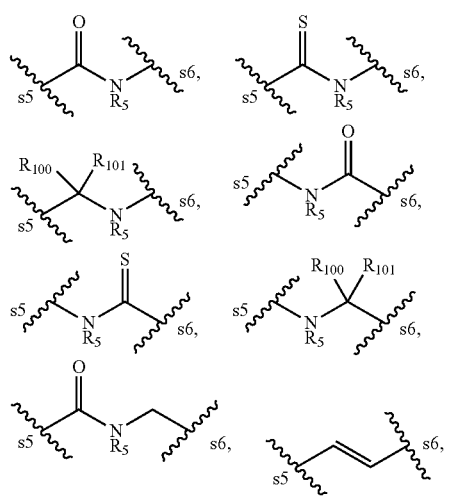

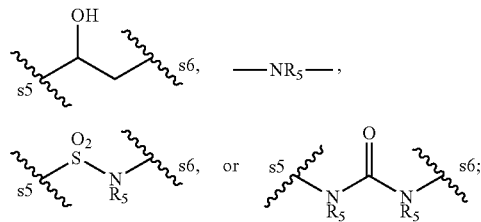

s5 is the site connected Ar$_1$ and s6 is the site connected to Ar$_2$;

Ar$_2$ is absent, a 6- to 18-membered aromatic ring, a 5- to 18-membered heteroaromatic ring or -Ar$_2$'-Ar$_2$"-, wherein Ar$_2$' and Ar$_2$" are each independently a 6- to 18-membered aromatic ring or a 5- to 18-membered heteroaromatic ring;

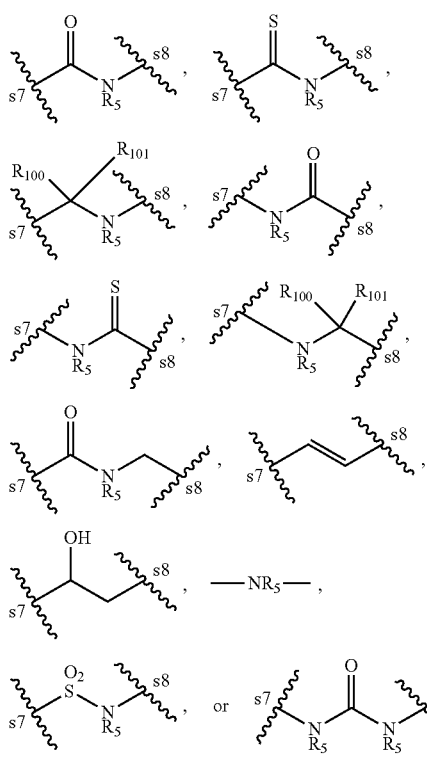

Ar$_3$ is a 6- to 18-membered aromatic ring, a 5- to 18-membered heteroaromatic ring or -Ar$_3$'-Ar$_3$"-, wherein Ar$_n$' and Ar$_n$" are each independently a 6- to 18-membered aromatic ring or a 5- to 18-membered heteroaromatic ring;

L is H, —C(=O)R$_a$, —NR$_b$R$_c$, or a linker bearing a reactive group that is capable of covalently linking the cytotoxic compound to a cell-binding agent (CBA);

R$_a$ is —OH, —Cl, —O(C$_1$-C$_6$)alkyl or —C(=O)OR$_a$ is a reactive ester group;

R$_b$ and R$_c$ are each independently —H, (C$_1$-C$_4$)alkyl or an amine protecting group; provided when X is R$^L$, L is H, —C(=O)R$_a$ or —NR$_b$R$_c$.

In some embodiments, for the compounds of formula (II) or (III), $Z_1$ is not

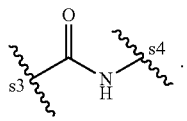 [SMILES: *NC(*)=O]

5

In some embodiments, the compound of formula (I) is not

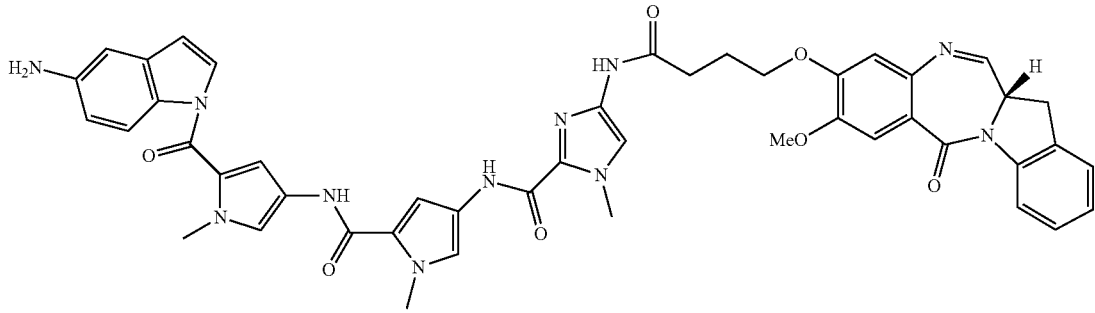 [SMILES: COc1cc2c(cc1OCCCC(=O)Nc1cn(C)c(C(=O)Nc3cc(C(=O)Nc4cc(C(=O)n5ccc6cc(N)ccc65)n(C)c4)n(C)c3)n1)N=C[C@@H]1Cc3ccccc3N1C2=O]

or a pharmaceutically acceptable salt thereof.

In some embodiments, for compounds of formula (I) or a pharmaceutically acceptable salt thereof, Y is —OR$^Y$, —OCOR$^{Y1}$, —OCOOR$^{Y1}$, or —SO$_3$H; and the remaining variables are as defined above in the first aspect. In some embodiments, for compounds of formula (I) or a pharmaceutically acceptable salt thereof, Y is —OH or —SO$_3$H. In some embodiments, Y is —SO$_3$H, —SO$_3$Na or —SO$_3$K. In some embodiments, Y is —SO$_3$H or —SO$_3$Na.

In a second aspect, the present invention is directed to a cell-binding agent-cytotoxic agent conjugate represented by the following formula:

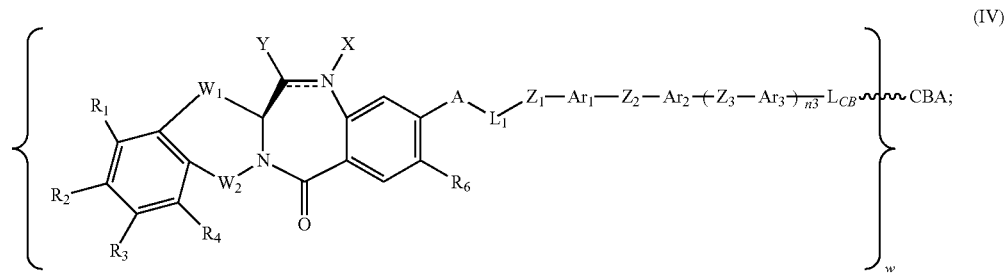

(IV)

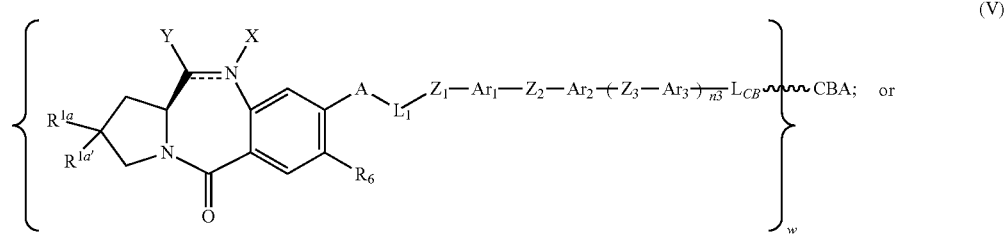

(V)

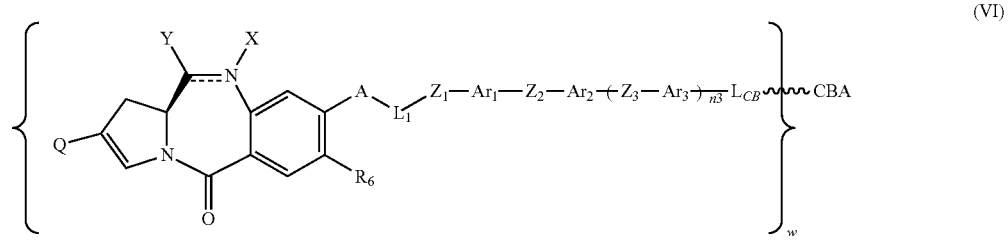

(VI)

or a pharmaceutically acceptable salt thereof, wherein:
$W_1$ is —$(CH_2)_{n1}$—;
$W_2$ is —$(CH_2)_{n2}$—
n1 is 1, 2 or 3;
n2 is 0, 1 or 2;
n3 is 0 or 1;
$R^{1a}$ and $R^{1a'}$ are each independently H, halide, —OH, or $(C_1-C_6)$alkyl; or $R^{1a}$ and $R^{1a'}$ together form a double bond containing group =B;
=B is selected from a $(C_2-C_6)$alkenyl or a carbonyl group, wherein the $(C_2-C_6)$alkenyl is optionally substituted with a halogen, —OH, $(C_1-C_3)$alkoxy or phenyl;
Q is $Q_1$-Ar-$Q_2$;
$Q_1$ is absent, $(C_1-C_6)$alkyl, or —CH=CH—;
Ar is absent or an aryl group;
$Q_2$ is —H, a $(C_1-C_6)$alkyl, a $(C_1-C_6)$alkenyl, a polyethylene glycol unit —$R^{c'}$—$(OCH_2CH_2)_n$—$R^c$, or a substituent selected from a halogen, guanidinium [—NH(C=NH)NH$_2$], —R, —OR, —NR'R", —NO$_2$, —NCO, —NR'COR", NR'(C=O)OR"— SR, —SOR', —SO$_2$R', —SO$_3$H, —OSO$_3$H, —SO$_2$NR'R", cyano, an azido, —COR', —OCOR' and —OCONR'R";
n is an integer from 1 to 10;
$R^{c'}$ is a $(C_1-C_4)$alkyl,
$R^c$ is H, or a $(C_1-C_4)$alkyl,
the double line $\doublebond$ between N and C represents a single bond or a double bond, provided that when it is a double bond X is absent and Y is —H, or a $(C_1-C_4)$ alkyl, and when it is a single bond, X is —H, an amine protecting moiety or $R^{L1}$; and
Y is H of a leaving group selected from —$OR^Y$, —$OCOR^{Y1}$, —$OCOOR^{Y1}$, —$OCONR^{Y1}R^{Y2}$, —$NR^{Y1}R^{Y2}$, —$NR^{Y1}COR^{Y2}$, —$NR^{Y1}NR^{Y1}R^{Y2}$, an optionally substituted 5- or 6-membered nitrogen-containing heterocycle (e.g., piperidine, tetrahydropyrrole, pyrazole, morpholine, etc. attached through the nitrogen atom), a guanidinum represented by —$NR^{Y1}$(C=NH)$NR^{Y1}R^{Y2}$, an amino acid residue, or a peptide represented by —NRCOP', —$SR^Y$, —$SOR^{Y1}$, halogen, cyano, azido, —OSO$_3$H, sulfite (—SO$_3$H or —SO$_2$H), metabisulfite (H$_2$S$_2$O$_5$), mono-, di-, tri-, and tetra-thiophosphate (PO$_3$SH$_3$, PO$_2$S$_2$H$_2$, POS$_3$H$_2$, PS$_4$H$_2$), thio phosphate ester ($R^i$O)$_2$PS(OR), $R^i$S—, $R^i$SO, $R^i$SO$_2$, $R^i$SO$_3$, thiosulfate (HS$_2$O$_3$), dithionite (HS$_2$O$_4$), phosphorodithioate (P(=S)(OR$^{k'}$)(S)(OH)), hydroxamic acid ($R^{k'}$C(=O)NOH), and formaldehyde sulfoxylate (HOCH$_2$SO$_2$—) or a mixture thereof, wherein $R^i$ is a linear or branched alkyl having 1 to 10 carbon atoms and is substituted with at least one substituent selected from —N($R^j$)$_2$, —CO$_2$H, —SO$_3$H, and —PO$_3$H; $R^i$ can be further optionally substituted with a substituent for an alkyl described herein; $R^j$ is a linear or branched alkyl having 1 to 6 carbon atoms; $R^{k'}$ is a linear, branched or cyclic alkyl, alkenyl or alkynyl having 1 to 10 carbon atoms, aryl, heterocyclyl or heteroaryl;
P' is an amino acid residue or a polypeptide containing between 2 to 20 amino acid residues,
$R^Y$, for each occurrence, is independently selected from the group consisting of —H, an optionally substituted linear, branched or cyclic alkyl, alkenyl or alkynyl having from 1 to 10 carbon atoms, a polyethylene glycol unit —(CH$_2$CH$_2$O)$_n$—$R^c$, an optionally substituted aryl having 6 to 18 carbon atoms, an optionally substituted 5- to 18-membered heteroaryl ring containing one or more heteroatoms independently selected from nitrogen, oxygen, and sulfur, or an optionally substituted 3- to 18-membered heterocyclic ring containing 1 to 6 heteroatoms independently selected from O, S, N and P;
$R^{Y1}$ and $R^{Y2}$ are each independently selected from —H, —OH, —$OR^Y$, —$NHR^Y$, —$NR^{Y2}$, —$COR^Y$, an optionally substituted linear, branched or cyclic alkyl, alkenyl or alkynyl having from 1 to 10 carbon atoms, a polyethylene glycol unit;
$R^{L1}$ is self-immolative linker bearing a linking moiety that is covalently bonded the cell-binding agent (CBA);
$R_1$, $R_2$, $R_3$ and $R_4$ are each independently selected from —H, a $(C_1-C_6)$alkyl, halogen, —OR, —NR'R", —NO$_2$, —NR'COR", —SR, —SOR', —SO$_2$R', —SO$_3$H, —OSO$_3$H, —SO$_2$NR'R", cyano, —COR', —OCOR', and —OCONR'R";
R, for each occurrence, is —H or a $(C_1-C_6)$alkyl;
R' and R" are each independently selected from —H, —OH, —OR, —NHR, —NR$_2$, —COR, or a $(C_1-C_6)$alkyl;
$R_6$ is —H, —R, —OR, —SR, —NR'R", —NO$_2$, or halogen;
A is absent or is selected from —O—, —C(=O)—, —CRR'O—, —CRR'—, —S—, —CRR'S—, —NR$_5$ and —CRR'N(R$_5$)—;
$L_1$ is a spacer;
$Z_1$ is a bond,

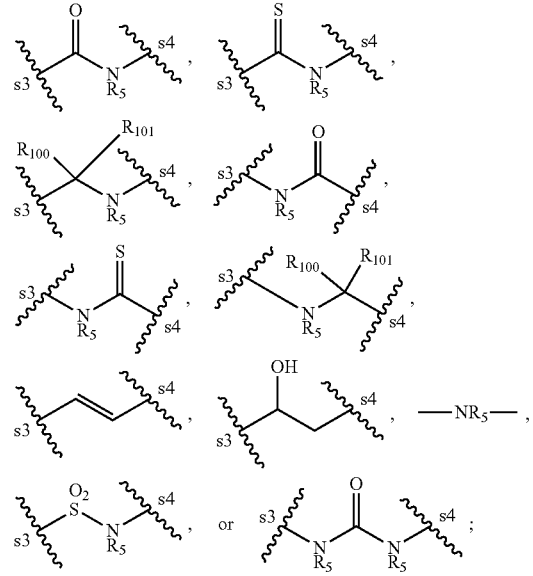

s3 is the site connected $L_1$ and s4 is the site connected to $Ar_1$;
$R_5$ is —H or a $(C_1-C_4)$alkyl;
$R_{100}$ and $R_{101}$, for each occurrence, are each independently —H, halogen, $(C_1-C_4)$alkyl, or $(C_1-C_4)$haloalkyl;
$Ar_1$ is a 6- to 18-membered aromatic ring, a 5- to 18-membered heteroaromatic ring, or -$Ar_1$'-$Ar_1$"-, wherein $Ar_1$' and $Ar_1$" are each independently a 6- to 18-membered aromatic ring or a 5- to 18-membered heteroaromatic ring;

$Z_2$ is absent,

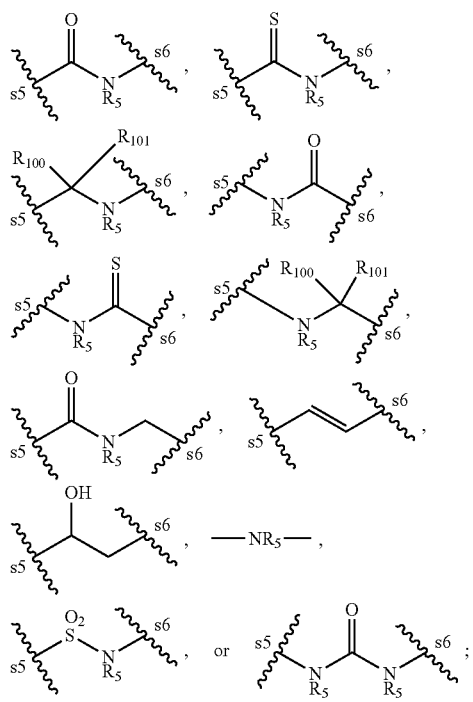

s5 is the site connected $Ar_1$ and s6 is the site connected to $Ar_2$;

$Ar_2$ is absent, a 6- to 18-membered aromatic ring, a 5- to 18-membered heteroaromatic ring or -$Ar_2'$-$Ar_2''$-, wherein $Ar_2'$ and $Ar_2''$ are each independently a 6- to 18-membered aromatic ring or a 5- to 18-membered heteroaromatic ring;

$Z_3$ is

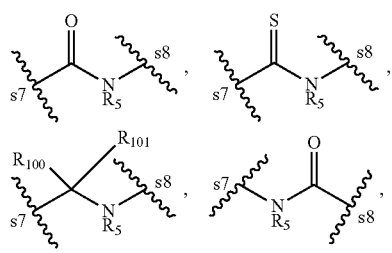

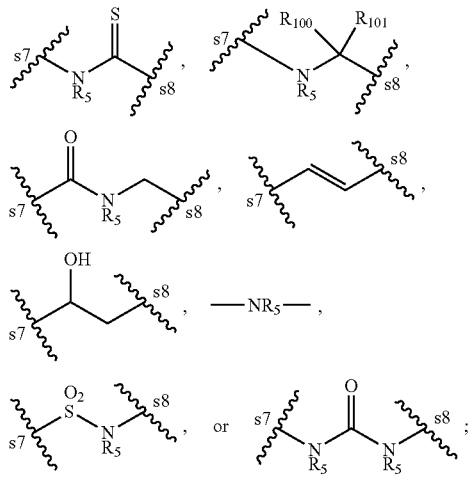

s7 is the site connected to $Ar_2$ and s8 is the site connected to $Ar_3$;

$Ar_3$ is a 6- to 18-membered aromatic ring, a 5- to 18-membered heteroaromatic ring or -$Ar_3'$-$Ar_3''$-, wherein $Ar_3'$ and $Ar_3''$ are each independently a 6- to 18-membered aromatic ring or a 5- to 18-membered heteroaromatic ring;

$L_{CB}$ is a linker bearing a linking moiety that is covalently linked to the cell-binding agent (CBA);

w is an integer from 1 to 20;

$R_a$ is —OH, —Cl, —O($C_1$-$C_6$)alkyl or —C(=O)$OR_a$ is a reactive ester group;

$R_b$ and $R_c$ are each independently —H, ($C_1$-$C_4$)alkyl or an amine protecting group; provided that when X is $R^{L1}$, L is H, —C(=O)$R_a$ or —$NR_bR_c$.

In some embodiments, for the conjugates of formula (V) or (VI), $Z_1$ is not

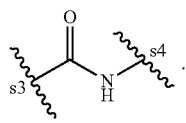

In some embodiments, the conjugate of formula (IV) does not comprise a compound represented by

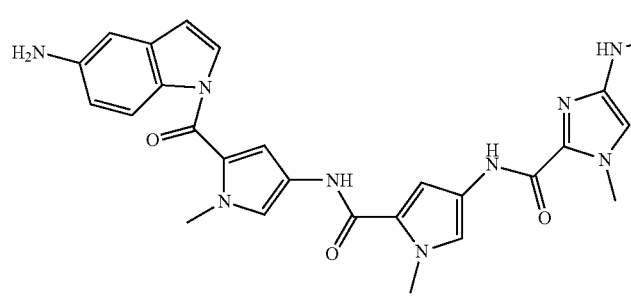

or a pharmaceutically acceptable salt thereof.

In some embodiments, for compounds of formula (I) or a pharmaceutically acceptable salt thereof, Y is —OR$^Y$, —OCOR$^{Y1}$, —OCOOR$^{Y1}$, or —SO$_3$H; and the remaining variables are as defined above in the first aspect. In some embodiments, for compounds of formula (I) or a pharmaceutically acceptable salt thereof, Y is —OH or —SO$_3$H. In some embodiments, Y is —SO$_3$H, —SO$_3$Na or —SO$_3$K. In some embodiments, Y is —SO$_3$H or —SO$_3$Na.

The present invention also includes a composition (e.g., a pharmaceutical composition) comprising the cytotoxic compounds of the present invention, derivatives thereof, or conjugates thereof, (and/or solvates, hydrates and/or salts thereof) and a carrier (a pharmaceutically acceptable carrier). The present invention additionally includes a composition (e.g., a pharmaceutical composition) comprising the cytotoxic compounds of the present invention, derivatives thereof, or conjugates thereof (and/or solvates, hydrates and/or salts thereof), and a carrier (a pharmaceutically acceptable carrier), further comprising a second therapeutic agent. The present compositions are useful for inhibiting abnormal cell growth or treating a proliferative disorder in a mammal (e.g., human). The present compositions are useful for treating conditions such as cancer, rheumatoid arthritis, multiple sclerosis, graft versus host disease (GVHD), transplant rejection, lupus, myositis, infection, immune deficiency such as AIDS, and inflammatory diseases in a mammal (e.g., human).

The present invention includes a method of inhibiting abnormal cell growth or treating a proliferative disorder in a mammal (e.g., human) comprising administering to said mammal a therapeutically effective amount of the cytotoxic compounds of the present invention, derivatives thereof, or conjugates thereof, (and/or solvates and salts thereof) or a composition thereof, alone or in combination with a second therapeutic agent. In some embodiments, the proliferative disorder is cancer. Also included in the present invention is the use of the cytotoxic compounds of the present invention, derivatives thereof, or conjugates thereof, (and/or solvates and salts thereof) or a composition thereof for the manufacture of a medicament for inhibiting abnormal cell growth or treating a proliferative disorder (e.g., cancer) in a mammal (e.g., human).

The present invention includes a method of synthesizing and using the cytotoxic compounds of the present invention, derivatives thereof, and conjugates thereof for in vitro, in situ, and in vivo diagnosis or treatment of mammalian cells, organisms, or associated pathological conditions.

DETAILED DESCRIPTION OF THE INVENTION

Figure 1:
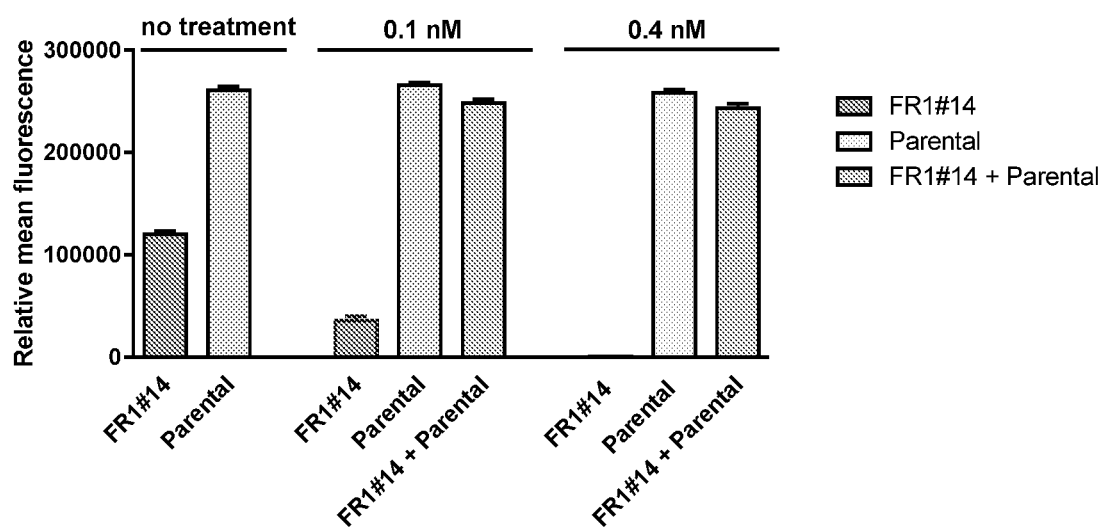
FIG. 1 shows bystander killing effects of a representative conjugate of the present invention.

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents that can be included within the scope of the present invention as defined by the claims. One skilled in the art will recognize many methods and materials similar or equivalent to those described herein, which could be used in the practice of the present invention.

It should be understood that any of the embodiments described herein, including those described under different aspects of the invention and different parts of the specification (including embodiments described only in the Examples) can be combined with one or more other embodiments of the invention, unless explicitly disclaimed or improper. Combination of embodiments are not limited to those specific combinations claimed via the multiple dependent claims.

Definitions

"Alkyl" or "linear or branched alkyl" as used herein refers to a saturated linear or branched monovalent hydrocarbon radical. In preferred embodiments, a straight chain or branched chain alkyl has thirty or fewer carbon atoms (e.g., $C_1$-$C_{30}$ for straight chain alkyl group and $C_3$-$C_{30}$ for branched alkyl), and more preferably twenty or fewer carbon atoms.

Even more preferably, the straight chain or branched chain alkyl has ten or fewer carbon atoms (i.e., $C_1$-$C_{10}$ for straight chain alkyl group and $C_3$-$C_{10}$ for branched alkyl). In other embodiments, the straight chain or branched chain alkyl has six or fewer carbon atoms (i.e., $C_1$-$C_6$ for straight chain alky group or $C_3$-$C_6$ for branched chain alkyl). Examples of alkyl include, but are not limited to, methyl, ethyl, 1-propyl, 2-propyl, 1-butyl, 2-methyl-1-propyl, —CH$_2$CH(CH$_3$)$_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like. Moreover, the term "alkyl" as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. As used herein, $(C_x-C_{xx})$alkyl or $C_{x-xx}$alky means a linear or branched alkyl having x-xx carbon atoms.

"Alkenyl" or "linear or branched alkenyl" refers to linear or branched-chain monovalent hydrocarbon radical of two to twenty carbon atoms with at least one site of unsaturation, i.e., a carbon-carbon double bond, wherein the alkenyl radical includes radicals having "cis" and "trans" orientations, or alternatively, "E" and "Z" orientations. Examples include, but are not limited to, ethylenyl or vinyl (—CH=CH$_2$), allyl (—CH$_2$CH=CH$_2$), and the like. Preferably, the alkenyl has two to ten carbon atoms. More preferably, the alkyl has two to four carbon atoms.

"Alkynyl" or "linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like. Preferably, the alkynyl has two to ten carbon atoms. More preferably, the alkynyl has two to four carbon atoms.

The terms "cyclic alkyl" and "cycloalkyl" can be used interchangeably. As used herein, the term refers to the radical of a saturated carbocyclic ring. In preferred embodiments, cycloalkyls have from 3 to 10 carbon atoms in their ring structure, and more preferably from 5 to 7 carbon atoms in the ring structure. In some embodiments, the two cyclic rings can have two or more atoms in common, e.g., the rings are "fused rings." Suitable cycloalkyls include, but are not limited to cycloheptyl, cyclohexyl, cyclopentyl, cyclobutyl and cyclopropyl. In some embodiments, the cycloalkyl is a monocyclic group. In some embodiments, the cycloalkyl is a bicyclic group. In some embodiments, the cycloalkyl is a tricyclic group.

The term "cycloalklalkyl" refers to an alkyl group described above that is substituted with a cycloalkyl group.

The term "cyclic alkenyl" refers to a carbocyclic ring radical having at least one double bond in the ring structure.

The term "cyclic alkynyl" refers to a carbocyclic ring radical having at least one triple bond in the ring structure.

The term "aryl" or "aromatic ring" as used herein, include substituted or unsubstituted single-ring aromatic groups in which each atom of the ring is carbon.

Preferably the ring is a 5- to 7-membered ring, more preferably a 6-membered ring. Aryl groups include, but are not limited to, phenyl, phenol, aniline, and the like. The terms "aryl" also includes "polycyclyl", "polycycle", and "polycyclic" ring systems having two or more rings in which two or more atoms are common to two adjoining rings, e.g., the rings are "fused rings," wherein at least one of the rings is aromatic, e.g., the other cyclic rings can be cycloalkyls, cycloalkenyls, cycloalkynyls, or aromatic rings. In some preferred embodiments, polycycles have 2-3 rings. In certain preferred embodiments, polycyclic ring systems have two cyclic rings in which both of the rings are aromatic. Each of the rings of the polycycle can be substituted or unsubstituted. In certain embodiments, each ring of the polycycle contains from 3 to 10 carbon atoms in the ring, preferably from 5 to 7. For example, aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl, and the like. In some embodiments, the aryl is a single-ring aromatic group. In some embodiments, the aryl is a two-ring aromatic group. In some embodiments, the aryl is a three-ring aromatic group.

The terms "heterocycle," "heterocyclyl," and "heterocyclic ring" as used herein, refers to substituted or unsubstituted non-aromatic ring structures of 3- to 18-membered rings, preferably 3- to 10-membered rings, more preferably 3- to 7-membered rings, whose ring structures include at least one heteroatom, preferably one to four heteroatoms, more preferably one or two heteroatoms. In certain embodiments, the ring structure can have two cyclic rings. In some embodiments, the two cyclic rings can have two or more atoms in common, e.g., the rings are "fused rings." Heterocyclyl groups include, for example, piperidine, piperazine, pyrrolidine, morpholine, lactones, lactams, and the like. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. Examples of heterocyclic rings include, but are not limited to, tetrahydrofurane, dihydrofuran, tetrahydrothiene, tetrahydropyran, dihydropyran, tetrahydrothiopyran, thiomorpholine, thioxane, homopiperazine, azetidine, oxetane, thietane, homopiperidine, piperidine, piperazine, pyrrolidine, morpholine, oxepane, thiepane, oxazepine, diazepine, thiazepine, 2-pyrroline, 3-pyrroline, indoline, 2H-pyrane, 4H-pyrane, dioxane, 1,3-dioxolane, pyrazoline, dithiane, dithiolane, dihydropyrane, dihydrothiene, dihydrofurane, pyrazolidinylimidazoline, imidazolidine, 3-azabicyco[3.1.0]hexane, 3-azabicyclo[4.1.0]heptane, and azabicyclo[2.2.2]hexane. Spiro moieties are also included within the scope of this definition. Examples of a heterocyclic group wherein ring atoms are substituted with oxo (=O) moieties are pyrimidinone and 1,1-dioxo-thiomorpholine.

The term "heteroaryl" or "heteroaromatic ring" as used herein, refers to substituted or unsubstituted aromatic single ring structures, preferably 6- to 18-membered rings, preferably 5- to 7-membered rings, more preferably 5- to 6-membered rings, whose ring structures include at least one heteroatom (e.g., O, N, or S), preferably one to four or one to three heteroatoms, more preferably one or two heteroatoms. When two or more heteroatoms are present in a heteroaryl ring, they may be the same or different. The term "heteroaryl" also includes "polycyclyl", "polycycle", and "polycyclic" ring systems having two or more cyclic rings in which two or more ring atoms are common to two adjoining rings, e.g., the rings are "fused rings," wherein at least one of the rings is heteroaromatic, e.g., the other cyclic rings can be cycloalkyls, cycloalkenyls, cycloalkynyls, aryls, heteroaromatics, and/or heterocyclyls. In some preferred embodiments, polycyclic heteroaryls have 2-3 rings. In certain embodiments, preferred polycyclic heteroaryls have two cyclic rings in which both of the rings are aromatic. In certain embodiments, each ring of the polycycle contains from 3 to 10 atoms in the ring, preferably from 5 to 7 atoms in the ring. For examples, heteroaryl groups include, but are not limited to, pyrrole, furan, thiophene, imidazole, oxazole, thiazole, pyrazole, pyridine, pyrazine, pyridazine, quinoline, pyrimidine, indolizine, indole, indazole, benzimidazole, benzothiazole, benzofuran, benzothiophene, cinnoline, phthalazine, quinazoline, carbazole, phenoxazine, quinoline, purine and the like. In some embodiments, the heteroaryl is a single-ring aromatic group. In some embodiments, the heteroaryl is a two-ring aromatic group. In some embodiments, the heteroaryl is a three-ring aromatic group.

The heterocycle or heteroaryl groups can be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocyclyl include the oxidized forms such as NO, SO, and $SO_2$.

In some embodiments, the heteroaromatic ring is a 5- to 18-membered ring.

The term "halo" or "halogen" refers to fluorine (F), chlorine (Cl), bromine (Br) or iodine (I). In some embodiments, the halogen is fluorine. In some embodiments, the halogen is chlorine. In some embodiments, the halogen is bromine. In some embodiments, the halogen is iodine. As used herein, the term "haloalkyl" refers to an alkyl, as defined herein, that is substituted by one or more halo groups as defined herein. The haloalkyl can be monohaloalkyl, dihaloalkyl or polyhaloalkyl. A monohaloalkyl can have one fluoro, chloro, bromo, or iodo substituent. Dihaloalkyl or polyhaloalkyl can be substituted with two or more of the same halo atoms or a combination of different halo groups. Examples of haloalkyl include, but are not limited to, flouromethyl, difluoromethyl, trifluoromethyl, chloroamethyl, dichloromethyl, trichloromethyl, pentafluoroethyl, heptafluoropropyl, diflurochloromethyl, dichlorofluoromethyl, difluoroehthyl, diflosoropropyl, dichloroethyl and dichloropropyl.

"Alkoxy" used herein refers to alkyl-O—, wherein alkyl is defined herein above. Examples of alkoxy include, not are not limited to, methoxy, ethoxy, propoxy, 2-propoxy, butoxy, tert-butoxy, pentyloxy, hexyloxy, and the like.

The alkyl, haloalkyl, alkoxy, alkenyl, alkynyl, cyclic alkyl, cyclic alkenyl, cyclic alkynyl, carbocyclyl, aryl, heterocyclyl and heteroaryl described above can be optionally substituted with one or more (e.g., 2, 3, 4, 5, 6 or more) substituents.

Unless specifically stated as "unsubstituted," references to chemical moieties herein are understood to also include substituted variants. For example, reference to an "alkyl" group or moiety implicitly includes both substituted and unsubstituted variants. Examples of substituents on chemical moieties includes but is not limited to, halogen, hydroxyl, carbonyl (such as carboxyl, alkoxycarbonyl, formyl, or acyl), thiocarbonyl (such as thioester, thioacetate, or thioformate), alkoxyl, alkylthio, acyloxy, phosphoryl, phosphate, phosphonate, amino, amido, amidine, imine, cyano, nitro, azido, sulfhydryl, alkylthio, sulfate, sulfonate, sulfamoyl, sulfonamido, sulfonyl, heterocyclyl, aralkyl, or aryl or heteroaryl moiety.

"Optional" or "optionally" means that the subsequently described circumstance may or may not occur, so that the application includes instances where the circumstance occurs and instances where it does not. For example, the phrase "optionally substituted" means that a nonhydrogen substituent may or may not be present on a given atom, and, thus, the application includes structures wherein a nonhydrogen substituent is present and structures wherein a nonhydrogen substituent is not present.

The term "substituted" refers to moieties having substituents replacing a hydrogen on one or more carbons, nitrogens, oxygens or sulfurs atoms. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a carbon of a substituent is described as being optionally substituted with one or more of a list of substituents, one or more of the hydrogens on the carbon (to the extent there are any) can separately and/or together be replaced with an independently selected optional substituent. If a nitrogen of a substituent is described as being optionally substituted with one or more of a list of substituents, one or more of the hydrogens on the nitrogen (to the extent there are any) can each be replaced with an independently selected optional substituent. One exemplary substituent can be depicted as —NR'R", wherein R' and R" together with the nitrogen atom to which they are attached, can form a heterocyclic ring. The heterocyclic ring formed from R' and R" together with the nitrogen atom to which they are attached can be partially or fully saturated. In some embodiments, the heterocyclic ring consists of 3 to 7 atoms. In other embodiments, the heterocyclic ring is selected from pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group can include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent can be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, aryl, heteroaryl, heterocyclyl, halogen, guanidinium [—NH(C=NH)NH$_2$], —OR$^{100}$, NR$^{101}$R$^{102}$, —NO$_2$, —NR$^{101}$COR$^{102}$, —SR$^{100}$, a sulfoxide represented by —SOR$^{101}$, a sulfone represented by —SO$_2$R$^{101}$, a sulfonate —SO$_3$M, a sulfate —OSO$_3$M, a sulfonamide represented by —SO$_2$NR$^{101}$R$^{102}$, cyano, an azido, —COR$^{101}$, —OCOR$^{101}$, —OCONR$^{101}$R$^{102}$ and a polyethylene glycol unit (—OCH$_2$CH$_2$)$_n$R$^{101}$ wherein M is H or a cation (such as Na$^+$ or K$^+$); R$^{101}$, R$^{102}$ and R$^{103}$ are each independently selected from H, linear, branched or cyclic alkyl, alkenyl or alkynyl having from 1 to 10 carbon atoms, a polyethylene glycol unit (—OCH$_2$CH$_2$)$_n$—R$^{104}$, wherein n is an integer from 1 to 24, an aryl having from 6 to 10 carbon atoms, a heterocyclic ring having from 3 to 10 carbon atoms and a heteroaryl having 5 to 10 carbon atoms; and R$^{104}$ is H or a linear or branched alkyl having 1 to 4 carbon atoms, wherein the alkyl, alkenyl, alkynyl, aryl, heteroaryl and heterocyclyl in the groups represented by R$^{100}$, R$^{101}$, R$^{102}$, R$^{103}$ and R$^{104}$ are optionally substituted with one or more (e.g., 2, 3, 4, 5, 6 or more) substituents independently selected from halogen, —OH, —CN, —NO$_2$ and unsubstituted linear or branched alkyl having 1 to 4 carbon atoms. Preferably, the substituents for the optionally substituted alkyl, alkenyl, alkynyl, cyclic alkyl, cyclic alkenyl, cyclic alkynyl, carbocyclyl, aryl, heterocyclyl and heteroaryl described above include halogen, —CN, —NR$^{102}$R$^{103}$, —CF$_3$, —OR$^{101}$, aryl, heteroaryl, heterocyclyl, —SR$^{101}$, —SOR$^{101}$, —SO$_2$R$^{101}$ and —SO$_3$M.

The number of carbon atoms in a group can be specified herein by the prefix "C$_{x\text{-}xx}$" or "C$_x$-C$_{xx}$", wherein x and xx are integers. For example, "C$_{1\text{-}4}$alkyl" or "C$_1$-C$_4$ alkyl" is an alkyl group having from 1 to 4 carbon atoms.

The term "compound" or "cytotoxic compound," "cytotoxic dimer" and "cytotoxic dimer compound" are used interchangeably. They are intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers," "geometric isomers," "tautomers," "solvates," "metabolites," "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "conjugate" as used herein refers to a compound described herein or a derivative thereof that is linked to a cell binding agent.

The term "precursor" of a given group refers to any group that can lead to that group by any deprotection, a chemical modification, or a coupling reaction.

The term "chiral" refers to molecules that have the property of non-superimposability of the mirror image partner, while the term "achiral" refers to molecules that are superimposable on their mirror image partner.

The term "stereoisomer" refers to compounds that have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities.

Mixtures of diastereomers can separate under high resolution analytical procedures such as crystallization, electrophoresis and chromatography.

"Enantiomers" refer to two stereoisomers of a compound that are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds," John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies that are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt can involve the inclusion of another molecule such as an acetate ion, a succinate ion or other counter ion. The counter ion can be any organic or inorganic moiety that stabilizes the charge on the parent compound. Furthermore, a pharmaceutically acceptable salt can have more than one charged atom in its structure.

Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt can be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt can be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound that further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amine-protecting group" or an "amino-protecting moiety" is a substituent attached to an amino group that blocks or protects the amino functionality in the compound.

Such groups are well known in the art (see for example P. Wuts and T. Greene, 2007, Protective Groups in Organic Synthesis, Chapter 7, J. Wiley & Sons, NJ) and exemplified by carbamates such as methyl and ethyl carbamate, FMOC, substituted ethyl carbamates, carbamates cleaved by 1,6-p-elimination (also termed "self immolative"), ureas, amides, peptides, alkyl and aryl derivatives. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see P. G. M. Wuts & T. W. Greene, Protective Groups in Organic Synthesis, John Wiley & Sons, New York, 2007.

The term "leaving group" refers to an group of charged or uncharged moiety that departs during a substitution or displacement. Such leaving groups are well known in the art and include, but not limited to, halogens, esters, alkoxy, hydroxyl, tosylates, triflates, mesylates, nitriles, azide, carbamate, disulfides, thioesters, thioethers and diazonium compounds.

The term "reactive ester" refers to an ester having an easily displaceable leaving group that can readily react with an amine group to form an amide bond. Examples of reactive esters include, but are not limited to, N-hydroxysuccinimide ester, N-hydroxy sulfosuccinimide ester, nitrophenyl (e.g., 2 or 4-nitrophenyl) ester, dinitrophenyl (e.g., 2,4-dinitrophenyl) ester, sulfo-tetraflurophenyl (e.g., 4 sulfo-2,3,5,6-tetrafluorophenyl) ester, or pentafluorophenyl ester.

The term "bifunctional crosslinking agent," "bifunctional linker" or "crosslinking agents" refers to modifying agents that possess two reactive groups; one of which is capable of reacting with a cell binding agent while the other one reacts with the cytotoxic compound to link the two moieties together. Such bifunctional crosslinkers are well known in the art (see, for example, Isalm and Dent in *Bioconjugation* chapter 5, p218-363, Groves Dictionaries Inc. New York, 1999). For example, bifunctional crosslinking agents that enable linkage via a thioether bond include N-succinimidyl-4-(N-maleimidomethyl)-cyclohexane-1-carboxylate (SMCC) to introduce maleimido groups, or with N-succinimidyl-4-(iodoacetyl)-aminobenzoate (SIAB) to introduce iodoacetyl groups. Other bifunctional crosslinking agents that introduce maleimido groups or haloacetyl groups on to a cell binding agent are well known in the art (see US Patent Applications 2008/0050310, 20050169933, available from Pierce Biotechnology Inc. P.O. Box 117, Rockland, IL 61105, USA) and include, but not limited to, bis-maleimidopolyethyleneglycol (BMPEO), BM(PEO)$_2$, BM(PEO)$_3$, N-(Q-maleimidopropyloxy)succinimide ester (BMPS), γ-maleimidobutyric acid N-succinimidyl ester (GMBS), 8-maleimidocaproic acid N-hydroxysuccinimide ester (EMCS), 5-maleimidovaleric acid NHS, HBVS, N-succinimidyl-4-(N-maleimidomethyl)-cyclohexane-1-carboxy-(6-amidocaproate), which is a "long chain" analog of SMCC (LC-SMCC), m-maleimidobenzoyl-N-hydroxysuccinimide ester (MBS), 4-(4-N-maleimidophenyl)-butyric acid hydrazide or HCl salt (MPBH), N-succinimidyl 3-(bromoacetamido)propionate (SBAP), N-succinimidyl iodoacetate (SIA), κ-maleimidoundecanoic acid N-succinimidyl ester (KMUA), N-succinimidyl 4-(p-maleimidophenyl)-butyrate (SMPB), succinimidyl-6-(β-maleimidopropionamido) hexanoate (SMPH), succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimidomethyl)cyclohexane-1-carboxylate (sulfo-SMCC), sulfosuccinimidyl(4-iodo-acetyl)aminobenzoate (sulfo-SIAB), m-maleimidobenzoyl-N-hydroxysulfosuccinimide ester (sulfo-MBS), N-(γ-maleimidobutryloxy)sulfosuccinimide ester (sulfo-GMBS), N-(ε-maleimidocaproyloxy) sulfosuccimido ester (sulfo-EMCS), N-(κ-maleimidoundecanoyloxy)sulfosuccinimide ester (sulfo-KMUS), and sulfosuccinimidyl 4-(p-maleimidophenyl)butyrate (sulfo-SMPB).

Heterobifunctional crosslinking agents are bifunctional crosslinking agents having two different reactive groups. Heterobifunctional crosslinking agents containing both an amine-reactive N-hydroxysuccinimide group (NHS group) and a carbonyl-reactive hydrazine group can also be used to link the cytotoxic compounds described herein with a cell-binding agent (e.g., antibody). Examples of such commercially available heterobifunctional crosslinking agents include succinimidyl 6-hydrazinonicotinamide acetone hydrazone (SANH), succinimidyl 4-hydrazidoterephthalate hydrochloride (SHTH) and succinimidyl hydrazinium nicotinate hydrochloride (SHNH). Conjugates bearing an acid-labile linkage can also be prepared using a hydrazine-bearing benzodiazepine derivative of the present invention. Examples of bifunctional crosslinking agents that can be used include succinimidyl-p-formyl benzoate (SFB) and succinimidyl-p-formylphenoxyacetate (SFPA).

Bifunctional crosslinking agents that enable the linkage of cell binding agent with cytotoxic compounds via disulfide bonds are known in the art and include N-succinimidyl-3-(2-pyridyldithio)propionate (SPDP), N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. Other bifunctional crosslinking agents that can be used to introduce disulfide groups are known in the art and are disclosed in U.S. Pat. Nos. 6,913,748, 6,716,821 and US Patent Publications 20090274713 and 20100129314, all of which are incorporated herein by reference. Alternatively, crosslinking agents such as 2-iminothiolane, homocysteine thiolactone or S-acetylsuccinic anhydride that introduce thiol groups can also be used.

A "linker," "linker moiety," or "linking group" as defined herein refers to a moiety that connects two groups, such as a cell binding agent and a cytotoxic compound, together. Typically, the linker is substantially inert under conditions for which the two groups it is connecting are linked. A bifunctional crosslinking agent can comprise two reactive groups, one at each ends of a linker moiety, such that one reactive group can be first reacted with the cytotoxic compound to provide a compound bearing the linker moiety and a second reactive group, which can then react with a cell binding agent. Alternatively, one end of the bifunctional crosslinking agent can be first reacted with the cell binding agent to provide a cell binding agent bearing a linker moiety and a second reactive group, which can then react with a cytotoxic compound. The linking moiety can contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913, 748; 7,276,497; 7,276,499; 7,368,565; 7,388,026 and 7,414, 073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in US 2009/0274713, US 2010/ 01293140 and WO 2009/134976, each of which is expressly incorporated herein by reference, each of which is expressly incorporated herein by reference.

The term "amino acid" refers to naturally occurring amino acids or non-naturally occurring amino acid. In some embodiments, the amino acid is represented by $NH_2$—C($R^{aa'}R^{aa}$)—C(=O)OH, wherein $R^{aa}$ and $R^{aa'}$ are each independently H, an optionally substituted linear, branched or cyclic alkyl, alkenyl or alkynyl having 1 to 10 carbon atoms, aryl, heteroaryl or heterocyclyl or $R^{aa}$ and the N-terminal nitrogen atom can together form a heterocyclic ring (e.g., as in proline). The term "amino acid residue" refers to the corresponding residue when one hydrogen atom is removed from the amine and/or carboxy end of the amino acid, such as —NH—C($R^{aa'}R^{aa}$)—C(=O)O—.

The term "peptide" refers to short chains of amino acid monomers linked by peptide (amide) bonds. In some embodiments, the peptides contain 2 to 20 amino acid residues. In other embodiments, the peptides contain 2 to 10 amino acid residus. In yet other embodiments, the peptides contain 2 to 5 amino acid residues. As used herein, when a peptide is a portion of a cytotoxic agent or a linker described herein represented by a specific sequence of amino acids, the peptide can be connected to the rest of the cytotoxic agent or the linker in both directions. For example, a dipeptide $X_1$-$X_2$ includes $X_1$-$X_2$ and $X_2$-$X_1$. Similarly, a tripeptide $X_1$-$X_2$-$X_3$ includes $X_1$-$X_2$-$X_3$ and $X_3$-$X_2$-$X_1$ and a tetrapeptide $X_1$-$X_2$-$X_3$-$X_4$ includes $X_1$-$X_2$-$X_3$-$X_4$ and $X_4$-$X_2$-$X_3$-$X_1$. $X_1$, $X_2$, $X_3$ and $X_4$ represents an amino acid residue.

The term "cation" refers to an ion with positive charge. The cation can be monovalent (e.g., $Na^+$, $K^+$, etc.), bi-valent (e.g., $Ca^{2+}$, $Mg^{2+}$, etc.) or multi-valent (e.g., $Al^{3+}$ etc.). Preferably, the cation is monovalent.

The term "cysteine engineered antibody" includes an antibody with at least one cysteine (Cys) that is not normally present at a given residue of the antibody light chain or heavy chain. Such Cys, which may also be referred to as "engineered Cys," can be introduced, for example, by standard recombinant technology (e.g., by replacing the coding sequence for a non-Cys residue at the target residue with a coding sequence for Cys). In certain embodiments, the Cys engineered antibody of the invention has an engineered Cys in the heavy chain. In certain embodiments, the engineered Cys is in or near the CH3 domain of the heavy chain. In certain embodiments, the engineered Cys is at residue 442 of the heavy chain (EU/OU numbering).

As used herein, all antibody amino acid residues described herein are numbered according to the EU index, Kabat et al., *Sequences of Proteins of Immunological Interest*, 5th Ed., NIH publication No. 91-3242, 1991 (EU/OU numbering, entire content incorporated herein by reference). The common isotypes are referred to as G1, G2, G4, etc.

The C442 residue can be conjugated with a cytotoxic drug/agent through the free thiol group of the C442 residue, such as through reacting with a thiol-reactive agent of the cytotoxic drug (e.g., a maleimido group).

As used herein, an "aqueous solution" refers to a solution in which the solvent is water or a mixture of water and one or more organic solvents.

The term "therapeutically effective amount" means that amount of active compound or conjugate that elicits the desired biological response in a subject. Such response includes alleviation of the symptoms of the disease or disorder being treated, prevention, inhibition or a delay in the recurrence of symptom of the disease or of the disease itself, an increase in the longevity of the subject compared with the absence of the treatment, or prevention, inhibition or delay in the progression of symptom of the disease or of the disease itself. Determination of the effective amount is well within the capability of those skilled in the art, especially in light of the detailed disclosure provided herein. Toxicity and therapeutic efficacy of compound I can be determined by standard pharmaceutical procedures in cell cultures and in experimental animals. The effective amount of compound or conjugate of the present invention or other therapeutic agent to be administered to a subject will depend on the stage, category and status of the multiple myeloma and characteristics of the subject, such as general health, age, sex, body weight and drug tolerance. The effective amount of compound or conjugate of the present invention or other therapeutic agent to be administered will also depend on administration route and dosage form. Dosage amount and interval can be adjusted individually to provide plasma levels of the active compound that are sufficient to maintain desired therapeutic effects.

As used herein, the term "treating" or "treatment" includes reversing, reducing, or arresting the symptoms, clinical signs, and underlying pathology of a condition in manner to improve or stabilize a subject's condition. As used herein, and as well understood in the art "treatment" is an approach for obtaining beneficial or desired results, including clinical results. Beneficial or desired clinical results can include, but are not limited to, alleviation, amelioration, or slowing the progression, of one or more symptoms or conditions associated with a condition, e.g., cancer, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Exemplary beneficial clinical results are described herein.

Compounds of the Present Invention

In a first aspect, the present invention is directed to cytotoxic compounds described herein.

In a 1$^{st}$ embodiment, the cytotoxic compound is represented by formula (I), (II) or (III), or a pharmaceutical acceptable salt thereof, wherein:

$W_1$ is —(CH$_2$)$_{n1}$—;
$W_2$ is —(CH$_2$)$_{n2}$—
n1 is 1, 2 or 3;
n2 is 0, 1 or 2;
n3 is 0 or 1;
$R^{1a}$ and $R^{1a'}$ are each independently H, halide, —OH, or (C$_1$-C$_6$)alkyl; or $R^{1a}$ and $R^{1a'}$ together form a double bond containing group =B;
=B is selected from a (C$_2$-C$_6$)alkenyl or a carbonyl group, wherein the (C$_2$-C$_6$)alkenyl is optionally substituted with a halogen, —OH, (C$_1$-C$_3$)alkoxy or phenyl;
Q is Q$_1$-Ar-Q$_2$;
Q$_1$ is absent, (C$_1$-C$_6$)alkyl, or —CH═CH—;
Ar is absent or an aryl group;
Q$_2$ is —H, a (C$_1$-C$_6$)alkyl, a (C$_1$-C$_6$)alkenyl, a polyethylene glycol unit —R$^{c'}$—(OCH$_2$CH$_2$)$_n$—R$^c$, or a substituent selected from a halogen, guanidinium [—NH(C═NH)NH$_2$], —R, —OR, —NR'R", —NO$_2$, —NCO, —NR'COR", NR'(C═O)OR"—SR, —SOR', —SO$_2$R', —SO$_3$H, —OSO$_3$H, —SO$_2$NR'R", cyano, an azido, —COR', —OCOR' and —OCONR'R";
n is an integer from 1 to 10;
R$^{c'}$ is a (C$_1$-C$_4$)alkyl;
R$^c$ is H, or a (C$_1$-C$_4$)alkyl, the double line ═ between N and C represents a single bond or a double bond, provided that when it is a double bond X is absent and Y is —H, or a (C$_1$-C$_4$)alkyl, and when it is a single bond, X is —H, an amine protecting moiety or R$^L$; and Y is —OH or —SO$_3$H;

R$^L$ is self-immolative linker bearing a reactive group that is capable of covalently linking the cytotoxic compound to a cell-binding agent (CBA);

R$_1$, R$_2$, R$_3$ and R$_4$ are each independently selected from —H, a (C$_1$-C$_6$)alkyl, halogen, —OR, —NR'R", —NO$_2$, —NR'COR", —SR, —SOR', —SO$_2$R', —SO$_3$H, —OSO$_3$H, —SO$_2$NR'R", cyano, —COR', —OCOR', and —OCONR'R";

R, for each occurrence, is —H or a (C$_1$-C$_6$)alkyl;

R' and R" are each independently selected from —H, —OH, —OR, —NHR, —NR$_2$, —COR, or a (C$_1$-C$_6$)alkyl;

R$_6$ is —H, —R, —OR, —SR, —NR'R", —NO$_2$, or halogen;

A is absent or is selected from —O—, —C(═O)—, —CRR'O—, —CRR'—, —S—, —CRR'S—, —NR$_5$ and —CRR'N(R$_5$)—;

L$_1$ is a spacer;
Z$_1$ is a bond,

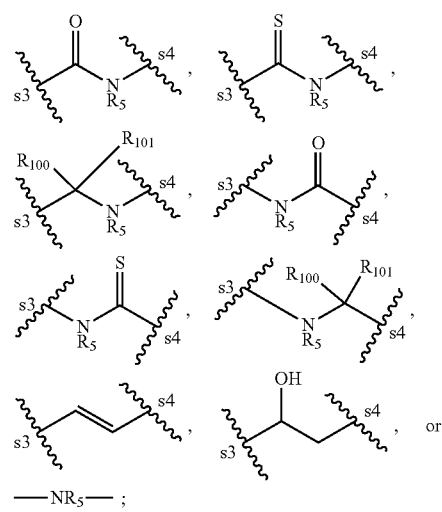

or —NR$_5$—;

s3 is the site connected L$_1$ and s4 is the site connected to Ar$_1$;

R$_5$ is —H or a (C$_1$-C$_4$)alkyl;

R$_{100}$ and R$_{101}$, for each occurrence, are each independently —H, halogen, (C$_1$-C$_4$)alkyl, or (C$_1$-C$_4$)haloalkyl;

Ar$_1$ is a 6- to 18-membered aromatic ring, a 5- to 18-membered heteroaromatic ring, or -Ar$_1$'-Ar$_1$"-, wherein Ar$_1$' and Ar$_1$" are each independently a 6- to 18-membered aromatic ring or a 5- to 18-membered heteroaromatic ring;

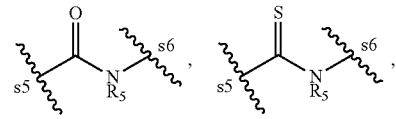

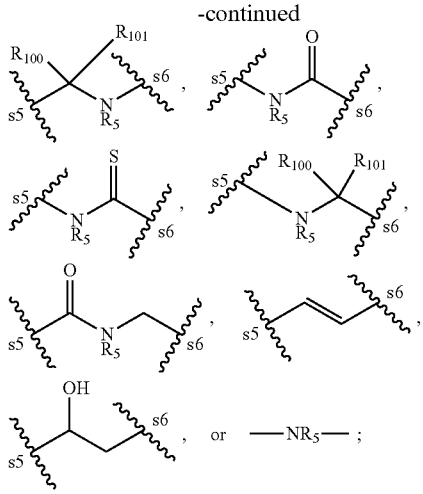

s5 is the site connected Ar$_1$ and s6 is the site connected to Ar$_2$;

Ar$_2$ is a 6- to 18-membered aromatic ring, a 5- to 18-membered heteroaromatic ring or -Ar$_2$'-Ar$_2$"-, wherein Ar$_2$' and Ar$_2$" are each independently a 6- to 18-membered aromatic ring or a 5- to 18-membered heteroaromatic ring;

Z$_3$ is

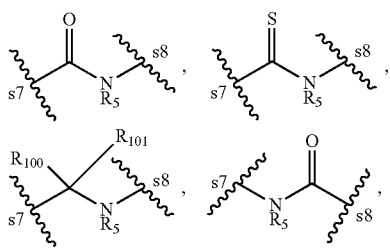

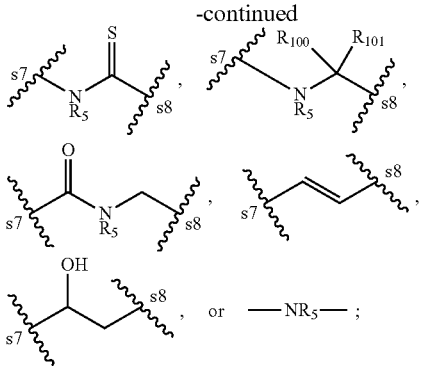

or —NR$_5$—;

Ar$_3$ is a 6- to 18-membered aromatic ring, a 5- to 18-membered heteroaromatic ring or -Ar$_3$'-Ar$_3$"-, wherein Ar$_3$' and Ar$_3$" are each independently a 6- to 18-membered aromatic ring or a 5- to 18-membered heteroaromatic ring;

L is H, —C(=O)R$_a$, —NR$_b$R$_c$ or a linker bearing a reactive group that is capable of covalently linking the cytotoxic compound to a cell-binding agent (CBA);

R$_a$ is —OH, —Cl, —O(C$_1$-C$_6$)alkyl or —C(=O)OR$_a$ is a reactive ester group;

R$_b$ and R$_c$ are each independently —H, (C$_1$-C$_4$)alkyl or an amine protecting group; and provided (i) when the compound is represented by formula (II) or (III), Z$_1$ is not

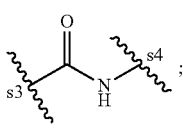

(ii) when the compound is represented by formula (I), the compound is not

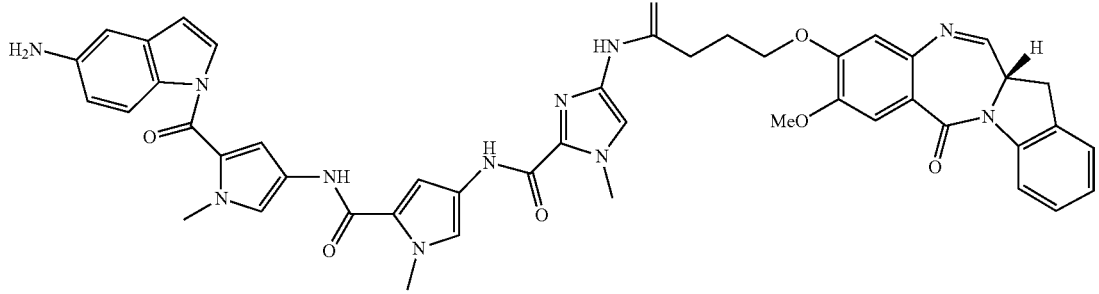

or a pharmaceutically acceptable salt thereof; and (iii) when X is R$^L$, L is H, —C(=O)R$_a$ or —NR$_b$R$_c$ In a specific embodiment, W$_1$ is —CH$_2$—, and W$_2$ is a bond; or W$_1$ and W$_2$ are both —CH$_2$—.

In another specific embodiment, L$_1$ is (C$_1$-C$_{10}$)alkyl, (C$_2$-C$_{10}$)alkenyl, (C$_2$-C$_{10}$)alkynyl, (C$_3$-C$_8$)cycloalkyl, aryl, heteroaryl, (C$_1$-C$_4$)alkyl-(C$_3$-C$_5$)cycloalkyl-(C$_1$-C$_4$)alkyl, (C$_1$-C$_4$)alkyl-aryl-(C$_1$-C$_4$)alkyl or (C$_1$-C$_4$)alkyl-heteroaryl-(C$_1$-C$_4$)alkyl.

In yet another specific embodiment, for formula (I), (II) or (III), $R_1$, $R_2$, $R_3$ and $R_4$ are each independently —H, a $(C_1$-$C_4)$alkyl, halogen, —$NO_2$, —OR, —$NR_2$ or cyano;
R is —H or a $(C_1$-$C_4)$alkyl;
$R_6$ is —OR;
A is —O— or —S—; and
$L_1$ is —$(CH_2)_{m1}$—;

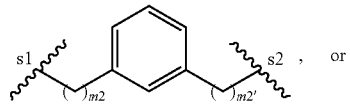, or

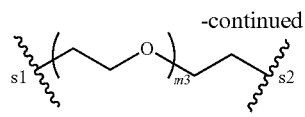

s1 is the site connected to A; s2 is the site connected to $Z_1$;
m1 is 1, 2, 3, 4, 5 or 6;
m2 is 1, 2 or 3;
m2' is 0, 1, 2 or 3; and
m3 is an integer from 1 to 10; and remaining variables are as defined in the 1st embodiment.

In a 2nd embodiment, the compound of the present invention is represented by the following formula:

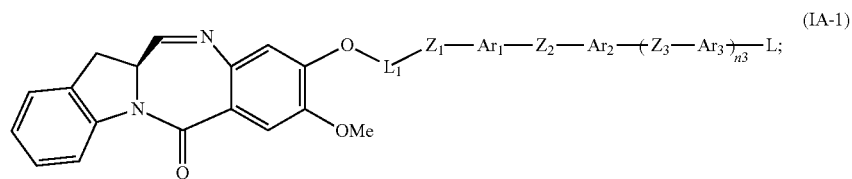
(IA-1)

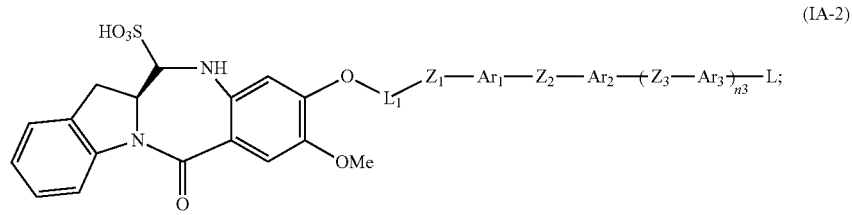
(IA-2)

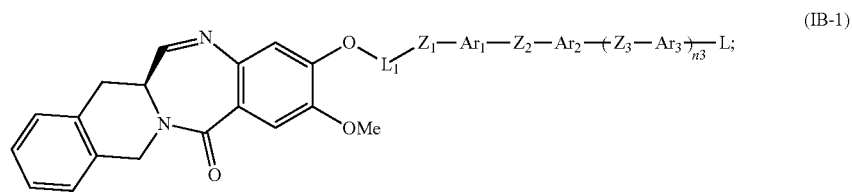
(IB-1)

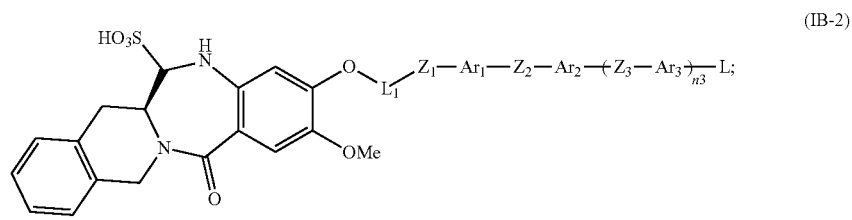
(IB-2)

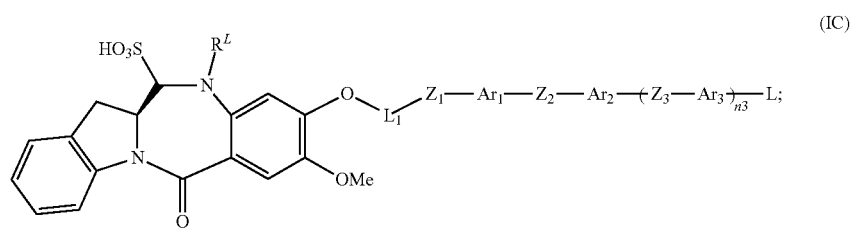
(IC)

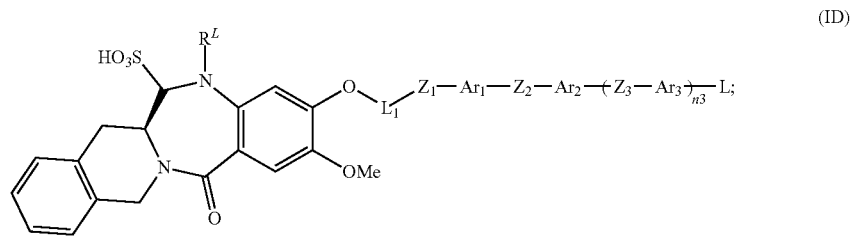
(ID)

-continued

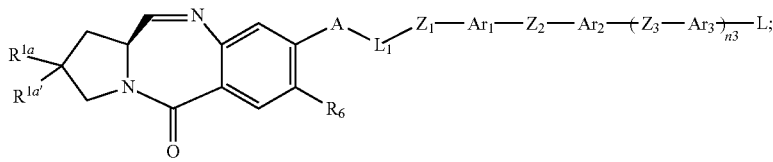
(IIA)

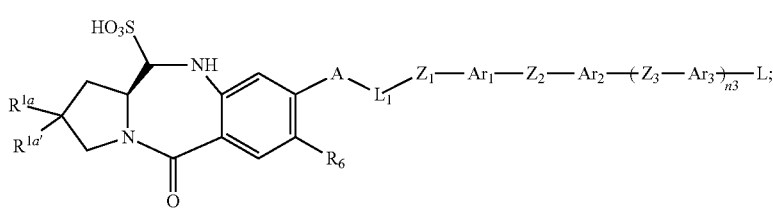
(IIB)

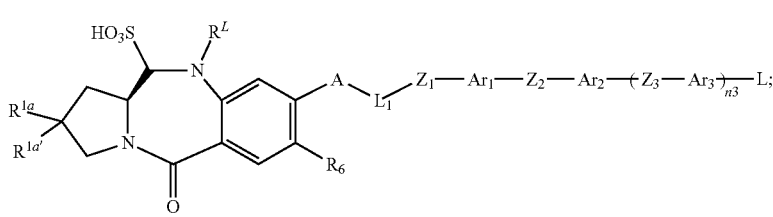
(IIC)

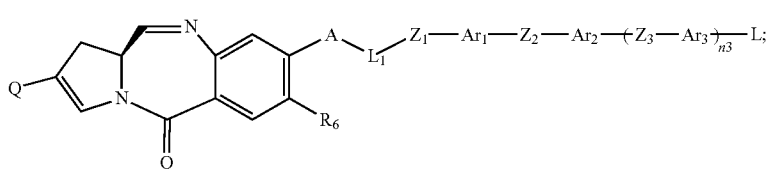
(IIIA)

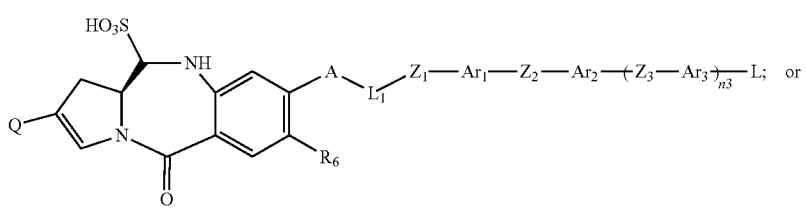
(IIIB)

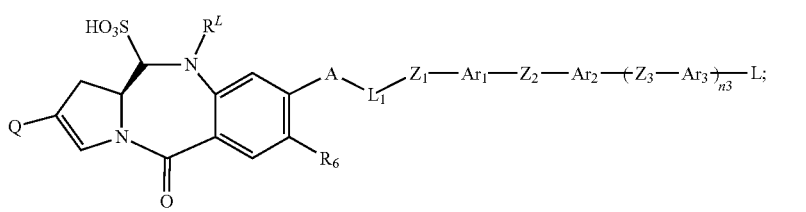
(IIIC)

or a pharmaceutically acceptable salt thereof, wherein the variables are as described in the first aspect or the 1st embodiment or any specific embodiments described therein.

In a 3rd embodiment, the compound of present invention is represented by formula (IC), (ID), (IIC) or (IIIC), or a pharmaceutically acceptable salt thereof, wherein:

L is H, —C(=O)$R_a$ or —$NR_bR_c$; and $R^L$ is represented by the following formula:

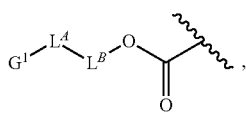

wherein:

$G^1$ is a spacer having an amine reactive group, a thiol reactive group or an aldehyde reactive group attached thereto;

$L^A$ is a peptide residue comprising 2 to 5 amino acid residues; and $L^B$ is a covalent bond or together with —OC(=O)— forms a self-immolative linker; and The remaining variables are as defined in the first aspect or the 1st embodiment or any specific embodiments described therein.

In a specific embodiment, —C(=O)O— and $L^B$ together form the group:

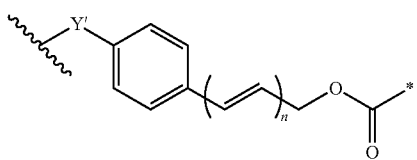

where the asterisk indicates the point of attachment to the N10 position, the wavy line indicates the point of attachment to the linker $L^A$, Y' is —NH—, —O—, —C(=O)NH— or —C(=O)O—, and n is 0 to 3.

In another specific embodiment, $R^L$ is represented by the following formula:

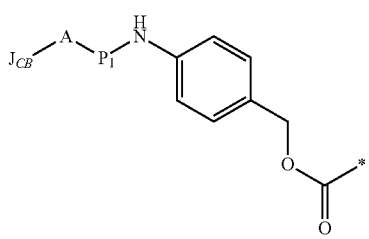

wherein:

$P_1$ is a peptide residue having 2 to 5 amino acid residues; and $J_{CB}$-A- is represented by:

(i)

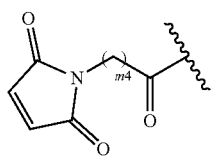

(ii)

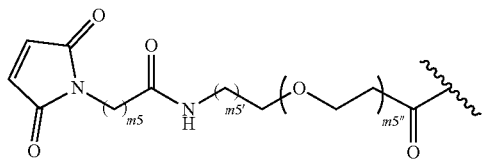

(ii')

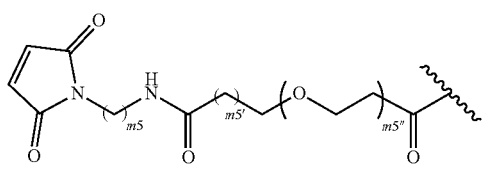

(iii)

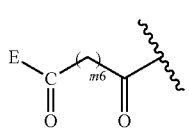

(iv)

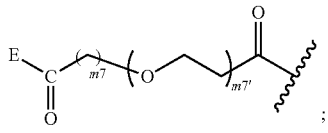

(v)

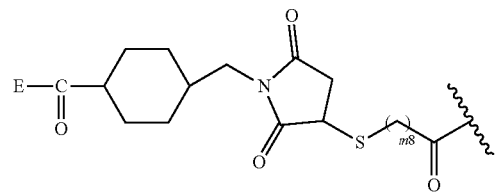

(vi)

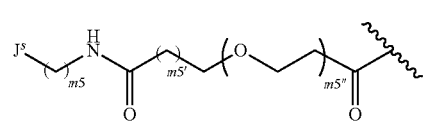

wherein: m4, m5, m5', m6, m7 and m8 are each independently an integer from 1 to 6; m5" and m7' are each independently 0 or an integer from 1 to 10; E is —OH, or —Cl or —C(=O)E is a reactive ester; and $J^s$ is

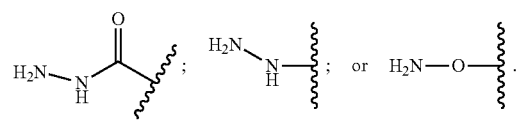

In another specific embodiment, $J_{CB}$-A- is represented by:

(i)

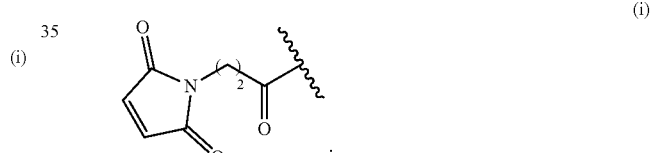

(ii)

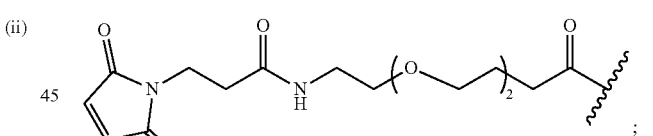

(ii')

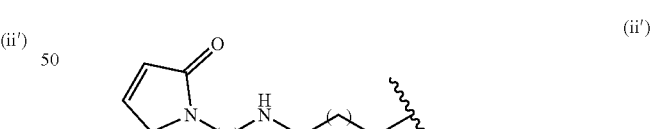

(iii)

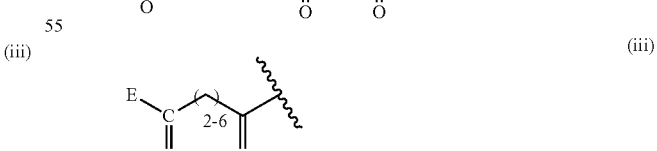

(iv)

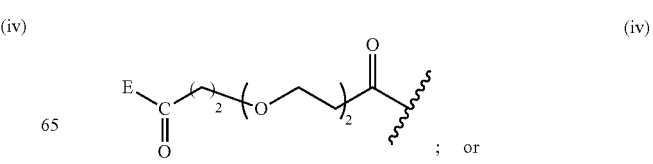

; or

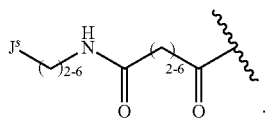

(v)

In another specific embodiment, P₁ is a peptide residue selected from Ala-Ala, Gln-Leu, Phe-Lys, Val-Ala, Val-Lys, Ala-Lys, Val-Cit, Phe-Cit, Leu-Cit, Ile-Cit, Phe-Arg, Trp-Cit, Lys-Lys, Phe-Ala, Phe-N⁹-tosyl-Arg, Phe-N⁹-nitro-Arg, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Gly-Gly-Gly, Phe-Phe-Lys, D-Phe-Phe-Lys, Gly-Phe-Lys, Leu-Ala-Leu, Ile-Ala-Leu and Val-Ala-Val; Ala-Leu-Ala-Leu, f-Ala-Leu-Ala-Leu and Gly-Phe-Leu-Gly. More specifically, P₁ is Ala-Ala, or Val-Ala.

In a 4ᵗʰ embodiment, for compounds of formula (I), (II), (III), (IA-1), (IA-2), (IB-1), (IB-2), (IC), (ID), (IIA), (IIB), (IIC), (IIIA), (IIIB) or (IIIC), or a pharmaceutically acceptable salt thereof, L₁ is represented by one of the following formulas.

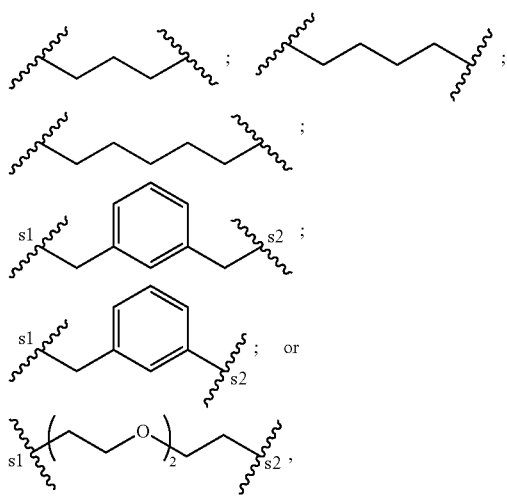

wherein s1 is the site connected to A and s2 is the site connected to Z₁; and the remaining variables are defined as in the first aspect or the 1ˢᵗ, 2ⁿᵈ or 3ʳᵈ embodiment.

In a 5ᵗʰ embodiment, for compounds of formula (I), (II), (III), (IA-1), (IA-2), (IB-1), (IB-2), (IC), (ID), (IIA), (IIB), (IIC), (IIIA), (IIIB) or (IIIC), or a pharmaceutically acceptable salt thereof, Z₁ is

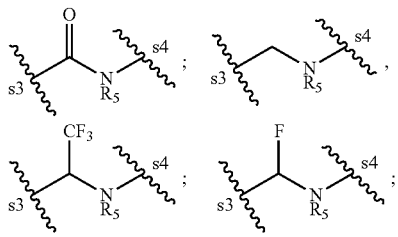

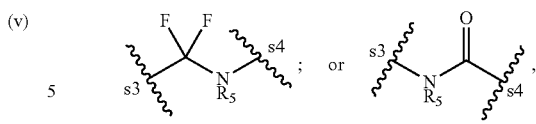

wherein R₅ is H or Me; and the remaining variables are as defined in the first aspect or the 1ˢᵗ, 2ⁿᵈ, 3ʳᵈ or 4ᵗʰ embodiment or any specific embodiment described therein. In a specific embodiment, Z₁ is not

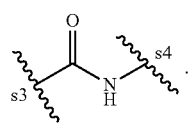 [SMILES: *NC(*)=O]

In a 6ᵗʰ embodiment, for compounds of formula (I), (II), (III), (IA-1), (IA-2), (IB-1), (IB-2), (IC), (ID), (IIA), (IIB), (IIC), (IIIA), (IIIB) or (IIIC), or a pharmaceutically acceptable salt thereof, Ar₁ is benzene, naphthalene, a 5- to 6-membered heteroaromatic ring, a 8 to 10-membered bicyclic heteroaromatic ring or -Ar₁'-Ar₁''-, wherein Ar₁' and Ar₁'' are each independently benzene or a 5- to 6-membered heteroaromatic ring; and the remaining variables are as defined in the first aspect or the 1ˢᵗ, 2ⁿᵈ, 3ʳᵈ, 4ᵗʰ or 5ᵗʰ embodiment or any specific embodiment described therein.

In a specific embodiment of the 6ᵗʰ embodiment, Ar₁ is benzene, naphthalene, pyrrole, imidazole, thiophene, thiazole, pyrazole, oxazole, isoxazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyridine-N-oxide, pyrazine, pyrimidine, pyridazine, 1,2,4-triazine, 1,3,5-triazine, tetrazole, indolizine, indole, isoindole, benzo[b]furan, benzo[b]thiophene, indazole, benzimidazole, benzthiazole, purine, 4H-quinolizine, quinoline, isoquinoline, cinnoline, phthalazine, quinazoline, quinoxaline, 1,8-naphthyridine, or pteridine.

In another specific embodiment of the 6ᵗʰ embodiment, An is pyrrole, imidazole, thiazole, pyridine, benzo[b]furan, benzene or -Ar₁'-Ar₁''-, wherein Ar₁' and Ar₃'' are each independently benzene, pyrrole, thiazole, or pyridine.

In yet another specific embodiment of the 6ᵗʰ embodiment, Ar₁ is represented by one of the following:

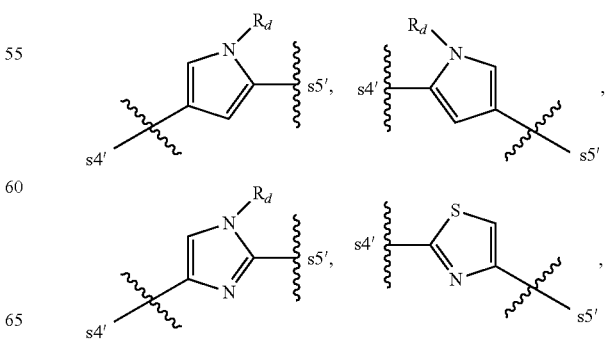

-continued

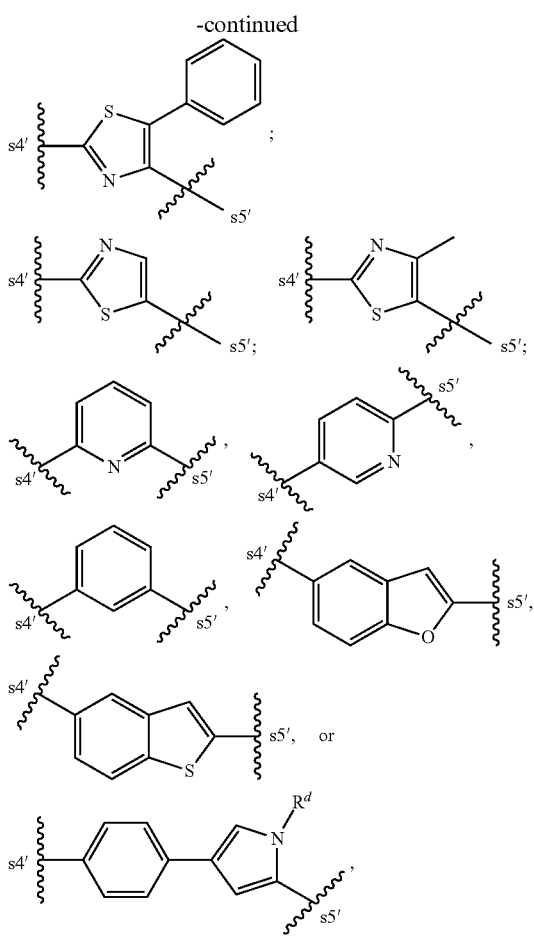

wherein $R_d$ is H, a $(C_1-C_6)$alkyl optionally substituted with halogen, —OH, or —$NR_bR_c$, wherein $R_b$ and $R_c$ are each independently H, $(C_1-C_4)$alkyl or an amine protecting group, phenyl or heteroaryl. More specifically, $R_d$ is methyl.

In a 7$^{th}$ embodiment, for compounds of formula (I), (II), (III), (IA-1), (IA-2), (IB-1), (IB-2), (IC), (ID), (IIA), (IIB), (IIC), (IIIA), (IIIB) or (IIIC), or a pharmaceutically acceptable salt thereof, $Z_2$ is

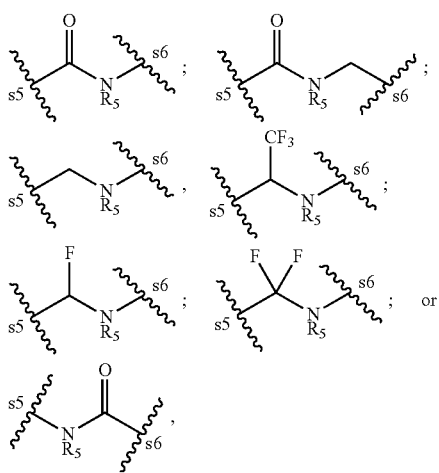

wherein $R_5$ is H or Me; and the remaining variables are as defined in the first aspect or the 1$^{st}$, 2$^{nd}$, 3$^{rd}$, 4$^{th}$, 5$^{th}$ or 6$^{th}$ embodiment or any specific embodiment described therein.

In a 8$^{th}$ embodiment, for compounds of formula (I), (II), (III), (IA-1), (IA-2), (IB-1), (IB-2), (IC), (ID), (IIA), (IIB), (IIC), (IIIA), (IIIB) or (IIIC), or a pharmaceutically acceptable salt thereof, $Ar_2$ is benzene, naphthalene, naphthalene, a 5- to 6-membered heteroaromatic ring, or a 8- to 10-membered bicyclic heteroaromatic ring or -$Ar_2'$-$Ar_2''$-, wherein $Ar_2'$ and $Ar_2''$ are each independently benzene or a 5- to 6-membered heteroaromatic ring; and the remaining variables are as defined in the first aspect of the 1$^{st}$, 2$^{nd}$, 3$^{rd}$, 4$^{th}$, 5$^{th}$, 6$^{th}$ or 7$^{th}$ embodiment or any specific embodiment described therein.

In a specific embodiment, $Ar_2$ is pyrrole, imidazole, thiophene, thiazole, pyrazole, oxazole, isoxazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyridine-N-oxide, pyrazine, pyrimidine, pyridazine, 1,2,4-triazine, 1,3,5-triazine, tetrazole, indolizine, indole, isoindole, benzo[b]furan, benzo[b]thiophene, indazole, benzimidazole, benzthiazole, purine, 4H-quinolizine, quinoline, isoquinoline, cinnoline, phthalazine, quinazoline, quinoxaline, 1,8-naphthyridine, pteridine, benzene, or naphthalene.

In another specific embodiment, $Ar_2$ is pyrrole, imidazole, benzene, benzo[b]thiophene, benzo[b]furan, benzimidazole, indole, quinoline, or isoquinoline or -$Ar_2'$-$Ar_2''$-, wherein $Ar_2'$ and $Ar_2''$ are each independently benzene, pyrrole, thiazole, or pyridine.

In yet another specific embodiment, $Ar_2$ is represented by one of the following:

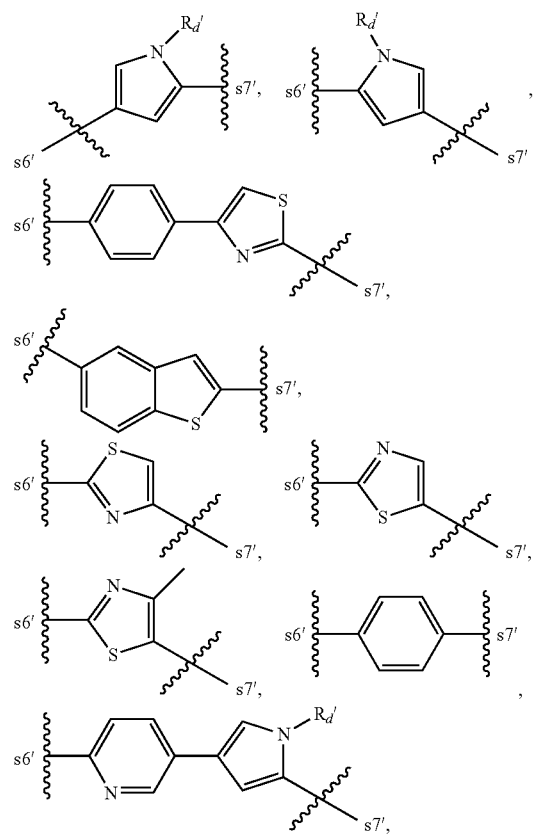

-continued

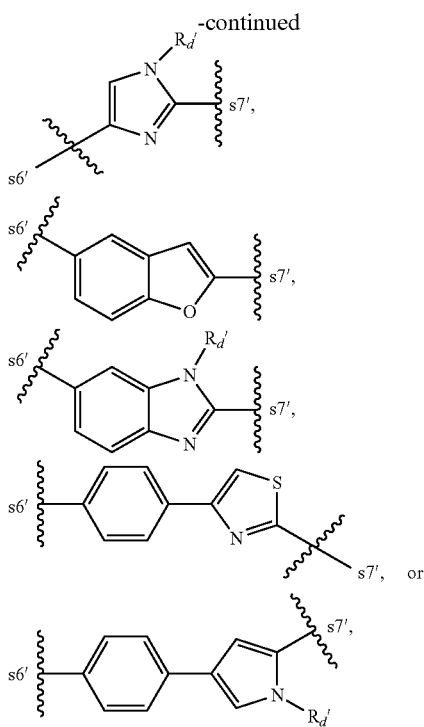

wherein $R_d{}'$ is H, a $(C_1\text{-}C_6)$alkyl optionally substituted with halogen, —OH, or —$NR_bR_c$, wherein $R_b$ and $R_c$ are each independently H, $(C_1\text{-}C_3)$alkyl, an amine protecting group, phenyl or heteroaryl. More specifically, $R_d{}'$ is methyl.

In a 9$^{th}$ embodiment, for compounds of formula (I), (II), (III), (IA-1), (IA-2), (IB-1), (IB-2), (IC), (ID), (IIA), (IIB), (IIC), (IIIA), (IIIB) or (IIIC), or a pharmaceutically acceptable salt thereof, n3 is 0; and the remaining variables are as defined in the first aspect or the 1$^{st}$, 2$^{nd}$, 3$^{rd}$, 4$^{th}$, 5$^{th}$, 6$^{th}$, 7$^{th}$ or 8$^{th}$ embodiment or any specific embodiment described therein.

In a 10$^{th}$ embodiment, for compounds of formula (I), (II), (III), (IA-1), (IA-2), (IB-1), (IB-2), (IC), (ID), (IIA), (IIB), (IIC), (IIIA), (IIIB) or (IIIC), or a pharmaceutically acceptable salt thereof, n3 is 1; $Z_3$ is

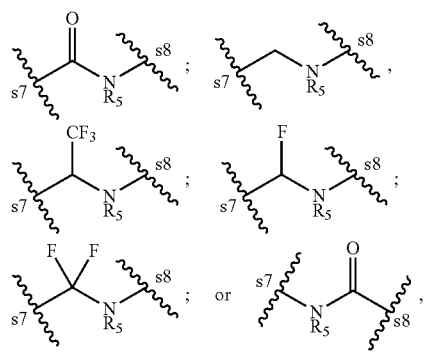

wherein $R_5$ is H or Me; and the remaining variables are as defined in the first aspect or the 1$^{st}$, 2$^{nd}$, 3$^{rd}$, 4$^{th}$, 5$^{th}$, 6$^{th}$, 7$^{th}$ or 8$^{th}$ embodiment or any specific embodiment described therein.

In a 11$^{th}$ embodiment, for compounds of formula (I), (II), (III), (IA-1), (IA-2), (IB-1), (IB-2), (IC), (ID), (IIA), (IIB), (IIC), (IIIA), (IIIB) or (IIIC), or a pharmaceutically acceptable salt thereof, $Ar_3$ is benzene, naphthalene, a 5- to 6-membered heteroaromatic ring, or a 8- to 10-membered bicyclic heteroaromatic ring or -$Ar_3{}'$-$Ar_3{}''$-, wherein $Ar_3{}'$ and $Ar_3{}''$ are each independently benzene or a 5- to 6-membered heteroaromatic ring; and the remaining variables are as defined in the first aspect or the 1$^{st}$, 2$^{nd}$, 3$^{rd}$, 4$^{th}$, 5$^{th}$, 6th, 7$^{th}$, 8$^{th}$ or 10$^{th}$ embodiment or any specific embodiment described therein.

In a specific embodiment, $Ar_3$ is pyrrole, imidazole, thiophene, thiazole, pyrazole, oxazole, isoxazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyridine-N-oxide, pyrazine, pyrimidine, pyridazine, 1,2,4-triazine, 1,3,5-triazine, tetrazole, indolizine, indole, isoindole, benzo[b]furan, benzo[b]thiophene, indazole, benzimidazole, benzthiazole, purine, 4H-quinolizine, quinoline, isoquinoline, cinnoline, phthalazine, quinazoline, quinoxaline, 1,8-naphthyridine, pteridine, benzene, or naphthalene.

In another specific embodiment, $Ar_3$ is represented by one of the following:

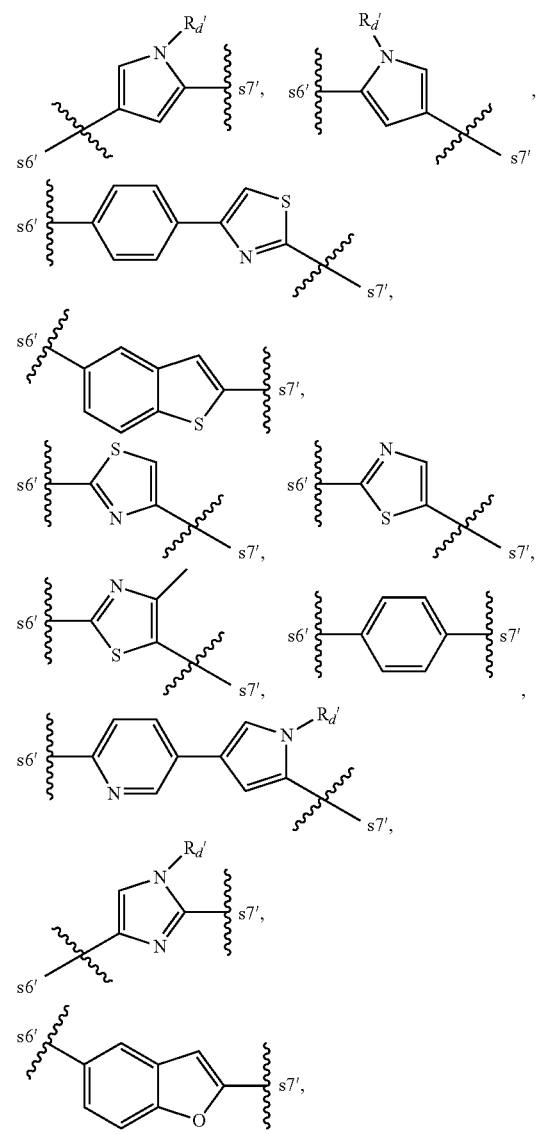

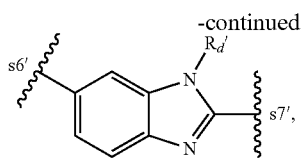
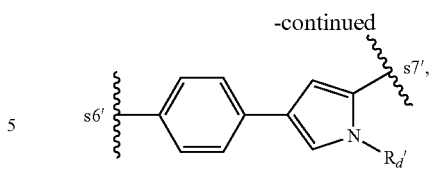
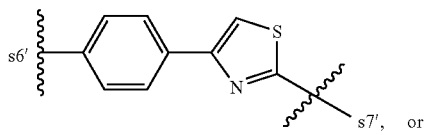
wherein $R_d'$ is H, a $(C_1-C_6)$alkyl optionally substituted with halogen, —OH, or —$NR_bR_c$, wherein $R_b$ and $R_c$ are each independently H, $(C_1-C_3)$alkyl, an amine protecting group, phenyl or heteroaryl.
In a 12$^{th}$ embodiment, the compound of the present invention is represented by the following formula:
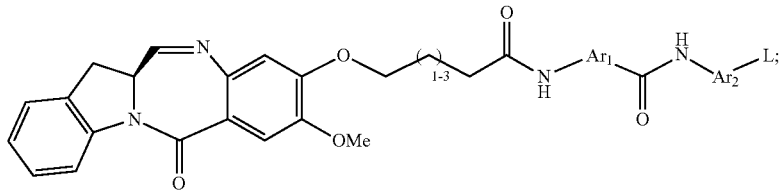
(IA-1a)
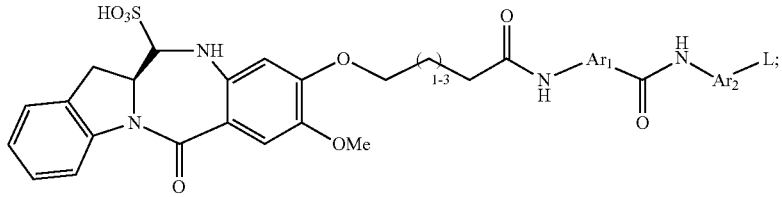
(IA-2a)
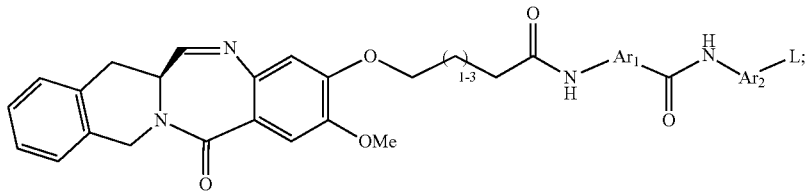
(IB-1a)
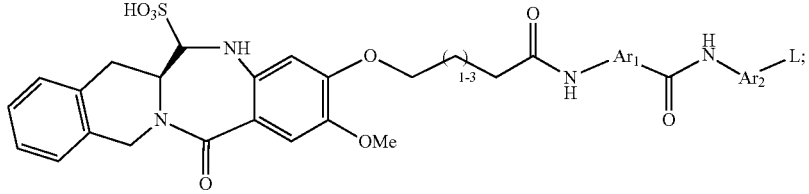
(IB-2a)
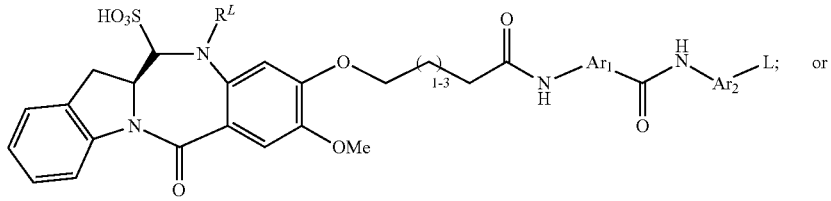
(IC-a)
or
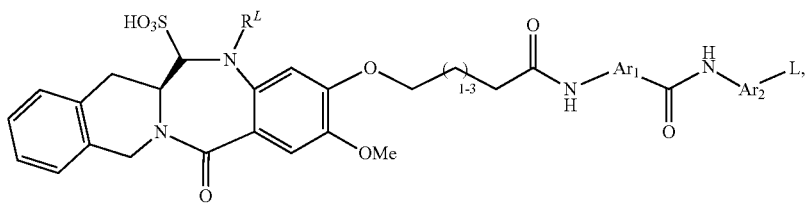
(ID-a)

or a pharmaceutically acceptable salt thereof, wherein:

Ar$_1$ is pyrrole, imidazole, thiazole, pyridine, benzo[b]furan, benzene or -Ar$_1$'-Ar$_1$"-, wherein Ar$_1$' and Ar$_1$" are each independently benzene, pyrrole, thiazole, or pyrrole;

Ar$_2$ is pyrrole, imidazole, benzene, benzo[b]thiophene, benzo[b]furan, benzimidazole, indole, quinoline, isoquinoline or -Ar$_2$'-Ar$_2$"-, wherein Ar$_2$' and Ar$_2$" are each independently benzene, pyrrole, thiazole, or pyridine; and the remaining variables are as defined in the first aspect or the 1$^{st}$, 2$^{nd}$, 3$^{rd}$ or 4$^{th}$ embodiment.

In a specific embodiment, for compounds of the 12$^{th}$ embodiment, Ar$_1$ is

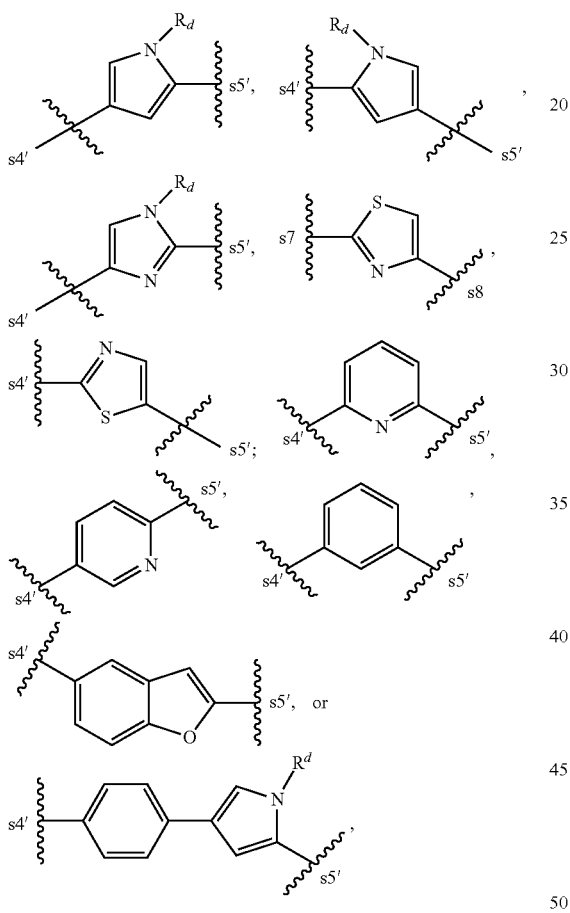

wherein R$_d$ is H, a (C$_1$-C$_6$)alkyl optionally substituted with halogen, —OH, or —NR$_b$R$_c$, wherein R$_b$ and R$_c$ are each independently H, (C$_1$-C$_4$)alkyl or an amine protecting group, phenyl or heteroaryl; and Ar$_2$ is

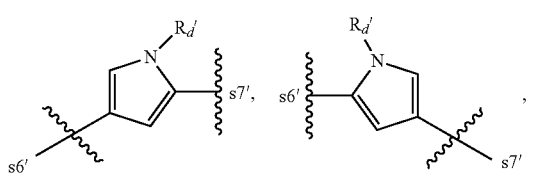

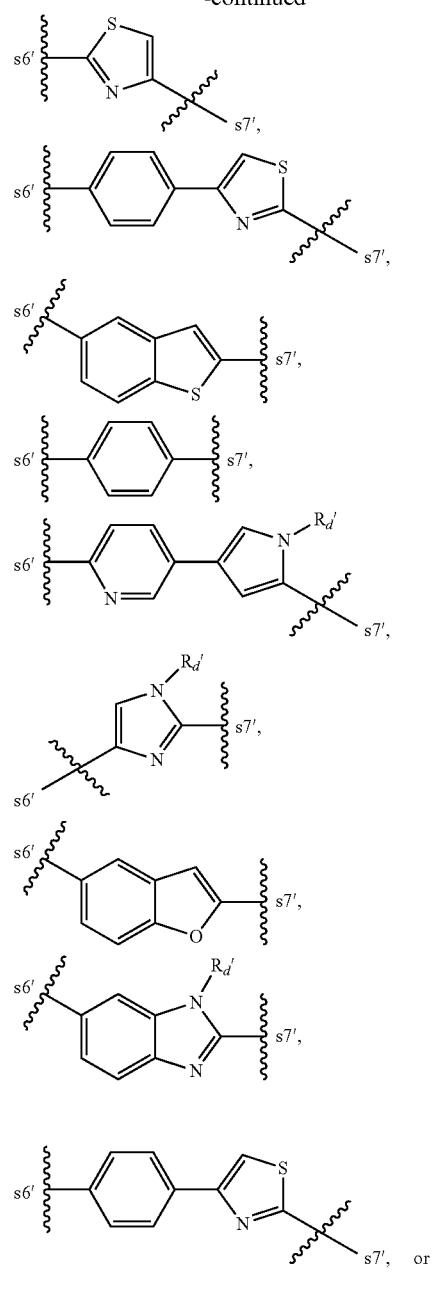

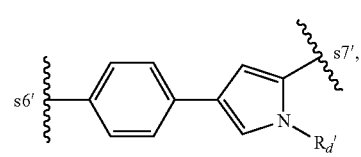

wherein R$_d$' is H, a (C$_1$-C$_6$)alkyl optionally substituted with halogen, —OH, or —NR$_b$R$_c$, wherein R$_b$ and R$_c$ are each independently H, (C$_1$-C$_3$)alkyl, an amine protecting group, phenyl or heteroaryl. More specifically, R$_d$ and R$_d$' are both methyl.

In a 13$^{th}$ embodiment, the compound of the present invention is represented by the following formula:

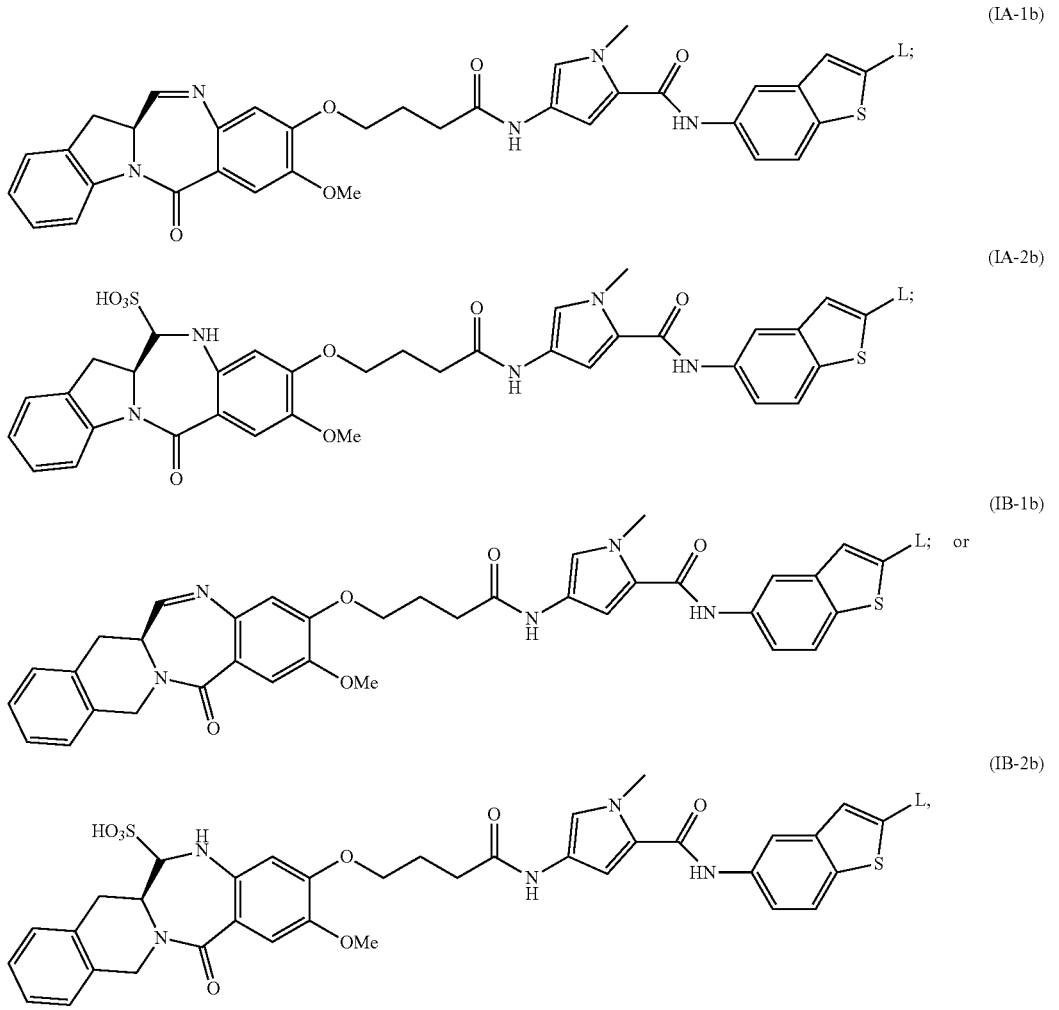

or a pharmaceutically acceptable salt thereof, wherein the variables are defined as in the first aspect or the 1st embodiment.

In a 14th embodiment, for compounds of formula (I), (II), (III), (IA-1), (IA-2), (IB-1), (IB-2), (IC), (ID), (IIA), (IIB), (IIC), (IIIA), (IIIB), (IIIC), (IA-1a), (IA-2a), (IB-1a), (IB-2a), (IC-a), (ID-a), (IA-1b), (IA-2b), (IB-1b), or (IB-2b), L is H, —C(=O)OH, —C(=O)O($C_1$-$C_3$)alkyl, a reactive ester, or —NH$_2$, and the remaining variables are as defined in the first aspect or the 1st, 2nd, 3rd, 4th, 5th, 6th, 7th, 8th, 9th, 10th, 11th, 12th or 13th embodiment or any specific embodiment described therein.

Also provided in the 14th embodiment, for compounds of formula (I), (II), (III), (IA-1), (IA-2), (IB-1), (IB-2), (IC), (ID), (IIA), (IIB), (IIC), (IIIA), (IIIB), (IIIC), (IA-1a), (IA-2a), (IB-1a), (IB-2a), (IC-a), (ID-a), (IA-1b), (IA-2b), (IB-1b), or (IB-2b), L is a linker bearing an amine reactive group that can form a covalent bond with a cell-binding agent, and the remaining variables are as defined in the first aspect or the 1st, 2nd, 3rd, 4th, 5th, 6th, 7th 8th, 9th 10th, 11th, 12th or 13th embodiment or any specific embodiment described therein. More specifically, the amine reactive group is a reactive ester.

In a 15th embodiment, for compounds of formula (I), (II), (III), (IA-1), (IA-2), (IB-1), (IB-2), (IC), (ID), (IIA), (IIB), (IIC), (IIIA), (IIIB), (IIIC), (IA-1a), (IA-2a), (IB-1a), (IB-2a), (IC-a), (ID-a), (IA-1b), (IA-2b), (IB-1b), or (IB-2b), L is represented by any one of the following formulae:

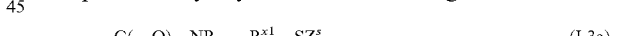
—C(=O)—NR$_{5a}$—R$^{x1}$—SZ$^s$      (L3a),

—NR$_{5a}$—C(=O)—R$^{x2}$—SZ$^s$      (L3b)

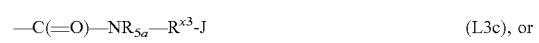
—C(=O)—NR$_{5a}$—R$^{x3}$-J      (L3c), or

—NR$_{5a}$—P$_2$—C(=O)—R$^{x4}$-J      (L3d), wherein:
R$_{5a}$ is H or ($C_1$-$C_3$)alkyl;
R$^{x1}$, R$^{x2}$, R$^{x3}$ and R$^{x4}$ are each independently a ($C_1$-$C_{10}$)alkyl, a ($C_3$-$C_8$)cycloalkyl, an aryl or a heteroaryl,
P$_2$ is an amino acid residue or a peptide containing between 2 to 20 amino acid residues;
J is —C(=O)R$_a$ or a reactive ester group;
R$_a$ is —OH, —Cl, —O($C_1$-$C_6$)alkyl;
Z$^s$ is H, —SR', —C(=O)R$^{e1}$ or a bifunctional linker moiety bearing a reactive group that can form a covalent bond with a cell-binding agent; and
R$^e$ is a ($C_1$-$C_6$)alkyl or is selected from phenyl, nitrophenyl (e.g., 2 or 4-nitrophenyl), dinitrophenyl (e.g., 2,4-dinitrophenyl), carboxynitrophenyl (e.g., 3-carboxy-4-nitrophenyl), pyridyl or nitropyridyl (e.g., 4-nitropyridyl); and $R^{e1}$ is a $(C_1\text{-}C_6)$alkyl; and the remaining variables are as defined in the first aspect or the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$ or $13^{th}$ embodiment or any specific embodiment described therein.

In a specific embodiment, $R^{x1}$, $R^{x2}$, $R^{x3}$ and $R^{x4}$ are each independently a $(C_1\text{-}C_6)$alkyl or —$R^{xc}$—$(CH_2CH_2O)_n$—$R^{xc'}$—, wherein n is an integer from 1 to 10; $R^{xc}$ is absent or a $(C_1\text{-}C_4)$alkyl; and $R^{xc'}$ is a $(C_1\text{-}C_4)$alkyl.

In another specific embodiment, L is represented by formula (L3a), $R^{x1}$ is —$(CH_2)_{p1}$—$(CR^{f1}R^{g1})$—, wherein $R^{f1}$ and $R^{g1}$ are each independently —H or -Me; and p1 is 0, 1, 2, 3, 4, or 5. More specifically, p1 is 1 and $R^1$ and $R^{g1}$ are both methyl.

In another specific embodiment, L is represented by formula (L3b), $R^{x2}$ is —$(CH_2)_{p2}$—$(CR^{f2}R^{g2})$—, wherein $R^{f2}$ and $R^{g2}$ are each independently —H or -Me; and p2 is 0, 1, 2, 3, 4 or 5. More specifically, $R^{x2}$ is —$(CH_2)_{p2}$—$(CR^{f2}R^{g2})$—, wherein $R^{f2}$ and $R^{g2}$ are each independently —H or -Me; and p2 is 0, 1, 2, 3, 4 or 5. More specifically, $R^{f2}$ and $R^{g2}$ are both methyl.

In yet another specific embodiment, L is represented by formula (L3c), $R^{x3}$ is —$(CH_2)_{p3}$—, wherein p3 is an integer from 2 to 6. More specifically, p3 is 2.

In yet another specific embodiment, L is represented by formula (L3d), $R^{x4}$ is —$(CH_2)_{p4}$—, wherein p4 is an integer from 2 to 6. More specifically, p4 is 4.

In another specific embodiment, for formula (L3d) described in the $15^{th}$ embodiment or any specific embodiment described therein, $P_2$ is a peptide containing 2 to 5 amino acid residues. More specifically, $P_2$ is selected from Ala-Ala, Gln-Leu, Gly-Gly-Gly, Ala-Val, Val-Ala, Cit-Val, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), f-Ala-Leu-Ala-Leu (SEQ ID NO: 2), Gly-Phe-Leu-Gly (SEQ ID NO: 3), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Met-Ala, Gln-Val, Asn-Ala, Gln-Phe and Gln-Ala. Even more specifically, $P_2$ is Gly-Gly-Gly, Ala-Val, Val-Ala, Ala-Ala, Ala-D-Ala, D-Ala-Ala, or D-Ala-D-Ala.

In another specific embodiment, for formula (L3a) or (L3b) described in the $15^{th}$ embodiment or any specific embodiment described therein, Z is H or —$SR^e$, wherein $R^e$ is a $(C_1\text{-}C_3)$alkyl, pyridyl or nitropyridyl (e.g., 4-nitropyridyl). Alternatively, $Z^s$ is represented by any one of the following:

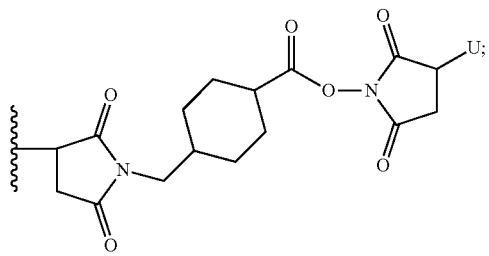
(a1)

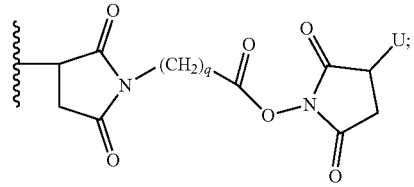
(a2)

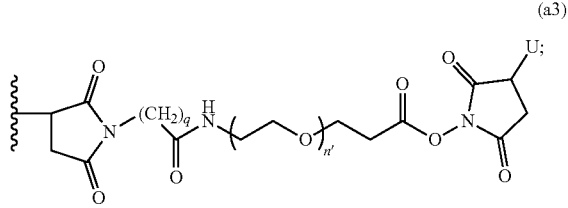
(a3)

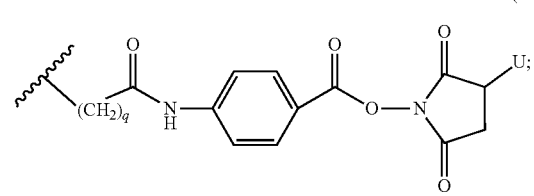
(a4)

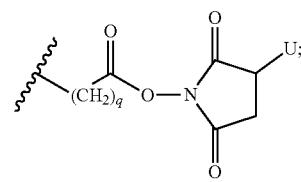
(a5)

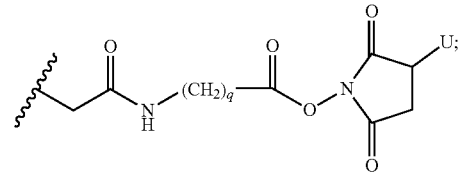
(a6)

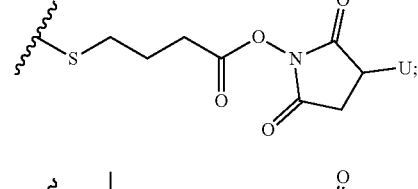
(a7)

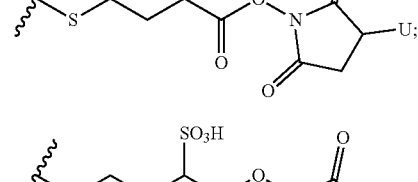
(a8)

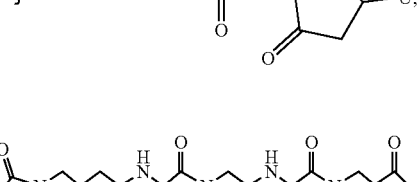
(a9)

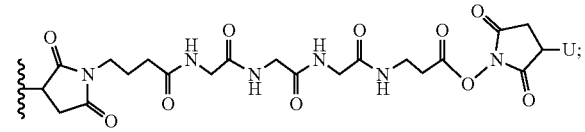
(a10)

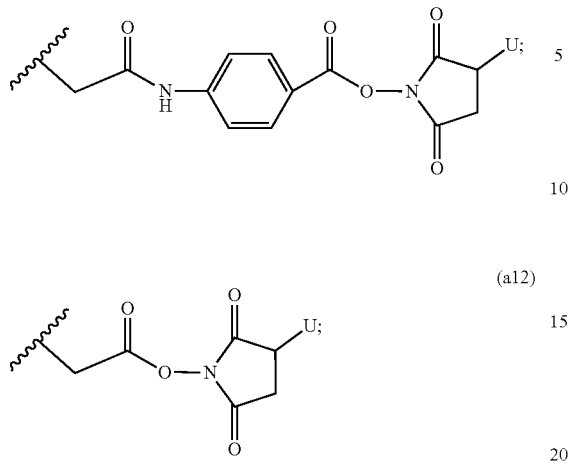

q is an integer from 1 to 5;
n' is an integer from 2 to 6; and
U is H or SO₃H.

In a specific embodiment, for formula (L3c) or (L3d) described in the 15$^{th}$ embodiment or any specific embodiment described therein, J is a reactive ester selected from N-hydroxysuccinimide ester, N-hydroxy sulfosuccinimide ester, nitrophenyl (e.g., 2 or 4-nitrophenyl) ester, dinitrophenyl (e.g., 2,4-dinitrophenyl) ester, sulfo-tetraflurophenyl (e.g., 4-sulfo-2,3,5,6-tetrafluorophenyl) ester, and pentafluorophenyl ester. More specifically, J is N-hydroxysuccinimide ester.

In a 16$^{th}$ embodiment, the compound of the present invention is any one of the following:

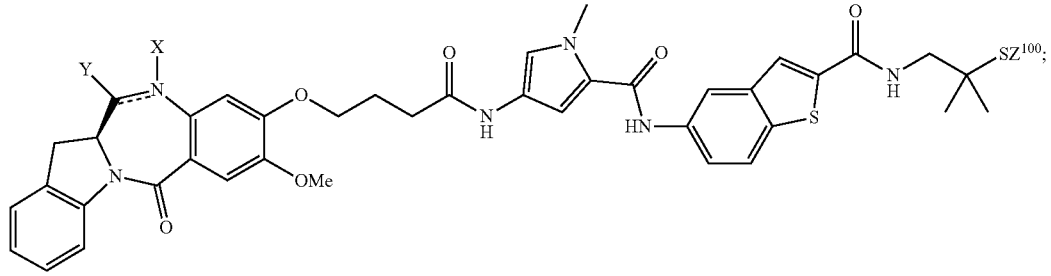
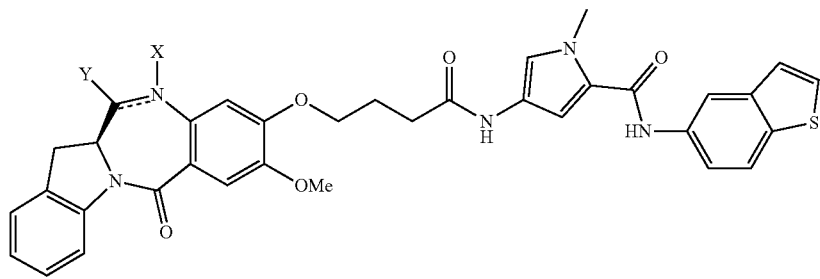
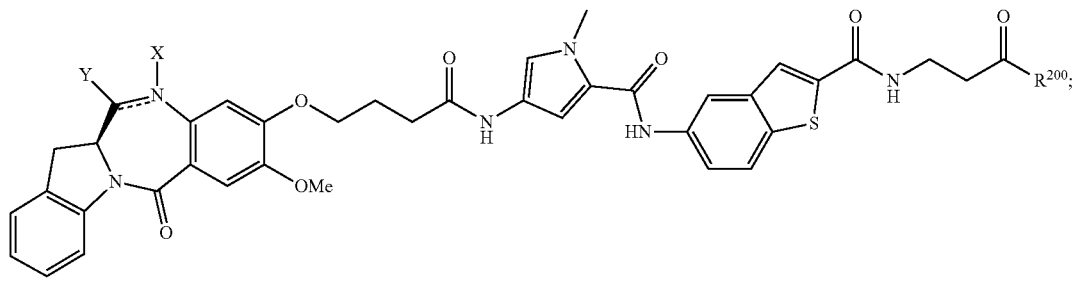
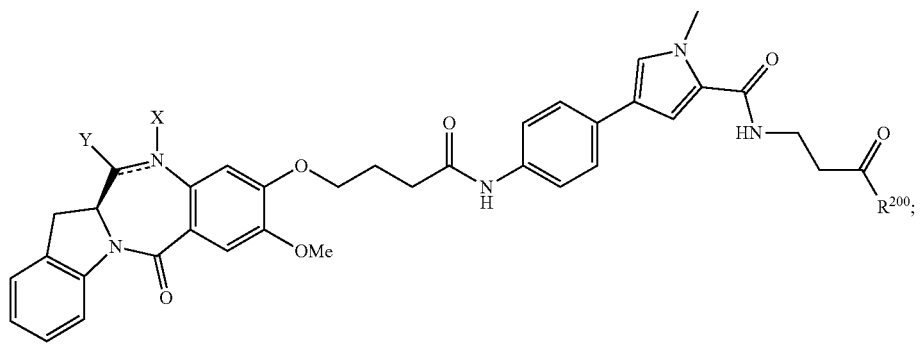
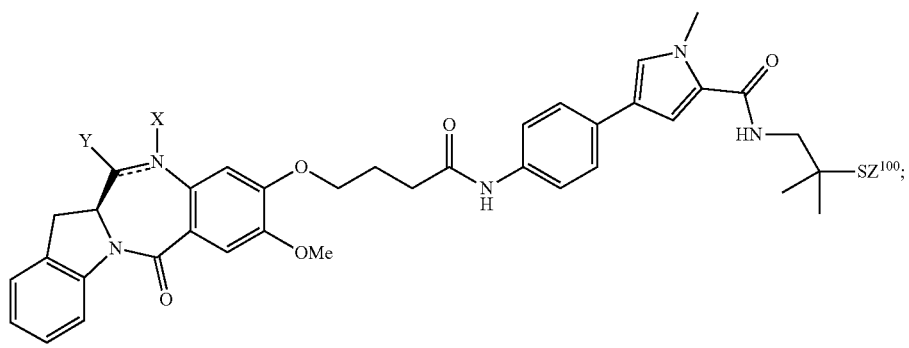

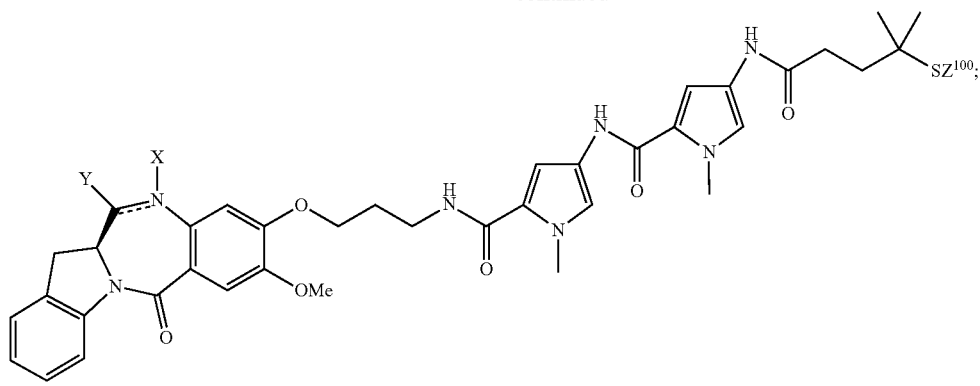
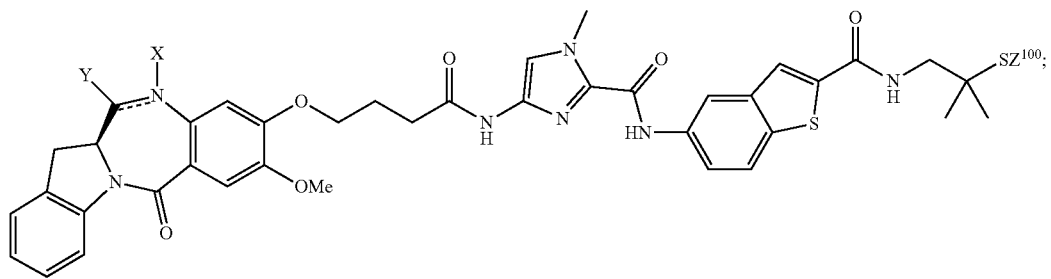
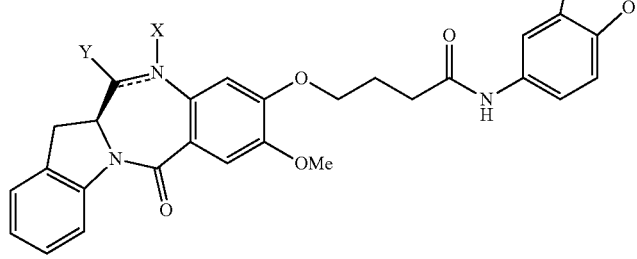
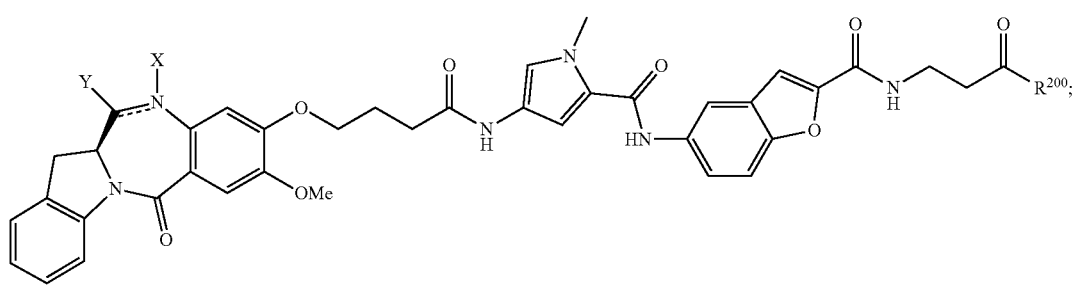
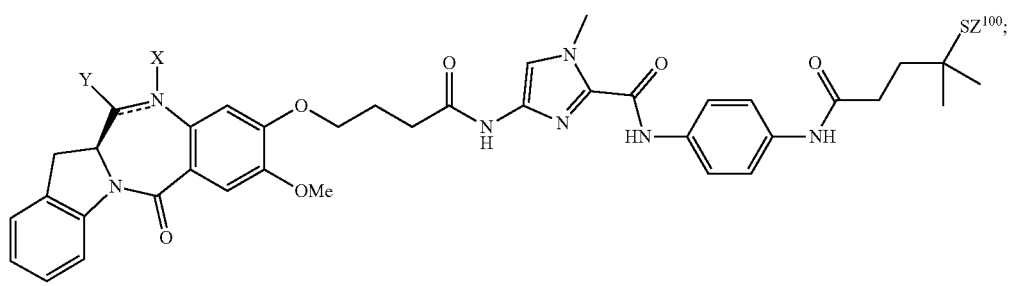

-continued
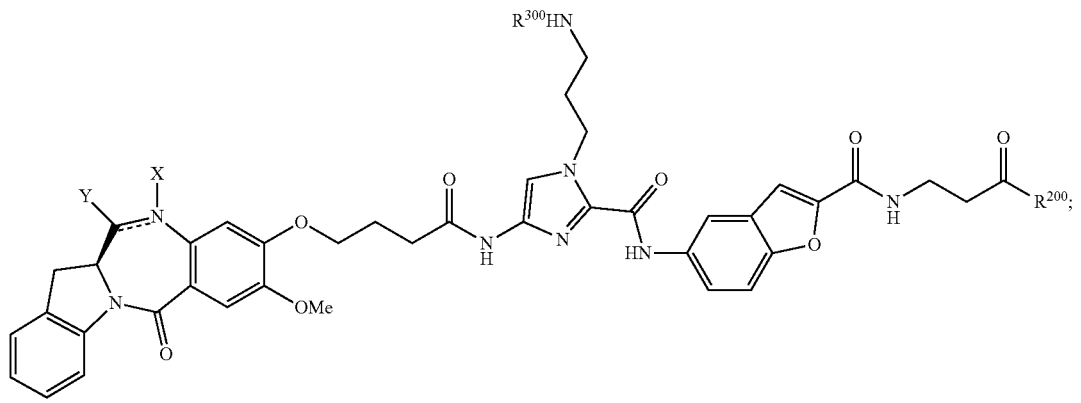
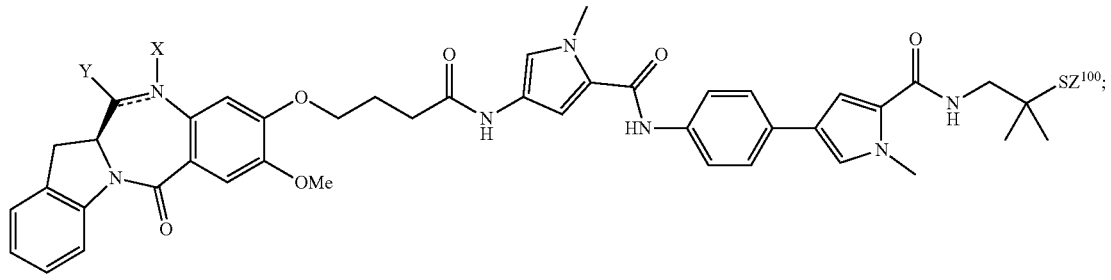
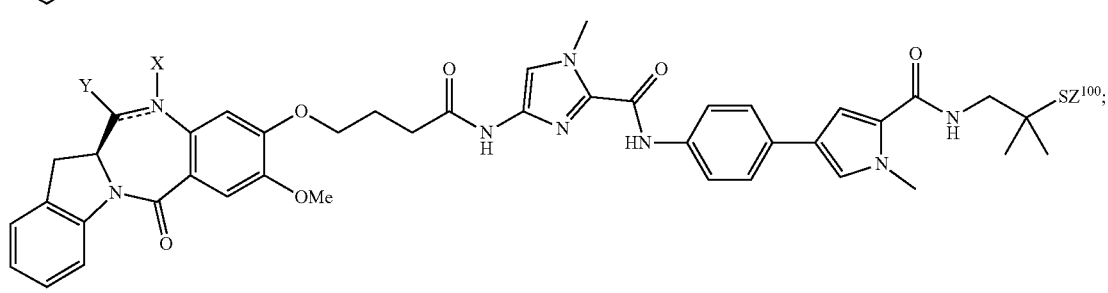
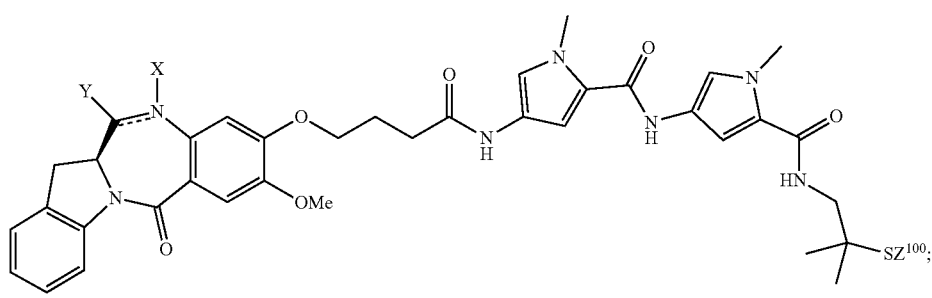
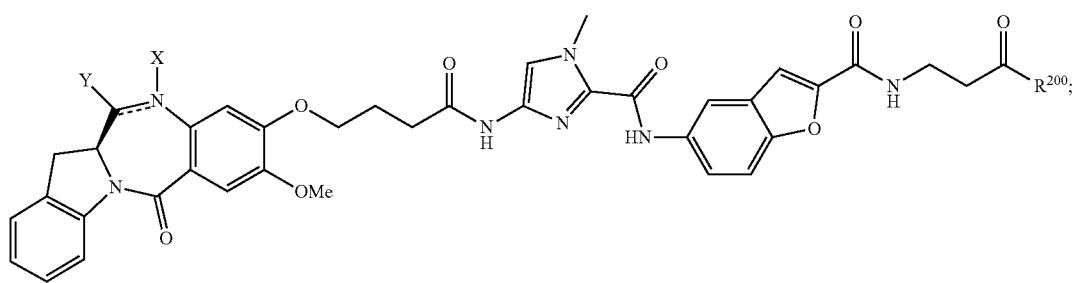

-continued
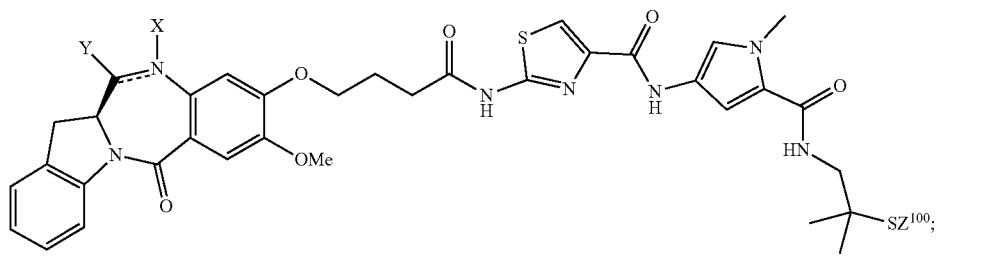
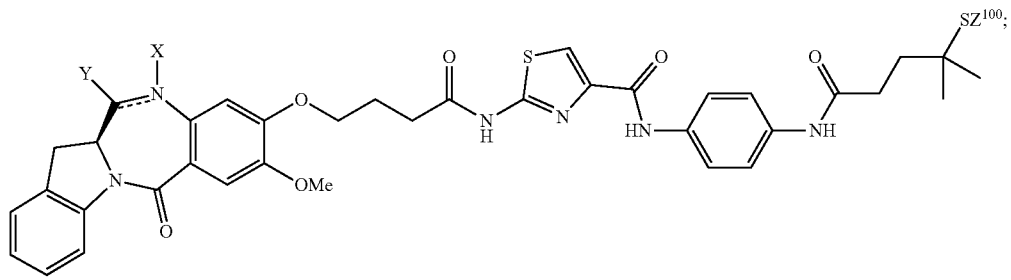
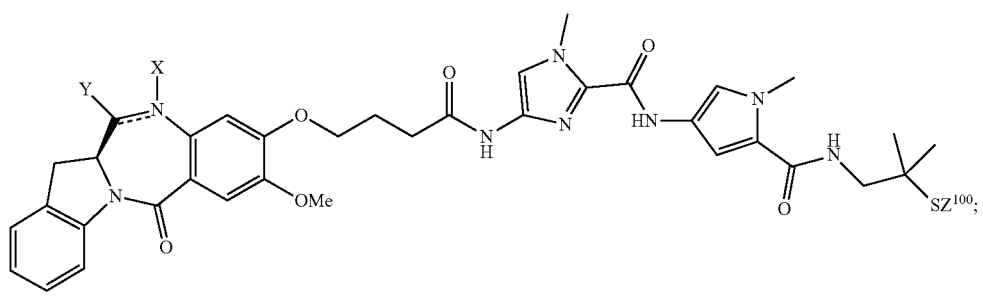
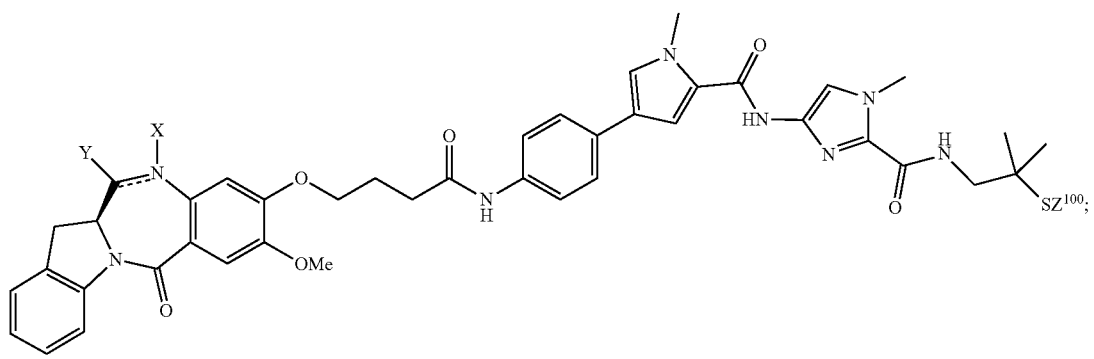
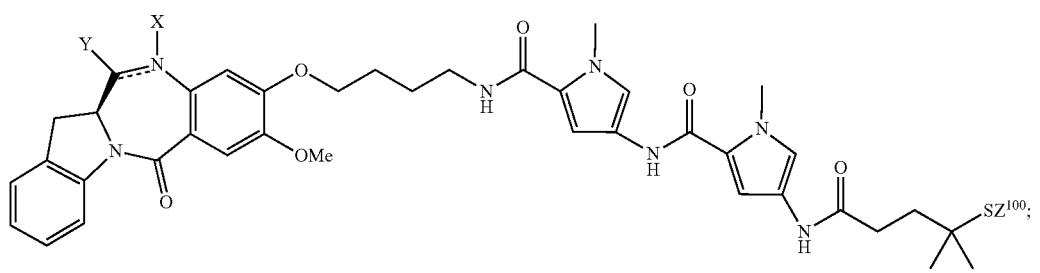

-continued
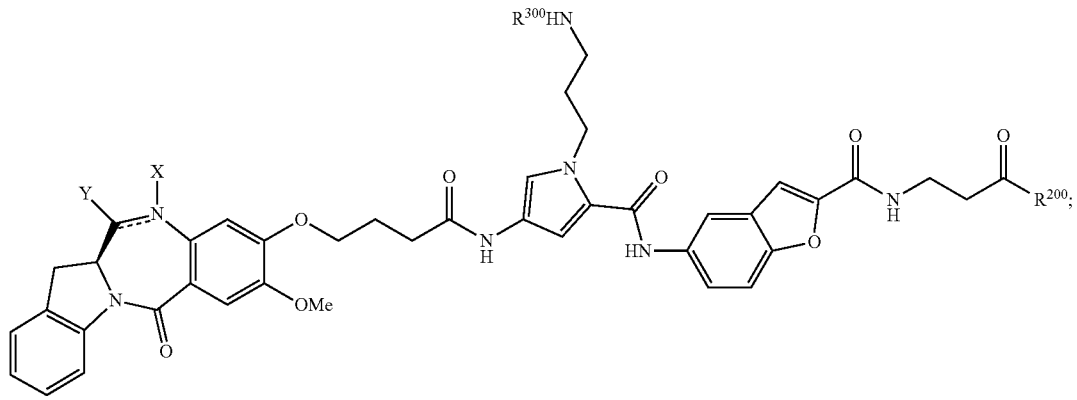
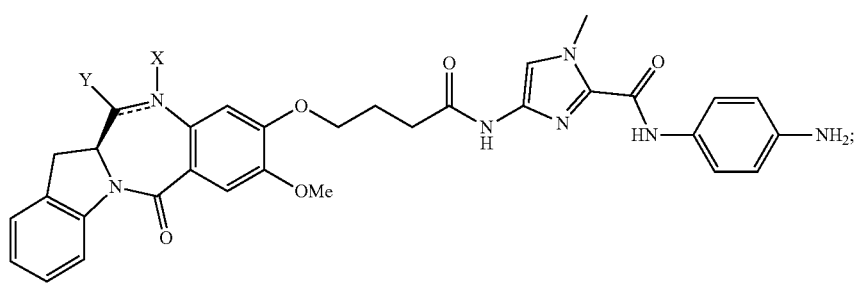
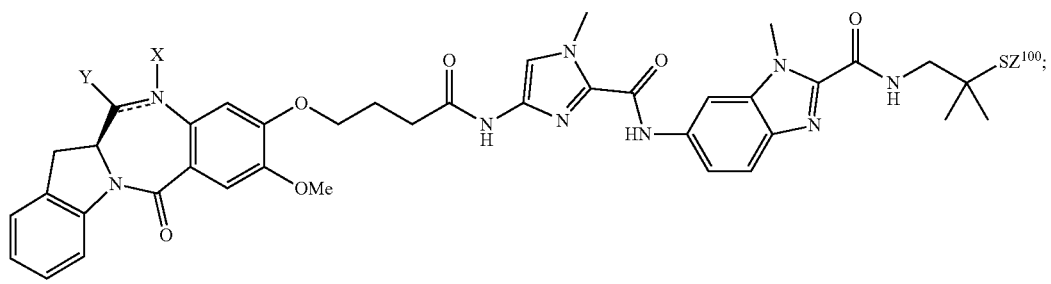
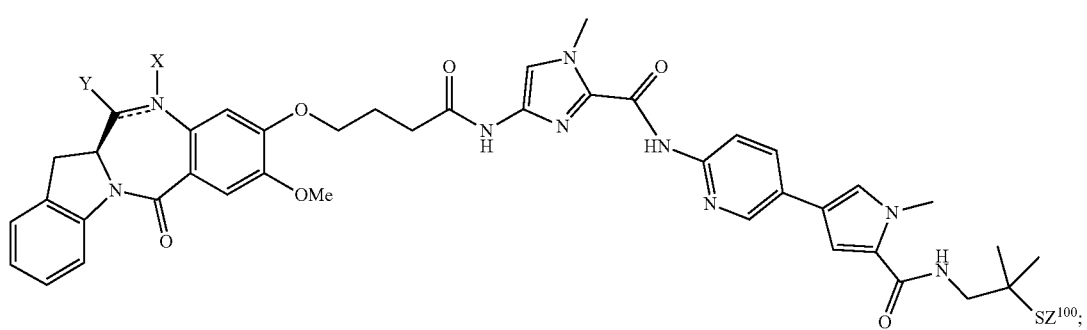
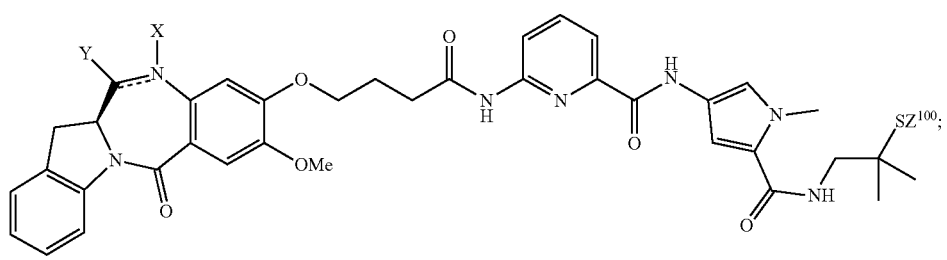

-continued
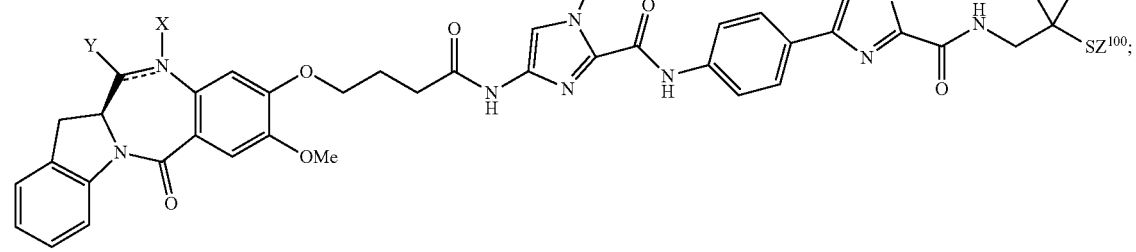
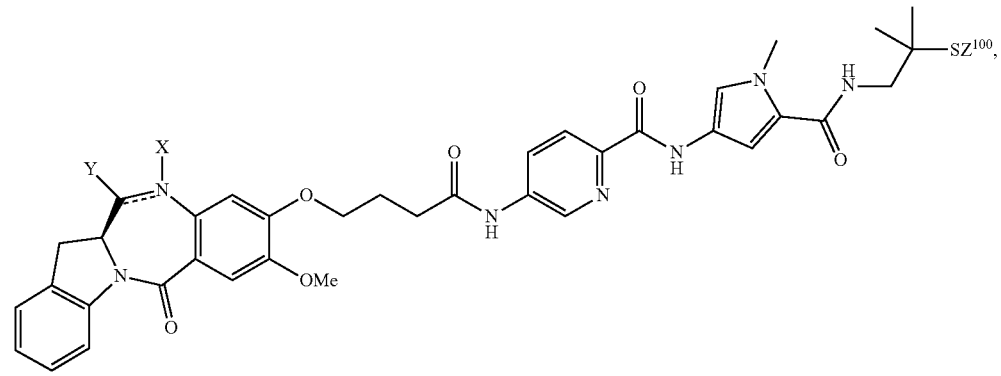
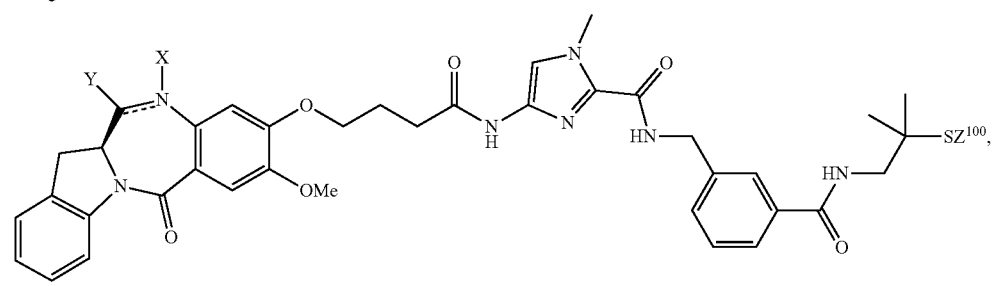
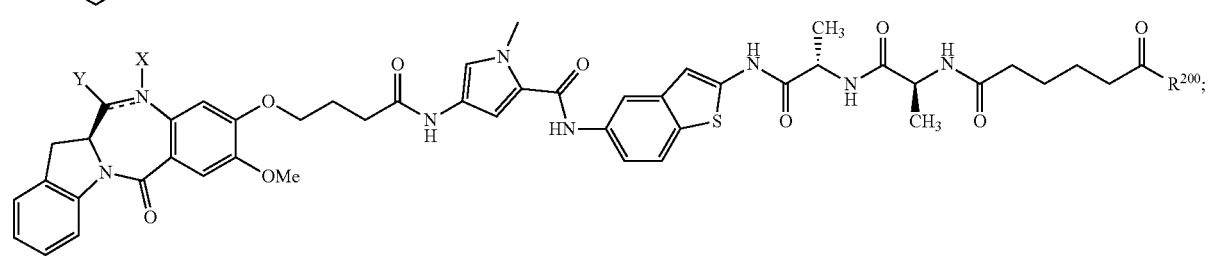
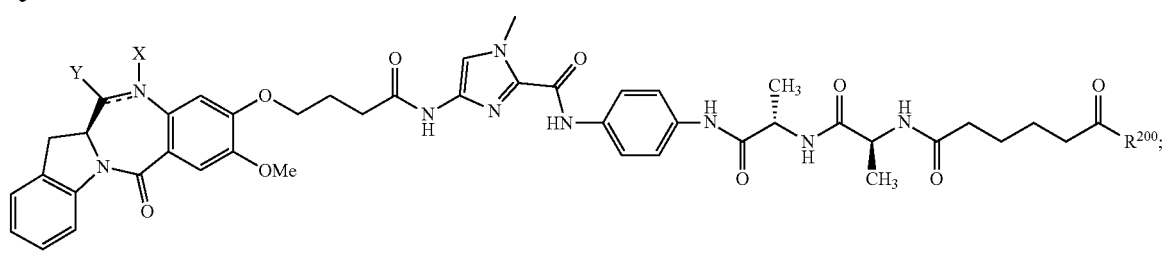
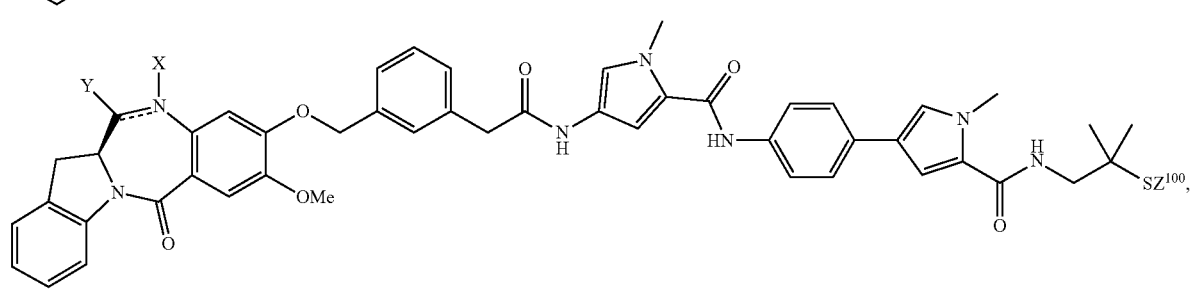

-continued
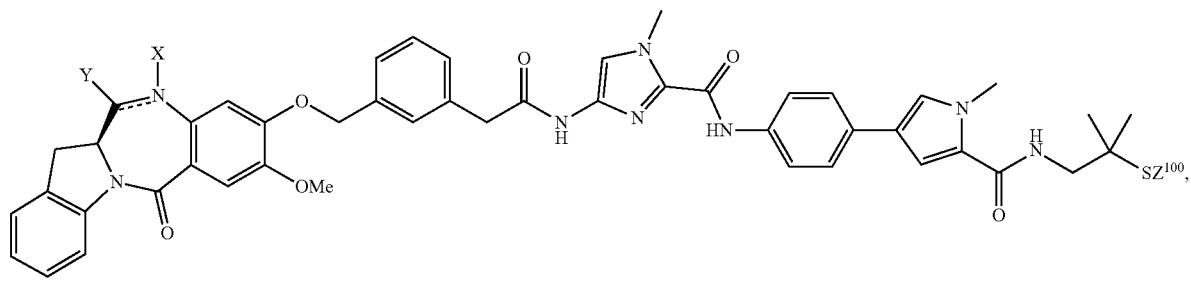
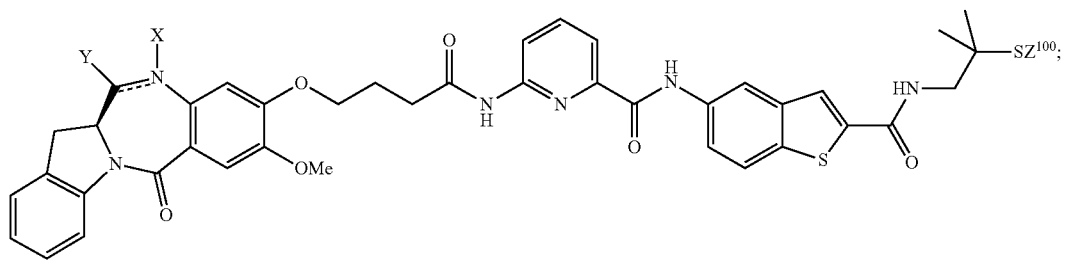
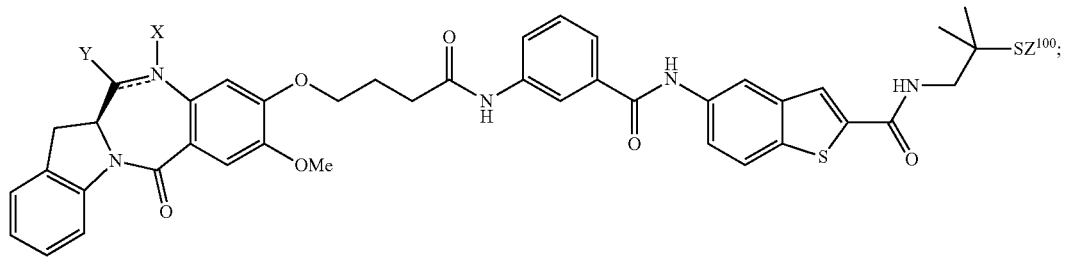
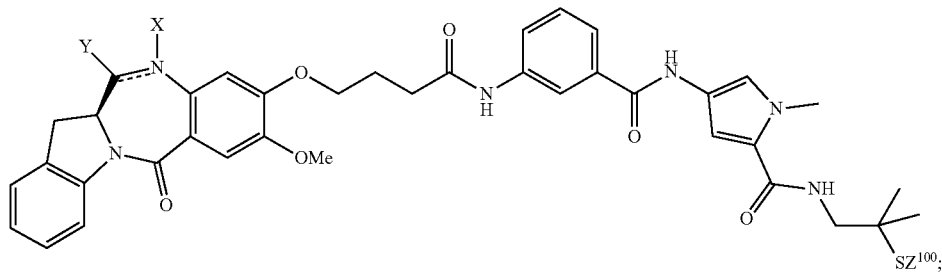
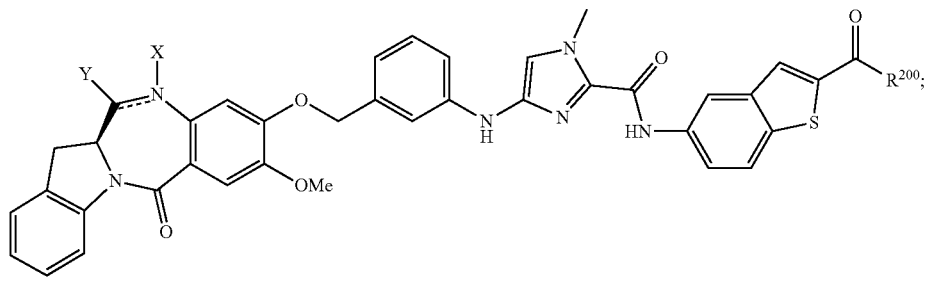
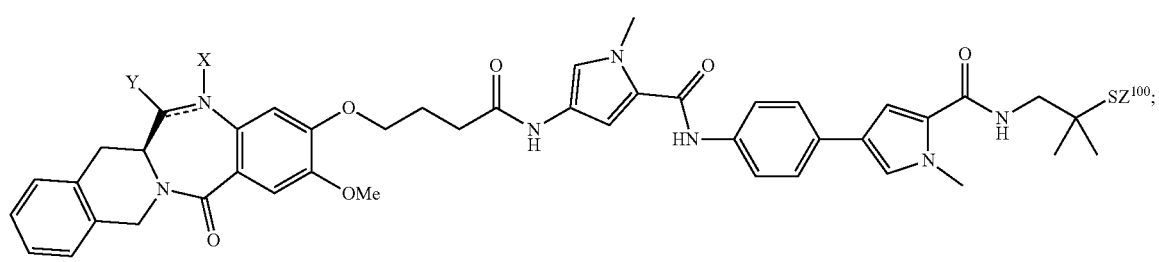

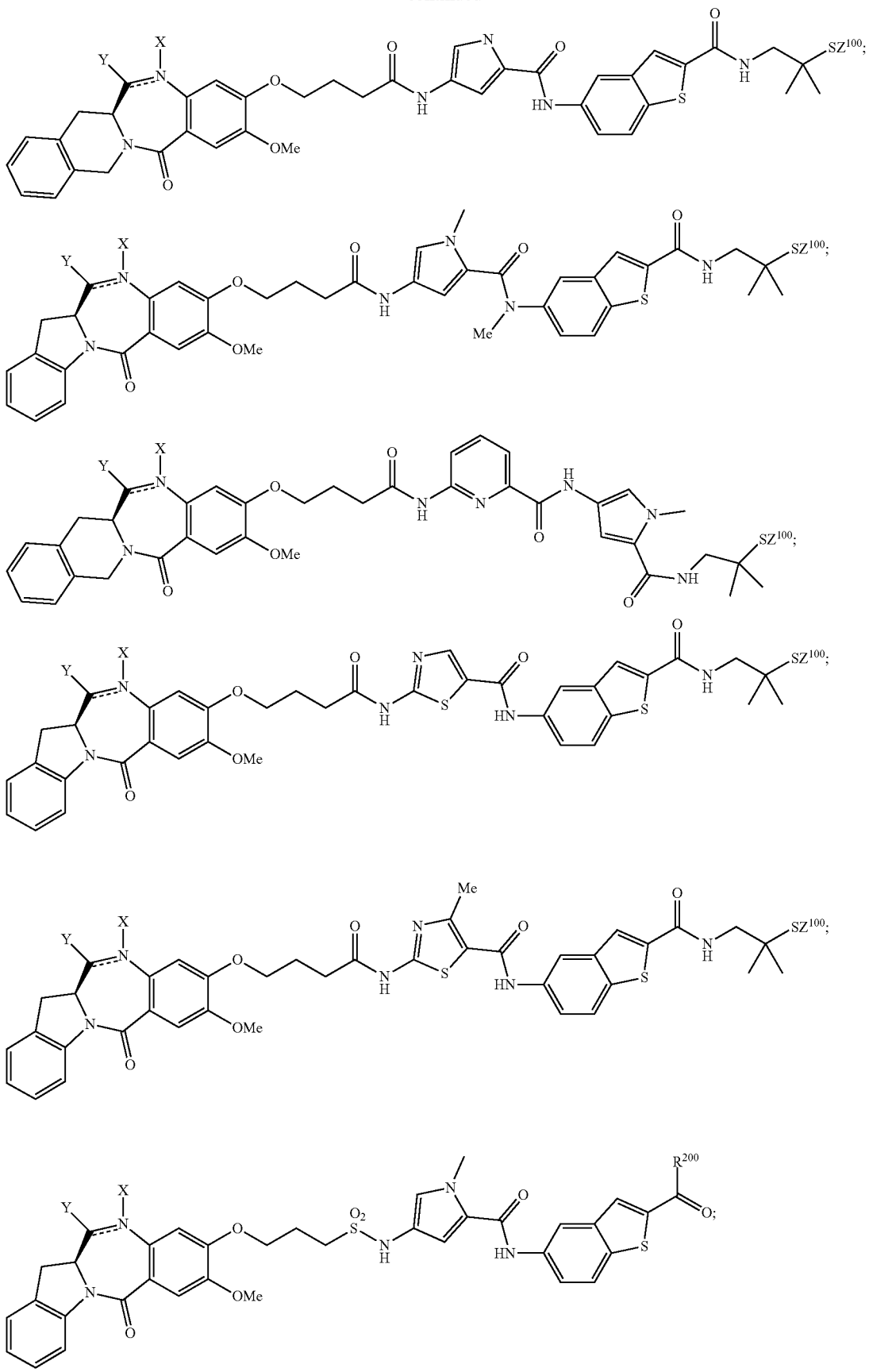

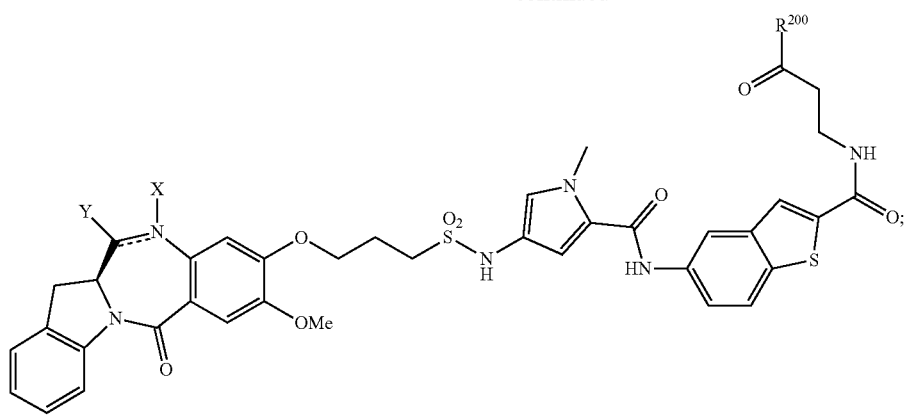
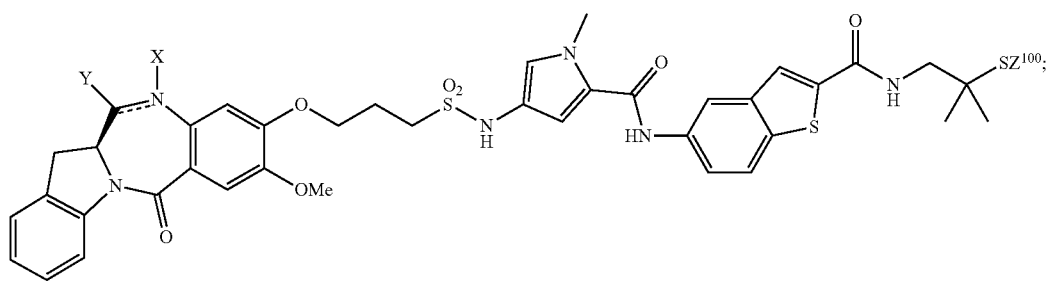
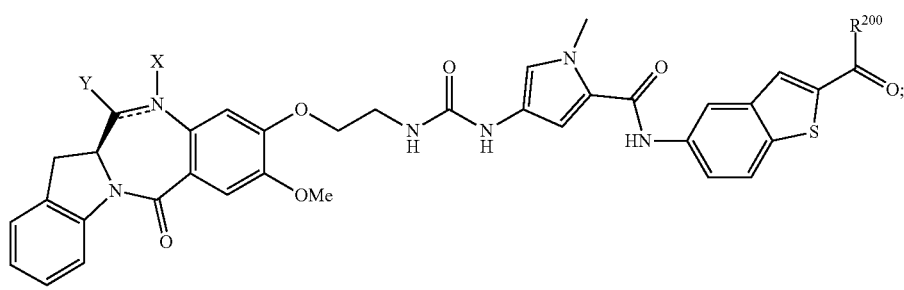
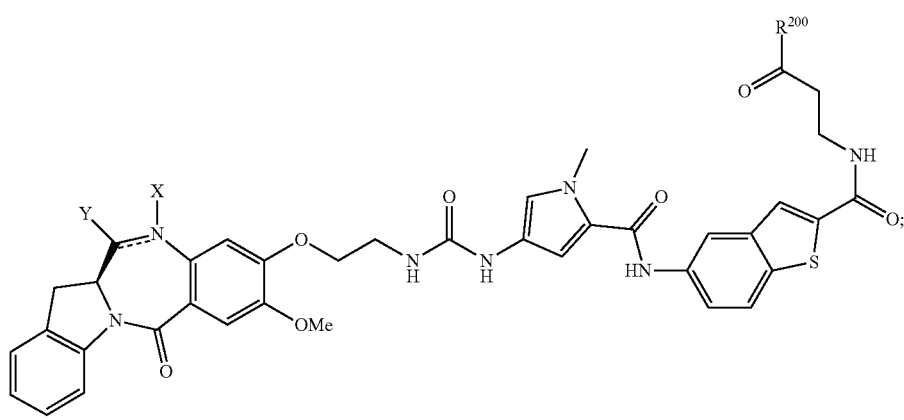
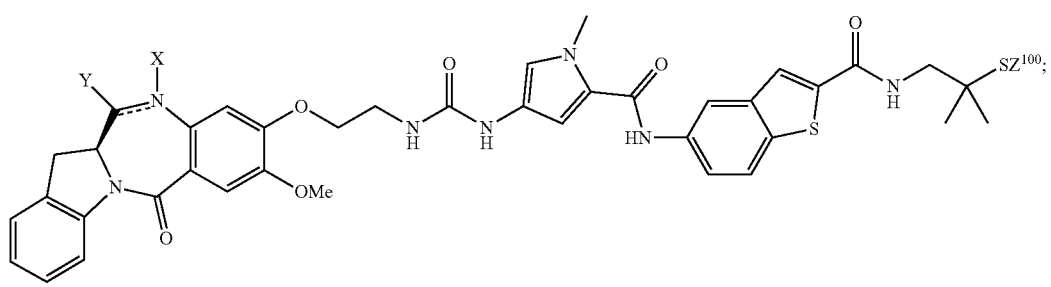

-continued
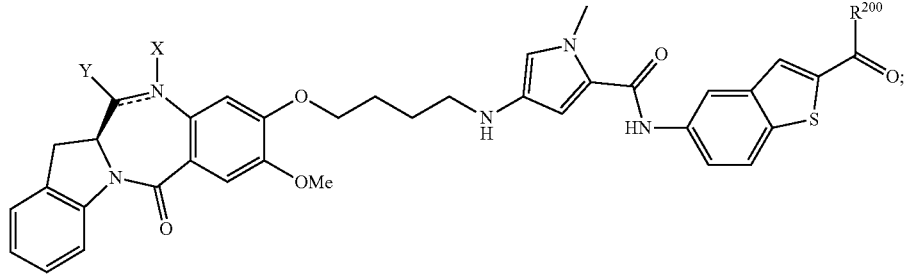
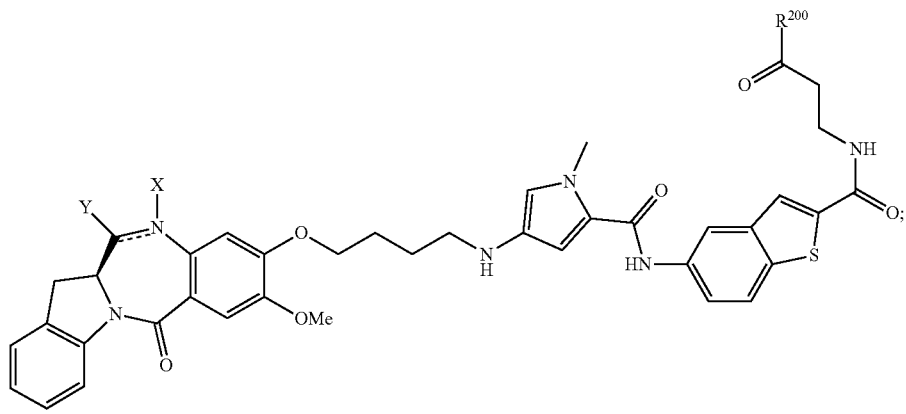
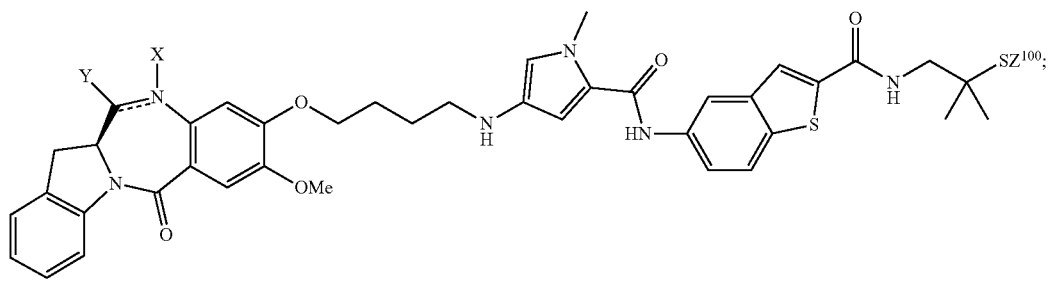
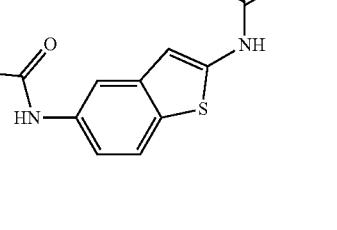
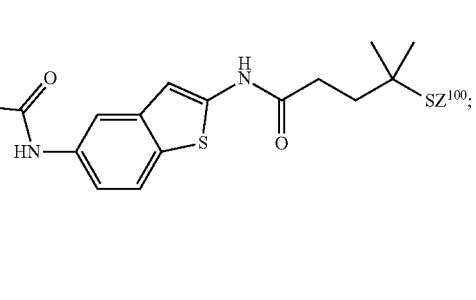
or or a pharmaceutically acceptable salt thereof, wherein $R^{200}$ is —OH, —O($C_1$-$C_3$)alkyl or
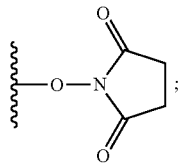 [SMILES: *ON1C(=O)CCC1=O]
$R^{300}$ is H or an amine protecting group (e.g., Boc); and $Z^{100}$ is H, $SR^e$ or is represented by one of the following formulae:
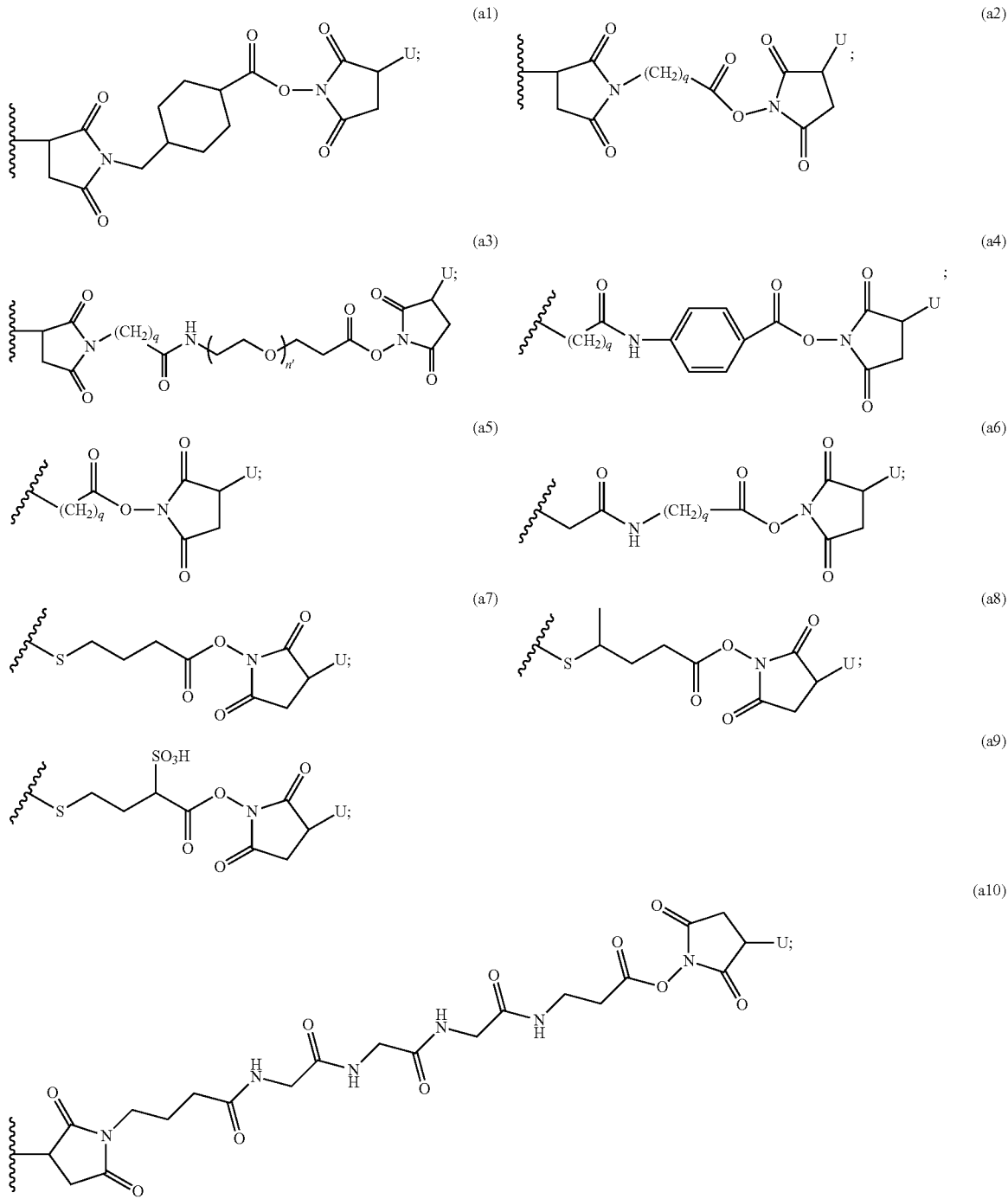

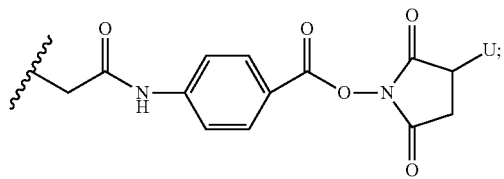 (a11)

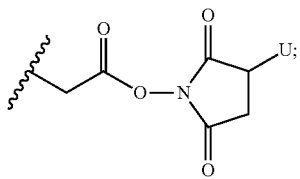 (a12)

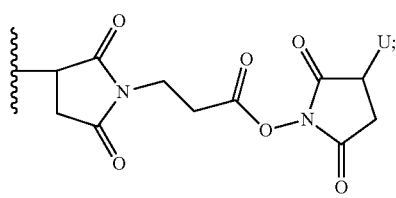 (a13)

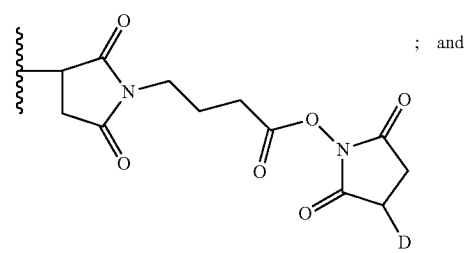 (a14)
; and

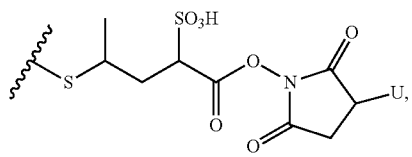 (a15)

$R^e$ is a $(C_1-C_3)$alkyl, pyridyl or nitropyridyl (e.g., 4-nitropyridyl);
q is an integer from 1 to 5;
n' is an integer from 2 to 6; and
U is H or $SO_3H$; and the remaining variables are as described in the 1$^{st}$ embodiment.

In a specific embodiment, $R^{200}$ is —OMe or

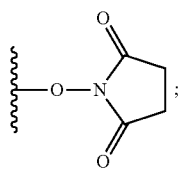 [SMILES: *ON1C(=O)CCC1=O];

and $Z^{100}$ is H or —SMe or is represented by formula (a7) or (a9).

In another specific embodiment, the double line ⚌ between N and C represents a single bond or a double bond, provided that when it is a double bond X is absent and Y is —H, and when it is a single bond, X is —H, and Y is —SO$_3$H.

In some embodiments, the pharmaceutically acceptable salt is a sodium or potassium salt. In some embodiments, the pharmaceutically acceptable salt is a sodium salt.

In another specific embodiment, the compound of the present invention is represented by the following formula:

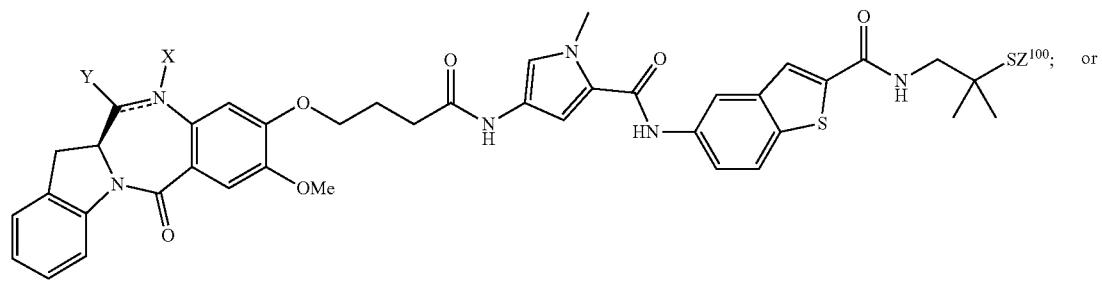 or

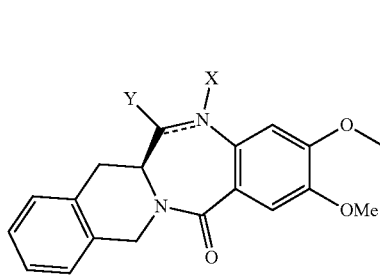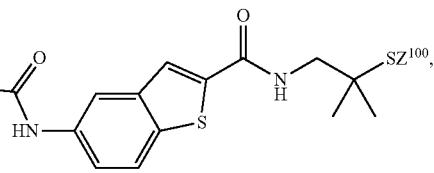

or a pharmaceutically acceptable salt thereof, wherein $Z^{100}$ is represented by formula (a7) or (a9).

In another specific embodiment, the compound of the present invention is represented by the following formula:

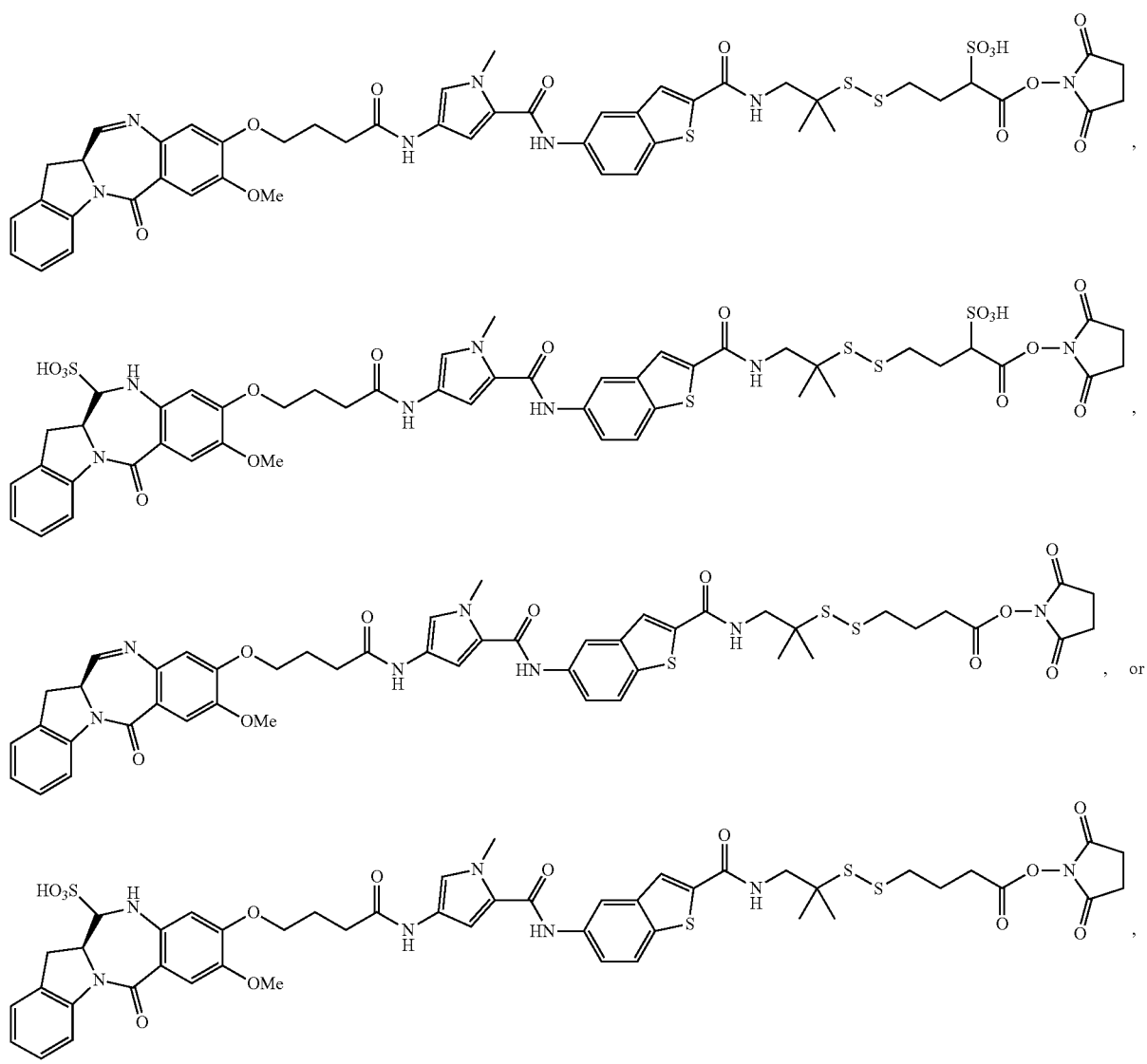

or a pharmaceutically acceptable salt thereof. In some embodiments, the pharmaceutically acceptable salt is a sodium or potassium salt. In some embodiments, the pharmaceutically acceptable salt is a sodium salt.

In a 17$^{th}$ embodiment, for compounds of formula (I), (II), (III), (IA-1), (IA-2), (IB-1), (IB-2), (IC), (ID), (IIA), (IIB), (IIC), (IIIA), (IIIB), (IIIC), (IA-1a), (IA-2a), (IB-1a), (IB-2a), (IC-a), (ID-a), (IA-1b), (IA-2b), (IB-1b), or (IB-2b), L is represented by the following formula:

$$—C(=O)—NR_{5a}—R^{x1}—S—Z^{c1} \quad (L4a),$$

$$—NR_{5a}—C(=O)—R^{x2}—SZ^{c1} \quad (L4b)$$

—C(=O)—NR$_{5a}$—R$^3$—C(=O)—Z$^{c2}$ (L4c), or

—NR$_{5a}$—P$_2$—C(=O)—R$^{x4}$—C(=O)—Z$^{c2}$ (L4d), wherein:
Z$^{c1}$ is

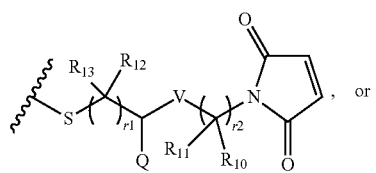 (L4a1)

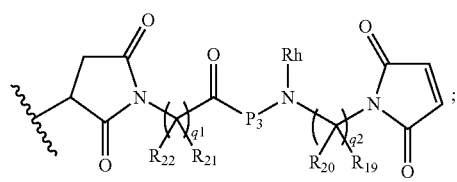 (L4b1)

Z$^{c2}$ is

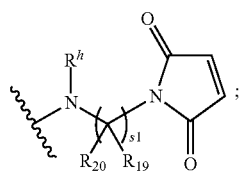

V is —C(=O)—NR$_9$—, or —NR$_9$—C(=O)—;
Q is —H, a charged substituent, or an ionizable group;
R$_9$, R$_{10}$, R$_{11}$, R$_{12}$, R$_{13}$, R$_{19}$, R$_{20}$, R$_{21}$ and R$_{22}$, for each occurrence, are independently —H or a (C$_1$-C$_4$) alkyl;
r1 and r2 are each independently 0 or an integer between 1 and 10;
q1 and q2 are each independently 0 or an integer between 1 and 10;
R$^h$ is —H or a (C$_1$-C$_3$)alkyl;
R$_{19}$ and R$_{20}$, for each occurrence, are independently —H or a (C$_1$-C$_4$)alkyl;
s1 is an integer between 1 and 10;
P$_3$ is an amino acid residue or a peptide residue containing 2 to 5 amino acid residues; and the remaining variables are as defined in the first aspect or the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$ or 13$^{th}$ embodiment or any specific embodiment described therein.

In a specific embodiment, L is represented by formula (L4a) or (L4b), and P$_3$ is selected from Ala-Ala, Gln-Leu, Gly-Gly-Gly, Ala-Val, Val-Cit, Val-Lys, Phe-Lys, Lys-Lys, Ala-Lys, Phe-Cit, Leu-Cit, Ile-Cit, Trp-Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), R-Ala-Leu-Ala-Leu (SEQ ID NO: 2), Gly-Phe-Leu-Gly (SEQ ID NO: 3), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. More specifically, P$_3$ is Gly-Gly-Gly, Ala-Val, Ala-Ala, Ala-D-Ala, D-Ala-Ala, or D-Ala-D-Ala.

In another specific embodiment, for formula (L4a) or (L4b), Z$^{c1}$ is represented by the following formula:

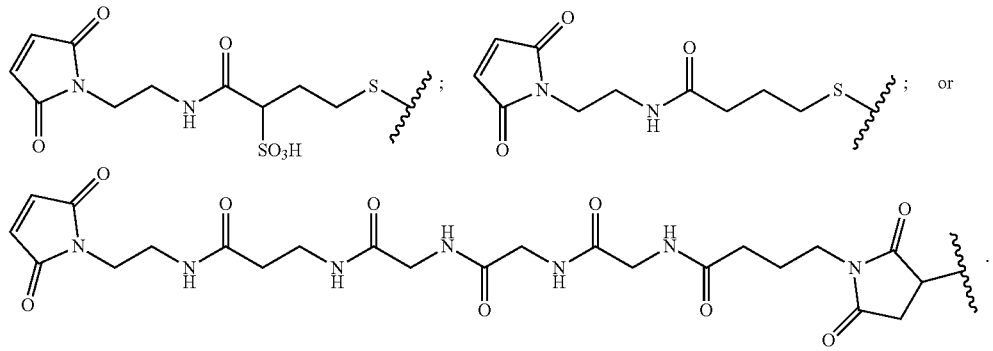

and the remaining variables are as define above in the 17$^{th}$ embodiment or any specific embodiment described therein.

In yet another specific embodiment, for formula (L4a) or (L4b), R$_{5a}$ is H or Me; R$^{x1}$ is —(CH$_2$)$_{p4}$—(CRR)—, and R$^{x2}$ is —(CH$_2$)$_{p5}$—(CR$^f$R$^g$)—, wherein R$^f$ and R$^g$ are each independently —H or a (C$_1$-C$_4$)alkyl; and p4 and p5 are each independently 0, 1, 2, 3, 4 or 5; and the remaining variables are as define above in the 17$^{th}$ embodiment or any specific embodiment described therein. More specifically, R$^f$ and R$^g$ are each independently —H or -Me.

In another specific embodiment, L is represented by formula (L4c) or (L4d), R$_{5a}$ is H or Me; R$^{x3}$ is —(CH$_2$)$_{p3}$—, wherein p3 is an integer from 2 to 6; and R$^{x4}$ is —(CH$_2$)$_{p4}$—, wherein p4 is an integer from 2 to 6; and the remaining variables are as define above in the 17$^{th}$ embodiment or any specific embodiment described therein.

In another specific embodiment, for formula (L4c) or (L4d), P$_2$ is a peptide residue containing 2 to 5 amino acid residues. More specifically, P$_2$ is selected from Ala-Ala, Gln-Leu, Gly-Gly-Gly, Ala-Val, Cit-Val, Val-Cit, Val-Lys, Phe-Lys, Lys-Lys, Ala-Lys, Phe-Cit, Leu-Cit, Ile-Cit, Trp, Cit, Phe-Ala, Phe-N⁹-tosyl-Arg, Phe-N⁹-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), -Ala-Leu-Ala-Leu (SEQ ID NO: 2), Gly-Phe-Leu-Gly (SEQ ID NO: 3), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Met-Ala, Gln-Val, Asn-Ala, Gln-Phe and Gln-Ala; and the remaining variables are as define above in the 17th embodiment or any specific embodiment described therein. Even more specifically, P₂ is Gly-Gly-Gly, Ala-Val, Val-Ala, Ala-Ala, Ala-D-Ala, D-Ala-Ala, or D-Ala-D-Ala.

In another specific embodiment, for formula (L4c) or (L4d), $Z^{c2}$ is represented by the following formula:

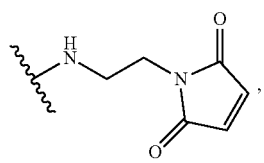 [SMILES: *NCCN1C(=O)C=CC1=O]

and the remaining variables are as define above in the 17th embodiment or any specific embodiment described therein.

In another specific embodiment, for formula (L4a), (L4b), (L4c) or (L4d), $R^h$ is H or Me; Q is —SO₃H; and $R_{19}$ and $R_{20}$ are both H; and s1 is an integer from 1 to 6; and the remaining variables are as define above in the 17th embodiment or any specific embodiment described therein.

In a 18th embodiment, the compound of the present invention is represented by the following formula:

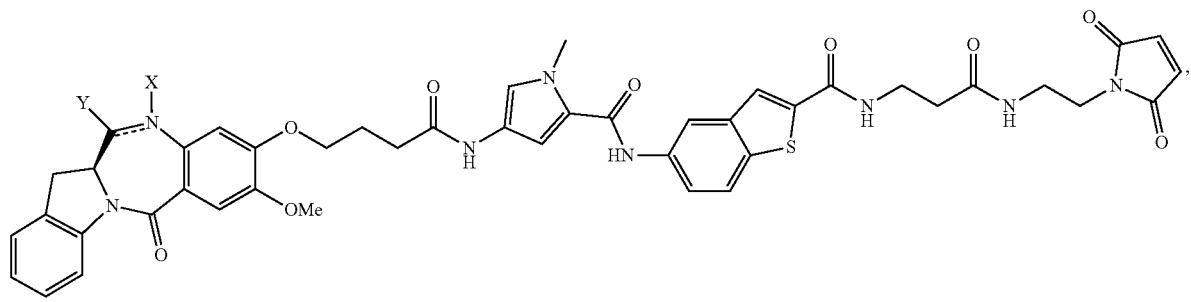

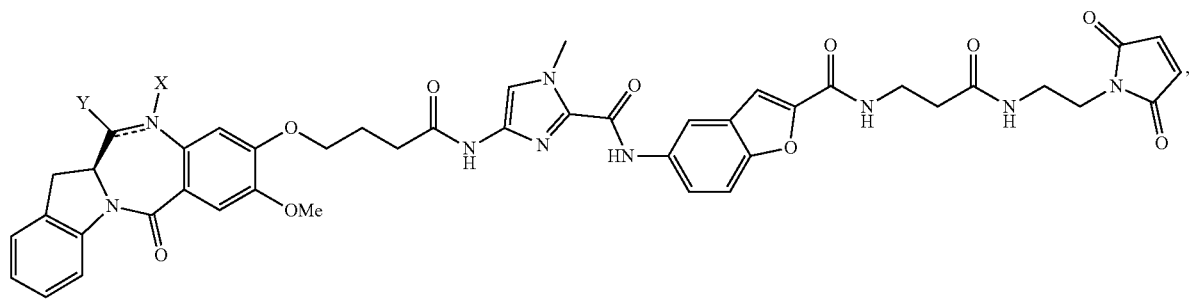

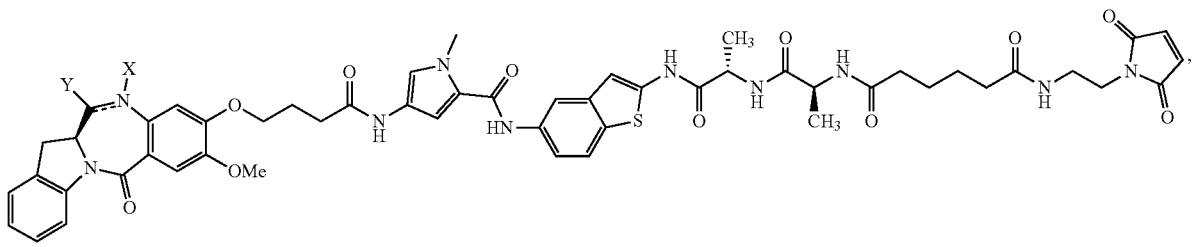

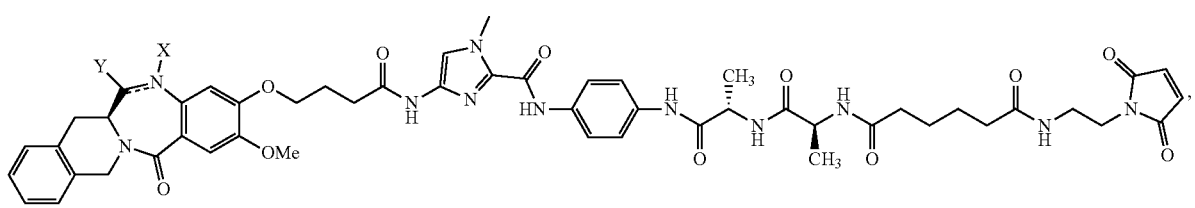

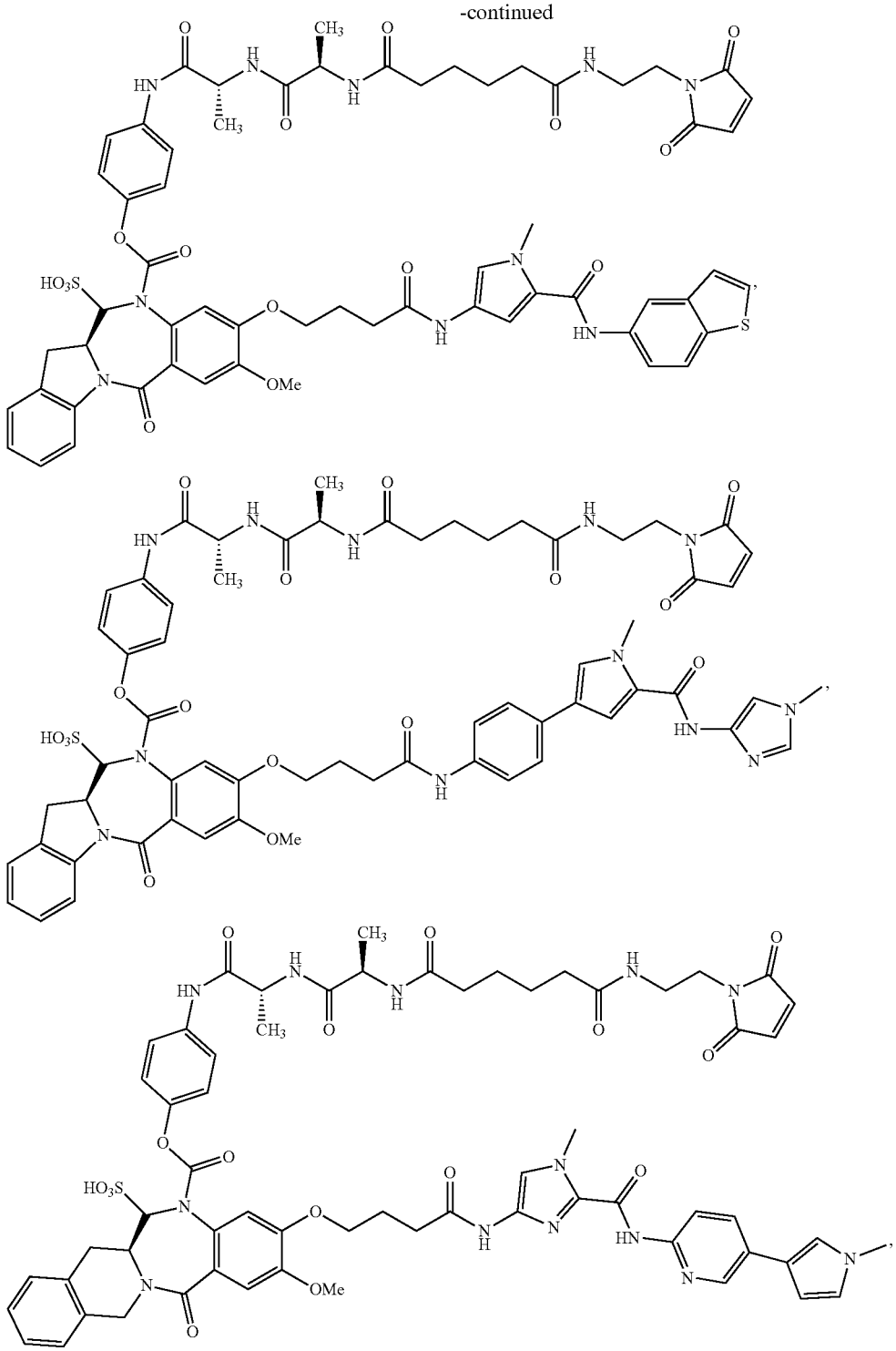

or a pharmaceutically acceptable salt thereof, wherein the double line ⚌ between N and C represents a single bond or a double bond, provided that when it is a double bond X is absent and Y is —H, and when it is a single bond, X is —H, and Y is —SO₃H. In some embodiments, the pharmaceutically acceptable salt is a sodium or potassium salt. In some embodiments, the pharmaceutically acceptable salt is a sodium salt.

In a 19$^{th}$ embodiment, for compounds of formula (I), (II), (III), (IA-1), (IA-2), (IB-1), (IB-2), (IC), (ID), (IIA), (IIB), (IIC), (IIIA), (IIIB), (IIIC), (IA-1a), (IA-2a), (IB-1a), (IB-2a), (IC-a), (ID-a), (IA-1b), (IA-2b), (IB-1b), or (IB-2b), L is represented by the following formula:

—C(=O)—NR$_{5a}$—R$^{x1}$—S—Z$^{s1}$-J$^s$     (L5a),

—NR$_{5a}$—C(=O)—R$^{x2}$—S—Z$^{s1}$-J$^s$     (L5b)

—C(=O)—NR$_{5a}$—R$^{x3}$—Z$_{a2}$—R$^{x3'}$-J$^s$ (L5c)

—NR$_{5a}$—R$^{x3}$—C(=O)—R$^{x4}$—Z$_{a2}$—R$^{x4'}$-J$^s$ (L5c1), or

—NR$_{5a}$—P$_3$—C(=O)—R$^{x4}$—Z$_{a2}$—R$^{x4'}$-J$^s$ (L5d), wherein:
R$^{x1}$, R$^{x2}$, R$^{x3}$, R$^{x3'}$, R$^{x4}$ and R$^{x4'}$ are each independently a (C$_1$-C$_6$)alkyl;
Z$^{s1}$ is

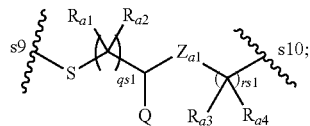

s9 is the site connected to the —S— group in formula (L5a) or (L5b);
s10 is the site connected to the group J$^s$;
Z$_{a1}$ is absent, —C(=O)—NR$_9$—, or —NR$_9$—C(=O)—;
R$_9$ is —H or a (C$_1$-C$_3$)alkyl;
Q is H, a charged substituent or an ionizable group;
R$_{a1}$, R$_{a2}$, R$_{a3}$, R$_{a4}$, for each occurrence, are independently H or (C$_1$-C$_3$)alkyl; and
qs1 and rs1 are each independently an integer from 0 to 10, provided that qs1 and rs1 are not both 0
Z$_{a2}$ is absent, —C(=O)—NR$_9$—, or —NR$_9$—C(=O)—;
R$_9$ is —H or a (C$_1$-C$_3$)alkyl;
J$^s$ is an aldehyde reactive group; and the remaining variables are as defined in the first aspect or the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$ or 13$^{th}$ embodiment or any specific embodiment described therein.

In a specific embodiment, J$^s$ is

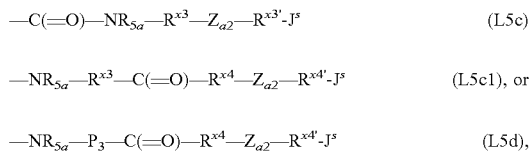

In another specific embodiment, L is represented by formula (L5c), (L5c1) or (L5d); R$_5$ and R$_9$ are both H or Me; and R$^{x1}$, R$^{x2}$, R$^{x3}$, R$^{x3'}$, R$^{x4}$ and R$^{x4'}$ are each independently —(CH$_2$)$_s$—; wherein s is 1, 2, 3, 4, 5 or 6; and the remaining variables are as defined in the 19$^{th}$ embodiment or any specific embodiments described therein.

In another specific embodiment, for formula (L5d), P$_3$ is selected from: Ala-Ala, Gln-Leu, Gly-Gly-Gly, Ala-Val, Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), f-Ala-Leu-Ala-Leu (SEQ ID NO: 2), Gly-Phe-Leu-Gly (SEQ ID NO: 3), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala; and the remaining variables are defined in the 19$^{th}$ embodiment or any specific embodiments described therein. More specifically, P$_3$ is Gly-Gly-Gly, Ala-Val, Ala-Ala, Ala-D-Ala, D-Ala-Ala, or D-Ala-D-Ala.

In yet another specific embodiment, for formula (L5a) or (L5b), Q is —SO$_3$H.

In another specific embodiment, L is represented by formula (L5a) or (L5b), and Z$^{s1}$ is represented by the following formula:

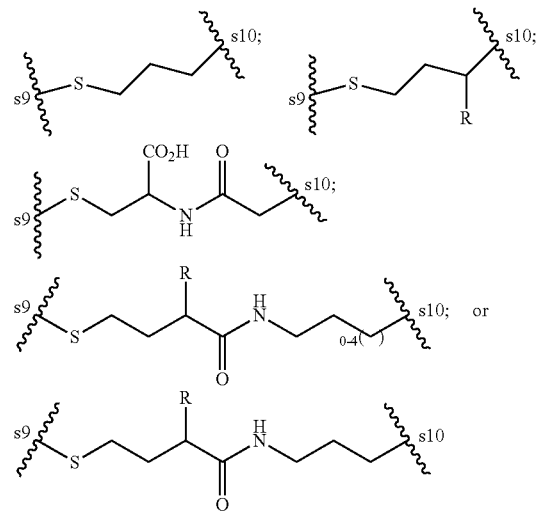

or a pharmaceutically acceptable salt thereof, wherein R is H or —SO$_3$H; and the remaining variables are defined in the 19$^{th}$ embodiment or any specific embodiments described therein.

More specifically, R$^{x1}$ is —(CH$_2$)$_p$—(CR$^f$R$^g$)—, and R$^{x2}$ is —(CH$_2$)$_p$—(CR$^f$R$^g$)—, wherein R$^f$ and R$^g$ are each independently —H or a (C$_1$-C$_4$)alkyl; and p is 0, 1, 2 or 3. Even more specifically, R$^f$ and R$^g$ are independently H or Me.

In a 20$^{th}$ embodiment, the compound of the present invention is represented by the following formula:

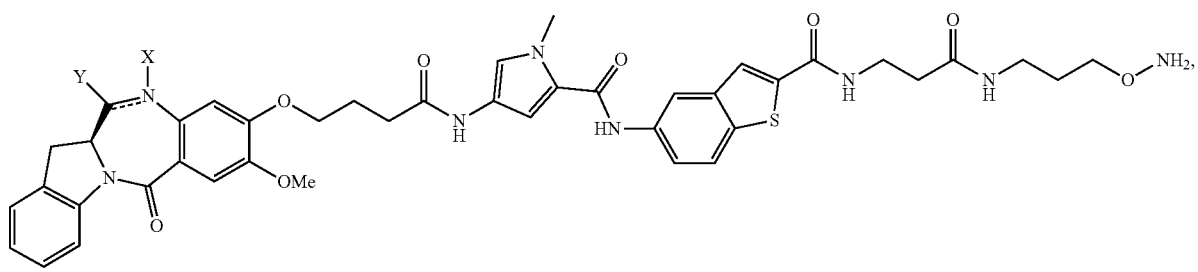

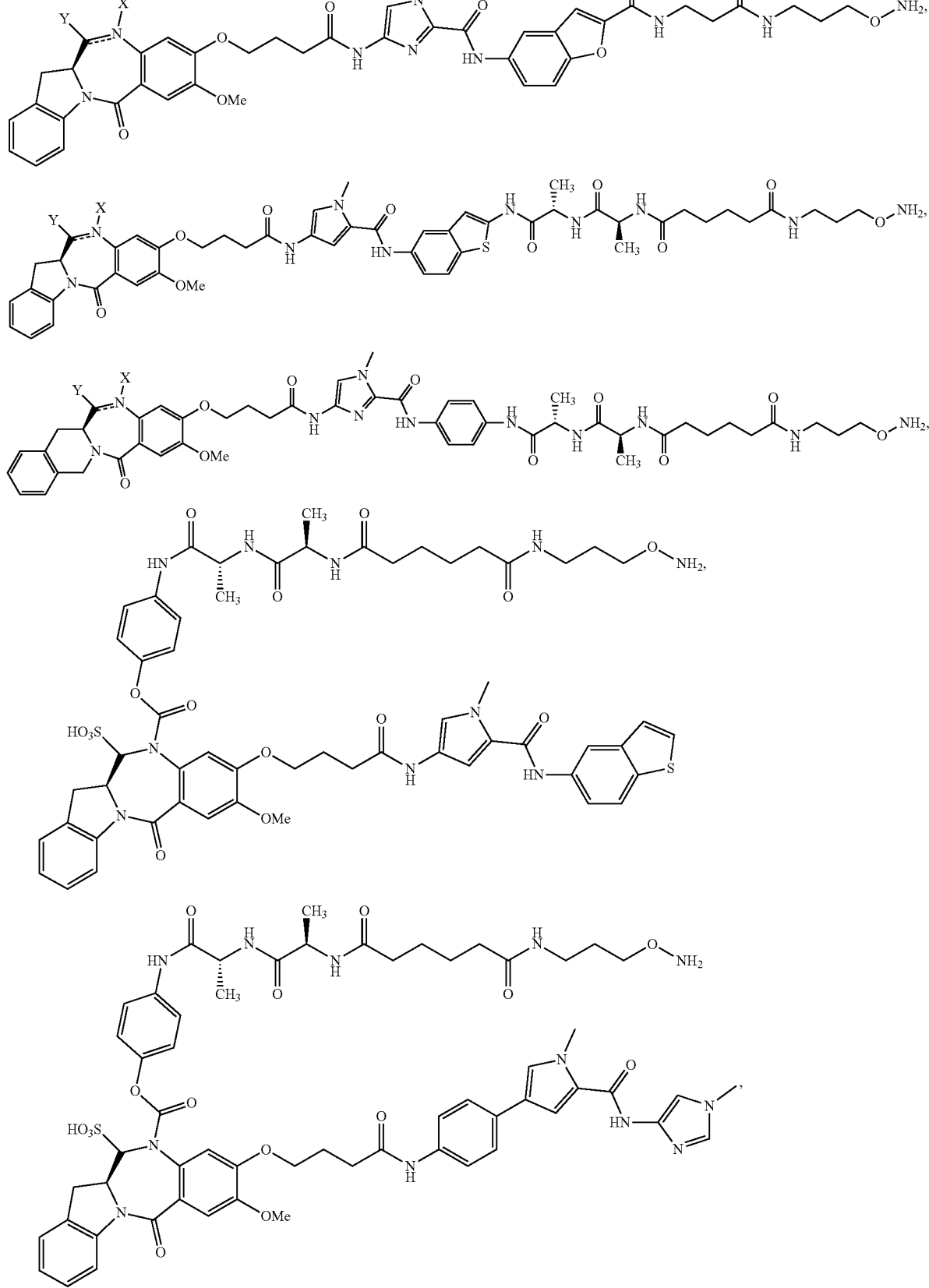

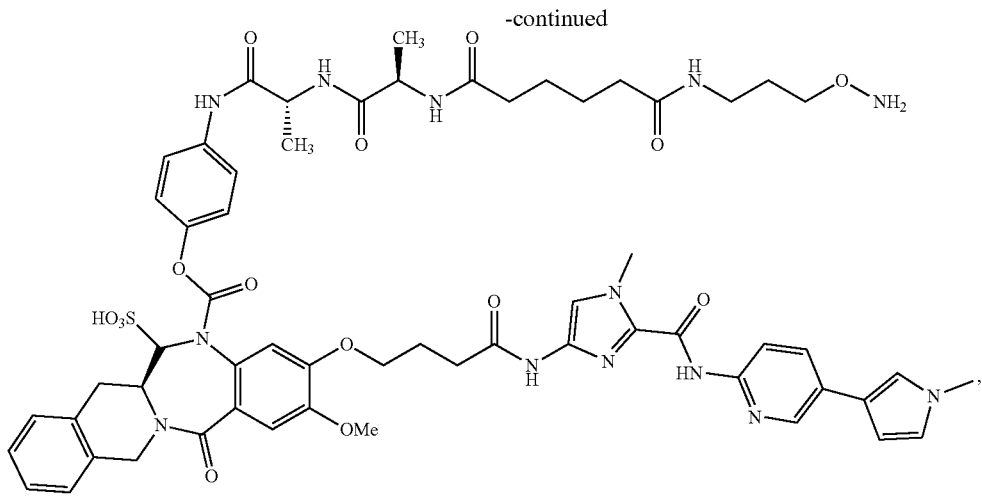

or a pharmaceutically acceptable salt thereof, wherein the double line ⚌ between N and C represents a single bond or a double bond, provided that when it is a double bond X is absent and Y is —H, and when it is a single bond, X is —H, and Y is —SO$_3$H. In some embodiments, the pharmaceutically acceptable salt is a sodium or potassium salt. In some embodiments, the pharmaceutically acceptable salt is a sodium salt.

In some embodiments, for compounds described above (e.g., compounds described in the first aspect or any embodiments described therein or in the 1$^{st}$ to 20$^{th}$ embodiments or any embodiments or specific embodiments described therein), the double line ⚌ between N and C represents a double bond, X is absent and Y is —H.

In some embodiments, for compounds described above (e.g., compounds described in the first aspect or any embodiments described therein or in the 1$^{st}$ to 20$^{th}$ embodiments or any embodiments or specific embodiments described therein), the double line ⚌ between N and C represents a single bond, X is —H, and Y is —SO$_3$H or —SO$_3$Na.

In some embodiments, for compounds described above (e.g., compounds described in the first aspect or any embodiments described therein or in the 1$^{st}$ to 20$^{th}$ embodiments or any embodiments or specific embodiments described therein), the pharmaceutically acceptable salt thereof is a sodium or potassium salt. In some embodiments, the pharmaceutically acceptable salt is a sodium salt.

Conjugates of the Present Invention

In a second aspect, the present invention provides a cell-binding agent-cytotoxic agent conjugate comprising a cell-binding agent described herein covalently linked to a cytotoxic compound described herein.

In a 21$^{st}$ embodiment, the conjugate of the present invention is represented by the following formula:

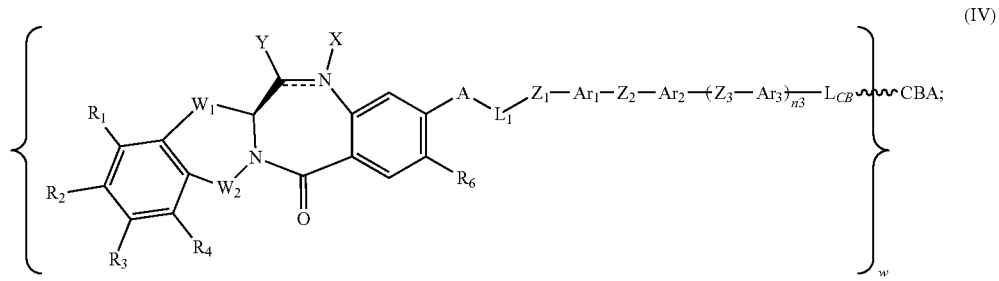

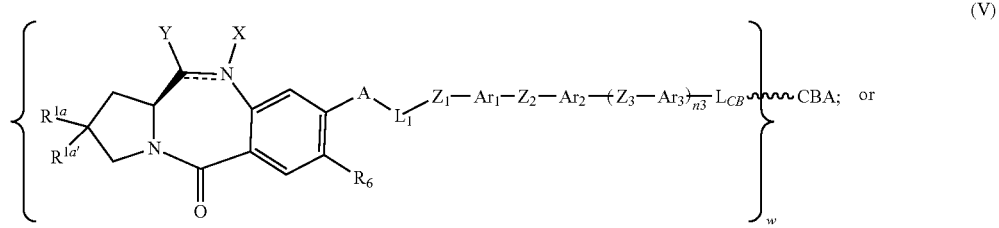

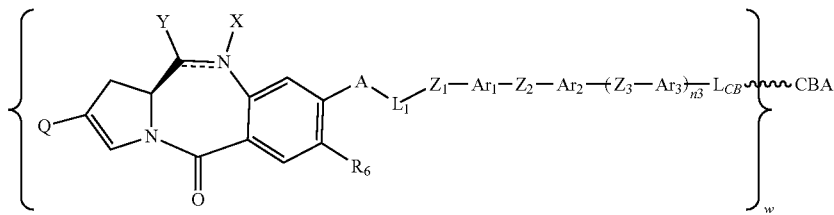

(VI)

or a pharmaceutically acceptable salt thereof, wherein:
- $W_1$ is —(CH$_2$)$_{n1}$—;
- $W_2$ is —(CH$_2$)$_{n2}$—
- n1 is 1, 2 or 3;
- n2 is 0, 1 or 2;
- n3 is 0 or 1;
- $R^{1a}$ and $R^{1a'}$ are each independently H, halide, —OH, or (C$_1$-C$_6$)alkyl; or $R^{1a}$ and $R^{1a'}$ together form a double bond containing group =B;
- =B is selected from a (C$_2$-C$_6$)alkenyl or a carbonyl group, wherein the (C$_2$-C$_6$)alkenyl is optionally substituted with a halogen, —OH, (C$_1$-C$_3$)alkoxy or phenyl;
- Q is Q$_1$-Ar-Q$_2$;
- Q$_1$ is absent, (C$_1$-C$_6$)alkyl, or —CH=CH—;
- Ar is absent or an aryl group;
- Q$_2$ is —H, a (C$_1$-C$_6$)alkyl, a (C$_1$-C$_6$)alkenyl, a polyethylene glycol unit —R$^{e'}$—(OCH$_2$CH$_2$)$_n$—R$^e$, or a substituent selected from a halogen, guanidinium [—NH(C=NH)NH$_2$], —R, —OR, —NR'R", —NO$_2$, —NCO, —NR'COR", NR'(C=O)OR"— SR, —SOR', —SO$_2$R', —SO$_3$H, —OSO$_3$H, —SO$_2$NR'R", cyano, an azido, —COR', —OCOR' and —OCONR'R";
- n is an integer from 1 to 10;
- R$^{e'}$ is a (C$_1$-C$_4$)alkyl,
- R$^e$ is H, or a (C$_1$-C$_4$)alkyl,
- the double line = between N and C represents a single bond or a double bond, provided that when it is a double bond X is absent and Y is —H, or a (C$_1$-C$_4$) alkyl, and when it is a single bond, X is —H, an amine protecting moiety or R$^{L1}$; and Y is —OH or —SO$_3$H;
- R$^{L1}$ is self-immolative linker bearing a linking moiety that is covalently bonded the cell-binding agent (CBA);
- R$_1$, R$_2$, R$_3$ and R$_4$ are each independently selected from —H, a (C$_1$-C$_6$)alkyl, halogen, —OR, —NR'R", —NO$_2$, —NR'COR", —SR, —SOR', —SO$_2$R', —SO$_3$H, —OSO$_3$H, —SO$_2$NR'R", cyano, —COR', —OCOR', and —OCONR'R";
- R, for each occurrence, is —H or a (C$_1$-C$_6$)alkyl;
- R' and R" are each independently selected from —H, —OH, —OR, —NHR, —NR$_2$, —COR, or a (C$_1$-C$_6$)alkyl;
- R$_6$ is —H, —R, —OR, —SR, —NR'R", —NO$_2$, or halogen;
- A is absent or is selected from —O—, —C(=O)—, —CRR'O—, —CRR'—, —S—, —CRR'S—, —NR$_5$ and —CRR'N(R$_5$)—;
- L$_1$ is a spacer;
- Z$_1$ is a bond

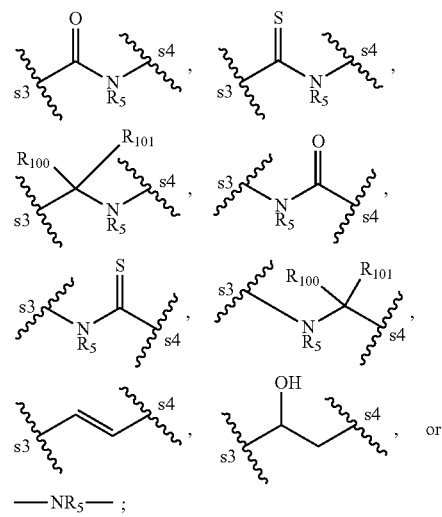

s3 is the site connected L$_1$ and s4 is the site connected to Ar$_1$;
- R$_5$ is —H or a (C$_1$-C$_4$)alkyl;
- R$_{100}$ and R$_{101}$, for each occurrence, are each independently —H, halogen, (C$_1$-C$_4$)alkyl, or (C$_1$-C$_4$)haloalkyl;
- Ar$_1$ is a 6- to 18-membered aromatic ring, a 5- to 18-membered heteroaromatic ring, or -Ar$_1$'-Ar$_1$"-, wherein Ar$_1$' and Ar$_1$" are each independently a 6- to 18-membered aromatic ring or a 5- to 18-membered heteroaromatic ring;
- Z$_2$ is

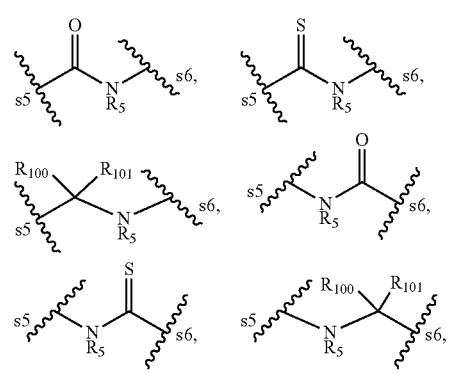

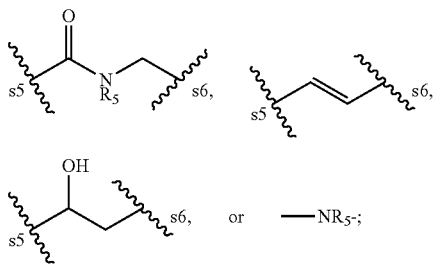

s5 is the site connected Ar₁ and s6 is the site connected to Ar₂;

Ar₂ is a 6- to 18-membered aromatic ring, a 5- to 18-membered heteroaromatic ring or -Ar₂'-Ar₂"-, wherein Ar₂' and Ar₂" are each independently a 6- to 18-membered aromatic ring or a 5- to 18-membered heteroaromatic ring;

Z₃ is

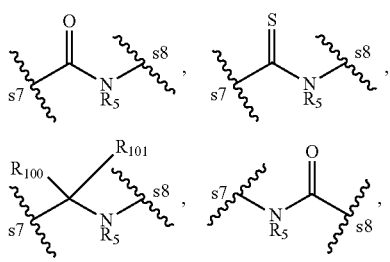

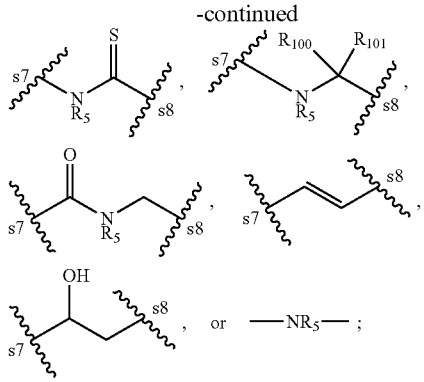

s7 is the site connected to Ar₂ and s8 is the site connected to Ar;

Ar₃ is a 6- to 18-membered aromatic ring, a 5- to 18-membered heteroaromatic ring or -Ar₃'-Ar₃"-, wherein Ar₃' and Ar₃" are each independently a 6- to 18-membered aromatic ring or a 5- to 18-membered heteroaromatic ring;

$L_{CB}$ is a linker bearing a linking moiety that is covalently linked to the cell-binding agent (CBA);

w is an integer from 1 to 20;

$R_a$ is —OH, —Cl, —O($C_1$-$C_6$)alkyl or —C(=O)OR$_a$ is a reactive ester group;

$R_b$ and $R_c$ are each independently —H, ($C_1$-$C_4$)alkyl or an amine protecting group; and provided (i) when the conjugate is represented by formula (V) or (VI), $Z_1$ is not

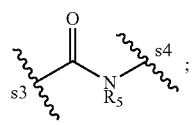

(ii) when the conjugate is represented by formula (IV), the conjugate does not comprise a compound represented by

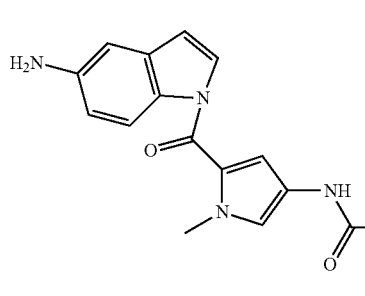

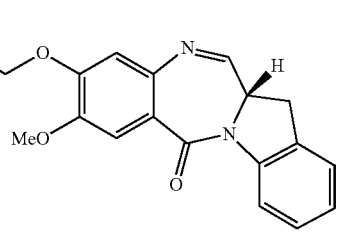

or a pharmaceutically acceptable salt thereof; and (iii) when X is R", L is H, —C(=O)R$_a$ or —NR$_b$R$_c$.

In a specific embodiment, W₁ is —CH₂—, and W₂ is a bond; or W₁ and W₂ are both —CH₂—.

In another specific embodiment, L₁ is ($C_1$-$C_{10}$)alkyl, ($C_2$-$C_{10}$)alkenyl, ($C_2$-$C_{10}$)alkynyl, ($C_3$-$C_8$)cycloalkyl, aryl, heteroaryl, ($C_1$-$C_4$)alkyl-($C_3$-$C_5$)cycloalkyl-($C_1$-$C_4$)alkyl, ($C_1$-$C_4$)alkyl-aryl-($C_1$-$C_4$)alkyl or ($C_1$-$C_4$)alkyl-heteroaryl-($C_1$-$C_4$)alkyl.

In yet another specific embodiment, for formula (IV), (V) or (VI),

R₁, R₂, R₃ and R₄ are each independently —H, a ($C_1$-$C_4$) alkyl, halogen, —NO₂, —OR, —NR₂ or cyano;

R is —H or a ($C_1$-$C_4$)alkyl;

R₆ is —OR;

A is —O— or —S—; and
$L_1$ is —$(CH_2)_{m1}$—;
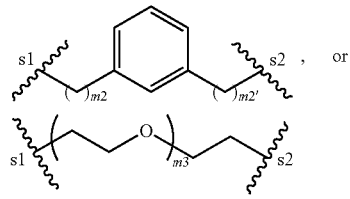
s1 is the site connected to A; s2 is the site connected to $Z_1$;
m1 is 1, 2, 3, 4, 5 or 6;
m2 is 1, 2 or 3;
m2' is 0, 1, 2 or 3; and
m3 is an integer from 1 to 10; and remaining variables are as defined in the second aspect or $21^{st}$ embodiment.
In a $22^{nd}$ embodiment, the conjugate of the present invention is represented by the following formula:
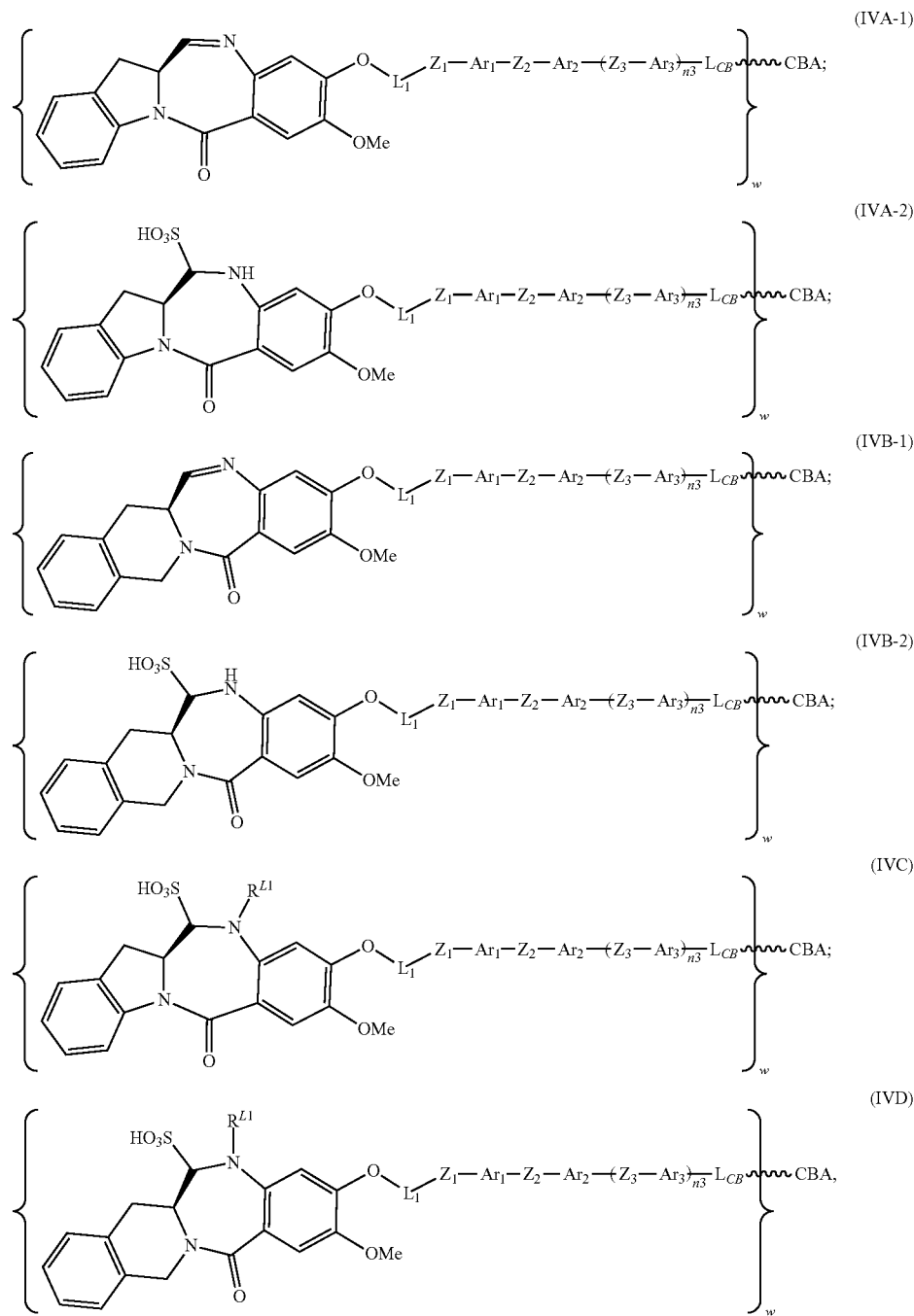

-continued

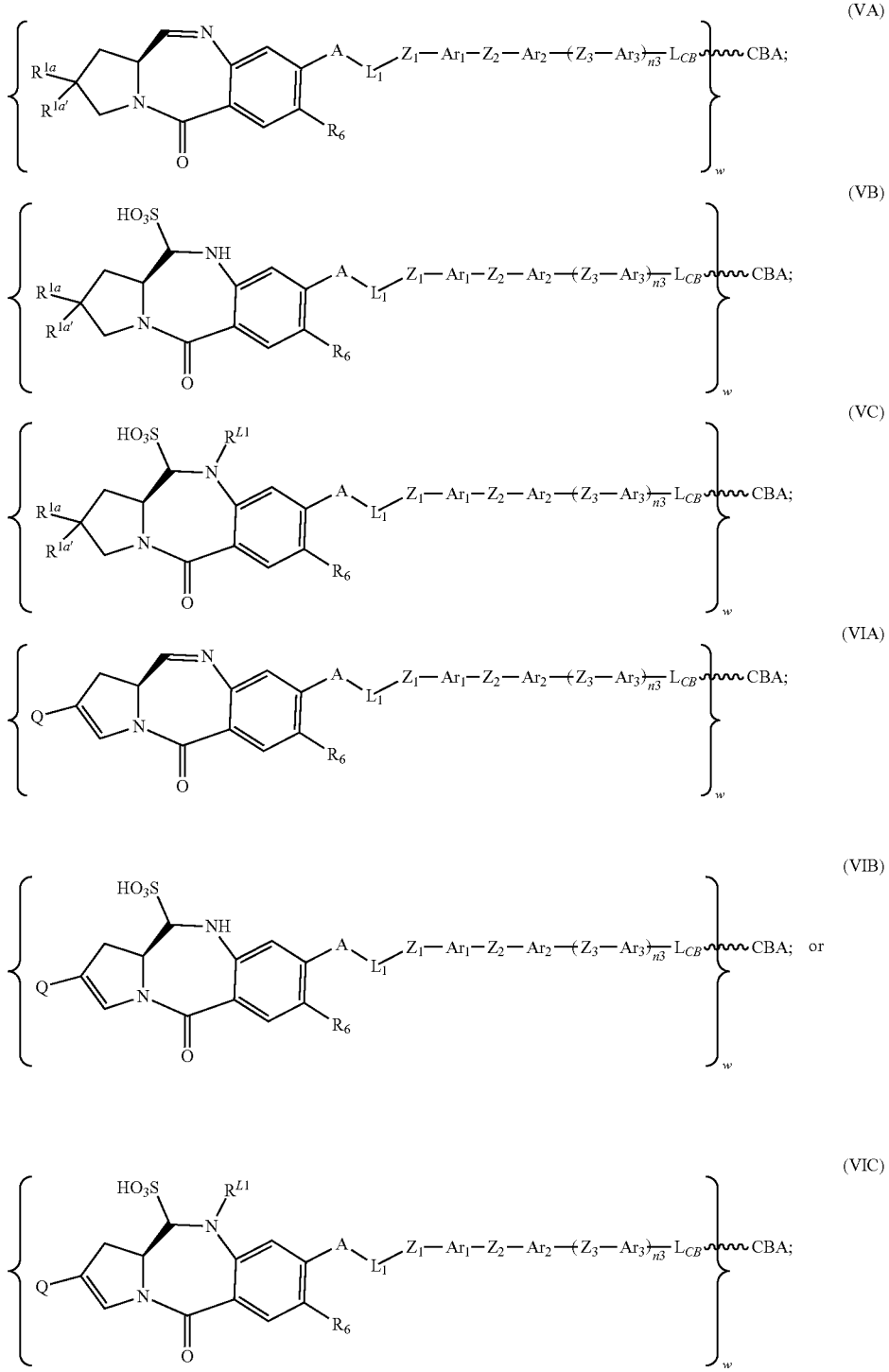

or a pharmaceutically acceptable salt thereof, wherein the variables are as described in the second aspect or the 21$^{st}$ embodiment or any specific embodiments described therein.

In a 23$^{rd}$ embodiment, the conjugate of present invention is represented by formula (IVC), (IVD), (VC) or (VIC), or a pharmaceutically acceptable salt thereof, wherein:

L is H, —C(=O)R$_a$ or —NR$_b$R$_c$; and

R$^{L1}$ is represented by the following formula:

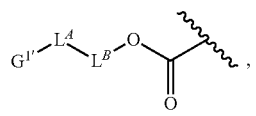

wherein:
G$^{1'}$ is a spacer having linking moiety covalently attached to the CBA, wherein the linking moiety is formed by reacting an amine reactive group, a thiol reactive group or an aldehyde reactive group of the spacer with the CBA;

L$^A$ is a peptide residue comprising 2 to 5 amino acid residues; and

L$^B$ is a covalent bond or together with —OC(=O)— forms a self-immolative linker; and The remaining variables are as defined in the 1$^{st}$ embodiment or any specific embodiments described therein.

In a specific embodiment, —C(=O)O— and L$^B$ together form the group:

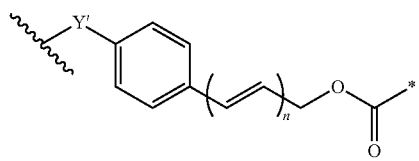

where the asterisk indicates the point of attachment to the N10 position, the wavy line indicates the point of attachment to the linker L$^A$, Y' is —NH—, —O—, —C(=O)NH— or —C(=O)O—, and n is 0 to 3.

In another specific embodiment, R$^{L1}$ is represented by the following formula:

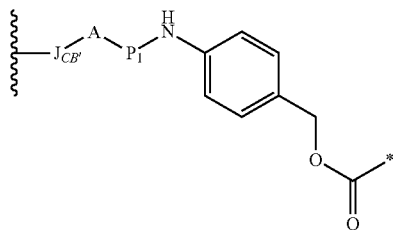

wherein:
P$_1$ is a peptide residue having 2 to 5 amino acid residues; and

J$_{CB'}$-A- is represented by:

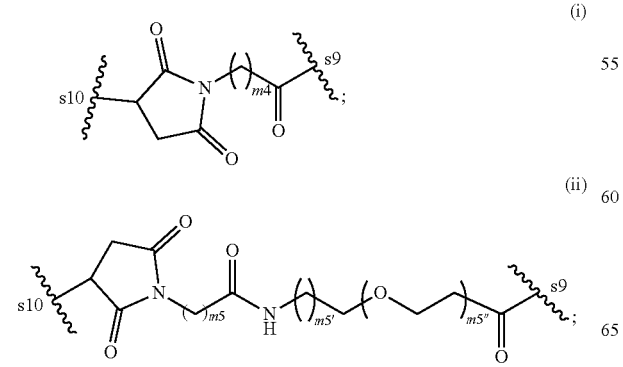

(ii')
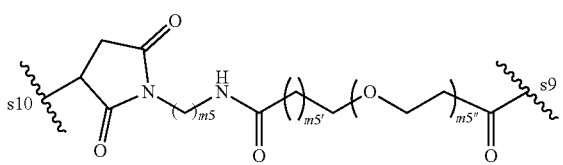

(iii)
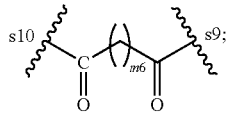

(iv)
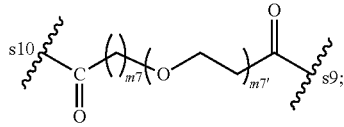

(v)
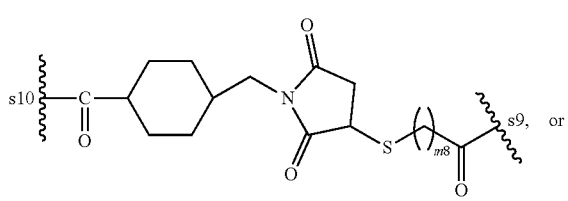

(vi)
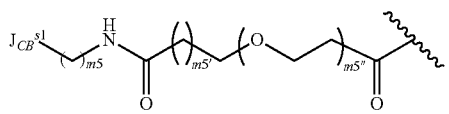

wherein: s10 is the site connected to the CBA; s9 is the site connected to P$_1$; m4, m5, m5', m6, m7 and m8 are each independently an integer from 1 to 6; m5" and m7' are each independently 0 or an integer from 1 to 10; E is —OH, or —Cl or —C(=O)E is a reactive ester, and J$_{CB}$ is

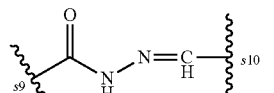

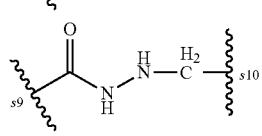

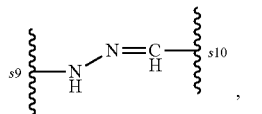

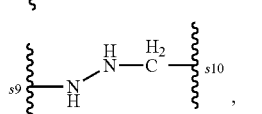

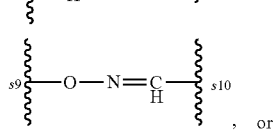

, or

-continued

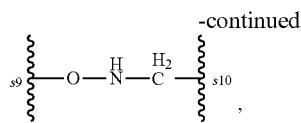

s9 is the site connected to $P_1$ and s10 is the site connected to CBA through an aldehyde group located on the CBA.

In another specific embodiment, $J_{CB'}$-A- is represented by:

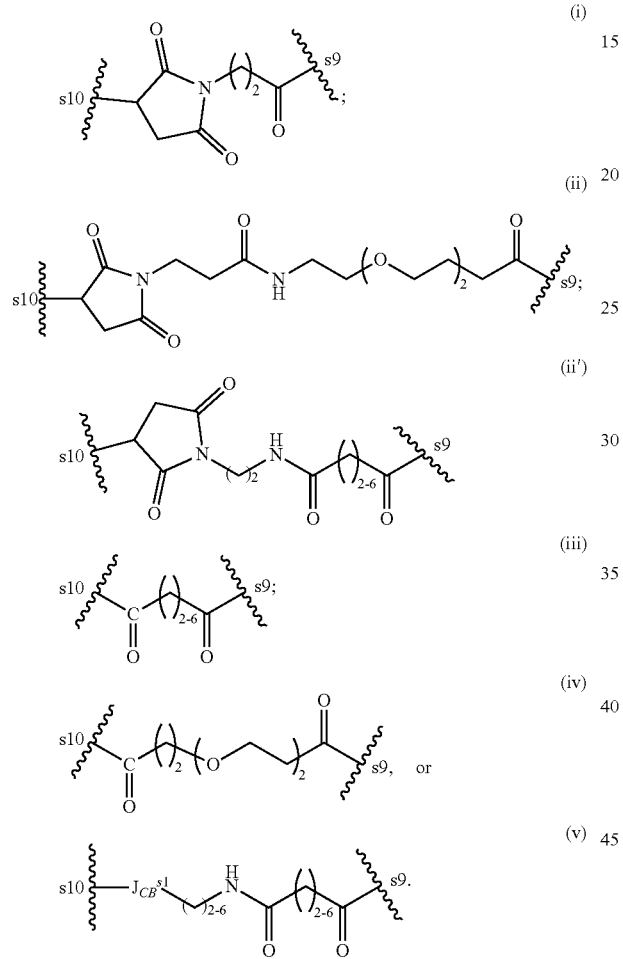

In another specific embodiment, $P_1$ is a peptide residue selected from Ala-Ala, Gln-Leu, Phe-Lys, Val-Ala, Val-Lys, Ala-Lys, Val-Cit, Phe-Cit, Leu-Cit, Ile-Cit, Phe-Arg, Trp-Cit, Lys-Lys, Phe-Ala, Phe-$N^9$-tosyl-Arg, Phe-$N^9$-nitro-Arg, Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Gly-Gly-Gly, Phe-Phe-Lys, D-Phe-Phe-Lys, Gly-Phe-Lys, Leu-Ala-Leu, Ile-Ala-Leu and Val-Ala-Val; Ala-Leu-Ala-Leu, f-Ala-Leu-Ala-Leu and Gly-Phe-Leu-Gly.

In a $4^{th}$ embodiment, for conjugates of formula (IV), (V), (IV), (IVA-1), (IVA-2), (IVB-1), (IVB-2), (IVC), (IVD), (VA), (VB), (VC), (VIA), (VIB) or (VIC), or a pharmaceutically acceptable salt thereof, $L_1$ is represented by one of the following formulas:

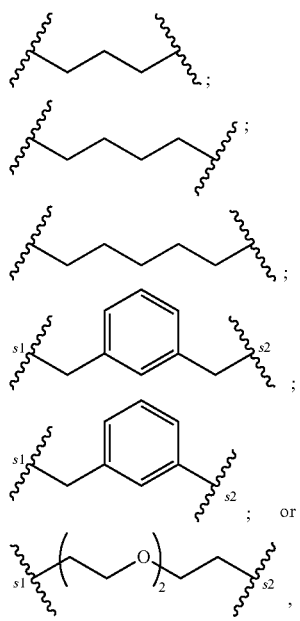

wherein s1 is the site connected to A and s2 is the site connected to $Z_1$; and the remaining variables are defined as in the second aspect or the $21^{st}$, $22^{nd}$ or $23^{rd}$ embodiment.

In a $25^{th}$ embodiment, for conjugates of formula (IV), (V), (VI), (IVA-1), (IVA-2), (IVB-1), (IVB-2), (IVC), (IVD), (VA), (VB), (VC), (VIA), (VIB) or (VIC), or a pharmaceutically acceptable salt thereof, $Z_1$ is

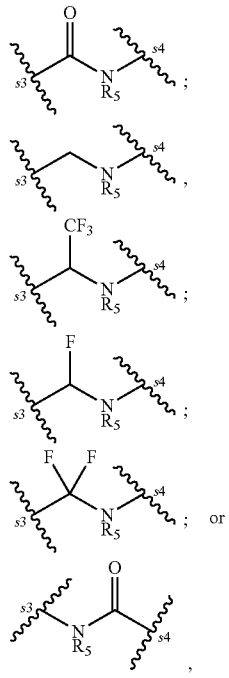

wherein $R_5$ is H or Me; and the remaining variables are as defined in the second aspect or the $21^{st}$, $22^{nd}$ $23^{rd}$ or $24^{th}$ embodiment or any specific embodiment described therein. In a specific embodiment, $Z_1$ is not

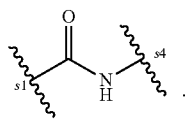

In a 26th embodiment, for conjugates of formula (IV), (V), (VI), (IVA-1), (IVA-2), (IVB-1), (IVB-2), (IVC), (IVD), (VA), (VB), (VC), (VIA), (VIB) or (VIC), or a pharmaceutically acceptable salt thereof, $Ar_1$ is benzene, naphthalene, a 5- to 6-membered heteroaromatic ring, a 8 to 10-membered bicyclic heteroaromatic ring or -$Ar_1'$-$Ar_1''$-, wherein $Ar_1'$ and $Ar_1''$ are each independently benzene or a 5- to 6-membered heteroaromatic ring; and the remaining variables are as defined in the second aspect or the $21^{st}$, $22^{nd}$, $23^{rd}$, $24^{th}$ or $25^{th}$ embodiment or any specific embodiment described therein.

In a specific embodiment of the $26^{th}$ embodiment, $Ar_1$ is benzene, naphthalene, pyrrole, imidazole, thiophene, thiazole, pyrazole, oxazole, isoxazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyridine-N-oxide, pyrazine, pyrimidine, pyridazine, 1,2,4-triazine, 1,3,5-triazine, tetrazole, indolizine, indole, isoindole, benzo[b]furan, benzo[b]thiophene, indazole, benzimidazole, benzthiazole, purine, 4H-quinolizine, quinoline, isoquinoline, cinnoline, phthalazine, quinazoline, quinoxaline, 1,8-naphthyridine, or pteridine.

In another specific embodiment of the $26^{th}$ embodiment, $Ar_1$ is pyrrole, imidazole, thiazole, pyridine, benzo[b]furan, benzene or -$Ar_1'$-$Ar_1''$-, wherein $Ar_1'$ and $Ar_1''$ are each independently benzene, pyrrole, thiazole, or pyridine.

In yet another specific embodiment of the $26^{th}$ embodiment, $Ar_1$ is represented by one of the following:

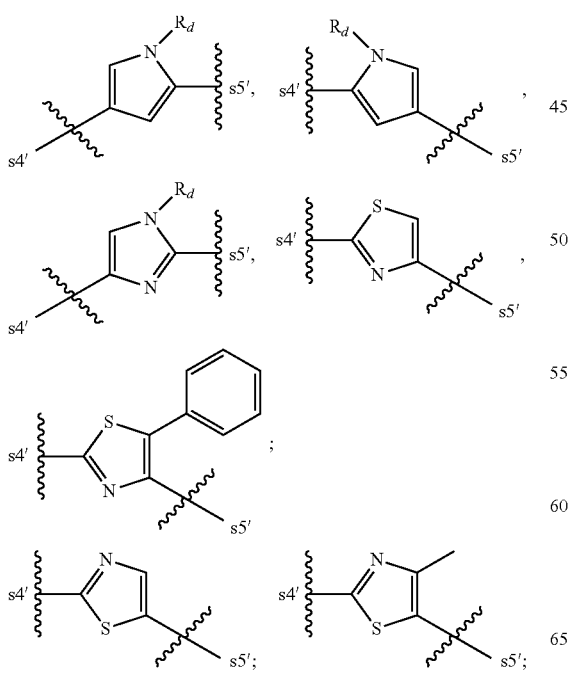

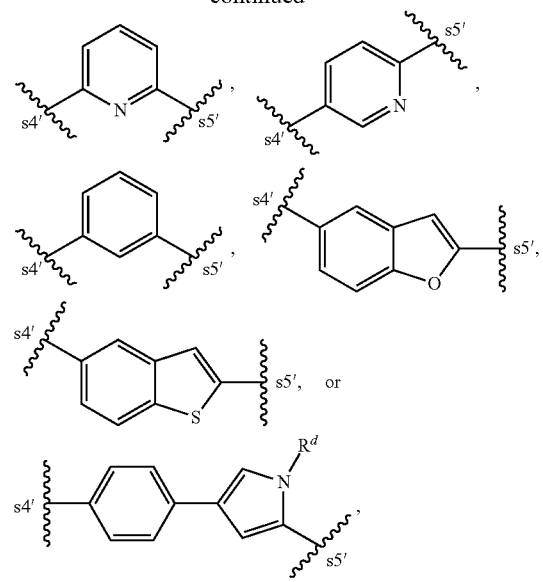

wherein $R_d$ is H, a ($C_1$-$C_6$)alkyl optionally substituted with halogen, —OH, or —$NR_bR_c$, wherein $R_b$ and $R_c$ are each independently H, ($C_1$-$C_4$)alkyl or an amine protecting group, phenyl or heteroaryl. More specifically, $R_d$ is methyl.

In a $27^{th}$ embodiment, for conjugates of formula (IV), (V), (VI), (IVA-1), (IVA-2), (IVB-1), (IVB-2), (IVC), (IVD), (VA), (VB), (VC), (VIA), (VIB) or (VIC), or a pharmaceutically acceptable salt thereof, $Z_2$ is

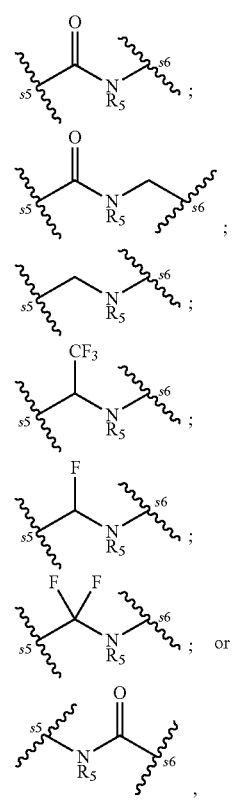

wherein R$_5$ is H or Me; and the remaining variables are as defined in the second aspect or the 21$^{st}$, 22$^{nd}$, 23$^{rd}$, 24$^{th}$, 25$^{th}$ or 26$^{th}$ embodiment or any specific embodiment described therein.

In a 28$^{th}$ embodiment, for conjugates of formula (IV), (V), (VI), (IVA-1), (IVA-2), (IVB-1), (IVB-2), (IVC), (IVD), (VA), (VB), (VC), (VIA), (VIB) or (VIC), or a pharmaceutically acceptable salt thereof, Ar$_2$ is benzene, naphthalene, naphthalene, a 5- to 6-membered heteroaromatic ring, or a 8- to 10-membered bicyclic heteroaromatic ring or -Ar$_2$'-Ar$_2$''-, wherein Ar$_2$' and Ar$_2$'' are each independently benzene or a 5- to 6-membered heteroaromatic ring; and the remaining variables are as defined in the second aspect or the 21$^{st}$, 22$^{nd}$, 23$^{rd}$, 24$^{th}$, 25$^{th}$, 26$^{th}$ or 27$^{th}$ embodiment or any specific embodiment described therein.

In a specific embodiment, Ar$_2$ is pyrrole, imidazole, thiophene, thiazole, pyrazole, oxazole, isoxazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyridine-N-oxide, pyrazine, pyrimidine, pyridazine, 1,2,4-triazine, 1,3,5-triazine, tetrazole, indolizine, indole, isoindole, benzo[b]furan, benzo[b]thiophene, indazole, benzimidazole, benzthiazole, purine, 4H-quinolizine, quinoline, isoquinoline, cinnoline, phthalazine, quinazoline, quinoxaline, 1,8-naphthyridine, pteridine, benzene, or naphthalene.

In another specific embodiment, Ar$_2$ is pyrrole, imidazole, benzene, benzo[b]thiophene, benzo[b]furan, benzimidazole, indole, quinoline, or isoquinoline or -Ar$_2$'-Ar$_2$''-, wherein Ar$_2$' and Ar$_2$'' are each independently benzene, pyrrole, thiazole, or pyridine.

In yet another specific embodiment, Ar$_2$ is represented by one of the following:

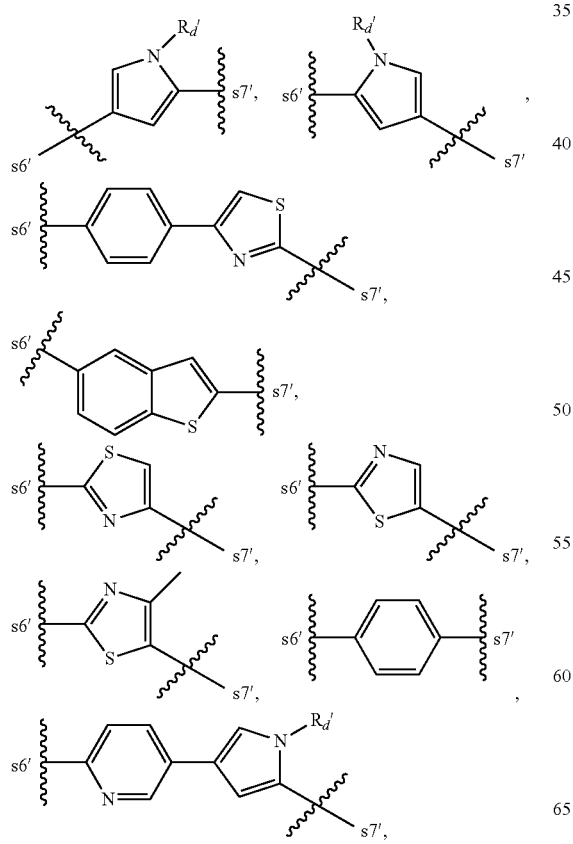

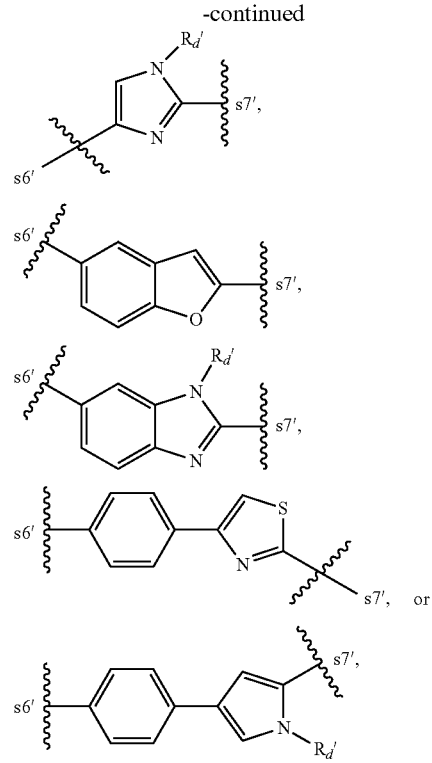

wherein R$_d$' is H, a (C$_1$-C$_6$)alkyl optionally substituted with halogen, —OH, or —NR$_b$R$_c$, wherein R$_b$ and R$_c$ are each independently H, (C$_1$-C$_3$)alkyl, an amine protecting group, phenyl or heteroaryl. More specifically, R$_d$' is methyl.

In a 29$^{th}$ embodiment, for conjugates of formula (IV), (V), (VI), (IVA-1), (IVA-2), (IVB-1), (IVB-2), (IVC), (IVD), (VA), (VB), (VC), (VIA), (VIB) or (VIC), or a pharmaceutically acceptable salt thereof, n3 is 0; and the remaining variables are as defined in the second aspect or the 21$^{st}$, 22$^{nd}$, 23$^{rd}$, 24$^{th}$, 25$^{th}$, 26$^{th}$, 27$^{th}$ or 28$^{th}$ embodiment or any specific embodiment described therein.

In a 30$^{th}$ embodiment, for conjugates of formula (IV), (V), (VI), (IVA-1), (IVA-2), (IVB-1), (IVB-2), (IVC), (IVD), (VA), (VB), (VC), (VIA), (VIB) or (VIC), or a pharmaceutically acceptable salt thereof, n3 is 1; Z$_3$ is

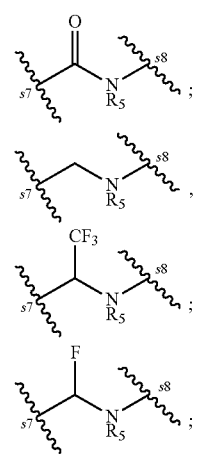

-continued

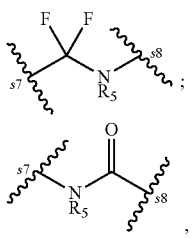

wherein R$_5$ is H or Me; and the remaining variables are as defined in the second aspect or the 21$^{st}$, 22$^{nd}$ 23$^{rd}$, 24$^{th}$, 25$^{th}$, 26$^{th}$, 27$^{th}$ or 28$^{th}$ embodiment or any specific embodiment described therein.

In a 31$^{st}$ embodiment, for conjugates of formula (IV), (V), (VI), (IVA-1), (IVA-2), (IVB-1), (IVB-2), (IVC), (IVD), (VA), (VB), (VC), (VIA), (VIB) or (VIC), or a pharmaceutically acceptable salt thereof, Ar$_3$ is benzene, naphthalene, a 5- to 6-membered heteroaromatic ring, or a 8- to 10-membered bicyclic heteroaromatic ring or -Ar$_3$'-Ar$_3$"-, wherein Ar$_3$' and Ar$_3$" are each independently benzene or a 5- to 6-membered heteroaromatic ring; and the remaining variables are as defined in the second aspect or the 21$^{st}$, 22$^{nd}$, 23$^{rd}$, 24$^{th}$, 25$^{th}$, 26$^{th}$, 27$^{th}$, 28$^{th}$ or 30$^{th}$ embodiment or any specific embodiment described therein.

In a specific embodiment, Ar$_3$ is pyrrole, imidazole, thiophene, thiazole, pyrazole, oxazole, isoxazole, isothiazole, 1,2,3-triazole, 1,2,4-triazole, 1,3,4-oxadiazole, 1,2,5-thiadiazole, 1,2,5-thiadiazole 1-oxide, 1,2,5-thiadiazole 1,1-dioxide, 1,3,4-thiadiazole, pyridine, pyridine-N-oxide, pyrazine, pyrimidine, pyridazine, 1,2,4-triazine, 1,3,5-triazine, tetrazole, indolizine, indole, isoindole, benzo[b]furan, benzo[b]thiophene, indazole, benzimidazole, benzthiazole, purine, 4H-quinolizine, quinoline, isoquinoline, cinnoline, phthalazine, quinazoline, quinoxaline, 1,8-naphthyridine, pteridine, benzene, or naphthalene.

In another specific embodiment, Ar$_3$ is represented by one of the following:

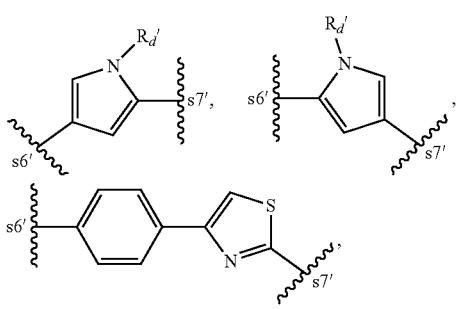

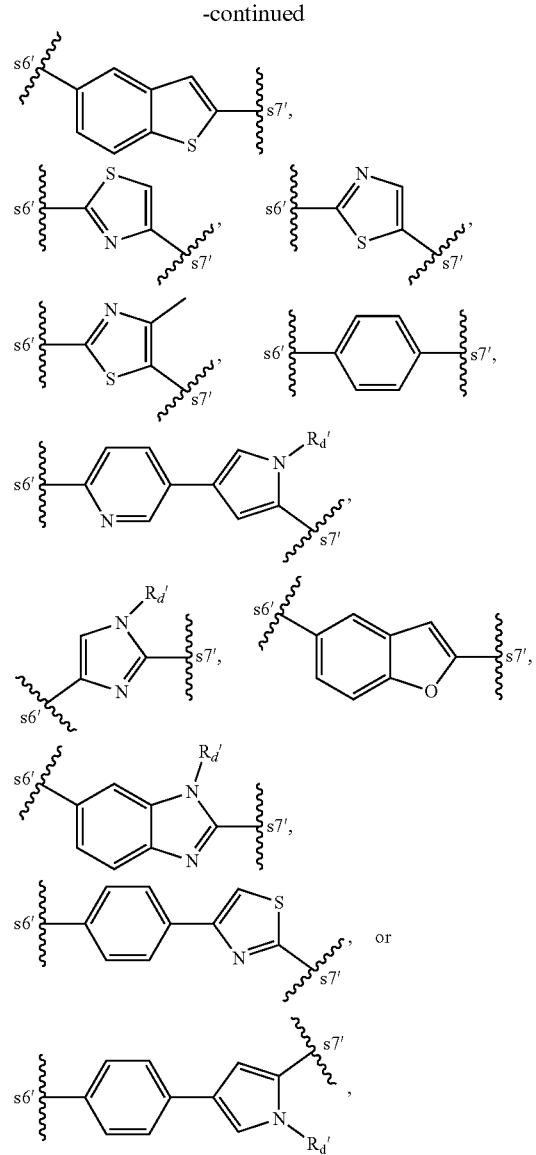

wherein R$_d$' is H, a (C$_1$-C$_6$)alkyl optionally substituted with halogen, —OH, or —NR$_b$R$_c$, wherein R$_b$ and R$_c$ are each independently H, (C$_1$-C$_3$)alkyl, an amine protecting group, phenyl or heteroaryl.

In a 32$^{nd}$ embodiment, the conjugate of the present invention is represented by the following formula:

(IVA-1a)

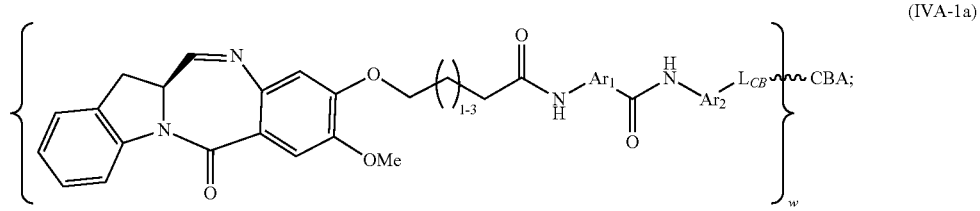

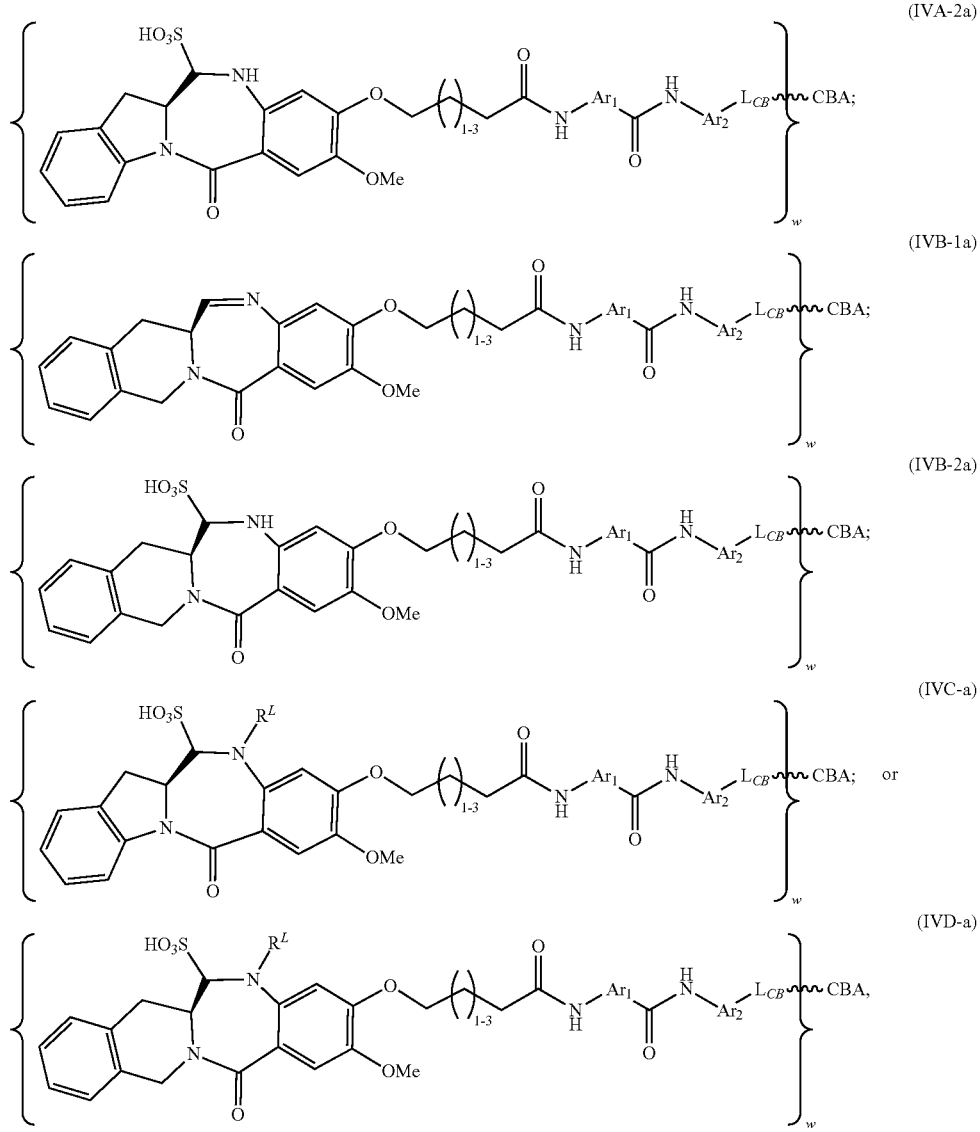

(IVA-2a)

(IVB-1a)

(IVB-2a)

(IVC-a)

(IVD-a)

or a pharmaceutically acceptable salt thereof, wherein:

Ar$_1$ is pyrrole, imidazole, thiazole, pyridine, benzo[b]furan, benzene or -Ar$_1$'-Ar$_1$''-, wherein Ar$_1$' and Ar$_1$'' are each independently benzene, pyrrole, thiazole, or pyrrole; and Ar$_2$ is pyrrole, imidazole, benzene, benzo[b]thiophene, benzo[b]furan, benzimidazole, indole, quinoline, isoquinoline or -Ar$_2$'-Ar$_2$''-, wherein Ar$_2$' and Ar$_2$'' are each independently benzene, pyrrole, thiazole, or pyridine; and the remaining variables are as defined in the second aspect or the 21$^{st}$, 22$^{nd}$, 23$^{rd}$ or 24$^{th}$ embodiment.

In a specific embodiment, for conjugates of the 32$^{nd}$ embodiment,

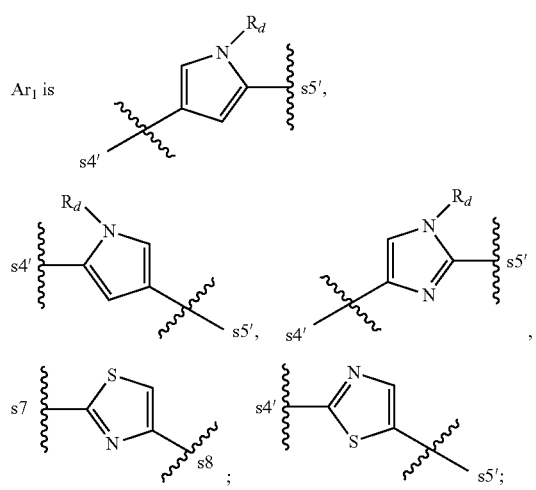

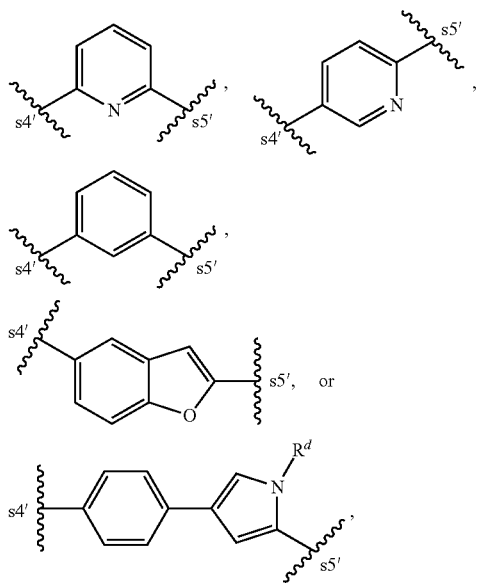

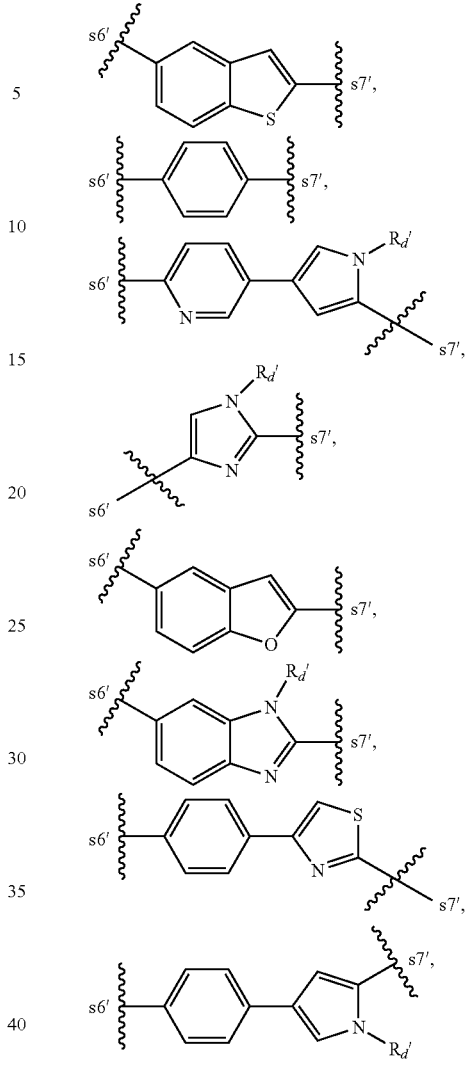

wherein $R_d$ is H, a $(C_1$-$C_6)$alkyl optionally substituted with halogen, —OH, or —$NR_bR_c$, wherein $R_b$ and $R_c$ are each independently H, $(C_1$-$C_4)$alkyl or an amine protecting group, phenyl or heteroaryl; and Ar$_2$ is

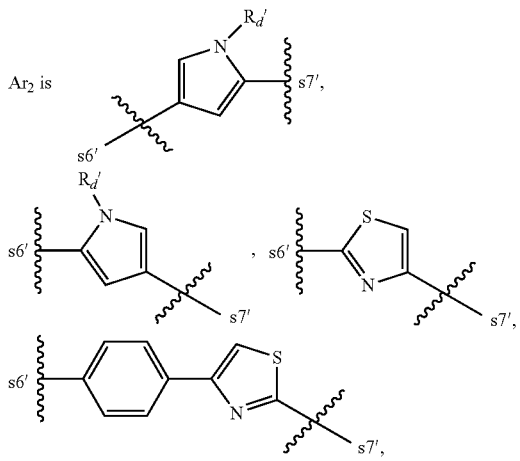

wherein $R_d{'}$ is H, a $(C_1$-$C_6)$alkyl optionally substituted with halogen, —OH, or —$NR_bR_c$, wherein $R_b$ and $R_c$ are each independently H, $(C_1$-$C_3)$alkyl, an amine protecting group, phenyl or heteroaryl. More specifically, $R_d$ and $R_{d'}$ are both methyl.

In a 33$^{rd}$ embodiment, the conjugate of the present invention is represented by the following formula:

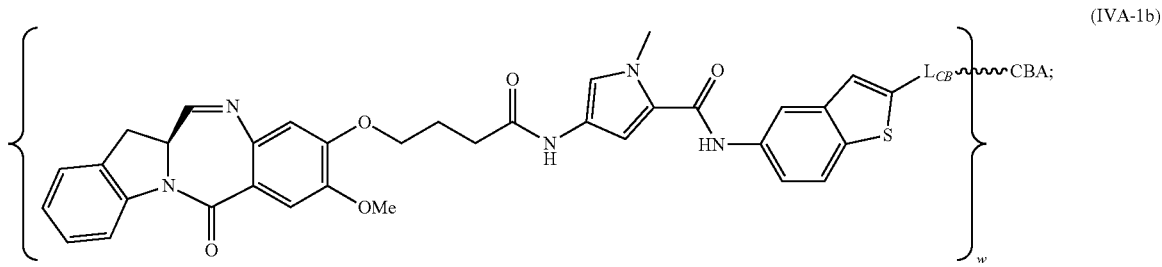

(IVA-1b)

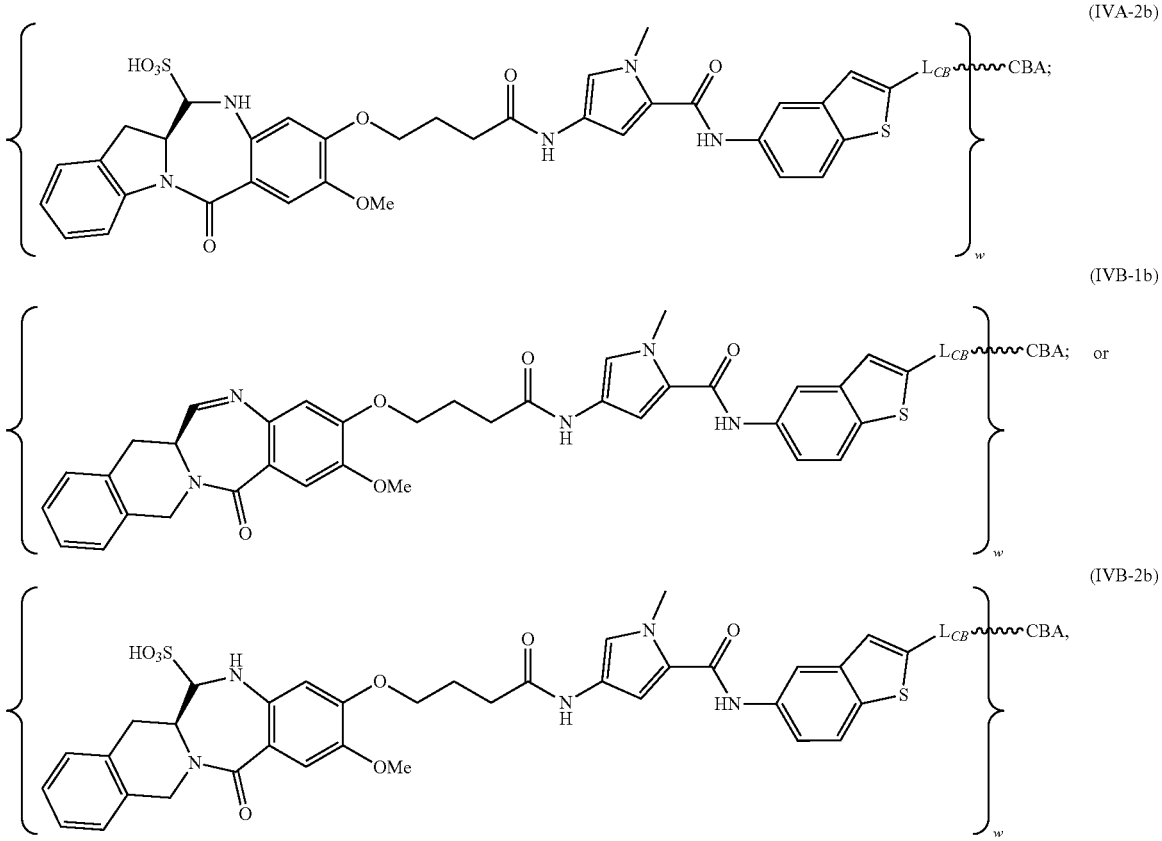

(IVA-2b)

(IVB-1b); or (IVB-2b)

or a pharmaceutically acceptable salt thereof, wherein the variables are defined as in the second aspect or the 21$^{st}$ embodiment.

In a 34$^{th}$ embodiment, for conjugates of formula (IV), (V), (VI), (IVA-1), (IVA-2), (IVB-1), (IVB-2), (IVC), (IVD), (VA), (VB), (VC), (VIA), (VIB), (VIC), (IVA-1a), (IVA-2a), (IVB-1a), (IVB-2a), (IVC-a), (IVD-a), (IVA-1b), (IVA-2b), (IVB-1b), or (IVB-2b), $L_{CB}$ is a linker bearing —C(=O)— group that is covalently linked to the cell-binding agent, and the remaining variables are as defined in the second aspect or the 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$ or 33$^{rd}$ embodiment or any specific embodiment described therein.

In a 35$^{th}$ embodiment, for conjugates of formula (IV), (V), (VI), (IVA-1), (IVA-2), (IVB-1), (IVB-2), (IVC), (IVD), (VA), (VB), (VC), (VIA), (VIB), (VIC), (IVA-1a), (IVA-2a), (IVB-1a), (IVB-2a), (IVC-a), (IVD-a), (IVA-1b), (IVA-2b), (IVB-1b), or (IVB-2b), $L_{CB}$ is represented by any one of the following formulae:

—C(=O)—NR$_{5a}$—R$^{x1}$—SZ$^{s1}$—  (L3a'),

—NR$_{5a}$—C(=O)—R$^{x2}$—SZ$^{s1}$—  (L3b')

—C(=O)—NR$_{5a}$—R$^{x3}$-J$^{CB}$-  (L3c'), or

—NR$_{5a}$—P$_2$—C(=O)—R$^{x4}$-J$_{CB}$-  (L3d'), wherein:

R$_{5a}$ is H or (C$_1$-C$_3$)alkyl;

R$^{x1}$, R$^{x2}$, R$^{x3}$ and R$^{x4}$ are each independently a (C$_1$-C$_{10}$)alkyl, a (C$_3$-C$_5$)cycloalkyl, an aryl or a heteroaryl, P$_2$ is an amino acid residue or a peptide containing between 2 to 20 amino acid residues;

J$_{CB}$ is —C(=O)— covalently linked to the CBA;

R$_a$ is —OH, —Cl, —O(C$_1$-C$_6$)alkyl;

Z$^{s1}$ is a bifunctional linker that is covalently linked to the cell-binding agent; and R$^e$ is a (C$_1$-C$_6$)alkyl or is selected from phenyl, nitrophenyl (e.g., 2 or 4-nitrophenyl), dinitrophenyl (e.g., 2,4-dinitrophenyl), carboxynitrophenyl (e.g., 3-carboxy-4-nitrophenyl), pyridyl or nitropyridyl (e.g., 4-nitropyridyl); and R$^{e1}$ is a (C$_1$-C$_6$)alkyl; and the remaining variables are as defined in the second aspect or the 21$^{st}$, 22$^{nd}$, 23$^{rd}$, 24$^{th}$, 25$^{th}$, 26$^{th}$, 27$^{th}$, 28$^{th}$, 29$^{th}$, 30$^{th}$, 31$^{st}$, 32$^{nd}$ or 33$^{rd}$ embodiment or any specific embodiment described therein.

In a specific embodiment, R$^{x1}$, R$^{x2}$, R$^{x3}$ and R$^{x4}$ are each independently a (C$_1$-C$_6$)alkyl or —R$^{xc}$—(CH$_2$CH$_2$O)$_n$—R$^{xc'}$—, wherein n is an integer from 1 to 10; R$^{xc}$ is absent or a (C$_1$-C$_4$)alkyl; and R$^{xc'}$ is a (C$_1$-C$_4$)alkyl.

In another specific embodiment, $L_{CB}$ is represented by formula (L3a'), R$^{x1}$ is —(CH$_2$)$_{p1}$—(CR$^{f1}$R$^{g1}$)—, wherein R$^{f1}$ and R$^{g1}$ are each independently —H or -Me; and p1 is 0, 1, 2, 3, 4, or 5. More specifically, p1 is 1 and R$^{f1}$ and R$^{g1}$ are both methyl.

In another specific embodiment, $L_{CB}$ is represented by formula (L3b'), R$^{x2}$ is —(CH$_2$)$_{p2}$—(CR$^{f2}$R$^{g2}$)—, wherein R$^{f2}$ and R$^{g2}$ are each independently —H or -Me; and p2 is 0, 1, 2, 3, 4 or 5. More specifically, RP and R$^{g2}$ are both methyl.

In yet another specific embodiment, $L_{CB}$ is represented by formula (L3c'), R$^{x3}$ is —(CH$_2$)$_{p3}$—, wherein p3 is an integer from 2 to 6. More specifically, p3 is 2.

In yet another specific embodiment, $L_{CB}$ is represented by formula (L3d'), $R^{x4}$ is —$(CH_2)_{p4}$—, wherein p4 is an integer from 2 to 6. More specifically, p4 is 4.

In another specific embodiment, for formula (L3d') described in the 35$^{th}$ embodiment or any specific embodiment described therein, $P_2$ is a peptide containing 2 to 5 amino acid residues. More specifically, $P_2$ is selected from Ala-Ala, Gln-Leu, Gly-Gly-Gly, Ala-Val, Val-Ala, Cit-Val, Val-Cit, Val-Lys, Phe-Lys, Lys-Lys, Ala-Lys, Phe-Cit, Leu-Cit, Ile-Cit, Trp, Cit, Phe-Ala, Phe-N$^9$-tosyl-Arg, Phe-N$^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), f-Ala-Leu-Ala-Leu (SEQ ID NO: 2), Gly-Phe-Leu-Gly (SEQ ID NO: 3), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Met-Ala, Gln-Val, Asn-Ala, Gln-Phe and Gln-Ala. Even more specifically, $P_2$ is Gly-Gly-Gly, Ala-Val, Val-Ala, Ala-Ala, Ala-D-Ala, D-Ala-Ala, or D-Ala-D-Ala.

In another specific embodiment, for formula (L3a') or (L3b') described in the 35$^{th}$ embodiment or any specific embodiment described therein, $Z^{s1}$ is represented by any one of the following:

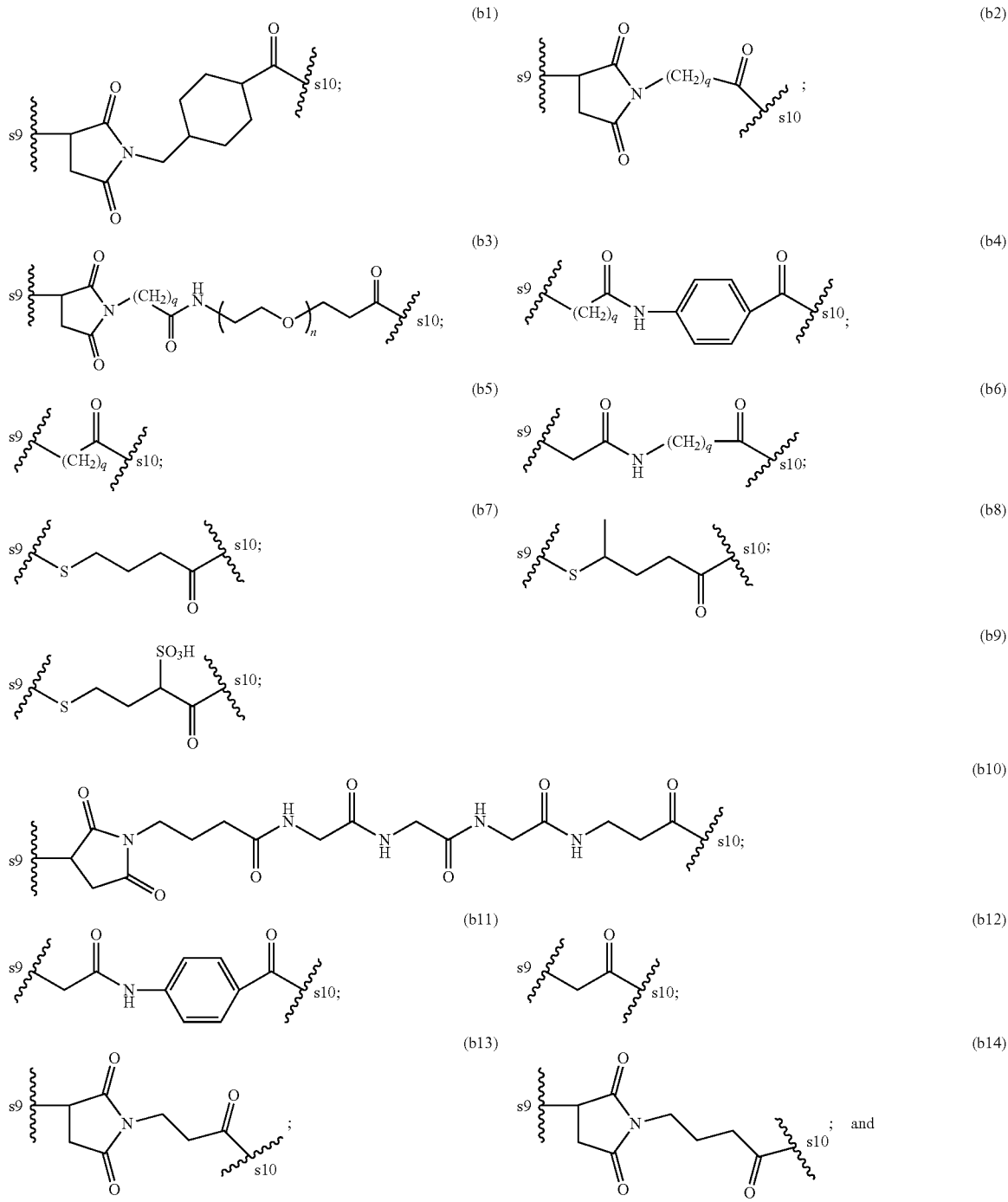

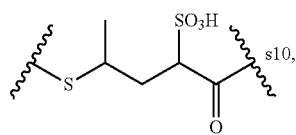
(b15)
s9 is the site connected to Ar$_3$ or Ar$_2$ when n3 is 0, and s10 is the site connected to the CBA through the ε-amino group on a lysine;
q is an integer from 1 to 5; and
n' is an integer from 2 to 6.
In a 36$^{th}$ embodiment, the conjugate of the present invention is any one of the following:
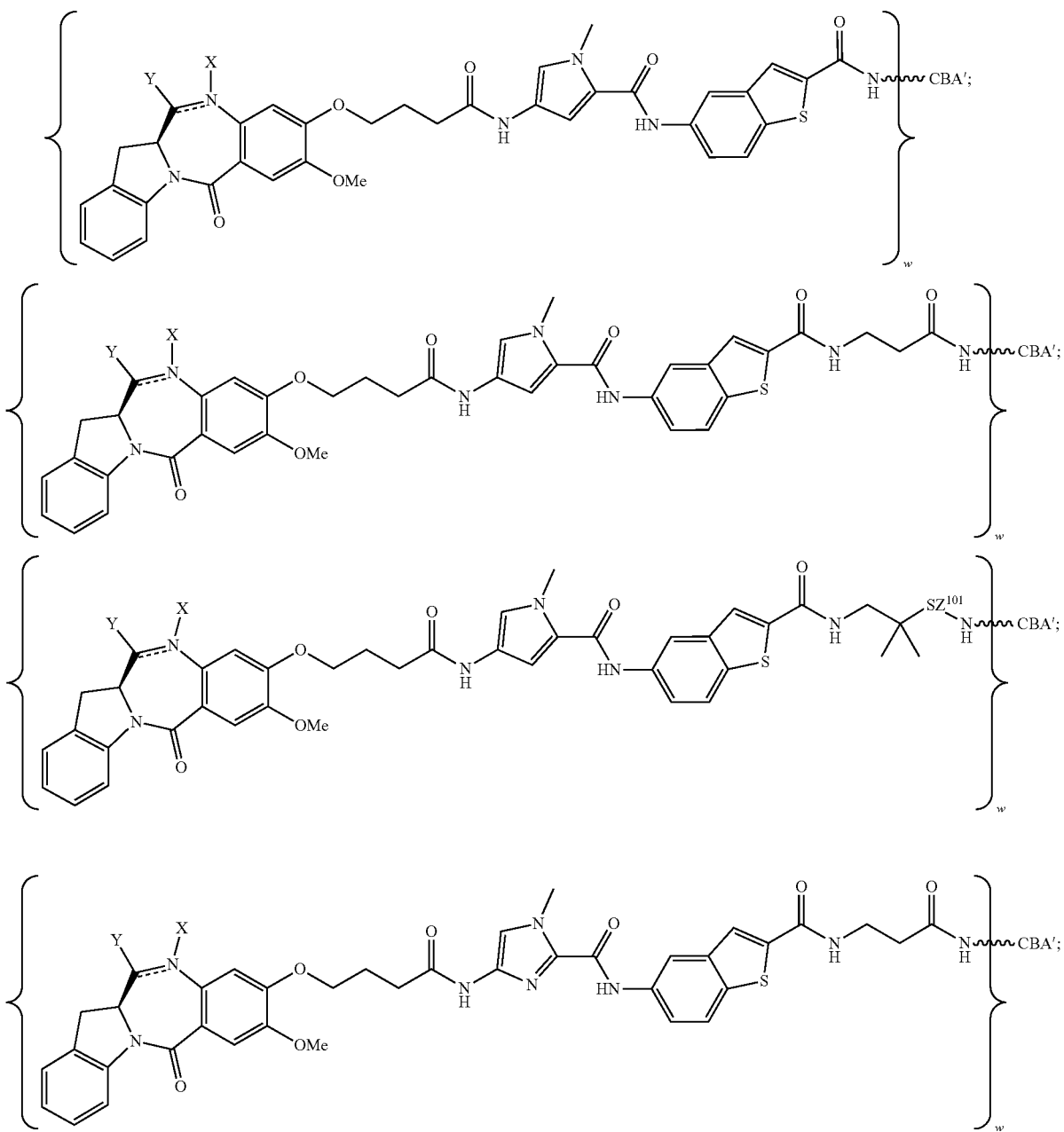

117 118
-continued
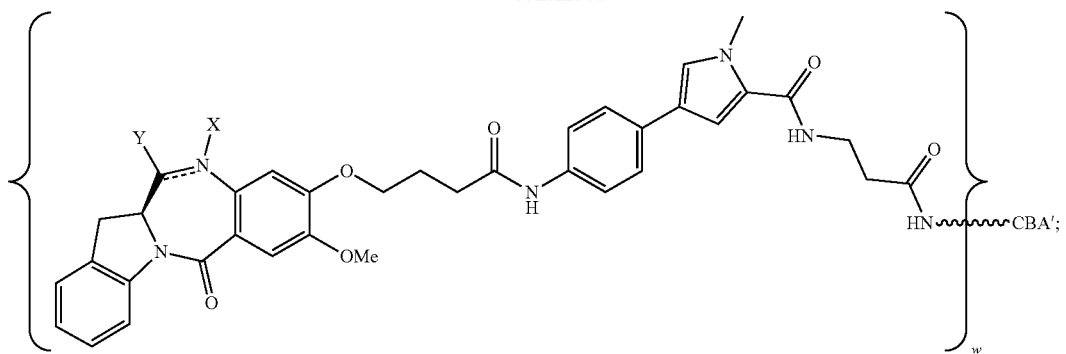
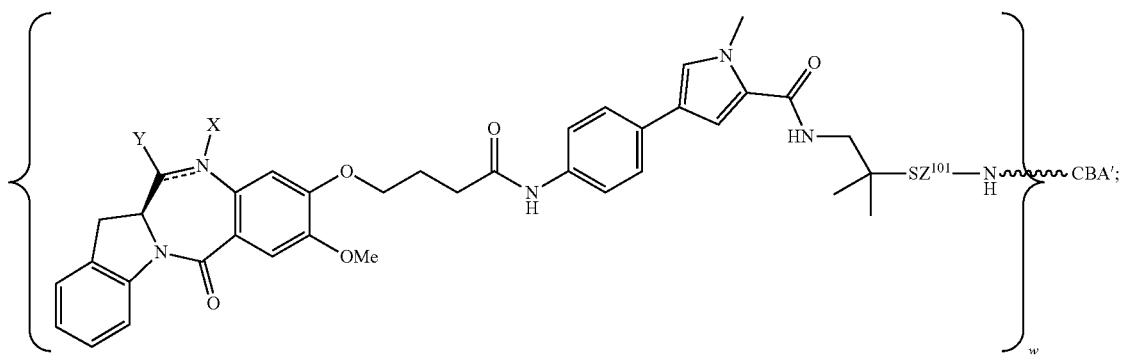
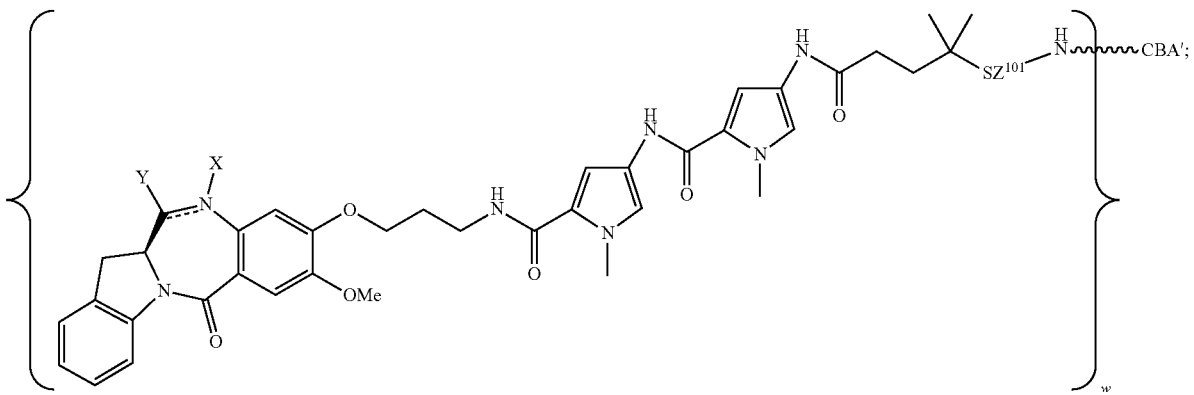
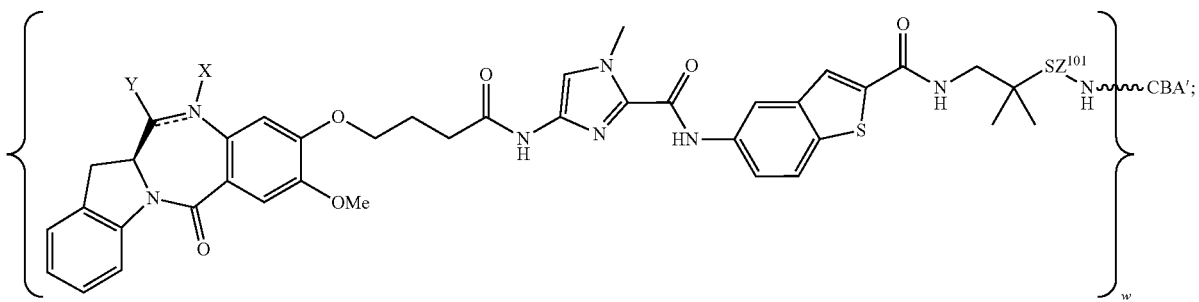

119                                         120
-continued
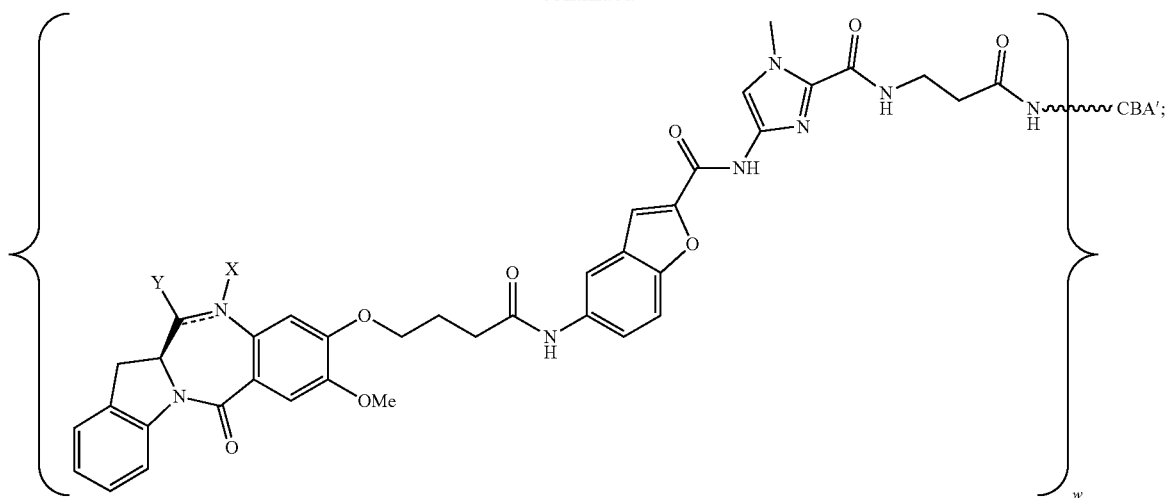
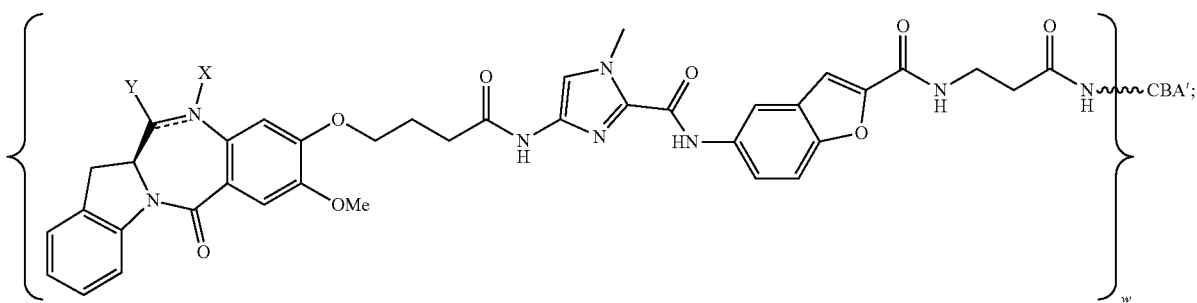
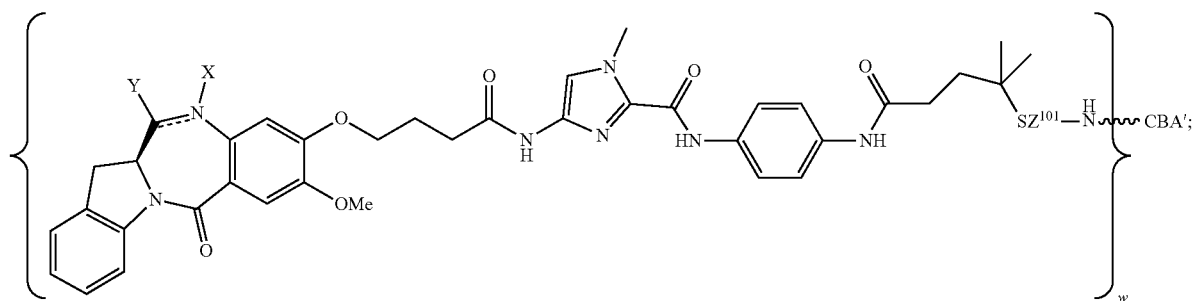
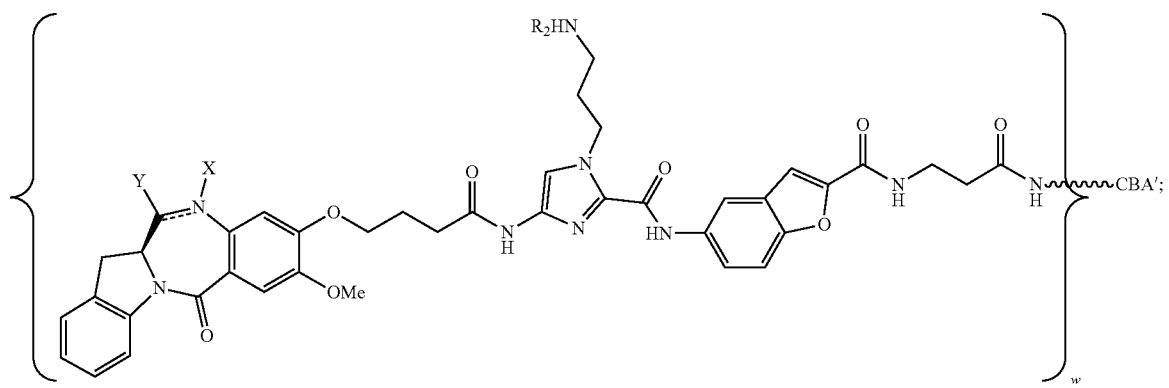

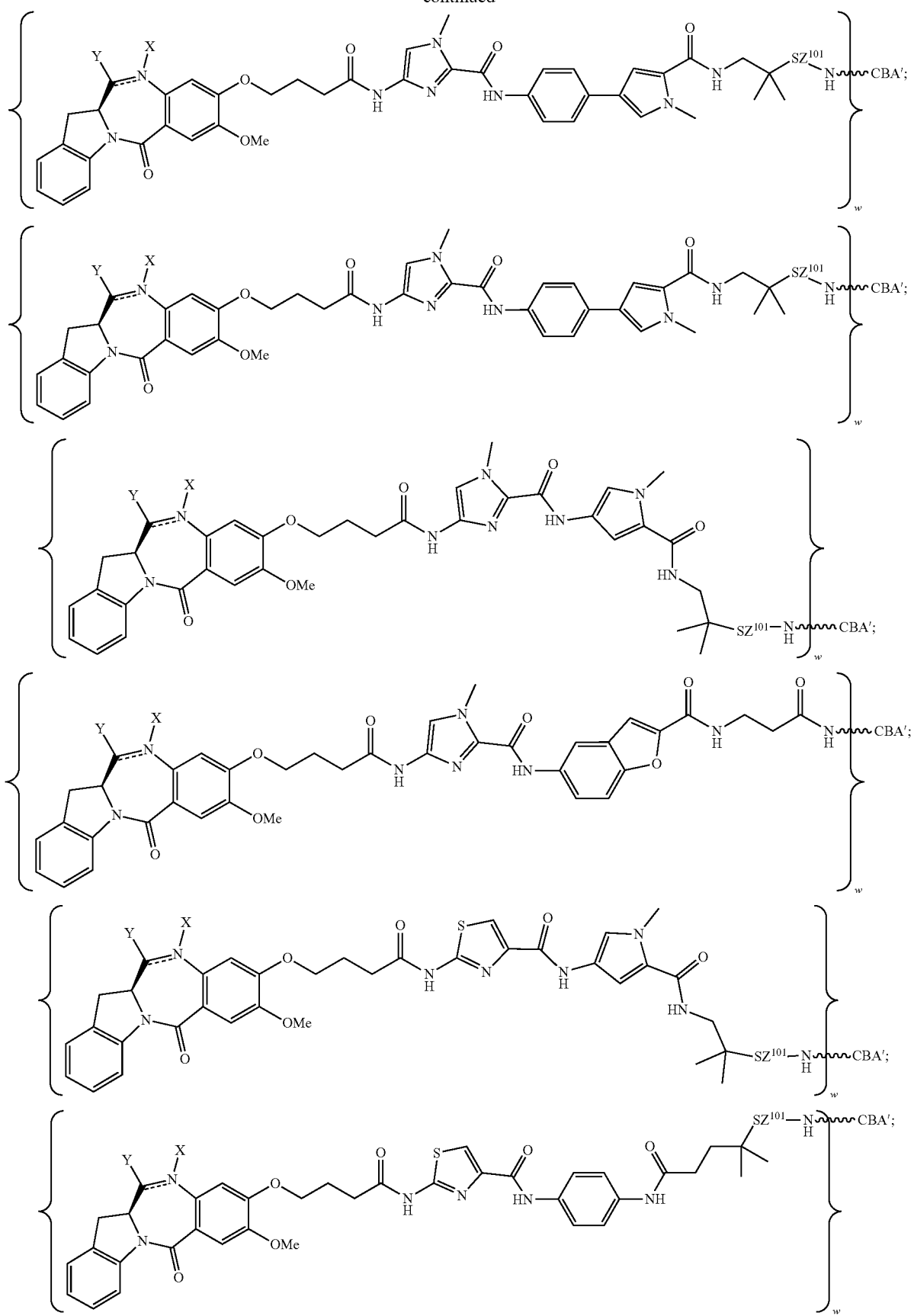

-continued
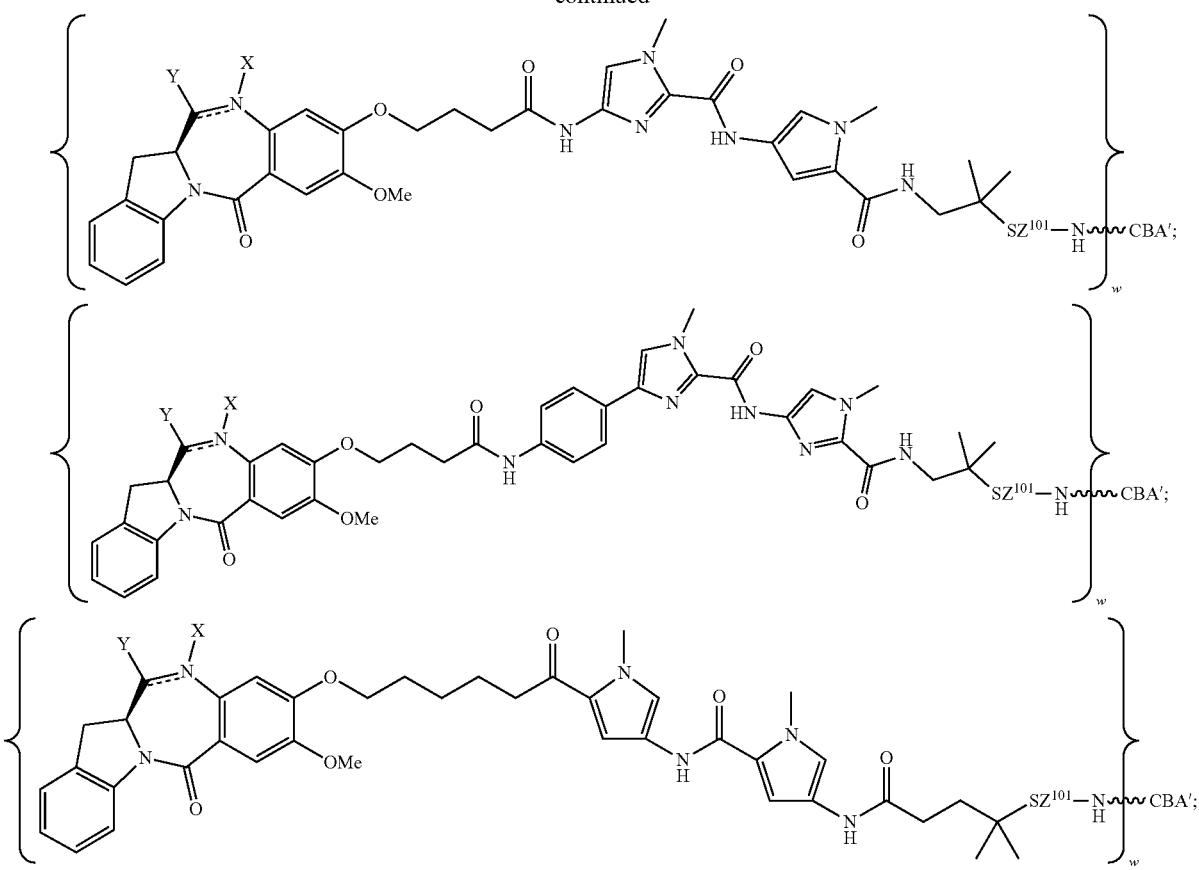
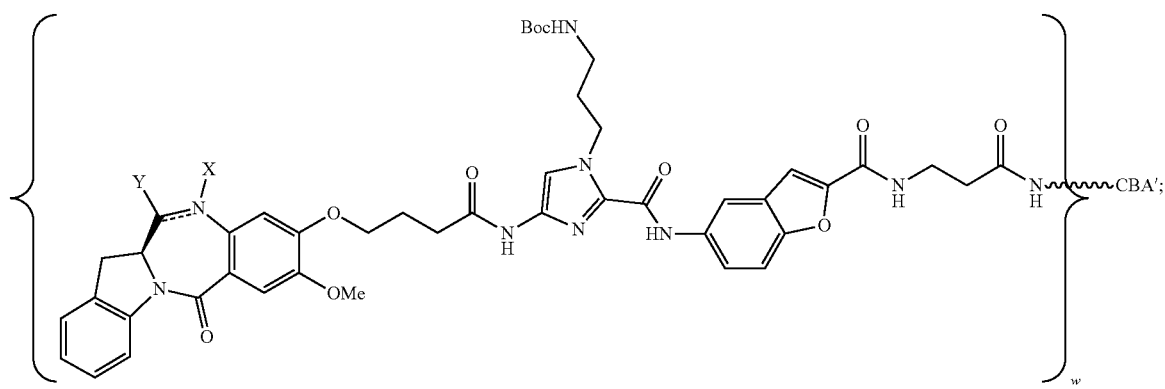
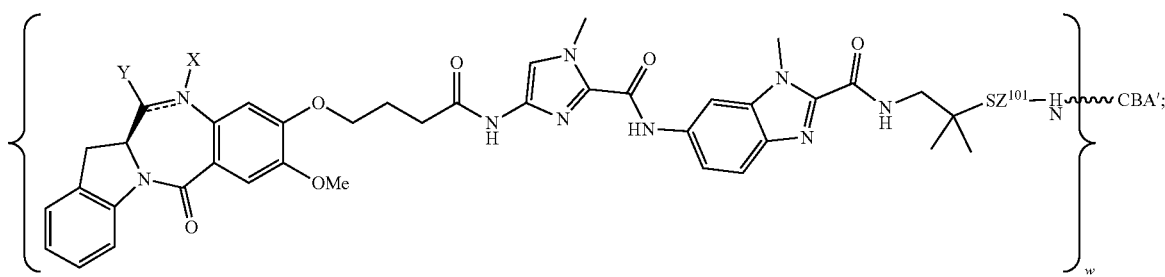

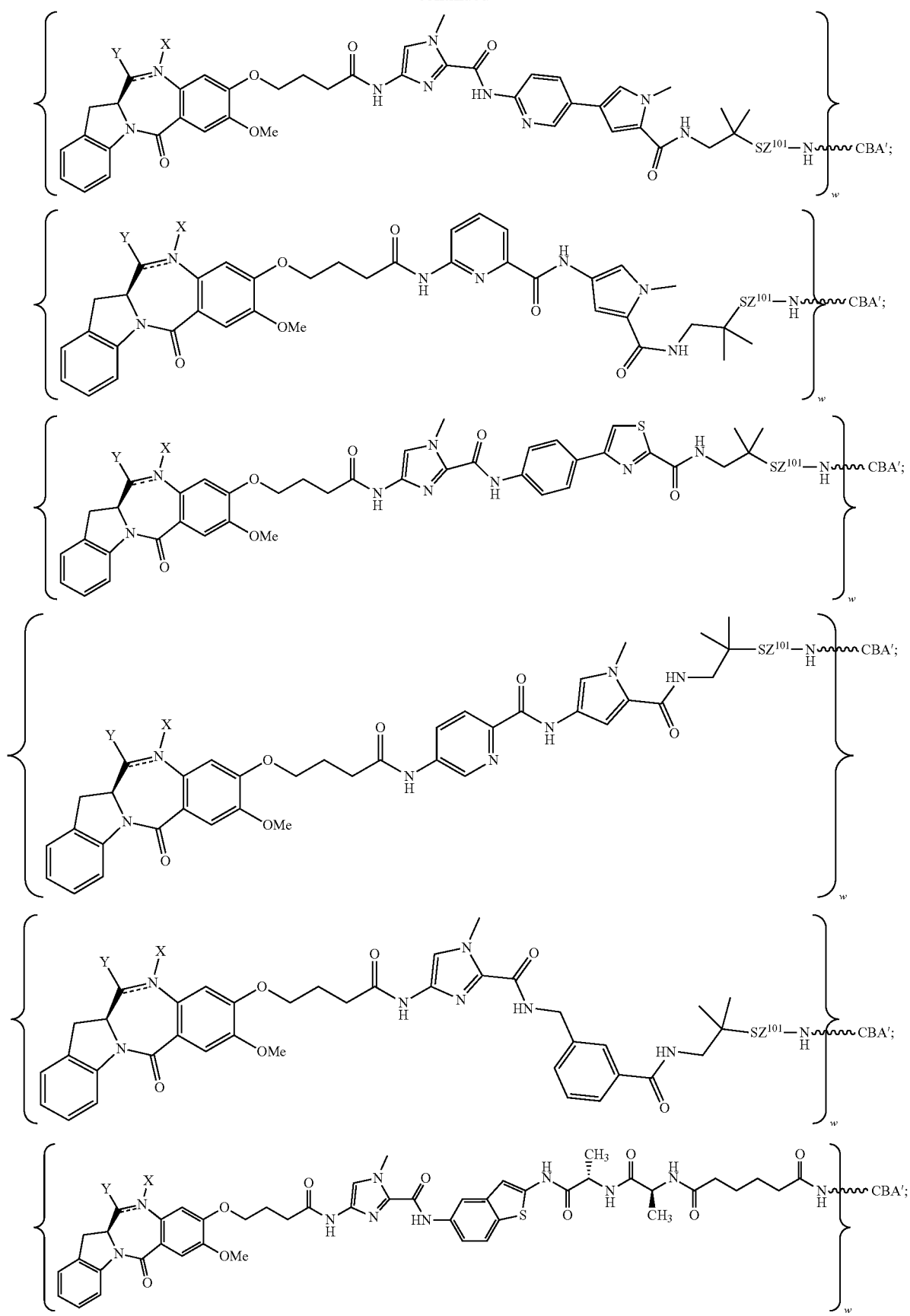

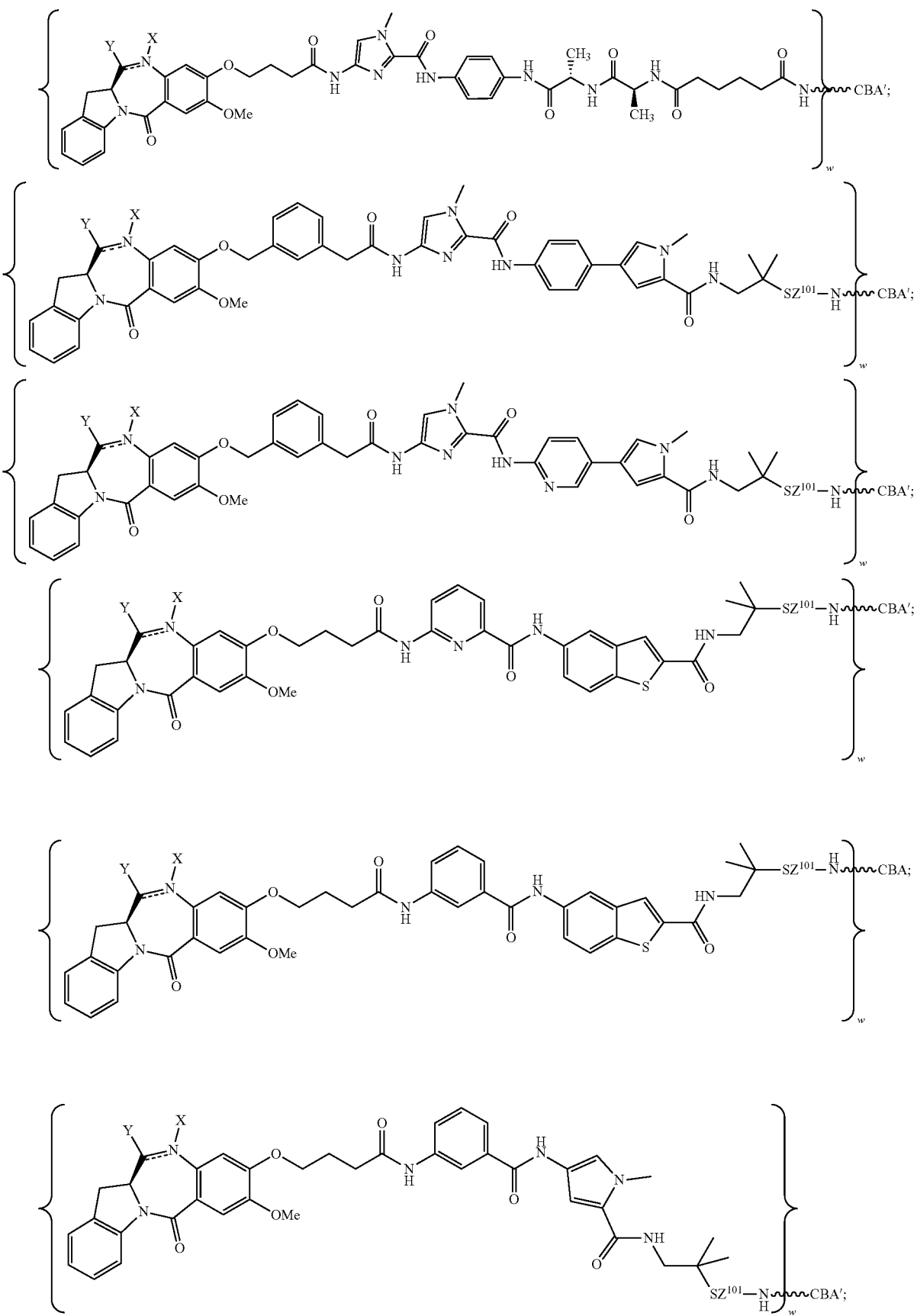

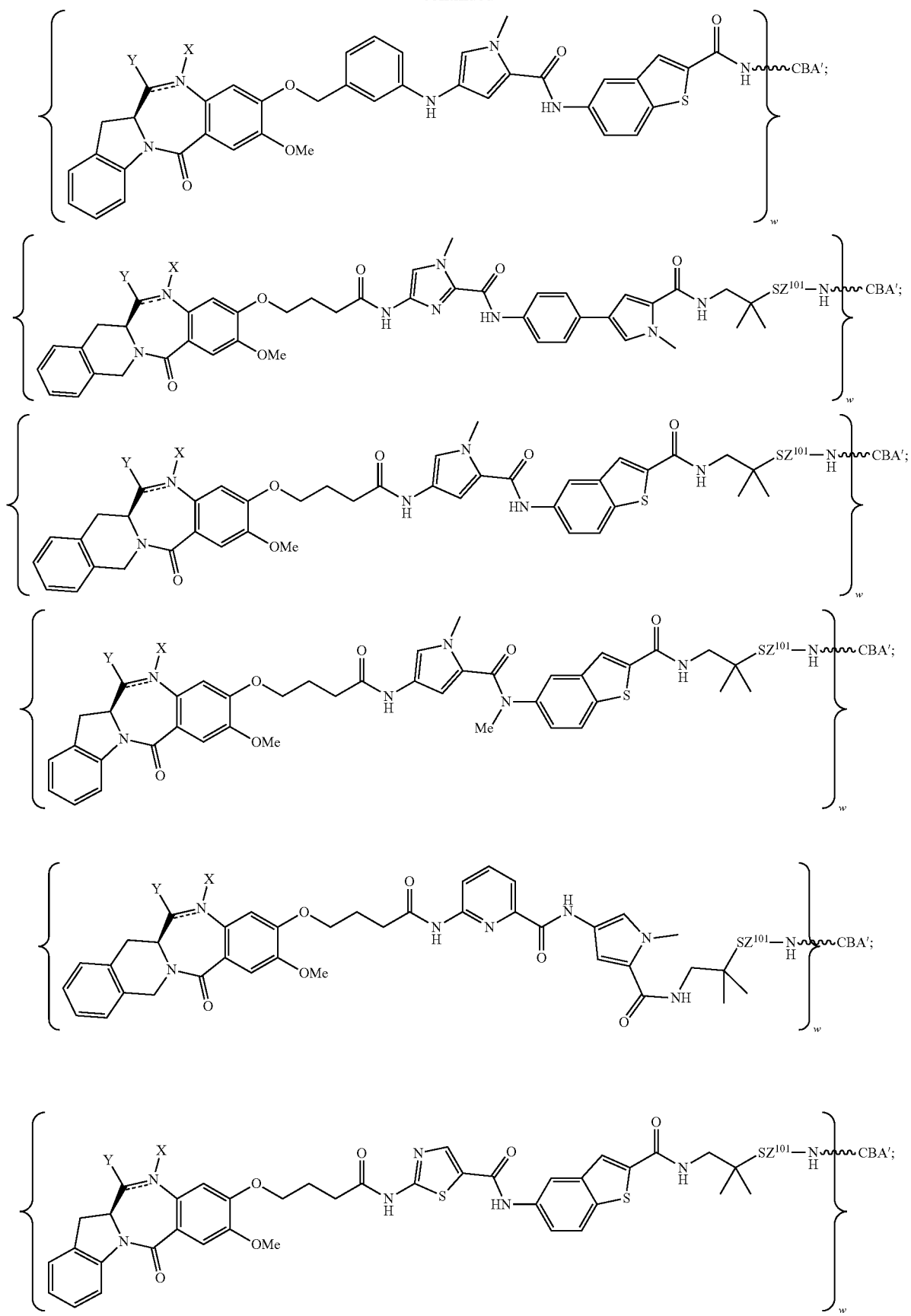

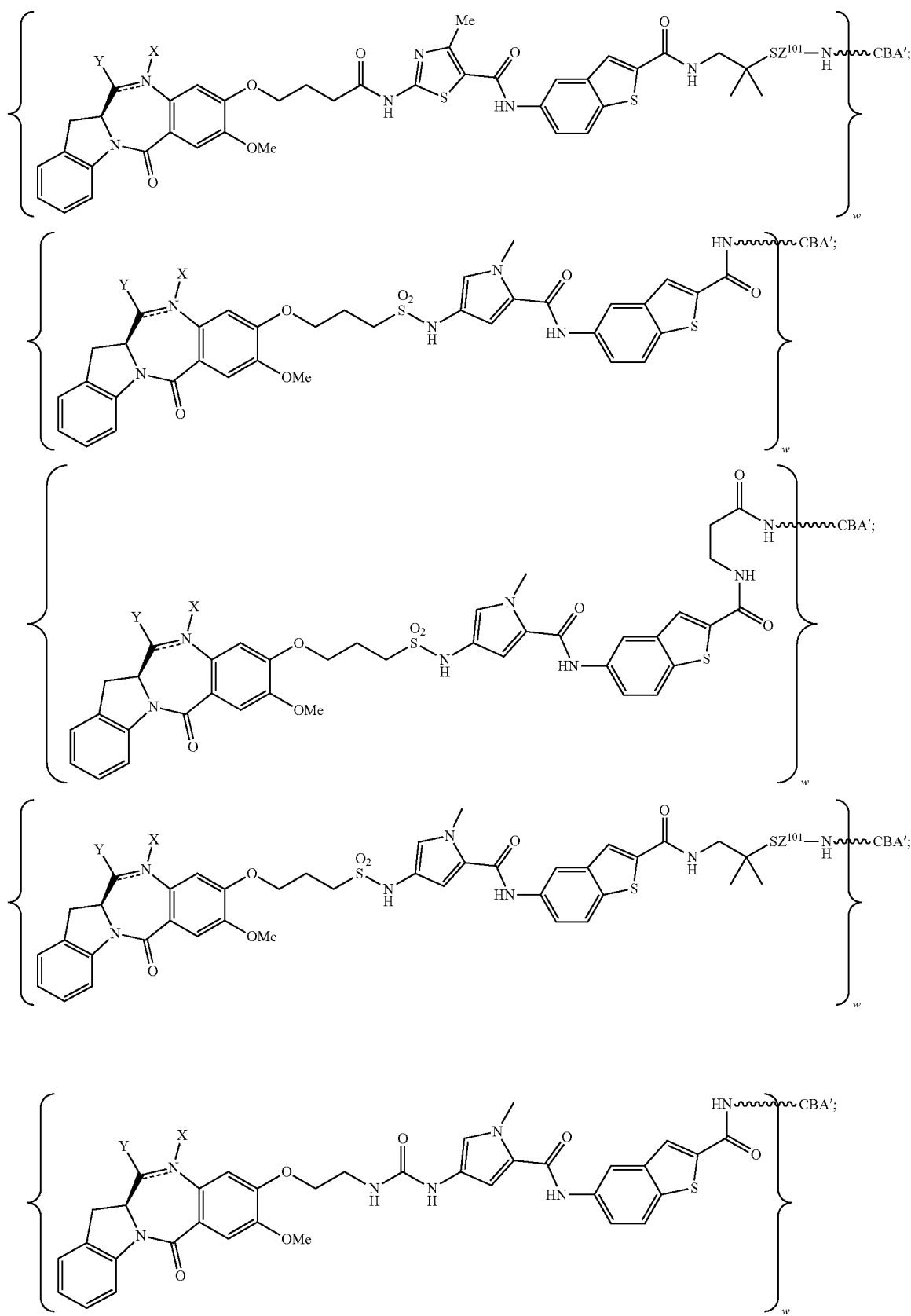

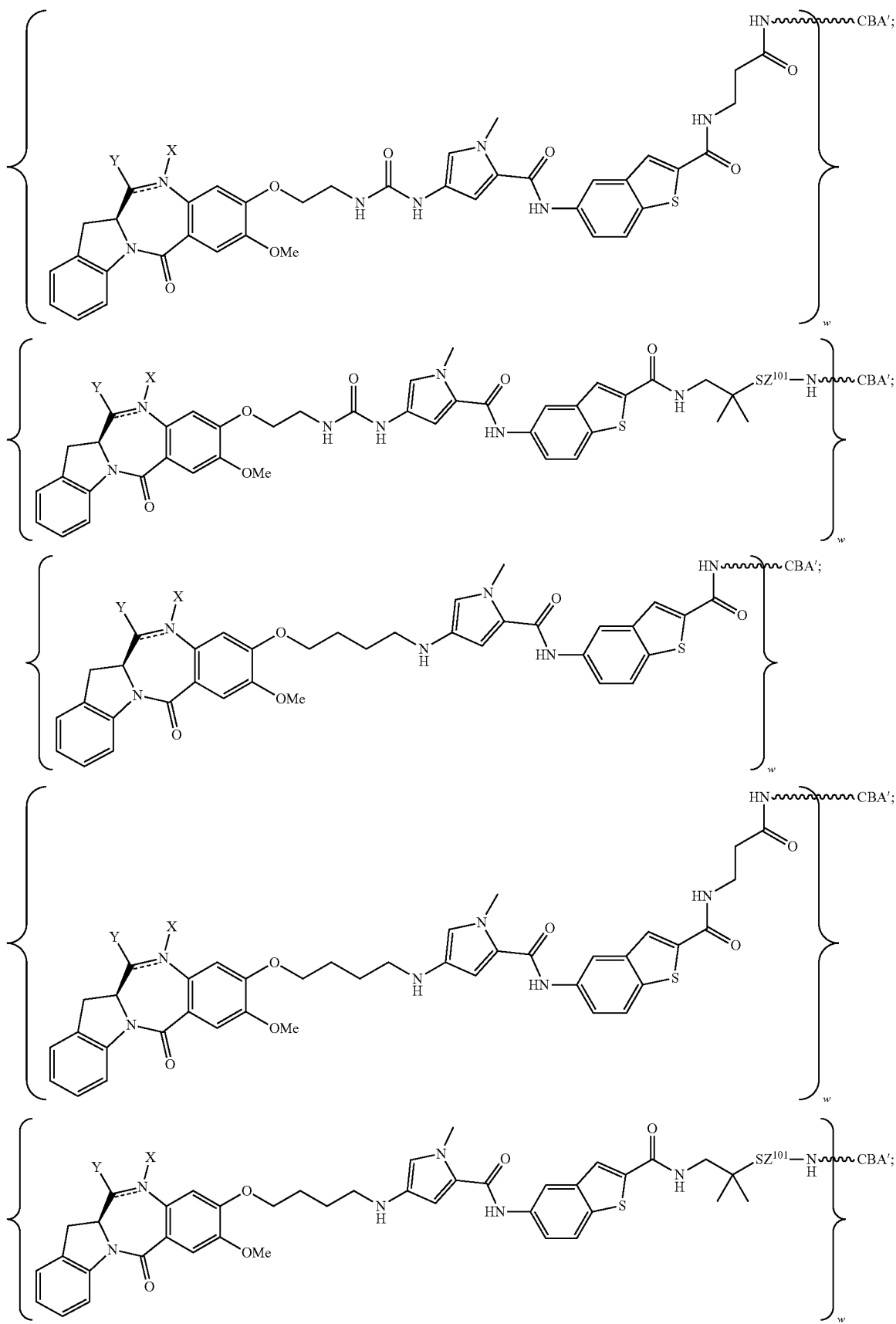

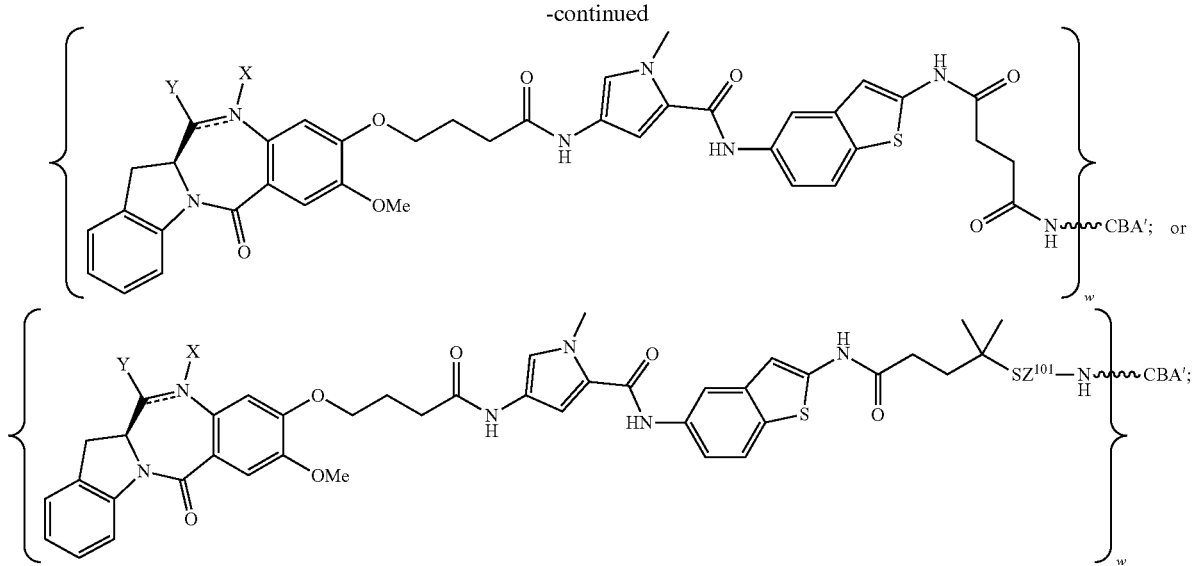
or a pharmaceutically acceptable salt thereof, wherein
represents the cell-binding agent covalently linked to the cytotoxic agent via the ε-amino group of a lysine; $Z^{101}$ is represented by one of the following formulae:
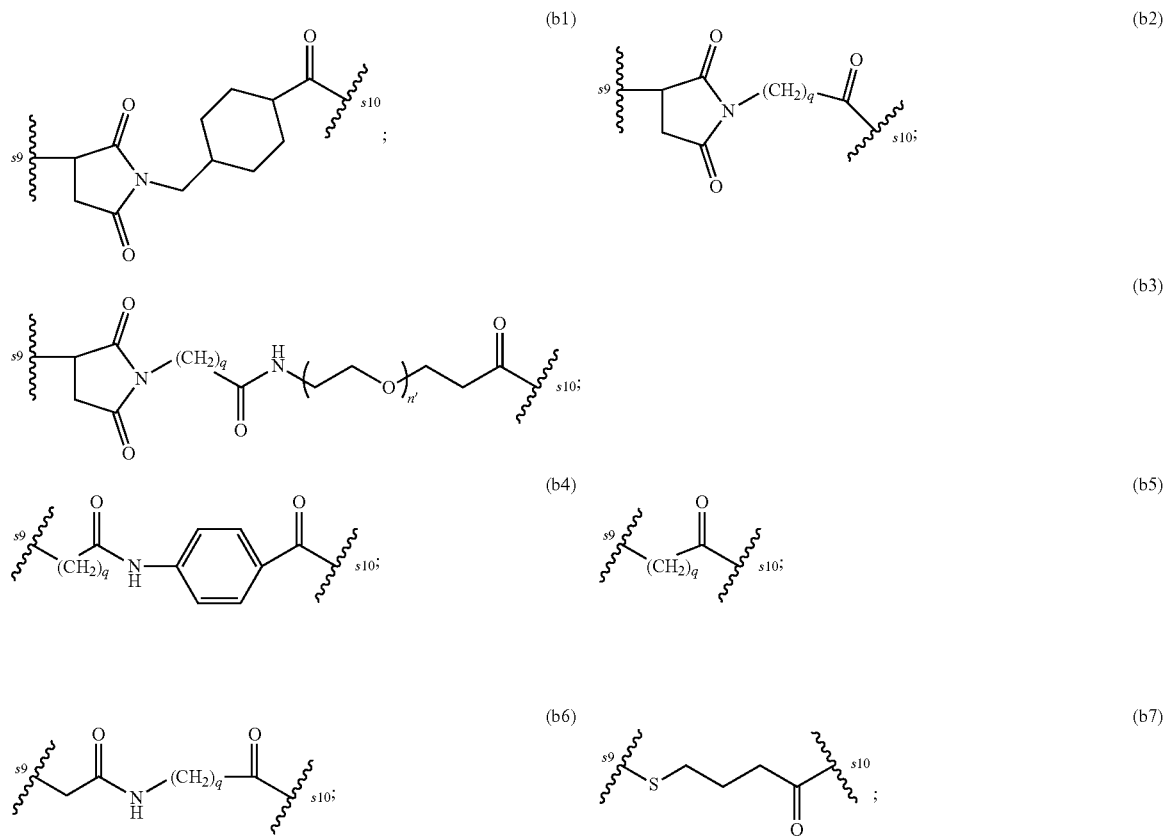

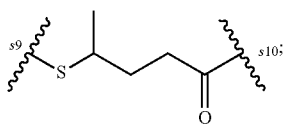 (b8)

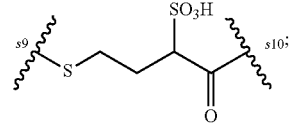 (b9)

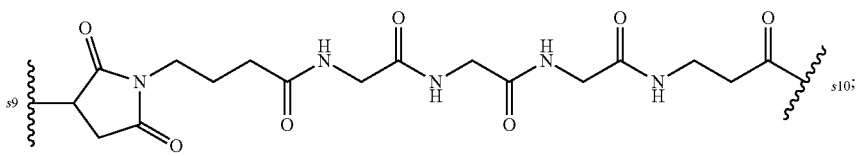 (b10)

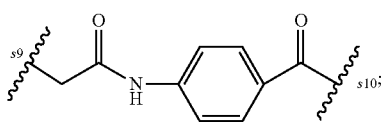 (b11)

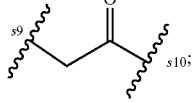 (b12)

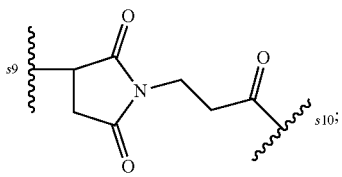 (b13)

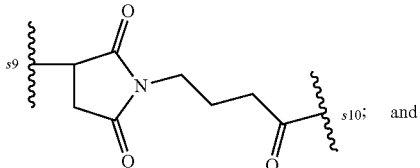 (b14) and

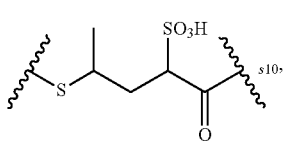 (b15)

q is an integer from 1 to 5;

n' is an integer from 2 to 6; and w is an integer from 1 to 10; and the remaining variables are as described in the 1st embodiment. In some embodiments, the pharmaceutically acceptable salt is a sodium or potassium salt. In some embodiments, the pharmaceutically acceptable salt is a sodium salt.

In a specific embodiment, $Z^{101}$ is represented by formula (b7) or (b9).

In another specific embodiment, the conjugate of the present invention is represented by the following formula:

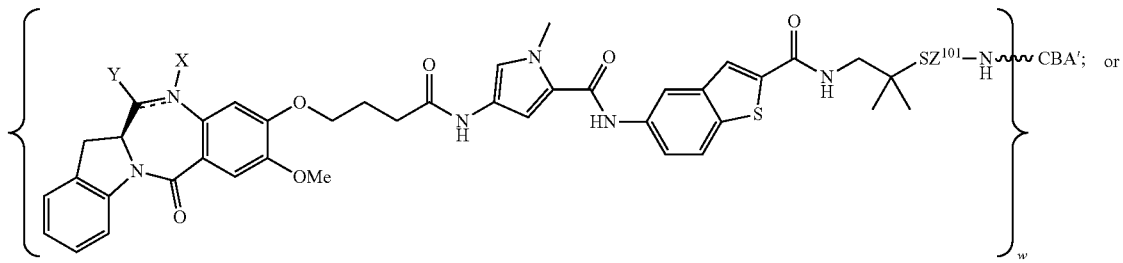

or

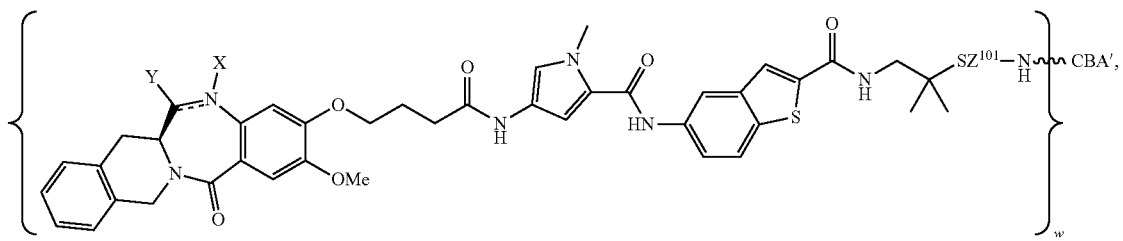

or a pharmaceutically acceptable salt thereof, wherein $Z^{101}$ is represented by formula (b7) or (b9).

In another specific embodiment, the conjugate of the present invention is represented by the following formula:

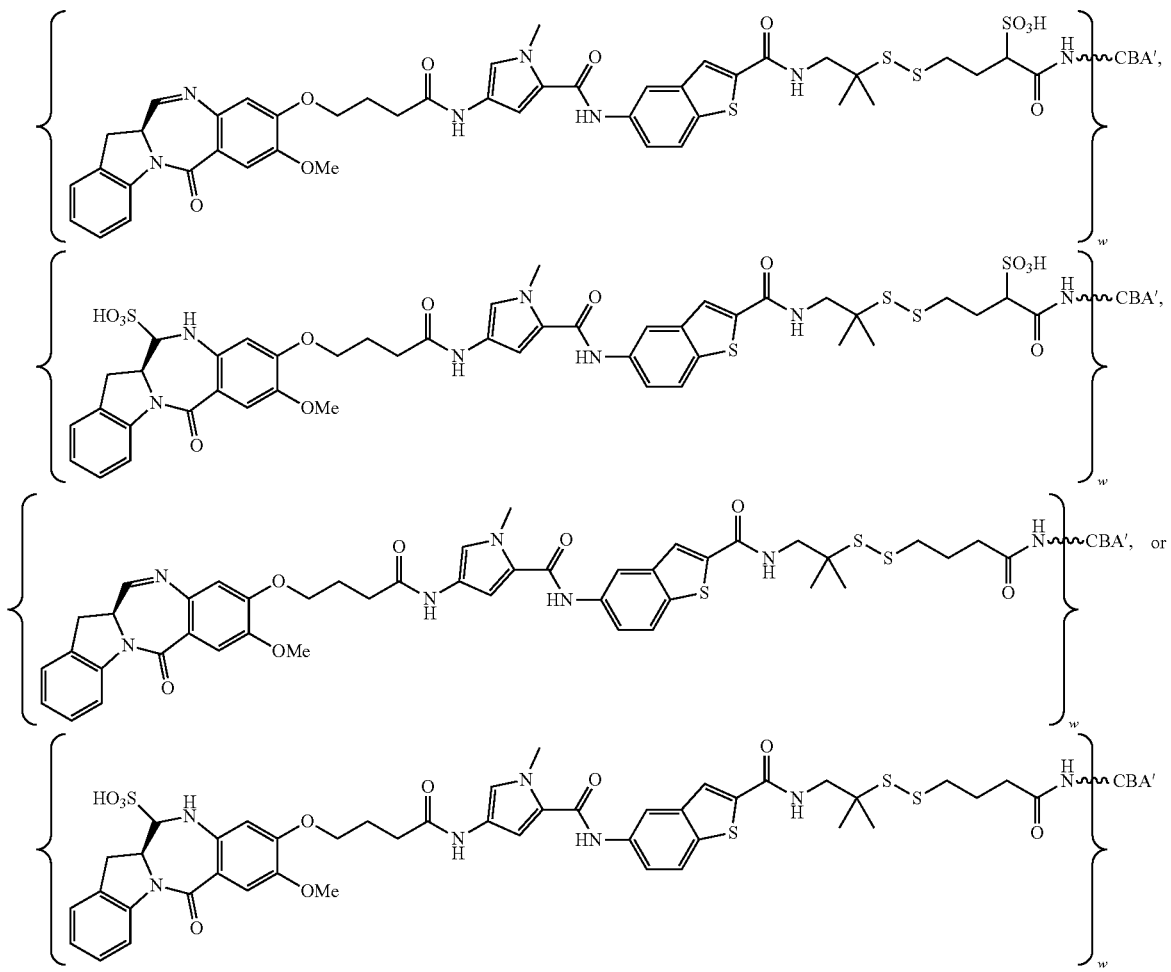

or a pharmaceutically acceptable salt thereof. In some embodiments, the pharmaceutically acceptable salt is a sodium or potassium salt. In some embodiments, the pharmaceutically acceptable salt is a sodium salt.

In a 37$^{th}$ embodiment, for conjugates of formula (IV), (V), (VI), (IVA-1), (IVA-2), (IVB-1), (IVB-2), (IVC), (IVD), (VA), (VB), (VC), (VIA), (VIB), (VIC), (IVA-1a), (IVA-2a), (IVB-1a), (IVB-2a), (IVC-a), (IVD-a), (IVA-1b), (IVA-2b), (IVB-1b), or (IVB-2b), $L_{CB}$ is represented by the following formula:

  (L4a'),

  (L4b')

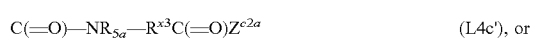  (L4c'), or

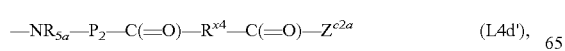  (L4d'), wherein:

$Z^{c1a}$ is

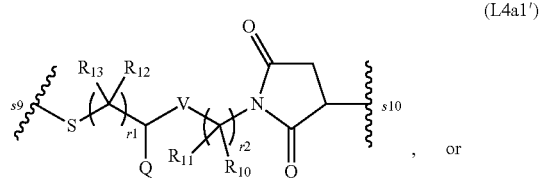 (L4a1')

, or

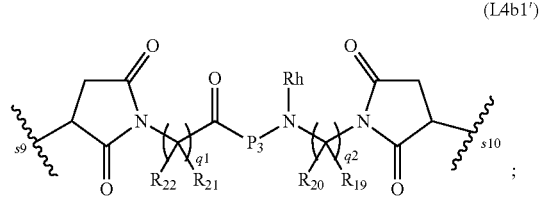 (L4b1')

;

$Z^{c2a}$ is

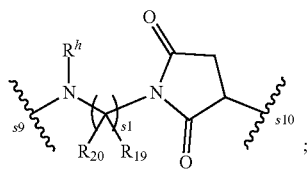

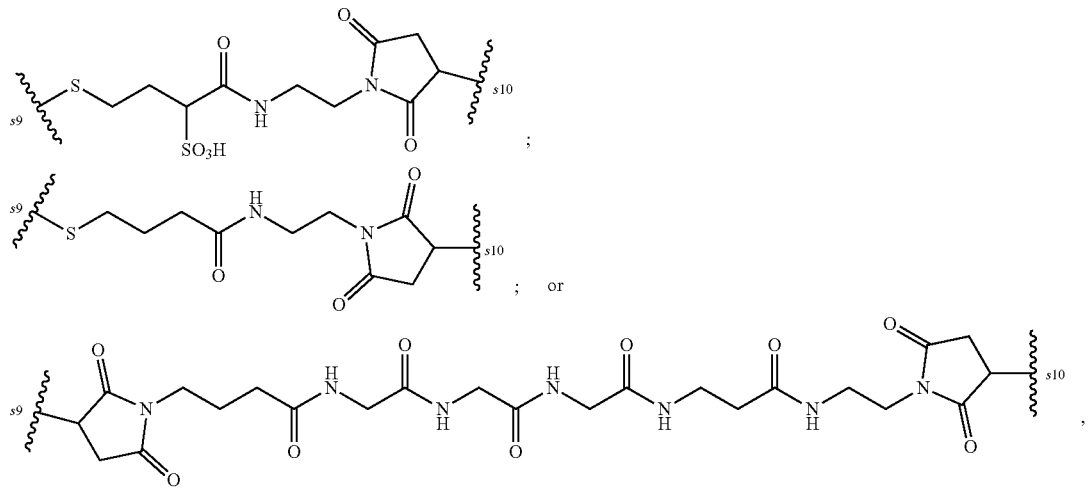

s9 is the site connected to $Ar_3$ or $Ar_2$ when n3 is 0, and s10 is the site connected to the CBA through the thiol group on a cysteine;

V is —C(=O)—$NR_9$—, or —$NR_9$—C(=O)—;

Q is —H, a charged substituent, or an ionizable group;

$R_9$, $R_{10}$, $R_{11}$, $R_{12}$, $R_{13}$, $R_{19}$, $R_{20}$, $R_{21}$ and $R_{22}$, for each occurrence, are independently —H or a ($C_1$-$C_4$)alkyl;

r1 and r2 are each independently 0 or an integer between 1 and 10;

q1 and q2 are each independently 0 or an integer between 1 and 10;

$R^h$ is —H or a ($C_1$-$C_3$)alkyl;

$R_{19}$ and $R_{20}$, for each occurrence, are independently —H or a ($C_1$-$C_4$)alkyl;

S1 is an integer between 1 and 10;

$P_3$ is an amino acid residue or a peptide residue containing 2 to 5 amino acid residues; and the remaining variables are as defined in the second aspect or the $21^{st}$, $22^{nd}$, $23^{rd}$, $24^{th}$ $25^{th}$, $26^{th}$, $27^{th}$, $28^{th}$, $29^{th}$, $30^{th}$, $31^{st}$, $32^{nd}$ or $33^{rd}$ embodiment or any specific embodiment described therein.

In a specific embodiment, $L_{CB}$ is represented by formula (L4a') or (L4b'), and $P_3$ is selected from Ala-Ala, Gln-Leu, Gly-Gly-Gly, Ala-Val, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), R-Ala-Leu-Ala-Leu (SEQ ID NO: 2), Gly-Phe-Leu-Gly (SEQ ID NO: 3), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala. More specifically, $P_3$ is Gly-Gly-Gly, Ala-Val, Ala-Ala, Ala-D-Ala, D-Ala-Ala, or D-Ala-D-Ala.

In another specific embodiment, for formula (L4a') or (L4b'), $Z^{c1a}$ is represented by the following formula:

and the remaining variables are as define above in the $37^{th}$ embodiment or any specific embodiment described therein.

In yet another specific embodiment, for formula (L4a') or (L4b'), $R_{5a}$ is H or Me; $R^{x1}$ is —$(CH_2)_{p4}$—(CRR)—, and $R^{x2}$ is —$(CH_2)_{p5}$—(CR$^f$R$^g$)—, wherein R$^f$ and R$^g$ are each independently —H or a ($C_1$-$C_4$)alkyl; and p4 and p5 are each independently 0, 1, 2, 3, 4 or 5; and the remaining variables are as define above in the $37^{th}$ embodiment or any specific embodiment described therein. More specifically, R$^f$ and R$^g$ are each independently H or Me.

In another specific embodiment, $L_{CB}$ is represented by formula (L4c') or (L4d'), $R_{5a}$ is H or Me; $R^{x3}$ is —$(CH_2)_{p3}$—, wherein p3 is an integer from 2 to 6; and $R^{x4}$ is —$(CH_2)_{p4}$—, wherein p4 is an integer from 2 to 6; and the remaining variables are as define above in the $37^{th}$ embodiment or any specific embodiment described therein.

In another specific embodiment, for formula (L4c') or (L4d'), $P_2$ is a peptide residue containing 2 to 5 amino acid residues. More specifically, $P_2$ is selected from Ala-Ala, Gln-Leu, Gly-Gly-Gly, Ala-Val, Cit-Val, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), -Ala-Leu-Ala-Leu (SEQ ID NO: 2), Gly-Phe-Leu-Gly (SEQ ID NO: 3), Val-Arg, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, Met-Ala, Gln-Val, Asn-Ala, Gln-Phe and Gln-Ala; and the remaining variables are as define above in the $37^{th}$ embodiment or any specific embodiment described therein. Even more specifically, $P_2$ is Gly-Gly-Gly, Ala-Val, Val-Ala, Ala-Ala, Ala-D-Ala, D-Ala-Ala, or D-Ala-D-Ala.

In another specific embodiment, for formula (L4c') or (L4d'), $Z^{c2a}$ is represented by the following formula:

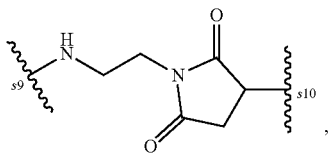 [SMILES: *NCCN1C(=O)CC(*)C1=O]

and the remaining variables are as define above in the 37$^{th}$ embodiment or any specific embodiment described therein.

In another specific embodiment, for formula (L4a'), (L4b'), (L4c') or (L4d'), $R^h$ is H or Me; Q is —SO$_3$H; and $R_{19}$ and $R_{20}$ are both H; and s1 is an integer from 1 to 6; and the remaining variables are as define above in the 77$^{th}$ embodiment or any specific embodiment described therein.

In a 38$^{th}$ embodiment, the conjugate of the present invention is represented by the following formula:

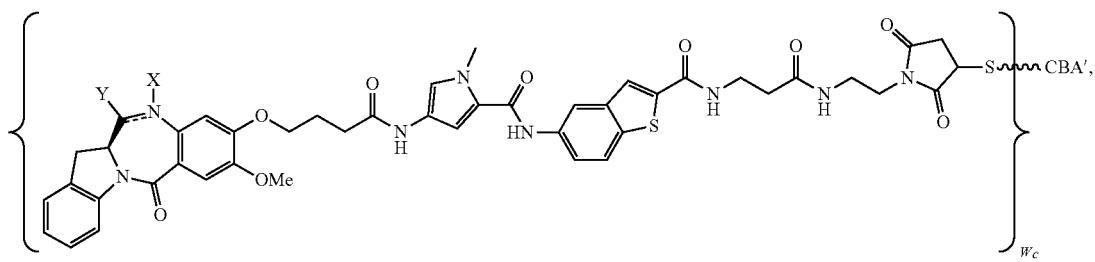

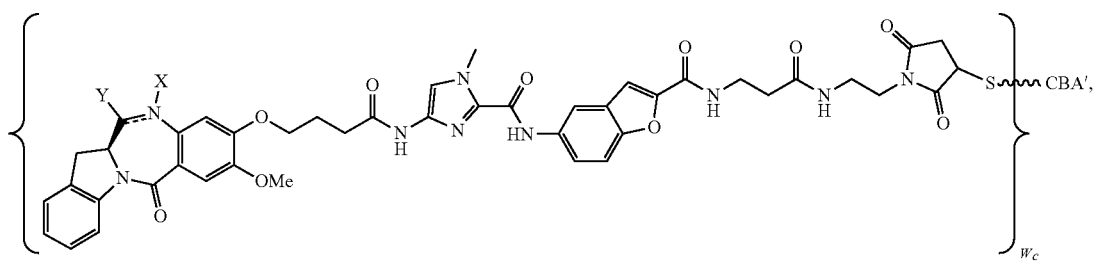

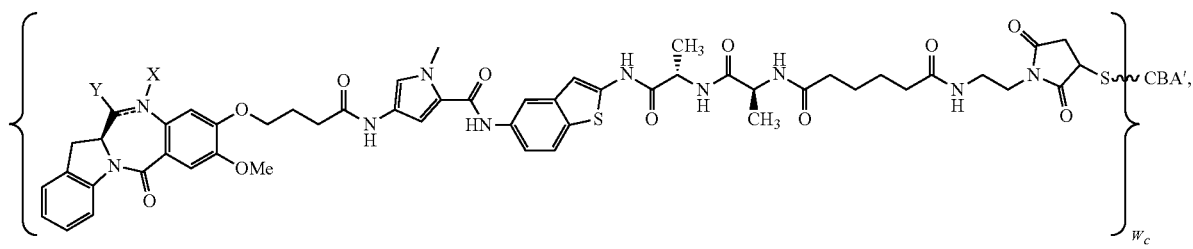

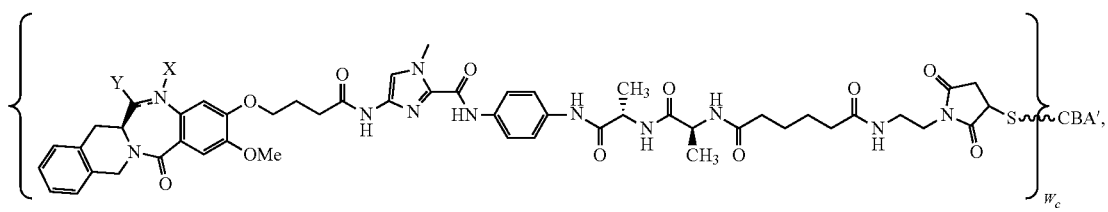

-continued

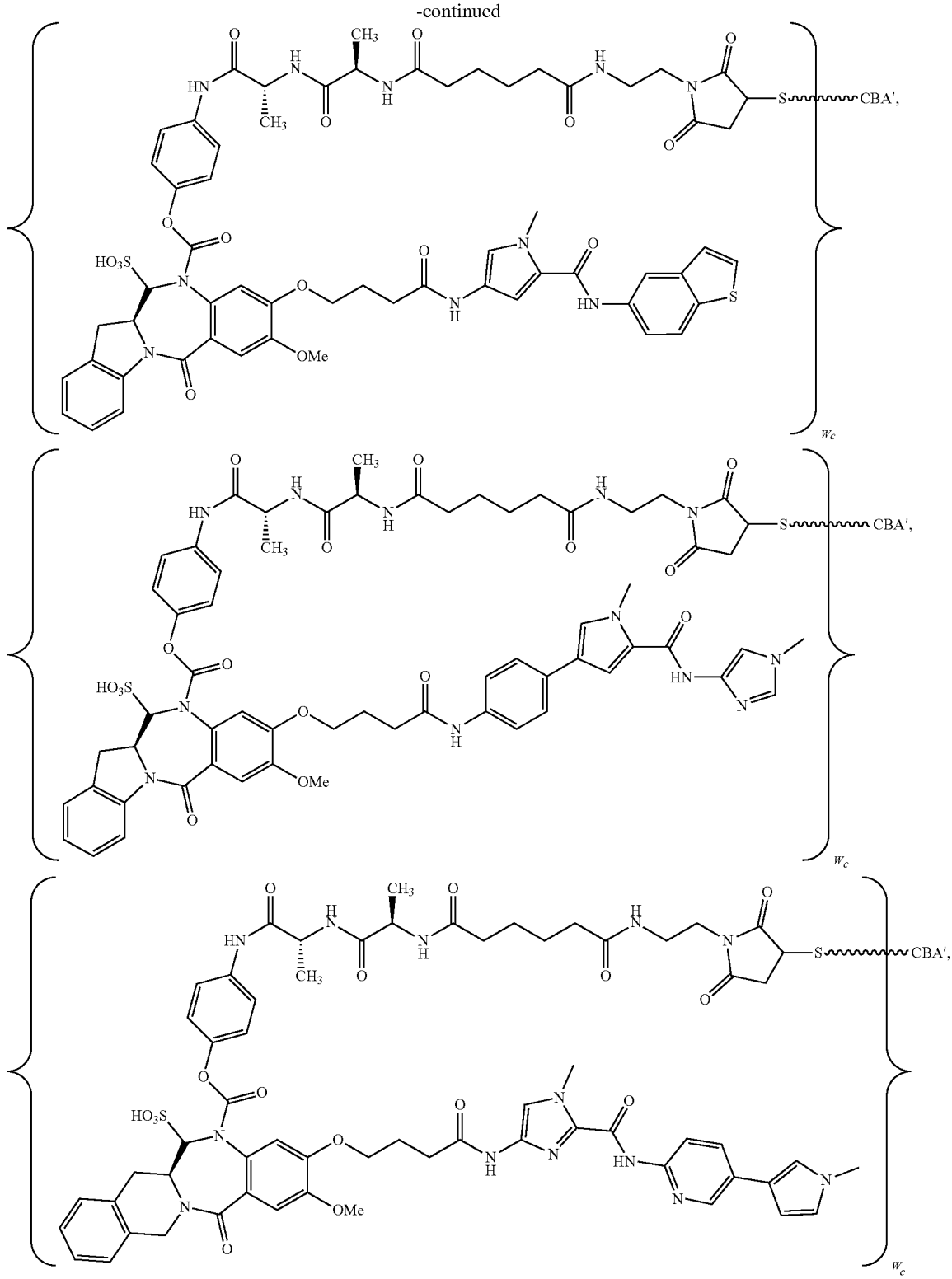

or a pharmaceutically acceptable salt thereof, wherein the double line ⚌ between N and C represents a single bond or a double bond, provided that when it is a double bond X is absent and Y is —H, and when it is a single bond, X is —H, and Y is —SO₃H, CBA'∼S— represents the cell-binding agent covalently linked to the cytotoxic agent via the thiol group of a lysine; $w_c$ is 1 or 2. In some embodiments, the pharmaceutically acceptable salt is a sodium or potassium salt. In some embodiments, the pharmaceutically acceptable salt is a sodium salt.

In a 39$^{th}$ embodiment, for compounds of formula (IV), (V), (VI), (IA-1), (IVA-2), (IVB-1), (IVB-2), (IVC), (IVD), (VA), (VB), (VC), (VIA), (VIB), (VIC), (IVA-1a), (IVA-2a), (IVB-1a), (IVB-2a), (IVC-a), (IVD-a), (IVA-1b), (IVA-2b), (IVB-1b), or (IVB-2b), $L_{CB}$ is represented by the following formula:

$$—C(=O)—NR_{5a}—R^{x1}—S—Z^{s1}-J_{CB}{}^{s1} \quad (L5a'),$$

$$—NR_{5a}—C(=O)—R_2—S—Z^{s1}-J_{CB}{}^{s1} \quad (L5b')$$

$$—C(=O)—NR_{5a}—R^{x3}—Z_{a2}—R^{x3}-J_{CB}{}^{s1} \quad (L5c')$$

$$—NR_{5a}—R^{x3}—C(=O)—R^{x4}—Z_{a2}—R^{x4'}-J_{CB}{}^{s1} \quad (L5c1'), \text{ or}$$

$$—NR_{5a}—P_3—C(=O)—R^{x4}—Z_{a2}—R^{x4'}-J_{CB}{}^{s1} \quad (L5d'),$$

wherein:
$R^{x1}$, Rx, $R^{x3}$, $R^{x4}$ and $R^{x4'}$ are each independently a $(C_1-C_6)$alkyl;
$Z^{s1}$ is

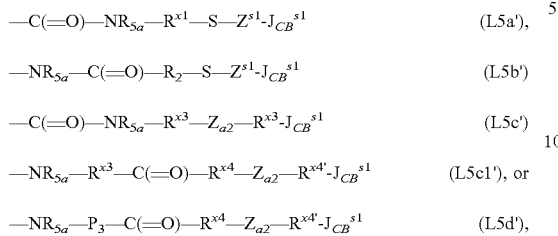

s9 is the site covalently linked to the group $J_{CB}'$;
s10 is the site covalently linked to the —S— group in formula (L5a) or (L5b);
$Z_{a1}$ is absent, —C(=O)—$NR_9$—, or —$NR_9$—C(=O)—;
$R_9$ is —H or a $(C_1-C_3)$alkyl;
Q is H, a charged substituent or an ionizable group;
$R_{a1}$, $R_{a2}$, $R_{a3}$, $R_{a4}$, for each occurrence, are independently H or $(C_1-C_3)$alkyl; and
qs1 and rs1 are each independently an integer from 0 to 10, provided that qs1 and rs1 are not both 0
$Z_{a2}$ is absent, —C(=O)—$NR_9$—, or —$NR_9$—C(=O)—;
$R_9$ is —H or a $(C_1-C_3)$alkyl;
$J_{CB}{}^{s1}$ is a moiety formed by reacting an aldehyde reactive group with an aldehyde group located on the CBA; and the remaining variables are as defined in the second aspect or the $21^{st}$, $22^{nd}$, $23^{rd}$, $24^{th}$, $25^{th}$, $26^{th}$, $27^{th}$, $28^{th}$, $29^{th}$, $30^{th}$, $31^{st}$ $32^{nd}$ or $33^{rd}$ embodiment or any specific embodiment described therein.

In a specific embodiment, $J_{CB}{}^{s1}$ is

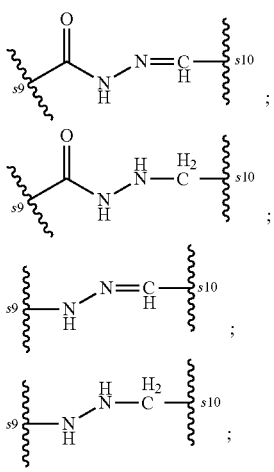

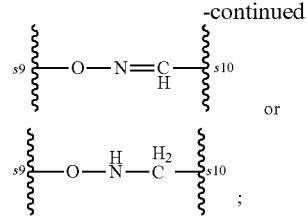

s9 is the site connected the rest of $L_{CB}$ and s10 is the site connected to CBA through an aldehyde group located on the CBA.

In another specific embodiment, $L_{CB}$ is represented by formula (L5c'), (L5c1') or (L5d'); $R_5$ and $R_9$ are both H or Me; and $R^{x1}$, $R^{x2}$, $R^{x3}$, $R^{x4}$ and $R^{x4'}$ are each independently —$(CH_2)_s$—; wherein s is 1, 2, 3, 4, 5 or 6; and the remaining variables are as defined in the $39^{th}$ embodiment or any specific embodiments described therein.

In another specific embodiment, for formula (L5d'), $P_3$ is selected from Ala-Ala, Gln-Leu, Gly-Gly-Gly, Ala-Val, Val-Cit, Val-Lys, Phe-Lys, Lys-Lys, Ala-Lys, Phe-Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ ID NO: 1), f-Ala-Leu-Ala-Leu (SEQ ID NO: 2), Gly-Phe-Leu-Gly (SEQ ID NO: 3), Val-Arg, Arg-Val, Arg-Arg, Val-D-Cit, Val-D-Lys, Val-D-Arg, D-Val-Cit, D-Val-Lys, D-Val-Arg, D-Val-D-Cit, D-Val-D-Lys, D-Val-D-Arg, D-Arg-D-Arg, Ala-Ala, Ala-D-Ala, D-Ala-Ala, D-Ala-D-Ala, Ala-Met, and Met-Ala; and the remaining variables are defined in the $19^{th}$ embodiment or any specific embodiments described therein. More specifically, $P_3$ is Gly-Gly-Gly, Ala-Val, Ala-Ala, Ala-D-Ala, D-Ala-Ala, or D-Ala-D-Ala.

In yet another specific embodiment, for formula (L5a') or (L5b'), Q is —$SO_3H$.

In another specific embodiment, $L_{CB}$ is represented by formula (L5a') or (L5b'), and $Z^{s1}$ is represented by the following formula:

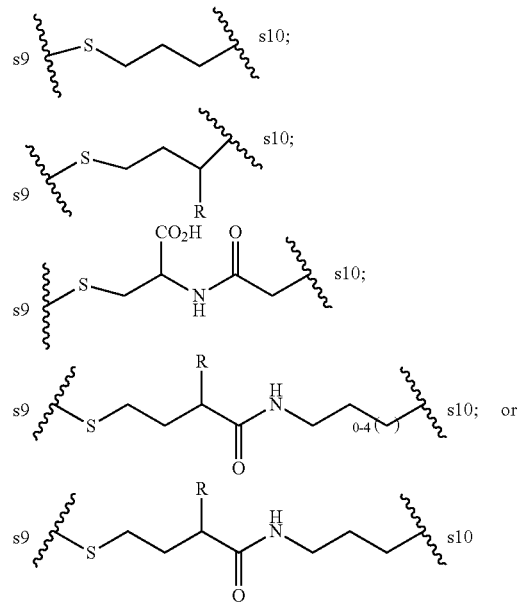

or a pharmaceutically acceptable salt thereof, wherein R is H or —SO$_3$H; and the remaining variables are defined in the 39$^{th}$ embodiment or any specific embodiments described therein.

More specifically, R$^{x1}$ is —(CH$_2$)$_p$—(CR$^f$R$^g$)—, and R$^{x2}$ is —(CH$_2$)$_p$—(CRR)—, wherein R$^f$ and R$^g$ are each independently —H or a (C$_1$-C$_4$)alkyl; and p is 0, 1, 2 or 3. Even more specifically, R$^f$ and R$^g$ are independently H or Me.

In a 40$^{th}$ embodiment, the conjugate of the present invention is represented by the following formula:

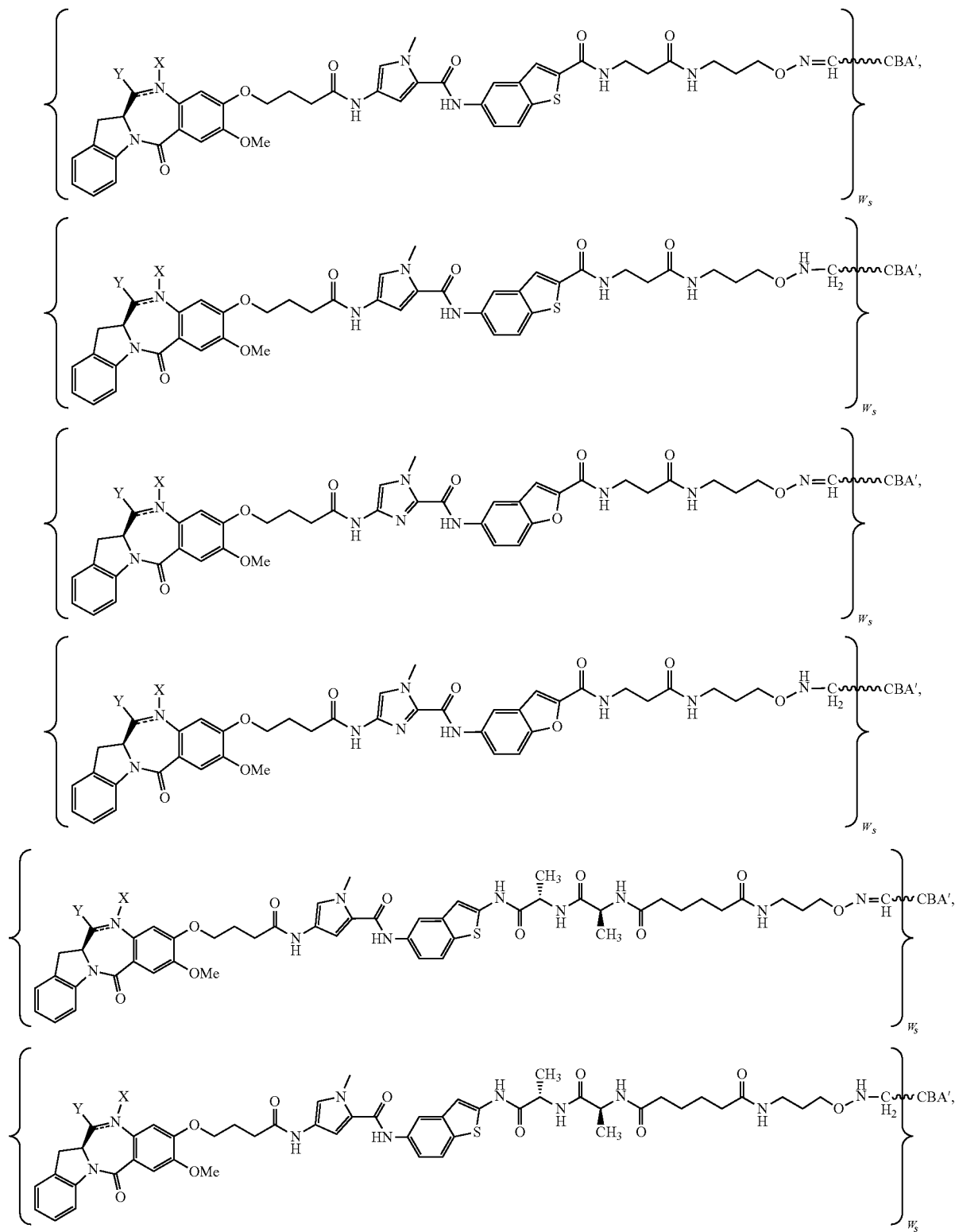

-continued
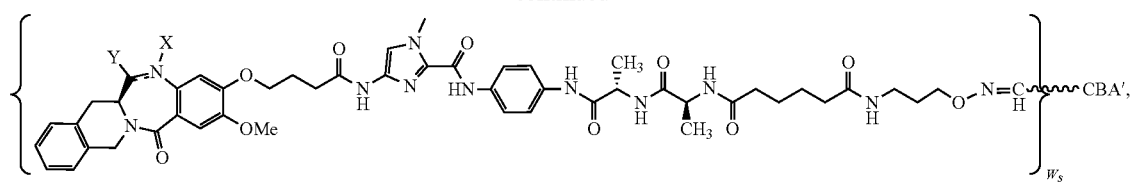
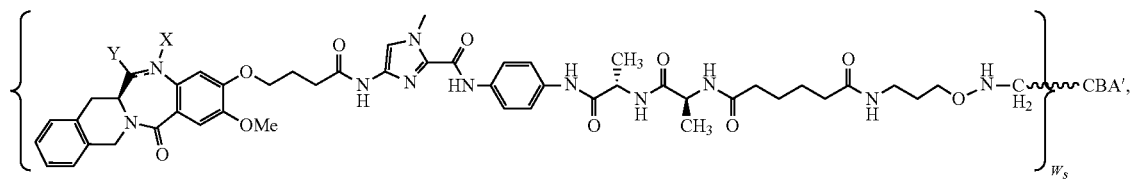
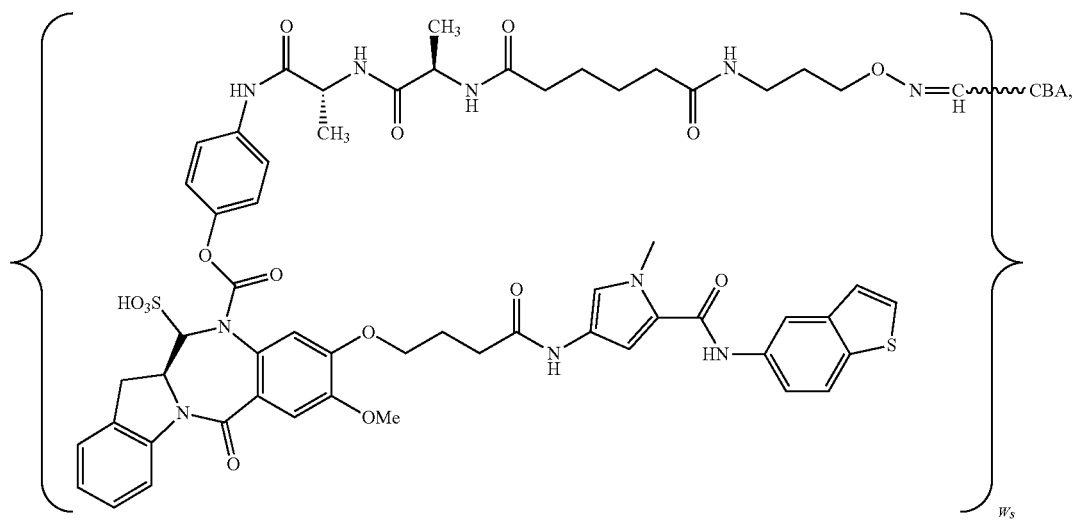
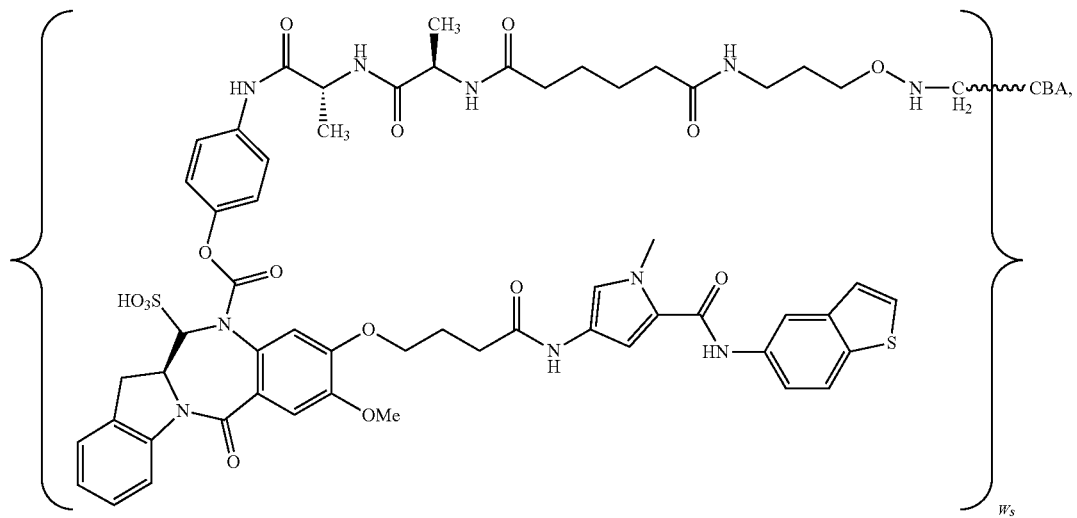

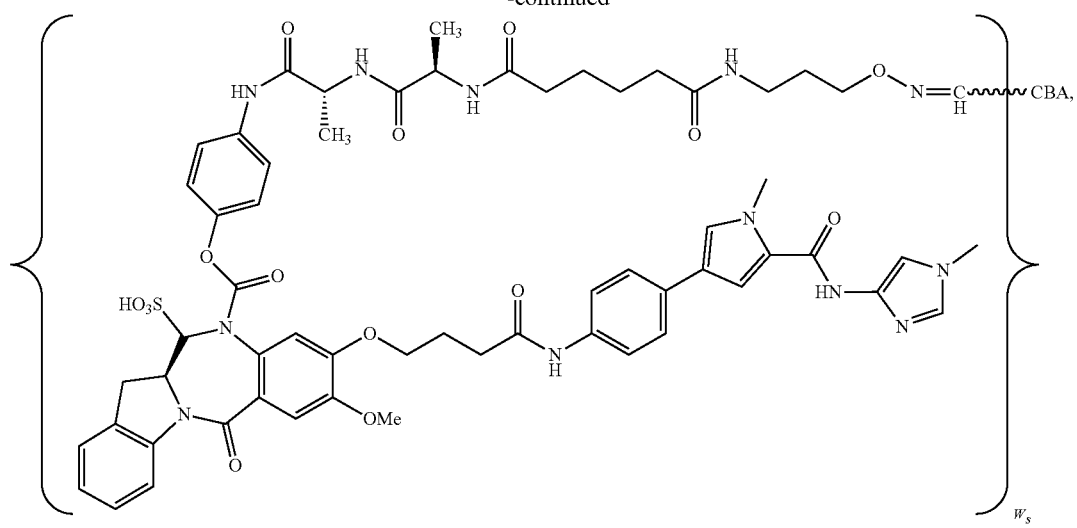
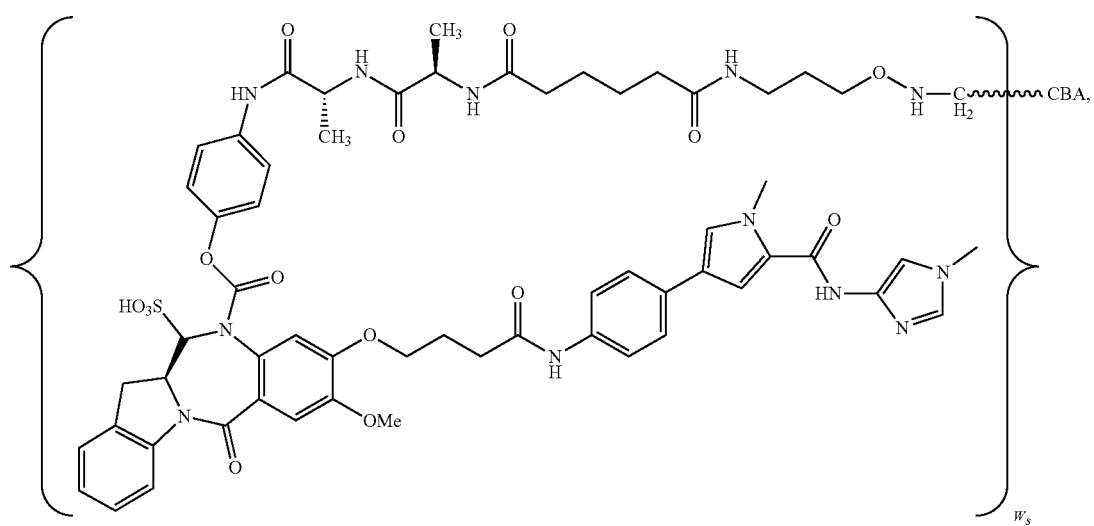
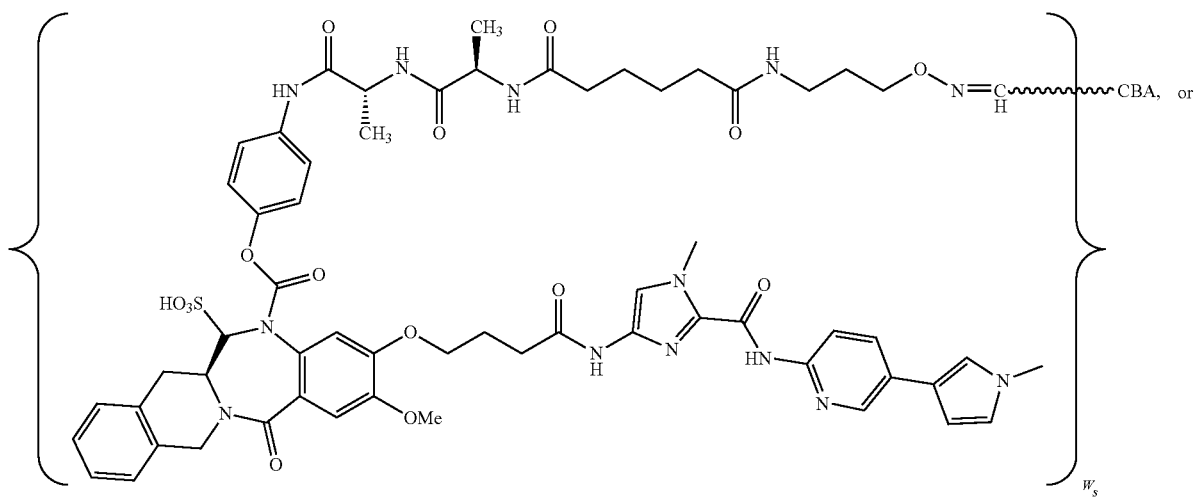

-continued

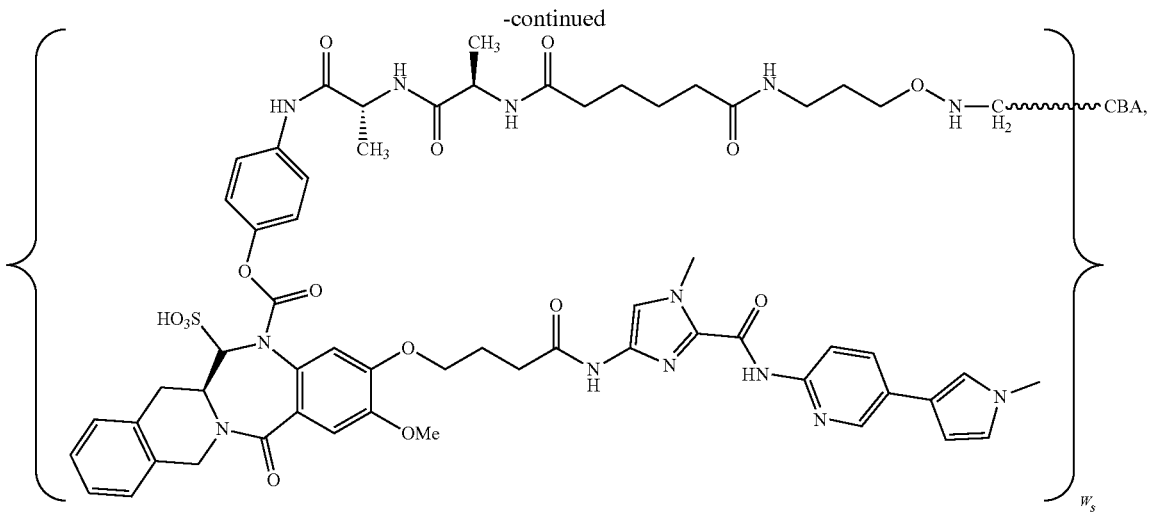

or a pharmaceutically acceptable salt thereof, wherein the double line ⹀ between N and C represents a single bond or a double bond, provided that when it is a double bond X is absent and Y is —H, and when it is a single bond, X is —H, and Y is —SO$_3$H,

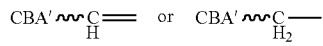

represents the cell-binding agent covalently linked to the cytotoxic agent via an aldehyde group located on the CBA; $w_s$ is 1 or 2.

In some embodiments, for conjugates described above (e.g., conjugates described in the second aspect or any embodiments described therein or in the $21^{st}$ to $40^{th}$ embodiments or any embodiments or specific embodiments described therein), the double line ⹀ between N and C represents a double bond, X is absent and Y is —H.

In some embodiments, for conjugates described above (e.g., conjugates described in the second aspect or any embodiments described therein or in the $21^{st}$ to $40^{th}$ embodiments or any embodiments or specific embodiments described therein), the double line ⹀ between N and C represents a single bond, X is —H, and Y is —SO$_3$H or —SO$_3$Na.

In some embodiments, for conjugates described above (e.g., conjugates described in the second aspect or any embodiments described therein or in the $21^{st}$ to $40^{th}$ embodiments or any embodiments or specific embodiments described therein), the pharmaceutically acceptable salt thereof is a sodium or potassium salt. In some embodiments, the pharmaceutically acceptable salt is a sodium salt.

Cell-Binding Agents

Cell-binding agents can be of any kind presently known, or that become known, including peptides and non-peptides. Generally, these can be antibodies (such as polyclonal antibodies and monoclonal antibodies, especially monoclonal antibodies), lymphokines, hormones, growth factors, vitamins (such as folate etc., which can bind to a cell surface receptor thereof, e.g., a folate receptor), nutrient-transport molecules (such as transferrin), or any other cell-binding molecule or substance.

Selection of the appropriate cell-binding agent is a matter of choice that partly depends upon the particular cell population that is to be targeted, but in many (but not all) cases, human monoclonal antibodies are a good choice if an appropriate one is available. For example, the monoclonal antibody MY9 is a murine IgG$_1$ antibody that binds specifically to the CD33 Antigen (J. D. Griffin et al., *Leukemia Res.*, 8:521 (1984)), and can be used if the target cells express CD33 as in the disease of acute myelogenous leukemia (AML).

In certain embodiments, the cell-binding agent is not a protein. For example, in certain embodiments, the cell binding agent may be a vitamin that binds to a vitamin receptor, such as a cell-surface receptor. In this regard, vitamin A binds to retinol-binding protein (RBP) to form a complex, which complex in turn binds the STRA6 receptor with high affinity and increases vitamin A in-take. In another example, folic acid/folate/vitamin B$_9$ binds the cell-surface folate receptor (FR), for example, FRα, with high affinity. Folic acid or antibodies that bind to FRα can be used to target the folate receptor expressed on ovarian and other tumors. In addition, vitamin D and its analog bind to vitamin D receptor.

In other embodiments, the cell-binding agent is a protein or a polypeptide, or a compound comprising a protein or polypeptide, including antibody, non-antibody protein, or polypeptide. Preferably, the protein or polypeptides comprise one or more Lys residues with side chain —NH$_2$ group. The Lys side chain —NH$_2$ groups can be covalently linked to the bifunctional crosslinkers, which in turn are linked to the dimer compounds of the invention, thus conjugating the cell-binding agents to the dimer compounds of the invention. Each protein-based cell-binding agents can contain multiple Lys side chain —NH$_2$ groups available for linking the compounds of the invention through the bifunctional crosslinkers.

In some embodiments, GM-CSF, a ligand/growth factor which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Epidermal growth factor can be used to target squamous cancers, such as lung and head and neck. Somatostatin can be used to target neuroblastomas and other tumor types. Estrogen (or estrogen analogues) can be used to target breast cancer. Androgen (or androgen analogues) can be used to target testes.

In certain embodiments, the cell-binding agent can be a lymphokine, a hormone, a growth factor, a colony stimulating factor, or a nutrient-transport molecule.

In certain embodiments, the cell-binding agent is an antibody mimetic, such as an ankyrin repeat protein, a Centyrin, or an adnectin/monobody.

In other embodiments, the cell-binding agent is an antibody, a single chain antibody, an antibody fragment that specifically binds to the target cell, a monoclonal antibody, a single chain monoclonal antibody, a monoclonal antibody fragment (or "antigen-binding portion") that specifically binds to a target cell, a chimeric antibody, a chimeric antibody fragment (or "antigen-binding portion") that specifically binds to the target cell, a domain antibody (e.g., sdAb), or a domain antibody fragment that specifically binds to the target cell.

In certain embodiments, the cell-binding agent is a humanized antibody, a humanized single chain antibody, or a humanized antibody fragment (or "antigen-binding portion"). In a specific embodiment, the humanized antibody is huMy9-6 or another related antibody, which is described in U.S. Pat. Nos. 7,342,110 and 7,557,189. In another specific embodiment, the humanized antibody is an anti-folate receptor antibody described in U.S. Provisional Application Nos. 61/307,797, 61/346,595, and 61/413,172 and U.S. application Ser. No. 13/033,723 (published as US 2012/0009181 A1). The teachings of all these applications are incorporated herein by reference in its entirety.

In certain embodiments, the cell-binding agent is a resurfaced antibody, a resurfaced single chain antibody, a resurfaced antibody fragment (or "antigen-binding portion"), or a bispecific antibody.

In certain embodiments, the cell-binding agent is a minibody, an avibody, a diabody, a tribody, a tetrabody, a nanobody, a probody, a domain antibody, or an unibody.

In other words, an exemplary cell binding agent may include an antibody, a single chain antibody, an antibody fragment that specifically binds to the target cell, a monoclonal antibody, a single chain monoclonal antibody, a monoclonal antibody fragment that specifically binds to a target cell, a chimeric antibody, a chimeric antibody fragment that specifically binds to the target cell, a bispecific antibody, a domain antibody, a domain antibody fragment that specifically binds to the target cell, an interferon (e.g., α, β, γ), a lymphokine (e.g., IL-2, IL-3, IL-4, and IL-6), a hormone (e.g., insulin, thyrotropin releasing hormone (TRH), melanocyte-stimulating hormone (MSH), and a steroid hormone (e.g., androgen and estrogen)), a vitamin (e.g., folate), a growth factor (e.g., EGF, TGF-alpha, FGF, VEGF), a colony stimulating factor, a nutrient-transport molecule (e.g., transferrin; see O'Keefe et al. (1985) *J. Biol. Chem.* 260:932-937, incorporated herein by reference), a Centyrin (a protein scaffold based on a consensus sequence of fibronectin type III (FN3) repeats; see U.S. Patent Publication 2010/0255056, 2010/0216708 and 2011/0274623 incorporated herein by reference), an Ankyrin Repeat Protein (e.g., a designed ankyrin repeat protein, known as DARPin; see U.S. Patent Publication Nos. 2004/0132028, 2009/0082274, 2011/0118146, and 2011/0224100, incorporated herein by reference, and also see C. Zahnd et al., *Cancer Res.* (2010) 70:1595-1605; Zahnd et al., *J. Biol. Chem.* (2006) 281(46):35167-35175; and Binz, H. K., Amstutz, P. & Pluckthun, A., *Nature Biotechnology* (2005) 23:1257-1268, incorporated herein by reference), an ankyrin-like repeats protein or synthetic peptide (see e.g., U.S. Patent Publication No. 2007/0238667; U.S. Pat. No. 7,101,675; WO 2007/147213; and WO 2007/062466, incorporated herein by reference), an Adnectin (a fibronectin domain scaffold protein; see US Patent Publication Nos. 2007/0082365; 2008/0139791, incorporated herein by reference), Avibody (including diabodies, triabodies, and tetrabodies; see U.S. Publication Nos. 2008/0152586 and 2012/0171115), dual receptor retargeting (DART) molecules (P. A. Moore et al., *Blood,* 2011; 117(17):4542-4551; Veri M C, et al., Arthritis Rheum, 2010 Mar. 30; 62(7):1933-43; Johnson S, et al., *J. Mol. Biol.,* 2010 Apr. 9; 399(3):436-49), cell penetrating supercharged proteins (*Methods in Enzymol.* 502, 293-319 (2012), and other cell-binding molecules or substances.

In certain embodiments, the cell-binding agent may be a ligand that binds to a moiety on the target cell, such as a cell-surface receptor. For example, the ligand may be a growth factor or a fragment thereof that binds to a growth factor receptor; or may be a cytokine or a fragment thereof that binds to a cytokine receptor. In certain embodiments, the growth factor receptor or cytokine receptor is a cell-surface receptor.

In certain embodiments, wherein the cell-binding agent is an antibody or an antigen-binding portion thereof (including antibody derivatives), or certain antibody mimetics, the CBA may bind to a ligand on the target cell, such as a cell-surface ligand, including cell-surface receptors.

Specific exemplary antigens or ligands may include renin; a growth hormone (e.g., human growth hormone and bovine growth hormone); a growth hormone releasing factor; a parathyroid hormone; a thyroid stimulating hormone; a lipoprotein; alpha-1-antitrypsin; insulin A-chain; insulin B-chain; proinsulin; a follicle stimulating hormone; calcitonin; a luteinizing hormone; glucagon; a clotting factor (e.g., factor vmc, factor IX, tissue factor, and von Willebrands factor); an anti-clotting factor (e.g., Protein C); an atrial natriuretic factor; a lung surfactant; a plasminogen activator (e.g., a urokinase, a human urine or tissue-type plasminogen activator); bombesin; a thrombin; hemopoietic growth factor; tumor necrosis factor-alpha and -beta; an enkephalinase; RANTES (i.e., the regulated on activation normally T-cell expressed and secreted); human macrophage inflammatory protein-i-alpha; a serum albumin (human serum albumin); Muellerian-inhibiting substance; relaxin A-chain; relaxin B-chain; prorelaxin; a mouse gonadotropin-associated peptide; a microbial protein (beta-lactamase); DNase; IgE; a cytotoxic T-lymphocyte associated antigen (e.g., CTLA-4); inhibin; activin; a vascular endothelial growth factor; a receptor for hormones or growth factors; protein A or D; a rheumatoid factor; a neurotrophic factor (e.g., bone-derived neurotrophic factor, neurotrophin-3, -4, -5, or -6), a nerve growth factor (e.g., NGF-β); a platelet-derived growth factor; a fibroblast growth factor (e.g., aFGF and bFGF); fibroblast growth factor receptor 2; an epidermal growth factor; a transforming growth factor (e.g., TGF-alpha, TGF-β1, TGF-β2, TGF-β3, TGF-β4, and TGF-β5); insulin-like growth factor-I and -II; des(1-3)-IGF-I (brain IGF-I); an insulin-like growth factor binding protein; melanotransferrin; CA6, CAK1, CALLA, CAECAM5, EpCAM; GD3; FLT3; PSMA; PSCA; MUC1; MUC16; STEAP; CEA; TENB2; an EphA receptor; an EphB receptor; a folate receptor; FOLR1; mesothelin; cripto; an alphav-beta$_6$; integrins; VEGF; VEGFR; EGFR; FGFR3; LAMP1, p-cadherin, transferrin receptor; IRTA1; IRTA2; IRTA3; IRTA4; IRTA5; CD proteins (e.g., CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD123, CD134, CD137, CD138, and CD152), one or more tumor-associated antigens or cell-surface receptors (see US Publication No. 2008/0171040 or US Publication No. 2008/0305044, incorporated in their entirety by reference); erythropoietin; an osteoinductive factor; an immunotoxin; a bone morphogenetic protein; an interferon (e.g., interferon-alpha, -beta, and -gamma); a colony stimulating factor (e.g., M-CSF, GM-CSF, and G-CSF); interleukins (e.g., IL-1 to IL-10); a superoxide dismutase; a T-cell receptor; a surface membrane protein; a decay accelerating factor; a viral antigen s (e.g., a portion of the HIV envelope); a transport protein, a homing receptor; an addressin; a regulatory protein; an integrin (e.g., CD11a, CD11b, CD11c, CD18, an ICAM, VLA-4, and VCAM;) a tumor associated antigen (e.g., HER2, HER3 and HER4 receptor); endoglin; c-Met; c-kit; 1GF1R; PSGR; NGEP; PSMA; PSCA; TMEFF2; LGR5; B7H4; and fragments of any of the above-listed polypeptides.

As used herein, the term "antibody" includes immunoglobulin (Ig) molecules. In certain embodiments, the antibody is a full-length antibody that comprises four polypeptide chains, namely two heavy chains (HC) and two light chains (LC) inter-connected by disulfide bonds. Each heavy chain is comprised of a heavy chain variable region (HCVR or VH) and a heavy chain constant region (CH). The heavy chain constant region is comprised of three domains, CH1, CH2, and CH3. Each light chain is comprised of a light chain variable region (LCVR or VL) and a light chain constant region, which is comprised of one domain, CL. The VH and VL regions can be further subdivided into regions of hypervariability, termed complementarity determining regions (CDRs). Interspersed with such regions are the more conserved framework regions (FRs). Each VH and VL is composed of three CDRs and four FRs, arranged from amino-terminus to carboxy-terminus in the following order: FR1, CDR1, FR2, CDR2, FR3, CDR3, and FR4.

In certain embodiments, the antibody is IgG, IgA, IgE, IgD, or IgM. In certain embodiments, the antibody is IgG1, IgG2, IgG3, or IgG4; or IgA1 or IgA2.

In certain embodiments, the cell-binding agent is an "antigen-binding portion" of a monoclonal antibody, sharing sequences critical for antigen-binding with an antibody (such as huMy9-6 or its related antibodies described in U.S. Pat. Nos. 7,342,110 and 7,557,189, incorporated herein by reference).

As used herein, the term "antigen-binding portion" of an antibody (or sometimes interchangeably referred to as "antibody fragments"), include one or more fragments of an antibody that retain the ability to specifically bind to an antigen. It has been shown that the antigen-binding function of an antibody can be performed by certain fragments of a full-length antibody. Examples of binding fragments encompassed within the term "antigen-binding portion" of an antibody include (without limitation): (i) a Fab fragment, a monovalent fragment consisting of the VL, VH, CL and CH1 domains (e.g., an antibody digested by papain yields three fragments: two antigen-binding Fab fragments, and one Fc fragment that does not bind antigen); (ii) a F(ab')$_2$ fragment, a bivalent fragment comprising two Fab fragments linked by a disulfide bridge at the hinge region (e.g., an antibody digested by pepsin yields two fragments: a bivalent antigen-binding F(ab')$_2$ fragment, and a pFc' fragment that does not bind antigen) and its related F(ab') monovalent unit; (iii) a Fd fragment consisting of the VH and CH1 domains (i.e., that portion of the heavy chain which is included in the Fab); (iv) a Fv fragment consisting of the VL and VH domains of a single arm of an antibody, and the related disulfide linked Fv; (v) a dAb (domain antibody) or sdAb (single domain antibody) fragment (Ward et al., Nature 341:544-546, 1989), which consists of a VH domain; and (vi) an isolated complementarity determining region (CDR). In certain embodiments, the antigen-binding portion is a sdAb (single domain antibody).

In certain embodiments, antigen-binding portion also include certain engineered or recombinant derivatives (or "derivative antibodies") that also include one or more fragments of an antibody that retain the ability to specifically bind to an antigen, in addition to elements or sequences that may not be found in naturally existing antibodies.

For example, although the two domains of the Fv fragment, VL and VH, are coded for by separate genes, they can be joined, using standard recombinant methods, by a synthetic linker that enables them to be made as a single protein chain in which the VL and VH regions pair to form monovalent molecules (known as single chain Fv (scFv); see, e.g., Bird et al. Science 242:423-426, 1988: and Huston et al., Proc. Natl. Acad. Sci. USA 85:5879-5883, 1988).

In all embodiments described herein, the N-terminum of an scFv may be a VH domain (i.e., N-VH-VL-C), or a VL domain (i.e., N-VL-VH-C).

Divalent (or bivalent) single-chain variable fragments (di-scFvs, bi-scFvs) can be engineered by linking two scFvs. This produces a single peptide chain with two VH and two VL regions, yielding a tandem scFvs (tascFv). More tandem repeats, such as tri-scFv, may be similarly produced by linking three or more scFv in a head-to-tail fashion.

In certain embodiments, scFvs may be linked through linker peptides that are too short (about five amino acids) for the two variable regions to fold together, forcing scFvs to dimerize, and form diabodies (see, e.g., Holliger et al., Proc. Natl. Acad. Sci. USA 90:6444-6448, 1993; Poljak et al., Structure 2:1121-1123, 1994). Diabodies may be bi-specific or monospecific. Diabodies have been shown to have dissociation constants up to 40-fold lower than corresponding scFvs, i.e., having a much higher affinity to the target.

Still shorter linkers (one or two amino acids) lead to the formation of trimers, or so-called triabodies or tribodies. Tetrabodies have also been produced similarly. They exhibit an even higher affinity to their targets than diabodies. Diabodies, triabodies, and tetrabodies are sometimes collectively called "AVIBODY™" cell binding agents (or "AVIBODY" in short). That is, AVIBODY having two, three, or four Target Binding Regions (TBRs) are commonly known as Dia-, Tria- and Tetra-bodies. See, for example, U.S. Publication Nos. 2008/0152586 and 2012/0171115 for details, the entire teachings of which are incorporated herein by reference.

All of these formats can be composed from variable fragments with specificity for two or more different antigens, in which case they are types of bi- or multi-specific antibodies. For example, certain bispecific tandem di-scFvs, are known as bi-specific T-cell engagers (BiTEs).

In certain embodiments, each scFv in the tandem scFv or diabody/triabody/tetrabody may have the same or different binding specificity, and each may independently have an N-terminal VH or N-terminal VL.

Single chain Fv (scFv) can also be fused to an Fc moiety, such as the human IgG Fc moiety to obtain IgG-like properties, but nevertheless they are still encoded by a single gene. As transient production of such scFv-Fc proteins in mammalians can easily achieve milligram amounts, this derivative antibody format is particularly suitable for many research applications.

Fcabs are antibody fragments engineered from the Fc constant region of an antibody. Fcabs can be expressed as soluble proteins, or they can be engineered back into a full-length antibody, such as IgG, to create mAb2. A mAb2 is a full-length antibody with an Fcab in place of the normal Fc region. With these additional binding sites, mAb2 bispecific monoclonal antibodies can bind two different targets at the same time.

In certain embodiments, the engineered antibody derivatives have reduced size of the antigen-binding Ig-derived recombinant proteins ("miniaturized" full-size mAbs), produced by removing domains deemed non-essential for function. One of the best examples is SMIPs.

A Small modular immunopharmaceutical, or SMIP, is an artificial protein largely built from parts of antibodies (immunoglobulins), and is intended for use as a pharmaceutical drug. SMIPs have similar biological half-life as antibodies, but are smaller than antibodies and hence may have better tissue penetration properties. SMIPs are single-chain proteins that comprise one binding region, one hinge region as a connector, and one effector domain. The binding region comprises a modified single-chain variable fragment (scFv), and the rest of the protein can be constructed from the Fc (such as CH2, and CH3 as the effector domain) and the hinge region of an antibody, such as IgG1. Genetically modified cells produce SMIPs as antibody-like dimers that are about 30% smaller than real antibodies.

Another example of such engineered miniaturized antibody is "unibody," in which the hinge region has been removed from IgG4 molecules. IgG4 molecules are unstable and can exchange light-heavy chain heterodimers with one another. Deletion of the hinge region prevents heavy chain-heavy chain pairing entirely, leaving highly specific monovalent light/heavy heterodimers, while retaining the Fc region to ensure stability and half-life in vivo.

A single-domain antibody (sdAb, including but not limited to those called nanobody by Ablynx) is an antibody fragment consisting of a single monomeric variable antibody domain. Like a whole antibody, it is able to bind selectively to a specific antigen, but is much smaller due to its molecular weight of only 12-15 kDa. In certain embodiments, the single-domain antibody is engineered from heavy-chain antibodies (hcIgG). The first such sdAb was engineered based on an hcIgG found in camelids, called $V_HH$ fragments. In certain embodiments, the single-domain antibody is engineered from IgNAR ("immunoglobulin new antigen receptor," see below) using a $V_{NAR}$ fragment. Cartilaginous fishes (such as shark) have such heavy-chain IgNAR antibodies. In certain embodiments, the sdAb is engineered by splitting the dimeric variable domains from common immunoglobulin G (IgG), such as those from humans or mice, into monomers. In certain embodiments, a nanobody is derived from a heavy chain variable domain. In certain embodiments, a nanobody is derived from light chain variable domain. In certain embodiments, the sdAb is obtained by screening libraries of single domain heavy chain sequences (e.g., human single domain HCs) for binders to a target antigen.

The single variable new antigen receptor domain antibody fragments ($V_{NARS}$, or $V_{NAR}$ domains) are derived from cartilaginous fish (e.g., shark) immunoglobulin new antigen receptor antibodies (IgNARs). Being one of the smallest known immunoglobulin-based protein scaffolds, such single domain proteins demonstrate favorable size and cryptic epitope recognition properties. Mature IgNAR antibodies consist of homodimers of one variable new antigen receptor ($V_{NAR}$) domain and five constant new antigen receptor ($C_{NAR}$) domains.

This molecule is highly stable, and possesses efficient binding characteristics. Its inherent stability can likely be attributed to both (i) the underlying Ig scaffold, which presents a considerable number of charged and hydrophilic surface exposed residues compared to the conventional antibody VH and VL domains found in murine antibodies; and (ii) stabilizing structural features in the complementary determining region (CDR) loops including inter-loop disulphide bridges, and patterns of intra-loop hydrogen bonds.

A minibody is an engineered antibody fragment comprising an scFv linked to a CH domain, such as the CH3γ1 (CH3 domain of IgG1) or CH4ε (CH4 domain of IgE). For example, an scFv specific for carcinoembryonic antigen (CEA) has been linked to the CH3γ1 to create a minibody, which has previously been demonstrated to possess excellent tumor targeting coupled with rapid clearance in vivo (Hu et al., *Cancer Res.* 56:3055-3061, 1996). The scFv may have a N-terminal VH or VL. The linkage may be a short peptide (e.g., two amino acid linker, such as ValGlu) that results in a non-covalent, hingeless minibody. Alternatively, the linkage may be an IgG1 hinge and a GlySer linker peptide that produces a covalent, hinge-minibody.

Natural antibodies are mono-specific, but bivalent, in that they express two identical antigen-binding domains. In contrast, in certain embodiments, certain engineered antibody derivatives are bi- or multi-specific molecules possess two or more different antigen-binding domains, each with different target specificity. Bispecific antibodies can be generated by fusing two antibody-producing cells, each with distinct specificity. These "quadromas" produced multiple molecular species, as the two distinct light chains and two distinct heavy chains were free to recombine in the quadromas in multiple configurations. Since then, bispecific Fabs, scFvs and full-size mAbs have been generated using a variety of technologies (see above).

The dual variable domain immunoglobulin (DVD-Ig) protein is a type of dual-specific IgG that simultaneously target two antigens/epitopes (DiGiammarino et al., *Methods Mol. Biol.*, 899:145-56, 2012). The molecule contains an Fc region and constant regions in a configuration similar to a conventional IgG. However, the DVD-Ig protein is unique in that each arm of the molecule contains two variable domains (VDs). The VDs within an arm are linked in tandem and can possess different binding specificities.

Trispecific antibody derivative molecules can also been generated by, for example, expressing bispecific antibodies with two distinct Fabs and an Fc. One example is a mouse IgG2a anti-Ep-CAM, rat IgG2b anti-CD3 quadroma, called BiUII, which is thought to permit the co-localization of tumor cells expressing Ep-CAM, T cells expressing CD3, and macrophages expressing FCγRI, thus potentiating the costimulatory and anti-tumor functions of the immune cells.

Probodies are fully recombinant, masked monoclonal antibodies that remain inert in healthy tissue, but are activated specifically in the disease microenvironment (e.g., through protease cleavage by a protease enriched or specific in a disease microenvironment). See Desnoyers et al., *Sci. Transl. Med.*, 5:207ra144, 2013. Similar masking techniques can be used for any of the antibodies or antigen-binding portions thereof described herein.

An intrabody is an antibody that has been modified for intracellular localization, for working within the cell to bind to an intracellular antigen. The intrabody may remain in the cytoplasm, or may have a nuclear localization signal, or may have a KDEL (SQ ID NO: 33) sequence for ER targeting. The intrabody may be a single-chain antibody (scFv), modified immunoglobulin VL domains with hyperstability, selected antibody resistant to the more reducing intracellular environment, or expressed as a fusion protein with maltose binding protein or other stable intracellular proteins. Such optimizations have improved the stability and structure of intrabodies, and may have general applicability to any of the antibodies or antigen-binding portions thereof described herein.

The antigen-binding portions or derivative antibodies of the invention may have substantially the same or identical (1) light chain and/or heavy chain CDR3 regions; (2) light chain and/or heavy chain CDR1, CDR2, and CDR3 regions; or (3) light chain and/or heavy chain regions, compared to an antibody from which they are derived/engineered. Sequences within these regions may contain conservative amino acid substitutions, including substitutions within the CDR regions. In certain embodiments, there is no more than 1, 2, 3, 4, or 5 conservative substitutions. In an alternative, the antigen-binding portions or derivative antibodies have a light chain region and/or a heavy chain region that is at least about 90%, 95%, 99% or 100% identical to an antibody from which they are derived/engineered. These antigen-binding portions or derivative antibodies may have substantially the same binding specificity and/or affinity to the target antigen compared to the antibody. In certain embodiments, the $K_d$ and/or $k_{off}$ values of the antigen-binding portions or derivative antibodies are within 10-fold (either higher or lower), 5-fold (either higher or lower), 3-fold (either higher or lower), or 2-fold (either higher or lower) of an antibody described herein.

In certain embodiments, the antigen-binding portions or derivative antibodies may be derived/engineered from fully human antibodies, humanized antibodies, or chimeric antibodies, and may be produced according to any art-recognized methods.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antibodies and humanized antibodies.

Cell-binding agent can also be peptides derived from phage display (see, for example, Wang et al., *Proc. Natl. Acad. Sci. USA* (2011) 108(17), 6909-6914) or peptide library techniques (see, for example, Dane et al., *Mol. Cancer. Ther.* (2009) 8(5):1312-1318).

In certain embodiments, the CBA of the invention also includes an antibody mimetic, such as a DARPin, an affibody, an affilin, an affitin, an anticalin, an avimer, a Fynomer, a Kunitz domain peptide, a monobody, or a nanofitin.

As used herein, the terms "DARPin" and "(designed) ankyrin repeat protein" are used interchangeably to refer to certain genetically engineered antibody mimetic proteins typically exhibiting preferential (sometimes specific) target binding. The target may be protein, carbohydrate, or other chemical entities, and the binding affinity can be quite high.

The DARPins may be derived from natural ankyrin repeat-containing proteins, and preferably consist of at least three, usually four or five ankyrin repeat motifs (typically about 33 residues in each ankyrin repeat motif) of these proteins. In certain embodiments, a DARPin contains about four- or five-repeats, and may have a molecular mass of about 14 or 18 kDa, respectively. Libraries of DARPins with randomized potential target interaction residues with diversities of over $10^{12}$ variants can be generated at the DNA level, for use in selecting DARPins that bind desired targets (e.g., acting as receptor agonists or antagonists, inverse agonists, enzyme inhibitors, or simple target protein binders) with picomolar affinity and specificity, using a variety of technologies such as ribosome display or signal recognition particle (SRP) phage display. See, for example, U.S. Patent Publication Nos. 2004/0132028, 2009/0082274, 2011/0118146, and 2011/0224100, WO 02/20565 and WO 06/083275 for DARPin preparation (the entire teachings of which are incorporated herein by reference), and also see C. Zahnd et al. (2010) *Cancer Res.*, 70:1595-1605; Zahnd et al. (2006) *J. Biol. Chem.*, 281(46):35167-35175; and Binz, H. K., Amstutz, P. & Pluckthun, A. (2005) *Nature Biotechnology*, 23:1257-1268 (all incorporated herein by reference). Also see U.S. Patent Publication No. 2007/0238667; U.S. Pat. No. 7,101,675; WO 2007/147213; and WO 2007/062466 (the entire teachings of which are incorporated herein by reference), for the related ankyrin-like repeats protein or synthetic peptide.

Affibody molecules are small proteins engineered to bind to a large number of target proteins or peptides with high affinity, thus imitating monoclonal antibodies. An Affibody consists of three alpha helices with 58 amino acids and has a molar mass of about 6 kDa. They have been shown to withstand high temperatures (90° C.) or acidic and alkaline conditions (pH 2.5 or pH 11), and binders with an affinity of down to sub-nanomolar range have been obtained from naïve library selections, and binders with picomolar affinity have been obtained following affinity maturation. In certain embodiments, affibodies are conjugated to weak electrophiles for binding to targets covalently.

Monobodies (also known as Adnectins), are genetically engineered antibody mimetic proteins capable of binding to antigens. In certain embodiments, monobodies consist of 94 amino acids and have a molecular mass of about 10 kDa. They are based on the structure of human fibronectin, more specifically on its tenth extracellular type III domain, which has a structure similar to antibody variable domains, with seven beta sheets forming a barrel and three exposed loops on each side corresponding to the three complementarity determining regions. Monobodies with specificity for different proteins can be tailored by modifying the loops BC (between the second and third beta sheets) and FG (between the sixth and seventh sheets).

A tribody is a self-assembly antibody mimetic designed based on the C-terminal coiled-coil region of mouse and human cartilage matrix protein (CMP), which self-assembles into a parallel trimeric complex. It is a highly stable trimeric targeting ligand created by fusing a specific target-binding moiety with the trimerization domain derived from CMP. The resulting fusion proteins can efficiently self-assemble into a well-defined parallel homotrimer with high stability. Surface plasmon resonance (SPR) analysis of the trimeric targeting ligands demonstrated significantly enhanced target-binding strength compared with the corresponding monomers. Cellular-binding studies confirmed that such tribodies have superior binding strength toward their respective receptors.

A Centyrin is another antibody mimetic that can be obtained using a library built upon the framework of a consensus FN3 domain sequence (Diem et al., *Protein Eng. Des. Sel.*, 2014). This library employs diversified positions within the C-strand, CD-loop, F-strand and FG-loop of the FN3 domain, and high-affinity Centyrin variants can be selected against specific targets.

In some embodiments, the cell-binding agent is an anti-folate receptor antibody. More specifically, the anti-folate receptor antibody is a humanized antibody or antigen binding fragment thereof that specifically binds a human folate receptor 1 (also known as folate receptor alpha (FR-α)). The terms "human folate receptor 1," "FOLR1," or "folate receptor alpha (FR-α)", as used herein, refers to any native human FOLR1, unless otherwise indicated. Thus, all of these terms can refer to either a protein or nucleic acid sequence as indicated herein. The term "FOLR1" encompasses "full-length," unprocessed FOLR1 as well as any form of FOLR1 that results from processing within the cell. The FOLR1 antibody comprises: (a) a heavy chain CDR1 comprising GYFMN (SEQ ID NO: 4); a heavy chain CDR2 comprising RIHPYDGDTFYNQXaa$_1$FXaa$_2$Xaa$_3$ (SEQ ID NO: 5); and a heavy chain CDR3 comprising YDGSRAMDY (SEQ ID NO: 6); and (b) a light chain CDR1 comprising KASQSVSFAGTSLMH (SEQ ID NO: 7); a light chain CDR2 comprising RASNLEA (SEQ ID NO: 8); and a light chain CDR3 comprising QQSREYPYT (SEQ ID NO: 9); wherein Xaa$_1$ is selected from K, Q, H, and R; Xaa$_2$ is selected from Q, H, N, and R; and Xaa$_3$ is selected from G, E, T, S, A, and V. Preferably, the heavy chain CDR2 sequence comprises RIHPYDGDTFYNQKFQG (SEQ ID NO: 10).

In another embodiment, the anti-folate receptor antibody is a humanized antibody or antigen binding fragment thereof that specifically binds the human folate receptor 1 comprising the heavy chain having the amino acid sequence of (SEQ ID NO: 11)
QVQLVQSGAEVVKPGASVKISCKASGYTFTGYFMNWVKQSPGQSLEWIGR

IHPYDGDTFYNQKFQGKATLTVDKSSNTAHMELLSLTSEDFAVYYCTRYD

GSRAMDYWGQGTTVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK.

In another embodiment, the anti-folate antibody receptor is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof that specifically binds the human folate receptor 1 comprising the light chain having the amino acid sequence of (SEQ ID NO: 12)
DIVLTQSPLSLAVSLGQPAIISCKASQSVSFAGTSLMHWYHQKPGQQPRL

LIYRASNLEAGVPDRFSGSGSKTDFTLNISPVEAEDAATYYCQQSREYPY

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC;
or
(SEQ ID NO: 13)
DIVLTQSPLSLAVSLGQPAIISCKASQSVSFAGTSLMHWYHQKPGQQPRL

LIYRASNLEAGVPDRFSGSGSKTDFTLTISPVEAEDAATYYCQQSREYPY

TFGGGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC.

In another embodiment the anti-folate receptor antibody is a humanized antibody or antigen binding fragment thereof that specifically binds the human folate receptor 1 comprising the heavy chain having the amino acid sequence of SEQ ID NO: 11, and the light chain having the amino acid sequence of SEQ ID NO: 12 or SEQ ID NO: 13. Preferably, the antibody comprises the heavy chain having the amino acid sequence of SEQ ID NO: 11 and the light chain having the amino acid sequence of SEQ ID NO: 13 (hu FOLR1).

In another embodiment, the anti-folate receptor antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate receptor antibody is a humanized antibody or antigen binding fragment thereof that specifically binds the human folate receptor 1, and comprising a heavy chain variable domain at least about 90%, 95%, 99% or 100% identical to IDC-490 DNA M (SEQ ID NO: 14)
QVQLVQSGAEVVKPGASVKISCKASGYTFTGYFMNWVKQSPGQSLEWIGR

IHPYDGDTFYNQKFQGKATLTVDKSSNTAHMELLSLTSEDFAVYYCTRYD

GSRAMDYWGQGTTVTVSS, and a light chain variable domain at least about 90%, 95%, 99% or 100% identical to (SEQ ID NO: 15)
DIVLTQSPLSLAVSLGQPAIISCKASQSVSFAGTSLMHWYHQKPGQQPRL

LIYRASNLEAGVPDRFSGSGSKTDFTLNISPVEAEDAATYYCQQSREYPY

TFGGGTKLEIKR;
or
(SEQ ID NO: 16)
DIVLTQSPLSLAVSLGQPAIISCKASQSVSFAGTSLMHWYHQKPGQQPRL

LIYRASNLEAGVPDRFSGSGSKTDFTLTISPVEAEDAATYYCQQSREYPY

TFGGGTKLEIKR.

In another embodiment, the anti-folate receptor antibody is huMov19 or M9346A (see, for example, U.S. Pat. Nos. 8,709,432, 8,557,966, and WO2011106528, all incorporated herein by reference).

In another embodiment, the cell-binding agent is an anti-EGFR antibody or an antibody fragment thereof. In some embodiments, the anti-EGFR antibody is a non-antagonist antibody, including, for example, the antibodies described in WO2012058592, herein incorporated by reference. In another embodiment, the anti-EGFR antibody is a non-functional antibody, for example, humanized ML66 or EGFR-8. More specifically, the anti-EGFR antibody is huML66.

In yet another embodiment, the anti-EGFR antibody comprising the heavy chain having the amino acid sequence of SEQ ID NO: 17, and the light chain having the amino acid sequence of SEQ ID NO: 18. As used herein, double underlined sequences represent the variable regions (i.e., heavy chain variable region or HCVR, and light chain variable region or LCVR) of the heavy or light chain sequences, while bold sequences represent the CDR regions (i.e., from N-terminal to C-terminal, CDR1, CDR2, and CDR3, respectively, of the heavy chain or light chain sequences).

| Antibody | Full-Length Heavy/Light Chain Amino Acid Sequence |
|---|---|
| huML66HC | QVQLQESGPGLVKPSETLSLTCTVSGLSLASNSVSWIRQPPGKGLEWMGVIWNHG GTDYNPSIKSRLSISRDTSKSQVFLKMNSLTAADTAMYFCVRKGGIYFDYWGQGV LVTVSS ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDKKVEPKSCDKT HTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQPEN NYKTTPPVLDSDGSFFLYSKLTVDKSRWQQGNVFSCSVMHEALHNHYTQKSLSLSPG (SEQ ID NO: 17) |
| huML66LC | DTVLTQSPSLAVSPGERATISCRASESVSTLMHWYQQKPGQQPKLLIYLASHRESG VPARFSGSGSGTDFTLTIDPMEAEDTATYYQQSRNDPWTFGQGTKLELKR TVAA PSVFIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGEC (SEQ ID NO: 18) |

In yet another embodiment, the anti-EGFR antibody comprises the heavy chain CDR1-CDR3 of SEQ ID NO: 17, and/or the light chain CDR1-CDR3 of SEQ ID NO: 18, and preferably specifically binds EGFR.

In yet another embodiment, the anti-EGFR antibody comprises a heavy chain variable region (HCVR) sequence at least about 90%, 95%, 97%, 99%, or 100% identical to SEQ ID NO: 17, and/or a light chain variable region (LCVR) sequence at least about 90%, 95%, 97%, 99%, or 100% identical to SEQ ID NO: 18, and preferably specifically binds EGFR.

In another embodiment, the anti-EGFR antibody are antibodies described in 8,790,649 and WO 2012/058588, herein incorporated by reference. In some embodiments, the anti-EGFR antibody is huEGFR-7R antibody.

In some embodiments, the anti-EGFR antibody comprises an immunoglobulin heavy chain region having the amino acid sequence of (SEQ ID NO: 19)
QVQLVQSGAEVAKPGASVKLSCKASGYTFTSYWMQWVKQRPGQGLECIGTIYPGD GDTTYTQKFQGKATLTADKSSSTAYMQLSSLRSEDSAVYYCARYDAPGYAMDYW GQGTLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFNWYV DGVEVHNAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESNGQPENNYKTTP PVLDSDGSFFLYSKLTVDKSRWQQGNVFSCSVMHEALHNHYTQKSLSLSPG and an immunoglobulin light chain region having the amino acid sequence of (SEQ ID NO: 20)
DIQMTQSPSSLSASVGDRVTITCRASQDINNYLAWYQHKPGKGPKLLIHYTSTLHPG IPSRFSGSGSGR DYSFSISSLEPEDIATYYCLQYDNLLYTFGQGTKLEIKR TVAAPSVFI

```
FPPSDEQLKSGTASVVCLLNNFYPREAKVQWKVDNALQSGNSQESVTEQDSKDSTYSLSSTL

TLSKADYEKHKVYACEVTHQGLSSPVTKSFNRGEC,
``` of an immunoglobulin light chain region having the amino acid sequence of

```
                                              (SEQ ID NO: 21)
DIQMTQSPSSLSASVGDRVTITCKASQDINNYLAWYQHKPGKGPKLLIHYTSTLHPG

IPSRFSGSGSGR DYSFSISSLEPEDIATYYCLQYDNLLYTFGQGTKLEIKR TVAAPSVFI

FPPSDEQLKSGTASVVCLLNNFYPREAKVQWKVDNALQSGNSQESVTEQDSKDSTY

SLSSTLTLSKADYEKHKVYACEVTHQGLSSPVTKSFNRGEC.
```

In another embodiment, the anti-EGFR antibody comprises an immunoglobulin heavy chain region having the amino acid sequence set forth in SEQ ID NO:19 and an immunoglobulin light chain region having the amino acid sequence set forth in SEQ ID NO:20.

In another embodiment, the anti-EGFR antibody comprises an immunoglobulin heavy chain region having the amino acid sequence set forth in SEQ ID NO:19 and an immunoglobulin light chain region having the amino acid sequence set forth in SEQ ID NO:21.

In yet another embodiment, the anti-EGFR antibody comprises the heavy chain CDR1-CDR3 of SEQ ID NO: 19, and/or the light chain CDR1-CDR3 of SEQ ID NO: 20 or 21, and preferably specifically binds EGFR.

In yet another embodiment, the anti-EGFR antibody comprises a heavy chain variable region (HCVR) sequence at least about 90%, 95%, 97%, 99%, or 100% identical to SEQ ID NO: 19, and/or a light chain variable region (LCVR) sequence at least about 90%, 95%, 97%, 99%, or 100% identical to SEQ ID NO: 20 or 21, and preferably specifically binds EGFR.

In another embodiment, the cell-binding agent is an anti-CD19 antibody, such as those described in U.S. Pat. No. 8,435,528 and WO2004/103272, herein incorporated by reference. In some embodiments, the anti-CD19 antibody comprises an immunoglobulin heavy chain region having the amino acid sequence of

```
                                              (SEQ ID NO: 22)
QVQLVQPGAEVVKPGASVKLSCKTSGYTFTSNWMHWVKQAPGQGLEWIGE

IDPSDSYTNYNQNFQGKAKLTVDKSTSTAYMEVSSLRSDDTAVYYCARGS

NPYYYAMDYWGQGTSVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

-continued
KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK
``` and an immunoglobulin light chain region having the amino acid sequence of

```
                                              (SEQ ID NO: 23)
EIVLTQSPAIMSASPGERVTMTCSASSGVNYMHWYQQKPGTSPRRWIYDT

SKLASGVPARFSGSGSGTDYSLTISSMEPEDAATYYCHQRGSYTFGGGTK

LEIKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSS

PVTKSFNRGEC.
```

In another embodiment, the anti-CD19 antibody is huB4 antibody.

In yet another embodiment, the anti-CD19 antibody comprises the heavy chain CDR1-CDR3 of SEQ ID NO: 22, and/or the light chain CDR1-CDR3 of SEQ ID NO: 23, and preferably specifically binds CD19.

In yet another embodiment, the anti-CD19 antibody comprises a heavy chain variable region (HCVR) sequence at least about 90%, 95%, 97%, 99%, or 100% identical to SEQ ID NO: 22, and/or a light chain variable region (LCVR) sequence at least about 90%, 95%, 97%, 99%, or 100% identical to SEQ ID NO: 23, and preferably specifically binds CD19.

In yet another embodiment, the cell-binding agent is an anti-Muc antibody, such as those described in U.S. Pat. No. 7,834,155, WO 2005/009369 and WO 2007/024222, herein incorporated by reference. In some embodiments, the anti-Muc antibody comprises an immunoglobulin heavy chain region having the amino acid sequence of

```
                                              (SEQ ID NO: 24)
QAQLVQSGAEVVKPGASVKMSCKASGYTFTSYNMHWVKQTPGQGLEWQGYIYPG

NGATNYNQKFQGKATLTADTSSSTAYMQISSLTSEDSAVYFCARGDSVPFAYWGQ

GTLVTVSAASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVD
```

```
GVEVHNAKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPGK
``` and an immunoglobulin light chain region having the amino acid sequence of

```
                                               (SEQ ID NO: 25)
EIVLTQSPATMSASPGERVTITCSAHSSVSFMHWFQQKPGTSPKLWIYSTSSLASGVP

AREGGSGSGTSYSLTISSMEAEDAATYYCQQRSSFPLTFGAGTKLELKRTVAAPSVFIFP

PSDEQLKSGTASVVCLLNNFYPREAKVQWKVDNALQSGNSQESVTEQDSKDSTYSLSSTLT

LSKADYEKHKVYACEVTHQGLSSPVTKSFNRGEC.
```

In another embodiment, the anti-Muc1 antibody is huDS6 antibody.

In yet another embodiment, the anti-Muc1 antibody comprises the heavy chain CDR1-CDR3 of SEQ ID NO: 24, and/or the light chain CDR1-CDR3 of SEQ ID NO: 25, and preferably specifically binds Muc1.

In yet another embodiment, the anti-Muc antibody comprises a heavy chain variable region (HCVR) sequence at least about 90%, 95%, 97%, 99%, or 100% identical to SEQ ID NO: 24, and/or a light chain variable region (LCVR) sequence at least about 90%, 95%, 97%, 99%, or 100% identical to SEQ ID NO: 25, and preferably specifically binds Muc1.

In another embodiment, the cell-binding agent is an anti-CD33 antibody or fragment thereof, such as the antibodies or fragments thereof described in U.S. Pat. Nos. 7,557,189, 7,342,110, 8,119,787 and 8,337,855 and WO2004/043344, herein incorporated by reference. In another embodiment, the anti-CD33 antibody is huMy9-6 antibody.

In some embodiments, the anti-CD33 antibody comprises an immunoglobulin heavy chain region having the amino acid sequence of

```
                                               (SEQ ID NO: 26)
QVQLQQPGAEVVKPGASVKMSCKASGYTFTSYYIHWIKQTPGQGLEWVGVIYPGN

DDISYNQKFQGKATLTADKSSTTAYMQLSSLTSEDSAVYYCAREVRLRYFDVWGQ

GTTVTVSSASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKVEPKSCDKTHTCP

PCPAPELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLDSDGSFFLYSKL

TVDKSRWQQGNVFSCSVMHEALHNHYTQKSLSLSPG,
``` and an immunoglobulin light chain region having the amino acid sequence of

```
                                               (SEQ ID NO: 27)
EIVLTQSPGSVSPGERVTMSCKSSQSVFFSSSQKNYLAWYQQIPGQSPRLLIYWA

STRESGVPDRFTGSGSGTDFTLTISSVQPEDLAIYYCHQYLSSRTFGQGTKLEIKRTV

AAPSVFIFPPSDEQLKSGTASVVCLLNNFYPREAKVQWKVDNALQSGNSQESVTEQDSKD

STYSLSSTLTLSKADYEKHKVYACEVTHQGLSSPVTKSFNRGEC.
```

In yet another embodiment, the anti-CD33 antibody comprises the heavy chain CDR1-CDR3 of SEQ ID NO: 26, and/or the light chain CDR1-CDR3 of SEQ ID NO: 27, and preferably specifically binds CD33.

In yet another embodiment, the anti-CD33 antibody comprises a heavy chain variable region (HCVR) sequence at least about 90%, 95%, 97%, 99%, or 100% identical to SEQ ID NO: 26, and/or a light chain variable region (LCVR)

sequence at least about 90%, 95%, 97%, 99%, or 100% identical to SEQ ID NO: 27, and preferably specifically binds CD33.

In another embodiment, the cell-binding agent is an anti-CD37 antibody or an antibody fragment thereof, such as those described in U.S. Pat. No. 8,765,917 and WO 2011/112978, herein incorporated by reference. In some embodiments, the anti-CD37 antibody is huCD37-3 antibody.

In some embodiments, the anti-CD37 antibody comprises an immunoglobulin light chain region having the amino acid sequence of (SEQ ID NO: 28)
DIQMTQSPSSLSVSVGERVTITCRASENIRSNLAWYQQKPGKSPKLLVNVATNLADGVPS
RFSGSGSGTDY SLKINSLQPEDFGTYYCQHYWGTTWTFGQGTKLEIKR TVAAPSVFIFPP
SDEQLKSGTASVVCLLNNFYPREAKVQWKVDNALQSGNSQESVTEQDSKDSTYSLSSTLTLS
KADYEKHKVYACEVTHQGLSSPVTKSFNRGEC an immunoglobulin heavy chain region having the amino acid sequence of (SEQ ID NO: 29)
QVQVQESGPGLVAPSQTLSITCTVSGFSLTTSGVSWVRQPPGKGLEWLG**VIWGDGS
TNYHPSLKSRLSIKKDHSKSQVFLKLNSLTAADTATYYCAKGGYSLAH**WGQGTLVTVSS
ASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPG, or an immunoglobulin heavy chain region having the amino acid sequence of (SEQ ID NO: 30)
QVQVQESGPLVAPSQTLSITCTVSGFSLTTSGVSWVRQPPGKGLEWLG**VIWGDGS
TNYHSSLKSRLSIKKDHSKSQVFLKLNSLTAADTATYYCAKGGYSLAH**WGQGTLVT
VSSASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQP
REPQVYTLPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPG In another embodiment, the anti-CD37 antibody comprises an immunoglobulin light chain region having the amino acid sequence set forth in SEQ ID NO:28 and an immunoglobulin heavy chain region having the amino acid sequence set forth in SEQ ID NO:29.

In yet another embodiment, the anti-CD37 antibody comprises an immunoglobulin light chain region having the amino acid sequence set forth in SEQ ID NO:28 and an immunoglobulin heavy chain region having the amino acid sequence set forth in SEQ ID NO:30.

In yet another embodiment, the anti-CD37 antibody comprises the heavy chain CDR1-CDR3 of SEQ ID NO: 29 or 30, and/or the light chain CDR1-CDR3 of SEQ ID NO: 28, and preferably specifically binds CD37.

In yet another embodiment, the anti-CD37 antibody comprises a heavy chain variable region (HCVR) sequence at least about 90%, 95%, 97%, 99%, or 100% identical to SEQ ID NO: 29 or 30, and/or a light chain variable region (LCVR) sequence at least about 90%, 95%, 97%, 99%, or 100% identical to SEQ ID NO: 28, and preferably specifically binds CD37.

In yet another embodiment, the anti-CD37 antibody comprises an immunoglobulin light chain region having the amino acid sequence of In certain embodiments, the oxidizing agent is a periodate. More specifically, the oxidizing agent is sodium periodate.

Excess molar equivalents of the oxidizing agent relative to the cell-binding agent can be used. In certain embodiments, about 2-100, 5-80, 10-50, 1-10 or 5-10 molar equivalents of the oxidizing agent can be used. In certain embodiments, about 10 or about 50 equivalents of the oxidizing agent can be used. When large amount of the oxidizing agent is used, short reaction time is used to avoid over-oxidation.

which can be oxidized with an oxidizing agent to form an oxidized cell-binding agent having a N-terminal aldehyde group.

Any suitable oxidizing agent can be used in step (a) of the methods described above. For example, when 50 equivalents of the oxidizing agent is used, the oxidation reaction is carried out for about 5 to about 60 minutes. Alternatively, when 10 equivalents of the oxidizing agent is used, the reaction is carried out for about 30 minutes to about 24 hours. In some embodiments, 5-10 molar equivalents of the oxidizing agent is used and the oxidation reaction is carried out for about 5 to about 60 minutes (e.g., about 10 to about 30 minutes, about 20 to about 30 minutes).

In certain embodiments, the oxidation reaction does not lead to significant non-targeted oxidation. For example, no signification extent (e.g., less than 20%, less than 10%, less than 5%, less than 3%, less than 2% or less than 1%) of methionine and/or glycans are oxidized during the oxidation process of N-terminal serine to generate the oxidized cell-binding agent having a N-terminal aldehyde group.

```
                                                          (SEQ ID NO: 31)
EIVLTQSPATMSASPGERVTMTCSATSSVTYMHWYQQKPGQSPKRWIYDTSNLPYG

VPARFSGSGSGTSYSLTISSMEAEDAATYYCQQWSDNPPTFGQGTKLEIKRTVAAPSVFIF

PPSDEQLKSGTASVVCLLNNFYPREAKVQWKVDNALQSGNSQESVTEQDSKDSTYSLSSTL

TLSKADYEKHKVYACEVTHQGLSSPVTKSFNRGEC
``` and an immunoglobulin heavy chain region having the amino acid sequence of

In certain embodiments, the cell-binding agent of the present invention (e.g., antibody) have a recombinantly

```
                                                          (SEQ ID NO: 32)
QVQLQESGPGLLKPSQSLSLTCTVSGYSITSGFAWHWIRQHPGNKLEWMGYILYSG

STVYSPSLKSRISITRDTSKNHFFLQLNSVTAADTATYYCARGYYGYGAWFAYWGQ

GTLVTVSAASTKGPSVFPLAPSSKSTSGGTAALGCLVKDYFPEPVTVSWNSGALTSGVHTF

PAVLQSSGLYSLSSVVTVPSSSLGTQTYICNVNHKPSNTKVDKKVEPKSCDKT

HTCPPCPAPELLGGPSVFLFPPKPKDTLMISRTPEVTCVVVDVSHEDPEVKFNWYVD

GVEVHNAKTKPREEQYNSTYRVVSVLTVLHQDWLNGKEYKCKVSNKALPAPIEKTI

SKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG.
```

In yet another embodiment, the anti-CD37 antibody comprises the heavy chain CDR1-CDR3 of SEQ ID NO: 32, and/or the light chain CDR1-CDR3 of SEQ ID NO: 31, and preferably specifically binds CD37.

In yet another embodiment, the anti-CD37 antibody comprises a heavy chain variable region (HCVR) sequence at least about 90%, 95%, 97%, 99%, or 100% identical to SEQ ID NO: 32, and/or a light chain variable region (LCVR) sequence at least about 90%, 95%, 97%, 99%, or 100% identical to SEQ ID NO: 31, and preferably specifically binds CD37.

In yet another embodiment, the anti-CD37 antibody is huCD37-50 antibody.

In certain embodiments, the cell-binding agent of the present invention (e.g., antibody) have a N-terminal serine, engineered Cys residue, such as a Cys residue at EU/OU numbering position 442 of the antibody. Thus the term "cysteine engineered antibody" includes an antibody with at least one Cys that is not normally present at a given residue of the antibody light chain or heavy chain. Such Cys, which may also be referred to as "engineered Cys," can be engineered using any conventional molecular biology or recombinant DNA technology (e.g., by replacing the coding sequence for a non-Cys residue at the target residue with a coding sequence for Cys). For example, if the original residue is Ser with a coding sequence of 5'-UCU-3', the coding sequence can be mutated (e.g., by site-directed mutagenesis) to 5'-UGU-3', which encodes Cys. In certain embodiments, the Cys engineered antibody of the invention has an engineered Cys in the heavy chain. In certain embodiments, the engineered Cys is in or near the $CH_3$ domain of the heavy chain. The engineered antibody heavy (or light) chain sequence can be inserted into a suitable recombinant expression vector to produce the engineered antibody having the engineered Cys residue in place of the original Ser residue.

Production of Cell-Binding Agent-Drug Conjugates

In order to link the cytotoxic compounds or derivative thereof of the present invention to the cell-binding agent, the cytotoxic compound can comprise a linking moiety with a reactive group bonded thereto. These compounds can be directly linked to the cell-binding agent. Representative processes for linking the cytotoxic compounds having a reactive group bonded thereof with the cell-binding agent to produce the cell-binding agent-cytotoxic agent conjugates are described in Example 1.

In some embodiments, a bifunctional crosslinking reagent can be first reacted with the cytotoxic compound to provide the compound bearing a linking moiety with one reactive group bonded thereto (i.e., drug-linker compound), which can then react with a cell binding agent. Alternatively, one end of the bifunctional crosslinking reagent can first react with the cell binding agent to provide the cell binding agent bearing a linking moiety with one reactive group bonded thereto, which can then react with a cytotoxic compound. The linking moiety can contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 2005/0169933, or charged linkers or hydrophilic linkers and are described in US 2009/0274713, US 2010/01293140 and WO 2009/134976, each of which is expressly incorporated herein by reference, each of which is expressly incorporated herein by reference.

In some embodiments, a solution of a cell-binding agent (e.g., an antibody) in aqueous buffer may be incubated with a molar excess of a bifunctional crosslinking agent, such as N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to introduce dithiopyridyl groups. The modified cell-binding agent (e.g., modified antibody) is then reacted with the thiol-containing cytotoxic compound described herein, to produce a disulfide-linked cell-binding agent-cytotoxic agent conjugate of the present invention.

In another embodiment, the thiol-containing cytotoxic compound described herein, can react with a bifunctional crosslinking agent such as N-succinimidyl-4-(2-pyridyldithio)pentanoate (SPP), N-succinimidyl-4-(2-pyridyldithio)butanoate (SPDB), N-succinimidyl-4-(2-pyridyldithio)2-sulfo butanoate (sulfo-SPDB) to form a cytotoxic agent-linker compound, which can then react with a cell-biding agent to produce a disulfide-linked cell-binding agent-cytotoxic agent conjugate of the present invention. The cytotoxic agent-linker compound can be prepared in situ without purification before reacting with the cell-binding agent. Alternatively, the cytotoxic agent-linker compound can be purified prior to reacting with the cell-binding agent.

The cell binding agent-cytotoxic agent conjugate may be purified using any purification methods known in the art, such as those described in U.S. Pat. No. 7,811,572 and US Publication No. 2006/0182750, both of which are incorporated herein by reference.

For example, the cell-binding agent-cytotoxic agent conjugate can be purified using tangential flow filtration, adsorptive chromatography, adsorptive filtration, selective precipitation, non-absorptive filtration or combination thereof. Preferably, tangential flow filtration (TFF, also known as cross flow filtration, ultrafiltration and diafiltration) and/or adsorptive chromatography resins are used for the purification of the conjugates.

Alternatively, the cell-binding agent (e.g., an antibody) may be incubated with a molar excess of an antibody modifying agent such as 2-iminothiolane, L-homocysteine thiolactone (or derivatives), or N-succinimidyl-S-acetylthioacetate (SATA) to introduce sulfhydryl groups. The modified antibody is then reacted with the appropriate disulfide-containing cytotoxic agent, to produce a disulfide-linked antibody-cytotoxic agent conjugate. The antibody-cytotoxic agent conjugate may then be purified by methods described above. The cell binding agent may also be engineered to introduce thiol moieties, such as cysteine-engineered antibodies disclosed in U.S. Pat. Nos. 7,772,485 and 7,855,275.

In another embodiment, a solution of a cell-binding agent (e.g., an antibody) in aqueous buffer may be incubated with a molar excess of an antibody-modifying agent such as N-succinimidyl-4-(N-maleimidomethyl)-cyclohexane-1-carboxylate to introduce maleimido groups, or with N-succinimidyl-4-(iodoacetyl)-aminobenzoate (SIAB) to introduce iodoacetyl groups. The modified cell-binding agent (e.g., modified antibody) is then reacted with the thiol-containing cytotoxic agent to produce a thioether-linked cell-binding agent-cytotoxic agent conjugate. The conjugate may then be purified by methods described above.

The number of cytotoxic molecules bound per antibody molecule can be determined spectrophotometrically by measuring the ratio of the absorbance at 280 nm and 330 nm. In some embodiments, an average of 1-10 cytotoxic compounds/antibody molecule(s) can be linked by the methods described herein. In some embodiments, the average number of linked cytotoxic compounds per antibody molecule is 2-5, and more specifically 2.5-4.0.

In some embodiments, when the antibody is linked to the cytotoxic agent through a cysteine thiol group, the conjugate has 1 or 2 cytotoxic compounds per antibody molecule. Similarly, when the antibody is linked to the cytotoxic agent through an aldehyde group, the conjugate has 1 or 2 cytotoxic compounds per antibody molecule.

Representative processes for preparing the cell-binding agent-drug conjugates of the present invention are described in 8,765,740 and U.S. Application Publication No. 2012/0238731. The entire teachings of these references are incorporated herein by reference.

Compositions and Methods of Use

The present invention includes a composition (e.g., a pharmaceutical composition) comprising the cytotoxic compounds described herein, derivatives thereof, or conjugates thereof, (and/or solvates, hydrates and/or salts thereof) and a carrier (a pharmaceutically acceptable carrier). The present invention also includes a composition (e.g., a pharmaceutical composition) comprising the cytotoxic compounds described herein, derivatives thereof, or conjugates thereof, (and/or solvates, hydrates and/or salts thereof) and a carrier (a pharmaceutically acceptable carrier), further comprising a second therapeutic agent. The present compositions are useful for inhibiting abnormal cell growth or treating a proliferative disorder in a mammal (e.g., human). The present compositions are also useful for treating depression, anxiety, stress, phobias, panic, dysphoria, psychiatric disorders, pain, and inflammatory diseases in a mammal (e.g., human).

The present invention includes a method of inhibiting abnormal cell growth or treating a proliferative disorder in a mammal (e.g., human) comprising administering to said mammal a therapeutically effective amount of cytotoxic compounds described herein, derivatives thereof, or conjugates thereof, (and/or solvates and salts thereof) or a composition thereof, alone or in combination with a second therapeutic agent.

The present invention also provides methods of treatment comprising administering to a subject in need of treatment an effective amount of any of the conjugates described above.

Similarly, the present invention provides a method for inducing cell death in selected cell populations comprising contacting target cells or tissue containing target cells with an effective amount of a cytotoxic agent comprising any of the cytotoxic compound-cell-binding agents of the present invention, a salt or solvate thereof. The target cells are cells to which the cell-binding agent can bind.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/mL to 25 mg/mL human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 μM to 1 μM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 mL of normal saline to which 5 to 10 mL of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer, autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

In some embodiments, the compounds and conjugates of the present invention can be used for treating cancer (e.g., ovarian cancer, pancreatic cancer, cervical cancer, melanoma, lung cancer (e.g., non small-cell lung cancer and small-cell lung cancer), colorectal cancer, breast cancer (e.g., triple negative breast cancer (TNBC)), gastric cancer, squamous cell carcinoma of the head and neck, prostate cancer, endometrial cancer, sarcoma, multiple myeloma, head and neck cancer, blastic plasmacytoid dendritic neoplasm (BPDN), lymphoma (e.g., non-Hodgkin lymphoma), myelodysplastic syndrome (MDS), peritoneal cancer, or leukemia (e.g., acute myeloid leukemia (AML), acute monocytic leukemia, promyelocytic leukemia, eosinophilic leukaemia, acute lymphoblastic leukemia (e.g., B-ALL), chronic lymphocytic leukemia (CLL), and chronic myeloid leukemia (CML))

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include:

Comprehensive index
By Manufacturer
Products (by company's or trademarked drug name)
Category index
Generic/chemical index (non-trademark common drug names)
Color images of medications
Product information, consistent with FDA labeling
Chemical information
Function/action
Indications & Contraindications
Trial research, side effects, warnings

EXAMPLES

The invention will now be illustrated by reference to non-limiting examples. Unless otherwise stated, all percents, ratios, parts, etc. are by weight. All reagents were purchased from the Aldrich Chemical Co., New Jersey, or other commercial sources. Nuclear Magnetic Resonance ($^1$H NMR) spectra were acquired on a Bruker 400 MHz instrument. Mass spectra were acquired on a Bruker Daltonics Esquire 3000 instrument, LCMS were acquired on an Agilent 1260 Infinity LC with an Agilent 6120 single quadrupole MS using electrospray ionization (column: Agilent Poroshell 120 C18, 3.0×50 mm, 2.7 µm, 8 min method: flow rate 0.75 mL/min, solvent A: water with 0.1% formic acid, solvent B: MeCN, 5 to 98% of MeCN over 7 min and 98% MeCN for 1 min; 15 min method: column: Agilent Poroshell 120 C18, 3.0×100 mm, 2.7 µm, flow rate 0.5 mL/min, solvent A: water with 0.1% formic acid, solvent B: MeCN, 25 to 80% of MeCN over 12 min, 80 to 95% MeCN over 0.5 min and 95% MeCN for 2.5 min) and UPLC were acquired on a Waters, Acquity system with a single quadrupole MS Zspray™ (column: Acquity BEH C18, 2.1×50 mm, 1.7 µm, 2.5 min method: flow rate 0.8 mL/min, solvent A: water with 0.1% formic acid, solvent B: MeCN, 5 to 95% of MeCN over 2.0 min and 95% MeCN for 0.5 min).

Example 1. Syntheses of the Compounds of the Invention

The following solvents, reagents, protecting groups, moieties and other designations may be referred to by their abbreviations in parenthesis:
Me=methyl; Et=ethyl; Pr=propyl; i-Pr=isopropyl; Bu=butyl; t-Bu=tert-butyl; Ph=phenyl, and Ac=acetyl
AcOH or HOAc=acetic acid
ACN or CH$_3$CN or MeCN=acetonitrile
Ala=alanine
aq=aqueous
Ar=argon
Bn=benzyl
Boc or BOC=tert-butoxycarbonyl
CBr$_4$=carbontetrabromide
Cbz or Z=benzyloxycarbonyl
DCM or CH$_2$Cl$_2$=dichloromethane
DCE=1,2-dichloroethane
DMAP=4-dimethylaminopyridine
DI water=deionized water
DIEA or DIPEA=N,N-diisopropylethylamine
DMA=N,N-dimethylacetamide
DMAP=4-dimethylaminopyridine
DMF=N,N-dimethylformamide
DMP=Dess-Martin Periodinane
DMSO=dimethyl sulfoxide
DPPA=diphenyl phosphorylazide
EDC=1-ethyl-3-(3-dimethylaminopropyl)carbodiimide
EEDQ=N-Ethoxycarbonyl-2-ethoxy-1,2-dihydroquinoline
ESI or ES=electrospray ionization
EtOAc=ethylacetate
g=grams
h=hour
HATU=(1-[Bis(dimethylamino)methylene]-1H-1,2,3-triazolo[4,5-b]pyridinium 3-oxid hexa-fluorophosphate)
HPLC=high-performance liquid chromatography
HOBt or HOBT=1-hydroxybenzotriazole
LC=liquid chromatography
LCMS=liquid chromatography mass spectrometry
min=minutes
mg=milligrams
mL=milliliters
mmol=millimoles
µg=micrograms
µL=microliters
µmol=micromoles
Me=methyl
MeOH=methanol
MS=mass spectrometry
MsCl=methanesulfonyl chloride (mesyl chloride)
Ms$_2$O=methanesulfonic anhydride
NaBH(OAc)$_3$ or STAB=sodium triacetoxyborohydride
NHS=N-hydroxysuccinamide
NMR=nuclear magnetic resonance spectroscopy
PPh$_3$ or TPP=triphenylphosphine
RPHPLC or RP-HPLC=reverse phase high-performance liquid chromatography
RT or rt=room temperature (ambient, about 25° C.)
sat or sat'd=saturated
TBSCl or TBDMSCl=tert-butyldimethylsilyl chloride
TBS=tert-butyldimethylsilyl
TCEP·HCl=tris(2-carboxyethyl)phosphine hydrochloride salt
TEA=triethylamine (Et$_3$N)
TFA=trifluoroacetic acid
THF=tetrahydrofuran

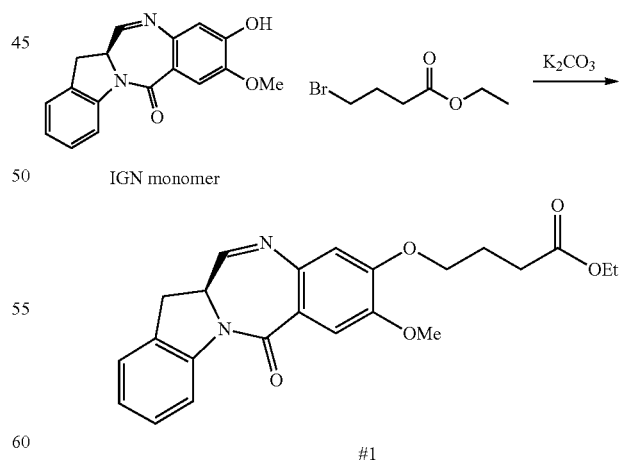

IGN monomer

1

IGN Monomer (3.0 g, 10.19 mmol) and ethyl 4-bromobutanoate (2.193 mL, 15.29 mmol) were dissolved in DMF (34.0 mL). K$_2$CO$_3$ (2.82 g, 20.39 mmol) was added and the reaction was stirred at rt overnight. The reaction mixture was diluted with EtOAc and was washed with sat'd NH$_4$Cl and brine, dried over Na$_2$SO$_4$, filtered, and concentrated. The crude product was coevaporated with ACN (2×), and then placed on the high vacuum to give compound #1, which was used directly without purification (4.16 g, 100% yield). LCMS=4.82 min (8 min method). Mass observed (ESI$^+$): 409.2 (M+H).

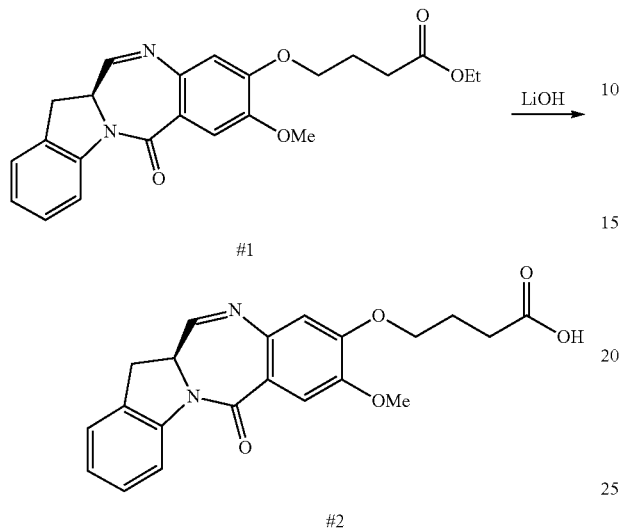

1

Compound #1 (4.16 g, 10.19 mmol) was suspended in MeOH (63.7 mL), Water (12.74 mL) and THF (25.5 mL). LiOH (0.747 g, 30.6 mmol) was added and was stirred at rt for 1 h. The reaction mixture was diluted with water and was acidified to pH-4 with 1 M HCl. The mixture was extracted with EtOAc (2×) and was washed with brine, dried over MgSO$_4$, filtered and concentrated. The crude material was purified by silica gel chromatography (DCM/MeOH) to give compound #2 (2.46 g, 64% yield). LCMS=3.99 min (8 min method). Mass observed (ESI$^+$): 381.1 (M+H), 399.1 (M+H$_2$O+H).

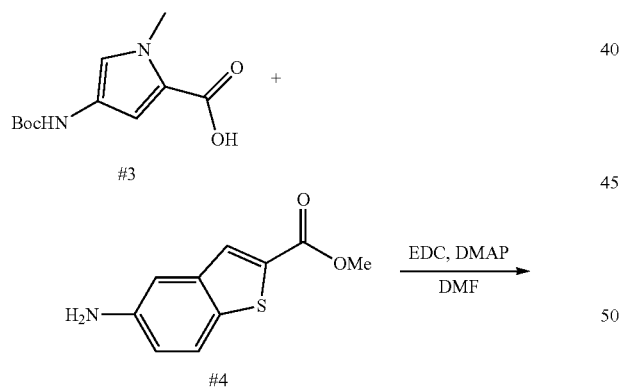

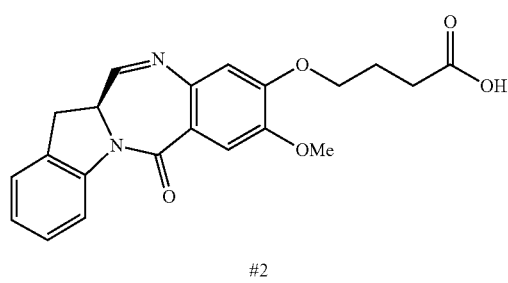

Compound #3 (255 mg, 1.062 mmol) and compound #4 (200 mg, 0.965 mmol) were dissolved in DMF (3.22 mL). EDC (222 mg, 1.158 mmol) was added to the reaction mixture, followed by DMAP (118 mg, 0.965 mmol) and the reaction was stirred at rt overnight. The reaction mixture was diluted with EtOAc and was washed with sat'd NH$_4$Cl, brine, dried over Na$_2$SO$_4$, filtered and concentrated. The crude product was purified by silica gel chromatography (0% to 40% EtOAc/hexanes) to obtain compound #5 as an orange-white solid (300 mg, 0.699 mmol, 72% yield). LCMS=6.014 min (8 min method). Mass observed (ESI$^+$): 430.05 (M+H). $^1$H NMR (400 MHz, DMSO-d$_6$): δ 1.46 (s, 9H), 3.83 (s, 3H), 3.89 (s, 3H), 6.97 (d, J=8.8 Hz, 2H), 7.79 (d, J=9.0 Hz, 1H), 7.97 (d, J=8.9 Hz, 1H), 8.18 (s, 1H), 8.49 (s, 1H), 9.14 (s, 1H), 9.98 (s, 1H).

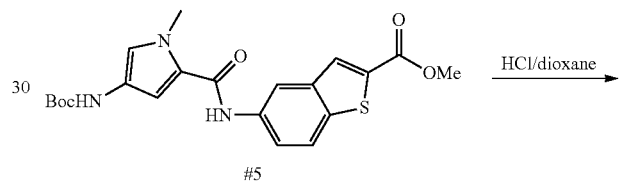

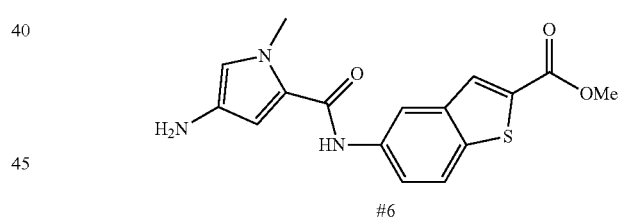

Anhydrous HCl (4 N in dioxane, 70.7 μL, 2.328 mmol) was added to neat compound #5 (10 mg, 0.023 mmol) at rt and was stirred for 1 h. The reaction mixture was concentrated to obtain compound #6 as an off white solid (8.5 mg, 0.023 mmol, 100% yield). LCMS=3.622 min (8 min method). Mass observed (ESI$^+$): 330.00 (M+H).

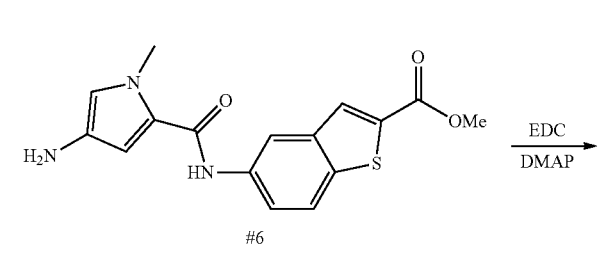

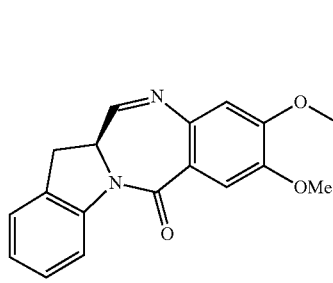

7

Compound #2 (14.43 mg, 0.039 mmol) and compound #6 (10 mg, 0.026 mmol) were dissolved in $CH_2Cl_2$ (263 µL). EDC (7.56 mg, 0.039 mmol) was added to the reaction mixture, followed by DMAP (4.82 mg, 0.039 mmol) and the reaction was stirred at rt for 2 h. The reaction mixture was diluted with DCM and was washed with sat'd $NH_4Cl$, water, dried over $Na_2SO_4$, filtered and concentrated. The crude product was purified by RPHPLC (C18 column, ACN/Water) to obtain compound #7 (4.7 mg, 6.79 µmol, 26% yield). LCMS=6.596 min (15 min method). Mass observed (ESI+): 692.30 (M+H).

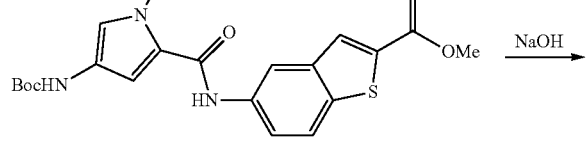

5

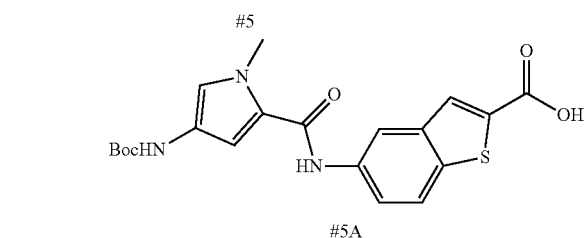

5A

Methyl ester #5 (100 mg, 0.233 mmol) was suspended in MeOH (2.33 mL). Sodium hydroxide solution (5 M aqueous, 466 µL, 0.466 mmol) was added and the reaction mixture was heated at 60° C. for 3 h. The reaction mixture was cooled to rt and was diluted with water. The solution was acidified to pH-3-4 with 1 M HCl. EtOAc was added and the layers were separated. The organic layer was washed with brine, dried over $Na_2SO_4$, filtered and concentrated to obtain compound #5A as an off white solid (93 mg, 0.224 mmol, 96% yield). LCMS=6.145 min (15 min method). Mass observed (ESI+): 416.10 (M+H).

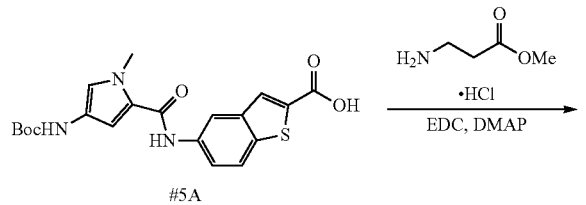

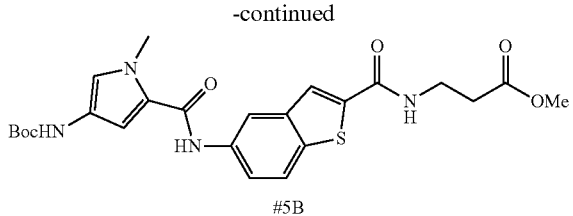

5B

Compound #5A (91 mg, 0.219 mmol) was dissolved in DMF (2.19 mL). Beta-alanine-OMe HCl was added to the solution (33.6 mg, 0.241 mmol), followed by EDC (50.4 mg, 0.263 mmol) and DMAP (26.8 mg, 0.219 mmol). The reaction mixture was stirred at rt for 3 days. The reaction mixture was diluted with EtOAc and washed with sat'd $NH_4Cl$, brine, dried over $Na_2SO_4$, filtered and concentrated. The crude product was slurried in EtOAc/hexanes (1:1, 15 mL) and filtered to obtain pure product #5B (80 mg, 0.160 mmol, 73% yield). LCMS=6.190 min (15 min method). Mass observed (ESI+): 401.10 (M-Boc+H), 501.10 (M+H). $^1$H NMR (400 MHz, DMSO-$d_6$): δ 1.46 (s, 9H), 2.63 (t, J=6.9 Hz, 2H), 3.51 (q, J=6.7 Hz, 2H), 3.62 (d, J=2.3 Hz, 3H), 3.83 (s, 3H), 6.96 (d, J=4.5 Hz, 2H), 7.74 (dd, J=8.8, 2.1 Hz, 1H), 7.91 (d, J=8.8 Hz, 1H), 7.98 (s, 1H), 8.33 (d, J=2.0 Hz, 1H), 8.80 (t, J=5.4 Hz, 1H), 9.14 (s, 1H), 9.93 (s, 1H).

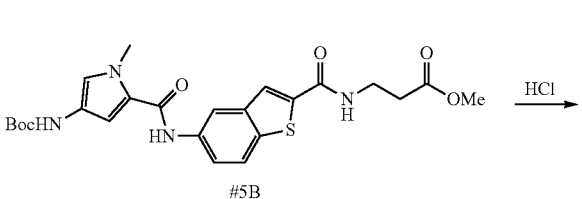

5B

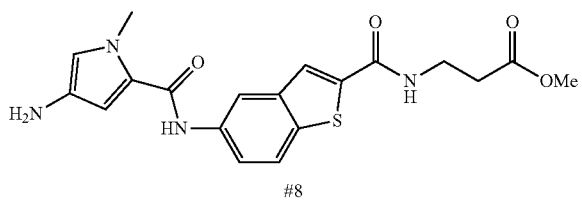

8

Compound #8 was synthesized from compound #5B in a similar fashion as compound #6 to obtain compound #8 as a yellowish-white solid (60 mg, 0.150 mmol, 94% yield). LCMS=2.538 min (15 min method). Mass observed (ESI+): 401.10 (M+H).

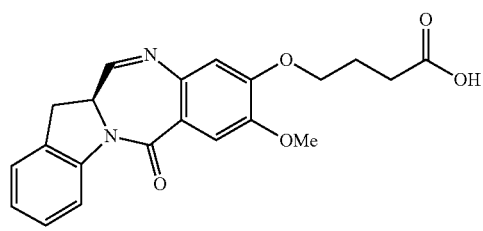
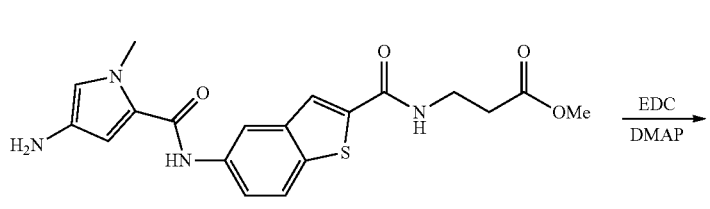
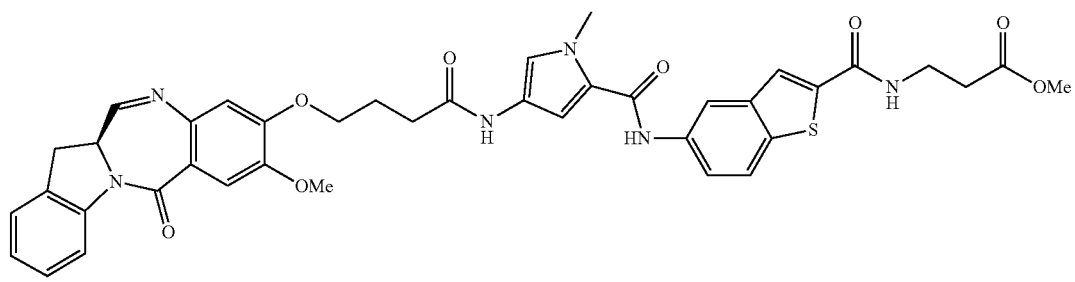
Compound #9 was synthesized similarly as compound #7 after RPHPLC purification (C18 column, ACN/H$_2$O) to obtain compound #9 as a white solid (26 mg, 0.034 mmol, 65% yield). LCMS=5.039 min (15 min method). Mass observed (ESI$^+$): 763.40 (M+H).
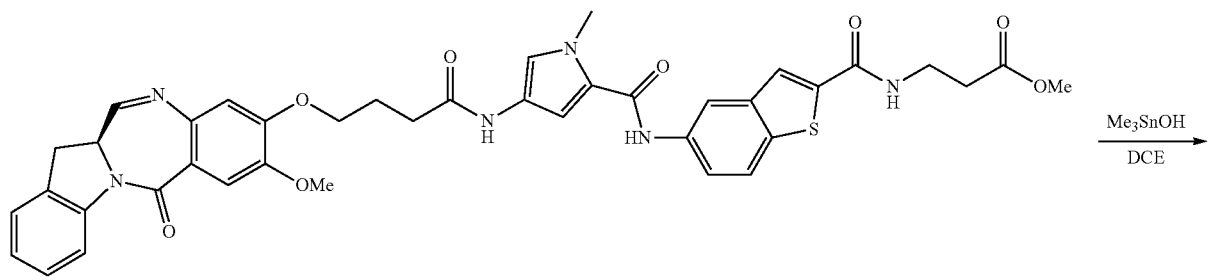
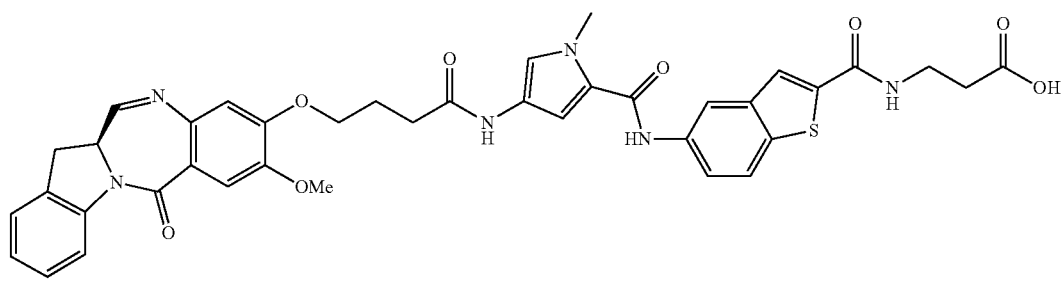

Compound #9 (6.4 mg, 8.39 µmol) was dissolved in DCE (419 µL). Trimethyltin hydroxide (15.17 mg, 0.084 mmol) was added and the reaction mixture was heated at 80° C. overnight. The solution was cooled to rt and was diluted with DCM/MeOH (5:1, 10 mL). The solution was washed with 0.5 M HCl and was re-extracted with DCM/MeOH (5:1, 2×5 mL). The organic layer was washed with brine, dried over $Na_2SO_4$, filtered and concentrated to obtain compound #10 (6.3 mg, 8.36 µmol, 100% yield). LCMS=4.432 min (8 min method). Mass observed (ESI+): 749.15 (M+H).

sium phosphate buffer pH 7.4 (7.50 mL). Methylmethanethiolsulfonate (2.499 mL, 26.5 mmol) was added and the reaction was stirred at rt overnight. The reaction mixture was diluted with EtOAc and was washed with brine. The organic layer was dried over $Na_2SO_4$, filtered and concentrated. The crude product was purified by silica gel chromatography (DCM/MeOH) to yield compound #12 as a white solid (1.34 g, 50% yield). $^1$H NMR (400 MHz, DMSO-d6): δ 1.34 (s, 6H), 2.45 (s, 3H), 2.94 (s, 2H), 8.13 (s, 2H).

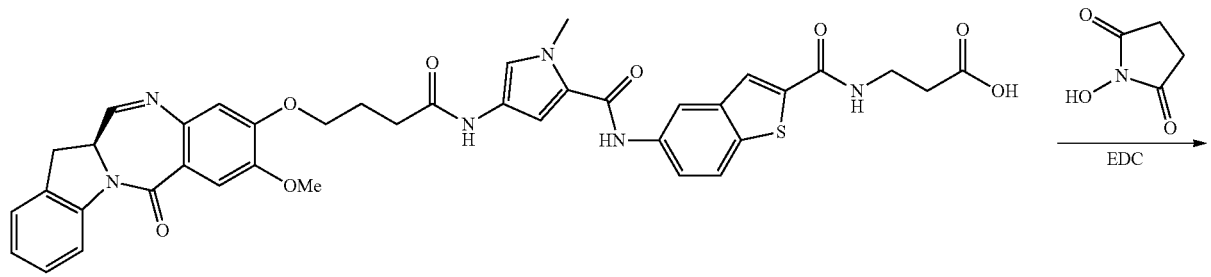

10

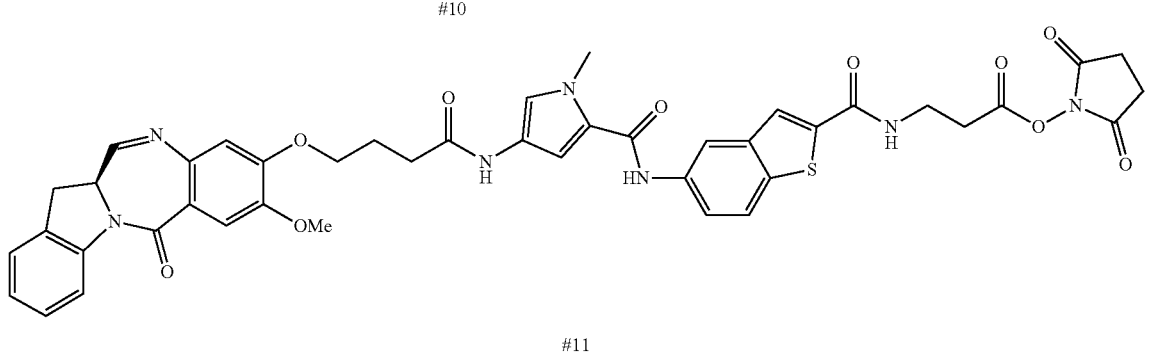

11

Compound #10 (8 mg, 10.68 µmol) was dissolved in DCM (427 µL). EDC (16.38 mg, 0.085 mmol) was added to the mixture at rt, followed by N-hydroxysuccinamide (6.15 mg, 0.053 mmol) and was stirred for 3.5 h. The reaction mixture was diluted with DCM and was washed with water (2×), dried over $Na_2SO_4$, filtered and concentrated. The residue was purified by RPHPLC (C18 column, ACN/Water) to obtain compound #11 as a white solid (2.5 mg, 2.96 µmol, 28% yield). LCMS=4.731 min (8 min method). Mass observed (ESI+):

5A

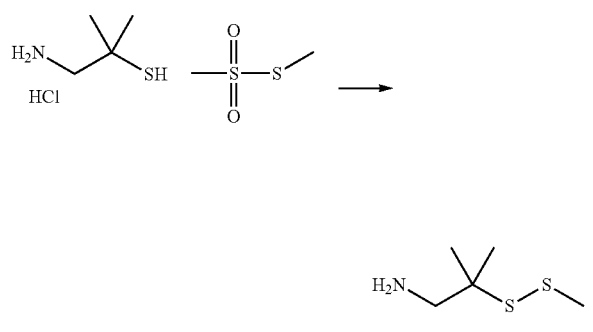

12

1-amino-2-methylpropane-2-thiol hydrochloride (2.5 g, 17.65 mmol) was suspended in MeOH (7.5 mL) and potas-

13

Compound #5A (100 mg, 0.241 mmol) and amine #12 (43.7 mg, 0.289 mmol) were dissolved in DMF (1.61 mL). EDC (69.2 mg, 0.361 mmol) was added to the solution at rt, followed by DMAP (14.70 mg, 0.120 mmol) and was stirred overnight. Water was added to the reaction mixture to precipitate the product. The resulting slurry was stirred for 15 min. The solution was filtered and the solid was dried under vacuum/N$_2$ for 2 h to obtain compound #13 as an off white solid (127 mg, 0.231 mmol, 96% yield). LCMS=6.408 min (8 min method). Mass observed (ESI$^+$): 549.15 (M+H). $^1$H NMR (400 MHz, DMSO-d$_6$): δ 1.31 (s, 6H), 1.46 (s, 9H), 2.45 (s, 3H), 3.48 (d, J=6.3 Hz, 2H), 3.83 (s, 3H), 6.97 (s, 2H), 7.72-7.79 (m, 1H), 7.92 (d, J=8.8 Hz, 1H), 8.11 (d, J=3.7 Hz, 1H), 8.31-8.41 (m, 2H), 8.70 (t, J=6.3 Hz, 1H), 9.14 (s, 1H), 9.94 (s, 1H).

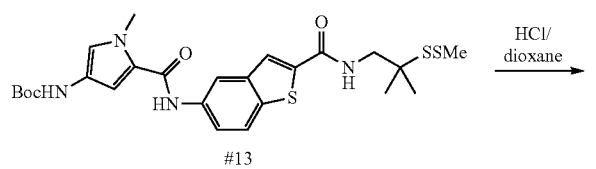

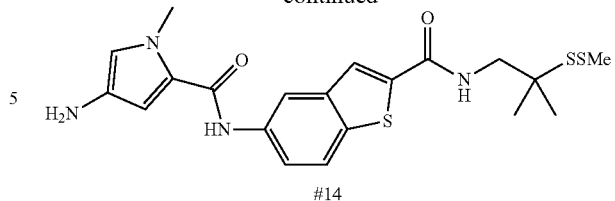

Anhydrous HCl (4 N in dioxane) (1.16 mL, 4.63 mmol) was added to neat compound #13 (127 mg, 0.231 mmol) at rt and the reaction was stirred for 3 h. The reaction mixture was concentrated to obtain compound #14 (112 mg, 0.231 mmol, 100% yield). LCMS=4.407 min (8 min method). Mass observed (ESI$^+$): 449.10 (M+H). $^1$H NMR (400 MHz, DMSO-d$_6$): δ 1.31 (s, 6H), 2.45 (s, 3H), 3.46-3.52 (m, 2H), 3.92 (s, 3H), 7.13 (t, J=2.0 Hz, 1H), 7.18 (d, J=2.0 Hz, 1H), 7.75 (dd, J=8.8, 2.1 Hz, 1H), 7.95 (d, J=8.6 Hz, 2H), 8.14 (d, J=4.5 Hz, 1H), 8.34 (d, J=2.1 Hz, 1H), 8.73 (t, J=6.4 Hz, 1H), 9.96 (bs, 2H), 10.12 (s, 1H).

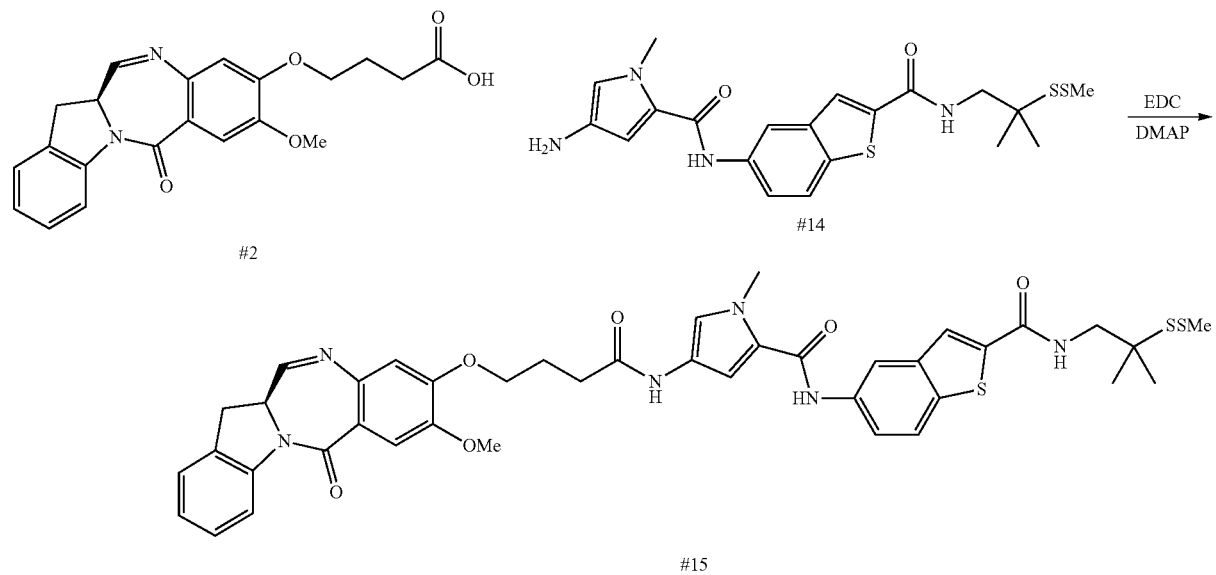

Compound #15 was synthesized similarly as compound #7 after RPHPLC purification (C18 column, ACN/H$_2$O) to obtain compound #15 as a white solid (48 mg, 0.059 mmol, 83% yield). LCMS=5.789 min (8 min method). Mass observed (ESI$^+$): 811.30 (M+H).

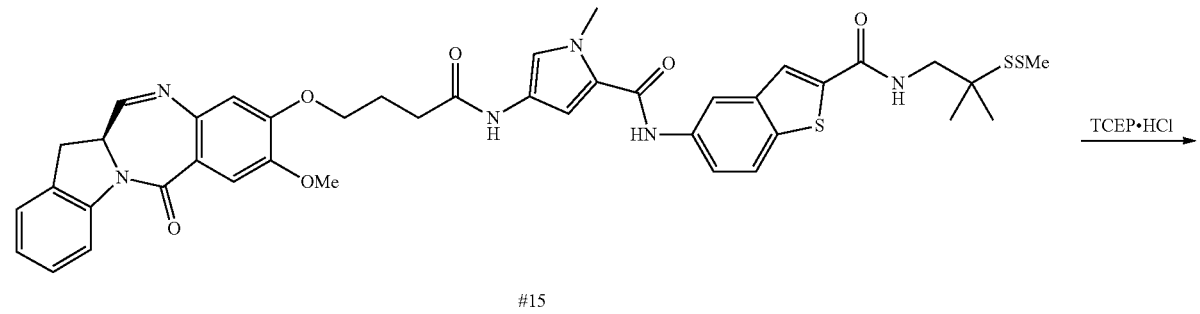

-continued

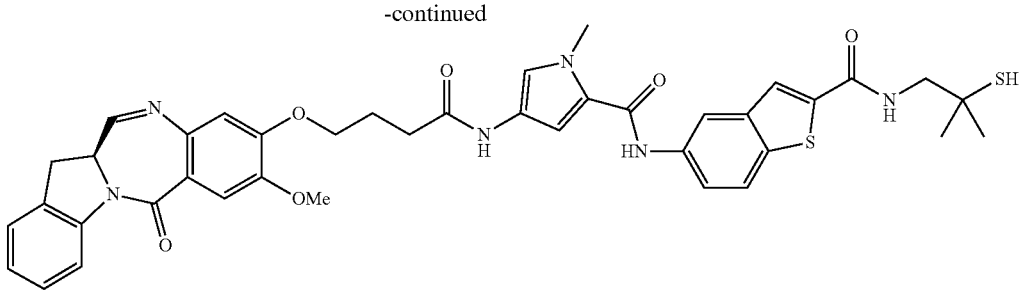

16

TCEP·HCl (45.1 mg, 0.157 mmol) was dissolved in water (0.5 mL). Sat'd NaHCO₃ solution (~0.470 mL) and 0.1 M pH 6.5 NaH₂PO₄ buffer solution (81 μL) was added to reach a pH between 6.5-7. In a separate flask, compound #15 (50 mg, 0.052 mmol) was dissolved in THF (1 mL) and CH₃CN (564 μL) at rt. The above TCEP/buffer mixture of pH=6.5-7 was added, followed by MeOH (403 μL). The yellow-brown solution was stirred at rt for 2 h. The reaction was diluted with DCM/MeOH (10:1, 30 mL) and water and the layers were separated. The organic layer was washed with brine, dried over Na₂SO₄, filtered and concentrated to give compound #16 (40 mg, 0.052 mmol, 100% yield). LCMS=5.312 min (8 min method). Mass observed (ESI⁺): 765.20 (M+H).

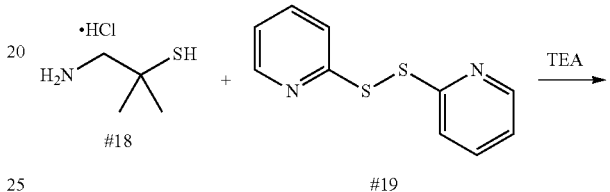

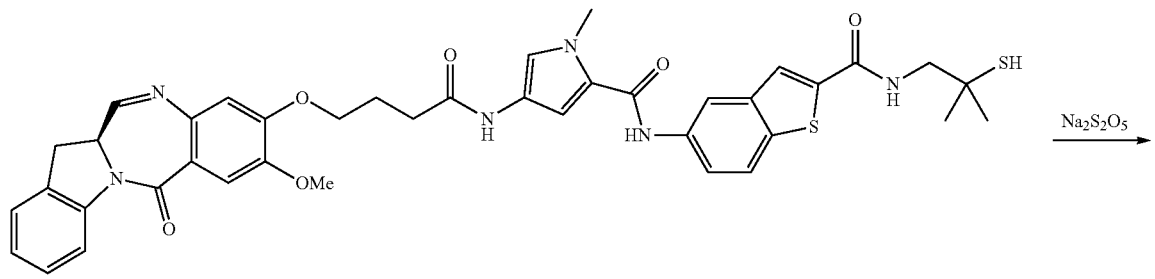

16

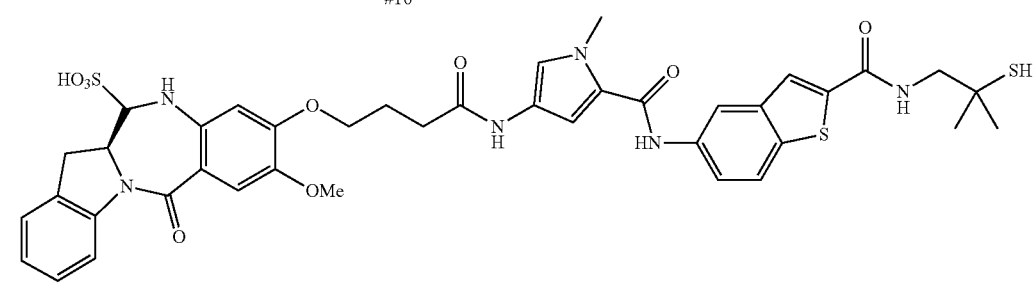

17

Compound #16 (47 mg, 0.061 mmol) was suspended in IPA (2.05 mL) and water (1.02 mL). Na₂S₂O₅ (63.9 mg, 0.614 mmol) was added and the reaction mixture was stirred at rt overnight. The reaction mixture was diluted with ACN/H₂O and was frozen and lyophilized. The crude product was purified by RPHPLC (C18 column, ACN/Water) to obtain compound #17 as a white solid (6.5 mg, 7.67 μmol, 13% yield). LCMS=4.646 min (8 min method). Mass observed=765.25 (ESI⁺, M-SO₃H+H), 845.10 (ESI⁻, M−H).

-continued

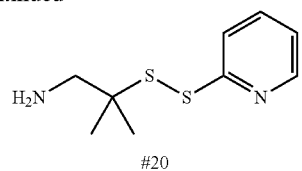

20

Dimethylcysteamine HCl, #18 (500 mg, 3.53 mmol) was dissolved in MeOH (11.765 mL). Aldrithiol, #19 (1.17 g, 5.29 mmol) was added and the reaction mixture was stirred at rt overnight. TEA (0.492 mL, 3.53 mmol) was added and the reaction was stirred at rt for 5 min and then concentrated. The crude residue was purified by silica gel chromatography (0% to 5% to 10% MeOH/DCM) to obtain compound #20 as an off white sticky solid (700 mg, 3.27 mmol, 93% yield). LCMS=2.874 min (8 min method). Mass observed (ESI⁺): 214.95 (M+H). ¹H NMR (400 MHz, CDCl₃): δ 1.49 (s, 6H), 2.95 (s, 2H), 7.17 (ddd, J=7.4, 5.0, 1.0 Hz, 1H), 7.42 (dt, J=8.0, 1.0 Hz, 1H), 7.54-7.64 (m, 1H), 8.65 (ddd, J=4.9, 1.9, 0.9 Hz, 1H).

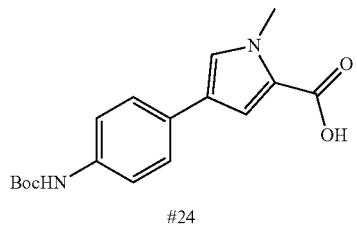

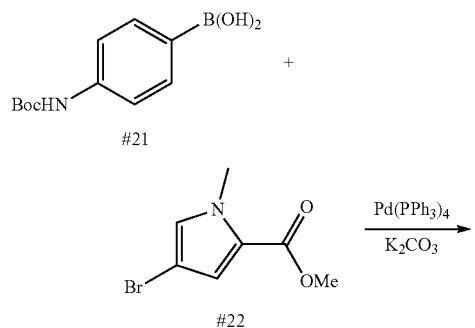

Compound #23 (480 mg, 1.453 mmol) was suspended in MeOH (4.84 mL). Sodium hydroxide solution (5 N aq, 581 µL, 2.91 mmol) was added and the reaction mixture was heated at 65° C. for 2 h. An additional solution of NaOH (5 N aq, 1.16 mL) was added and was heated at 65° C. for 45 min. The reaction mixture was cooled to rt and was diluted with water. The solution was acidified to pH~3-4 with 5 M aq HCl. The solution was extracted with EtOAc (2×) and the layers were separated. The organic layer was washed with brine, dried over Na₂SO₄, filtered and concentrated to obtain compound #24 (420 mg, 1.328 mmol, 91% yield). LCMS=5.203 min (8 min method). Mass observed (ESI⁺): 317.25 (M+H).

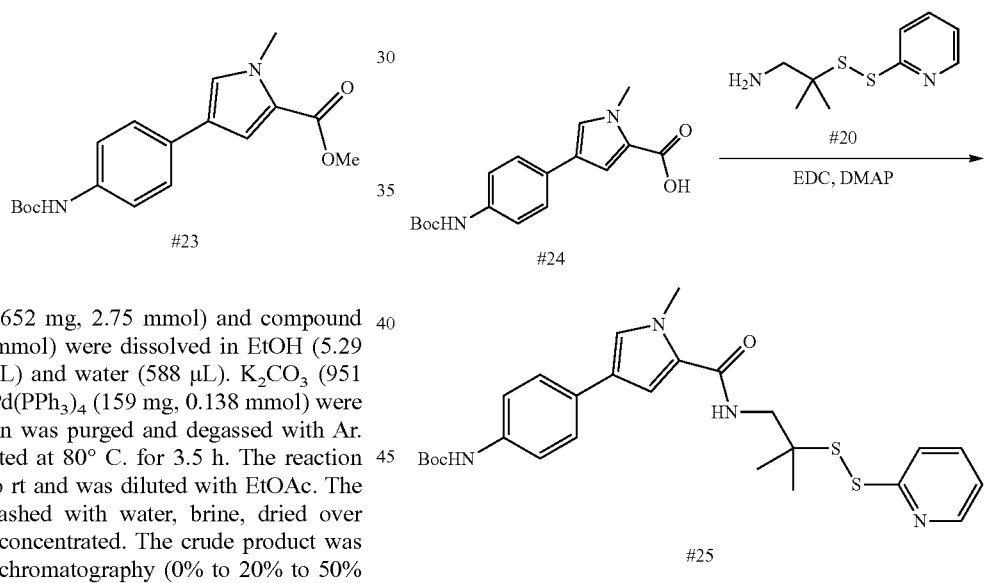

Boronic acid #21 (652 mg, 2.75 mmol) and compound #22 (500 mg, 2.293 mmol) were dissolved in EtOH (5.29 mL), toluene (1.76 mL) and water (588 µL). K₂CO₃ (951 mg, 6.88 mmol) and Pd(PPh₃)₄ (159 mg, 0.138 mmol) were added and the solution was purged and degassed with Ar. The reaction was heated at 80° C. for 3.5 h. The reaction mixture was cooled to rt and was diluted with EtOAc. The organic layer was washed with water, brine, dried over Na₂SO₄, filtered and concentrated. The crude product was purified by silica gel chromatography (0% to 20% to 50% EtOAc/hexanes) to obtain compound #23 as a yellow solid (432 mg, 1.308 mmol, 57% yield). ¹H NMR (400 MHz, CDCl₃): δ 1.52 (s, 9H), 3.84 (s, 3H), 3.95 (s, 3H), 6.44 (s, 1H), 7.03 (d, J=2.1 Hz, 1H), 7.16 (d, J=2.0 Hz, 1H), 7.32-7.34 (m, 2H), 7.37-7.44 (m, 2H).

Compound #25 was synthesized similarly as compound #7 to obtain compound #25 as a solid (160 mg, 0.312 mol, 99% yield). LCMS=6.794 min (8 min method). Mass observed (ESI⁺): 512.80 (M+H).

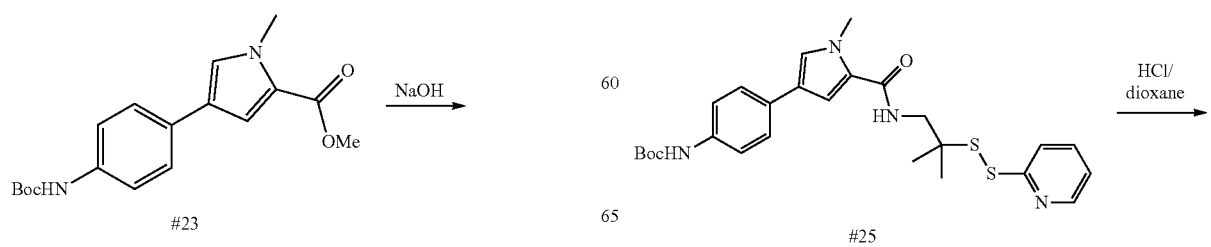

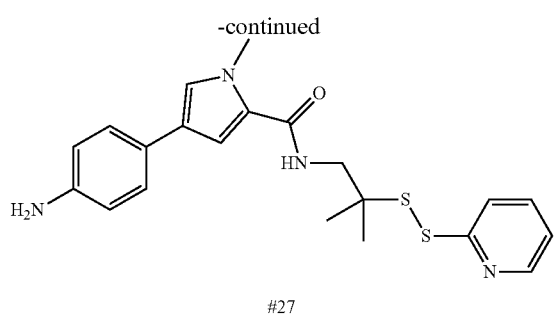

27

Compound #27 was synthesized similarly as compound #6 from compound #25 to obtain compound #27 as an off white solid (130 mg, 0.29 mmol, 93% yield). LCMS=4.443 min (8 min method). Mass observed (ESI$^+$): 412.95 (M+H). $^1$H NMR (400 MHz, DMSO-d$_6$): δ 1.28 (s, 6H), 2.73 (s, 1H), 2.89 (s, 1H), 3.39 (d, J=6.4 Hz, 2H), 3.85 (s, 3H), 7.20-7.28 (m, 2H), 7.35 (d, J=8.5 Hz, 2H), 7.47 (d, J=1.9 Hz, 1H), 7.58-7.65 (m, 2H), 7.78-7.86 (m, 2H), 8.27 (t, J=6.3 Hz, 1H), 8.43 (dt, J=4.8, 1.5 Hz, 1H).

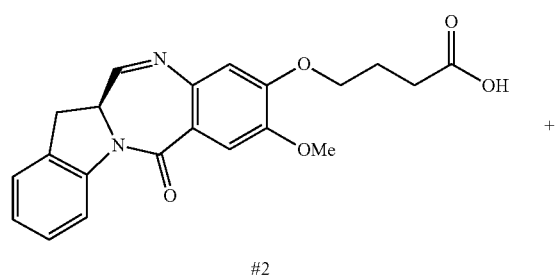

2

+

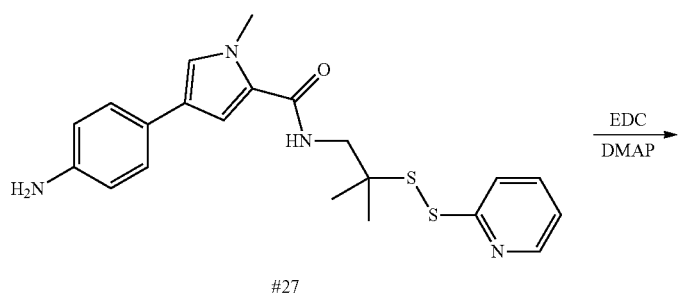

27

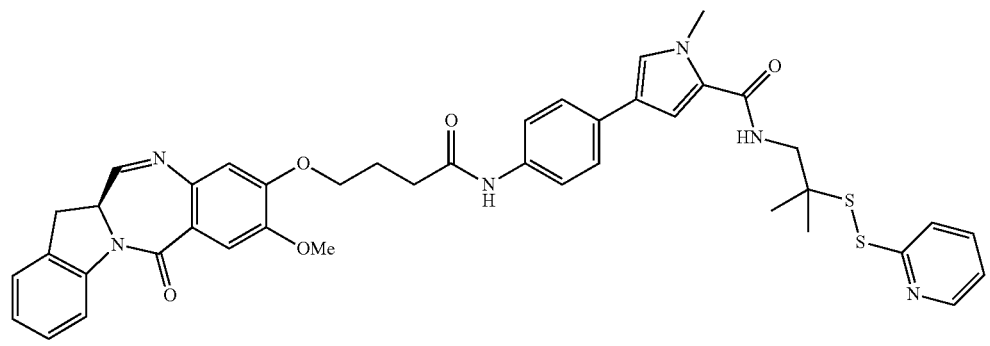

28

Compound #28 was synthesized similarly as compound #7 after purification by RPHPLC (C18 column, ACN/Water) to obtain compound #28 as an off white solid (52 mg, 0.067 mmol, 51% yield). LCMS=5.881 min (8 min method). Mass observed (ESI$^+$): 774.75 (M+H).

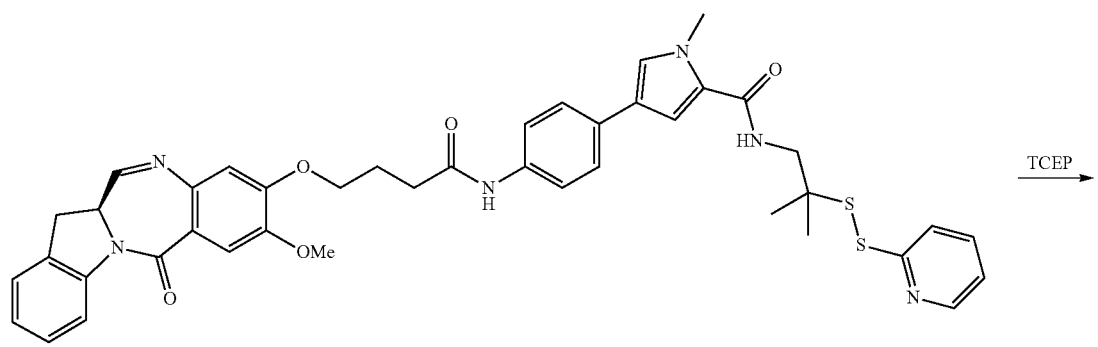
28
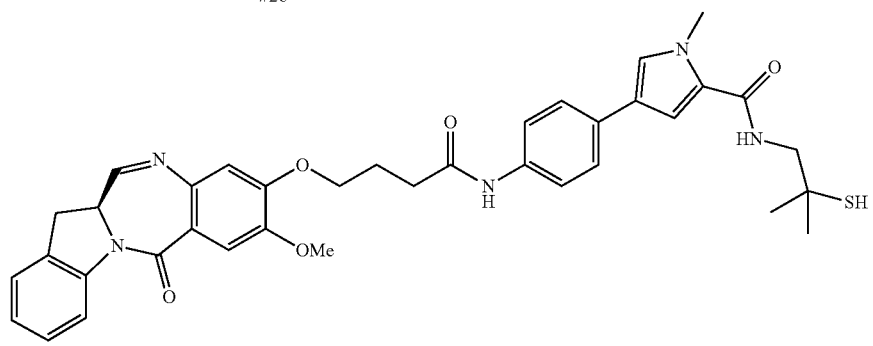
29
Compound was synthesized similarly as compound #16 from compound #28 to obtain compound #29 as a white solid (45 mg, 0.067 mmol, 100% yield). LCMS=5.352 min (8 min method). Mass observed (ESI+): 665.85 (M+H).
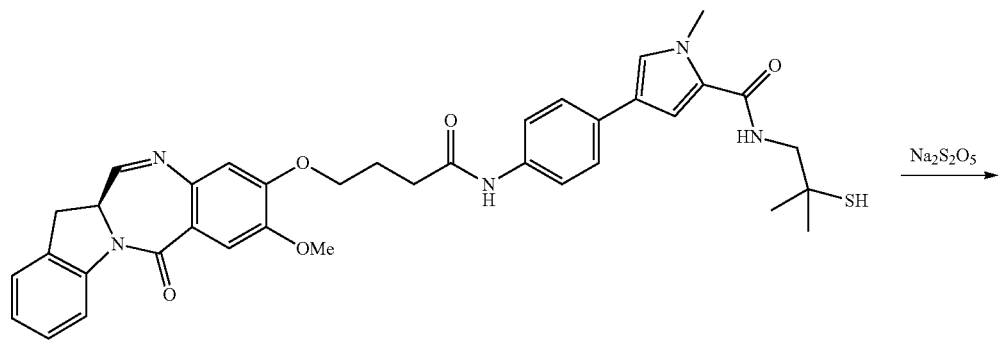
29
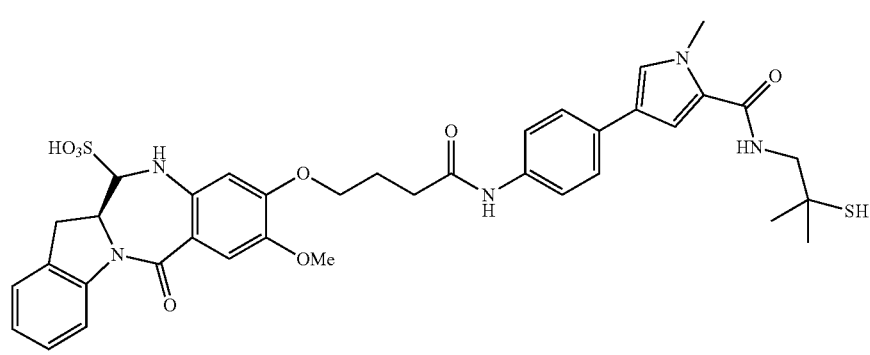
30

Compound #30 was synthesized similarly as compound #17 from compound #29 to obtain compound #30 as a white solid after purification by RPHPLC (C18 column, ACN/Water) (17 mg, 0.023 mmol, 34% yield). LCMS=4.471 min (8 min method). Mass observed=665.85 (ESI⁺, M-SO₃H+ H), 745.80 (ESI⁻, M−H).

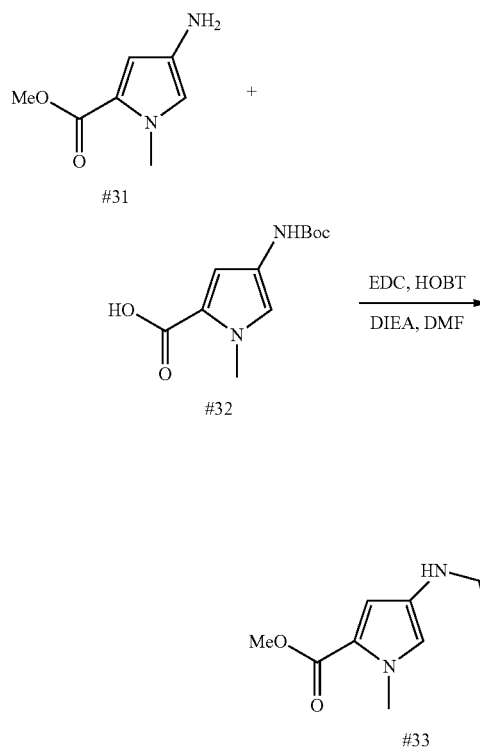

Compound #31 (300 mg, 1.574 mmol) and compound #32 (397 mg, 1.652 mmol) were dissolved in DMF (7.87 mL). EDC (332 mg, 1.731 mmol) and HOBt (265 mg, 1.731 mmol) were added to the reaction mixture, followed by DIEA (550 µL, 3.15 mmol) and the reaction was stirred for 3 days. The reaction mixture was diluted with EtOAc and washed with sat'd NH₄Cl, sat'd NaHCO₃, water (3×), dried over Na₂SO₄, filtered and concentrated to obtain compound #33 as a brown foam (551 mg, 1.464 mmol, 93% yield). LCMS=5.446 min (8 min method). Mass observed (ESI⁺): 376.95 (M+H).

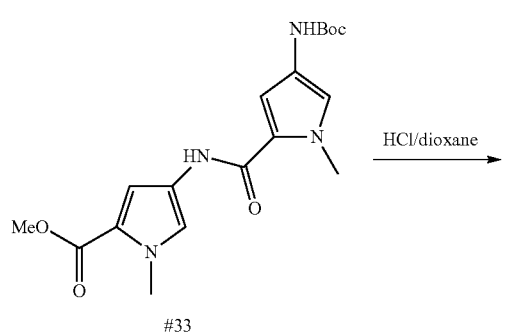

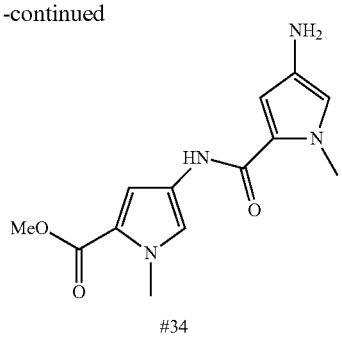

Compound #34 was synthesized similarly as compound #6 from compound #33 to obtain compound #34 as a brown solid (430 mg, 1.375 mmol, 94% yield). LCMS=3.436 min (8 min method). Mass observed (ESI⁺): 276.95 (M+H). ¹H NMR (400 MHz, DMSO-d₆): δ 3.73 (s, 3H), 3.84 (s, 3H), 3.88 (s, 3H), 6.92 (d, J=2.0 Hz, 1H), 7.00 (d, J=2.0 Hz, 1H), 7.11 (d, J=2.0 Hz, 1H), 7.46 (d, J=1.9 Hz, 1H), 10.06 (s, 2H), 10.12 (s, 1H).

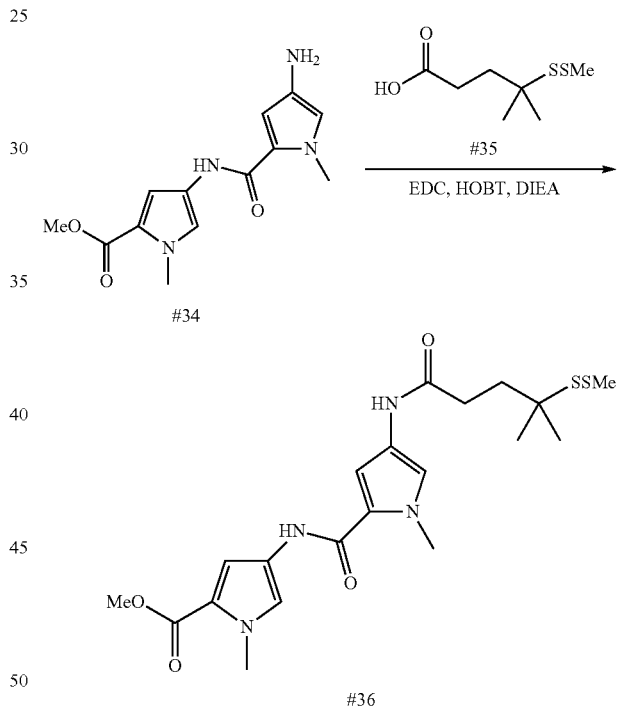

Compound #34 (130 mg, 0.416 mmol) and compound #35 (89 mg, 0.457 mmol) were dissolved in DMF (2.08 mL). EDC (88 mg, 0.457 mmol) and HOBt (70.0 mg, 0.457 mmol) were added to the reaction mixture, followed by DIEA (160 µL, 0.914 mmol) and the reaction was stirred at rt overnight. The reaction mixture was diluted with EtOAc and was washed with sat'd NH₄Cl, sat'd NaHCO₃, brine, water (3×), dried over Na₂SO₄, filtered and concentrated. The crude product was purified by silica gel chromatography (0% to 60% to 100% EtOAc/hexanes) to obtain compound #36 (97 mg, 0.214 mmol, 52% yield). LCMS=5.616 min (8 min method). Mass observed (ESI⁺): 452.85 (M+H). ¹H NMR (400 MHz, CDCl₃): δ 1.33 (s, 6H), 1.99-2.08 (m, 2H), 2.38-2.47 (m, 5H), 3.81 (s, 3H), 3.90 (s, 3H), 3.91 (s, 3H), 6.60 (d, J=1.9 Hz, 1H), 6.73 (d, J=2.0 Hz, 1H), 7.05-7.12 (m, 2H), 7.40 (d, J=2.0 Hz, 1H), 7.45 (s, 1H).

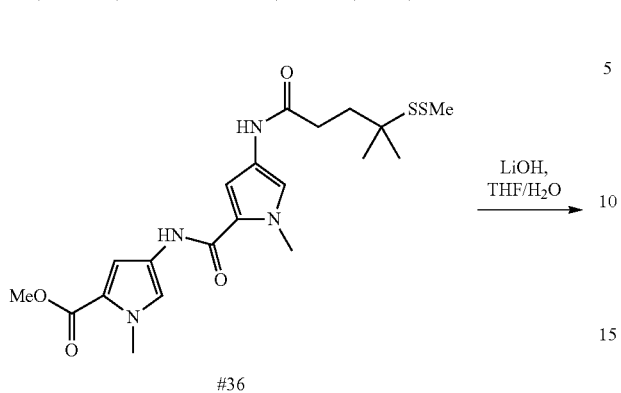
36

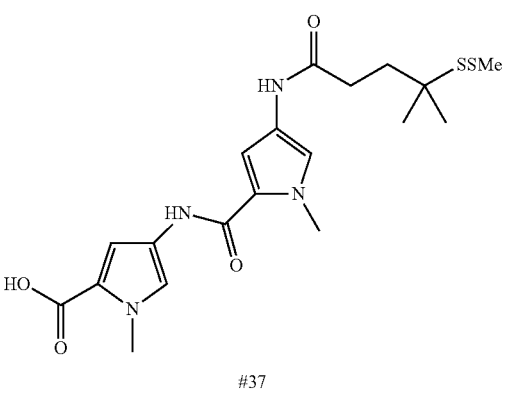
37

Compound #36 (97 mg, 0.214 mmol) was dissolved in THF (1.61 mL) and water (536 µL). LiOH (25.7 mg, 1.072 mmol) was added and the reaction mixture was heated at 50° C. for 5 h. An additional LiOH (25 mg) was added and was heated at 60° C. overnight. The reaction mixture was cooled to rt and was diluted with water. The solution was acidified to pH ~3-4 with 1 M aq HCl. The cloudy solution was extracted with EtOAc (3×), dried over Na₂SO₄, filtered and concentrated to obtain compound #37 as a brown foam (75 mg, 0.171 mmol, 80% yield). LCMS=5.006 min (8 min method). Mass observed (ESI⁺): 438.90 (M+H).

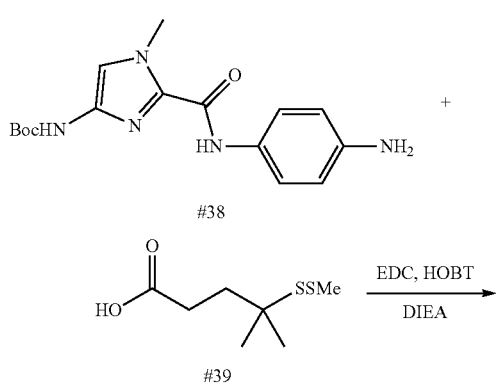
38
39

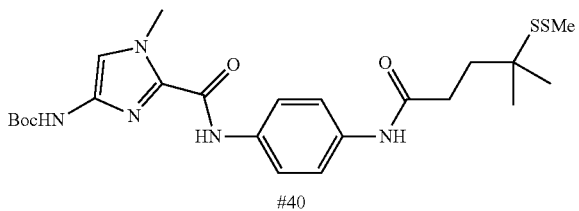
40

Compound #38 (500 mg, 1.509 mmol) and compound #39 (323 mg, 1.660 mmol) were dissolved in DMF (7.54 mL). EDC (318 mg, 1.660 mmol) and HOBt (254 mg, 1.660 mmol) were added to the reaction mixture, followed by DIEA (527 µl, 3.02 mmol) and the reaction was stirred at rt overnight. The reaction mixture was diluted with EtOAc, washed with sat'd NH₄Cl, sat'd NaHCO₃, water (3×), dried over Na₂SO₄, filtered and concentrated to obtain compound #40 (735 mg, 1.448 mmol, 96% yield). LCMS=6.218 min (8 min method). Mass observed (ESI⁺): 507.85 (M+H). ¹H NMR (400 MHz, CDCl₃): δ 1.33 (d, J=4.9 Hz, 6H), 1.52 (s, 9H), 2.01-2.11 (m, 2H), 2.43 (d, J=3.7 Hz, 3H), 2.44-2.50 (m, 1H), 4.23 (s, 3H), 4.20 (s, 1H), 7.21 (s, 1H), 7.36 (s, 1H), 7.52 (d, J=8.7 Hz, 2H), 7.77 (d, J=10.9 Hz, 1H), 7.86 (d, J=8.8 Hz, 2H), 10.83 (d, J=12.9 Hz, 1H).

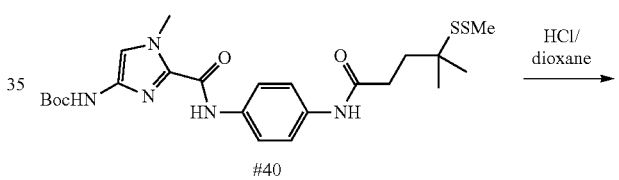
40

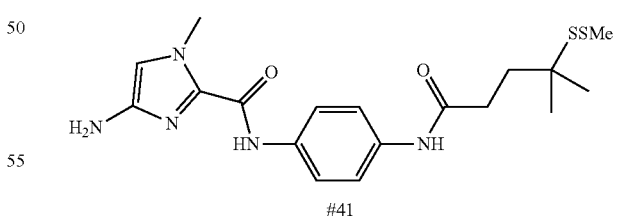
41

Anhydrous HCl (4 N in dioxane, 5.43 mL, 21.72 mmol) was added to neat compound #40 (735 mg, 1.448 mmol) and was stirred at rt overnight. ACN was added to the reaction mixture and the slurry was filtered and dried under vacuum/N₂ to obtain compound #41 as a white solid (600 mg, 1.351 mmol, 93% yield). LCMS=3.618 min (8 min method). Mass observed (ESI⁺): 407.85 (M+H).

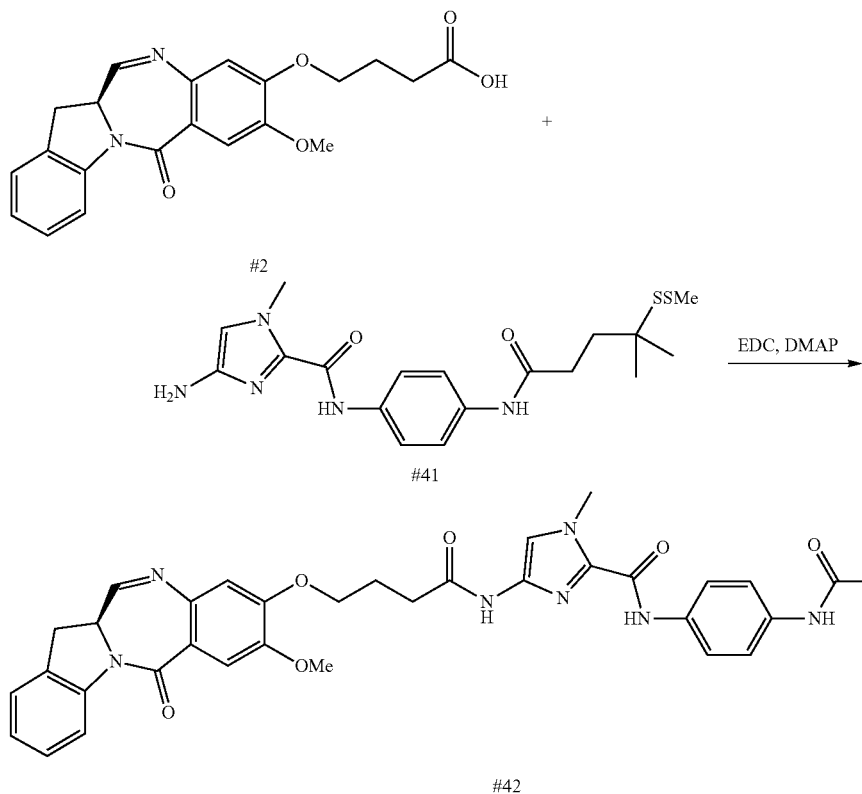

Compound #42 was synthesized similarly as compound #7 to obtain compound #42 as a white solid (5.0 mg, 6.49 μmol, 8% yield). LCMS=5.638 min (8 min method). Mass observed (ESI⁺): 769.80 (M+H).

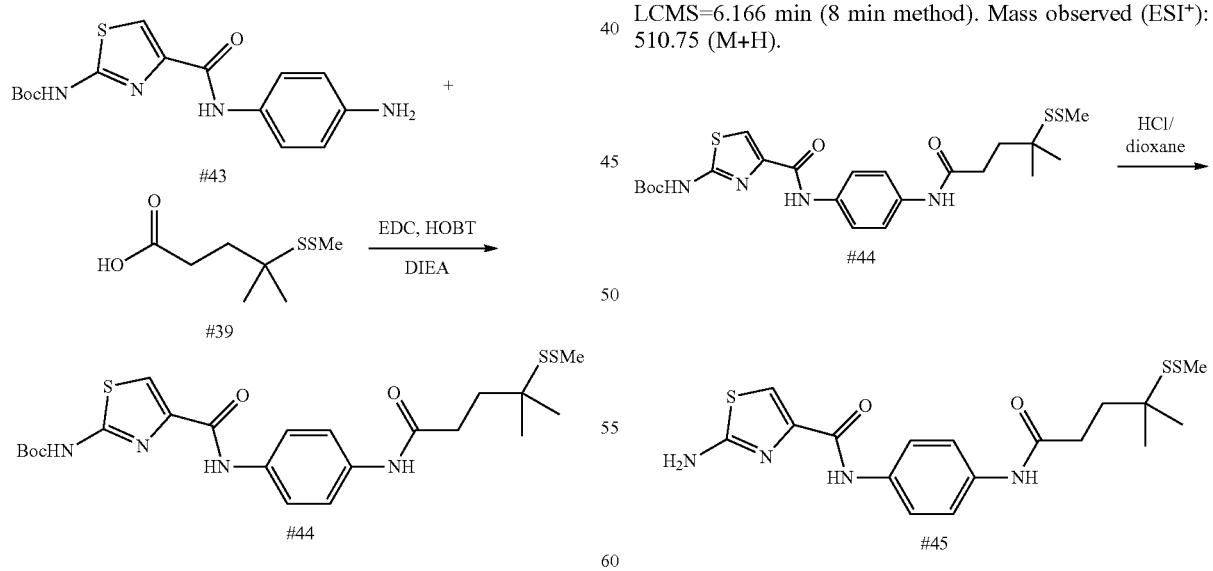

Compound #43 (500 mg, 1.495 mmol) and compound #39 (320 mg, 1.645 mmol) were dissolved in DMF (7.478 mL). EDC (315 mg, 1.645 mmol) and HOBt (252 mg, 1.645 mmol) were added to the reaction mixture, followed by DIEA (261 μL, 1.495 mmol) and the reaction was stirred at rt overnight. The reaction mixture was diluted with EtOAc and was washed with sat'd NH₄Cl, sat'd NaHCO₃, water (3×), dried over Na₂SO₄, filtered and concentrated. The crude product was purified by silica gel chromatography (0% to 50% EtOAc/hexanes) to obtain compound #44 as a colorless sticky oil (644 mg, 1.261 mmol, 84% yield). LCMS=6.166 min (8 min method). Mass observed (ESI⁺): 510.75 (M+H).

Compound #45 was synthesized similarly as compound #6 from compound #44 to obtain compound #45 as a white solid (550 mg, 1.230 mmol, 98% yield). ¹H NMR (400 MHz, DMSO-d₆): δ 1.29 (s, 6H), 1.85-1.94 (m, 2H), 2.37-2.42 (m, 2H), 2.42 (s, 3H), 7.54 (d, J=2.0 Hz, 1H), 7.56 (s, 1H), 7.58-7.68 (m, 3H), 9.99 (s, 1H), 10.03 (s, 1H).

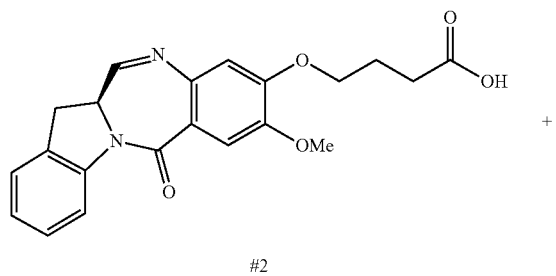

2

+

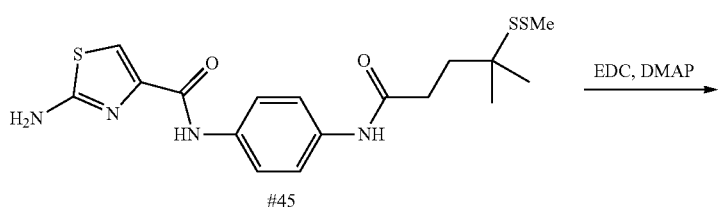

45

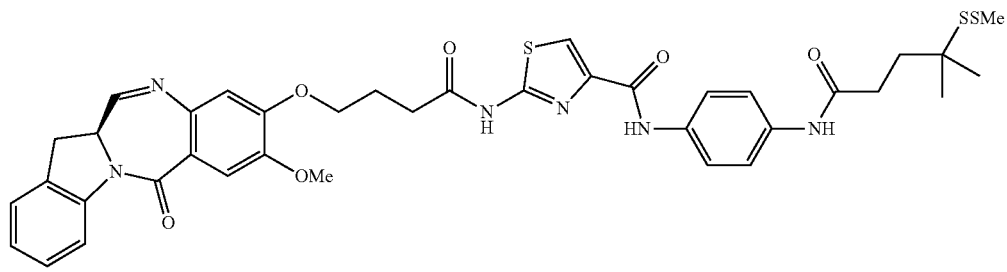

46

Compound #46 was synthesized similarly as compound #7 to obtain compound #46 as a white solid after purification by RPHPLC (C18 column, ACN/Water) (5 mg, 6.47 μmol, 8% yield). LCMS=5.655 min (8 min method). Mass observed (ESI+): 772.70 (M+H).

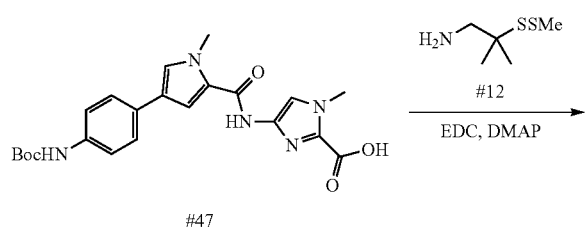

47

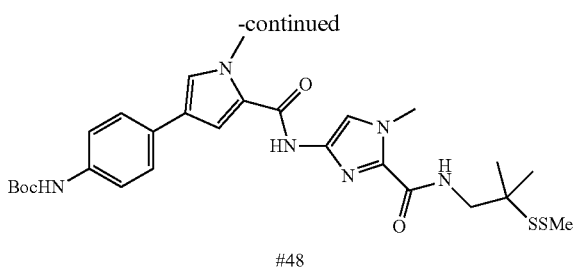

48

Compound #47 (250 mg, 0.569 mmol) and compound #12 (103 mg, 0.683 mmol) were dissolved in DMF (5.69 mL). EDC (164 mg, 0.853 mmol) and DMAP (34.7 mg, 0.284 mmol) were added to the reaction mixture was stirred at rt overnight. Water (5 mL) was added to the reaction mixture to precipitate the product. The resulting slurry was stirred for 5 min and filtered. The solid cake was washed with water (2×10 mL) and dried under vacuum/$N_2$. The crude product was purified by silica gel chromatography (0% to 50% to 100% EtOAc/hexanes) to obtain compound #48 (240 mg, 0.419 mmol, 74% yield). LCMS=6.730 min (8 min method). Mass observed (ESI+): 572.85 (M+H). $^1$H NMR (400 MHz, CDCl$_3$): δ 1.36 (s, 6H), 1.53 (s, 9H), 2.46 (s, 3H), 3.54 (d, J=6.3 Hz, 2H), 4.02 (d, J=13.7 Hz, 6H), 6.50 (s, 1H), 6.97 (d, J=1.8 Hz, 1H), 7.02 (d, J=1.8 Hz, 1H), 7.32-7.52 (m, 6H), 8.14 (s, 1H).

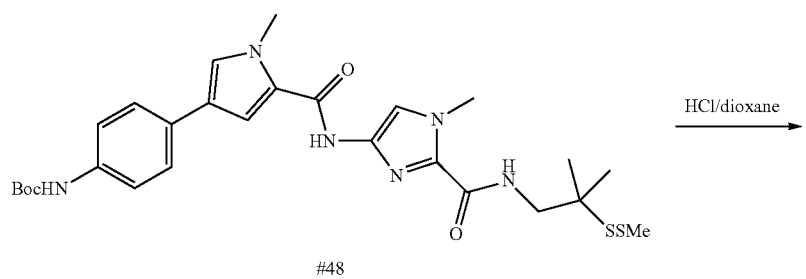
48
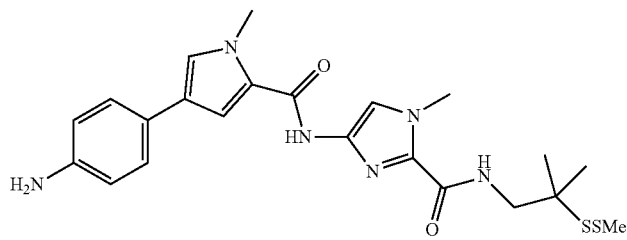
49
Compound #49 was synthesized similarly as compound #6 from compound #48 to obtain compound #49 as a solid (150 mg, 0.317 mmol, 76% yield). $^1$H NMR (400 MHz, DMSO-$d_6$): δ 1.29 (s, 6H), 2.46 (s, 3H), 3.46 (d, J=6.4 Hz, 2H), 3.92 (s, 3H), 3.96 (s, 3H), 7.36 (d, J=8.5 Hz, 2H), 7.53 (d, J=1.9 Hz, 1H), 7.57 (s, 1H), 7.60-7.63 (m, 3H), 7.75 (t, J=6.5 Hz, 1H), 10.18 (bs, 2H), 10.45 (s, 1H).
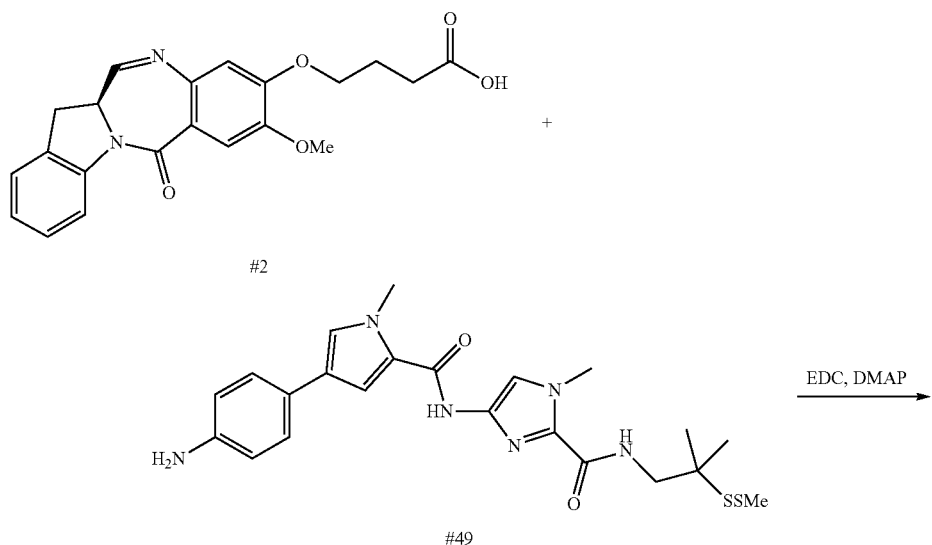
2
49
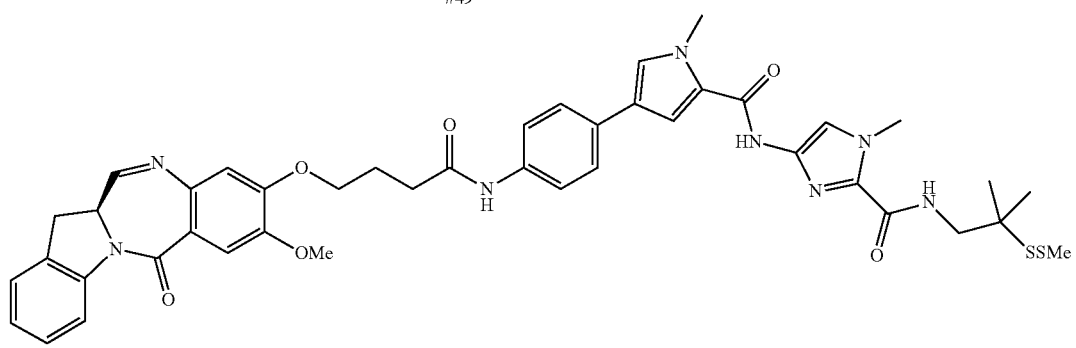
50

Compound #50 was synthesized similarly as compound #7 to obtain compound #50 as a white solid after purification by RPHPLC (C18 column, ACN/Water) (15 mg, 0.017 mmol, 13% yield). LCMS=5.899 min (8 min method). Mass observed (ESI+): 834.75 (M+H).

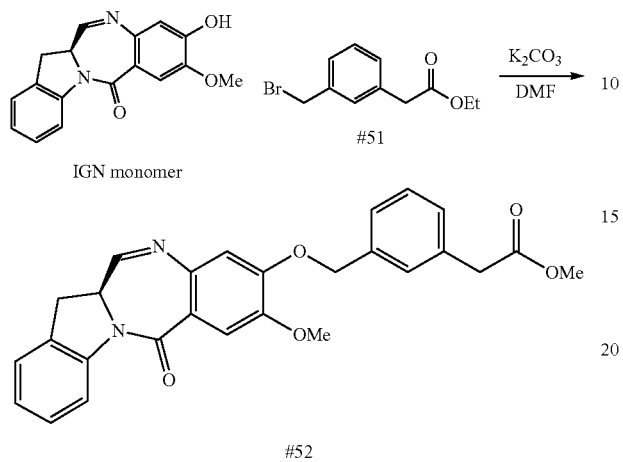

IGN monomer (105 mg, 0.355 mmol) and compound #51 (100 mg, 0.323 mmol) were dissolved in DMF (3.23 mL). K₂CO₃ (66.9 mg, 0.484 mmol) was added to the reaction mixture and was stirred at rt for 3.5 h. Water and EtOAc were added to the solution. The layers were separated and the organic layer was washed with water (3×), dried over Na₂SO₄, filtered and concentrated to obtain compound #52 (150 mg, 0.319 mmol, 99% yield). UPLCMS=1.72 min (2.5 min method). Mass observed (ESI+): 471.40 (M+H), 489.40 (M+H₂O+H).

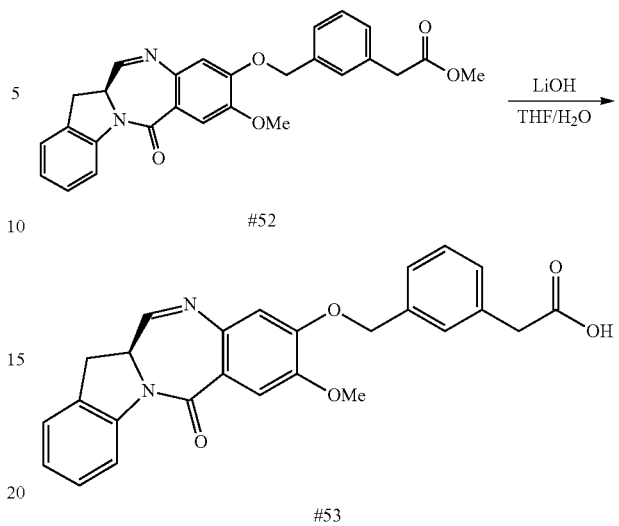

Compound #52 (150 mg, 0.319 mmol) was dissolved in THF (2.39 mL) and water (797 µL). LiOH (15.27 mg, 0.638 mmol) was added and the reaction mixture was stirred at rt for 1.5 h. The solution was diluted with water and acidified to pH~ 4 with 0.5 M aq HCl. EtOAc was added and the layers were separated. The aq. layer was extracted with EtOAc (2×). The combined organic layer was washed with water, dried over Na₂SO₄, filtered and concentrated to obtain compound #53 as an orange solid (130 mg, 0.294 mmol, 92% yield). UPLCMS=1.49 min (2.5 min method). Mass observed (ESI+): 443.30 (M+H), 461.30 (M+H₂O+H).

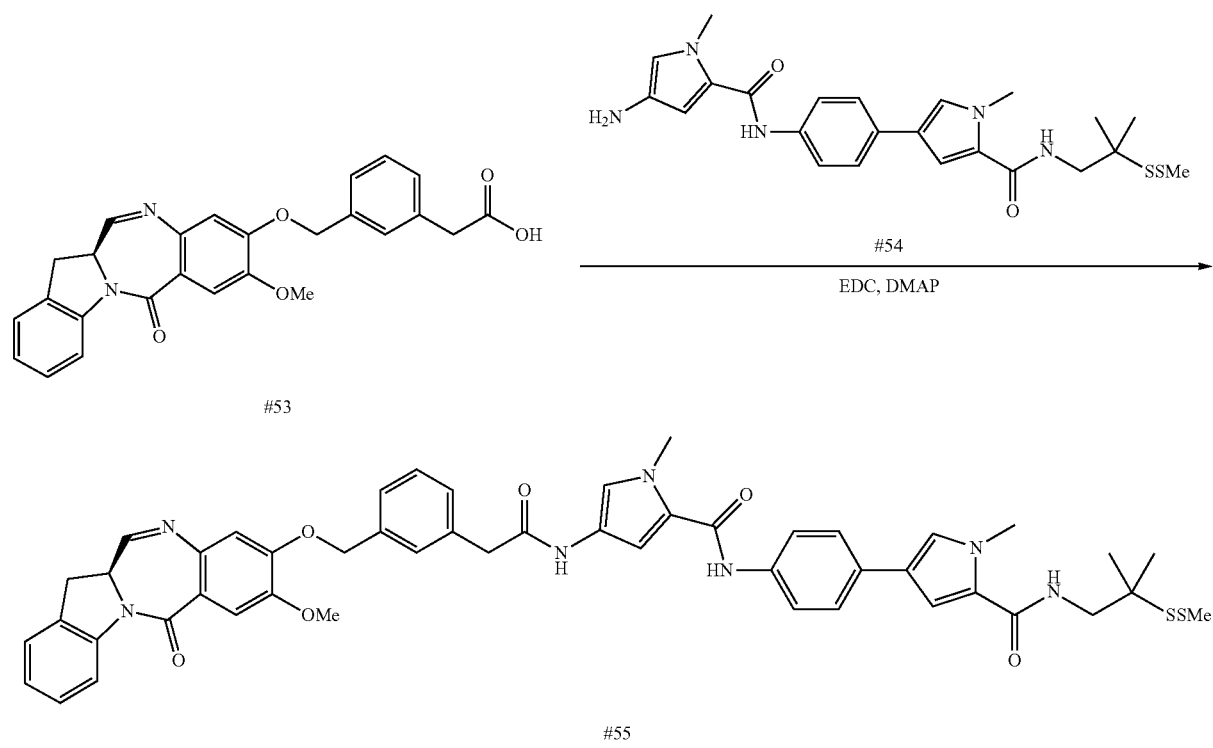

Compound #55 was synthesized similarly as compound #7 from compound #53 to obtain compound #55 as a white solid after purification by RPHPLC (C18 column, ACN/Water) (10 mg, 0.011 mmol, 14% yield). LCMS=6.310 min (8 min method). Mass observed (ESI⁺): 896.30 (M+H).

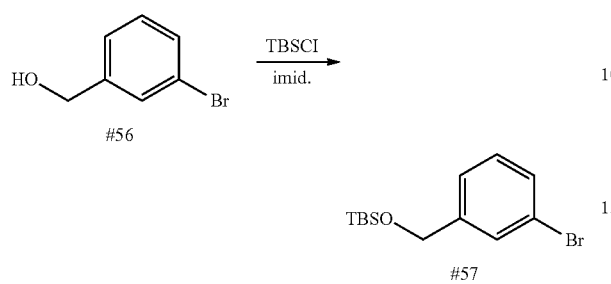

(3-bromophenyl)methanol, #56 (0.641 mL, 5.35 mmol) was dissolved in DMF (17.82 mL). TBSCl (0.967 g, 6.42 mmol) and imidazole (0.473 g, 6.95 mmol) were added to the reaction mixture and it was stirred at rt overnight. The reaction mixture was diluted with EtOAc and washed with sat'd NH₄Cl, water (3×), dried over Na₂SO₄, filtered and concentrated. The crude product was purified by silica gel chromatography (0% to 20% to 100% EtOAc/hexanes) to obtain compound #57 a colorless oil (1.50 g, 4.98 mmol, 93% yield). ¹H NMR (400 MHz, CDCl₃): δ 0.10 (s, 6H), 0.94 (s, 9H), 4.71 (bd, J=0.8 Hz, 2H), 7.17-7.21 m, 1H), 7.22-7.25 (m, 1H), 7.35-7.38 (m, 1H), 7.46-7.48 (m, 1H).

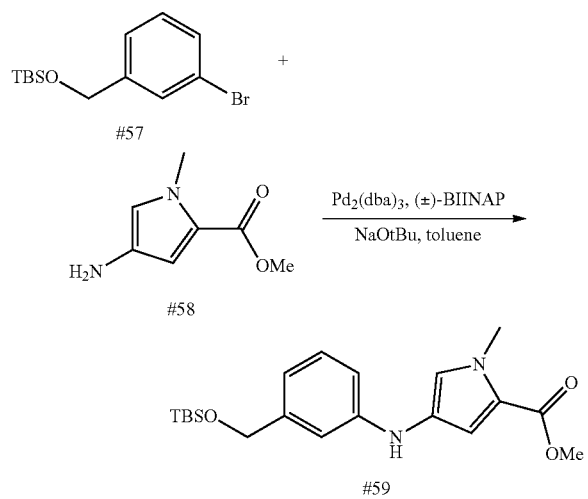

Compound #57 (528 mg, 1.751 mmol) and compound #58 (300 mg, 1.946 mmol) were dissolved in toluene (9.73 mL). Pd₂(dba)₃ (178 mg, 0.195 mmol) and BINAP (121 mg, 0.195 mmol) were added, followed by NaOtBu (262 mg, 2.72 mmol). The solution was degassed with Ar for a few minutes and was heated at 80° C. for 4 h. The reaction was cooled to rt and was diluted with EtOAc. The solution was filtered through Celite and the cake was washed with EtOAc and the filtrate concentrated. The crude product was purified by silica gel chromatography (0% to 30% EtOAc/hexanes) to obtain compound #59 as a brown-orange oil (279 mg, 0.745 mmol, 38% yield). UPLCMS=2.11 min (2.5 min method). Mass observed (ESI⁺): 375.8 (M+H). ¹H NMR (400 MHz, CDCl₃): δ 0.08 (s, 6H), 0.92 (s, 9H), 3.80 (s, 3H), 3.90 (s, 3H), 4.64-4.69 (m, 2H), 6.63-6.73 (m, 3H), 6.76-6.84 (m, 2H), 7.12 (t, J=7.8 Hz, 2H).

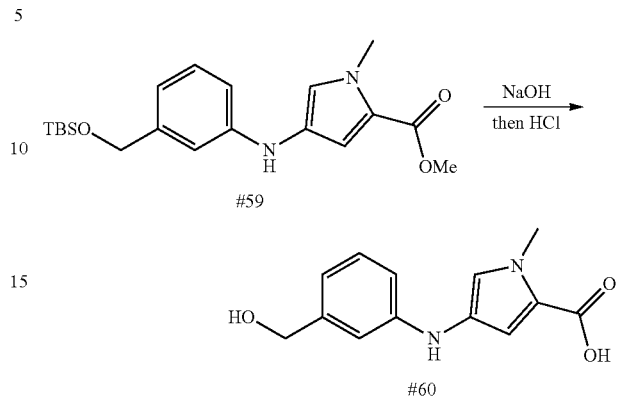

Compound #59 (270 mg, 0.721 mmol) was dissolved in MeOH (3.60 mL). NaOH (5 N, aq) (721 µL, 3.60 mmol) was added and the reaction mixture and was heated at 60° C. for 3 h. The solution was cooled to rt and 1 M HCl (aq) was added until pH~ 4. The solution was diluted with ACN and water and was lyophilized. The crude product was purified by flash reverse phase C18 (10% to 70% ACN/H₂O with 0.1% formic acid) to obtain compound #60 as a solid (50 mg, 0.203 mmol, 28% yield). UPLCMS=1.20 min (2.5 min method). Mass observed (ESI⁺): 247.1 (M+H).

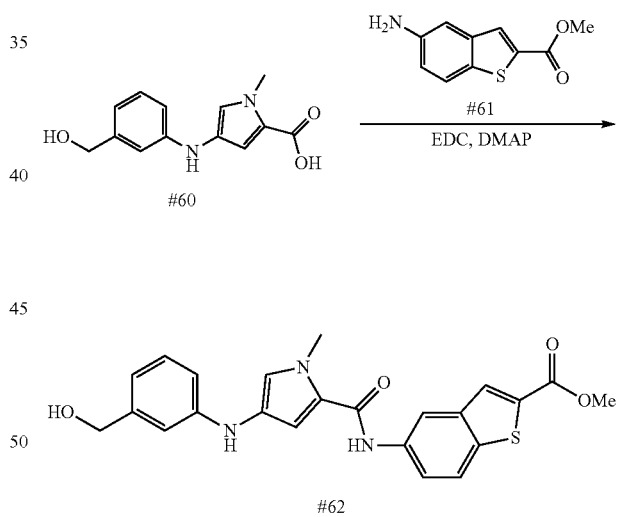

Compound #60 (29 mg, 0.118 mmol) and compound #61 (37 mg, 0.177 mmol) were dissolved in DMF (1.18 mL). EDC (34 mg, 0.177 mmol) was added to the reaction mixture, followed by DMAP (14 mg, 0.118 mmol). The reaction was stirred at rt for 2 h. The solution was diluted with water and EtOAc and the layers were separated. The organic layer was washed with sat'd NH₄Cl, water (3×), dried over Na₂SO₄, filtered and concentrated. The crude residue was purified by RPHPLC (C18 column, ACN/H₂O) to obtain compound #62 as a solid (10 mg, 0.023 mmol, 20% yield). UPLCMS=1.69 min (2.5 min method). Mass observed (ESI⁺): 436.3 (M+H).

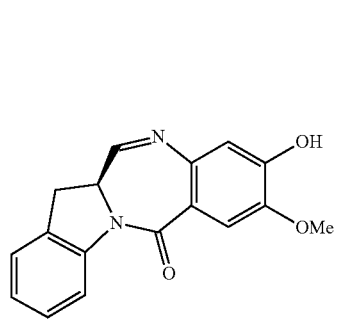

IGN monomer

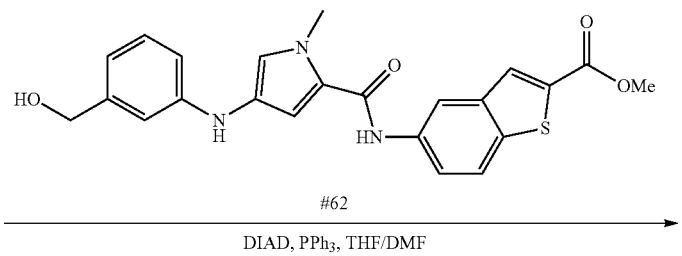

DIAD, PPh₃, THF/DMF

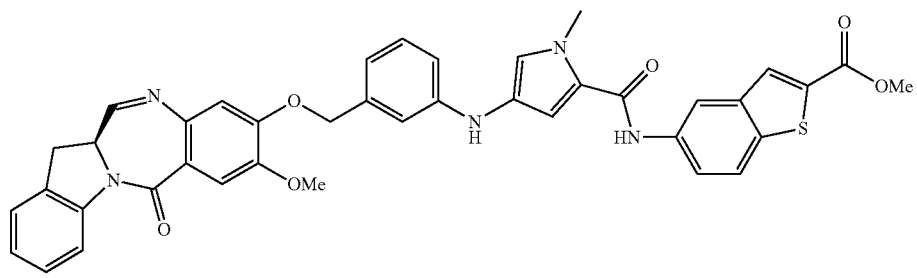

63

Compound #62 (10 mg, 0.023 mmol) and IGN monomer (8.11 mg, 0.028 mmol) were dissolved in THF (638 μL) and DMF (128 μL). PPh₃ (7.23 mg, 0.028 mmol) was added to the reaction mixture at rt, followed by DIAD (5.36 μL, 0.028 mmol) and was stirred at rt for 3 h. The reaction mixture was diluted with water and DCM and the layers were separated. The organic layer was washed with water, dried over Na₂SO₄, filtered and concentrated. The crude product was purified by RPHPLC (C18 column, ACN/Water) to obtain compound #63 as a white solid (3.0 mg, 4.21 mmol, 18% yield). UPLCMS=6.272 min (8 min method). Mass observed (ESI⁺): 712.6 (M+H).

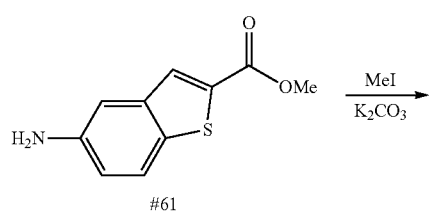

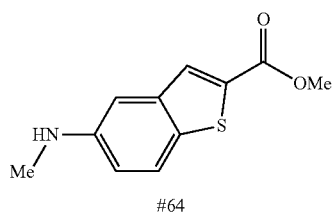

Compound #61 (300 mg, 1.448 mmol) was dissolved in DMF (4.83 mL). MeI (109 μL, 1.737 mmol) was added, followed by K₂CO₃ (300 mg, 2.171 mmol) and the reaction was stirred at rt overnight. Water was added to the reaction mixture to precipitate the product. The resulting slurry was filtered to obtain a brown solid. The crude product was purified by silica gel chromatography (10% to 100% EtOAc/ hexanes) to obtain compound #64 as an orange solid (95 mg, 0.434 mmol, 30% yield). UPLCMS=1.32 min (2.5 min method). Mass observed (ESI⁺): 222.4 (M+H).

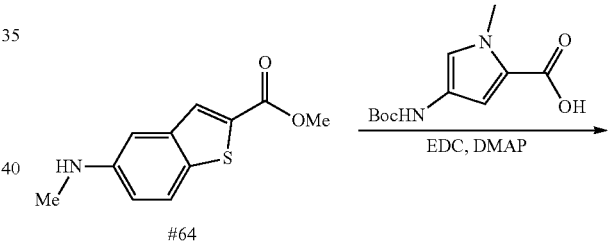

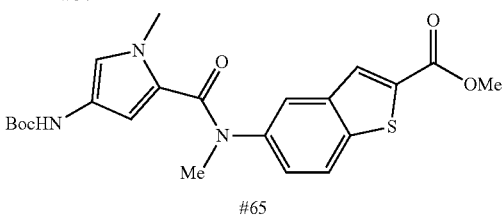

Compound #65 was synthesized similarly as compound #13 from compound #64 to obtain compound #65 as a white solid after C18 purification (24 mg, 0.054 mmol, 13% yield). UPLCMS=1.75 min (2.5 min method). Mass observed (ESI⁺): 444.4 (M+H).

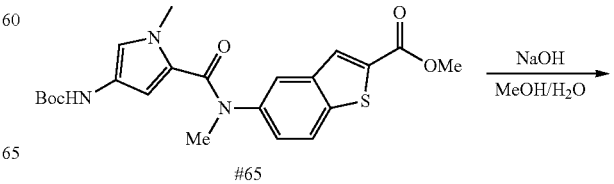

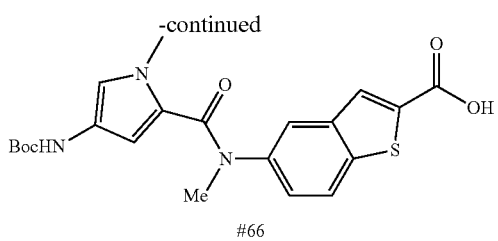

Compound #66 was synthesized similarly as compound #5A to obtain product #66 which was taken onto the next without purification (23 mg, 0.054 mmol, 99% yield). UPLCMS=1.53 min (2.5 min method). Mass observed (ESI+): 430.4 (M+H).

Compound #67 was synthesized similarly as compound #13 to obtain crude product #67 which was taken onto the next step without further purification (31 mg, 0.055 mmol, 95% yield). LCMS=6.208 min (8 min method). Mass observed (ESI+): 563.0 (M+H).

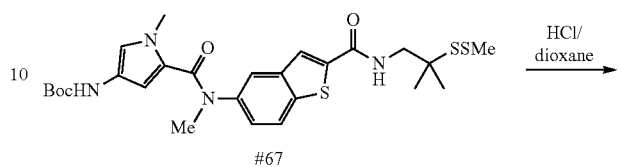

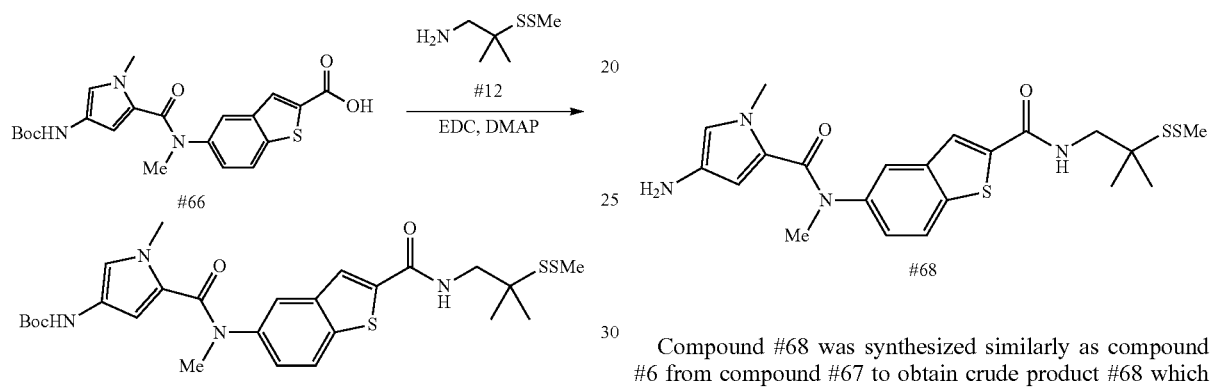

Compound #68 was synthesized similarly as compound #6 from compound #67 to obtain crude product #68 which was taken onto the next step without further purification (24 mg, 0.052 mmol, 94% yield). UPLCMS=1.37 min (2.5 min method). Mass observed (ESI+): 463.9 (M+H).

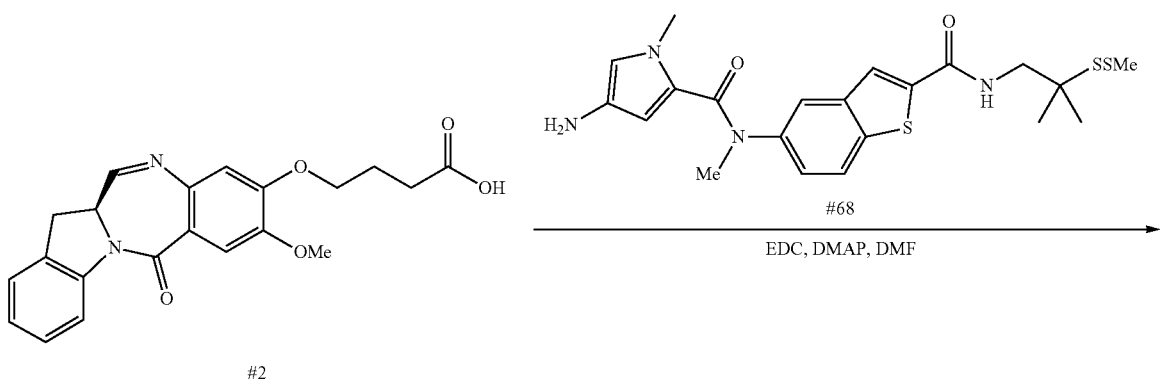

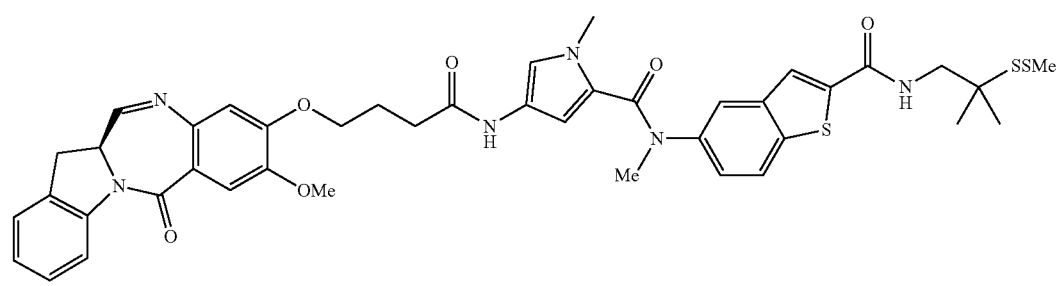

Compound #69 was synthesized similarly as compound #7 to obtain compound #69 after purification by RPHPLC (C18 column, ACN/Water) (15 mg, 0.018 mmol, 35% yield). LCMS=5.763 min (8 min method). Mass observed (ESI$^+$): 824.8 (M+H).

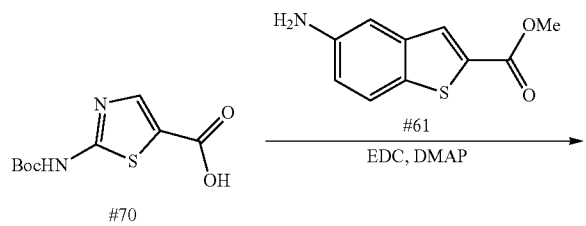

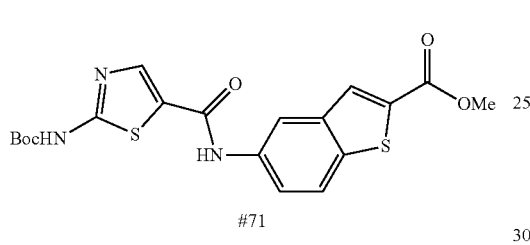

Compound #71 was synthesized similarly as compound #13 to obtain compound #71 as a solid, which was taken onto the next step without purification (230 mg, 0.531 mmol, 43% yield). UPLCMS=1.66 min (2.5 min method). Mass observed (ESI$^+$): 434.2 (M+H). $^1$H NMR (400 MHz, DMSO-d$_6$): δ 1.51 (s, 9H), 3.89 (s, 3H), 7.78 (dd, J=8.9, 2.1 Hz, 1H), 8.03 (dt, J=8.8, 0.7 Hz, 1H), 8.19-8.29 (m, 2H), 8.44 (d, J=2.1 Hz, 1H), 10.37 (s, 1H), 11.84 (s, 1H).

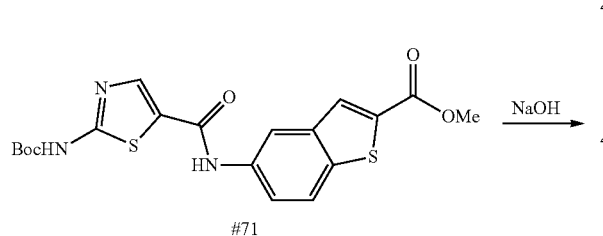

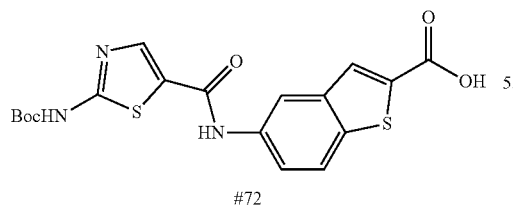

Compound #72 was synthesized similarly as compound #5A from compound #71 to obtain compound #72 which was taken onto the next step without purification (170 mg, 0.405 mmol, 76% yield). UPLCMS=1.47 min (2.5 min method). Mass observed (ESI$^+$): 420.2 (M+H). $^1$H NMR (400 MHz, DMSO-d$_6$): δ 1.51 (s, 9H), 7.76 (dd, J=8.8, 2.1 Hz, 1H), 8.00 (d, J=8.9 Hz, 1H), 8.11 (d, J=0.7 Hz, 1H), 8.27 (s, 1H), 8.42 (d, J=2.0 Hz, 1H), 10.37 (s, 1H), 11.84 (s, 1H), 13.49 (s, 1H).

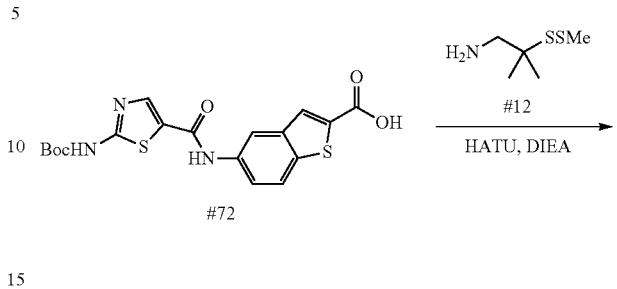

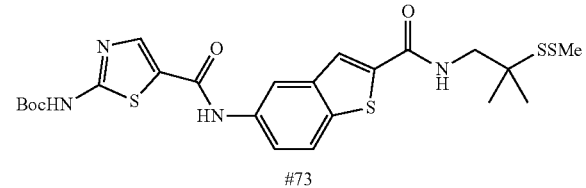

Compound #72 (170 mg, 0.405 mmol) and compound #12 (67 mg, 0.446 mmol) were dissolved in DMF (2.03 mL). HATU (170 mg, 0.446 mmol) was added to the reaction mixture, followed by DIEA (142 µL, 0.811 mmol). The reaction mixture was stirred at rt overnight. Water was added to the reaction mixture to precipitate the product. The resulting slurry was filtered and dried under vacuum/N$_2$ to obtain compound #73 as a solid (176 mg, 0.318 mmol, 79% yield). UPLCMS=1.85 min (2.5 min method). Mass observed (ESI$^+$): 553.4 (M+H).

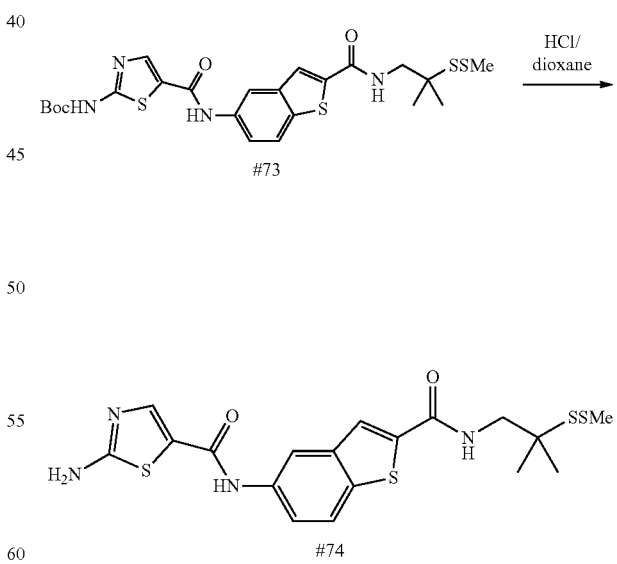

Compound #74 was synthesized similarly as #6 from compound #73 to obtain compound #74 which was taken onto the next without purification (140 mg, 0.309 mmol, 97% yield). UPLCMS=1.51 min (2.5 min method). Mass observed (ESI$^+$): 453.8 (M+H).

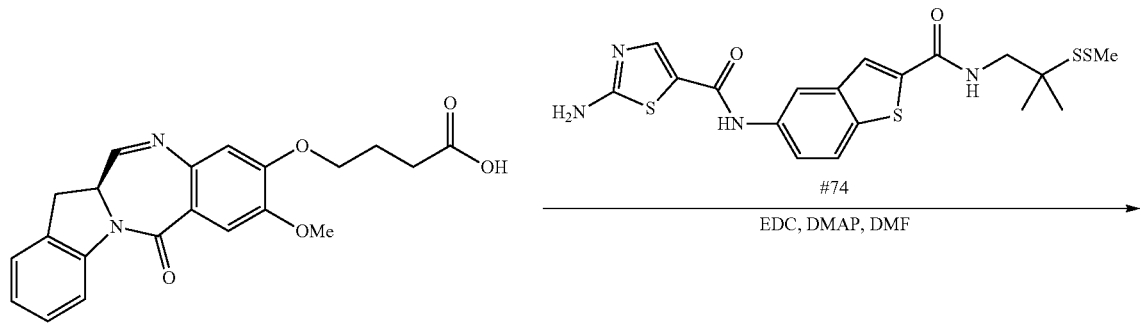

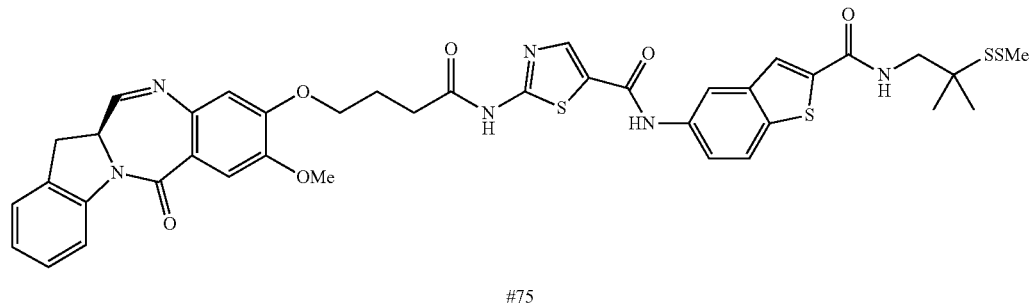

Compound #75 was synthesized similarly as compound #7 to obtain compound #75 after purification by RPHPLC (C18 column, ACN/Water) (45 mg, 0.055 mmol, 42% yield). LCMS=5.909 min (8 min method). Mass observed (ESI+): 814.80 (M+H).

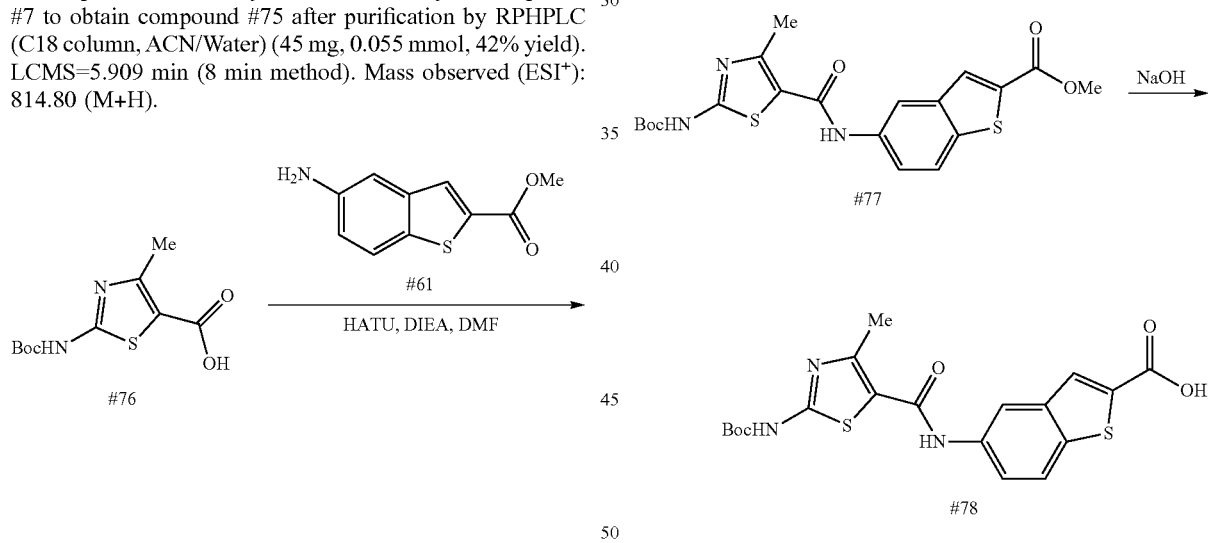

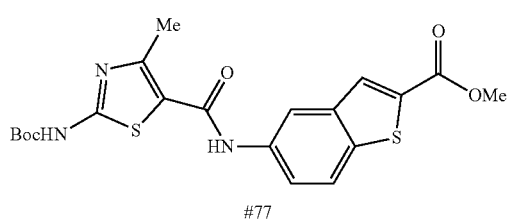

Compound #77 was synthesized similarly as compound #13 to obtain compound #77 (479 mg, 1.07 mmol, 92% yield). UPLCMS=1.70 min (2.5 min method). Mass observed (ESI+): 448.4 (M+H).

Compound #78 was synthesized similarly as compound #5A from compound #77 to obtain compound #78 which was taken onto the next step without purification (450 mg, 1.038 mmol, 97% yield). UPLCMS=1.56 min (2.5 min method). Mass observed (ESI+): 434.2 (M+H).

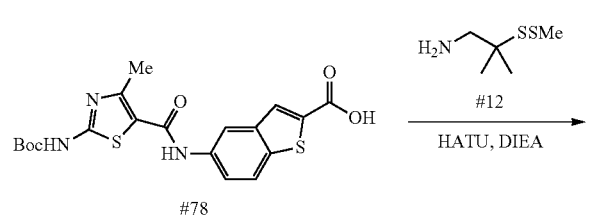

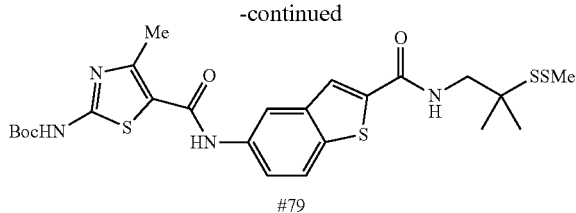

79

Compound #79 was synthesized similarly as compound #13 after purification by silica gel chromatography (0% to 10% MeOH/DCM) to obtain compound #79 (240 mg, 0.423 mmol, 41% yield). UPLCMS=1.84 min (2.5 min method). Mass observed (ESI+): 567.4 (M+H).

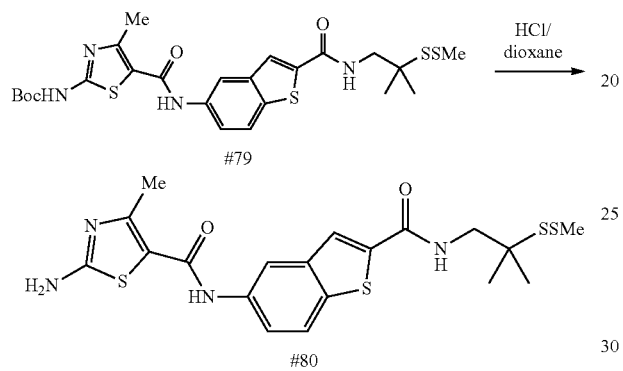

Compound #80 was synthesized similarly as #6 from compound #79 to obtain compound #80 which was taken onto the next step without purification (198 mg, 0.424 mmol, 100% yield). UPLCMS=1.52 min (2.5 min method). Mass observed (ESI+): 467.5 (M+H).

Compound #81 was synthesized similarly as compound #7 to obtain compound #81 after purification by RPHPLC (C18 column, ACN/Water) (33 mg, 0.040 mmol, 30% yield). LCMS=5.983 min (8 min method). Mass observed (ESI+): 828.90 (M+H).

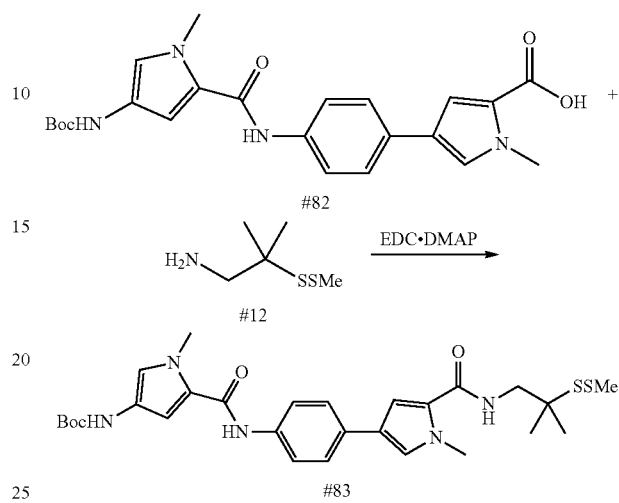

Compound #82 (300 mg, 0.684 mmol) and compound #12 (135 mg, 0.889 mmol) were dissolved in DMF (4.56 mL). EDC (236 mg, 1.232 mmol) and DMAP (62.7 mg, 0.513 mmol) were added and the reaction and was stirred overnight at rt. Addition of water caused precipitation of the product which was filtered and washed with water. The solid was dissolved in MeOH/DCM, dried over MgSO4, filtered and concentrated to give compound #83 (296 mg, 76% yield) as a brownish solid that was used without further purification. LCMS=6.53 min (8 min method). Mass observed (ESI+): 569.8 (M+H).

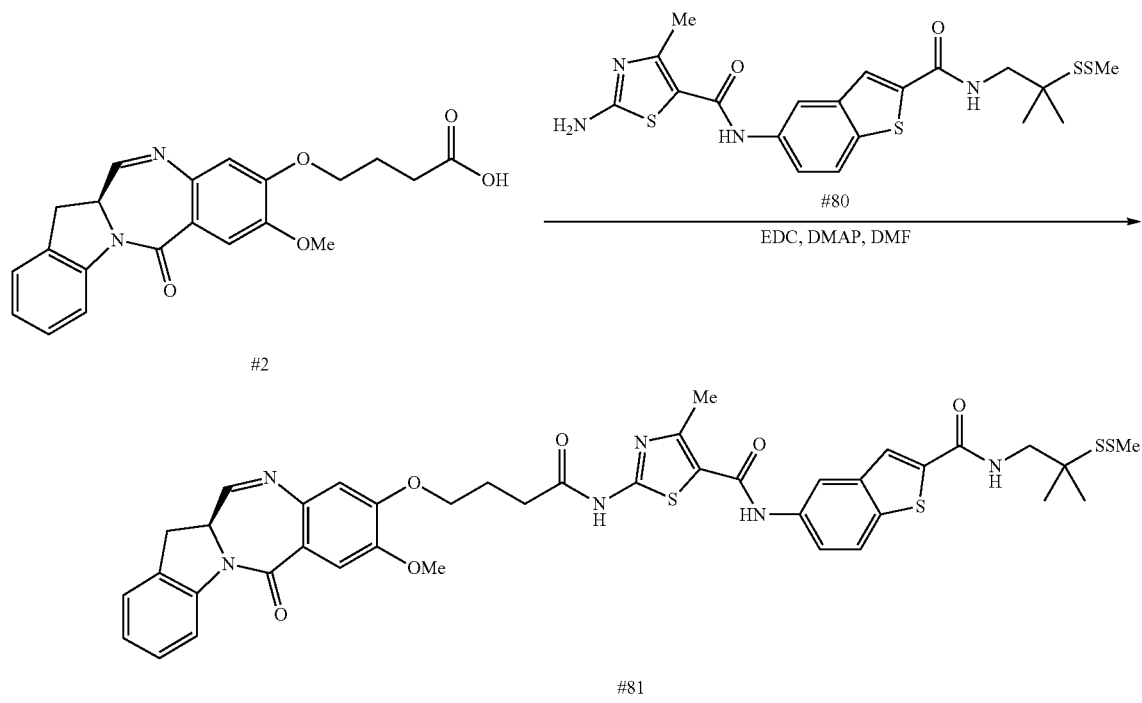

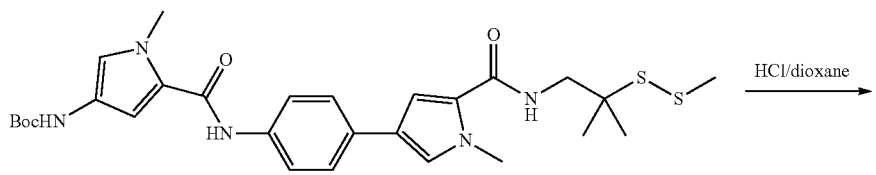

83

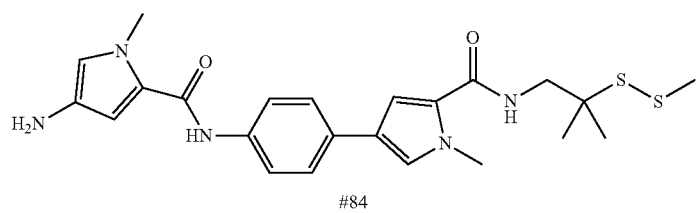

84

Compound #83 (296 mg, 0.518 mmol) was stirred in neat hydrogen chloride (4 N in dioxane, 1.94 mL, 7.77 mmol) under $N_2$ at rt for 2.5 h until precipitate had formed. The reaction was slurried with hexanes and then filtered and washed with additional hexanes. The solid was dissolved in DCM with a few drops of methanol and washed with sat'd NaHCO$_3$ solution. The organic layer was dried over MgSO$_4$, filtered and concentrated to give compound #84 (240 mg, 98% yield) as a brown solid that was carried on without further purification. LCMS=4.42 min (8 min method). Mass observed (ESI$^+$): 471.9 (M+H).

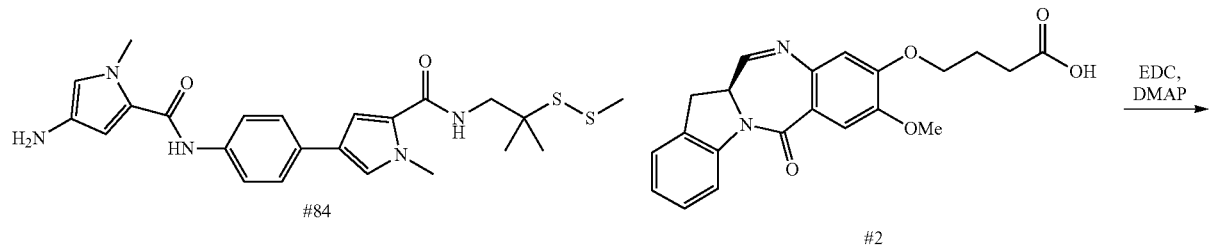

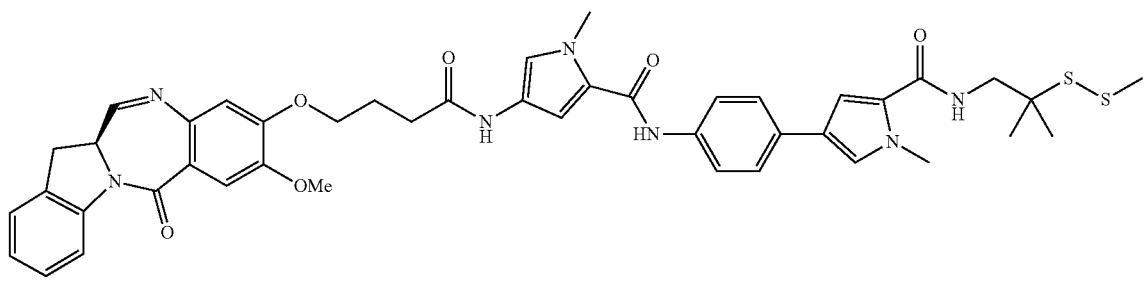

85

Compound #2 (105 mg, 0.276 mmol) and compound #84 (130 mg, 0.276 mmol) were dissolved in DCM (2.76 mL). EDC (79 mg, 0.413 mmol) and DMAP (16.84 mg, 0.138 mmol) were added and the mixture was stirred at rt for 2 h. The reaction was diluted with DCM and washed with water. The layers were separated and the organics were dried over MgSO$_4$, filtered and concentrated to give compound #85 (238 mg, 100% yield) that was used directly in the next reaction without purification. LCMS=5.85 min (8 min method). Mass observed (ESI$^+$): 833.7 (M+H).

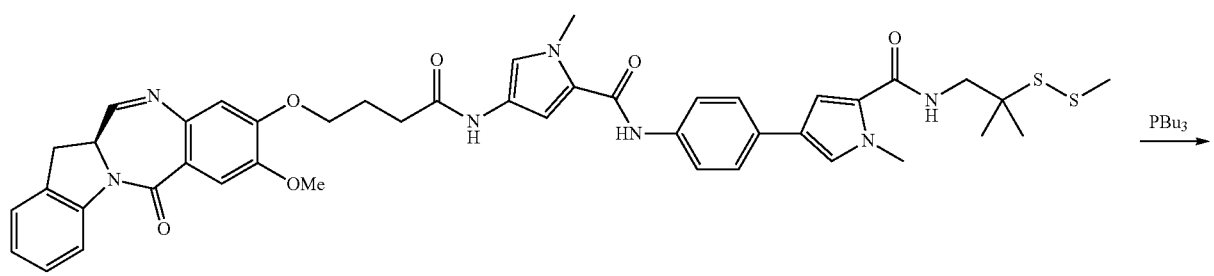

85

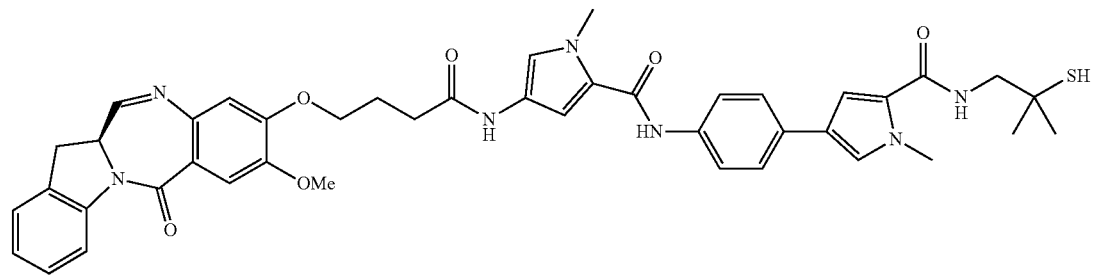

86

Compound #85 (100 mg, 0.120 mmol) was dissolved in THF (0.9 mL) and water (0.045 mL) under Ar. Tributylphosphine (0.033 mL, 0.132 mmol) was added and the reaction stirred at rt for 80 min. The reaction mixture was concentrated to obtain compound #86 (126 mg, 100% yield, 75% purity). LCMS=6.6 min (15 min method). Mass observed (ESI$^+$): 788.2 (M+H).

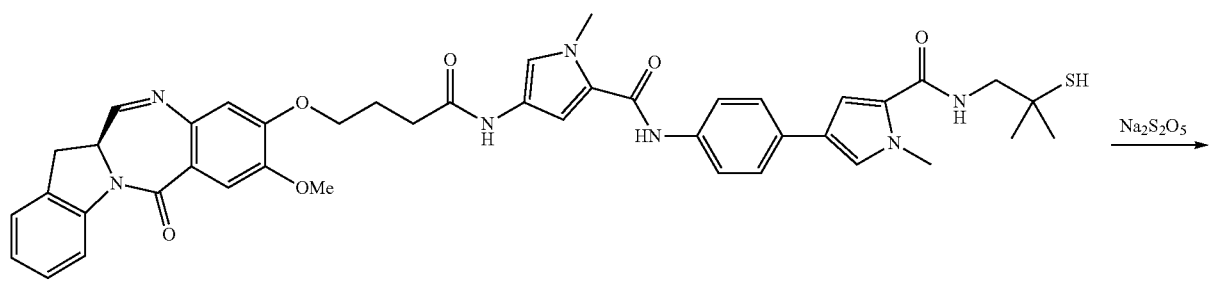

86

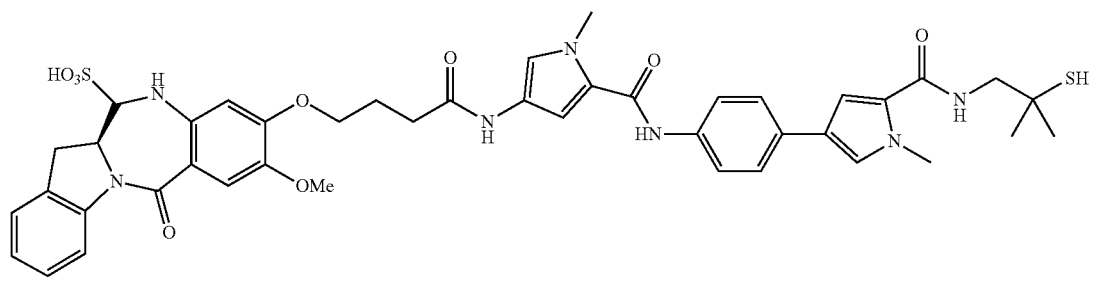

87

Compound #86 (126 mg, 0.160 mmol, 75% purity) was suspended in 2-Propanol (5.33 mL) and water (2.66 mL). Na$_2$S$_2$O$_5$ (100 mg, 0.959 mmol) was added and was stirred at rt overnight. The reaction mixture was diluted with ACN/H$_2$O, frozen and lyophilized. The crude mixture was dissolved in 3:1:1 (THF:ACN:water) and was purified via RPHPLC (C18 column, ACN/water) to give compound #87 (12 mg, 11% yield). LCMS=4.1 min (15 min method). Mass observed (ESI$^-$): 868.4 (M−H).

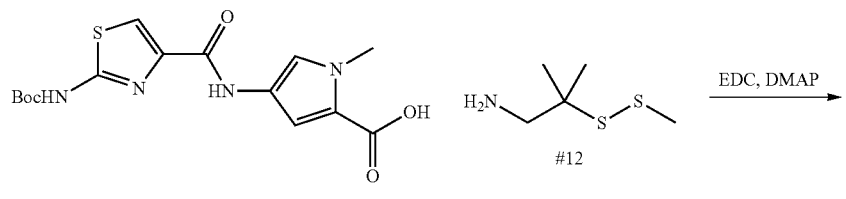

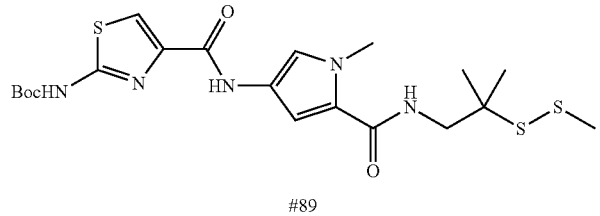

Compound #89 was prepared from compound #88 similarly as compound #83 to obtain compound #89 as a fluffy yellow solid (412 mg, 100% yield). LCMS=5.78 min (8 min method). Mass observed (ESI⁺): 499.8 (M+H).

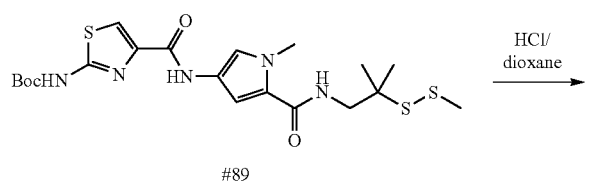

Compound #89 (409 mg, 0.819 mmol) was stirred in neat hydrogen chloride (4 M in dioxane, 3.07 mL, 12.28 mmol) under $N_2$ at rt. MeOH (1.5 mL) was added and the reaction was stirred at rt overnight. The reaction mixture was concentrated and then the crude product was redissolved in DCM/MeOH. The solution was washed with sat'd $NaHCO_3$, dried over $MgSO_4$, filtered and concentrated to give compound #90 (284 mg, 87% yield), which was used without further purification. LCMS=4.50 min (8 min method). Mass observed (ESI⁺): 399.8 (M+H).

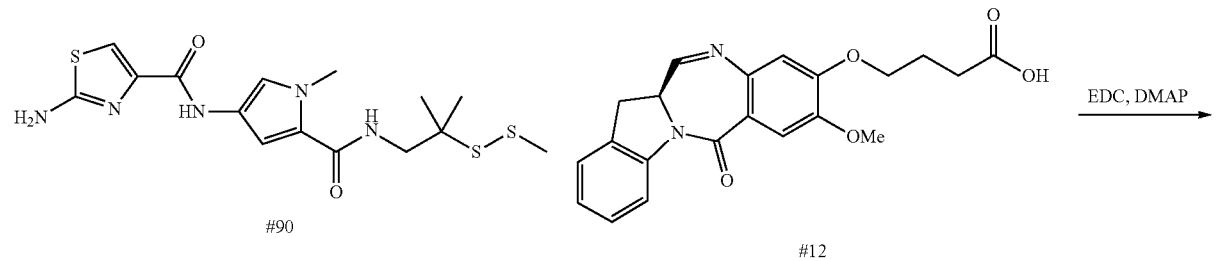

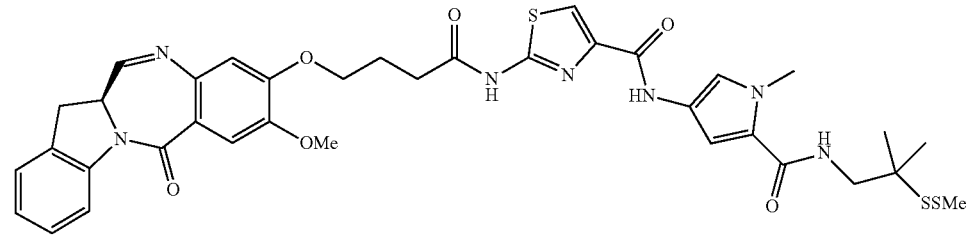

Compound #91 was prepared similarly as compound #85 to give compound #91 after purification by RPHPLC (C18 column, ACN/water) (1.8 mg, 12% yield). LCMS=5.3 min (8 min method). Mass observed (ESI+): 761.7 (M+H).

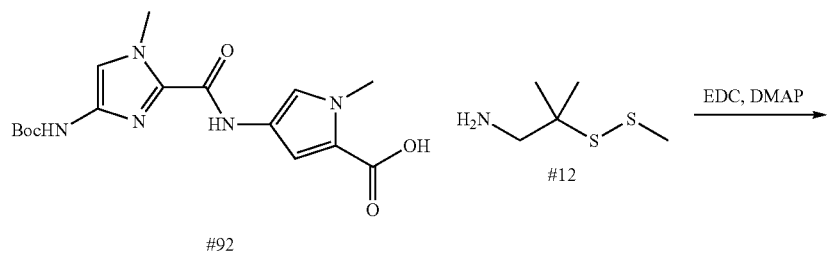

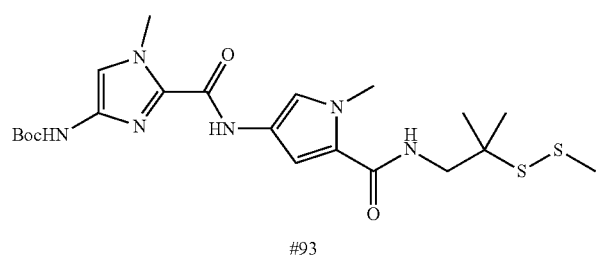

Compound #93 was prepared from compound #92 similarly as compound #83 to obtain compound #93, which was used without further purification (405 mg, 99% yield). LCMS=5.83 min (8 min method). Mass observed (ESI+): 496.9 (M+H).

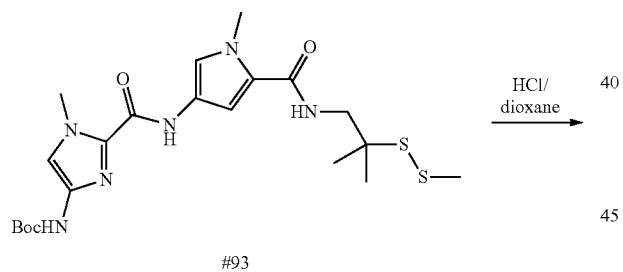

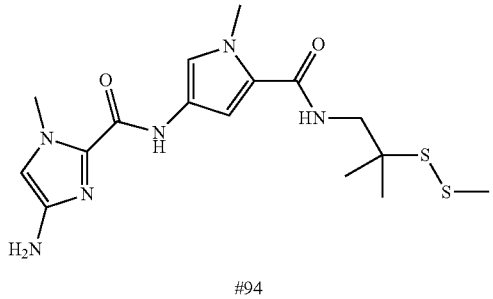

Compound #94 was prepared similarly as compound #84 from compound #93 to obtain compound #94, which was used without further purification (290 mg, 90% yield). LCMS=3.9 min (8 min method). Mass observed (ESI+): 396.9 (M+H).

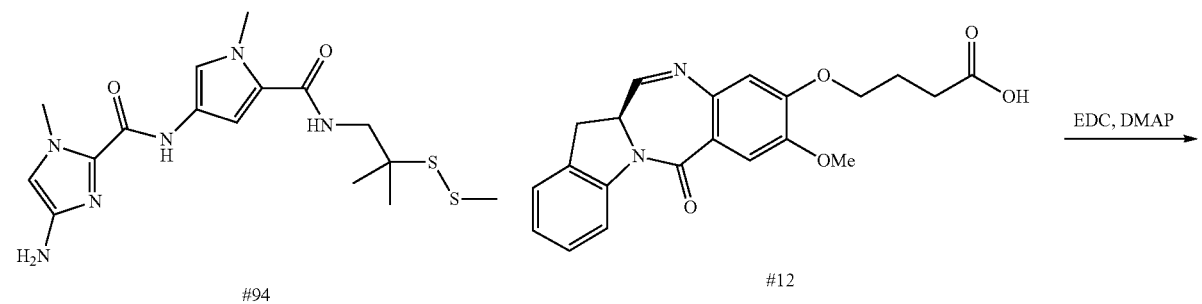

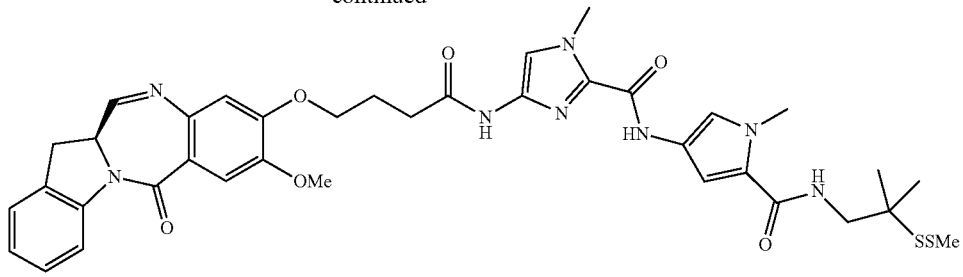

95

Compound #95 was prepared similarly as compound #85 to give compound #95 after purification by RPHPLC (C18 column, ACN/water) (5.7 mg, 25% yield). LCMS=5.22 min (8 min method). Mass observed (ESI+): 758.7 (M+H).

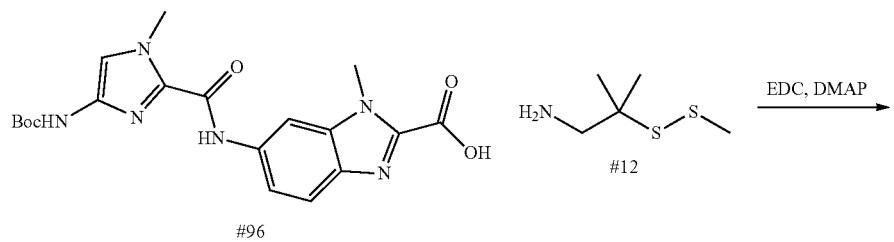

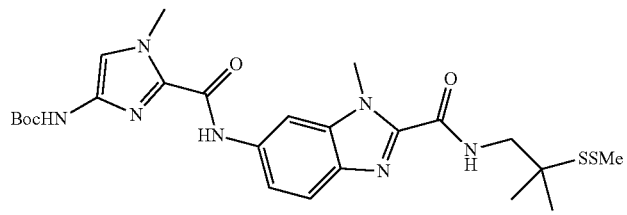

97

Compound #96 (1.0 g, 2.413 mmol) and compound #12 (0.402 g, 2.65 mmol) were dissolved in DMF (4.56 mL). EDC (0.509 g, 2.65 mmol), HOBt (0.406 g, 2.65 mmol) and DIPEA (0.843 mL, 4.83 mmol) were added and the reaction was stirred overnight at rt. Addition of water caused precipitation of the product which was filtered and washed with water. The crude solid was purified via silica gel chromatography (Hexanes/EtOAc) to give compound #97 (323 mg, 24% yield). LCMS=6.54 min (8 min method). Mass observed (ESI+): 548.3 (M+H). $^1$H NMR (400 MHz, CDCl$_3$): δ 1.37 (s, 6H), 1.53 (s, 9H), 2.47 (s, 3H), 3.63 (d, J=6.4 Hz, 2H), 4.09 (s, 3H), 4.23 (s, 3H), 6.82 (s, 1H), 7.16-7.23 (m, 2H), 7.74 (d, J=8.7 Hz, 1H), 8.07 (s, 1H), 8.29 (s, 1H), 9.20 (s, 1H).

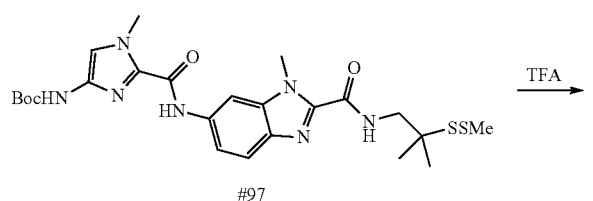

97

TFA →

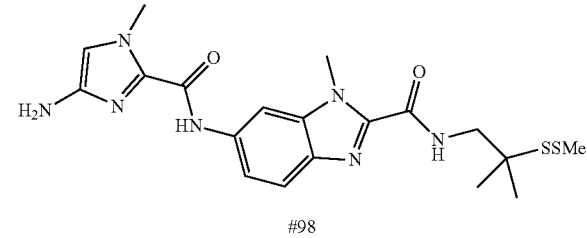

98

Compound #97 (157 mg, 0.287 mmol) was dissolved in DCM (717 μL) and was cooled to 0° C. A freshly mixed solution of DCM (358 μL) and TFA (358 μL) was added and the ice bath was removed. The reaction was stirred at rt until completion by LCMS. The reaction mixture was diluted with DCM and was quenched with sat'd NaHCO$_3$. The organic layer was washed with brine, dried over MgSO$_4$, filtered and concentrated to give compound #98 (127 mg, 99% yield) that was used without further purification. LCMS=4.77 min (8 min LCMS method). Mass observed (ESI+): 448.2 (M+H).

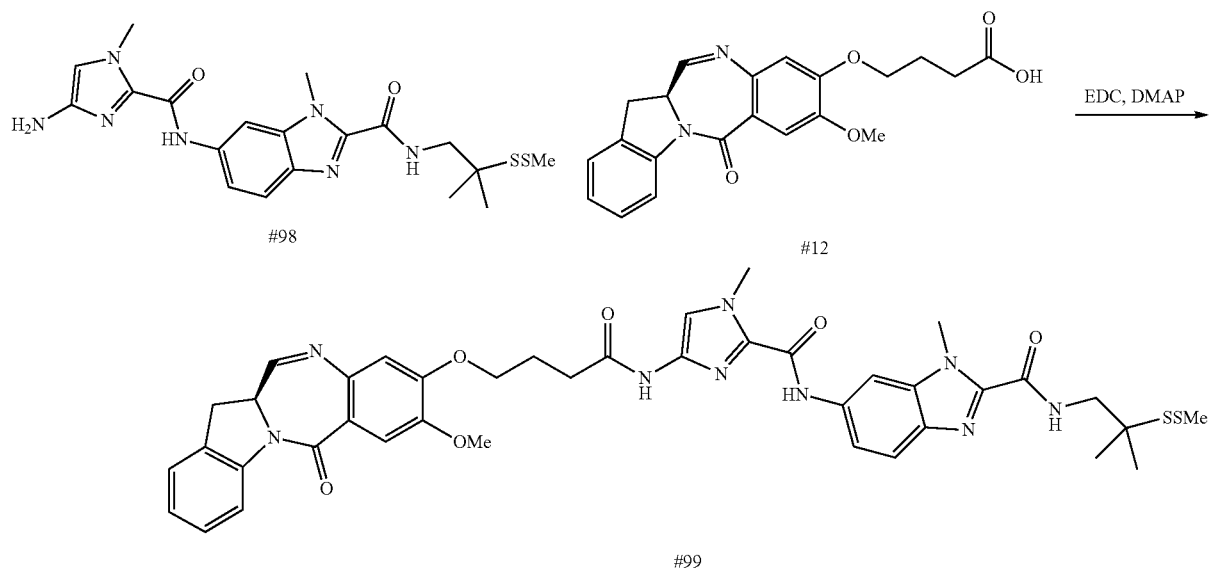

Compound #99 was prepared similarly as compound #85. Approximately ⅓ of the crude product was purified via RPHPLC (C18 column, Acetonitrile/water with 0.1% formic acid) to give compound #99 (6.3 mg, 14% yield). LCMS=5.8 min (8 min method). Mass observed (ESI+): 810.3 (M+H).

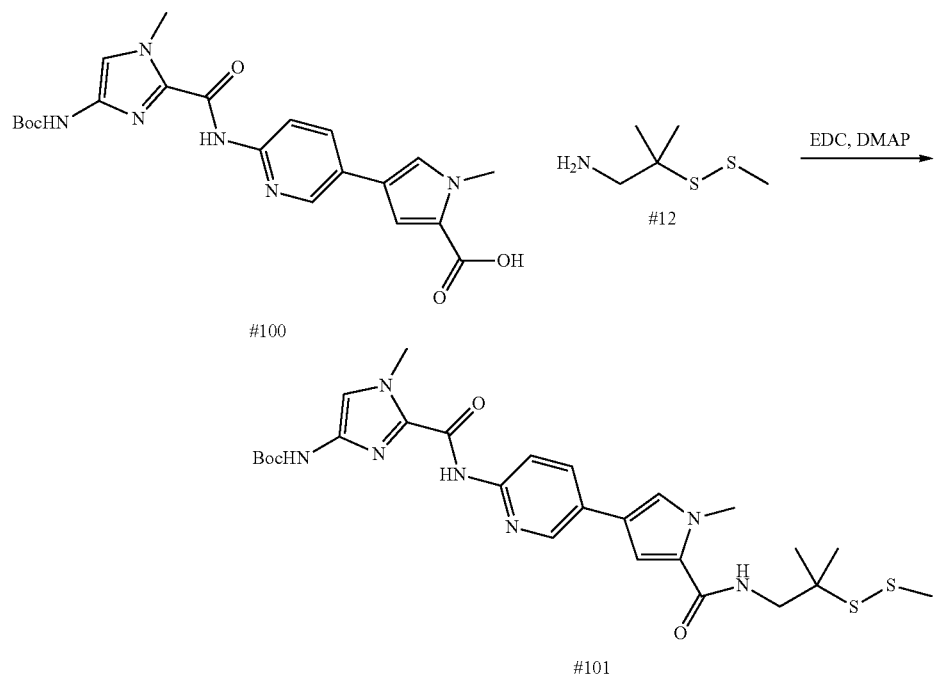

Compound #100 (520 mg, 1.181 mmol) and compound #12 (232 mg, 1.535 mmol) were dissolved in DMF (7.87 mL). EDC (407 mg, 2.125 mmol), DMAP (108 mg, 0.885 mmol) and DIPEA (412 µL, 2.361 mmol) were added and the reaction was stirred overnight at rt. Addition of water caused precipitation of the product which was filtered and washed with water. The resulting solid was dissolved in MeOH/DCM and dried over MgSO$_4$, filtered and concentrated. The crude product was purified via silica gel chromatography (Hexanes/EtOAc) to give compound #101 (215 mg, 32% yield) as a white solid. LCMS=6.63 min (8 min method). Mass observed (ESI+): 574.2 (M+H).

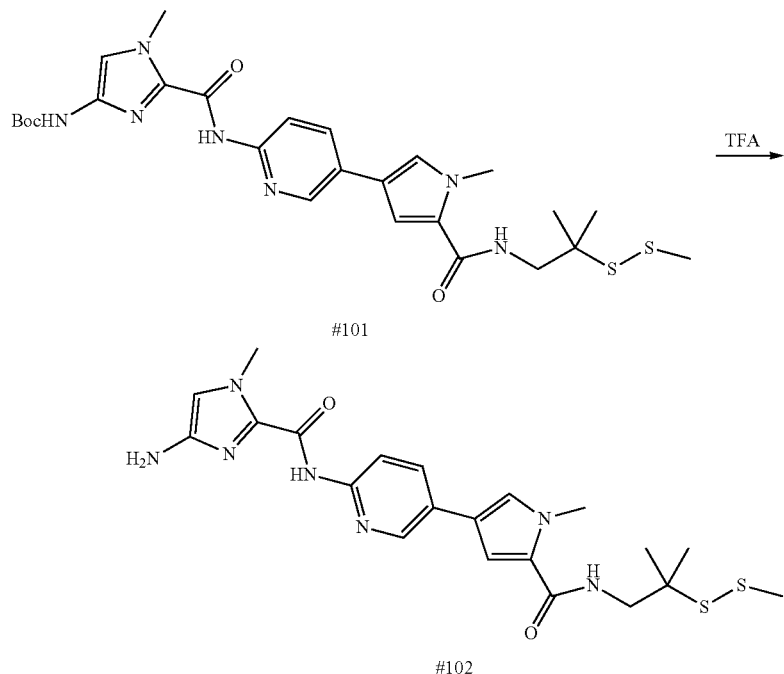

Compound #102 was prepared similarly as compound #98 using compound #101, which was used without purification to give compound #102 (91 mg, 81% yield). LCMS=4.87 min (8 min method). Mass observed (ESI+): 474.1 (M+H).

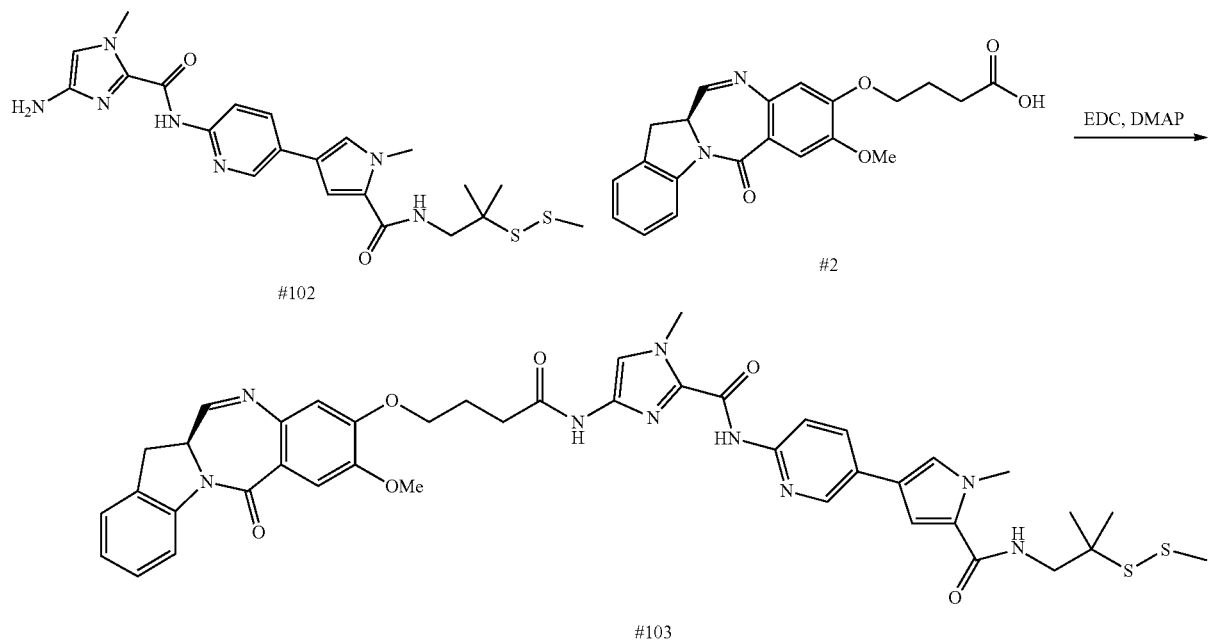

Compound #103 was prepared similarly as compound #85. Half of the crude material was purified via RPHPLC (C18 column, ACN/Water with 0.1% formic acid) to give compound #103 (6 mg, 15% yield). LCMS=5.97 min (8 min method). Mass observed (ESI+): 836.3 (M+H).

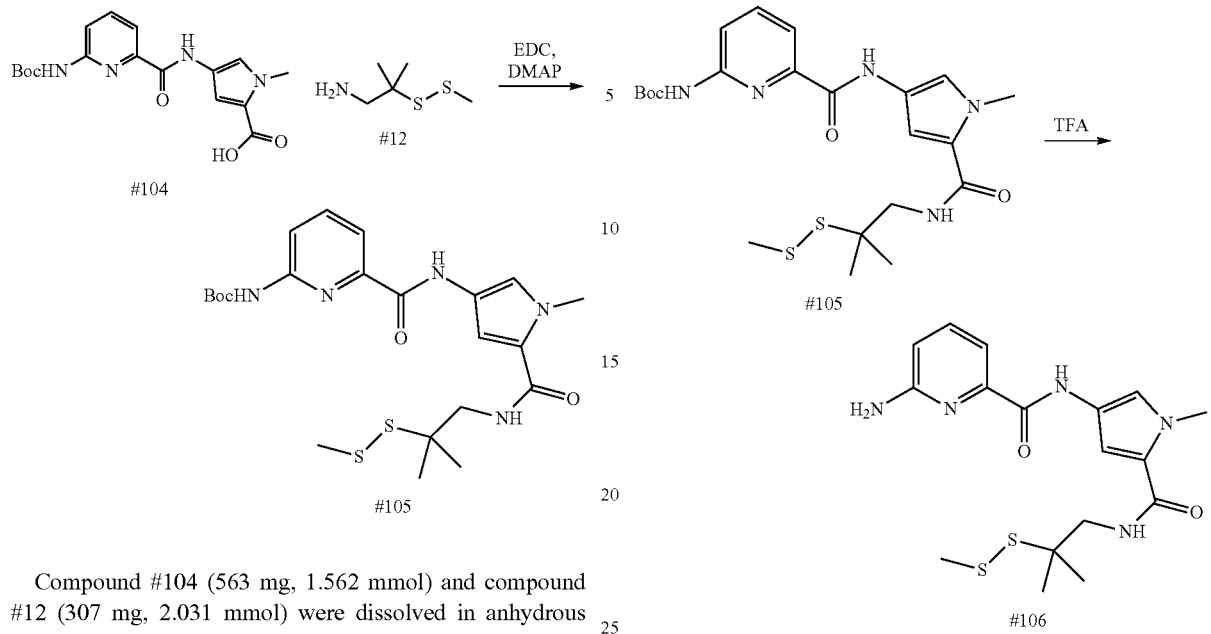

Compound #104 (563 mg, 1.562 mmol) and compound #12 (307 mg, 2.031 mmol) were dissolved in anhydrous DMF (10.4 mL). EDC (898 mg, 4.69 mmol) and DMAP (286 mg, 2.343 mmol) were added and the reaction and was stirred overnight at rt. The reaction mixture was diluted with water and was extracted with EtOAc (2×). The combined organics were washed with water, dried over MgSO$_4$, filtered, and concentrated. The crude product was purified by silica gel chromatography (Hexanes/EtOAc) to give compound #105 (541 mg, 70% yield). LCMS=6.45 min (8 min LCMS method). Mass observed (ESI$^+$): 494.2 (M+H).

Compound #106 was prepared similarly as compound #98 using compound #105 to obtain compound #106, which was used without purification (202 mg, 95% yield). LCMS=4.45 min (8 min method). Mass observed (ESI$^+$): 394.1 (M+H). $^1$H NMR (400 MHz, DMSO-d6): δ 1.26 (s, 6H), 2.44 (s, 3H), 3.39 (d, J=6.3 Hz, 2H), 3.81 (s, 3H), 6.18 (s, 2H), 6.66 (d, J=8.3 Hz, 1H), 7.00 (d, J=1.9 Hz, 1H), 7.22 (d, J=7.2 Hz, 1H), 7.32 (d, J=1.9 Hz, 1H), 7.53-7.62 (m, 1H), 8.01 (t, J=6.4 Hz, 1H), 10.01 (s, 1H).

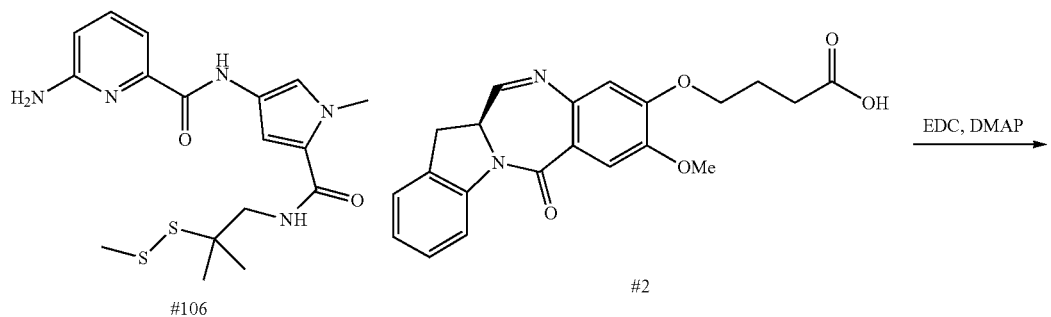

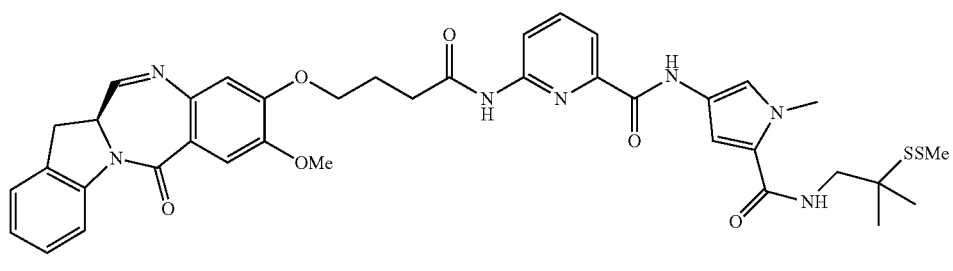

Compound #106 (318 mg, 0.836 mmol) and compound #2 (329 mg, 0.836 mmol) were dissolved in DCM (8.36 mL). EDC (481 mg, 2.508 mmol) and DMAP (102 mg, 0.836 mmol) were added and the reaction was stirred at rt for 5 h. The reaction mixture was diluted with DCM and was washed with brine, dried over MgSO$_4$, filtered and concentrated. The crude product was purified via RPHPLC (C18 column, ACN/Water with 0.1% formic acid) to give compound #107 (102 mg, 16% yield). LCMS=5.64 min (8 min method). Mass observed (ESI$^+$): 756.3 (M+H).

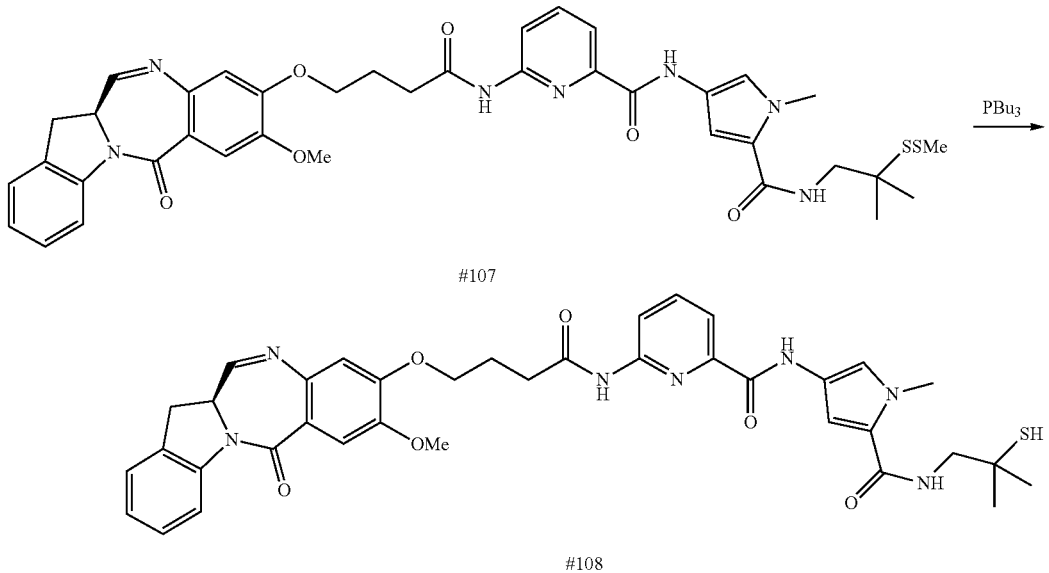

Compound #108 was prepared similarly as compound #86 using compound #107 to obtain compound #108, which was used without further purification (100% yield). LCMS=5.15 min, 5.93 min (8 min method). Mass observed (ESI$^+$): 710.3 (M+H for both retention times.

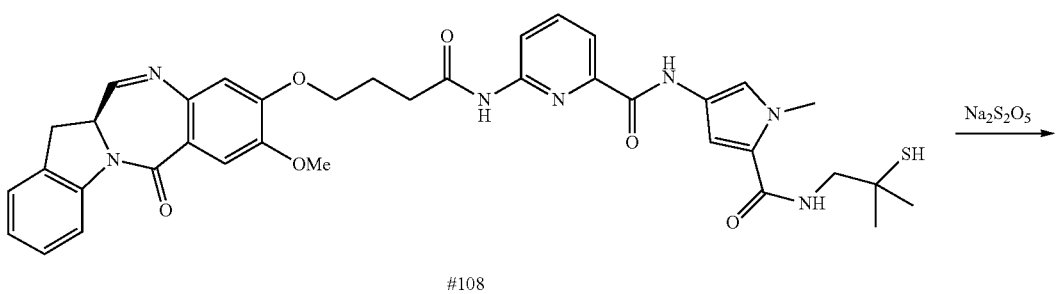

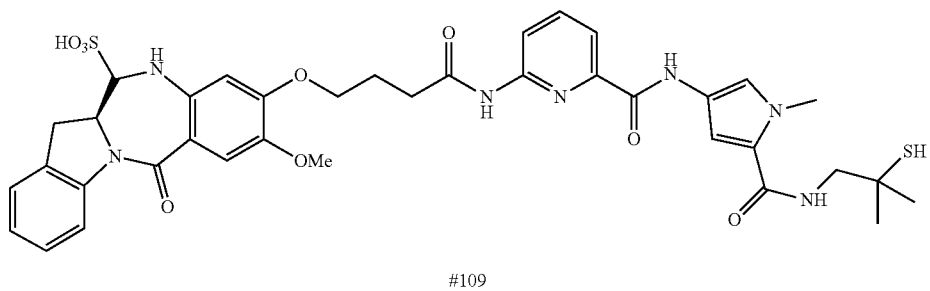

Compound #109 was prepared similarly as compound #87 using compound #108 to obtain compound #109 after purification by RPHPLC (C18 column, ACN/water) (73 mg, 68% yield). LCMS=5.17 min (15 min method). Mass observed (ESI−): 790.2 (M−H).

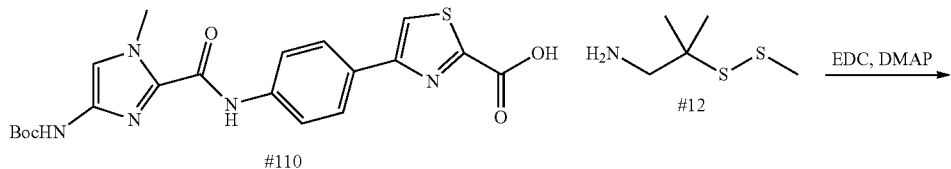

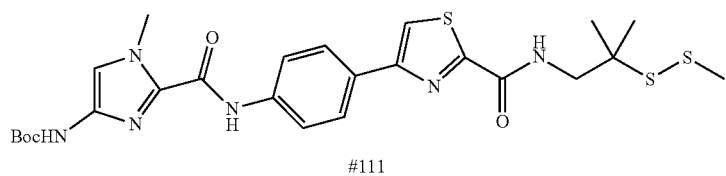

Compound #111 was prepared from compound #110 similarly as compound #83 to obtain compound #111 after purification by silica gel chromatography (Hexanes/EtOAc) (364 mg, 53% yield). LCMS=7.02 min (8 min method). Mass observed (ESI+): 577.2 (M+H).

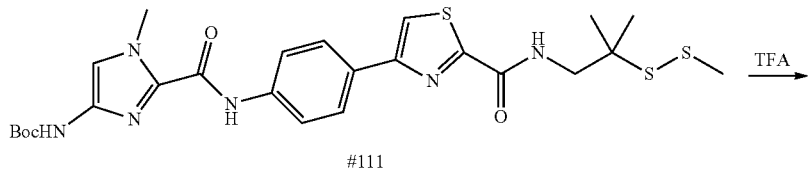

Compound #112 was prepared similarly as compound #98 using compound #111 to obtain compound #112 after purification by silica gel chromatography (Hexanes/EtOAc) (109 mg, 70% yield). LCMS=5.31 min (8 min method). Mass observed (ESI+): 477.1 (M+H).

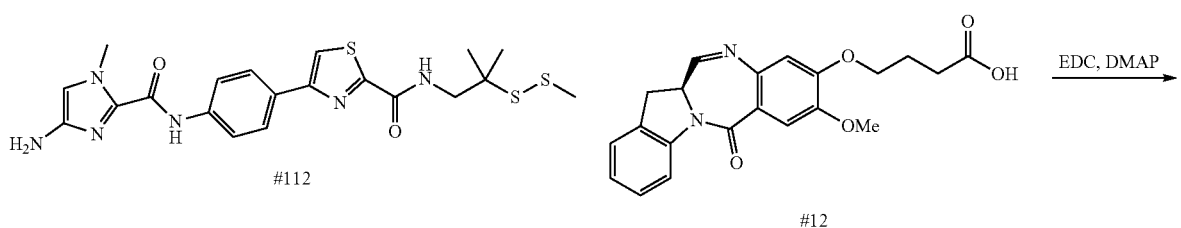

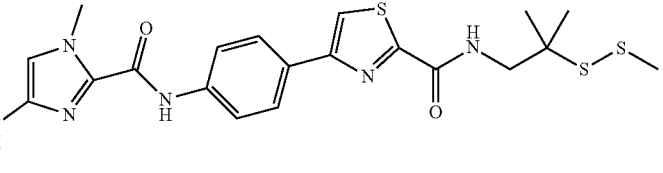
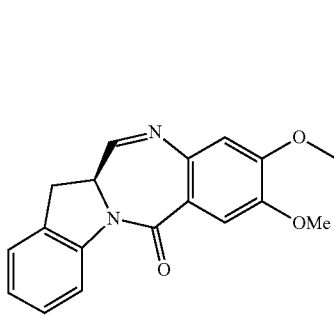

113

Compound #113 was prepared similarly as compound #85. One third of the crude product was purified via RPHPLC (C18 column, ACN/water with 0.1% formic acid) to give compound #113 (2.2 mg, 6% yield). LCMS=6.20 min (8 min method). Mass observed (ESI⁺): 839.3 (M+H).

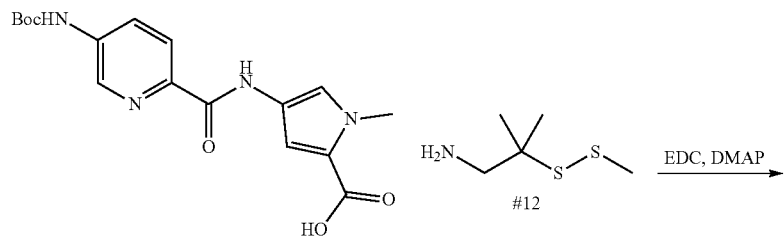

114     #12     EDC, DMAP

115

Compound #115 was prepared from compound #114 similarly as compound #83 after purification by silica gel chromatography (Hexanes/EtOAc) (560 mg, 73% yield). LCMS=6.11 min (8 min method). Mass observed (ESI⁺): 494.3 (M+H).

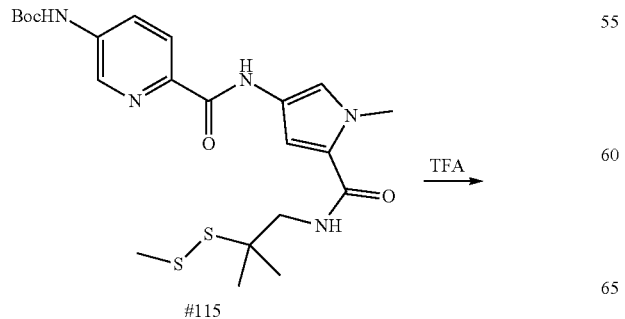

115     TFA →

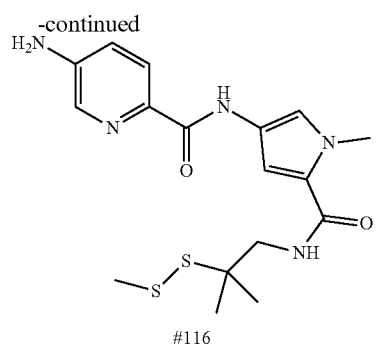

116

Compound #115 (291 mg, 0.589 mmol) was dissolved in DCM (1.47 mL) and was cooled to 0° C. A freshly mixed solution of DCM (737 μL) and TFA (737 μL) was added and the ice bath was removed. The reaction was stirred at rt until completion by LCMS. The reaction mixture was diluted with DCM and Methanol and was quenched with sat'd NaHCO₃ solution. The organic layer was washed with brine, dried over MgSO₄, filtered and concentrated to give compound #116 (229 mg, 99% yield), that was used without further purification. LCMS=4.76 min (8 min method). Mass observed (ESI⁺): 394.1 (M+H).

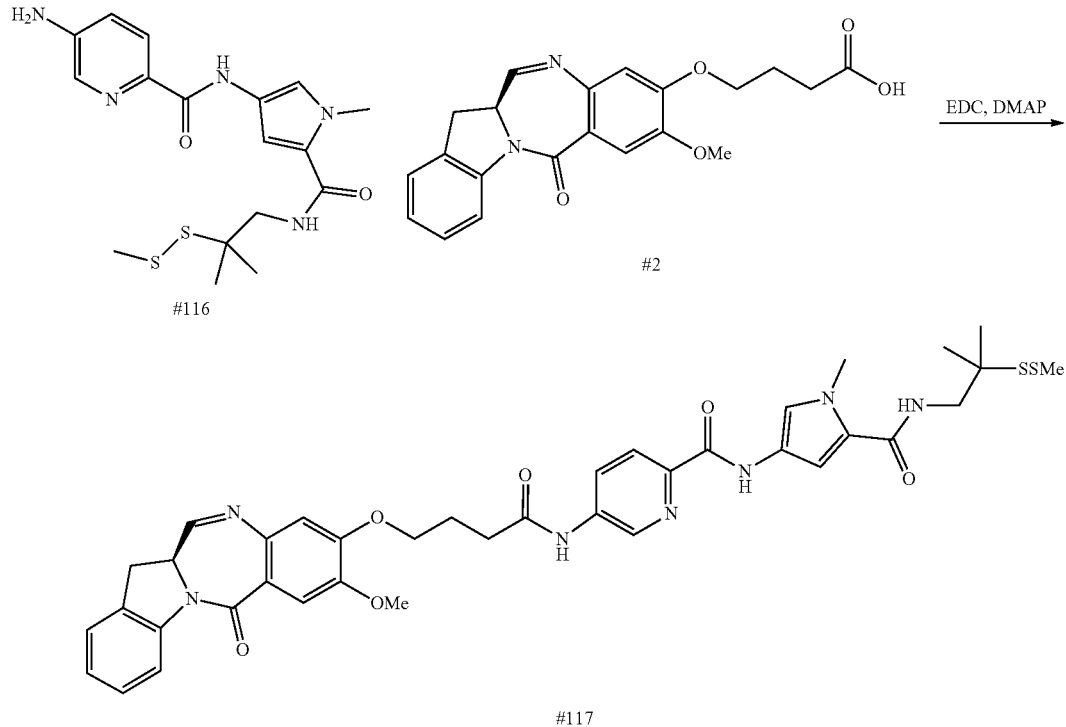

Compound #117 was prepared similarly as compound #85. Half of the crude product was purified via RPHPLC (C18 column, ACN/Water with 0.1% formic acid) to give compound #117 (4.4 mg, 7.6% yield). LCMS=5.53 min (8 min method). Mass observed (ESI⁺): 756.3 (M+H).

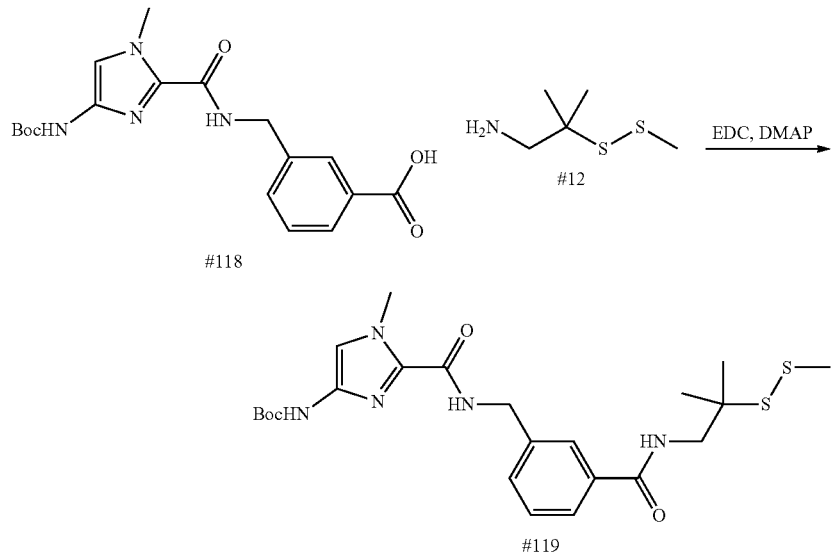

249

Compound #119 was prepared from compound #118 similarly as compound #83 to obtain compound #119 after purification by silica gel chromatography (Hexanes/EtOAc) (656 mg, 77% yield). LCMS=5.74 min (8 min method). Mass observed (ESI+): 508.2 (M+H).

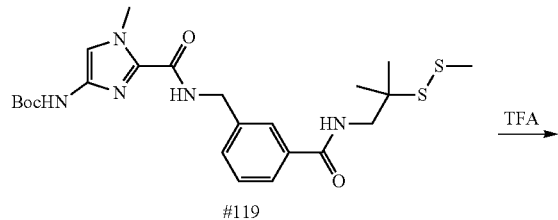

250

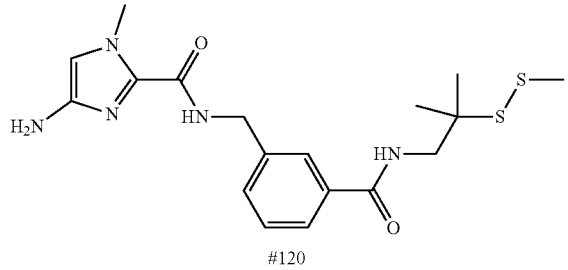

Compound #120 was prepared similarly as compound #98 to obtain compound #120 after purification by silica gel chromatography (DCM/MeOH) (178 mg, 97% yield). LCMS=3.96 min (8 min method). Mass observed (ESI+): 408.1 (M+H).

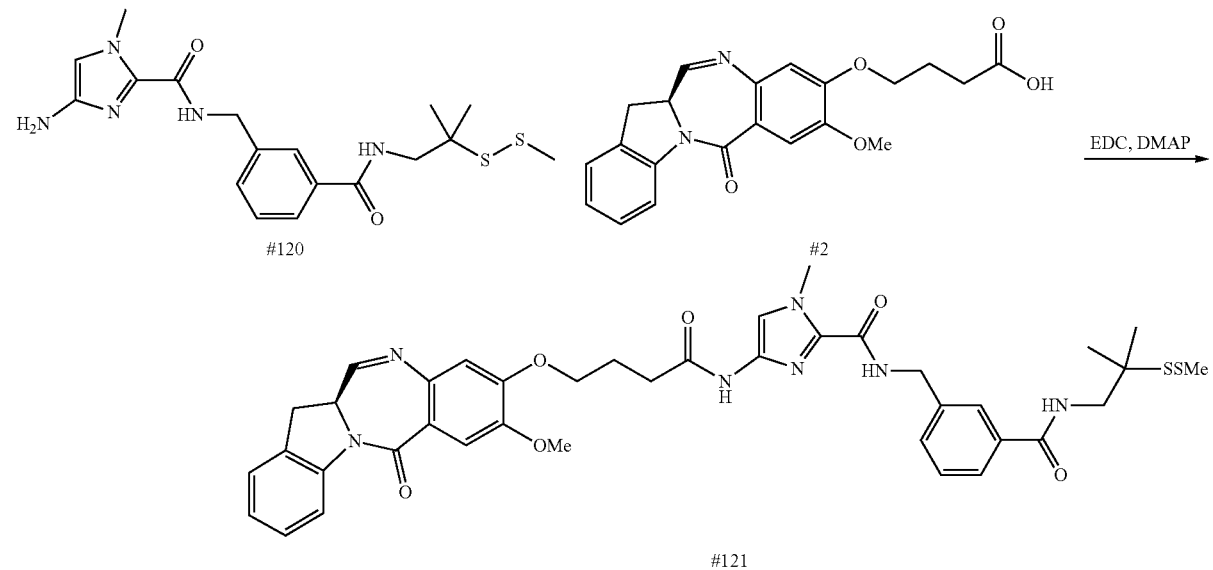

Compound #121 was prepared similarly as compound #85. One fourth of the crude product was purified via RPHPLC (C18 column, ACN/water with 0.1% formic acid) to give compound #121 (6.5 mg, 21% yield). LCMS=5.32 min (8 min method). Mass observed (ESI+): 770.3 (M+H).

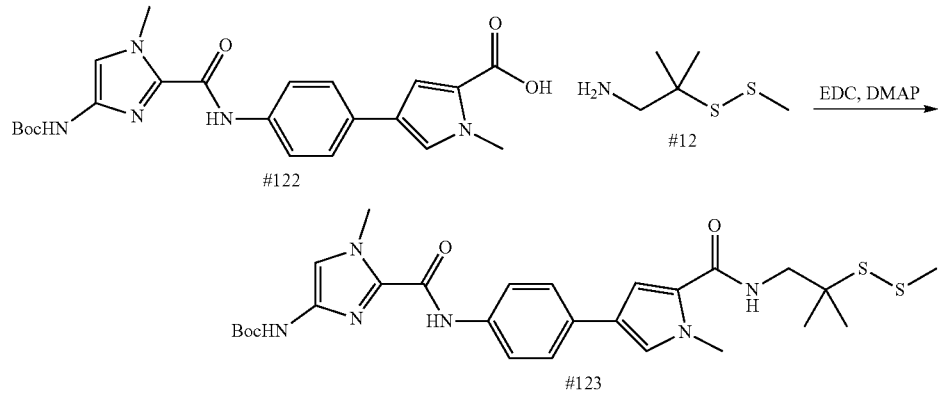

To a mixture of compound #122 (250 mg, 0.569 mmol) and compound #12 (112 mg, 0.740 mmol) in DMF (3.79 mL) was added EDC (196 mg, 1.024 mmol) and DMAP (52.1 mg, 0.427 mmol) at rt. After stirring for 18 h, water was added to the reaction mixture. The resulting solid was filtered, washed with water, and dried under vacuum to yield compound #123 (280 mg, 85% yield). LCMS=6.62 min (8 min method). Mass observed (ESI⁺): 572.8 (M+H).

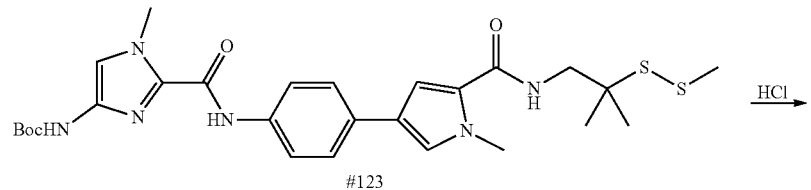

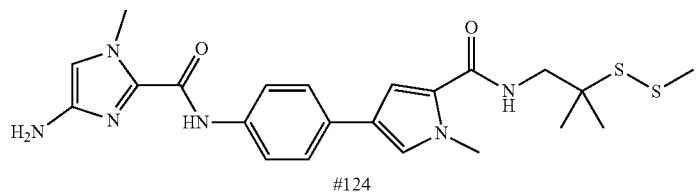

Compound #123 (280 mg, 0.489 mmol) was stirred in HCl (4 N in dioxane, 1.8 mL, 7.33 mmol) under $N_2$ at rt. After stirring for 3 h, hexanes was added to the reaction mixture. The resulting solid was filtered and washed with hexanes. The solid was re-dissolved in 5% MeOH/DCM and was washed with sat'd aq NaHCO₃ solution. The organic layer was dried over MgSO₄, filtered and concentrated to yield compound #124 (140 mg, 65% yield). ¹H NMR (400 MHz, DMSO-$d_6$): δ 1.28 (s, 6H), 2.44 (s, 3H), 3.41 (d, J=6.3 Hz, 2H), 3.85 (s, 3H), 3.88 (s, 3H), 4.47 (s, 2H), 6.45 (s, 1H), 7.20 (d, J=2.0 Hz, 1H), 7.36 (d, J=1.9 Hz, 1H), 7.46 (d, J=8.7 Hz, 2H), 7.74 (d, J=8.7 Hz, 2H), 8.03 (t, J=6.4 Hz, 1H), 9.82 (s, 1H). LCMS=4.85 min (8 min method). Mass observed (ESI⁺): 472.9 (M+H).

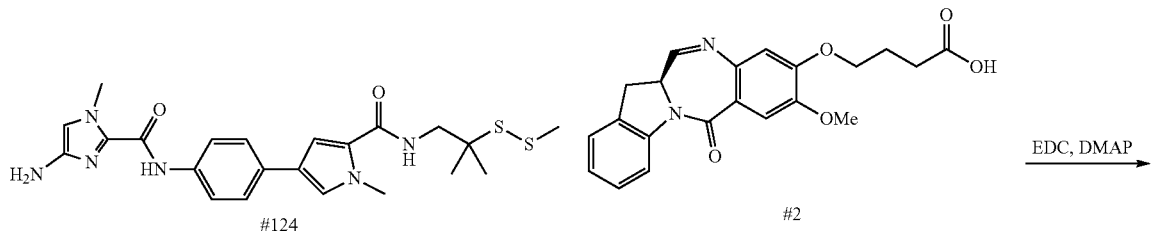

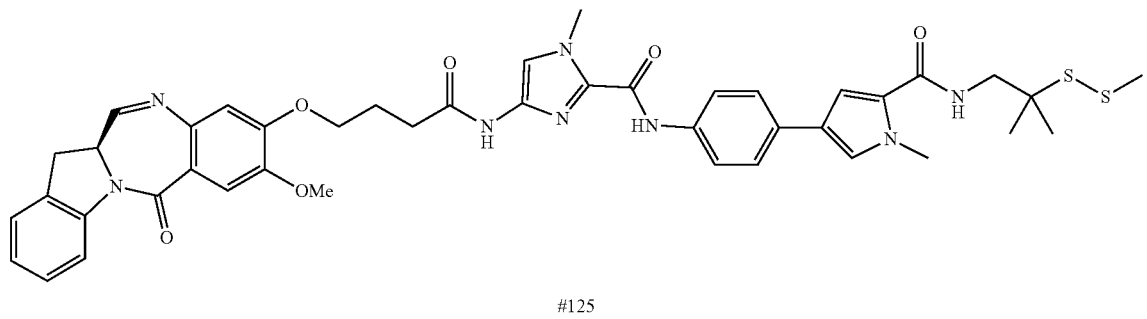

To a mixture of compound #124 (72.7 mg, 0.154 mmol) and compound #2 (45 mg, 0.118 mmol) in DCM (1.18 mL) was added EDC (34.0 mg, 0.177 mmol) and DMAP (7.23 mg, 0.059 mmol) at rt. After stirring for 2 h, the reaction mixture was diluted with DCM and was washed with water. The organic layer was dried over MgSO$_4$, filtered and concentrated. Approximately one quarter of the crude material was purified by RPHPLC (C18 Kromasil column, Acetonitrile/0.1% formic acid in H$_2$O, 50-80%) to obtain compound #125 (5 mg, 20% yield). LCMS=5.89 min (8 min method). Mass observed (ESI$^+$): 834.8 (M+H).

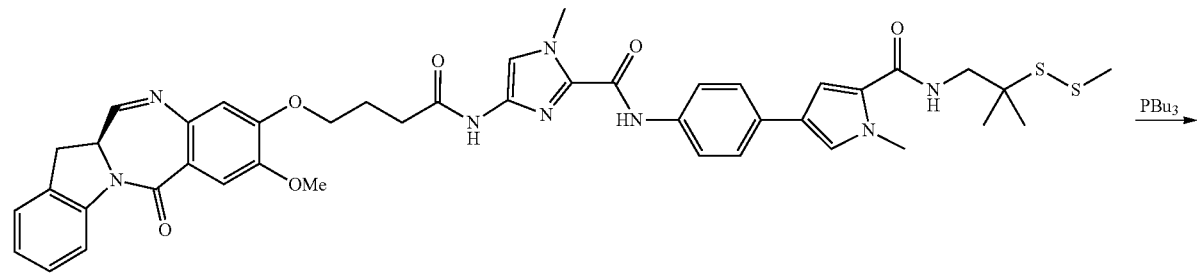

125

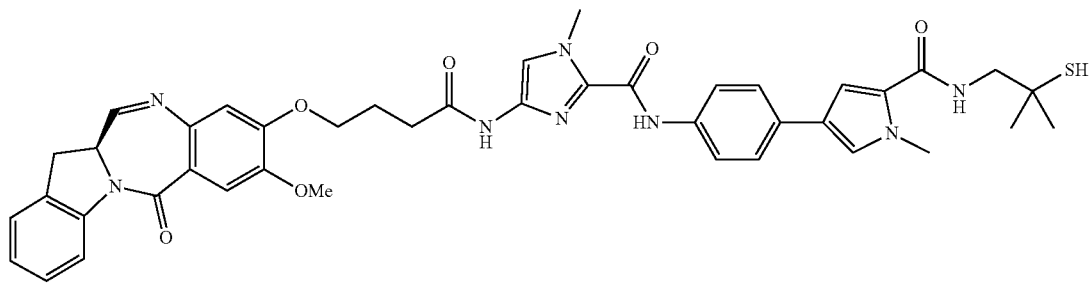

126

To a mixture of compound #125 (96 mg, 0.115 mmol) in THF (912 µL) and water (45.6 µL) was added PBu$_3$ (86 µL, 0.345 mmol) at rt. After 5 h, the reaction mixture was concentrated to dryness to obtain compound #126 as a yellow solid, which was carried onto the next step without purification. LCMS=5.46 min (8 min method). Mass observed (ESI$^+$): 789.9 (M+H).

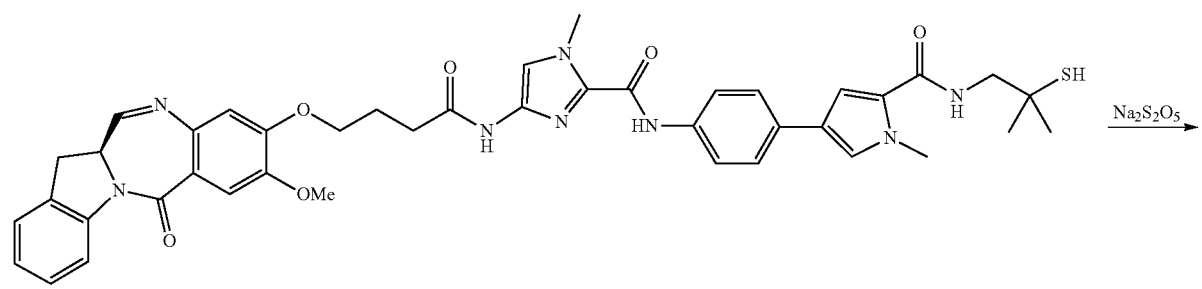

126

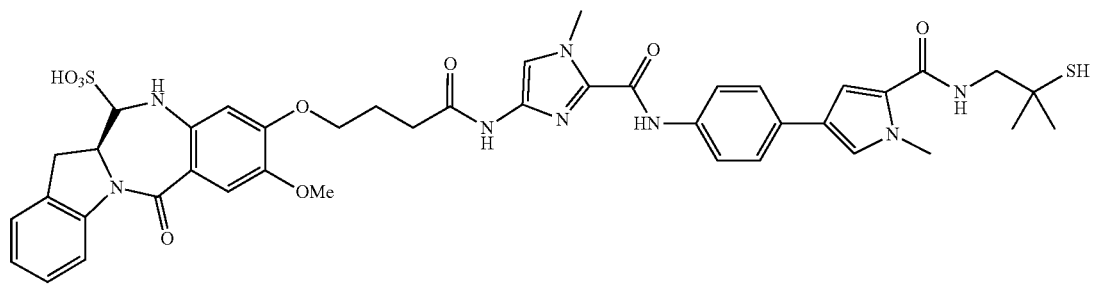

127

To a suspension of compound #126 (54.4 mg, 0.069 mmol) in 2-Propanol (4.6 mL) and water (2.30 ml) was added sodium metabisulfite (39.4 mg, 0.207 mmol) at rt. After stirring for 20 h, the reaction mixture was frozen and lyophilized. The resulting solid was re-dissolved in 3 mL ACN/H$_2$O/THF (1:1:1) and centrifuged. The supernatant was purified by RPHPLC (C18 Kromasil, ACN/H$_2$O) to obtain compound #127 (7.1 mg, 7% over 2 steps). LCMS=3.29 min (8 min method). Mass observed=788.7 (ESI$^+$, M-SO$_3$H+H), 868.7 (ESI, M−H).

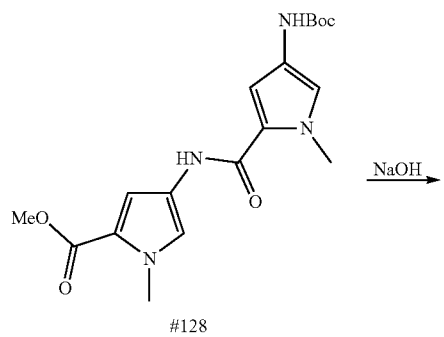

128

To a suspension of compound #128 (0.37 g, 0.983 mmol) in MeOH (7.56 mL) was added NaOH (1.96 mL, 1.966 mmol, 1 M aq) and the mixture was stirred at 60° C. for 4 h. The reaction mixture was cooled to rt and was diluted with water. Acidification of the mixture to pH~ 3 with HCl (1.5 mL, 5% aq solution) resulted in the formation of a white precipitate that was extracted with EtOAc (2×100 mL). The organic extracts were washed with water, brine, dried over Na$_2$SO$_4$, filtered and concentrated to obtain compound #129 (166 mg, 0.458 mmol) (335 mg, 94%) as an off-white solid. $^1$H NMR (400 MHz, DMSO-d$_6$): δ 1.44 (d, J=6.5 Hz, 9H), 3.80 (s, 3H), 3.81 (s, 3H), 6.83 (d, J=2.0 Hz, 2H), 6.88 (s, 1H), 7.40 (d, J=2.0 Hz, 1H), 9.09 (s, 1H), 9.81 (s, 1H), 12.11 (s, 1H). LCMS=4.51 min (8 min method). Mass observed (ESI$^+$): 362.9 (M+H).

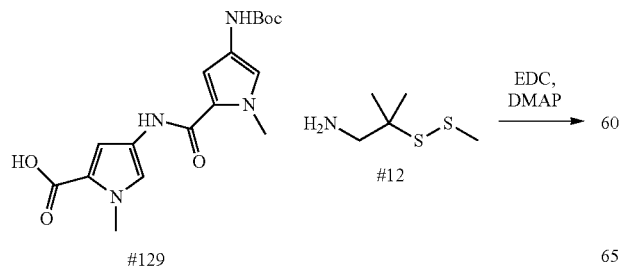

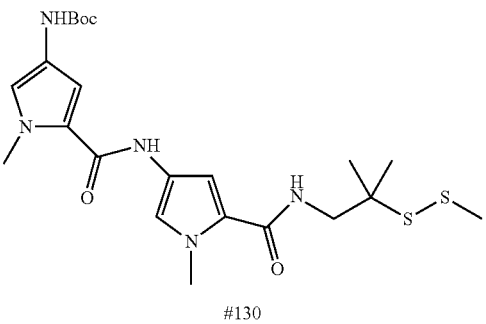

130

To a mixture of compound #129 (166 mg, 0.458 mmol) and compound #12 (90 mg, 0.596 mmol) in DMF (3.0 mL) was added EDC (158 mg, 0.825 mmol) and DMAP (42.0 mg, 0.344 mmol) at rt. After stirring for 20 h, water was added to the mixture and the resulting precipitate was filtered and washed with water. The solid was re-dissolved in DCM and washed with water. The organic layer was washed with water, dried over MgSO$_4$, filtered and concentrated to give compound #130 (227 mg, 100% yield). LCMS=5.81 min (8 min method). Mass observed (ESI$^+$): 495.9 (M+H).

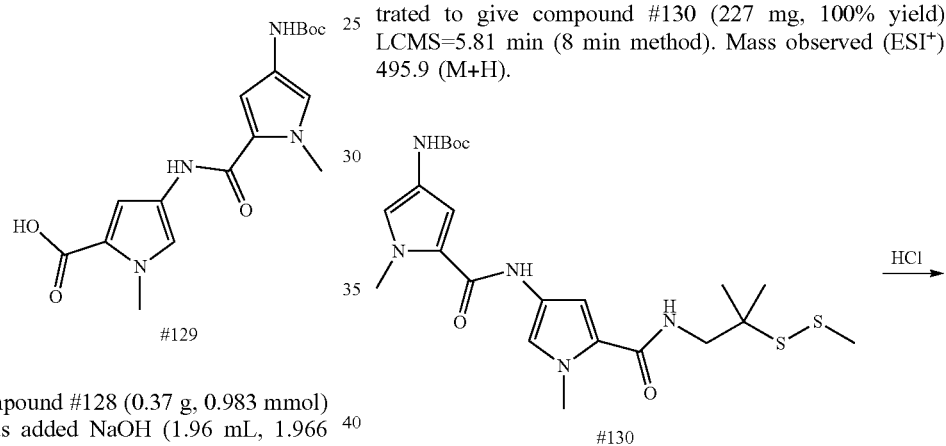

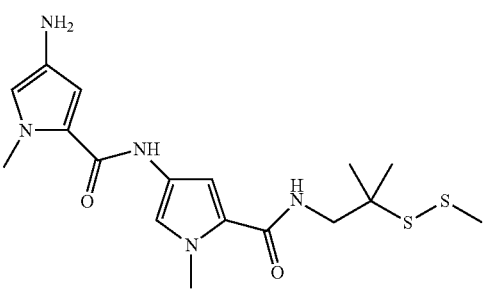

131

Compound #130 (227 mg, 0.458 mmol) was stirred in HCl (4 N in dioxane, 1.7 mL, 6.87 mmol) for 3 h at rt. Hexanes was added to the mixture and the resulting solid was filtered and washed with hexanes. The solid was re-dissolved in 5% MeOH/DCM and washed with sat'd aq. NaHCO$_3$ solution. The organic layer was dried over MgSO$_4$, filtered and concentrated to give compound #131 (147 mg, 81% yield) as a brown solid, which was carried on without further purification. LCMS=4.46 min (8 min method). Mass observed (ESI$^+$): 395.9 (M+H).

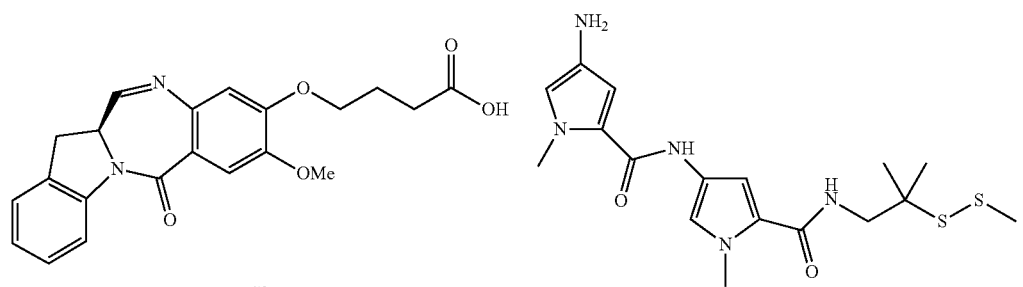

To a mixture of compound #2 (75 mg, 0.197 mmol) and compound #131 (146 mg, 0.296 mmol) in DCM (1.97 mL) was added EDC (56.7 mg, 0.296 mmol) and DMAP (12.04 mg, 0.099 mmol) at rt. After stirring for 1 h, the reaction mixture was extracted with dichloromethane and water. The organic extracts were dried over MgSO$_4$, filtered and concentrated. The crude material was purified by preparative TLC (DCM/MeOH) followed by RPHPLC (C18, 0.1% formic acid in H$_2$O/ACN) to obtain compound #132 (3 mg, 2% yield). LCMS=5.24 min (8 min method). Mass observed (ESI$^+$): 757.7 (M+H).

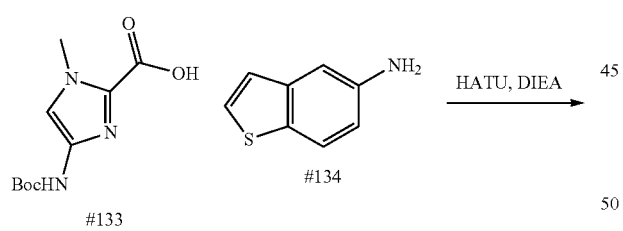

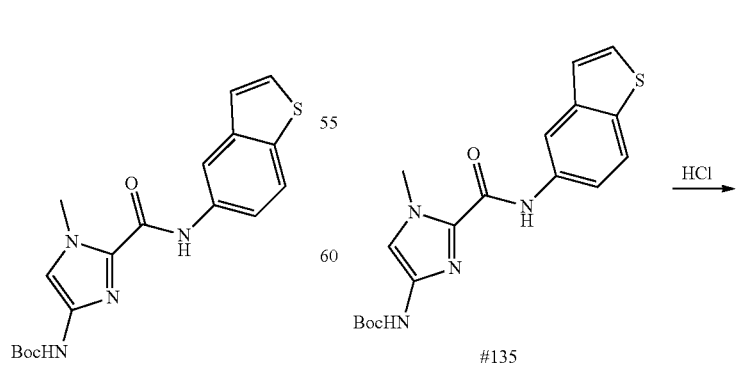

To a solution of compound #133 (520 mg, 2.157 mmol) and compound #134 (308 mg, 1.961 mmol) in DCM (10.05 mL) was added HATU (1.12 g, 2.94 mmol) and DIEA (0.685 mL, 3.92 mmol) at rt. After stirring for 18 h, the mixture was diluted with DCM and was washed with sat'd aq NaHCO$_3$ and brine. The organic layer was dried over MgSO$_4$, filtered and concentrated. The crude material was purified by silica gel chromatography (hexanes/EtOAc) to yield compound #135 as a purplish solid (0.63 g, 86% yield). $^1$H NMR (400 MHz, CDCl$_3$): δ 1.52 (s, 9H), 4.08 (s, 3H), 6.84 (s, 1H), 7.18 (s, 1H), 7.31 (d, J=5.4 Hz, 1H), 7.40-7.50 (m, 2H), 7.82 (d, J=8.6 Hz, 1H), 8.31 (d, J=2.1 Hz, 1H), 9.07 (s, 1H). LCMS=11.4 min (15 min method). Mass observed (ESI$^+$): 373.1 (M+H).

-continued

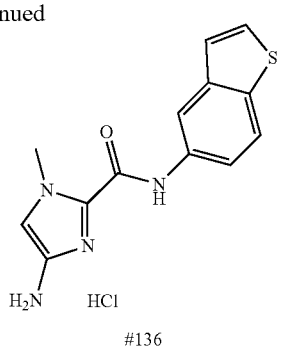
136

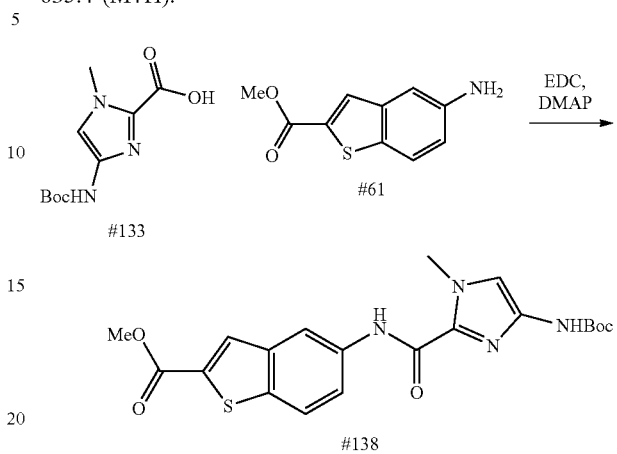

J=8.0 Hz, 1H), 7.85 (d, J=8.0 Hz, 1H), 8.02 (s, 1H), 8.25 (d, J=8.0 Hz, 1H), 8.28 (d, J=4.0 Hz, 1H), 9.03 (s, 1H). LCMS=9.62 min (15 min method). Mass observed (ESI$^+$): 635.4 (M+H).

Compound #135 (300 mg, 0.805 mmol) was stirred in HCl (4 M in dioxane, 3.0 mL, 12.08 mmol) at rt. After stirring for 18 h, the mixture was extracted with DCM and water. The organic layer was dried over MgSO$_4$, filtered and concentrated to yield compound #136 (0.13 g, 43% yield), which was used in next step without further purification. LCMS=5.38 min (15 min method). Mass observed (ESI$^+$): 273.1 (M+H).

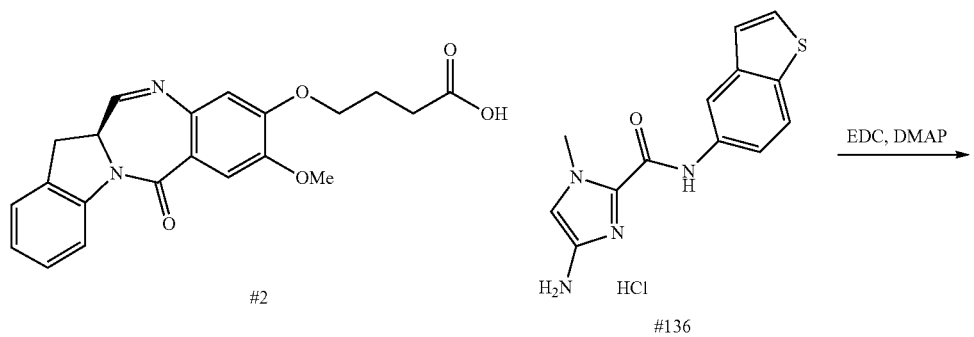

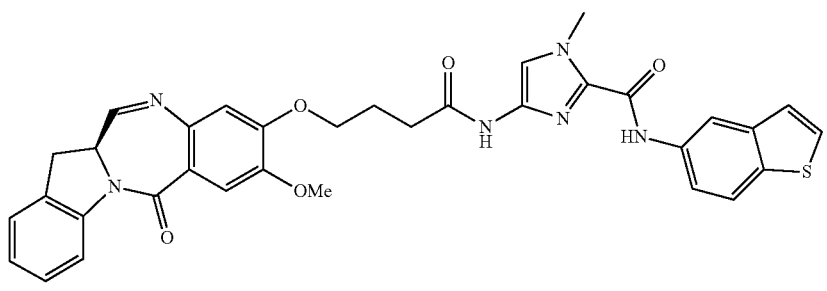
137

To a mixture of compound #2 (100 mg, 0.237 mmol) and compound #136 (132 mg, 0.355 mmol) in DCM (2.3 mL) was added EDC (71.6 mg, 0.355 mmol) and DMAP (14.45 mg, 0.118 mmol) at rt. After stirring for 2 h, the mixture was extracted with DCM and water. The organic layer was dried over MgSO$_4$, filtered, and concentrated. The crude material was purified by silica gel chromatography (DCM/MeOH), followed by RP-HPLC (C18 Kromasil, ACN/H$_2$O) to yield compound #137 (50 mg, 33% yield). $^1$H NMR (400 MHz, CDCl$_3$): δ 2.26-2.35 (m, 2H), 2.56-2.74 (m, 2H), 3.46 (dd, J=16.7, 4.0 Hz, 1H), 3.65 (dd, J=16.7, 10.9 Hz, 1H), 3.98 (s, 3H), 4.09 (s, 3H), 4.10-4.16 (m, 1H), 4.19-4.24 (m, 1H), 4.41-4.46 (m, 1H), 6.86 (s, 1H), 7.09 (t, J=7.5 Hz, 1H), 7.20-7.37 (m, 3H), 7.38-7.48 (m, 3H), 7.59 (s, 1H), 7.80 (d, To a mixture of compound #133 (508 mg, 2.106 mmol) and compound #61 (300 mg, 1.404 mmol) in DMF (7.021 mL) was added EDC (567 mg, 2.81 mmol) and DMAP (429 mg, 3.51 mmol) at rt. After stirring for 3 h, the reaction was diluted with EtOAc and then washed with water, sat'd aq. NaHCO$_3$ and brine. The organic layer was dried over MgSO$_4$, filtered and concentrated to obtain compound #138, which was used in the next step without purification (0.6 g, 100% yield). LCMS=8.36 min (15 min method). Mass observed (ESI$^-$): 429.0 (M−H).

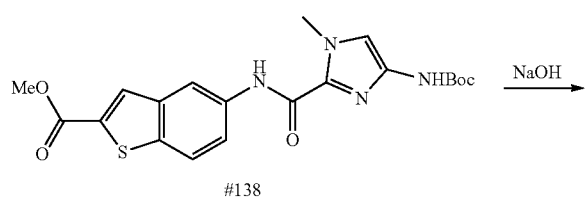

138

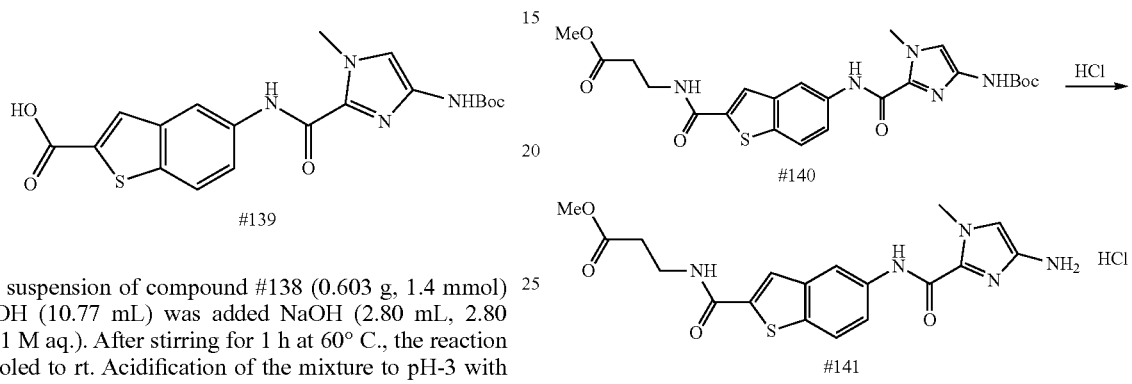

To compound #139 (148 mg, 0.355 mmol) in DMF (3.55 ml) was added b-alanine methylester hydrochloride (59.5 mg, 0.426 mmol), EDC (82 mg, 0.426 mmol), and DMAP (43.4 mg, 0.355 mmol) at rt. After stirring for 20 h, the mixture was diluted with EtOAc and washed with sat'd aq NH$_4$Cl and brine. The organic layer was dried over Na$_2$SO$_4$, filtered and concentrated. The crude product was slurried with EtOAc/hexanes (1:1) and the resulting solid was filtered and dried to yield compound #140, which was used in the next step without further purification (178 mg, 100% yield). LCMS=6.48 min (15 min method). Mass observed (ESI$^-$): 500.1 (M−H).

To a suspension of compound #138 (0.603 g, 1.4 mmol) in MeOH (10.77 mL) was added NaOH (2.80 mL, 2.80 mmol, 1 M aq.). After stirring for 1 h at 60° C., the reaction was cooled to rt. Acidification of the mixture to pH-3 with HCl (2.5 mL, 5% aq solution) resulted in the formation of a white precipitate that was extracted with EtOAc (2×100 mL). The organic extracts were washed with water, brine, dried over Na$_2$SO$_4$, filtered and concentrated to obtain compound #139, which was used in next step without further purification (0.26 g, 44% yield). $^1$H NMR (400 MHz, DMSO-d$_6$): δ 1.46 (s, 9H), 3.96 (s, 3H), 7.29 (s, 1H), 7.78 (dd, J=8.9, 2.1 Hz, 1H), 7.99 (d, J=8.8 Hz, 1H), 8.09 (s, 1H), 8.50 (d, J=2.0 Hz, 1H), 9.43 (s, 1H), 10.05 (s, 1H). LCMS=6.29 min (15 min method). Mass observed (ESI$^+$): 317.1 (M-Boc+H).

Compound #140 (178 mg, 0.355 mmol) was stirred in HCl (4 N in dioxane, 1.77 mL, 7.10 mmol) at rt for 3 h. The mixture was concentrated to dryness, then re-dissolved in MeOH/DCM (1:4) and washed with water. The organic layer was dried over Na$_2$SO$_4$, filtered and concentrated to give compound #141 (72 mg, 46% yield), which was used in next step without further purification. LCMS=1.48 min (15 min method). Mass observed (ESI$^-$): 400.0 (M−H).

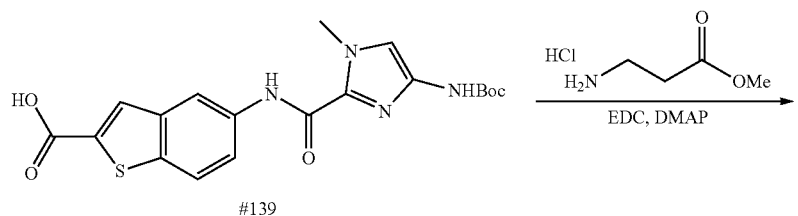

139

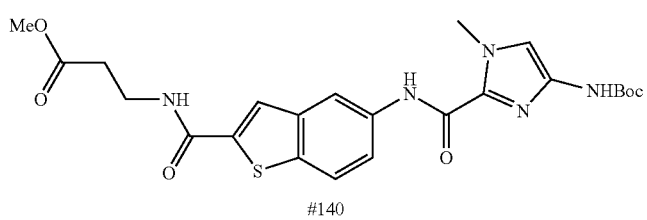

140

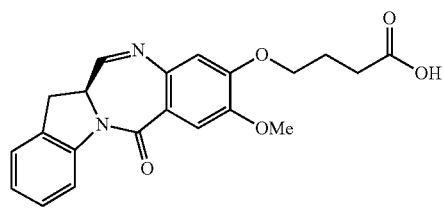

2

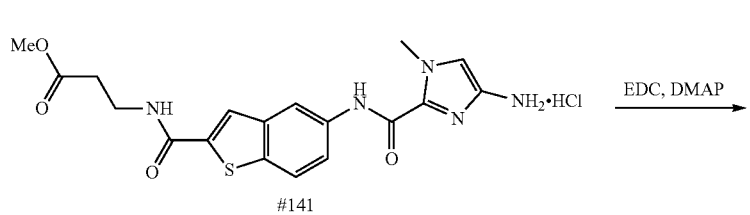

141

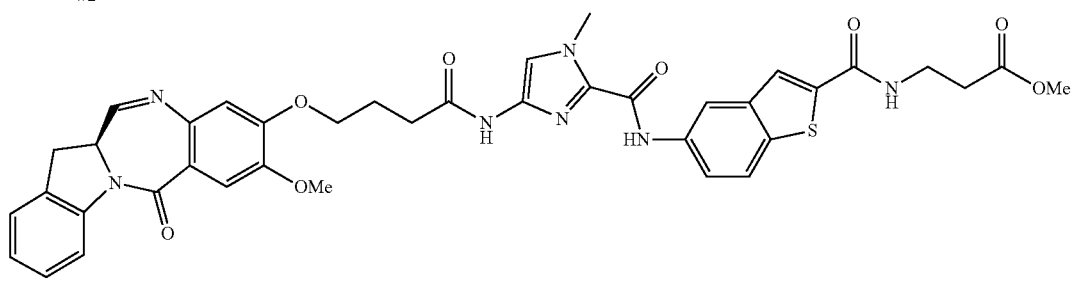

142

To a mixture of compound #2 (45 mg, 0.118 mmol) and compound #141 (72.5 mg, 0.166 mmol) in DCM (1.18 mL) was added EDC (34.0 mg, 0.177 mmol) and DMAP (7.23 mg, 0.059 mmol) at rt. After stirring for 2 h, the reaction was diluted with DCM and washed with water. The organic layer was dried over MgSO$_4$, filtered, and concentrated. The crude material was purified by silica gel chromatography (DCM/MeOH) to obtain compound #142 (30 mg, 33% yield). LCMS=4.85 min (8 min method). Mass observed (ESI$^+$): 763.7 (M+H).

To a solution of compound #142 (25 mg, 0.033 mmol) in DCE (1.63 mL) was added trimethylstannanol (59.2 mg, 0.327 mmol). The mixture was stirred at 80° C. for 18 h. The reaction was cooled to rt and was extracted with MeOH/DCM (1:4) and HCl solution (0.5 M, aq). The organic extracts were washed with brine, dried over MgSO$_4$, filtered and concentrated to yield compound #143, which was used in the next step without further purification (24 mg, 99% yield). LCMS=4.08 min (15 min method). Mass observed=750.5 (ESI$^+$, M+H), 748.3 (ESI$^-$, M−H).

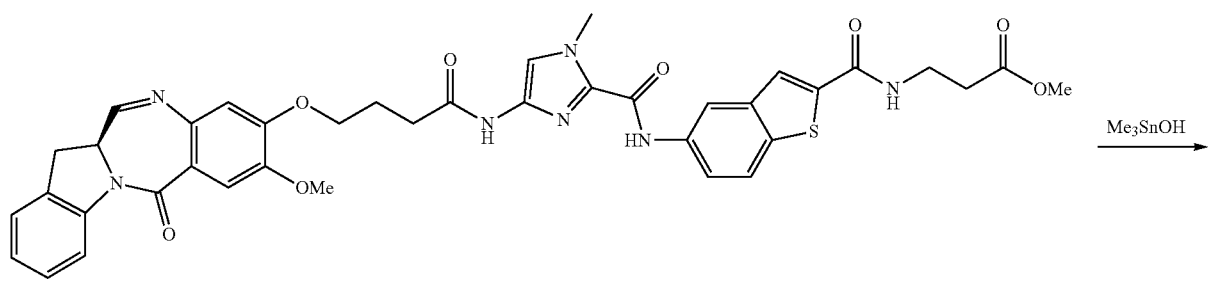

142

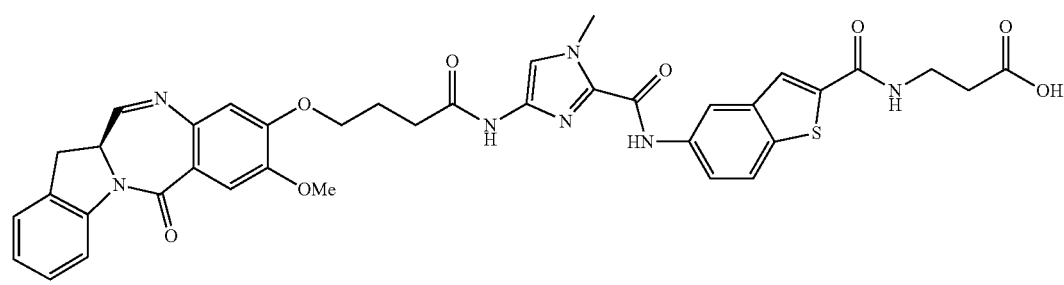

143

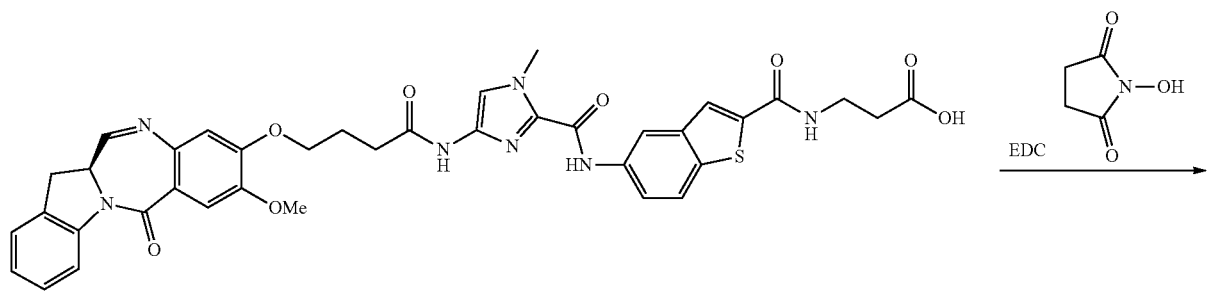

143

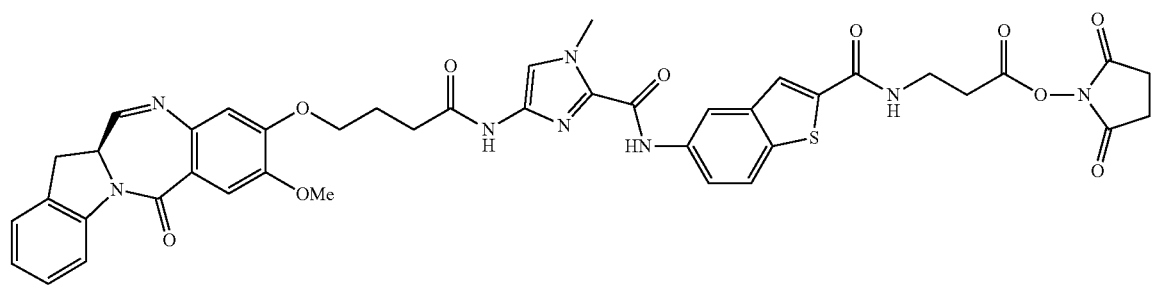

144

To a suspension of compound #143 (29.5 mg, 0.039 mmol) in DMF (787 μL) was added NHS (22.64 mg, 0.197 mmol) and EDC (60.3 mg, 0.315 mmol) at rt. After stirring for 3 h, the reaction mixture was diluted with water. The resulting off-white solid was filtered and washed with water. The crude material was purified by silica gel chromatography (DCM/MeOH) to yield compound #144 (5 mg, 15% yield). LCMS=4.83 min (8 min method). Mass observed (ESI+): 846.6 (M+H).

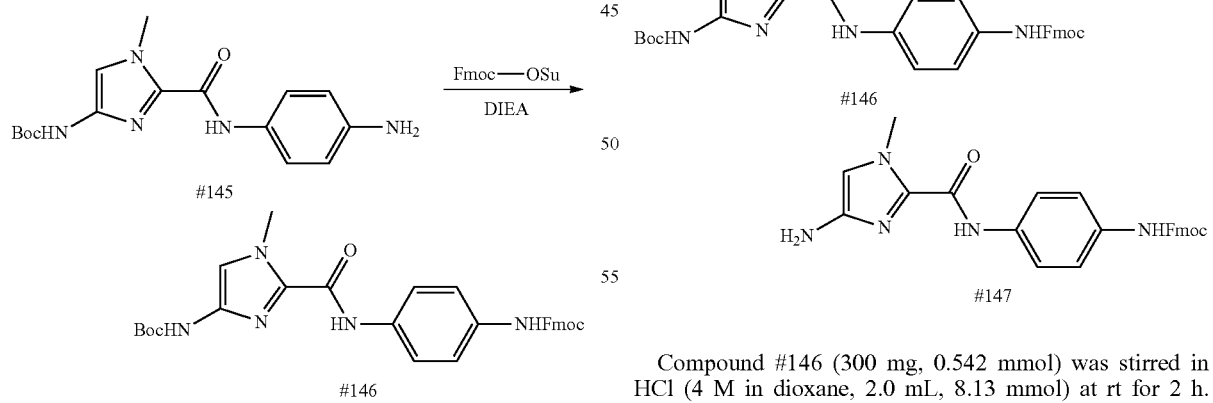

To a solution of compound #145 (1.04 g, 3.14 mmol) 1,2-dimethoxyethane/H$_2$O (1:1, 12 mL) was added DIEA (1.093 ml, 6.28 mmol) and Fmoc-OSu (1.270 g, 3.77 mmol) in 1,2-dimethoxyethane (6 mL). After stirring for 48 h at rt, the reaction mixture was concentrated and was then diluted with water. The resulting mixture was extracted with 20% MeOH/DCM. The organic extracts were washed with water and brine, dried over MgSO$_4$, filtered through Celite and concentrated. The crude residue was purified by silica gel chromatography (DCM/MeOH) to give compound #146 (308 mg, 17% yield). LCMS=6.78 min (8 min method). Mass observed (ESI+): 554.3 (M+H).

Compound #146 (300 mg, 0.542 mmol) was stirred in HCl (4 M in dioxane, 2.0 mL, 8.13 mmol) at rt for 2 h. Hexanes was added and the resulting solid was filtered and was washed with hexanes. The solid was re-dissolved in 5% MeOH/DCM and was washed with sat'd aq NaHCO$_3$ solution. The organic layer was washed with brine, then dried over MgSO$_4$, filtered and concentrated to yield compound #147, which was used in next step without purification (175 mg, 71% yield). LCMS=5.04 min (8 min method). Mass observed (ESI+): 454.2 (M+H).

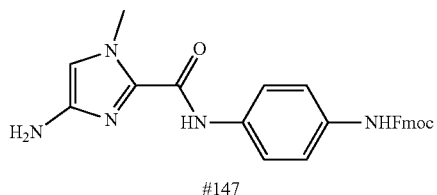

147

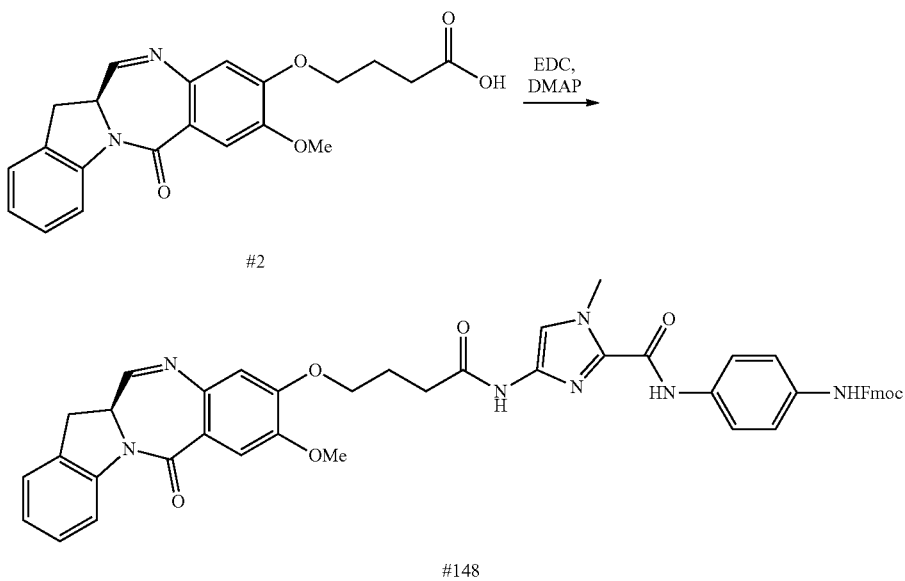

To a mixture of compound #147 (86 mg, 0.189 mmol) and compound #2 (65 mg, 0.145 mmol) in DCM (2.9 mL) was added EDC (41.8 mg, 0.218 mmol) and DMAP (8.87 mg, 0.073 mmol). After stirring at rt for 3.5 h, the mixture was extracted with DCM and water. The organic layer was dried with over MgSO$_4$, filtered and concentrated. The crude material was purified by silica gel chromatography (DCM/ MeOH) to give compound #148 (25 mg, 21% yield). LCMS=6.18 min (8 min method). Mass observed (ESI$^+$): 816.3 (M+H).

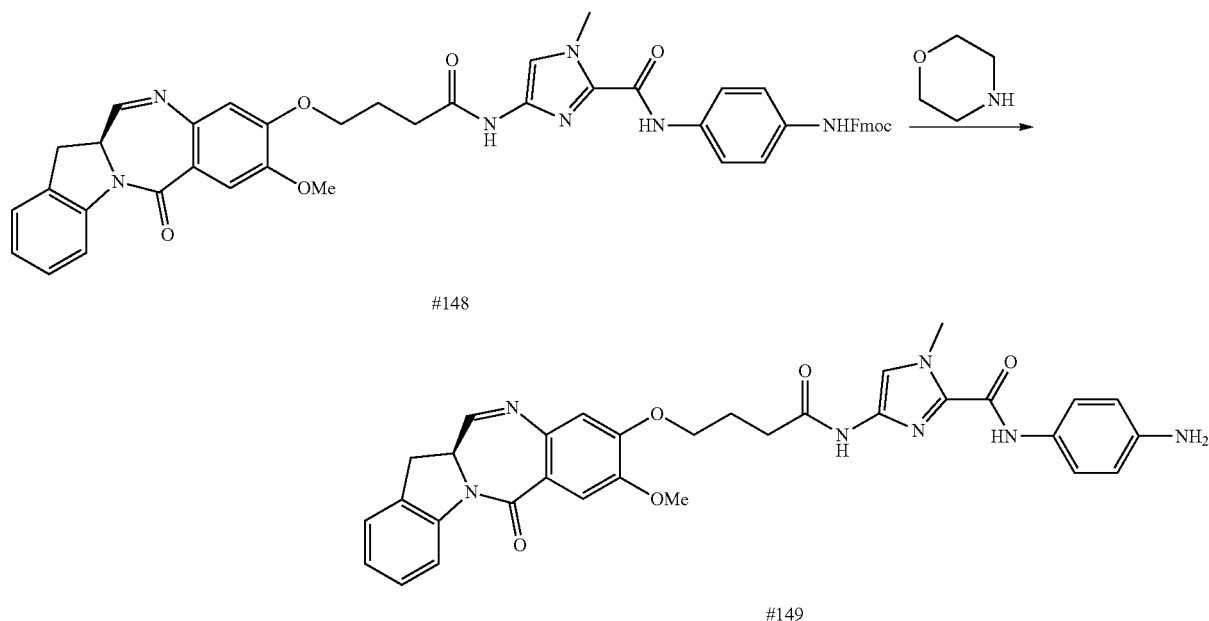

Compound #148 (25 mg, 0.031 mmol) was dissolved in DMF (0.26 mL) and morpholine (0.059 mL, 0.674 mmol) was added at rt and the reaction was stirred for 3.5 h. The reaction mixture was diluted with ACN and water, centrifuged, and the supernatant was purified by RP-HPLC (C18 Kromasil, 0.1% formic acid in H₂O/ACN) to give compound #149 as a white powder (5.7 mg, 31% yield). LCMS=3.43 min (15 min method). Mass observed (ESI⁺): 594.4 (M+H).

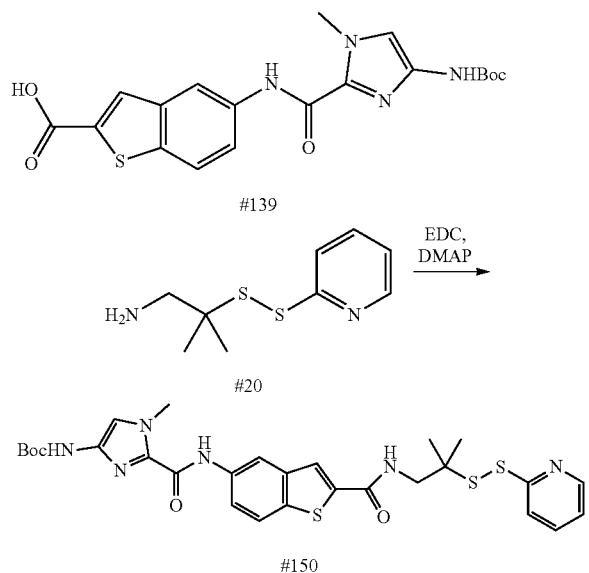

To a mixture of compound #139 (110 mg, 0.264 mmol) and compound #20 (73.6 mg, 0.343 mmol) in DMF (1.76 mL) was added EDC (91 mg, 0.475 mmol) and DMAP (24.20 mg, 0.198 mmol) at rt. After stirring for 18 h, water was added and the resulting off-white solid was filtered and dried under vacuum to give compound #150, which was used in next step without purification (162 mg, 100% yield). ¹H NMR (400 MHz, DMSO-d₆): δ 1.31 (s, 6H), 1.46 (s, 9H), 3.47 (d, J=6.2 Hz, 2H), 3.96 (s, 3H), 7.20-7.31 (m, 2H), 7.75-7.88 (m, 3H), 7.97 (d, J=8.8 Hz, 1H), 8.11 (s, 1H), 8.40 (d, J=2.0 Hz, 1H), 8.45 (dt, J=4.8, 1.3 Hz, 1H), 8.85 (t, J=6.4 Hz, 1H), 9.42 (s, 1H), 10.05 (s, 1H). LCMS=6.79 min (8 min method). Mass observed (ESI⁺): 610.8 (M+H).

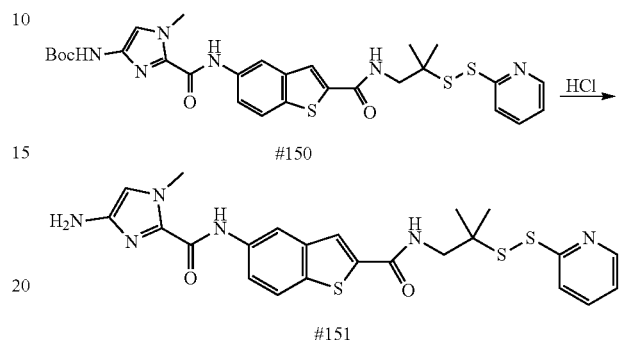

Compound #150 (162 mg, 0.264 mmol) was stirred in HCl (4 N in dioxane, 1.32 mL, 5.28 mmol) at rt. After 3 h, the mixture was concentrated and the resulting residue was re-dissolved in 20% MeOH/DCM and washed with water. The organic layer was dried over MgSO₄, filtered and concentrated to give compound #151, which was used in next step without further purification (100 mg, 74% yield). ¹H NMR (400 MHz, DMSO-d₆): δ 1.30 (s, 6H), 3.45 (dd, J=12.6, 6.3 Hz, 2H), 3.57 (s, 3H), 3.90 (s, 2H), 4.49 (s, 1H), 7.22-7.25 (m, 1H), 7.76-7.89 (m, 3H), 7.94 (d, J=8.8 Hz, 1H), 8.11 (s, 1H), 8.37-8.48 (m, 2H), 8.84 (t, J=5.9 Hz, 1H), 10.07 (s, 1H).

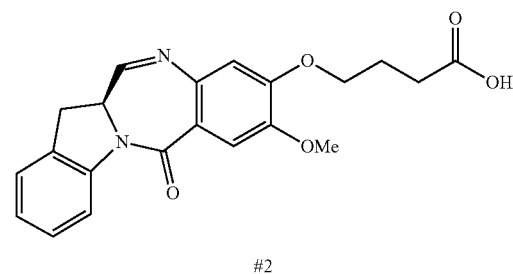

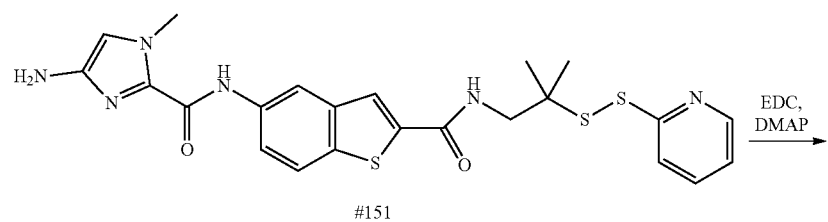

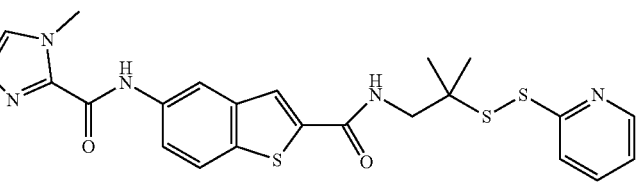

152

To a mixture of compound #2 (30 mg, 0.079 mmol) and compound #151 (60.6 mg, 0.118 mmol) in DCM (789 μL) was added EDC (22.68 mg, 0.118 mmol) and DMAP (4.82 mg, 0.039 mmol) at rt. After stirring for 2 h, the mixture was extracted with DCM and water. The organic extracts were dried over MgSO₄, filtered and concentrated. Half of the crude material was purified by RP-HPLC (C18 Kromasil, ACN/0.1% formic acid in water) to obtain compound #152 (7 mg, 20% yield). LCMS=8.22 min (15 min method). Mass observed (ESI⁺): 875.5 (M+H).

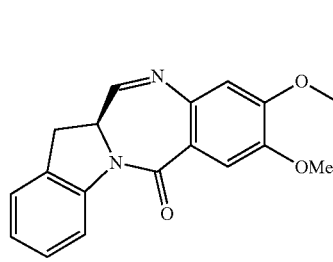

151

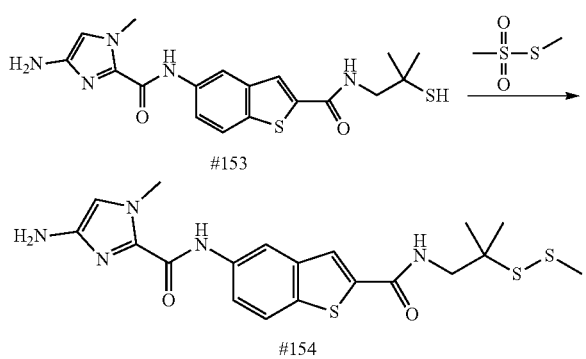

153

TCEP·HCl (50.3 mg, 0.176 mmol) was dissolved in a mixture of sat'd aq NaHCO₃ and sodium phosphate buffer pH=6.5 (2:1, 0.6 mL). This solution was added to compound #151 (30 mg, 0.059 mmol) in ACN, MeOH, and THF (1.5:1:1, 1.4 mL) at rt. After stirring for 3 h, the mixture was extracted with DCM. The organic layer was washed with brine, dried over MgSO₄, filtered, and concentrated to yield compound #153, which was used in next step without purification (24 mg, 100% yield). LCMS=4.76 min (8 min method). Mass observed (ESI⁺): 403.8 (M+H).

154

To a suspension of compound #153 (23.81 mg, 0.059 mmol) in MeOH (2 mL) and potassium phosphate buffer (2.0 mL, pH=7.4) was added methylmethanethiolsulfonate (0.223 mL, 2.360 mmol) at rt. After stirring for 18 h, the mixture was extracted with EtOAc and brine. The organic layer was dried over MgSO₄, filtered, and concentrated. The crude material was purified by silica gel chromatography (MeOH/DCM) to yield compound #154 (8.8 mg, 33% yield). LCMS=5.89 min (8 min method). Mass observed (ESI⁺): 449.8 (M+H).

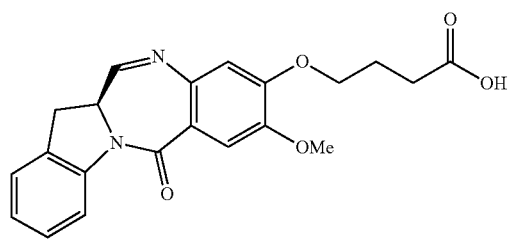

2

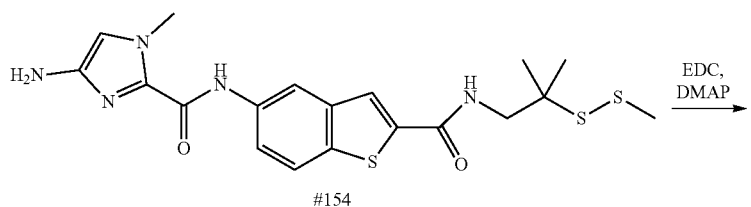

154

-continued

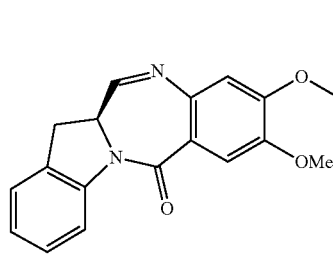
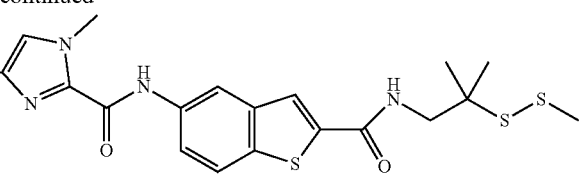

155

To a mixture of compound #2 (5 mg, 0.013 mmol) and compound #154 (8.86 mg, 0.020 mmol) in DCM (263 μL) was added EDC (3.78 mg, 0.020 mmol) and DMAP (0.803 mg, 6.57 μmol) at rt. After stirring for 1 h, the reaction was extracted with DCM and water. The organic extracts were dried over MgSO$_4$, filtered and concentrated. The crude product was purified by RP-HPLC (C18 Kromasil, ACN/H$_2$O) to yield compound #155 (2.5 mg, 23% yield). LCMS=5.91 min (8 min method). Mass observed (ESI$^+$): 811.7 (M+H).

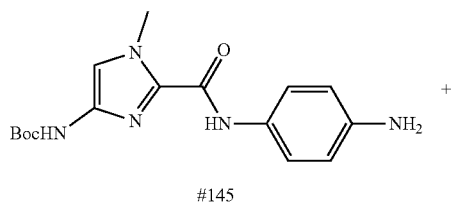

145

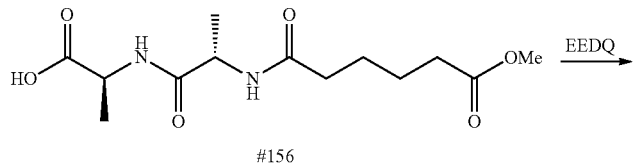

156

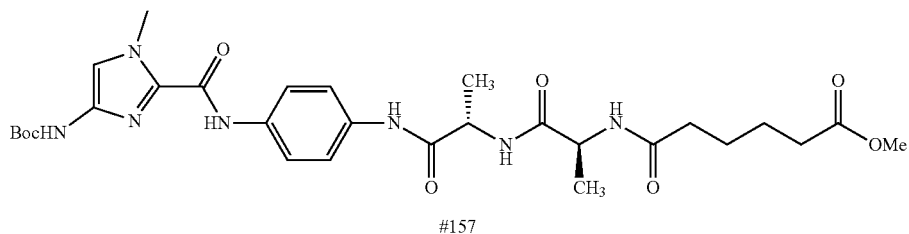

157

To a mixture of compound #145 (1.5 g, 4.53 mmol) and compound #156 (1.64 g, 5.43 mmol) in DCM (30.2 mL) and MeOH (15.09 mL) was added EEDQ (1.679 g, 6.79 mmol) at rt. After stirring for 18 h, the reaction mixture was concentrated and then EtOAc was added to precipitate the product. The resulting solid was filtered, rinsed with ethyl acetate, and dried to obtain compound #157 (1.85 g, 60% yield) as a purplish white solid, which was used in next step without further purification. $^1$H NMR (400 MHz, DMSO-d$_6$): δ 1.17 (t, J=7.1 Hz, 7H), 1.21 (d, J=7.1 Hz, 3H), 1.31 (d, J=7.1 Hz, 3H), 1.45 (s, 9H), 1.51 (p, J=3.6 Hz, 4H), 1.98 (s, 6H), 2.14 (s, 2H), 2.29 (t, J=4.7 Hz, 2H), 3.57 (s, 3H), 3.94 (s, 3H), 4.03 (q, J=7.1 Hz, 4H), 4.26 (h, J=7.4 Hz, 1H), 7.58 (d, J=8.9 Hz, 2H), 7.66 (d, J=8.9 Hz, 2H), 8.05 (dd, J=13.5, 7.1 Hz, 2H), 9.74 (s, 1H), 9.85 (s, 1H). LCMS=4.74 min (8 min method). Mass observed (ESI$^+$): 616.3 (M+H).

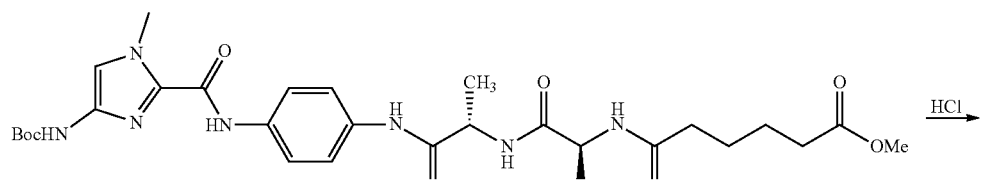

157

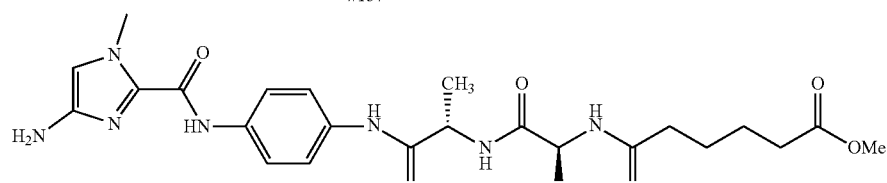

158

Compound #157 (0.60 g, 0.877 mmol) was stirred in HCl (4 N in dioxane, 3.29 mL, 13.16 mmol) and MeOH (1.0 mL) at rt. After stirring for 4 h, hexanes was added and the resulting solid was filtered and washed with hexanes. The solid was re-dissolved in MeOH/DCM (1:4) and washed with sat'd aq. NaHCO$_3$ solution. The organic layer was washed with brine, dried over Na$_2$SO$_4$, filtered, and concentrated to obtain compound #158 (345 mg, 76% yield). LCMS=2.96 min (8 min method). Mass observed (ESI$^+$): 516.3 (M+H).

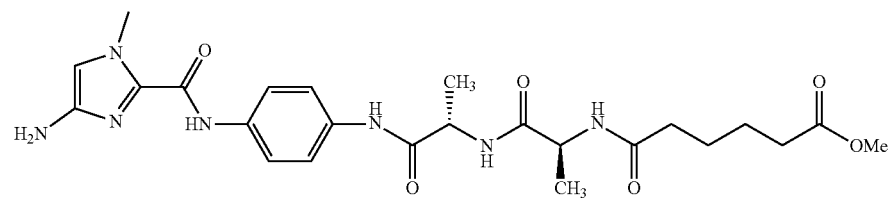

158

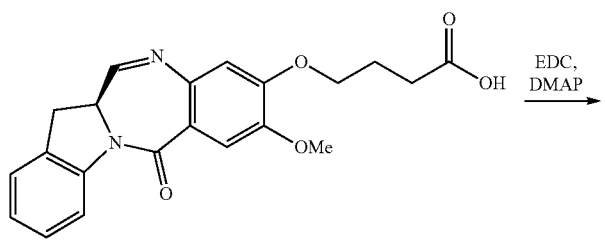

2

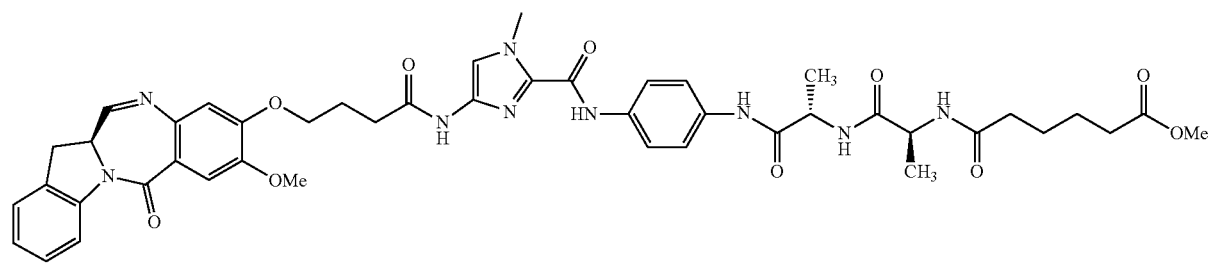

159

To a mixture of compound #158 (130 mg, 0.189 mmol) and compound #2 (65 mg, 0.145 mmol) in DCM (2.9 mL) was added EDC (41.8 mg, 0.218 mmol) and DMAP (8.87 mg, 0.073 mmol) at rt. After stirring for 18 h, the reaction was extracted with DCM and water. The organic layer was dried over MgSO$_4$, filtered and concentrated to obtain compound #159 (57 mg, 45% yield). LCMS=4.45 min (8 min method). Mass observed (ESI$^+$): 516.3 (M+H).

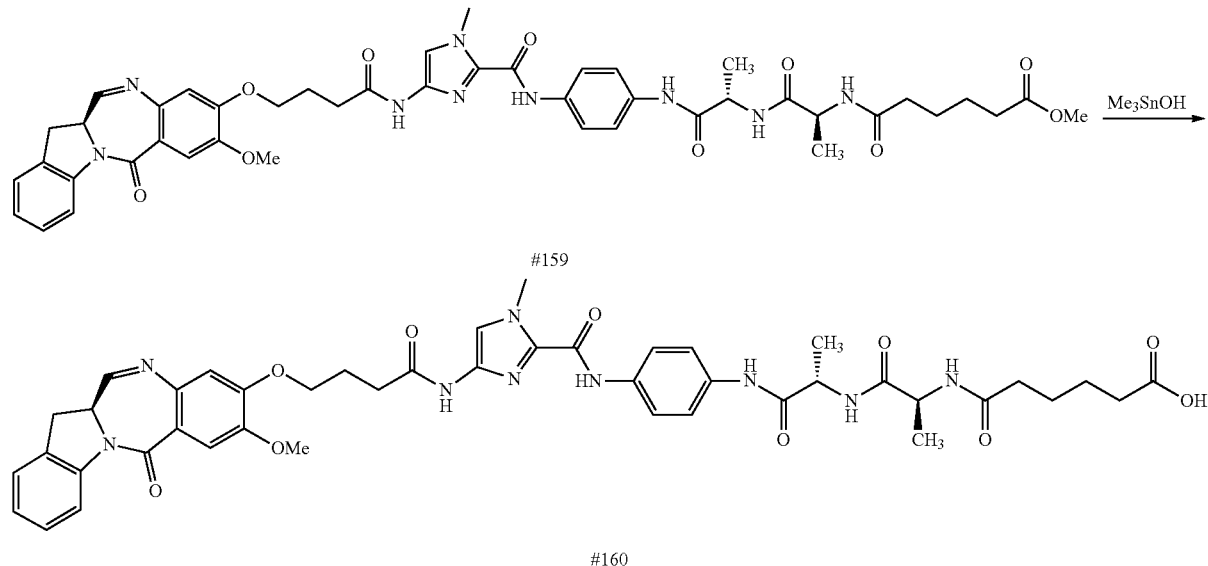

159

160

To a solution of compound #159 (0.21 g, 0.144 mmol) in DCE (7.18 mL) was added Me$_3$SnOH (0.26 g, 1.435 mmol). The reaction mixture was stirred at 80° C. for 18 h. The reaction mixture was then cooled to rt and was diluted with MeOH/DCM (1:4) and carefully acidified to pH~ 4 with HCl (aq, 0.5 M). The solution was extracted with MeOH/DCM (1:2). The organic extracts were washed with brine, dried over MgSO$_4$, filtered, and concentrated. The crude material was purified by silica gel chromatography (MeOH/DCM) to obtain compound #160 (19 mg, 15% yield). LCMS=4.17 min (8 min method). Mass observed (ESI$^+$): 864.3 (M+H).

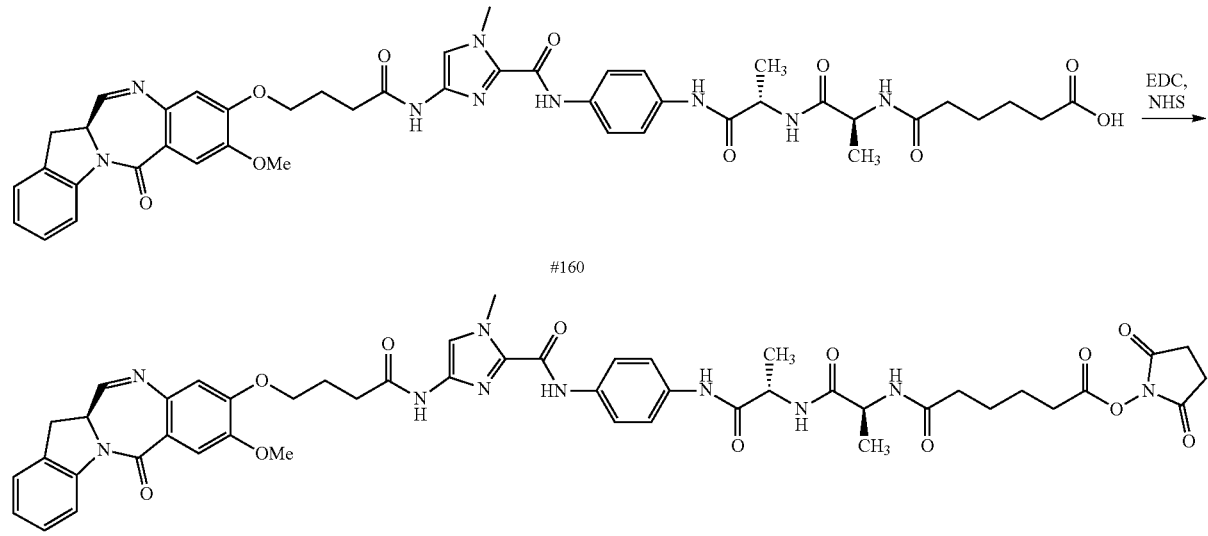

160

161

To a mixture of compound #160 (19 mg, 0.022 mmol) and NHS (7.59 mg, 0.066 mmol) in DCM (1.1 mL) was added EDC (21.08 mg, 0.110 mmol) at rt. After stirring for 5 h, the mixture was extracted with DCM and water. The organic layer was dried over MgSO₄, filtered, and concentrated. The crude material was purified by RP-HPLC (C18 Kromasil, 0.1% formic acid in H₂O/ACN) to obtain compound #161 as a white solid (3.6 mg, 17% yield). LCMS=4.45 min (8 min method). Mass observed (ESI⁺): 961.3 (M+H).

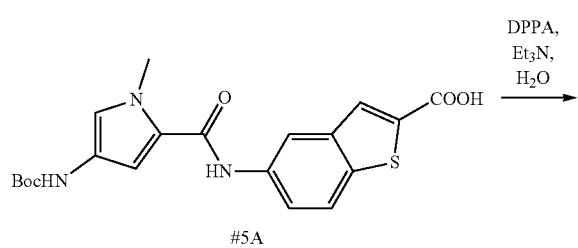

5A

-continued

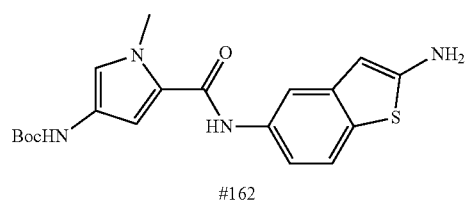

162

Compound #5A (1.50 g, 3.61 mmol) was dissolved in DMF (18.0 mL). DPPA (0.933 mL, 4.330 mmol) and TEA (0.604 mL, 4.33 mmol) were added. The reaction mixture was allowed to stir at rt under Ar for 2 h. Next, water (1.30 mL, 72.2 mmol) was added to the mixture and the mixture was heated to 80° C. and allowed to stir at this temperature for 8 h. After 8 h, the mixture was cooled to rt and was diluted with EtOAc (50 mL). The reaction mixture was washed with DI water (2×25 mL) and brine (20 mL). The organics were dried over Na₂SO₄, filtered, and concentrated. The crude residue was purified via silica gel chromatography (DCM/MeOH) to give #162 (0.682 g, 1.763 mmol, 49% yield). UPLCMS (2.5 min method)=1.57 min. Mass observed (ESI⁺): 387.5 (M+H).

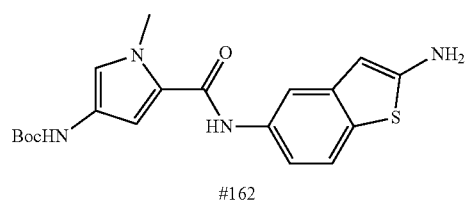

162

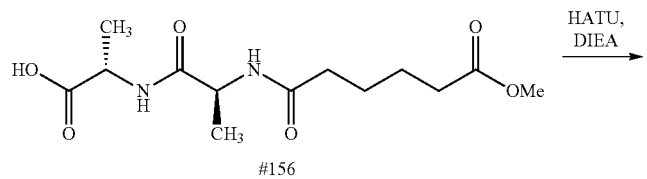

156

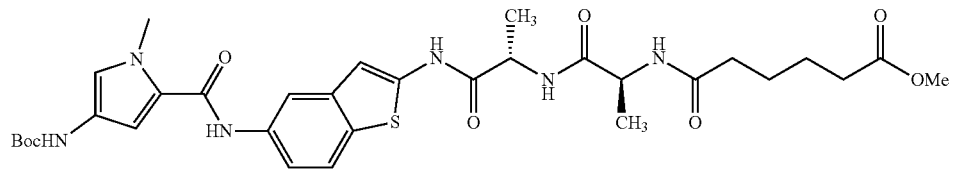

163

Compound #162 (0.500 g, 1.294 mmol) and compound #156 (0.587 g, 1.941 mmol) were dissolved in DMF (4.13 mL). HATU (0.984 g, 2.59 mmol) and DIEA (0.604 mL, 6.47 mmol) were added. The reaction mixture was allowed to stir at rt under Ar overnight. After stirring overnight, the reaction mixture was diluted with EtOAc (20 mL) and was washed with DI water (2×25 mL) and brine (10 mL). The organics were dried over Na₂SO₄, filtered, and concentrated. The crude residue was purified via silica gel chromatography (DCM/MeOH) to give #163 (0.514 g, 0.766 mmol, 59% yield). UPLCMS (2.5 min method)=1.59 min. Mass observed (ESI⁺): 671.4 (M+H).

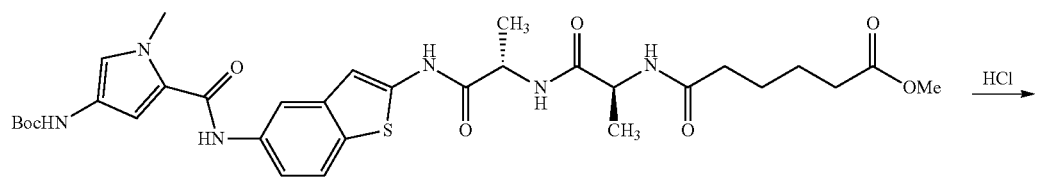

163

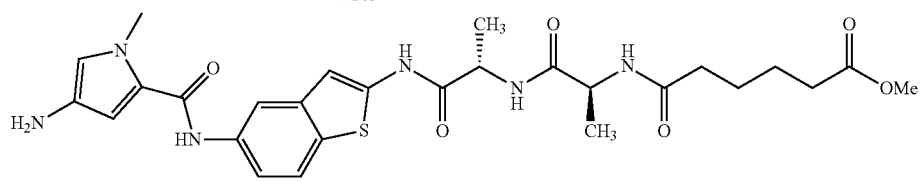

164

Compound #163 (0.212 g, 0.317 mmol) was dissolved in DCM (3 mL). HCl (4 N in dioxane, (3.0 mL, 12.0 mmol) was added and the reaction mixture was allowed to stir at rt under Ar for 45 min. After stirring 45 min, the reaction mixture was concentrated and placed on high vacuum to dryness to give crude #164 (0.181 g, 0.317 mmol, 100% yield) which was used directly in the next step. UPLCMS (2.5 min method)=1.11 min. Mass observed (ESI$^+$): 571.7 (M+H).

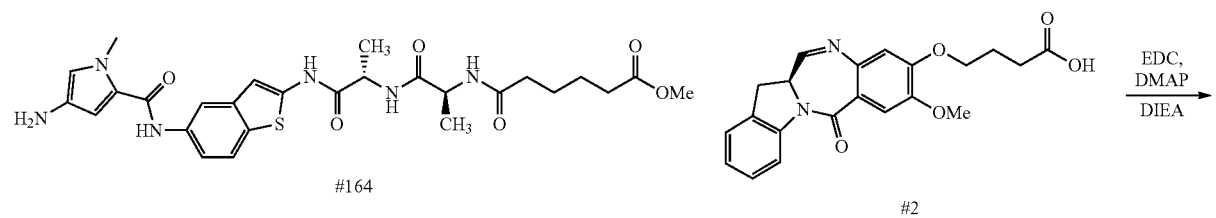

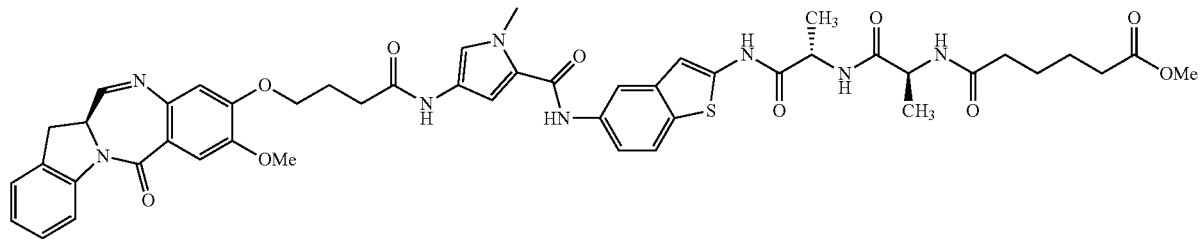

165

Compound #164 (0.181 g, 0.317 mmol) and compound #2 (0.133 g, 0.349 mmol) were dissolved in DMF (3.0 mL). EDC HCl (0.091 g, 0.476 mmol), DIEA (0.111 mL, 0.634 mmol), and DMAP (38.7 mg, 0.317 mmol) were added. The reaction mixture was allowed to stir at rt under Ar overnight. After stirring overnight, DI water (10 mL) was added to the reaction mixture to precipitate the product. The slurry was stirred at rt for 5 min and was then filtered. The crude residue was purified via silica gel chromatography (DCM/MeOH) to give #165 (0.0723 g, 0.077 mmol, 24% yield). UPLCMS (2.5 min method)=1.49 min. Mass observed (ESI$^+$): 933.8 (M+H).

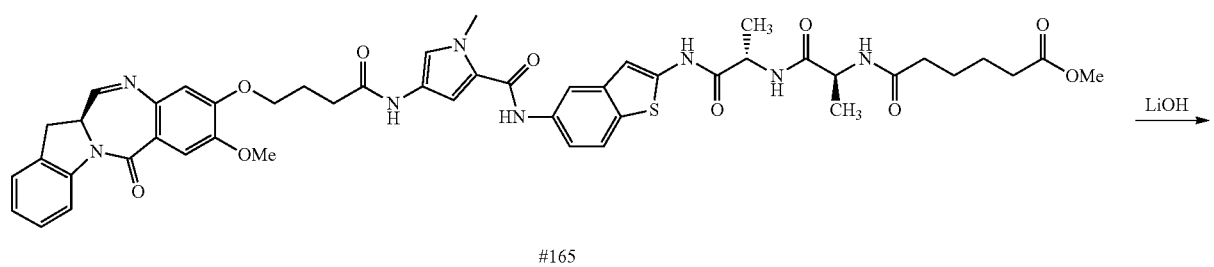

165

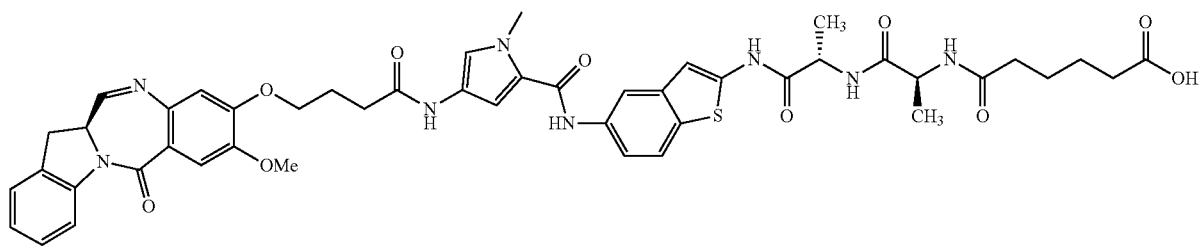

166

Compound #165 (0.056 g, 0.060 mmol) was dissolved in THF (2.25 mL). DI water (0.750 mL) and LiOH (14.4 mg, 0.60 mmol) was added. The reaction mixture was allowed to stir at rt under Ar for 2 h. After stirring 2 h, the reaction mixture was diluted with DCM/MeOH (10:3, 5 mL) and DI water (5 mL) then acidified with 1.0 M aq HCl until pH~ 3. The aqueous layer was extracted with DCM/MeOH (10:3, 2×20 mL). The combined organics were dried over $Na_2SO_4$, filtered, concentrated, and placed on high vacuum to dryness to give crude #166, which was used directly in the next step (0.052 g, 0.060 mmol, 100% yield). UPLCMS (2.5 min method)=1.41 min. Mass observed (ESI$^+$): 919.7 (M+H).

Compound #166 (0.0552 g, 0.060 mmol) and NHS (0.0207 g, 0.180 mmol) were dissolved in DMF (0.500 mL) and DCM (3.85 mL). EDC HCl (0.0576 g, 0.300 mmol) was added. The reaction mixture was allowed to stir at rt under Ar for 90 min. After stirring 90 min, the reaction mixture was diluted with DCM (5 mL) and washed with DI water (2×10 mL). The organic layer was dried over $Na_2SO_4$, filtered, and concentrated. The crude residue was purified by RPHPLC (C18 column, $CH_3CN/H_2O$, gradient, 50% to 80%) to obtain #167 (0.0183 g, 0.018 mmol, 30% yield). LCMS (8.0 min method)=4.74 min. Mass observed (ESI$^+$): 1116.25 (M+H).

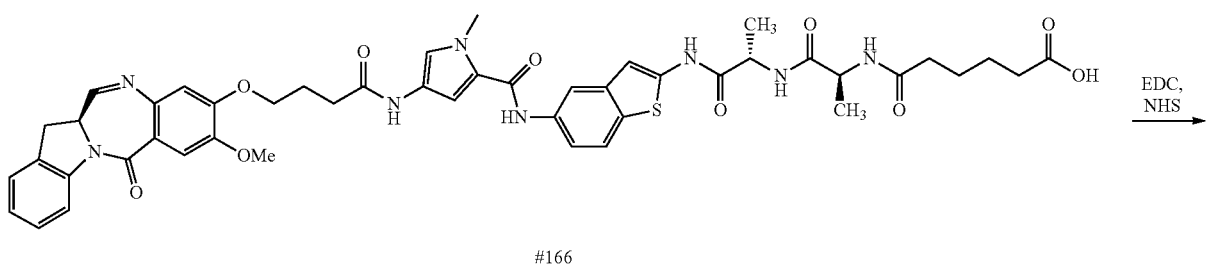

166

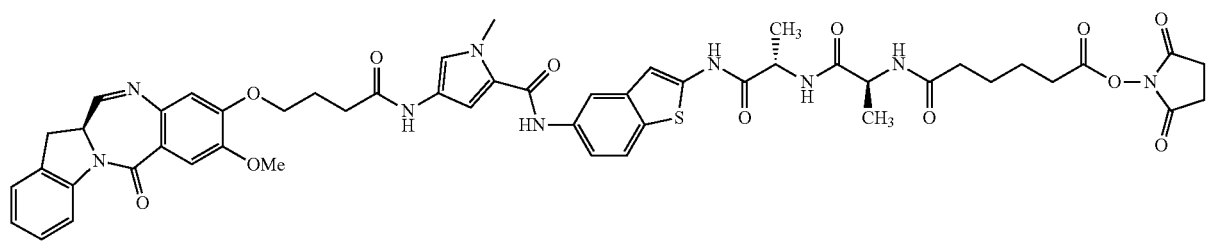

167

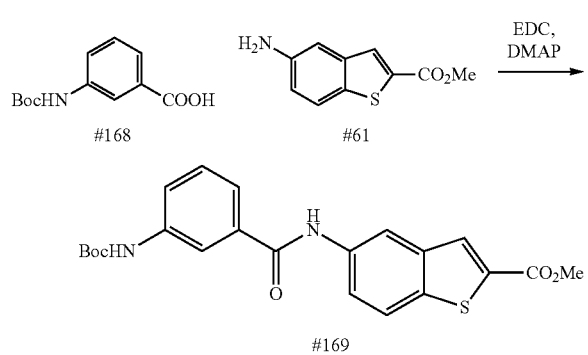

Compound #168 (1.259 g, 5.31 mmol) and compound #61 (1.00 g, 4.83 mmol) were dissolved in DMF (6.0 mL). EDC HCl (1.11 g, 0.476 mmol) and DMAP (0.295 g, 2.41 mmol) were added. The reaction mixture was allowed to stir at rt under Ar overnight. After stirring overnight, DI water (25 mL) was added to the reaction mixture to precipitate the product. The slurry was stirred at rt for 5 min and was then filtered. The resulting solids were placed on high vacuum to dryness to give crude #169, which was used directly in the next step (2.058 g, 5.31 mmol, 100% yield). UPLCMS (2.5 min method)=1.84 min. Mass observed (ESI$^+$): 427.2 (M+H).

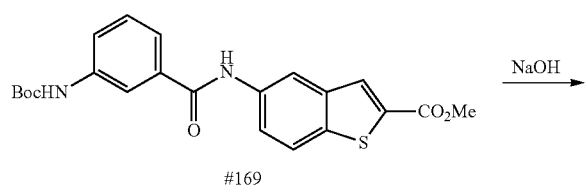

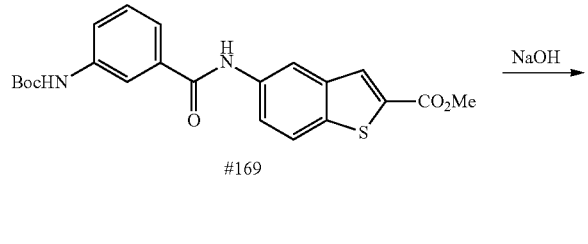

Compound #169 (1.01 g, 2.368 mmol) was dissolved in MeOH (6.0 mL). NaOH (aqueous, 5 N, 0.947 mL, 4.74 mmol) was added. The reaction mixture was allowed to stir at 60° C. under Ar for 2.5 h. After stirring 2.5 h, the reaction was cooled to rt, then acidified with 1.0 M aq HCl until pH-3-4. The aqueous layer was extracted with EtOAC (3×50 mL). The combined organics were dried over Na$_2$SO$_4$, filtered, concentrated, and placed on high vacuum to dryness to give crude #170, which was used directly in the next step (0.587 g, 1.42 mmol, 60% yield). UPLCMS (2.5 min method)=1.65 min. Mass observed (ESI$^+$): 413.2 (M+H).

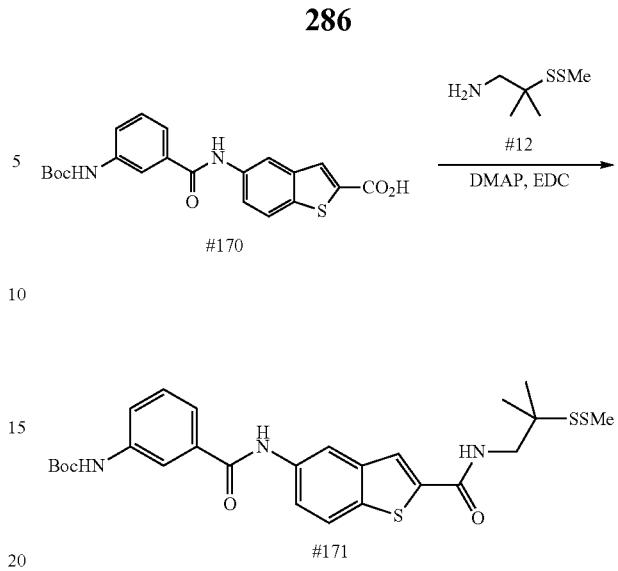

Compound #170 (0.313 g, 0.758 mmol) and compound #12 (0.104 g, 0.689 mmol) were dissolved in DMF (6.89 mL). EDC HCl (0.396 g, 2.07 mmol) and DMAP (0.126 g, 1.03 mmol) were added. The reaction mixture was allowed to stir at rt under Ar overnight. After stirring overnight, DI water (10 mL) was added to the reaction mixture to precipitate the product. The slurry was stirred at rt for 5 min and then filtered. The crude residue was purified via silica gel chromatography (EtOAc/hexanes) to give #171 (0.2148 g, 0.077 mmol, 57% yield). UPLCMS (2.5 min method)=1.94 min. Mass observed (ESI$^+$): 546.3 (M+H).

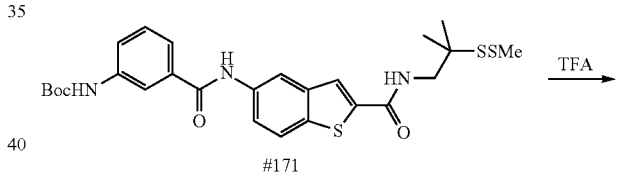

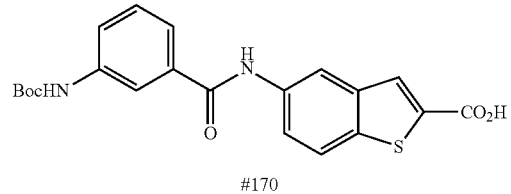

Compound #171 (0.110 g, 0.202 mmol) was dissolved in DCM (2.30 mL). A mixture of DCM/TFA was added (2:1, 1.728 mL). The reaction mixture was allowed to stir at rt under Ar for 2.5 h. After stirring 2.5 h, the reaction mixture was diluted with DCM (20 mL) and washed with sat'd NaHCO$_3$ (25 mL) and brine (10 mL). The organic layer was dried over Na$_2$SO$_4$, filtered, concentrated, and placed on high vacuum to dryness to give crude #172, which was used directly in the next step (0.077 g, 0.173 mmol, 86% yield). UPLCMS (2.5 min method)=1.66 min. Mass observed (ESI$^+$): 446.9 (M+H).

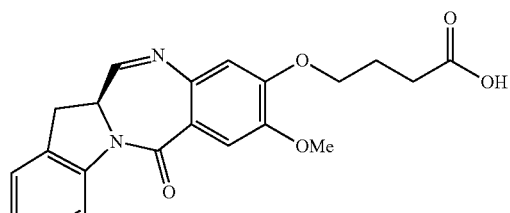

2

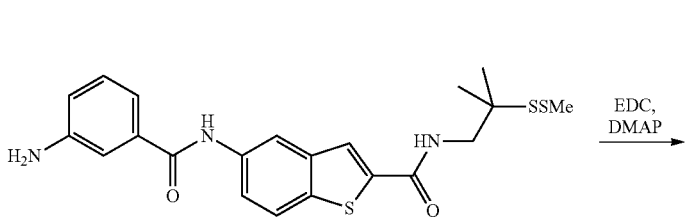

172

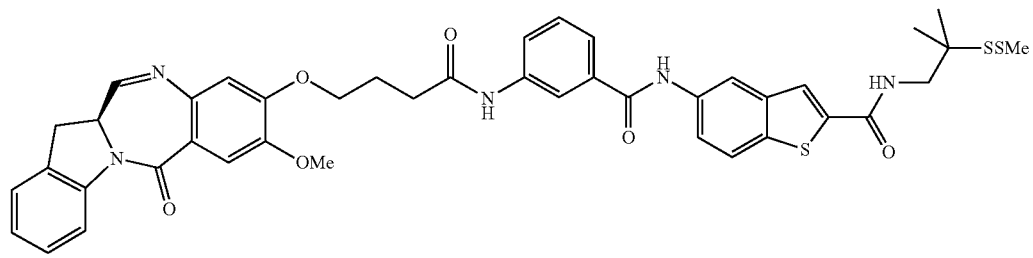

173

Compound #2 (0.077 g, 0.173 mmol) and #172 (0.059 g, 0.156 mmol) were dissolved in DMF (2.0 mL). EDC HCl (0.865 g, 0.166 mmol) and DMAP (0.042 g, 0.346 mmol) were added. The reaction mixture was allowed to stir at rt under Ar for 2 h. After stirring 2 h, additional EDC HCl (0.865 g, 0.166 mmol) and DMAP (0.0423 g, 0.346 mmol) were added to the reaction mixture. After stirring 1 h, DI water (5 mL) was added to the reaction mixture to precipitate the product. The slurry was stirred at rt for 5 min and was then filtered. The crude residue was purified by RPHPLC (C18 column, $CH_3CN/H_2O$, gradient, 40% to 70%) to obtain #173 (0.0233 g, 0.018 mmol, 17% yield). UPLCMS (2.5 min method)=1.84 min. Mass observed ($ESI^+$): 808.9 (M+H).

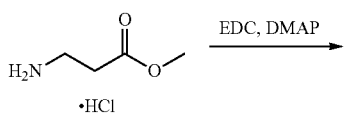

133

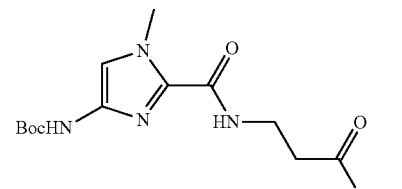

174

Compound #133 (2.0 g, 8.29 mmol) and beta-alanine methylester HCl (1.504 g, 10.78 mmol) were dissolved in DMF (41.5 mL). EDC (2.07 g, 10.78 mmol) and DMAP (0.506 g, 4.15 mmol) were added and the reaction was stirred at rt under Ar overnight. The reaction mixture was concentrated and the crude material was purified by silica gel chromatography to give compound #174 (1.45 g, 54% yield). LCMS=4.35 min (8 min method). Mass observed ($ESI^+$): 327.0 (M+H).

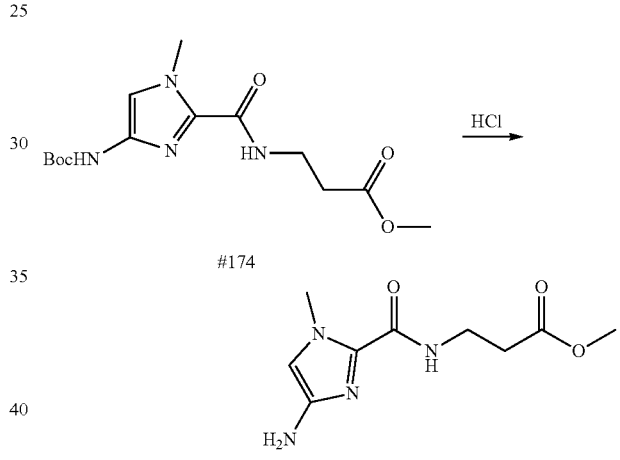

174

175

Compound #174 (1.17 g, 3.59 mmol) was treated with HCl (4 N in dioxane) (13.44 mL, 53.8 mmol) and was stirred at rt under Ar for 20 min. The precipitate was filtered to yield compound #175 (573 mg, 61% yield). LCMS=1.00 min (8 min method). Mass observed ($ESI^+$): 227.0 (M+H).

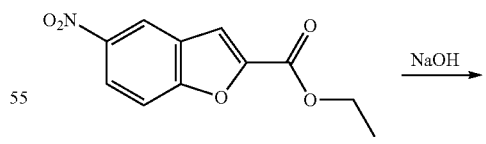

176

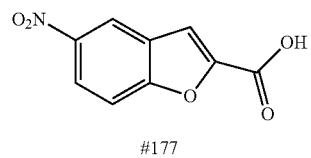

177

To a solution of ethyl 5-nitrobenzofuran-2-carboxylate, #176 (5.0 g, 21.26 mmol) in MeOH/THF (1:1, 100 mL) was added a solution of NaOH (7.96 g, 199 mmol) in H$_2$O (59.5 mL). The resulting solution was stirred at rt for 3 h. The reaction was quenched with aq HCl to pH=1. The precipitate was filtered and dissolved in THF. The filtrate was extracted with THF/EtOAc (1:2, 100 mL×3) and the organic layer was combined with the solubilized precipitate, dried over MgSO$_4$, filtered and concentrated. The crude solid was recrystallized with THF/EtOAc/hexanes to yield compound #177 (4.40 g, 100% yield). LCMS=3.75 min (8 min method). Mass observed (ESI$^+$): 207.9 (M+H).

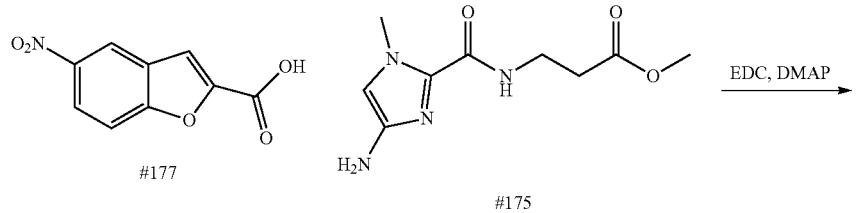

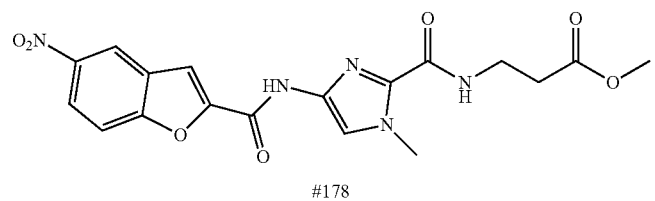

Compound #177 (342 mg, 1.649 mmol) and compound #175 (287 mg, 1.269 mmol) were dissolved in DMF (10 mL). EDC (316 mg, 1.649 mmol) and DMAP (77 mg, 0.634 mmol) were added and the reaction was stirred under Ar at rt overnight. The crude reaction mixture was directly purified by silica gel chromatography to yield compound #178 (63 mg, 12% yield). LCMS=4.74 min (8 min method). Mass observed (ESI$^+$): 415.9 (M+H). $^1$H NMR (400 MHz, DMSO-d6): δ 2.60 (t, J=6.7 Hz, 2H), 3.50 (q, J=6.5 Hz, 2H), 3.62 (s, 3H), 3.97 (s, 3H), 7.62 (s, 1H), 7.96 (d, J=9.1 Hz, 1H), 8.02 (t, J=6.1 Hz, 1H), 8.07 (s, 1H), 8.35 (dd, J=9.1, 2.5 Hz, 1H), 8.83 (d, J=2.4 Hz, 1H), 11.30 (s, 1H).

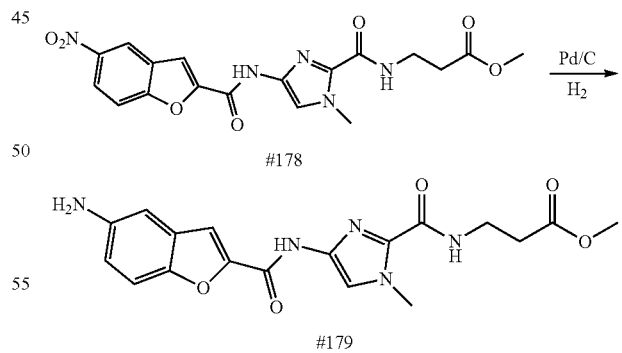

Compound #178 (63 mg, 0.152 mmol) was dissolved in MeOH/Water (9:1, 10 mL). Pd/C (5%, 8.07 mg, 0.076 mmol) was added and the reaction was reacted in a parr shaker with H$_2$ (15 psi) at rt overnight. The reaction mixture was filtered through Celite, rinsed with MeOH, and concentrated to yield compound #179 (53 mg, 91% yield). LCMS=3.27 min (8 min method). Mass observed (ESI$^+$): 385.9 (M+H).

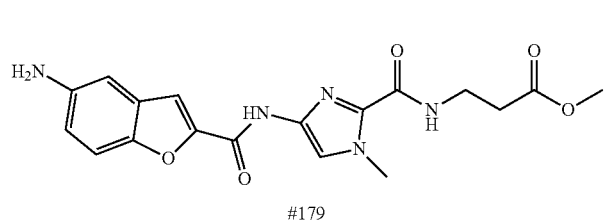

179

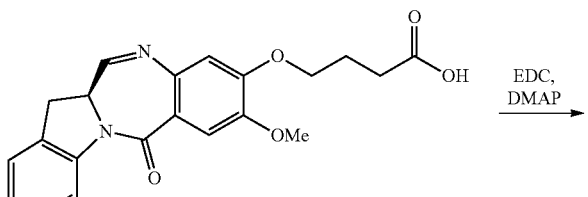

2

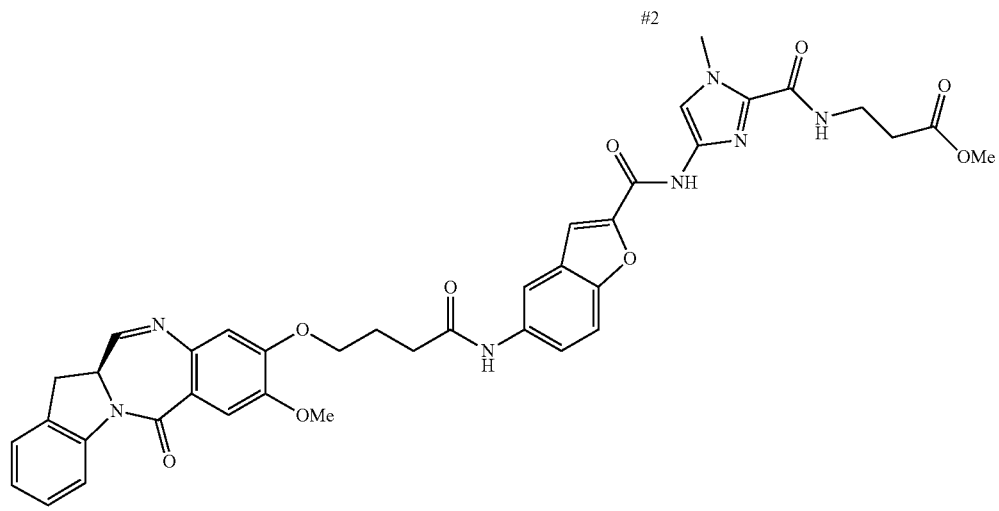

180

Compound #179 (40.2 mg, 0.106 mmol) was dissolved in DMF (5 mL). Compound #2 (53 mg, 0.138 mmol), EDC (26.4 mg, 0.138 mmol) and DMAP (6.46 mg, 0.053 mmol) were added and the reaction was stirred under Ar at rt. After 2 h, the reaction was quenched with water and was extracted with DCM. The organic layer was dried over $Na_2SO_4$, filtered and concentrated. The crude product was purified by silica gel chromatography (DCM/THF) to obtain compound #180 (9.2 mg, 10% yield). LCMS=4.80 min (8 min method). Mass observed (ESI$^+$): 747.8 (M+H).

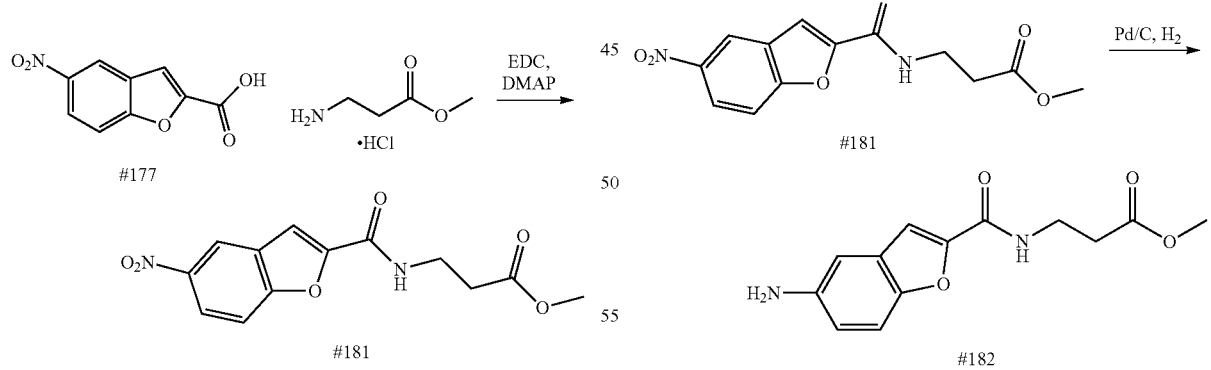

Compound #177 (2.0 g, 9.66 mmol) and beta-alanine methylester HCl (1.752 g, 12.55 mmol) were dissolved in DMF (48.3 mL). EDC (2.41 g, 12.55 mmol) and DMAP (0.59 g, 4.83 mmol) were added and the reaction was stirred under Ar at rt for 2 d. An additional amount of beta-alanine methylester HCl (337 mg), EDC (462 mg), and DMAP (147 mg) were added and stirred for an additional night. The reaction was cooled in an ice bath and then water was added to precipitate the desired compound. The solution was filtered to obtain compound #181 (2.82 g, 100% yield), which used without further purification. LCMS=4.33 min (8 min method). Mass observed (ESI$^+$): 293.0 (M+H). $^1$H NMR (400 MHz, CDCl$_3$): δ 2.70 (t, J=5.8 Hz, 2H), 3.75 (s, 3H), 3.76-3.81 (m, 2H), 7.30 (s, 1H), 7.59 (s, 1H), 7.63 (d, J=9.1 Hz, 1H), 8.34 (dd, J=9.1, 2.3 Hz, 1H), 8.62 (d, J=2.3 Hz, 1H).

Compound #182 was synthesized similarly as compound #179 from compound #181 to obtain compound #182, which was used without further purification (1.73 g, 55% yield). LCMS=2.0 min (8 min method). Mass observed (ESI$^+$): 263.0 (M+H). $^1$H NMR (400 MHz, DMSO-d6): δ 2.59 (t, J=7.0 Hz, 2H), 3.48 (q, J=7.0 Hz, 2H), 3.60 (s, 3H), 6.70-6.80 (m, 2H), 7.23-7.32 (m, 2H), 8.58 (t, J=5.7 Hz, 1H).

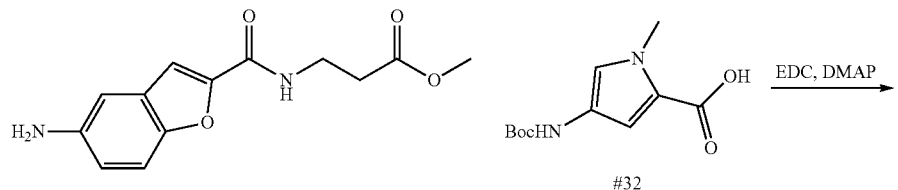

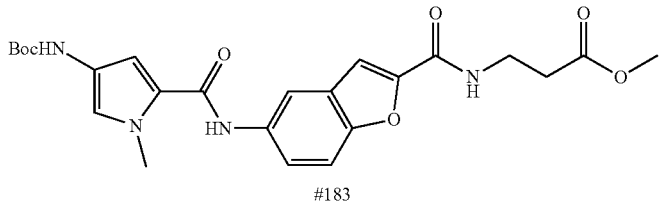

Compound #182 (865 mg, 3.30 mmol) and compound #32 (1.03 g, 4.29 mmol) were dissolved in DMF (16.5 mL). EDC (822 mg, 4.29 mmol) and DMAP (201 mg, 1.649 mmol) were added and the reaction was stirred at rt overnight. The reaction mixture was cooled to 0° C. in an ice bath and water was added to precipitate the desired product. The solution was filtered to yield compound #183, which was used without further purification (1.18 g, 74% yield). LCMS=5.13 min (8 min method). Mass observed (ESI−): 482.9 (M−H).

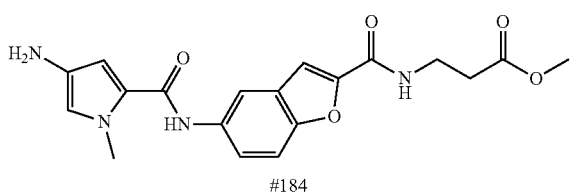

-continued

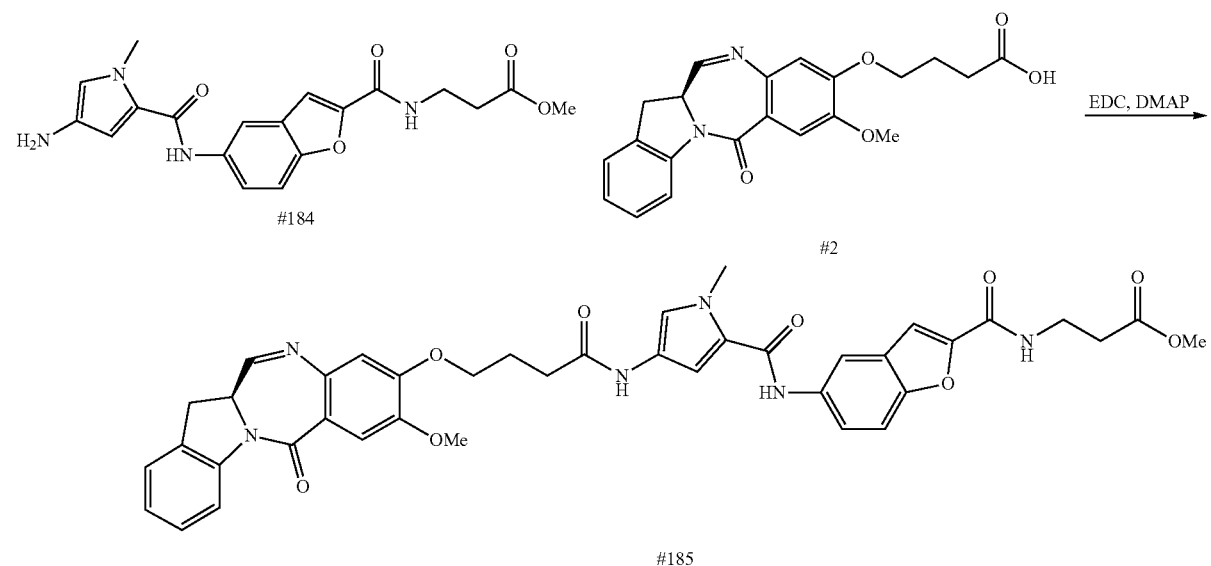

Compound #183 (250 mg, 0.516 mmol) was treated with HCl (4 N in dioxane, 1.93 mL, 7.74 mmol). After 90 min, hexanes was added and the reaction mixture was filtered, washed with hexanes and dried under vacuum to give compound #184, which was used without further purification (164 mg, 76% yield). LCMS=3.39 min (8 min method). Mass observed (ESI+): 384.9 (M+H).

Compound #185 was prepared similarly as compound #7. Purification by silica gel chromatography (DCM/THF) gave compound #185 (7.3 mg, 3% yield). LCMS=4.71 min (8 method). Mass observed (ESI−): 744.9 (M−H).

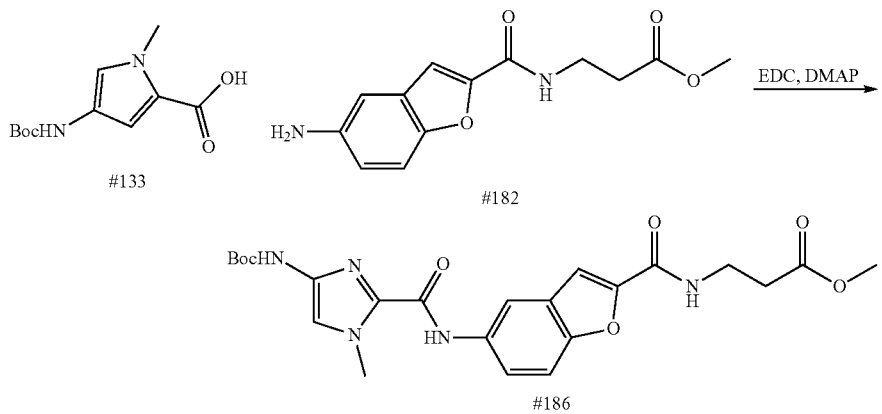

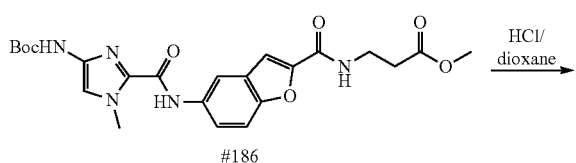

Compound #186 was synthesized similarly as compound #13 from compound #133 to give compound #186, which was used without further purification (487 mg, 42% yield). LCMS=5.2 min (8 min method). Mass observed (ESI⁻): 483.9 (M−H).

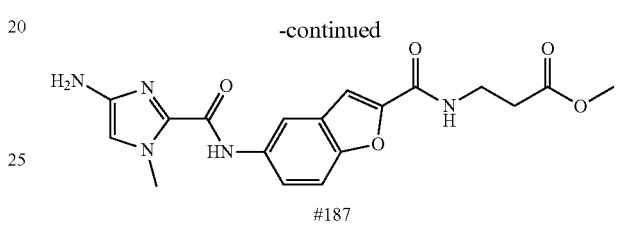

-continued

Compound #187 was prepared similarly as compound #6 from compound #186 to yield compound #187 (190 mg, 100%). LCMS=3.36 min (8 min method). Mass observed (ESI⁺): 386.0 (M+H).

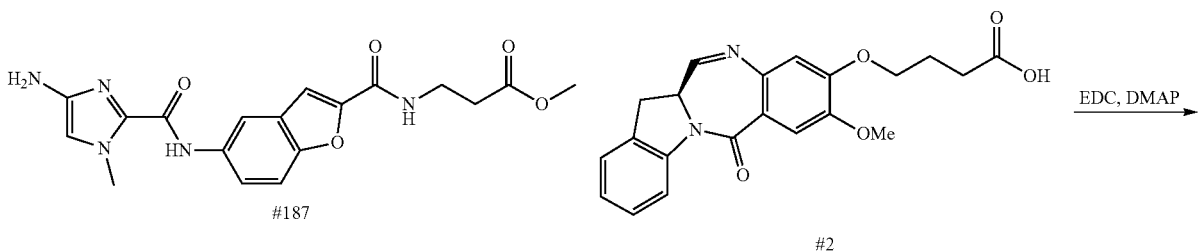

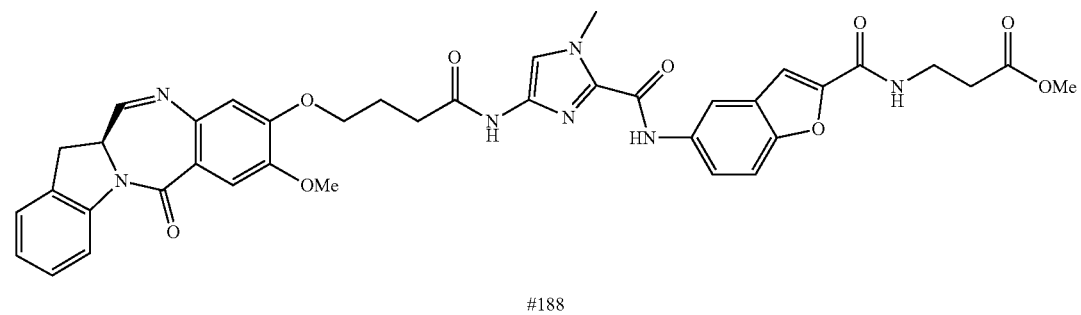

Compound #188 was prepared similarly as compound #7 after purification by silica gel chromatography (DCM/THF), followed by RPHPLC (C18 column, ACN/0.1% formic acid in H₂O) to give compound #188 (1.9 mg, 2% yield). LCMS=4.66 min (8 min method). Mass observed (ESI⁺): 746.7 (M+H).

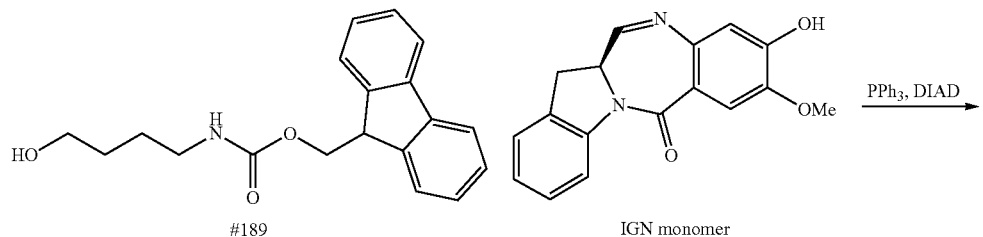

Compound #189 (532 mg, 1.709 mmol) and IGN monomer (553 mg, 1.879 mmol) were dissolved in THF (6.83 mL) and DMF (300 μL) and cooled to 0° C. PPh₃ (672 mg, 2.56 mmol) was added, followed by a slow addition of DIAD (498 μL, 2.56 mmol). The reaction was allowed to warm to rt and was stirred under Ar overnight. The crude product was purified via RPHPLC (C18 column, ACN/H₂O) to obtain compound #190 (115 mg, 11.4%). LCMS=4.68 min (4 min method). Mass observed (ESI⁺): 587.8 (M+H).

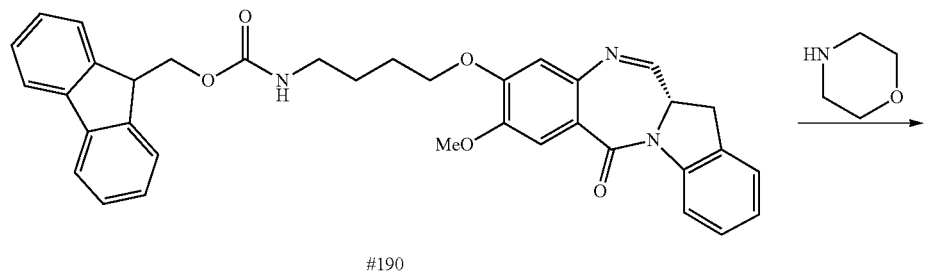

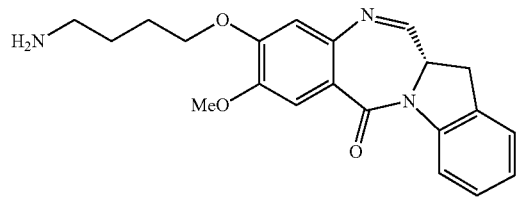

Compound #190 (115 mg, 0.196 mmol) was treated with morpholine (20% in DMF) (2 mL, 22.96 mmol) and was stirred at rt under Ar for 3 h. The crude reaction mixture was purified directly by RPHPLC (C18 column, ACN/H₂O) to obtain compound #191 (45 mg, 63% yield). LCMS=3.26 min (4 min method). Mass observed (ESI⁺): 366.0 (M+H).

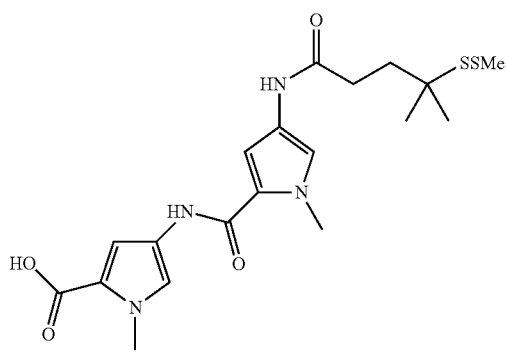

37

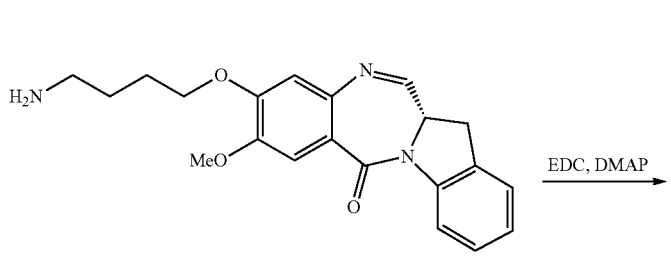

191

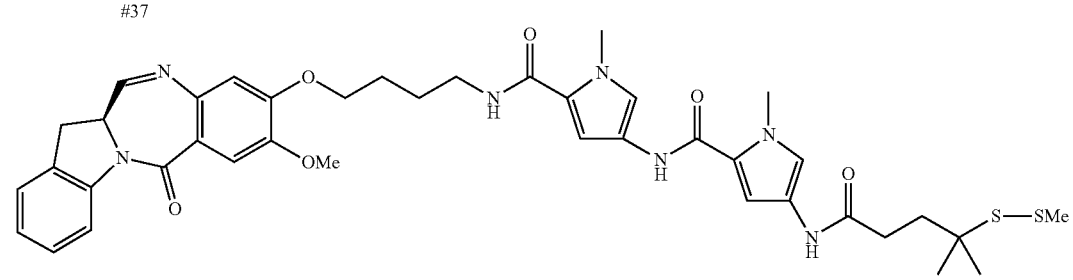

192

Compound #191 (26 mg, 0.070 mmol) and Compound #37 (28 mg, 0.064 mmol) were dissolved in DMF. EDC (13.5 mg, 0.070 mmol) and DMAP (3.9 mg, 0.032 mmol) were added and the reaction was stirred overnight. The crude product was purified by RPHPLC (C18 column, ACN/0.1% formic acid in $H_2O$) to give compound #192 (1 mg, 2% yield). LCMS=5.66 mins (8 min method). Mass observed (ESI$^+$): 785.7 (M+H).

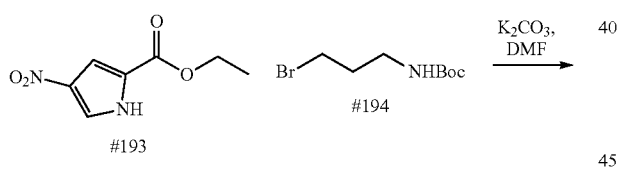

193     #194

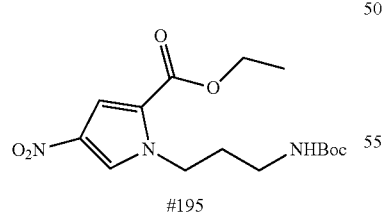

195

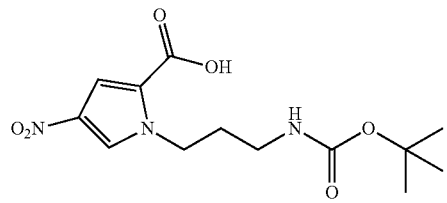

196

Compound #193 (3 g, 16.29 mmol) was dissolved in DMF (35 mL). Compound #194 (4.66 g, 19.55 mmol) and $K_2CO_3$ (4.50 g, 32.6 mmol) were added and the reaction was stirred at 40° C. under Ar for 4 h. The reaction was cooled to rt and was filtered. The crude filtrate was purified by RPHPLC (C18 column, ACN/$H_2O$) to yield compound #195 (5.5 g, 99% yield). LCMS=5.84 min (8 min method). Mass observed (ESI$^+$): 241.9 (M-Boc+H).

Compound #195 (1.0 g, 2.93 mmol) was dissolved in EtOH (24.89 mL) and water (2.489 mL). NaOH (5 N, aq. 2.502 mL, 12.51 mmol) was added and the reaction mixture was stirred at room temperature under Ar for 3 h. AcOH (1.254 ml, 21.91 mmol) was added to the reaction mixture and was. The crude product was purified by RPHPLC (C18 column, ACN/$H_2O$) to give compound #196 (867 mg, 94% yield). LCMS=4.68 min (8 min method). Mass observed (ESI$^-$): 312.0 (M–H).

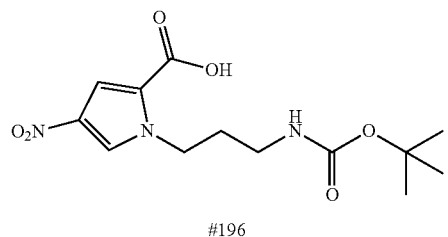
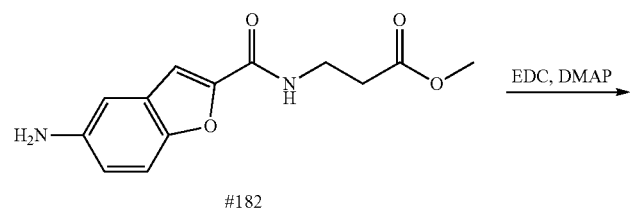

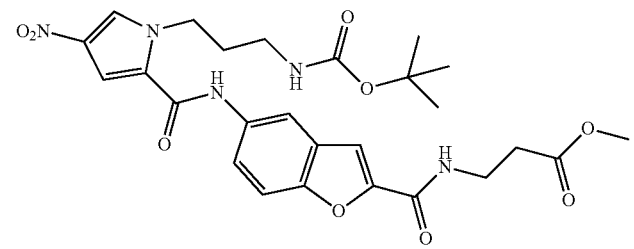

Compound #196 (348 mg, 1.110 mmol) and compound #182 (291 mg, 1.110 mmol) were dissolved in DMF (5.548 mL). EDC (277 mg, 1.442 mmol) and DMAP (67.8 mg, 0.555 mmol) were added and the reaction was stirred under Ar at rt overnight. The crude reaction was placed in an ice water bath and water was added to precipitate the product. The precipitate was filtered and dried by vacuum to give compound #197 (543 mg, 88% yield). LCMS=5.43 (8 min method). Mass observed (ESI−): 555.9 (M−H). ¹H NMR (400 MHz, CDCl₃): δ 1.44 (s, 9H), 2.06 (p, J=6.9 Hz, 2H), 2.69 (t, J=5.9 Hz, 2H), 3.18 (q, J=6.3 Hz, 2H), 3.73-3.82 (m, 5H), 4.46 (t, J=6.9 Hz, 2H), 7.22 (t, J=6.1 Hz, 1H), 7.28 (d, J=1.9 Hz, 1H), 7.41-7.48 (m, 2H), 7.48-7.55 (m, 1H), 7.75 (s, 1H), 7.84 (s, 1H), 8.02 (d, J=1.7 Hz, 1H).

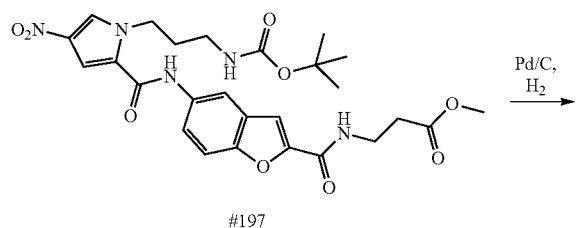

-continued

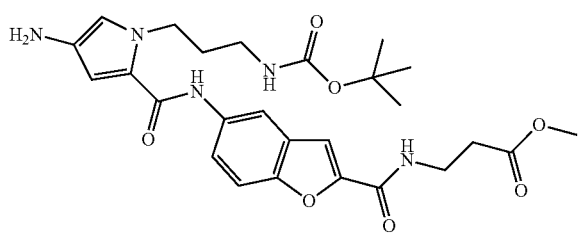

Compound #197 (250 mg, 0.448 mmol) was dissolved in MeOH/Water (95:5, 50 mL). Pd/C (5%, 23.86 mg, 0.224 mmol) was added and the reaction was reacted in a parr shaker with H₂ (30 psi) at rt overnight. The reaction mixture was filtered through Celite, rinsed with MeOH, and concentrated to yield compound #198 (237 mg, 100% yield).

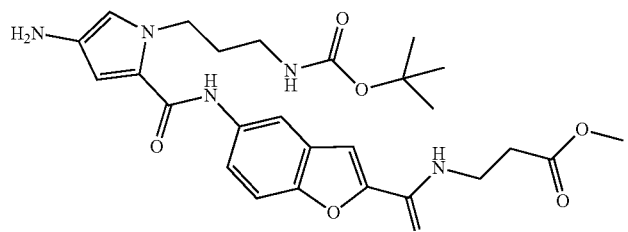

-continued
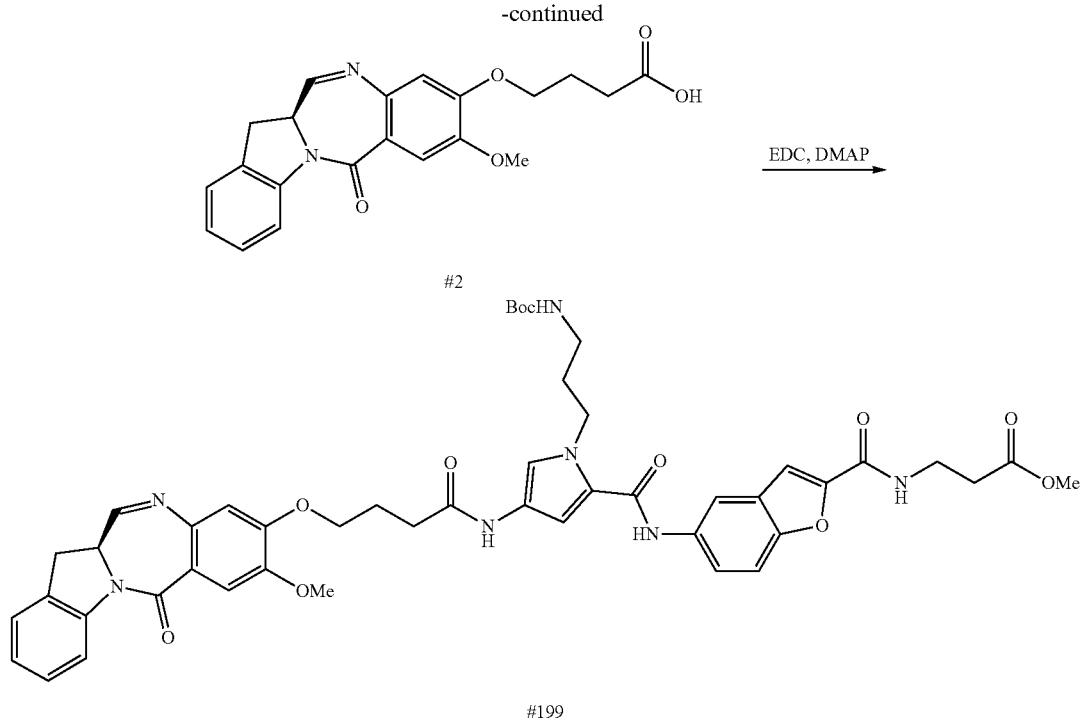
199
Compound #199 was prepared similarly as compound #7 from compound #198 to obtain compound #199 after purification by RPHPLC (C18 column, ACN/0.1% formic acid in H₂O) (5.1 mg, 3% yield). LCMS=5.23 min (8 min method). Mass observed (ESI⁺): 790.3 (M-Boc+H).
Synthesis of IGN THIQ Monomer
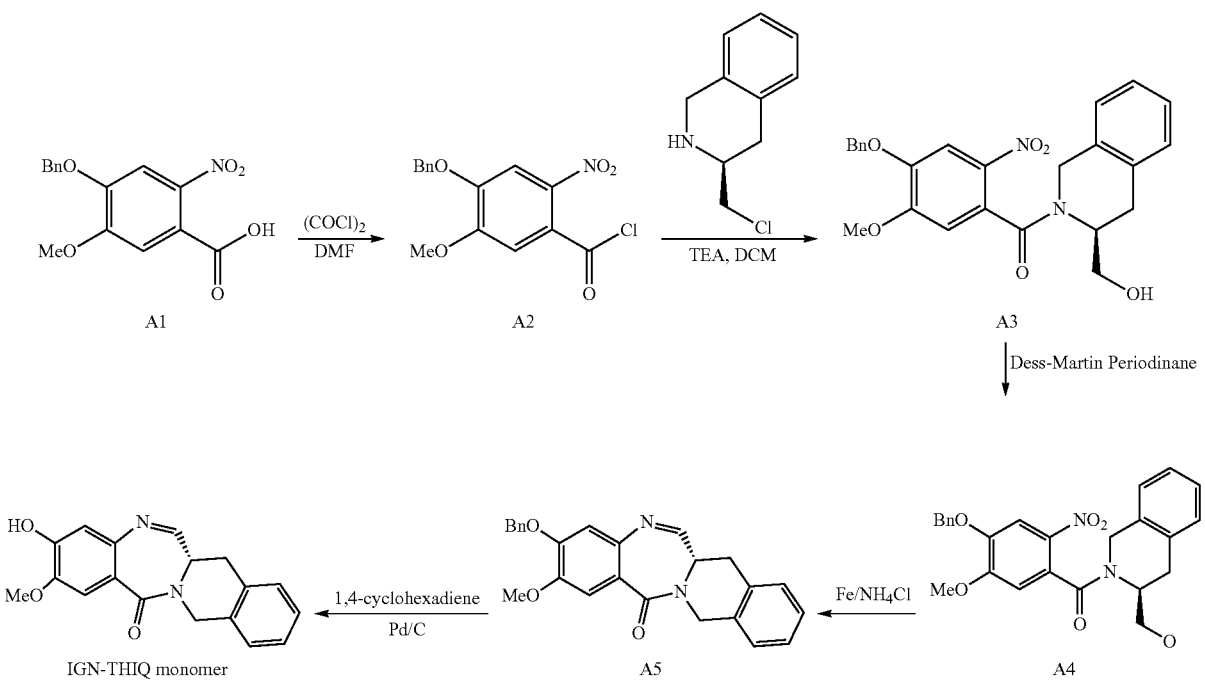

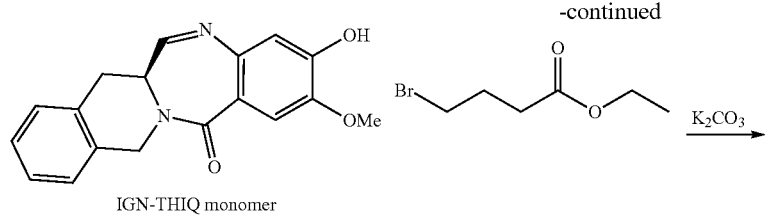

IGN-THIQ monomer

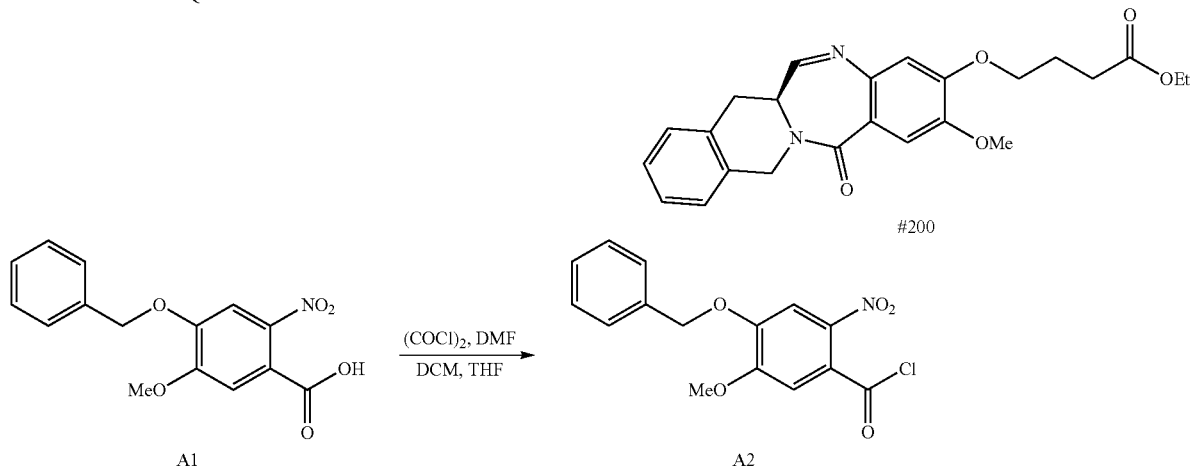

200

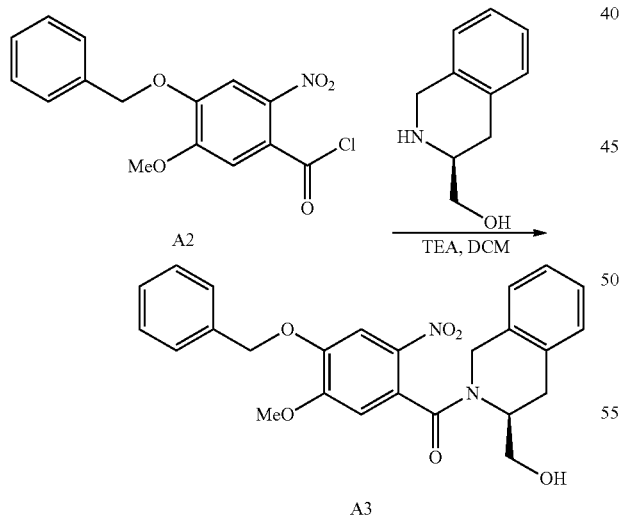

Step 1: Oxalyl chloride (3.61 mL, 41.2 mmol) was added dropwise to a stirred solution of compound A1 (5.0 g, 16.49 mmol) in DCM (42.8 mL), THF (4.28 mL) and DMF (0.020 mL, 0.264 mmol) at 0° C. under Ar. The reaction mixture was warmed to rt and was stirred for 3 h. The reaction mixture was concentrated and placed under high vacuum to obtain compound A2 as a pale yellow solid and was taken onto the next step without purification (5.3 g, 16.49 mmol, 100% yield)

Step 2: Compound A2 (5.3 g, 16.47 mmol) and (S)-(1,2,3,4-tetrahydroisoquinolin-3-yl)methanol (2.96 g, 18.12 mmol) were dissolved in DCM (47.1 mL). The reaction mixture was cooled to 0° C. and TEA (3.44 mL, 24.71 mmol) was added dropwise under Ar. The reaction mixture was then warmed to rt and was stirred overnight. The solution was concentrated and the crude product was purified by silica gel chromatography (EtOAc/hexanes, gradient, 0% to 80%) to obtain compound A3 (7.22 g, 16.10 mmol, 98% yield). LCMS=5.482 min (8 min method). Mass observed (ESI$^+$): 449.25 (M+H).

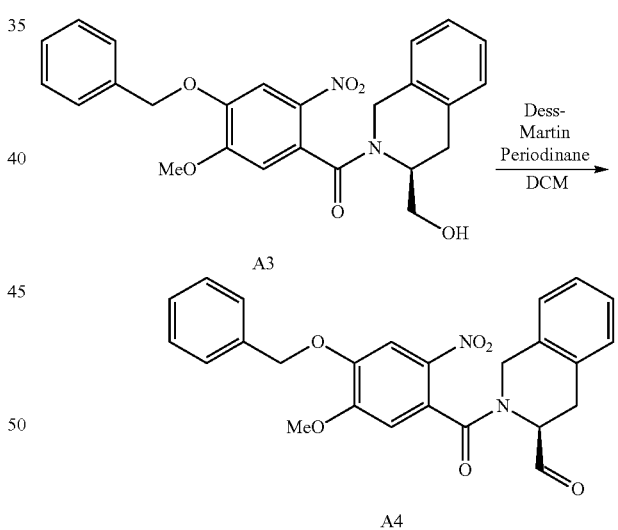

Step 3: Compound A3 (6.0 g, 13.38 mmol) was dissolved in DCM (53.5 mL). Dess-Martin Periodinane (6.24 g, 14.72 mmol) was added slowly, portion-wise at 0° C. The reaction was then warmed to rt and was stirred for 3 h under Ar. The reaction was quenched with sat'd aq. sodium thiosulfate solution (20 mL), followed by a slow addition of sat'd NaHCO$_3$ (20 mL) and H$_2$O (20 mL). The mixture was stirred vigorously for ~1 h. The layers were separated and the organic layer was washed with sat'd aq. sodium thiosulfate, sat'd NaHCO$_3$, brine, dried over Na$_2$SO$_4$, filtered and concentrated. The crude product was purified by silica gel chromatography (EtOAc/hexanes, 10% to 100%) to obtain compound A4 as pale yellow foam (5.45 g, 12.21 mmol, 91% yield). Mass observed (ESI⁺): 447.15 (M+H).

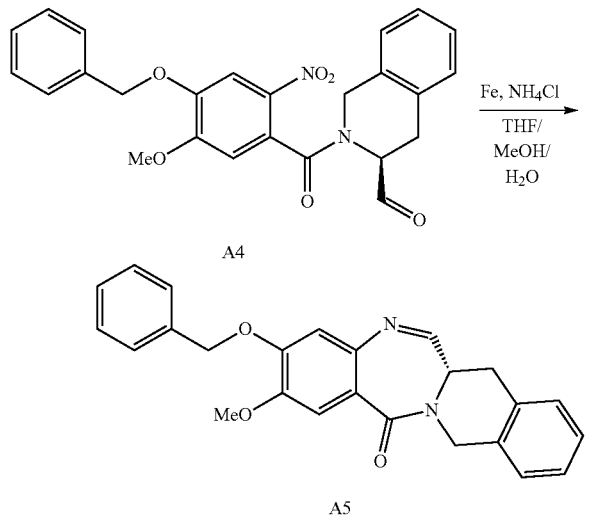

Step 4: Compound A4 (5.45 g, 12.21 mmol) was dissolved in THF (6.98 mL), methanol (34.9 mL) and water (6.98 mL) at rt. NH₄Cl (9.79 g, 183 mmol) was added, followed by iron powder (3.41 g, 61.0 mmol). The reaction was then heated reaction at 50° C. under Ar overnight. The reaction mixture was cooled to rt and was filtered through Celite. The cake was washed with DCM and the layers were separated. The organic layer was washed with brine, dried over Na₂SO₄, filtered and concentrated. The crude product was purified by silica gel chromatography (EtOAc/hexanes, 10% to 100%) to obtain compound A5 as a pale yellow foam (4.09 g, 10.26 mmol, 84% yield). ¹H NMR (400 MHz, CDCl₃): δ 7.55 (s, 1H), 7.46-7.43 (m, 3H), 7.39-7.34 (m, 3H), 7.33-7.29 (m, 4H), 6.85 (s, 1H), 5.20 (dd, 2H, J=12.3, 12.3 Hz), 5.00 (d, 1H, J=15.5 Hz), 4.56 (d, 1H, J=15.7 Hz), 3.97 (s, 3H), 3.88-4.00 (m, 1H), 3.26 (dd, 1H, J=15.4, 5.5 Hz), 3.14 (dd, 1H, J=15.3 4.2 Hz). LCMS=5.084 min (8 min method). Mass observed (ESI⁺): 399.15 (M+H).

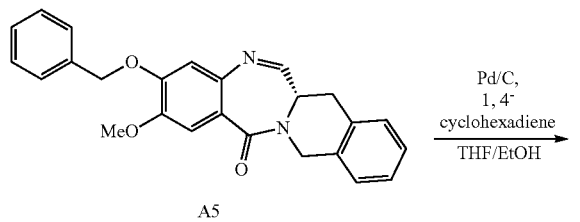

Step 5: Compound A5 (4.09 g, 9.75 mmol) was dissolved in EtOH (48.8 mL) and THF (16.25 mL). The solution was degassed with Ar for 5 min. Pd/C (10%) (2.075 g, 1.950 mmol) was added slowly and the solution was degassed for 5 min. Cyclohexa-1,4-diene (7.38 mL, 78 mmol) was added and the reaction was stirred at rt with continuous bubbling of Ar overnight. The reaction mixture was filtered through Celite and was washed with MeOH/DCM (1:1, 50 mL), followed by MeOH (30 mL) and was concentrated. The crude product was purified by silica gel chromatography (EtOAc/hexanes, 0% 100%) to obtain THIQ-benzodiazepine monomer 6 (1.53 g, 4.27 mmol, 44% yield). LCMS=3.504 min (8 min method). Mass observed (ESI⁺): 309.15 (M+H), 327.15 (M+H₂O).

Compound #200 was prepared similarly as compound #1 to give compound #200, which was used without purification (100% yield). LCMS=4.74 min (8 min method). Mass observed (ESI⁺): 423.0 (M+H).

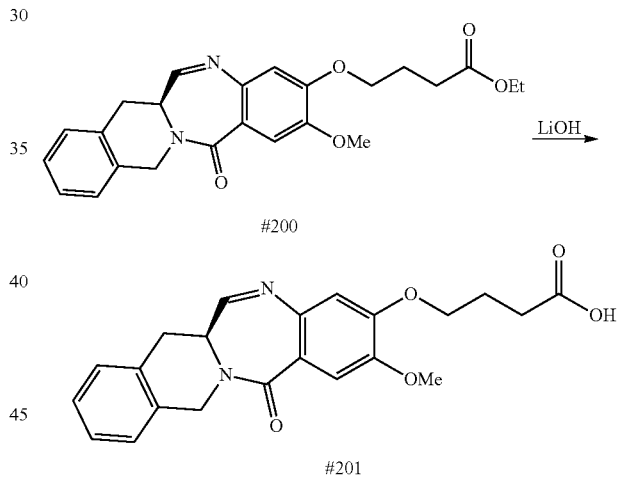

Compound #201 was prepare similarly as compound using compound 200 to obtain compound #201 after purification by silica gel chromatography (DCM/MeOH) (599 mg, 53% yield). LCMS=3.93 min (8 min method). Mass observed (ESI⁺): 395.0 (M+H).

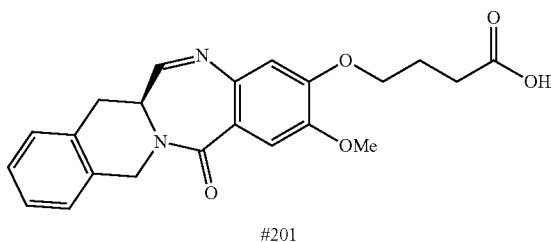

-continued

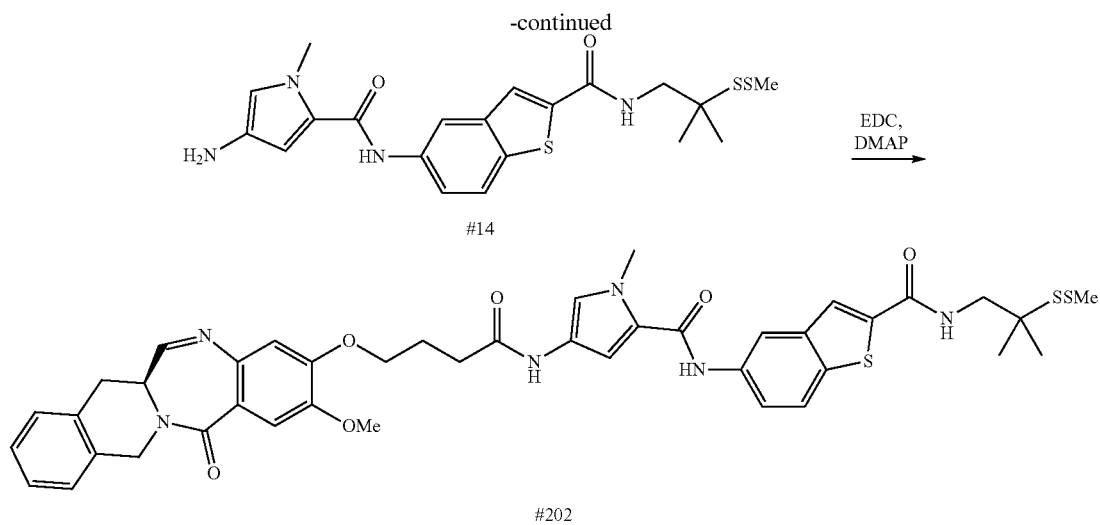

14

202

Compound #201 (0.040 g, 0.101 mmol) and compound #14 (0.048 g, 0.106 mmol) were dissolved in DMF (1.0 mL). EDC HCl (0.058 g, 0.304 mmol) and DMAP (0.0124 g, 0.101 mmol) were added. The reaction mixture was allowed to stir at rt under Ar for 1 h. After stirring for 1 h, the reaction mixture was quenched with sat'd NH$_4$Cl (5 mL) and the resulting mixture was extracted with EtOAc (3×20 mL). The combined organics were washed with brine (10 mL), dried over Na$_2$SO$_4$, filtered, and concentrated. The crude residue was purified by RPHPLC (C18 column, CH$_3$CN/H$_2$O, gradient, 50% to 85%) to obtain compound #202 (0.026 g, 0.032 mmol, 31% yield). UPLCMS (2.5 min method)=1.82 min. Mass observed (ESI$^+$): 825.8 (M+H).

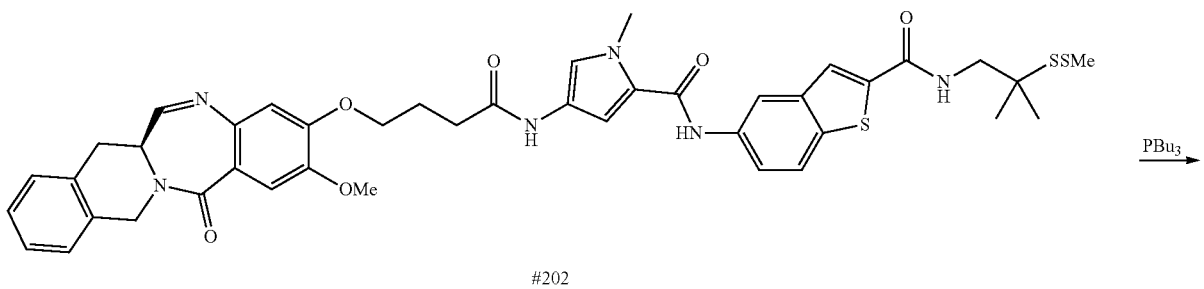

202

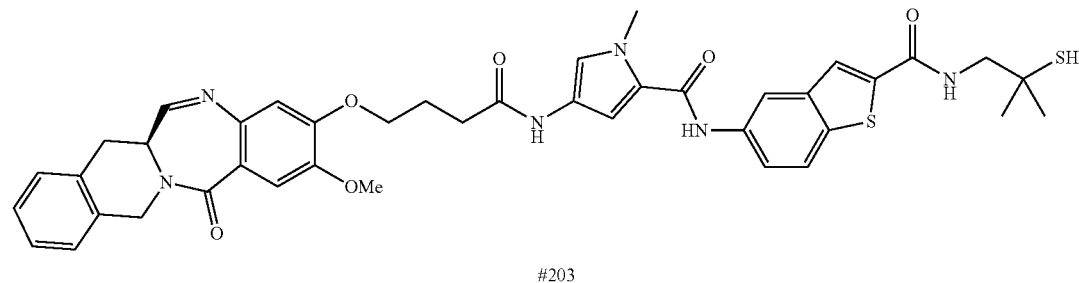

203

Compound #202 (0.026 g, 0.032 mmol) was dissolved in THF (1.50 mL) and DI water (0.075 mL). Tributylphosphine (0.0087 mL, 0.035 mmol) was added and the reaction mixture was allowed to stir at rt under Ar for 3.5 h. After stirring 3.5 h, the reaction mixture was concentrated and placed on high vacuum to dryness to give crude #203, which was used directly in the next step (0.0246 g, 0.032 mmol, 100% yield). UPLCMS (2.5 min method)=1.71 min. Mass observed (ESI$^+$): 779.8 (M+H).

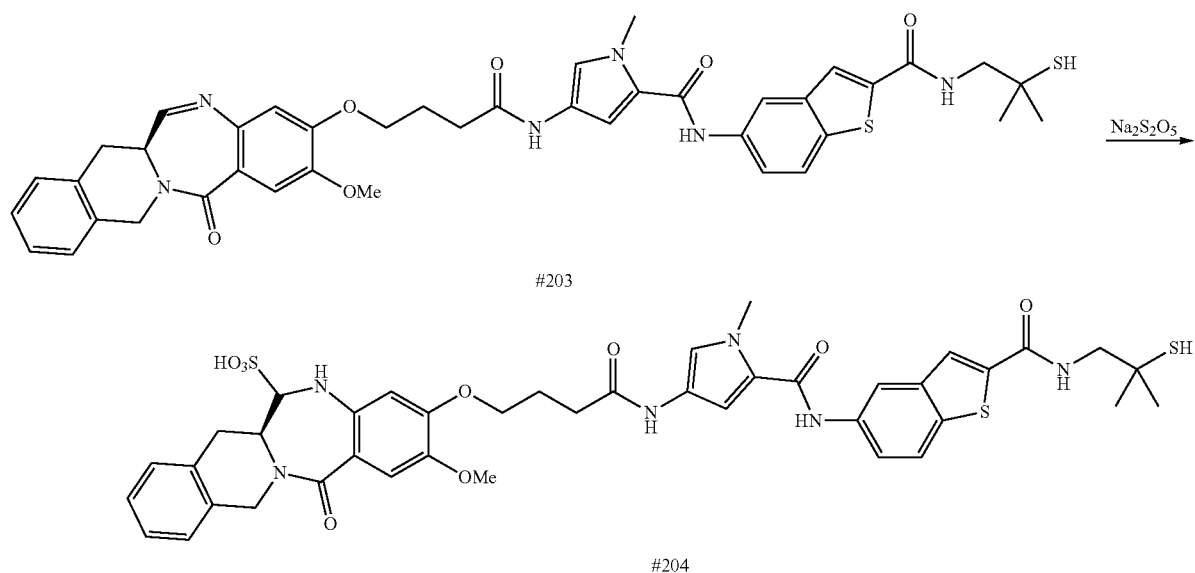

Compound #203 (0.025 g, 0.032 mmol) was suspended in IPA (0.853 mL) and water (0.427 mL). Sodium metabisulfite (0.036 g, 0.192 mmol) was added. The reaction mixture was allowed to stir at rt under Ar for 3 h. After stirring for 3 h, the reaction mixture was diluted with ACN (20 mL) and DI water (20 mL), then frozen and lyophilized. The fluffy white solid was purified by RPHPLC (C18 column, ACN/H$_2$O, gradient, 30% to 50%) to obtain #204 (6.1 mg, 0.007 mmol, 22% yield). LCMS (8.0 min method)=5.511 min. Mass observed (ESI$^-$): 859.8 (M−H).

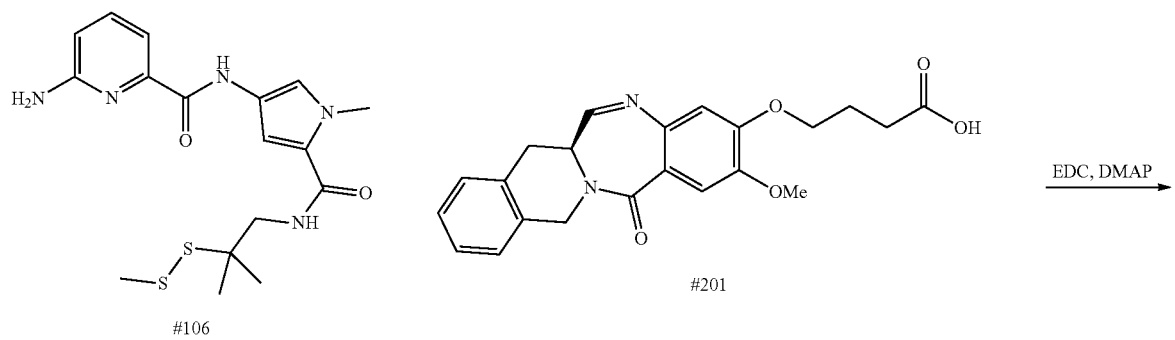

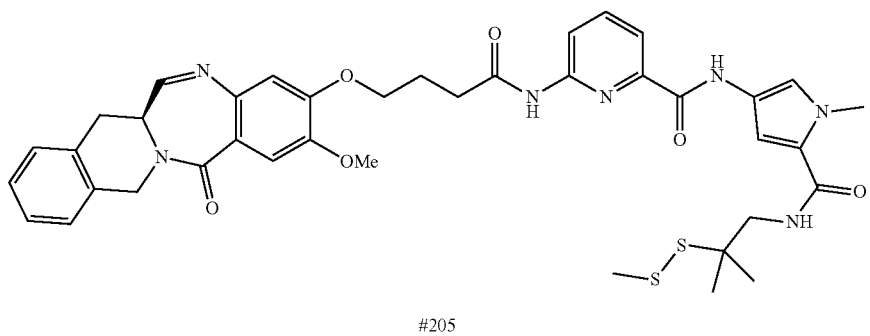

Compound #106 (39.9 mg, 0.101 mmol) and compound #201 (40 mg, 0.101 mmol) were dissolved in DCM (1.01 mL). EDC (58.3 mg, 0.304 mmol) and DMAP (14.87 mg, 0.122 mmol) were added and the reaction was stirred for 2 h. The reaction mixture was diluted with DCM and water and the layers were separated. The aq layer was extracted with DCM (1x) and the combined organics were dried over MgSO$_4$, filtered and concentrated. The crude product was purified by RPHPLC (C18 column, ACN/water) to give compound #205 (3.4 mg, 4.4% yield). LCMS=5.61 min (8 min method). Mass observed (ESI$^+$): 770.0 (M+H).

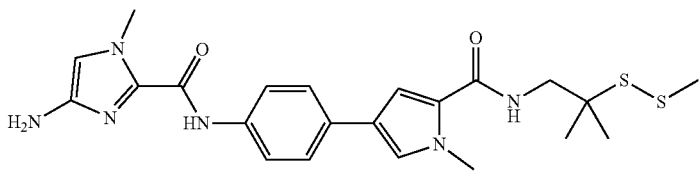

124

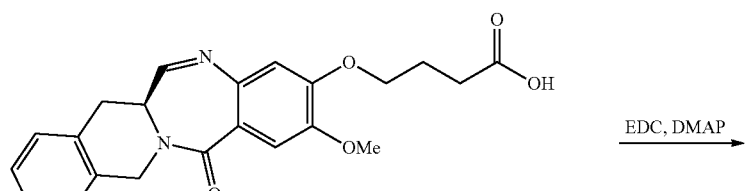

201

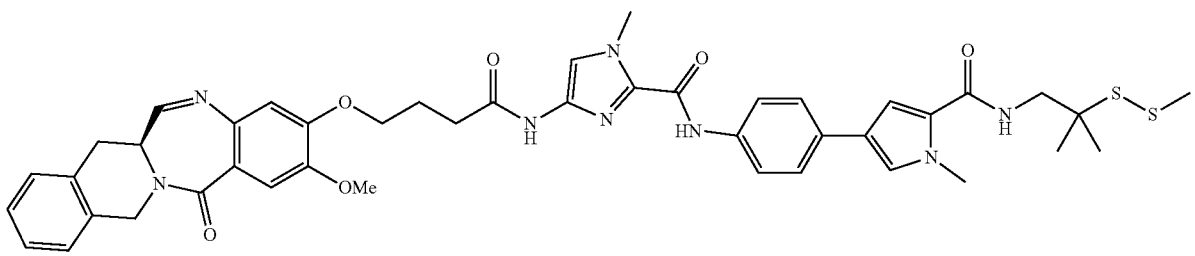

206

Compound #124 (61.0 mg, 0.155 mmol) and compound #201 (95 mg, 0.201 mmol) were dissolved in DCM (1.55 mL). EDC (59 mg, 0.309 mmol) and DMAP (13.2 mg, 0.108 mmol) were added and the reaction mixture stirred at rt for 2 h. The reaction mixture was diluted with DCM, washed with water, dried over MgSO$_4$, filtered and concentrated. The crude product was purified by RPHPLC (C18 column, ACN/water with 0.1% formic acid) to give compound #206 (38.5 mg, 29% yield). LCMS=5.96 min (8 min method). Mass observed (ESI$^+$): 849.0 (M+H).

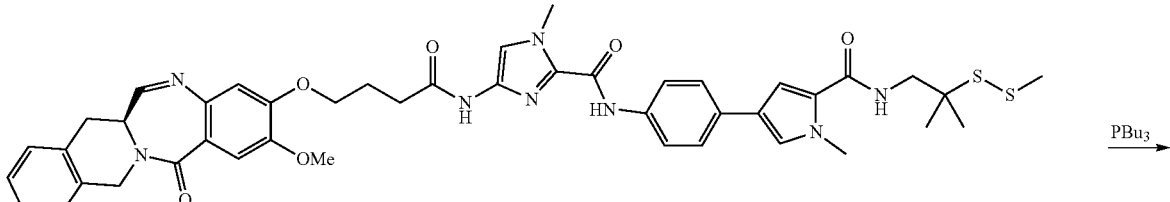

206

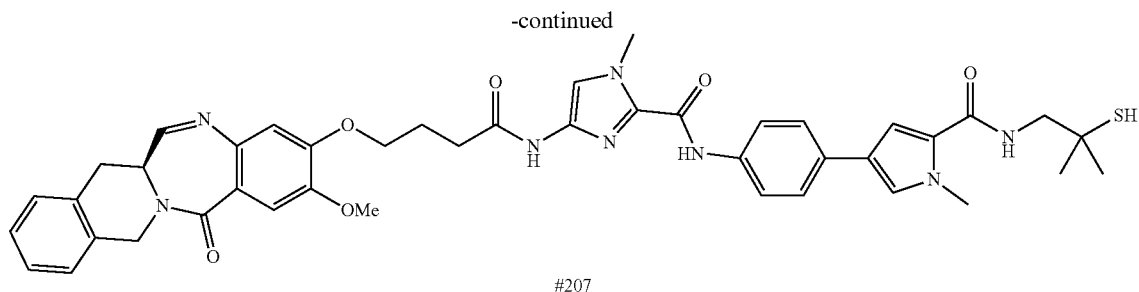

207

Compound #206 (38.5 mg, 0.045 mmol) was dissolved in THF (2.16 mL) and water (108 μL) under Ar. Tributylphosphine (12.46 μL, 0.050 mmol) was added and the reaction was stirred at rt for 2 h. The reaction mixture was concentrated to obtain compound #207 (36 mg, 100% yield). LCMS=5.48 min and 6.09 min (8 min method). Mass observed (ESI⁺): 803.0 (M+H) for both retention times.

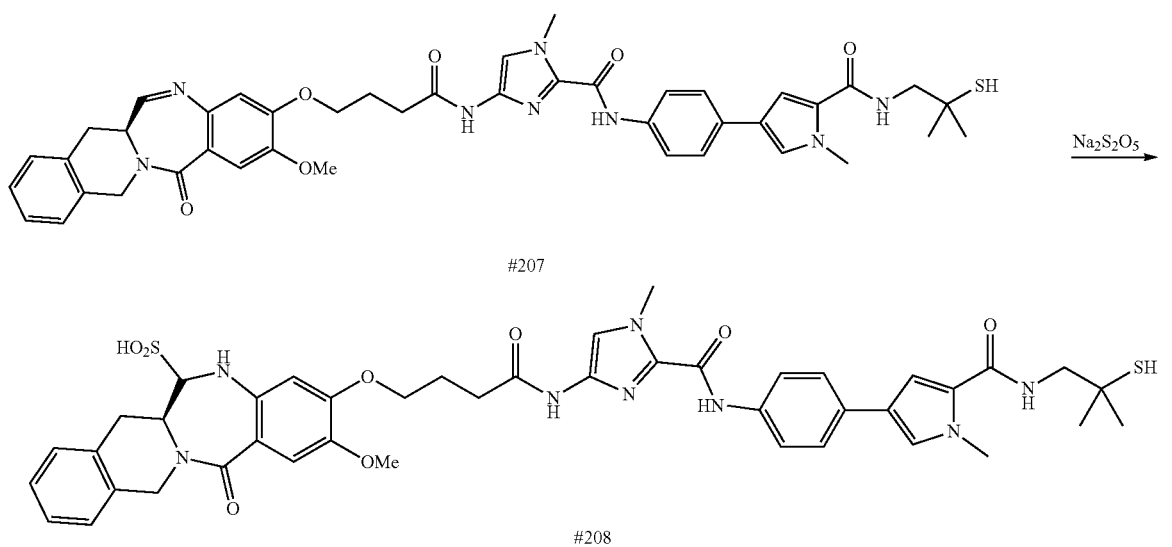

207

208

Compound #207 (36.1 mg, 0.045 mmol) was suspended in IPA (600 μL) and water (300 μL) and Na₂S₂O₅ (34.2 mg, 0.180 mmol) was added. The mixture was stirred at rt for 3 h and was then diluted with ACN/H₂O, frozen and lyophilized. The crude product was purified by RPHPLC (C18 column, ACN/water) to give compound #208 (22.5 mg, 56% yield). LCMS=4.79 min (8 min method). Mass observed (ESI⁻): 883.0 (M−H).

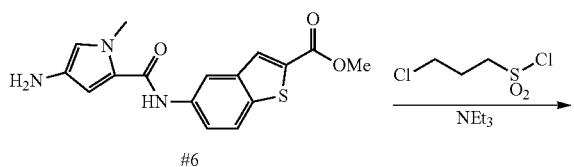

6

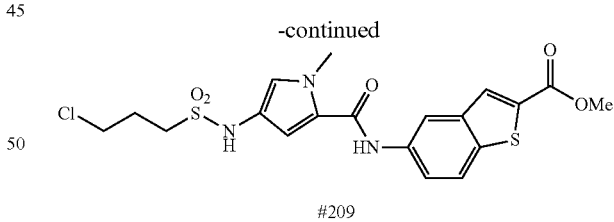

209

Compound #06 (150 mg, 0.566 mmol) and 3-chloropropone-1-sulfonyl chloride (0.086 mL, 0.683 mmol) was dissolved in DMF (3.0 mL). Triethylamine (0.063 mL, 0.455 mmol) was added and the reaction stirred at room temperature for 16 h. The crude reaction was diluted with EtOAc/MeOH and the organic layer washed with 1 N HCl, Sat. NaHCO₃ and brine, dried over MgSO₄, filtered and concentrated. The crude product was purified by silica gel chromatography (Hexane/Ethyl Acetate) to give compound #209 (48 mg, 22% yield). UPLCMS=1.60 min (2.5 min method). Mass observed (ESI⁺): 470.0, 471.9 (M+H).

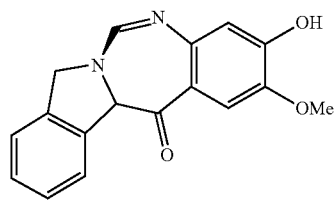 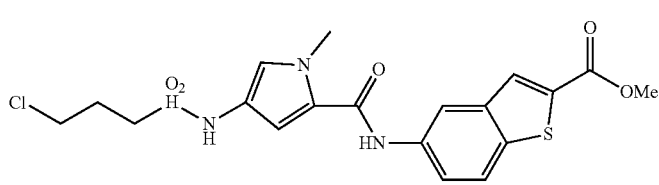

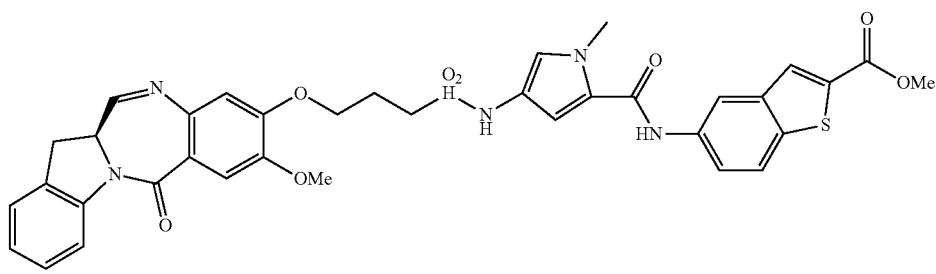

IGN Monomer (30 mg, 0.064 mmol) was dissolved in THF (0.3 mL) and sodium hydride (3.8 mg, 0.095 mmol) was added to form a suspension. Compound #209 (30 mg, 0.064 mmol) in DMF (0.3 mL) was added and stirred for 16 h. The solution was purified by silica gel chromatography (DCM/MeOH) followed by purification by RPHPLC (C18 column, ACN/water) to give compound #210 (1.3 mg, 3%). UPLCMS=1.68 min (2.5 min method). Mass observed (ESI⁺): 728.5 (M+H).

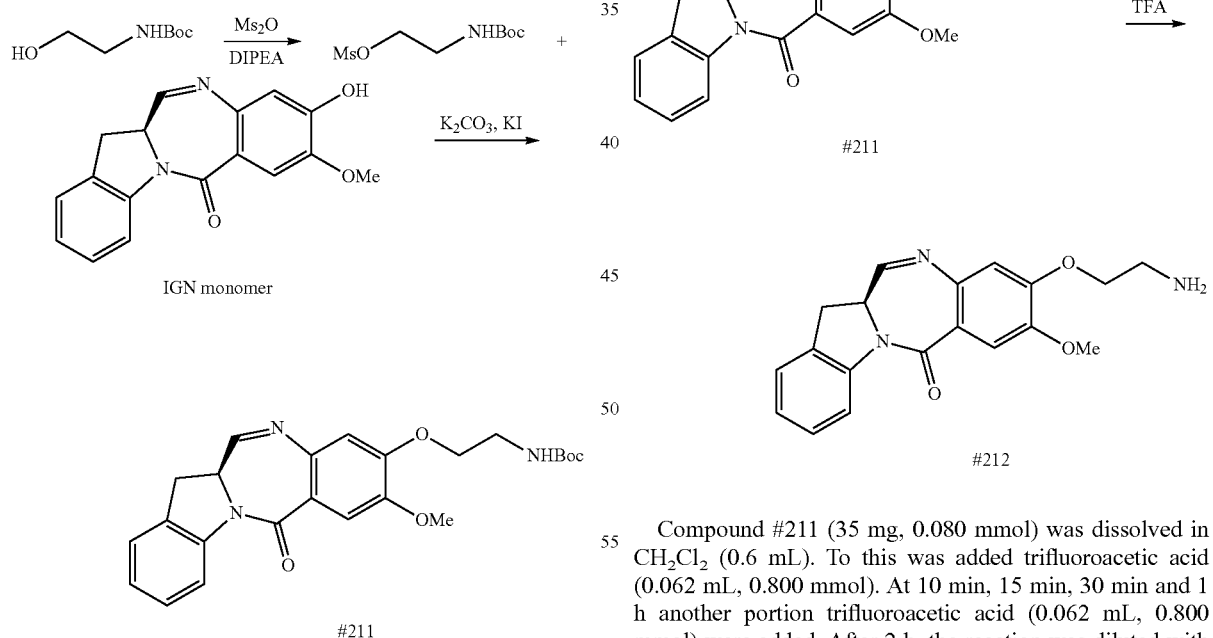

N-Boc-ethanolamine (0.096 mL, 0.620 mmol) and methanesulfonic anhydride (141, 0.809 mmol) were dissolved in CH₂Cl₂. DIPEA (0.271 mL, 1.551 mmol) was added. After 30 minutes, the reaction was diluted with EtOAc washed with water and brine, dried with MgSO₄, filtered and concentrated. The mesylate, IGN Monomer (194 mg, 0.659 mmol), potassium carbonate (171 mg, 1.237 mmol) and potassium iodide (38 mg, 0.229 mmol) were stirred in DMF (6.0 mL) at 40° C. After 16 h, the reaction was purified directly by silica gel chromatography using DCM:MeOH to give compound #211 (35 mg, 13%) and was used as is. UPLCMS=1.44 min (2.5 min method). Mass observed (ESI⁺): 456.2 (M+H₂O+H).

Compound #211 (35 mg, 0.080 mmol) was dissolved in CH₂Cl₂ (0.6 mL). To this was added trifluoroacetic acid (0.062 mL, 0.800 mmol). At 10 min, 15 min, 30 min and 1 h another portion trifluoroacetic acid (0.062 mL, 0.800 mmol) were added. After 2 h, the reaction was diluted with CH₂Cl₂ and extracted with water. The aqueous layer was adjusted to pH 11 and the aqueous layer was extracted with EtOAc/MeOH, followed by saturation with NaCl and extraction with EtOAc/MeOH. The combined organic were dried and concentrated under reduced pressure to give compound #212 (4 mg, 15%) and was used as is. UPLCMS=1.09 min (2.5 min method). Mass observed (ESI⁺): 338.2 (M+H), 356.4 (M+H₂O+H).

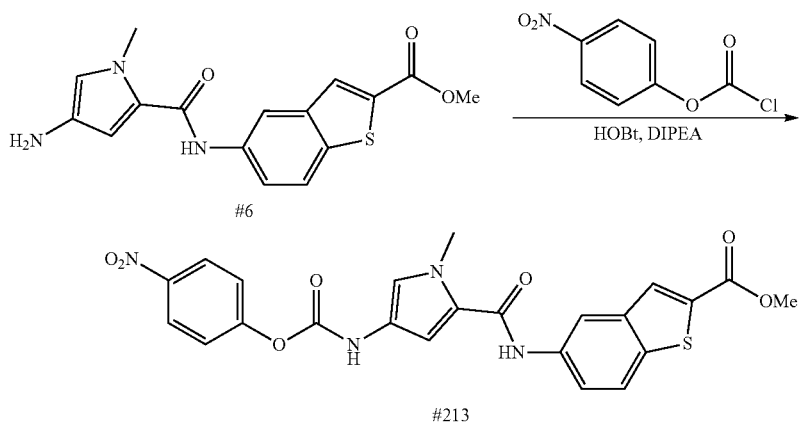

Compound #06 (150 mg, 0.566 mmol), 4-nitro-phenol chloroformate (127 mg, 0.630 mmol), HOBt (17 mg, 0.11 mmol) was dissolved in $CH_2Cl_2$ (4 mL). DIPEA (0.10 mL, 0.57 mmol) was added and the reaction was stirred for 20 h. The reaction was diluted with $CH_2C12$ washed 3× with Sat. $NaHCO_3$, water and brine, dried with $MgSO_4$, filtered and concentrated. Compound #213 (170 mg, 83%) was used as is. UPLCMS=1.70 min (2.5 min method). Mass observed (ESI$^+$): 495.1 (M+H).

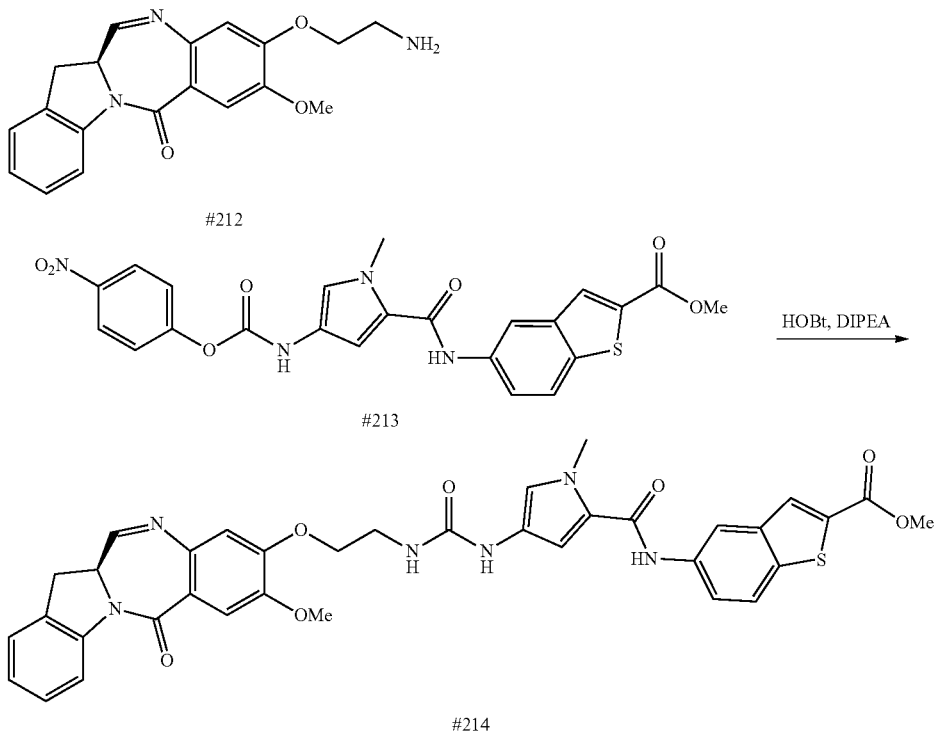

Compound #212 (4 mg, 0.012 mmol), Compound #213 (7.6 mg, 0.015 mmol) and HOBt (3.2 mg, 0.021 mmol) was dissolved in DMF (0.1 mL). DIPEA (0.021 mL, 0.119 mmol) was added and the reaction stirred 16 h. Product was purified directly by RPHPLC (C18 column, ACN/water) to give compound #214 (1.9 mg, 23%). UPLCMS=1.53 min (2.5 min method). Mass observed (ESI$^+$): 693.4 (M+H), 711.3 (M+H+$H_2O$).

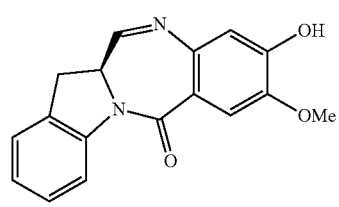

IGN monomer

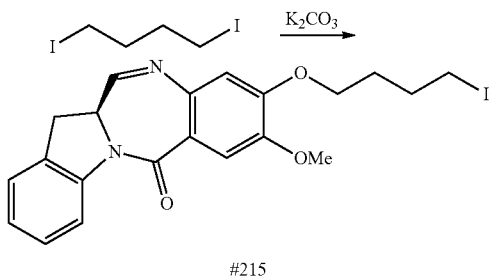

215

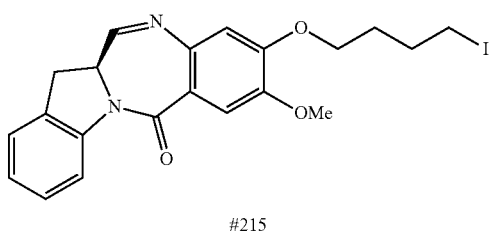

215

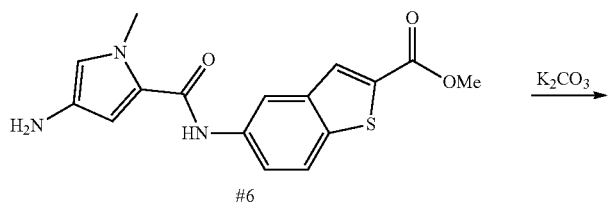

6

To a suspension of IGN Monomer (0.5 g, 1.699 mmol) and K$_2$CO$_3$ (0.760 g, 5.5 mmol) in DMF (10 mL) was added 1,4 diiodobutane (1.0 mL, 7.58 mmol). After 16 h, the reaction was diluted with EtOAc and washed with water, dried with MgSO$_4$, filtered and concentrated. Produc was purified by silica gel chromatography using DCM/MeOH to give compound #215 (0.542 g, 67%). UPLCMS=1.61 min (2.5 min method). Mass observed (ESI$^+$): 477.0 (M+H), 495.1 (M+H+H$_2$O). $^1$H NMR (400 MHz, Chloroform-d) δ 1.84-2.05 (m, 4H), 3.20 (t, J=6.6 Hz, 2H), 3.42 (dd, J=16.7, 4.0 Hz, 1H), 3.63 (dd, J=16.7, 10.9 Hz, 1H), 3.87 (s, 3H), 3.95-4.09 (m, 2H), 4.40 (dt, J=10.9, 4.2 Hz, 1H), 6.73 (s, 1H), 7.03 (td, J=7.5, 1.1 Hz, 1H), 7.13-7.27 (m, 2H), 7.47 (s, 1H), 7.79 (d, J=4.5 Hz, 1H), 8.18 (d, J=8.1 Hz, 1H). $^{13}$C NMR (101 MHz, Chloroform-d) δ 6.2, 29.9, 30.1, 32.6, 55.0, 56.2, 67.9, 110.5, 111.9, 116.9, 120.5, 124.8, 124.8, 128.2, 129.5, 140.1, 142.0, 148.2, 151.2, 163.1, 163.9.

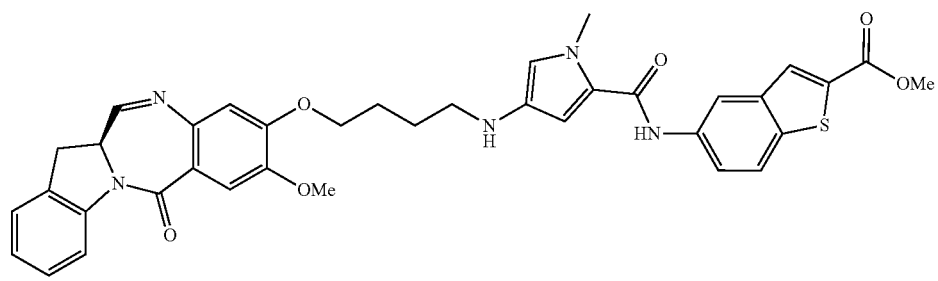

216

Compound #06 was dissolved in CH$_2$Cl$_2$ washed with 1 N NaOH dried with MgSO$_4$, filtered and concentrated before use. Compound #06 (31.9, 0.097 mmol) and Compound #215 (31 mg, 0.065 mmol) were stirred with K$_2$CO$_3$ in DMF (0.6 mL). After 3 h, the reaction was purified directly by RPHPLC (C18 column, ACN/water) to give compound #216 (2.2 mg, 5%). UPLCMS=1.46 min (2.5 min method). Mass observed (ESI$^+$): 678.5 (M+H), 696.5 (M+H+H$_2$O).

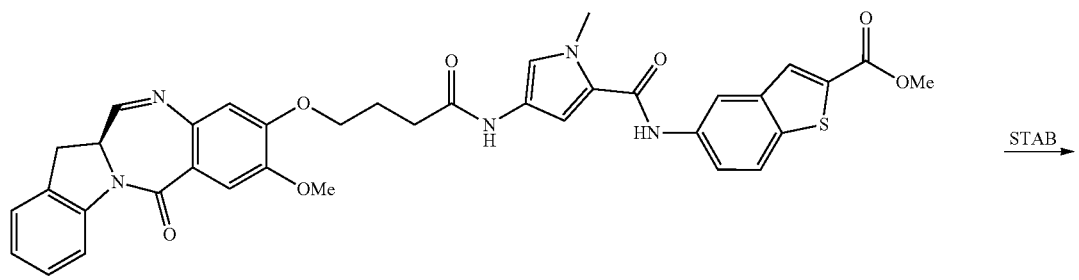

7

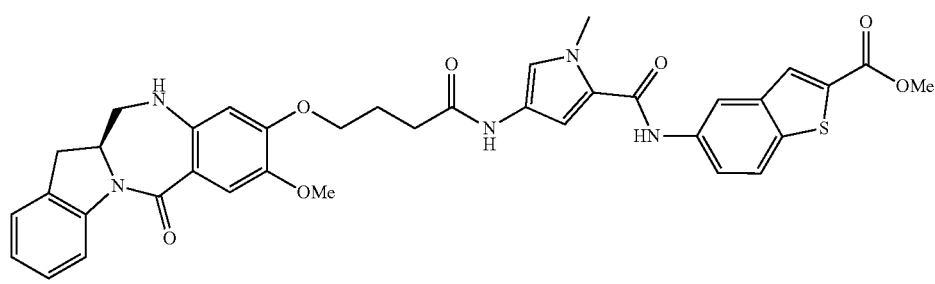

217

Compound #07 (10 mg, 0.014 mmol) was dissolved in DCE (1 mL). STAB (6.13 mg, 0.029 mmol) was added and the reaction stirred for 2 h. The reaction was purified directly by silica gel chromatography to give compound #217 (1.8 mg, 18%). UPLCMS=1.67 min (2.5 min method). Mass observed (ESI+): 694.4 (M+H).

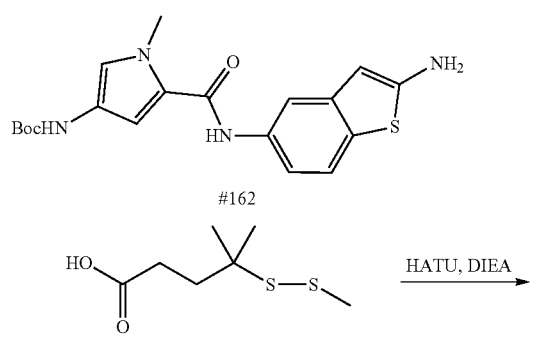

-continued

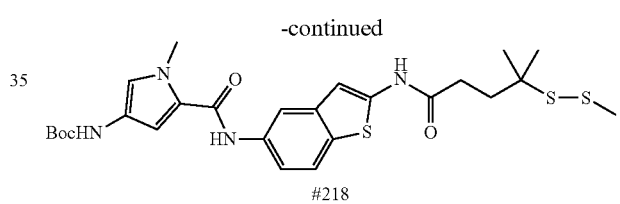

218

Compound #162 (403 mg, 1.043 mmol), 4-methyl-4-(methyldisulfanyl)pentanoic acid (0.304 mg, 1.565 mmol) and HATU (610 mg, 1.604 mmol) were dissolved in DMF (10 mL). DIEA (0.4 mL, 2.290 mmol) was added and stirred for 2 h. The reaction mixture was diluted with EtOAc and was washed with 1N HCl, Sat. NaHCO₃ and brine, dried with MgSO₄, filtered and concentrated. The crude residue was purified via silica gel chromatography (DCM/MeOH) to give #218 (344 mg, 59% yield). UPLCMS (2.5 min method) =1.82 min. Mass observed (ESI+): 563.4 (M+H). $^1$H NMR (400 MHz, Chloroform-d) δ 1.28 (s, 6H), 1.52 (s, 9H), 2.08-1.89 (m, 2H), 2.40 (s, 3H), 2.52-2.43 (m, 2H), 3.89 (s, 3H), 6.45 (s, 1H), 6.62 (s, 1H), 6.66 (s, 1H), 6.87 (s, 1H), 7.14 (dd, J=8.4, 2.2 Hz, 1H), 7.58 (d, J=8.4 Hz, 1H), 7.82 (s, 1H), 7.73 (s, 1H), 8.97 (s, 1H).

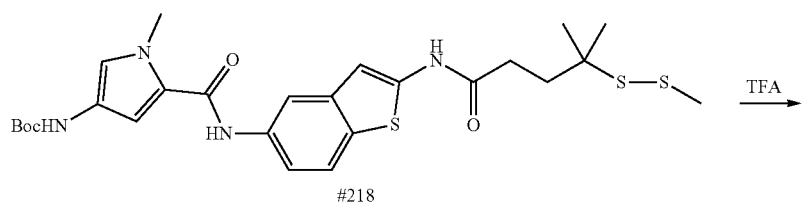

218

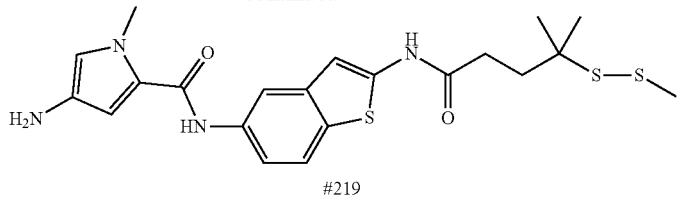

219

Compound #218 (344, 0.611 mmol) and TFA (0.5 mL, 6.49 mmmol) in CH₂Cl₂ (5 mL) was stirred for 6 h. The reaction was concentrated under reduced pressure, dissolved in toluene and concentrated again three times and dried under reduced pressure to give Compound #219 as the TFA salt (315 mg, 89% yield). UPLCMS (2.5 min method)=1.44 min. Mass observed (ESI⁺): 463.6 (M+H).

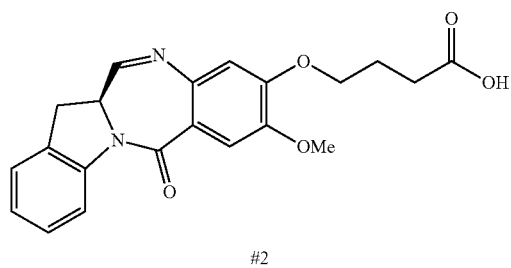

2

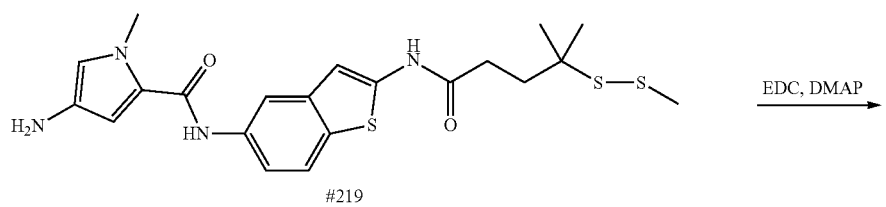

219

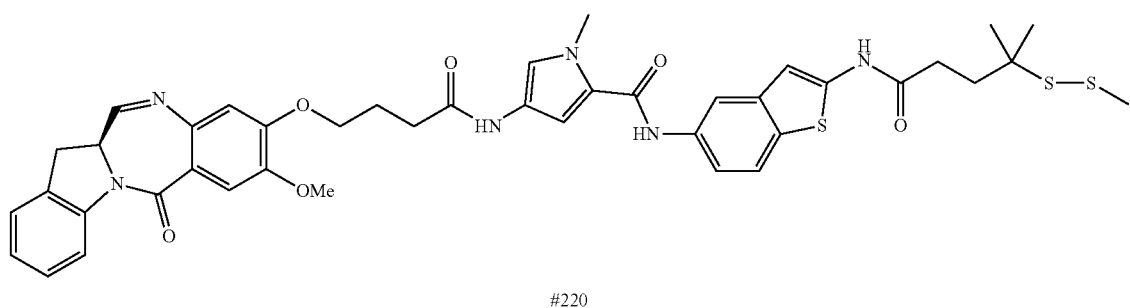

220

Compound #219 (94 mg, 0.163 mmol), compound #2 (49.4 mg, 0.130 mmol) and EDC (43.4 mg, 0.226 mmol) was dissolved in DMF (1.3 ml). DMAP (27 mg, 0.221 mmol) was added and the reaction stirred for 3 h. The crude solution was diluted with water and triturated for 5 min, the solid filtered and washed with water. The solid was redissolved in DCM/MeOH and dried with MgSO₄, filtered and concentrated under reduced pressure. Product was purified by silica gel chromatography (DCM/MeOH) followed by RPHPLC (C18 column, ACN/water) to give compound #220 (14 mg, 14%). UPLCMS (2.5 min method)=1.72 min. Mass observed (ESI⁺): 825.5 (M+H), 843.8 (M+H+H₂O).

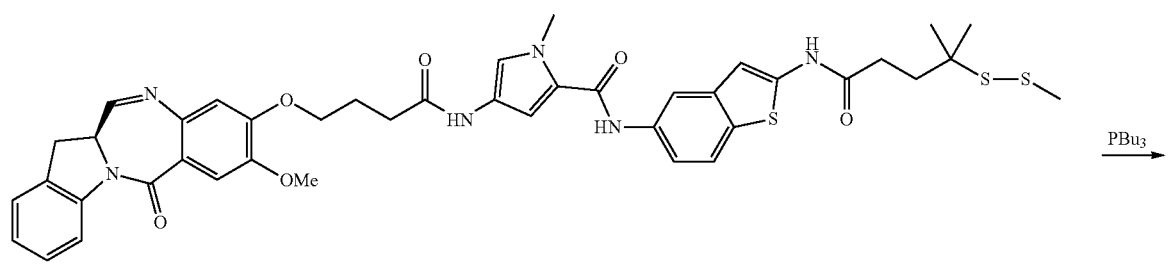

220

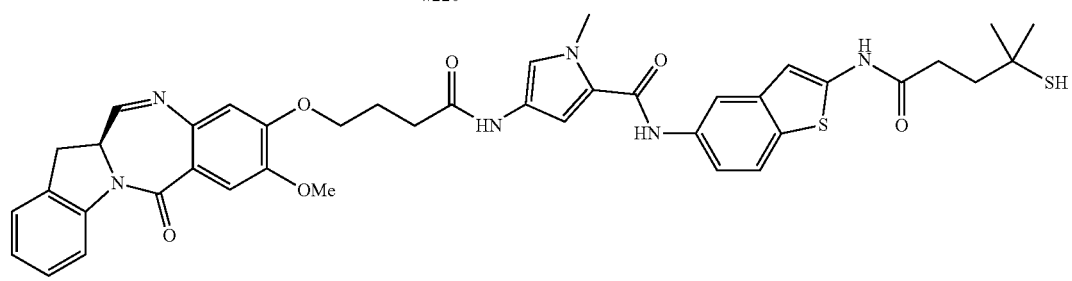

221

Compound #220 (14 mg, 0.017 mmol) was dissolved in THF (0.17 mL) and water (0.01 mL). Tributylphosphine (4.6 µL, 0.019 mmoL was added and the reaction was stirred for 1.5 h and the reaction concentrated under reduced pressure to give crude compound #221 (13 mg, 100%), which was used as is.

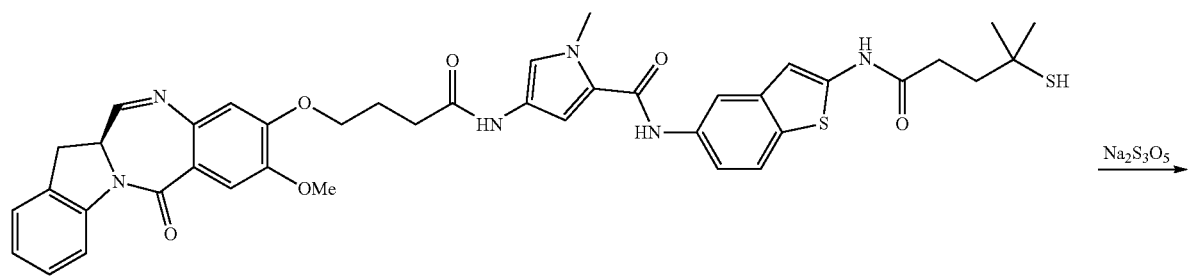

221

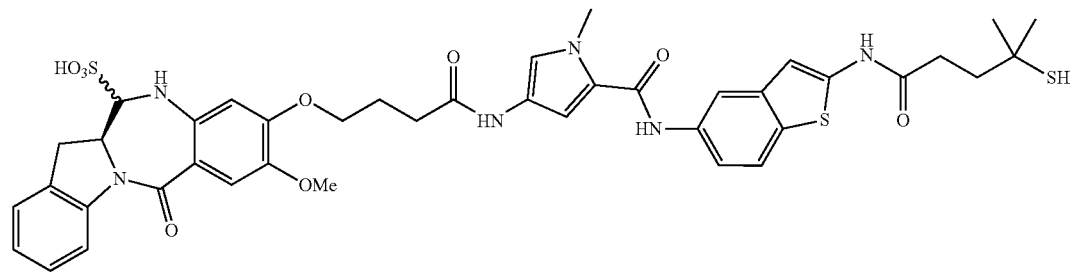

222

Compound #221 (13 mg, 0.017 mmol) was suspended in IPA (0.4 mL) and water (0.2 mL) and $Na_2S_2O_5$ (14.2 mg, 0.075 mmol) was added. The mixture was stirred overnight and $Na_2S_2O_5$ (14.2 mg, 0.075 mmol) was added and stirred 4 hours. The reaction was diluted with ACN/$H_2O$ and lyophilized. The crude product was purified RPHPLC (C18 column, ACN/water) to give compound #222 (3 mg, 20%). LCMS=5.11 min (8 min method). Mass observed (ESI-): 858.9 (M-H).

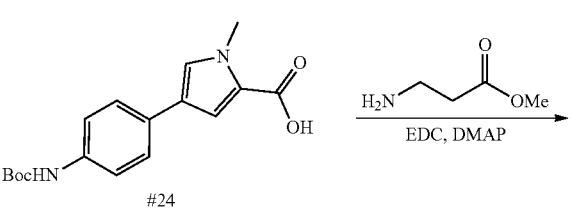

24

329
-continued
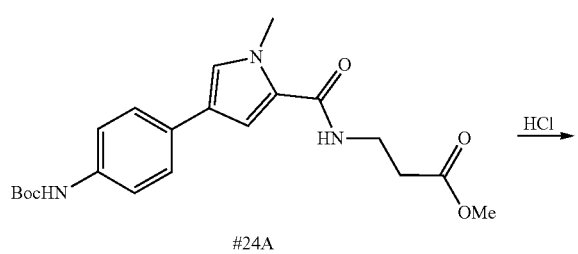
24A
330
-continued
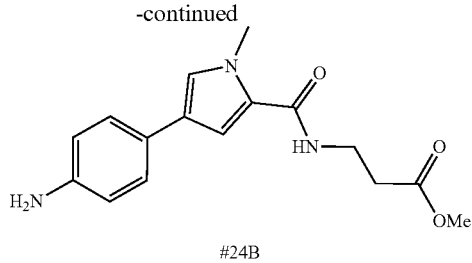
24B
Compounds #24A and #24B were synthesized similar as compounds #5B and #8.
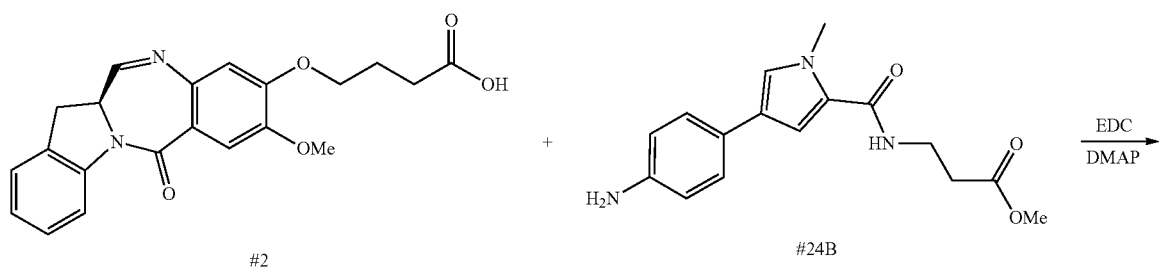
Compound #223 was synthesized similar as compound #9.
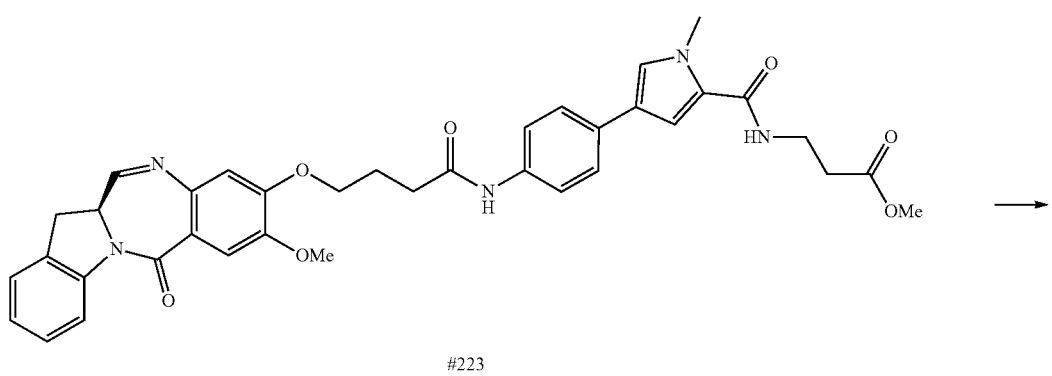

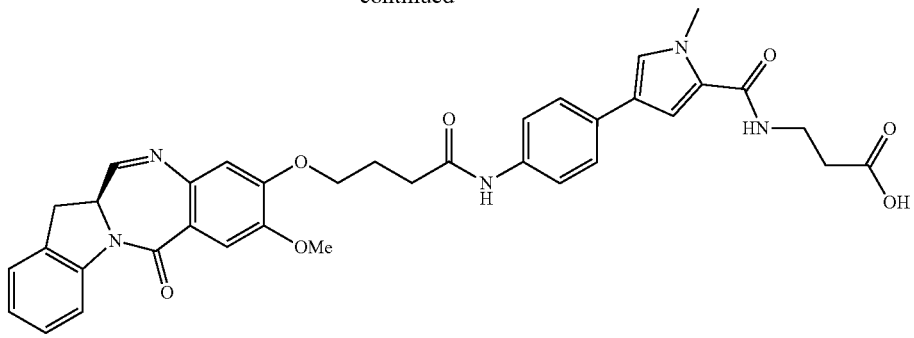

224

Compound #224 was synthesized similar as compound #10.

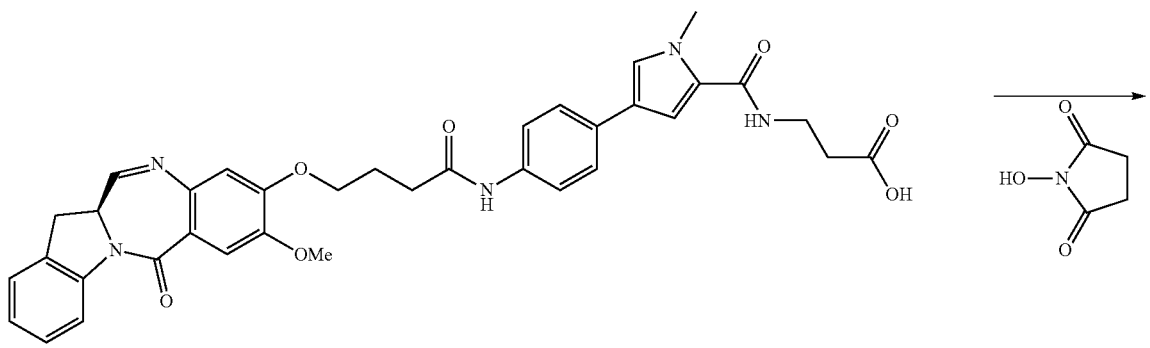

224

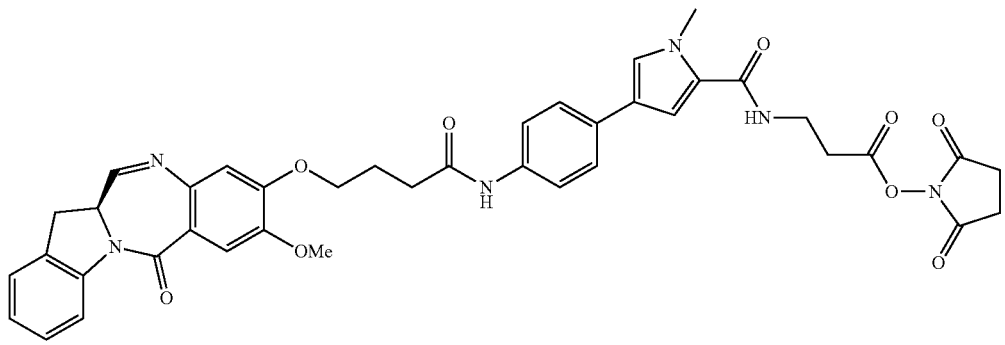

225

Compound #225 was synthesized similar as compound #11.

Example 2. Synthesis of the Conjugates of the Invention huMov19-Sulfo-SPDB-17

Prior to conjugation, sulfo-SPDB-17 was prepared by mixing a stock solution of sulfo-SPDB in N,N-dimethylacetamide (DMA) with a stock solution of compound 17 in DMA in the presence of diisopropylethylamine (DIEA) such that the final composition was 1.5 mM sulfo-SPDB, 1.95 mM compound 17, and 10 mM DIEA. The reaction was allowed to proceed for 4.5 hr. at 25° C. The crude sulfo-SPDB-17 was then added to a solution containing huMov19 antibody and buffered with 15 mM 2-[4-(hydroxyethyl)piperzin-1-yl]ethanesulfonic acid (HEPES), pH 8.5 with 15% (v/v) DMA to a final ratio of 9.6 mol sulfo-SPDB-16 to 1 mol antibody. The conjugation reaction was allowed to proceed overnight at 25° C. The conjugate was purified into 20 mM histidine, 50 mM sodium chloride, 8.5% sucrose, 0.01% Tween-20, 50 μM sodium bisulfite, pH 6.2 using Sephadex G-25 columns and then dialyzed against this same buffer using a membrane with 10 kDa molecular weight cutoff.

Figure 4:
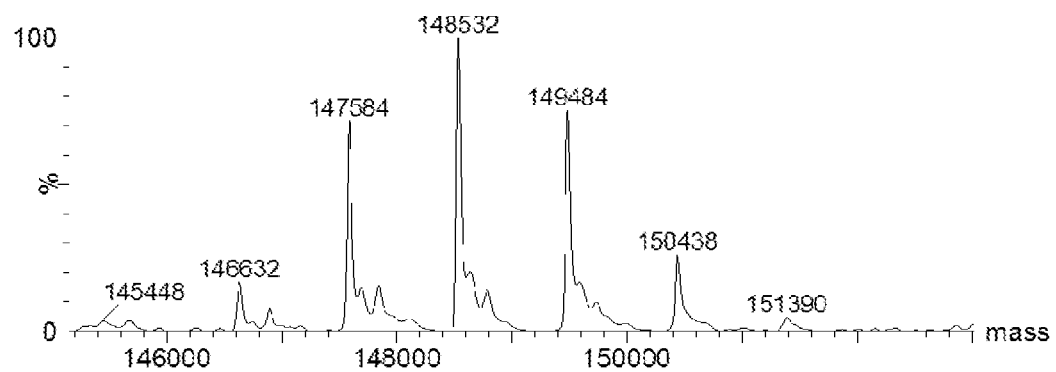
FIG. 4 shows LC-MS profile of conjugate huMov19-sulfo-SPDB-17.

The conjugate was found to have an average of 2.9 mol 17/mol antibody by UV-vis, 97.7% monomer by SEC, and 0.4% unconjugated compound 17 by tandem SEC/RP-UPLC. LC-MS of the deglycosylated conjugate is shown in FIG. 4.

huMov19-144 (or huMov19-143)

A stock solution of compound 144 in DMA was sulfonated by adding 5 equivalents of sodium bisulfite as an aqueous solution such that the final mixture consisted of 90% (v/v) DMA and 10% (v/v) water. The reaction was allowed to proceed for 4 hr. at 25° C. The crude, sulfonated compound 144 thus prepared was added to a solution of huMov19 antibody in 15 mM HEPES, pH 8.5 with 10% (v/v) DMA, such that the final ratio of mol 144/mol huMov19 was 5.2. The conjugation reaction was allowed to proceed for 5 hr. at 25° C.

Figure 5:
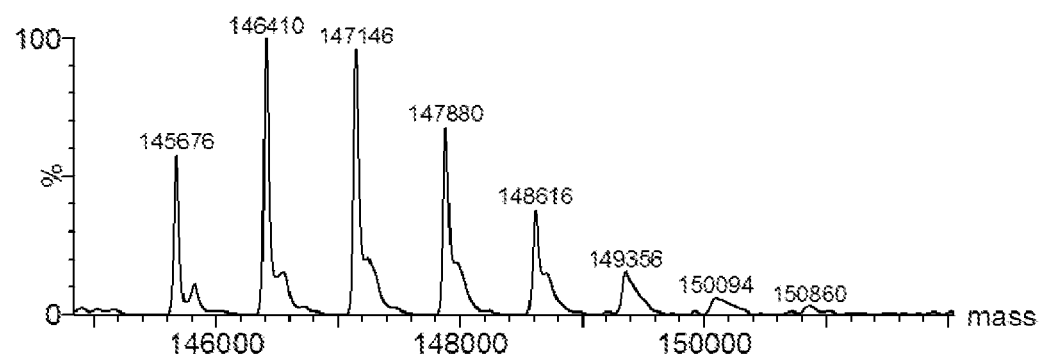
FIG. 5 shows LC-MS profile of conjugate huMov19-144.

The conjugate was purified into 20 mM histidine, 50 mM sodium chloride, 8.5% sucrose, 0.01% Tween-20, 50 µM sodium bisulfite, pH 6.2 using Sephadex G-25 columns and then dialyzed against this same buffer using a membrane with 10 kDa molecular weight cutoff. The conjugate was found to have an average of 2.9 mol 144/mol antibody by UV-vis, 97.7% monomer by SEC, and 0.5% unconjugated 144 by tandem SEC/RP-UPLC. LC-MS of the deglycosylated conjugate is shown in FIG. 5 huMov19-255

Figure 6:
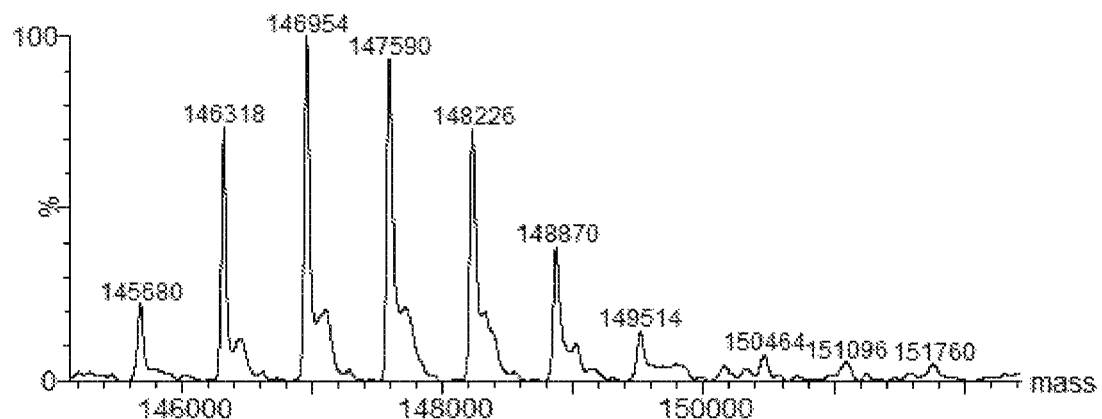
FIG. 6 shows LC-MS profile of conjugate huMov19-225.

A stock solution of compound #225 in DMA was sulfonated by adding 5 equivalents of sodium bisulfite as an aqueous solution such that the final mixture consisted of 90% (v/v) DMA and 10% (v/v) water. The reaction was allowed to proceed for 4 hr. at 25° C. The crude, sulfonated compound #225 thus prepared was added to a solution of huMov19 antibody in 15 mM HEPES, pH 8.5 with 10% (v/v) DMA, such that the final ratio of mol 225/mol huMov19 was 5.0. The conjugation reaction was allowed to proceed for 5 hr. at 25° C. The conjugate was purified into 20 mM histidine, 50 mM sodium chloride, 8.5% sucrose, 0.01% Tween-20, 50 µM sodium bisulfite, pH 6.2 using Sephadex G-25 columns. The conjugate was found to have an average of 3.1 mol 225/mol antibody by UV-vis, 98.0% monomer by SEC, and <1.8% unconjugated 225 by tandem SEC/RP-UPLC. LC-MS of the deglycosylated conjugate is shown FIG. 6.

huMov19-30

Prior to conjugation, sulfo-SPDB-30 was prepared by mixing a stock solution of sulfo-SPDB in DMA with a stock solution of compound 30 in DMA in the presence of DIEA such that the final composition was 1.5 mM sulfo-SPDB, 1.95 mM compound 30, and 10 mM DIEA. The reaction was allowed to proceed for 3.5 hr. at 25° C. The crude sulfo-SPDB-30 was then added to a solution containing huMov19 antibody and buffered with 15 mM HEPES, pH 8.5 with 15% (v/v) DMA to a final ratio of 9.2 mol sulfo-SPDB-30 to 1 mol antibody. The conjugation reaction was allowed to proceed overnight at 25° C.

The conjugate was purified into 20 mM histidine, 50 mM sodium chloride, 8.5% sucrose, 0.01% Tween-20, 50 µM sodium bisulfite, pH 6.2 using Sephadex G-25 columns and then dialyzed against this same buffer using a membrane with 10 kDa molecular weight cutoff.

Figure 7:
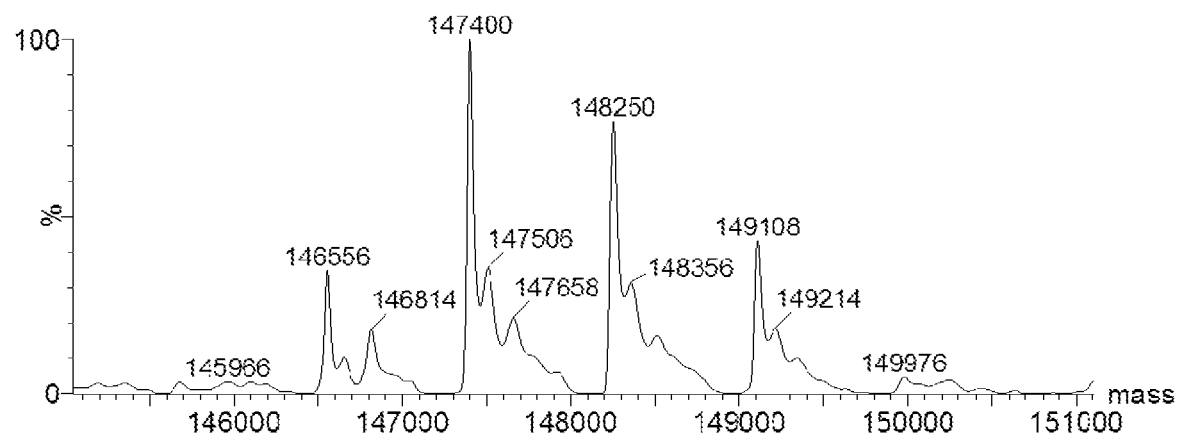
FIG. 7 shows LC-MS profile of conjugate huMov19-30.

The conjugate was found to have an average of 2.5 mol 30/mol antibody by UV-vis, 98.7% monomer by SEC, and <2.0% unconjugated 30 by tandem SEC/RP-UPLC. LC-MS of the deglycosylated conjugate is shown in FIG. 7.

huMov19-sulfo-SPDB-155

Prior to conjugation, sulfo-SPDB-155 was prepared by mixing a stock solution of sulfo-SPDB in DMA with a stock solution of compound 155 in DMA in the presence of DIEA such that the final composition was 1.5 mM sulfo-SPDB, 1.95 mM compound 155, and 10 mM DIEA. The reaction was allowed to proceed for 4 hr. at 25° C. The crude sulfo-SPDB-155 was then added to a solution containing huMov19 antibody and buffered with 15 mM HEPES, pH 8.5 with 15% (v/v) DMA to a final ratio of 8.1 mol sulfo-SPDB-155 to 1 mol antibody. The conjugation reaction was allowed to proceed overnight at 25° C.

The conjugate was purified into 20 mM histidine, 50 mM sodium chloride, 8.5% sucrose, 0.01% Tween-20, 50 µM sodium bisulfite, pH 6.2 using Sephadex G-25 columns and then dialyzed against this same buffer using a membrane with 10 kDa molecular weight cutoff.

Figure 8:
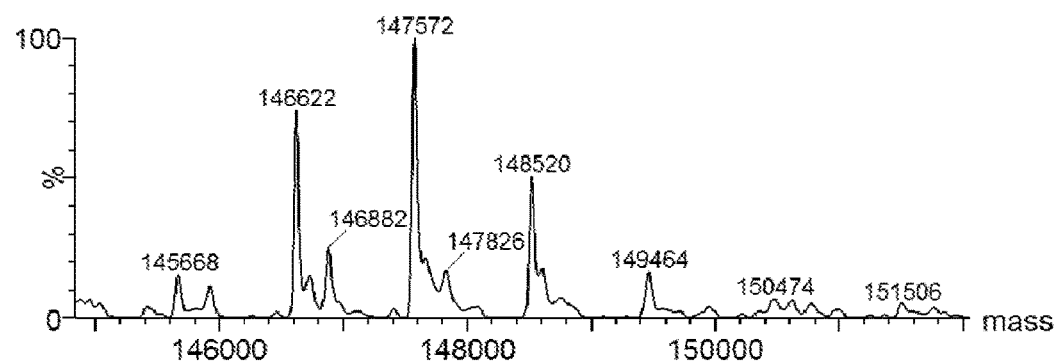
FIG. 8 shows LC-MS profile of conjugate huMov19-sulfo-SPDB-155.

The conjugate was found to have an average of 2.5 mol 155/mol antibody by UV-vis, 98.4% monomer by SEC, and 0.9% unconjugated 155 by tandem SEC/RP-UPLC. LC-MS of the deglycosylated conjugate is shown in FIG. 8.

huMov19-sulfo-SPDB-87

Prior to conjugation, sulfo-SPDB-87 was prepared by mixing a stock solution of sulfo-SPDB in DMA with a stock solution of compound 87 in DMA in the presence of DIEA such that the final composition was 1.5 mM sulfo-SPDB, 1.95 mM compound 87, and 10 mM DIEA. The reaction was allowed to proceed for 5.5 hr. at 25° C. The crude sulfo-SPDB-87 was then added to a solution containing huMov19 antibody and buffered with 15 mM HEPES, pH 8.5 with 15% (v/v) DMA to a final ratio of 7.8 mol sulfo-SPDB-87 to 1 mol antibody. The conjugation reaction was allowed to proceed overnight at 25° C.

The conjugate was purified into 20 mM histidine, 50 mM sodium chloride, 8.5% sucrose, 0.01% Tween-20, 50 µM sodium bisulfite, pH 6.2 using Sephadex G-25 columns and then dialyzed against this same buffer using a membrane with 10 kDa molecular weight cutoff.

Figure 9:
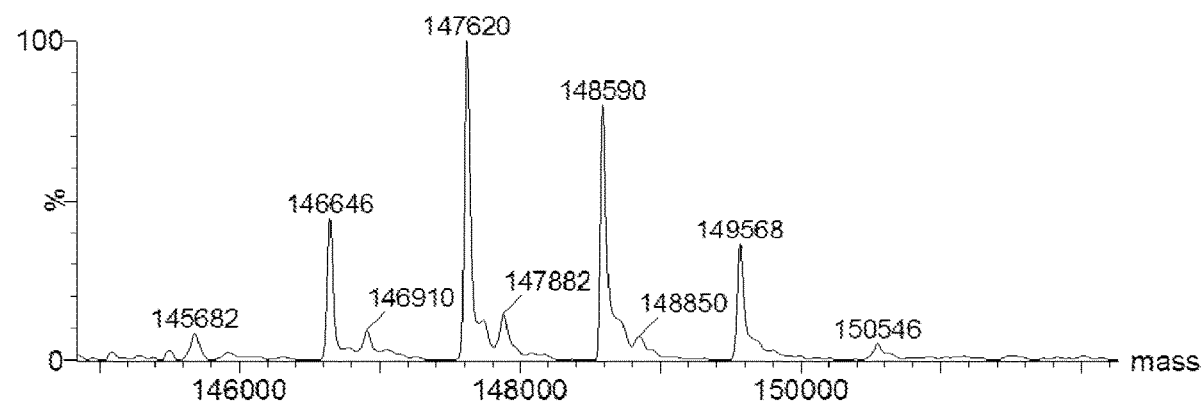
FIG. 9 shows LC-MS profile of conjugate huMov19-sulfo-SPDB-87.

The conjugate was found to have an average of 2.7 mol 87/mol antibody by UV-vis, 94.8% monomer by SEC, and 0.5% unconjugated 87 by tandem SEC/RP-UPLC. LC-MS of the deglycosylated conjugate is shown in FIG. 9.

huMov19-sulfo-SPDB-127

Prior to conjugation, sulfo-SPDB-127 was prepared by mixing a stock solution of sulfo-SPDB in DMA with a stock solution of compound 127 in DMA in the presence of DIEA such that the final composition was 1.5 mM sulfo-SPDB, 1.95 mM compound 127, and 10 mM DIEA. The reaction was allowed to proceed for 5.5 hr. at 25° C. The crude sulfo-SPDB-127 was then added to a solution containing huMov19 antibody and buffered with 15 mM HEPES, pH 8.5 with 15% (v/v) DMA to a final ratio of 7.4 mol sulfo-SPDB-127 to 1 mol antibody. The conjugation reaction was allowed to proceed overnight at 25° C.

Figure 10:
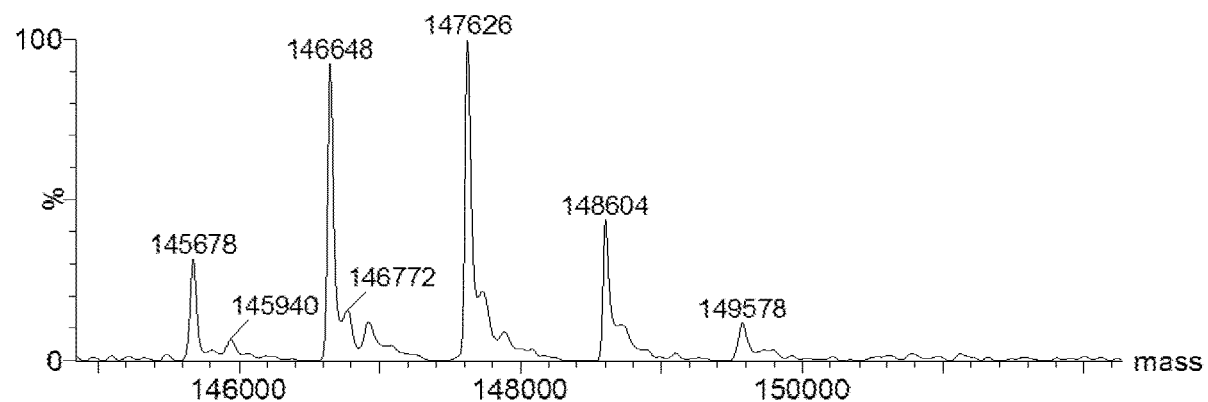
FIG. 10 shows LC-MS profile of conjugate huMov19-sulfo-SPDB-127.

The conjugate was purified into 20 mM histidine, 50 mM sodium chloride, 8.5% sucrose, 0.01% Tween-20, 50 µM sodium bisulfite, pH 6.2 using Sephadex G-25 columns and then dialyzed against this same buffer using a membrane with 10 kDa molecular weight cutoff. The conjugate was found to have an average of 2.6 mol 127/mol antibody by UV-vis, 94.0% monomer by SEC, and 1.3% unconjugated 127 by tandem SEC/RP-UPLC. LC-MS of the deglycosylated conjugate is shown in FIG. 10.

huMov19-sulfo-SPDB-109

Prior to conjugation, sulfo-SPDB-109 was prepared by mixing a stock solution of sulfo-SPDB in DMA with a stock solution of compound 109 in DMA in the presence of DIEA such that the final composition was 1.5 mM sulfo-SPDB, 1.95 mM compound 109, and 10 mM DIEA. The reaction was allowed to proceed for 4.0 hr. at 25° C. The crude sulfo-SPDB-109 was then added to a solution containing huMov19 antibody and buffered with 15 mM HEPES, pH 8.5 with 15% (v/v) DMA to a final ratio of 9.1 mol sulfo-SPDB-109 to 1 mol antibody. The conjugation reaction was allowed to proceed overnight at 25° C.

The conjugate was purified into 20 mM histidine, 8.5% sucrose, 0.01% Tween-20, 50 μM sodium bisulfite, pH 6.2 using Sephadex G-25 columns and then dialyzed against this same buffer using a membrane with 10 kDa molecular weight cutoff.

Figure 11:
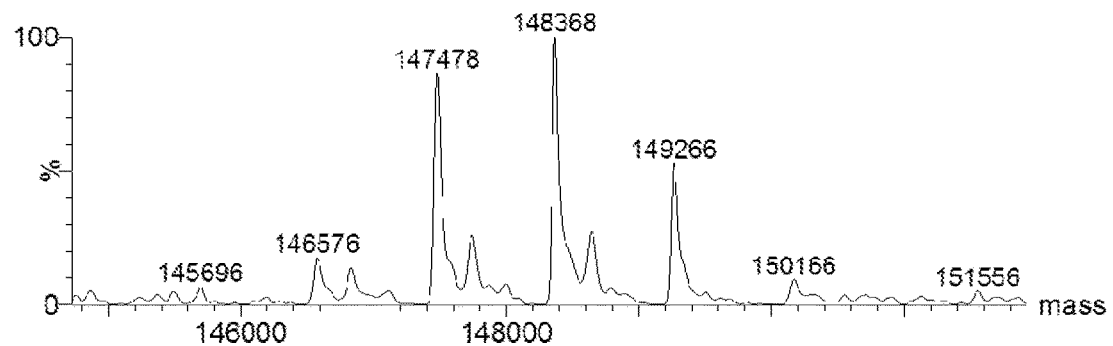
FIG. 11 shows LC-MS profile of conjugate huMov19-sulfo-SPDB-109.

The conjugate was found to have an average of 2.8 mol 109/mol antibody by UV-vis, 97.5% monomer by SEC, and 4.4% unconjugated 109 by tandem SEC/RP-UPLC. LC-MS of the deglycosylated conjugate is shown in FIG. 11.

huMov19-167 (or huMov19-166)

A stock solution of compound 167 in DMA was sulfonated by adding 5 equivalents of sodium bisulfite as an aqueous solution such that the final mixture consisted of 90% (v/v) DMA and 10% (v/v) water. The reaction was allowed to proceed for 3 hr. at 25° C. The crude, sulfonated 167 thus prepared was added to a solution of huMov19 antibody in 15 mM HEPES, pH 8.5 with 10% (v/v) DMA, such that the final ratio of mol 167/mol huMov19 was 5.4. The conjugation reaction was allowed to proceed for 5 hr. at 25° C.

The conjugate was purified into 20 mM histidine, 8.5% sucrose, 0.01% Tween-20, 50 μM sodium bisulfite, pH 6.2 using Sephadex G-25 columns and then dialyzed against this same buffer using a membrane with 10 kDa molecular weight cutoff.

Figure 12:
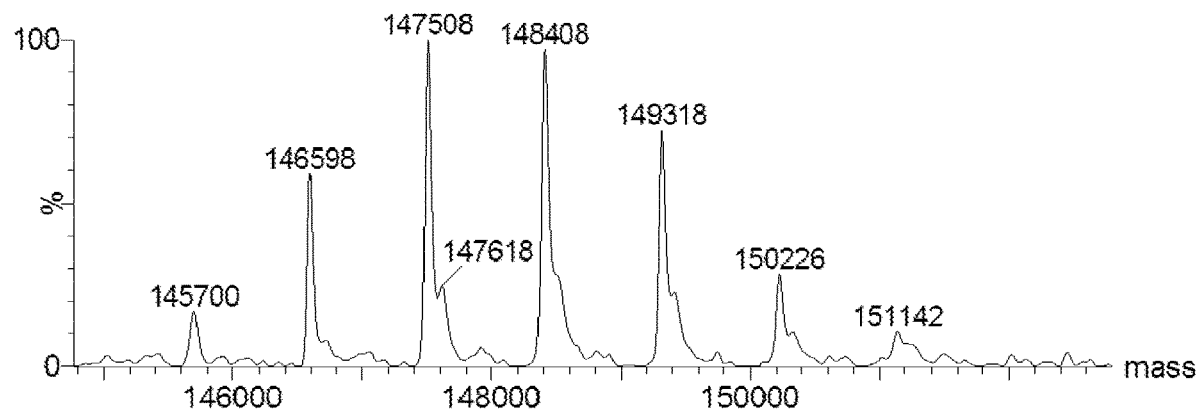
FIG. 12 shows LC-MS profile of conjugate huMov19-167.

The conjugate was found to have an average of 3.1 mol 167/mol antibody by UV-vis, 95.7% monomer by SEC, and <0.5% unconjugated 167 by tandem SEC/RP-UPLC. LC-MS of the deglycosylated conjugate is shown in FIG. 12.

huMov19-161 (or huMov19-160)

A stock solution of compound 161 in DMA was sulfonated by adding 5 equivalents of sodium bisulfite as an aqueous solution such that the final mixture consisted of 90% (v/v) DMA and 10% (v/v) water. The reaction was allowed to proceed for 3 hr. at 25° C. The crude, sulfonated 161 thus prepared was added to a solution of huMov19 antibody in 15 mM HEPES, pH 8.5 with 15% (v/v) DMA, such that the final ratio of mol 161/mol huMov19 was 9.8. The conjugation reaction was allowed to proceed for 4.5 hr. at 25° C.

The conjugate was purified into 20 mM histidine, 8.5% sucrose, 0.01% Tween-20, 50 μM sodium bisulfite, pH 6.2 using Sephadex G-25 columns and then dialyzed against this same buffer using a membrane with 10 kDa molecular weight cutoff.

Figure 13:
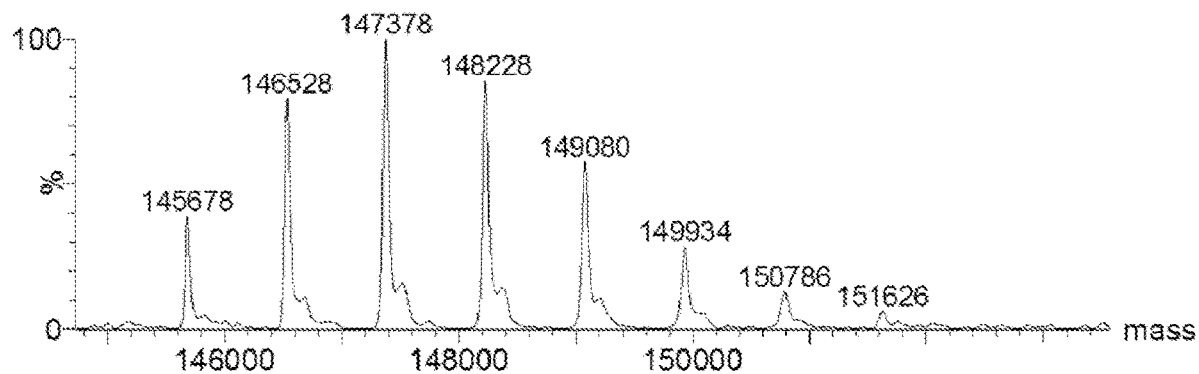
FIG. 13 shows LC-MS profile of conjugate huMov19-161.

The conjugate was found to have an average of 2.4 mol 161/mol antibody by UV-vis, 98.9% monomer by SEC, and 3.3% unconjugated 161 by tandem SEC/RP-UPLC. LC-MS of the deglycosylated conjugate is shown in FIG. 13.

huMov19-sulfo-SPDB-208

Prior to conjugation, sulfo-SPDB-208 was prepared by mixing a stock solution of sulfo-SPDB in DMA with a stock solution of compound 208 in DMA in the presence of DIEA such that the final composition was 1.5 mM sulfo-SPDB, 1.95 mM compound 208, and 10 mM DIEA. The reaction was allowed to proceed for 3.5 hr. at 25° C. The crude sulfo-SPDB-208 was then added to a solution containing huMov19 antibody and buffered with 15 mM HEPES, pH 8.5 with 15% (v/v) DMA to a final ratio of 10 mol sulfo-SPDB-208 to 1 mol antibody. The conjugation reaction was allowed to proceed overnight at 25° C.

The conjugate was purified into 20 mM histidine, 8.5% sucrose, 0.01% Tween-20, 50 μM sodium bisulfite, pH 6.2 using Sephadex G-25 columns and then dialyzed against this same buffer using a membrane with 10 kDa molecular weight cutoff.

Figure 14:
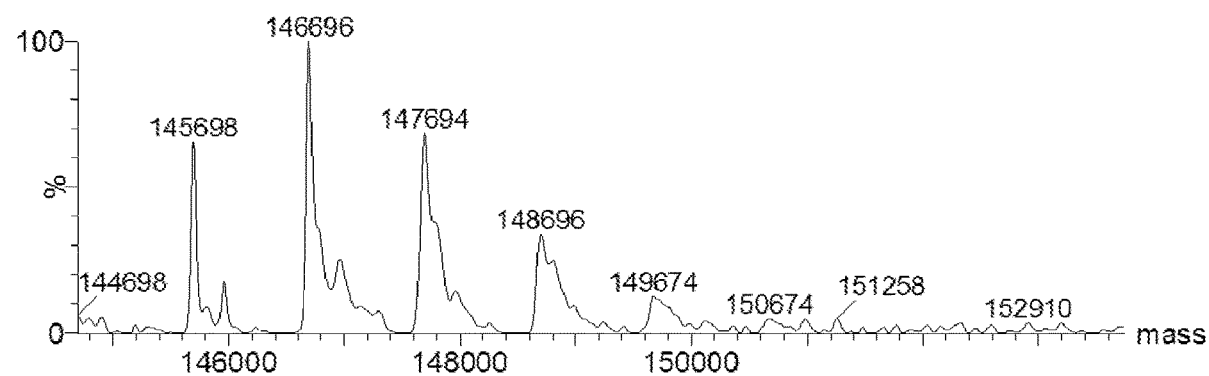
FIG. 14 shows LC-MS profile of conjugate huMov19-sulfo-SPDB-208.

The conjugate was found to have an average of 1.3 mol 208/mol antibody by UV-vis, 91.9% monomer by SEC, and 2.0% unconjugated 208 by tandem SEC/RP-UPLC. LC-MS of the deglycosylated conjugate is shown in FIG. 14.

huMov19-sulfo-SPDB-204

Prior to conjugation, sulfo-SPDB-204 was prepared by mixing a stock solution of sulfo-SPDB in DMA with a stock solution of compound 204 in DMA in the presence of DIEA such that the final composition was 1.5 mM sulfo-SPDB, 1.95 mM compound 204, and 10 mM DIEA. The reaction was allowed to proceed for 3.5 hr. at 25° C. The crude sulfo-SPDB-204 was then added to a solution containing huMov19 antibody and buffered with 15 mM HEPES, pH 8.5 with 15% (v/v) DMA to a final ratio of 10 mol sulfo-SPDB-204 to 1 mol antibody. The conjugation reaction was allowed to proceed overnight at 25° C.

The conjugate was purified into 20 mM histidine, 8.5% sucrose, 0.01% Tween-20, 50 μM sodium bisulfite, pH 6.2 using Sephadex G-25 columns and then dialyzed against this same buffer using a membrane with 10 kDa molecular weight cutoff.

Figure 15:
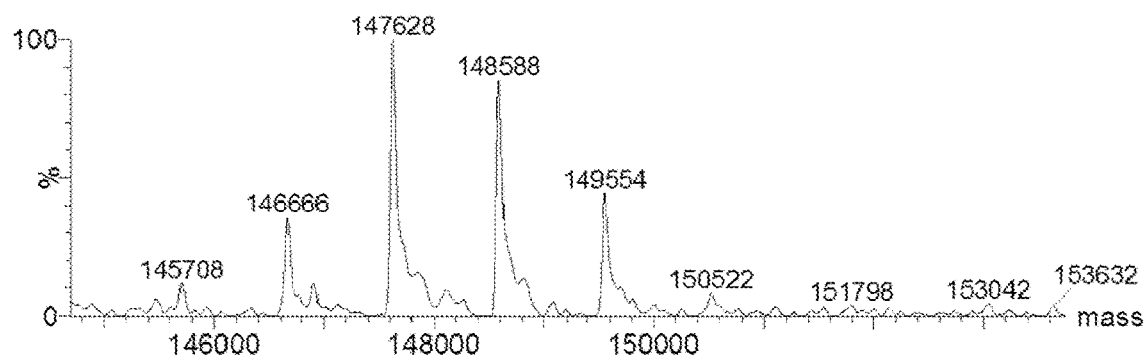
FIG. 15 shows LC-MS profile of conjugate huMov19-sulfo-SPDB-204.

The conjugate was found to have an average of 2.9 mol 204/mol antibody by UV-vis, 95.8% monomer by SEC, and 3.7% unconjugated 204 by tandem SEC/RP-UPLC. LC-MS of the deglycosylated conjugate is shown in FIG. 15.

Example 3. Cytotoxicity Assay

Following cell lines were used for the study: KB (cervical carcinoma, ATCC), NCI-H2110 (Non Small Cell Lung Carcinoma, ATCC), Namalwa (Burkitt's lymphoma, ATCC), Ishikawa (endometrial adenocarcinoma, ECACC), EOL-1 (Acute Myeloid Leukemia, ECACC), JEG-3 (choriocarcinoma, ATCC), JHOS-4 (ovarian adenocarcinoma, Riken Bioresource Center), OV-90 (ovarian adenocarcinoma, ATCC), SKOV-6 (ovarian adenocarcinoma, Memorial Sloan Kettering Cancer Center), Igrov-1 (ovarian adenocarcinoma, National Cancer Institute), KB-GRC1-MDR (cervical carcinoma/Pgp positive, gift from Dr. Roninson at the Ordway Research Institute) and T47D (breast epithelial cancer, ATCC). The cells were maintained and plated for the cytotox experiments in media recommended by the manufacturers. Cells were plated in the 96-well flat bottom plates at a seeding density of 800 cells per well (Ishikawa, JEG-3 or SK-OV-6), 1,000 cells per well (KB, Namalwa, EOL-1, OV-90 and Igrov-1) or 2,000 cell per well (NCI H2110, JHOS-4 and T47D). Conjugates or free drug compounds were diluted in RPMI-1640 (Life Technologies) supplemented with heat-inactivated 100 FBS (Life Technologies) and 0.1 mg/ml gentamycin (Life Technologies), and added to the plated cells. To determine specificity of cytotoxic activity of the conjugates an excess of unconjugated antibody was added to a separate set of diluted conjugates (+block samples, $IC_{50}$ table). The plates were incubated at 37° C., 500 $CO_2$ for either 4 days (JHOS-4 and T47D cells) or 5 days (KB, NCI H2110, Ishikawa, EOL-1, JEG-3, OV-90, SK-OV-6, NC-H441 and Igrov-1 cells). Alamar blue assay (Invitrogen) was used to determine viability of JHOS-4 and T47D cells, and WST-8 assay (Donjindo Molecular Technologies, Inc.) was applied for viability of KB, NCI H2110, Namalwa, Ishikawa, EOL-1, JEG-4, OV-90, SK-OV-6, NCI-H4441 and Igrov-1 cells. The assays were performed in accordance with the manufacturer's protocols. Killing curves and $IC_{50}$ were generated using a sigmoidal dose-response nonlinear regression curve fit (GraphPad Software Inc.). As shown in Tables 1-6, the cytotoxic compounds and conjugates of the present invention are highly potent against various cancer cells in in vitro cytotoxicity assays.

TABLE 1

IC$_{50}$ values for free cytotoxic compounds (Molar, M) determined by in vitro cytotoxicity assays

| Compound # | KB | NCI-H2110 | Namalwa | EOL-1 | Ishikawa | KB-MDR |
|---|---|---|---|---|---|---|
| 7 | ND | ND | 2.00E−11 | ND | ND | ND |
| 9 | 4.00E−11 | 2.00E−10 | 3.00E−11 | 1.00E−11 | N7e−11D | ND |
| 15 | 8.00E−11 | 3.00E−10 | 9.00E−12 | 4.00E−12 | ND | 3.00E−09 |
| 30 | ND | ND | 7.00E−10 | 1.00E−10 | ND | ND |
| 42 | 3.00E−11 | 4.00E−10 | 3.00E−11 | 9.00E−12 | 2.00E−10 | ND |
| 46 | 1.00E−10 | 6.00E−10 | 3.00E−11 | 1.00E−11 | ND | ND |
| 50 | 1.00E−10 | 2.00E−10 | 2.00E−11 | ND | ND | ND |
| 55 | 9.00E−09 | 2.00E−09 | 4.00E−09 | ND | ND | ND |
| 63 | 1.00E−09 | 3.00E−09 | 3.00E−10 | ND | 6.00E−10 | >5e−9 |
| 69 | >5e−9 | >5e−9 | 4.00E−09 | ND | >5e−9 | >5e−9 |
| 75 | >5e−9 | >5e−9 | 2.00E−09 | ND | >5e−9 | >5e−9 |
| 81 | >5e−9 | >5e−9 | 3.00E−09 | ND | >5e−9 | >5e−9 |
| 85 | 1.00E−11 | 1.00E−10 | 3.00E−11 | 8.00E−12 | 1.00E−10 | >5e−9 |
| 91 | 6.00E−10 | 4.00E−09 | 2.00E−10 | 6.00E−11 | ND | ND |
| 95 | 9.00E−10 | 2.00E−09 | 2.00E−10 | ND | ND | ND |
| 99 | 5.00E−10 | 1.00E−09 | 1.00E−10 | ND | 7.00E−10 | ND |
| 103 | 7.00E−11 | 2.00E−10 | 2.00E−11 | ND | 5.00E−11 | 4.00E−10 |
| 107 | 2.00E−11 | 6.00E−11 | 6.00E−12 | ND | 1.00E−11 | 2.00E−10 |
| 113 | 2.00E−10 | 4.00E−10 | 7.00E−11 | ND | 2.00E−10 | 3.00E−09 |
| 117 | 6.00E−10 | 2.00E−09 | 3.00E−10 | ND | 1.00E−09 | >5e−9 |
| 121 | 2.00E−09 | 2.00E−09 | 6.00E−10 | ND | 2.00E−09 | >5e−9 |
| 125 | 4.00E−11 | 6.00E−11 | 1.00E−11 | 4.00E−12 | 5.00E−11 | 9.00E−10 |
| 132 | 4.00E−10 | 2.00E−09 | 9.00E−11 | 4.00E−11 | ND | ND |
| 137 | 5.00E−11 | 1.00E−10 | 2.00E−11 | 1.00E−11 | ND | ND |
| 142 | ND | ND | 1.00E−11 | 6.00E−12 | ND | ND |
| 149 | 2.00E−10 | 4.00E−10 | 6.00E−11 | ND | 1.00E−10 | ND |
| 151 | ND | ND | 1.00E−10 | 5.00E−11 | ND | ND |
| 155 | ND | ND | 3.00E−11 | 9.00E−12 | ND | ND |
| 173 | >5e−9 | >5e−9 | 3.00E−09 | ND | >5e−9 | >5e−9 |
| 180 | 1.00E−9 | 2.00E−09 | 3.00E−10 | ND | ND | ND |
| 185 | 2.00E−10 | 5.00E−10 | 2.00E−10 | ND | ND | ND |
| 188 | 8.00E−11 | 5.00E−10 | 6.00E−11 | 2.00E−11 | ND | ND |
| 192 | 9.00E−10 | 2.00E−09 | 4.00E−10 | ND | ND | ND |
| 199 | ND | 5.00E−09 | ND | ND | ND | ND |
| 199 | 1.00E−09 | 3.00E−09 | >5e−10 | ND | ND | ND |
| 202 | 5.00E−12 | 3.00E−11 | 2.00E−12 | ND | 7.00E−12 | 3.00E−10 |
| 205 | 4.00E−10 | 8.00E−10 | 1.00E−10 | ND | 3.00E−10 | 4.00E−09 |
| 206 | 6.00E−12 | 1.00E−11 | 1.00E−12 | ND | 4.00E−12 | 1.00E−10 |
| 210 | 8.00E−10 | 2.00E−9 | | | | |
| 214 | >5.00E−9 | >5.00E−9 | | | | |
| 216 | 5.00E−10 | 9.00E−9 | | | | |

ND = not determined

TABLE 2

IC$_{50}$ values (Molar, M) for additional cytotoxic compounds determined by in vitro cytotoxic assays

| Compound # | T47D | JHOS-4 | JEG-3 | OV-90 | Igrov-1 | SK-OV-6 |
|---|---|---|---|---|---|---|
| 15 | 7e−11 | 6e−10 | 3e−10 | 2e−10 | 2e−11 | 1e−10 |
| 107 | 1e−10 | 2e−9 | 3e−11 | 3e−11 | 7e−12 | 2e−11 |
| 216 | 2.00e−9 | | | | | |

TABLE 3

IC$_{50}$ values (Molar, M) for M9346A-Conjugates determine by in vitro cytotoxicity assays

| Antibody-linker | Compound # | KB − block | KB + block | H2110 − block | H2110 + block | T47D − block | T47D + block |
|---|---|---|---|---|---|---|---|
| M- | 10 | 2.00E−11 | >4e−9 | 3.50E−08 | >4e−8 | 2.00E−11 | 2.00E−08 |
| M-sSPDB | 17 | 4.00E−11 | 1.00E−09 | 6.00E−09 | 7.00E−09 | 2.00E−10 | 5.00E−09 |
| M-sSPDB | 30 | >4e−9 | >4e−9 | >4e−8 | >4e−8 | 1.00E−08 | 1.00E−08 |
| M-sSPDB | 87 | 3.00E−11 | 7.00E−10 | 1.00E−09 | 2.00E−09 | 2.00E−09 | 6.00E−09 |
| M-sSPDB | 109 | 4.00E−09 | 4.00E−09 | 7.00E−09 | 7.00E−09 | 7.00E−09 | 7.00E−09 |
| M-sSPDB | 127 | 1.00E−10 | 1.00E−09 | 3.00E−09 | 3.00E−09 | 1.00E−09 | 2.00E−09 |

TABLE 3-continued

IC$_{50}$ values (Molar, M) for M9346A-Conjugates determine by in vitro cytotoxicity assays

| Antibody-linker | Compound # | KB − block | KB + block | H2110 − block | H2110 + block | T47D − block | T47D + block |
|---|---|---|---|---|---|---|---|
| M- | 143 or 144 | 1.00E−11 | 3.00E−09 | 2.00E−09 | 4.00E−08 | 1.00E−11 | 1.00E−08 |
| M-sSPDB | 155 | 3.00E−11 | 4.00E−10 | 3.00E−09 | 4.00E−09 | 1.00E−10 | 4.00E−09 |
| M- | 160 or 161 | 5.00E−11 | 2.00E−08 | >4e−8 | >4e−8 | >4e−8 | >4e−8 |
| M- | 166 or 167 | 5.00E−11 | >4e−9 | 4.00E−09 | >4e−8 | 4.00E−10 | 4.00E−09 |
| M-sSPDB | 204 | 4.00E−12 | 3.00E−10 | 2.00E−10 | 1.00E−09 | 3.00E−11 | 2.00E−09 |
| M-sSPDB | 208 | 7.00E−12 | 2.00E−10 | 1.00E−10 | 2.00E−10 | 6.00E−11 | 6.00E−10 |

TABLE 4

IC$_{50}$ values (Molar, M) for M9346A-Conjugate values determined by in vitro cytotoxicity assays

| Antibody-linker | compound # | Ishikawa − block | Ishikawa + block | HEC-1B − block | HEC-1B + block | JHOS-4 − block | JHOS-4 + block |
|---|---|---|---|---|---|---|---|
| M-sSPDB | 17 | 3.00E−09 | 3.00E−09 | 8.00E−09 | 8.00E−09 | 4.00E−09 | 4.00E−08 |
| M-sSPDB | 87 | 5.00E−10 | 1.00E−09 | 5.00E−09 | 7.00E−09 | ND | ND |
| M-sSPDB | 127 | 3.00E−10 | 3.00E−10 | 3.00E−09 | 3.00E−09 | ND | ND |
| M-sSPDB | 109 | ND | ND | ND | ND | 5.00E−09 | 7.00E−09 |
| M- | 167 | 9.00E−09 | 2.00E−08 | 3.00E−09 | 3.00E−09 | ND | ND |

ND = not determined

TABLE 5

IC$_{50}$ values (Molar, M) for M9346A-Conjugate determined by in vitro cytotoxicity assays

| Antibody-linker | Compound # | JEG-3 − block | JEG-3 + block | OV-90 − block | OV-90 + block | Igrov-1 − block | Igrov-1 + block |
|---|---|---|---|---|---|---|---|
| M-sSPDB | 17 | 1e−9 | 4e−9 | 3e−9 | 4e−9 | 2e−11 | 8e−10 |
| M-sSPDB | 127 | 2e−9 | 2e−9 | 3e−9 | 4e−9 | 2e−10 | 6e−10 |

TABLE 6

IC$_{50}$ values (Molar, M) for M9346A-Conjugate determined by in vitro cytotoxicity assays

| Antibody-linker | Compound # | H441 − block | H441 + block |
|---|---|---|---|
| M-sSPDB | 17 | 8e−9 | 9e−9 |
| M-sSPDB | 127 | 5e−9 | 5e−9 |

TABLE 7

In vitro bystander activity in 300.19 cell system, −/+FRα

| Antibody-linker | Compound # | % FRα-negative cells killed at 4e−10M conjugate |
|---|---|---|
| M- | 11 | 0 |
| M-sSPDB | 17 | 9 |
| M-sSPDB | 127 | 6 |
| M- | 167 | 13 |

Similar results for M-sSPDB-127 are shown in FIG. 1.

Example 4. Bystander Cytotoxicity Assay (300.19−/+FRα System)

A mixed culture of FRα-positive cells 300-19 transfected with human FRα and FRα-negative cells 300-19 was exposed to conjugates at concentrations that are not toxic for the negative cells but highly toxic for the receptor-positive cells (killing 100% of the cells). Cells were incubated for 4 days, and the inhibition of cell proliferation was determined by Cell Titer Glo (Promega) according to the manufacturer's protocol.

Example 5. Bystander Cytotoxicity Assay (Human Tumor Cell Lines System)

A mixed culture of different FRα-positive human tumor cell lines (KB, OV-90, JEG-3 or T47D) and FRα-negative human tumor cells (Namalwa) expressing Luciferase were exposed to varying concentrations of each conjugate. Cells were incubated for 5 days, and the inhibition of Namalwa cell proliferation was determined by ONE Glo (Promega) according to the manufacturer's protocol. Killing curves and IC$_{50}$ were generated using a sigmoidal dose-response non-linear regression curve fit (GraphPad Software Inc.)

TABLE 8

In vitro bystander IC$_{50}$ (Molar, M) in human tumor cells, −/+ FRα

| Antibody-linker | Compound # | FRα-negative Namalwa-Luc alone (non-specific activity of ADC) | FRα-positive + Namalwa-Luc mixed | | | |
|---|---|---|---|---|---|---|
| | | | KB | OV-90 | JEG-3 | T47D |
| M-sSPDB | 17  | 4e−9  | 6e−11 | 9e−11 | 7e−10 | 7e−11 |
| M-sSPDB | 109 | 2e−9  | 3e−9  | 2e−9  | 2e−9  | ND    |
| M-      | 160 | 1e−8  | 3e−10 | 1e−8  | 3e−9  | ND    |
| M-      | 166 | 8e−9  | 3e−10 | ND    | 2e−9  | ND    |
| M-sSPDB | 208 | 2e−10 | 3e−11 | 2e−10 | ND    | 3e−11 |
| M-sSPDB | 204 | 1e−9  | 4e−12 | 4e−10 | ND    | 4e−11 |

ND = not determined

Example 6. Binding Assay (Flow Cytometry)

20,000 T47D cells per well in the 96-well round bottom plate were incubated for 2 hours at 4° C. with unconjugated antibody or conjugates diluted to various concentrations in FACS buffer (0.01 M PBS, pH 7.4 (Life Technologies) supplemented with 0.5% BSA (Boston BioProducts)). The cells were then washed in cold FACS buffer, stained with FITC-labeled Goat Anti-Human-IgG-Fcγ specific antibody (Jackson ImmunoResearch) for 1 hr at 4° C., washed with the cold FACS buffer, fixed in 1% formaldehyde/0.01 M PBS overnight and then read using a FACS Calibur (BD Biosciences). Binding curves and EC$_{50}$ were generated using a sigmoidal dose-response nonlinear regression curve fit (GraphPad Software Inc.)

TABLE 9

EC$_{50}$ values (Molar, M) determined by in vitro binding assays using flow cytometry

| Antibody-linker | Compound # | Conjugate | Un-conjugated Antibody control* |
|---|---|---|---|
| M-      | 10  | 3.00E−10 | 3.00E−10 |
| M-sSPDB | 17  | 2.00E−10 | 2.00E−10 |
| M-sSPDB | 30  | 3.00E−10 | 2.00E−10 |
| M-sSPDB | 87  | 4.00E−10 | 2.00E−10 |
| M-sSPDB | 109 | 3.00E−10 | 2.00E−10 |
| M-sSPDB | 127 | 2.00E−10 | 2.00E−10 |
| M-      | 143 | 2.00E−10 | 1.00E−10 |
| M-sSPDB | 155 | 3.00E−10 | 1.00E−10 |
| M-      | 160 | 2.00E−10 | 2.00E−10 |
| M-      | 166 | 2.00E−10 | 2.00E−10 |
| M-sSPDB | 204 | 6.00E−10 | 5.00E−10 |
| M-sSPDB | 208 | 7.00E−10 | 5.00E−10 |

*The EC$_{50}$ values for each conjugate and the unconjugated antibody control were generated in independent experiments which might explain slight variability of the unconjugated control antibody EC$_{50}$ values.

Example 7. In Vivo Efficacy Study in SCID Mice Bearing KB Cervical Cancer Xenografts Female CB.17 SCID mice, six weeks old were obtained from Charles River Laboratories. Mice were inoculated with 1×10$^7$ KB cells in 0.1 ml serum free medium by subcutaneous injection in the area on the right hind flank. When tumor volumes reached approximately 100 mm$^3$ (day 7 post inoculation) animals were randomized based on tumor volume into groups of six mice. Mice received a single IV administration of vehicle control (0.2 ml/mouse) or test article (50 or 100 μg/kg) based on concentration of compound 16.

Tumor size was measured two times per week in three dimensions using a caliper. The tumor volume was expressed in mm$^3$ using the formula V=Length×Width×Height×12. A mouse was considered to have a partial regression (PR) when tumor volume was reduced by 50% or greater, complete tumor regression (CR) when no palpable tumor could be detected and tumor-free survivor (TFS) is the number of mice tumor free at the end of the study. Body weight of all the mice was measured twice per week as a rough index of drug toxicity. Tumor volume and body weight were determined by StudyLog software.

Log$_{10}$ cell kill (LCK) was calculated with the formula:

$$LCK=(T-C)/T_d \times 3.32,$$

where (T−C), or tumor growth delay (TGD), is the median time (in days) for the treatment group and control group tumors to reach a predetermined size of 1000 mm$^3$ (tumor-free survivors excluded) (Bissery, M. et al. Experimental Antitumor Activity of Taxotere (RP 56976, NSC 628503), a Taxol Analogue. Cancer Res. 51, 4845-4852, Sep. 1991), T$_d$ is the tumor doubling time in mice (estimated from nonlinear exponential curve fit of daily median of control tumor growth) and x is the number of cell doublings per log of cell growth. Body weights (BW) of mice were expressed as percent change in body weight from the pre-treatment body weight as follows:

$$\% \text{ BW change}=[(BW_{post}/BW_{pre})-1]\times 100$$

where BW$_{post}$ is weight after treatment and BW$_{pre}$ is the starting body weight prior to treatment. Percent body weight loss (BWL) at nadir was expressed as the mean change in body weight post treatment. Animals were sacrificed when the tumor volume was larger than 1000 mm3 or necrotic, or if body weight dropped by 20% more at any point in the study.

Figure 2:
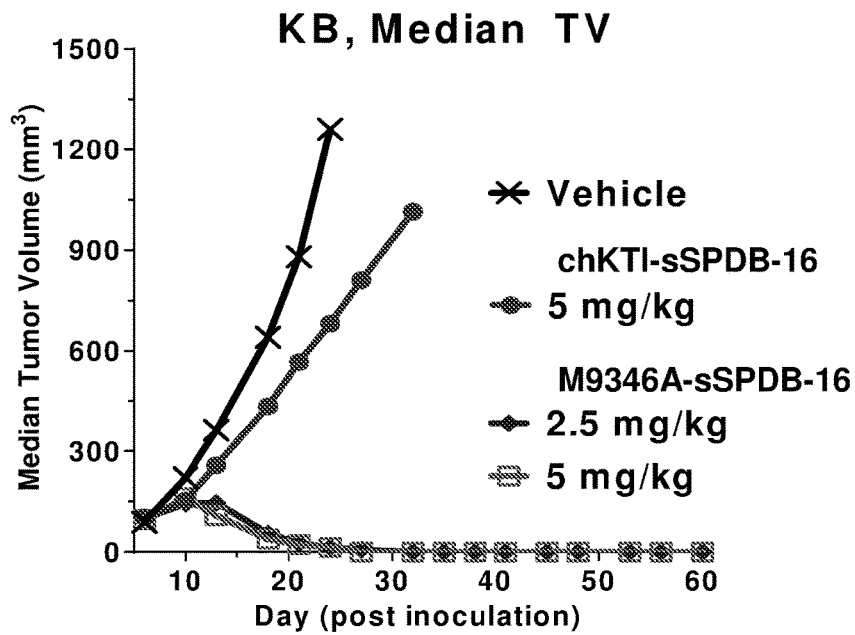
FIG. 2 shows in vivo antitumor activity of a representative conjugate of the present invention in mice bearing KB cervical cancer xenografts at 2.5 mg/kg or 5 mg/kg dose.

As shown in FIG. 2, the conjugate was highly active at 2.5 and 5 mg/kg corresponding to antibody dose (equivalent to 50 and 100 μg/kg compound 16 respectively).

Example 8. In Vivo Efficacy Study in SCID Mice Bearing OV90 Ovarian Cancer Xenografts Female, CB.17 SCID mice, at 6 weeks of age, were obtained from Charles River Laboratories. Mice were inoculated with 1×10$^7$ OV-90 cells in 0.1 ml serum free medium+Matrigel (1:1) by subcutaneous injection in the area on the right hind flank. When tumor volumes reached approximately 100 mm$^3$ (day 13/14 post inoculation), animals were randomized based on tumor volume into groups of six mice. Mice received a single IV administration of vehicle control (0.2 ml/mouse) or test article (25, 50 or 100 μg/kg) based on concentration of compound 16. Tumor size and tumor volume were determined as described in Example 6.

Figure 3:
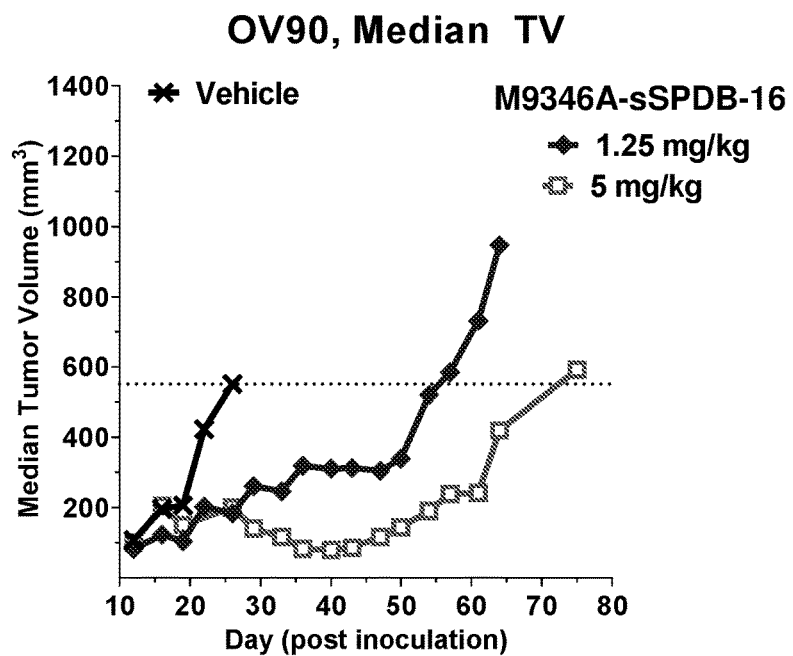
FIG. 3 shows in vivo antitumor activity of a representative conjugate of the present invention in mice bearing OV90 ovarian cancer xenografts at 1.25 mg/kg or 5 mg/kg dose.

As shown in FIG. 3, M9346A-sSPDB-16 conjugate shows dose dependent in vivo antitumor activity at low doses against an ovarian xenograft model with low heterogenous FRα expression.

We claim:

1. A compound represented by formula (I):

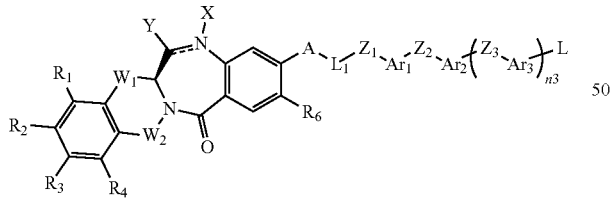

or a pharmaceutically acceptable salt thereof,
wherein:

==== is a double bond;

A is —O—;

$L_1$ is —$(CH_2)_{m1}$—;

m1 is 1, 2, 3, 4, 5, or 6;

$Z_1$ is s3-C(O)$NR_5$-s4, wherein s3 is the site connected to $L_1$ and s4 is the site connected to $Ar_1$;

$Ar_1$ is:

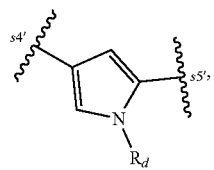

wherein:

$R_d$ is H, $C_1$-$C_6$ alkyl, $NR_bR_c$, or OH, wherein the $C_1$-$C_6$ alkyl is optionally substituted with 1 or more independently selected halogen substituents;

$R_b$ is H, $C_1$-$C_4$ alkyl, C(O)$OCH_3$, C(O)$OCF_3$, C(O)OC$(CH_3)_3$, C(O)$OCH_2$-phenyl, C(O)$OCH_2$-fluorenyl, phenyl, or heteroaryl;

$R_c$ is H, $C_1$-$C_4$ alkyl, C(O)$OCH_3$, C(O)$OCF_3$, C(O)OC$(CH_3)_3$, C(O)$OCH_2$-phenyl, C(O)$OCH_2$-fluorenyl, phenyl, or heteroaryl; and s4' is the site connected to $Z_1$ and s5' is the site connected to $Z_2$;

$Z_2$ is s5-C(O)$NR_5$-s6, wherein s5 is the site connected to $Ar_1$ and s6 is the site connected to $Ar_2$;

Ar₂ is:

[chemical structures: pyrrole and benzothiophene derivatives with s6' and s7' connection sites]

wherein:
- $R_{d'}$ is H, $C_1$-$C_6$ alkyl, $NR_bR_c$, or OH, wherein the $C_1$-$C_6$ alkyl is optionally substituted with 1 or more independently selected halogen substituents;
- $R_b$ is H, $C_1$-$C_4$ alkyl, $C(O)OCH_3$, $C(O)OCF_3$, $C(O)OC(CH_3)_3$, $C(O)OCH_2$-phenyl, $C(O)OCH_2$-fluorenyl, phenyl, or heteroaryl;
- $R_c$ is H, $C_1$-$C_4$ alkyl, $C(O)OCH_3$, $C(O)OCF_3$, $C(O)OC(CH_3)_3$, $C(O)OCH_2$-phenyl, $C(O)OCH_2$-fluorenyl, phenyl, or heteroaryl; and
- s6' is the site connected to $Z_2$ and s7' is the site connected to: (i) $Z_3$, when n3 is not 0, or (ii) L, when n3 is 0;
- $Z_3$ is s7-C(OH)CH₂-s8, s7-CR$^{100}$R$^{101}$NR₅-s8, —CH=CH—, s7-C(O)NR₅-s8, s7-C(O)NR₅CH₂-s8, s7-C(S)NR₅-s8, —NR₅—, s7-NR₅CR$^{100}$R$^{101}$-s8, s7-NR₅C(O)-s8, —NR₅C(O)NR₅—, s7-NR₅C(S)-s8, or s7-S(O)₂NR₅-s8, wherein s7 is the site connected to Ar₂ and s8 is the site connected to Ar₃;
- $R_{100}$ is H, halogen, $C_1$-$C_4$ alkyl, or $C_1$-$C_4$ haloalkyl;
- $R_{101}$ is H, halogen, $C_1$-$C_4$ alkyl, or $C_1$-$C_4$ haloalkyl;
- Ar₃ is $C_6$-$C_{18}$ aryl, 5- to 18-membered heteroaryl, or -Ar₃'-Ar₃"-;
- Ar₃' is $C_6$-$C_{18}$ aryl or 5- to 18-membered heteroaryl;
- Ar₃" is $C_6$-$C_{18}$ aryl or 5- to 18-membered heteroaryl;
- L is:
  (i) $C(O)R_a$; and
  wherein:
  (a) $R_a$ is Cl, OH, or $OC_1$-$C_6$ alkyl; or
  (b) $R_a$ is:

[chemical structures: NHS ester, sulfo-NHS ester, pentafluorophenyl ester, 2-nitrophenyl, 4-nitrophenyl, 2,4-dinitrophenyl esters]

(ii) formula (L3a) or formula (L3c):

$$C(O)NR_{5a}—R^{x1}—SZ^s \quad (L3a); or$$

$$C(O)NR_{5a}—R^{x3}-J \quad (L3c),$$

wherein:
- $R_{5a}$ is H or $C_1$-$C_3$ alkyl;
- $R^{x1}$ is $C_1$-$C_{10}$ alkylene, $C_3$-$C_8$ cycloalkylene, arylene, or heteroarylene;
- $R^{x3}$ is $C_1$-$C_{10}$ alkylene, $C_3$-$C_8$ cycloalkylene, arylene, or heteroarylene;
- $Z^s$ is H, $C(O)R^{e1}$, or $SR^e$;
- $R^e$ is $C_1$-$C_6$ alkyl, phenyl, 2-nitrophenyl, 4-nitrophenyl, 2,4-dinitrophenyl, 3-carboxy-4-nitrophenyl, pyridinyl, or 4-nitropyridinyl; and
- $R^{e1}$ is $C_1$-$C_6$ alkyl;
- J is $C(O)R_a$; and
- (a) $R_a$ is Cl, OH, or $OC_1$-$C_6$ alkyl; or
- (b) $R_a$ is:

[chemical structures: NHS ester, sulfo-NHS ester, pentafluorophenyl ester, 2-nitrophenyl, 4-nitrophenyl, 2,4-dinitrophenyl esters]

-continued

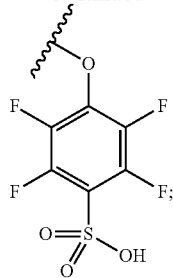

or (iii) formula (L4a) or formula (L4c):

wherein:
R$_{5a}$ is H or C$_1$-C$_3$ alkyl;
R$^{x1}$ is C$_1$-C$_{10}$ alkylene, C$_3$-C$_8$ cycloalkylene, arylene, or heteroarylene;
R$^{x3}$ is C$_1$-C$_{10}$ alkylene, C$_3$-C$_8$ cycloalkylene, arylene, or heteroarylene;
Z$^{c1}$ is formula (L4a1) or formula (L4b1):

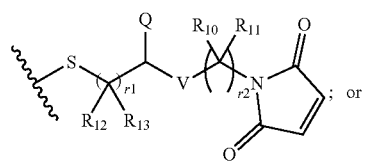

wherein:
Q is H;
V is —C(O)NR$_9$— or —NR$_9$C(O)—;
R$_9$ is H or C$_1$-C$_4$ alkyl;
each R$_{10}$ is independently H or C$_1$-C$_4$ alkyl;
each R$_{11}$ is independently H or C$_1$-C$_4$ alkyl;
each R$_{12}$ is independently H or C$_1$-C$_4$ alkyl;
each R$_{13}$ is independently H or C$_1$-C$_4$ alkyl;
each R$_{19}$ is independently H or C$_1$-C$_4$ alkyl;
each R$_{20}$ is independently H or C$_1$-C$_4$ alkyl;
each R$_{21}$ is independently H or C$_1$-C$_4$ alkyl;
each R$_{22}$ is independently H or C$_1$-C$_4$ alkyl;
R$^h$ is H or C$_1$-C$_3$ alkyl;
P$_3$ is an amino acid residue or a peptide containing 2, 3, 4, or 5 amino acid residues;
q1 is 0, 1, 2, 3, 4, 5, 6, 7, 8, 9, or 10;
q2 is 0, 1, 2, 3, 4, 5, 6, 7, 8, 9, or 10;
r1 is 0, 1, 2, 3, 4, 5, 6, 7, 8, 9, or 10; and
r2 is 0, 1, 2, 3, 4, 5, 6, 7, 8, 9, or 10; and Z$^{c2}$ is:

wherein:
each R$_{19}$ is independently H or C$_1$-C$_4$ alkyl;
each R$_{20}$ is independently H or C$_1$-C$_4$ alkyl;
R$^h$ is H or C$_1$-C$_3$ alkyl; and
s1 is 1, 2, 3, 4, 5, 6, 7, 8, 9, or 10; or (iv) formula (L5a) or formula (L5c):

C(O)NR$_{5a}$—R$^{x1}$—SZ$^{s1}$-J$^s$     (L5a); or

C(O)NR$_{5a}$—R$^{x3}$—Z$_{a2}$—R$^{x3'}$-J$^s$     (L5c), wherein:
R$_{5a}$ is H or C$_1$-C$_3$ alkyl;
R$^{x1}$ is C$_1$-C$_6$ alkylene;
R$^{x3}$ is C$_1$-C$_6$ alkylene;
R$^{x3'}$ is C$_1$-C$_6$ alkylene;
Z$_{a2}$ is absent, —C(O)NR$_9$—, or —NR$_9$C(O)—;
R$_9$ is H or C$_1$-C$_4$ alkyl;
J$^s$ is C(O)NHNH$_2$, NHNH$_2$, or ONH$_2$; and
Z$^{s1}$ is:

wherein:
Q is H;
each R$_{a1}$ is independently H or C$_1$-C$_3$ alkyl;
each R$_{a2}$ is independently H or C$_1$-C$_3$ alkyl;
each R$_{a3}$ is independently H or C$_1$-C$_3$ alkyl;
each R$_{a4}$ is independently H or C$_1$-C$_3$ alkyl;
Z$_{a1}$ is absent, —C(O)NR$_9$—, or —NR$_9$C(O)—;
qs1 is 0, 1, 2, 3, 4, 5, 6, 7, 8, 9, or 10;
rs1 is 0, 1, 2, 3, 4, 5, 6, 7, 8, 9, or 10;
s9 is the site connected to —S— in formula (L5a); and
s10 is the site connected to J$^s$ in formula (L5a);
with the proviso that qs1 and rs1 are not both 0;
R$^1$ is H, halogen, CN, NO$_2$, C$_1$-C$_6$ alkyl, C(O)R', NR'R'', NR'C(O)R'', OR, OC(O)R', OC(O)NR'R'', OS(O)$_2$OH, SR, S(O)R', S(O)$_2$R', S(O)$_2$NR'R'', or S(O)$_2$OH;
R$^2$ is H, halogen, CN, NO$_2$, C$_1$-C$_6$ alkyl, C(O)R', NR'R'', NR'C(O)R'', OR, OC(O)R', OC(O)NR'R'', OS(O)$_2$OH, SR, S(O)R', S(O)$_2$R', S(O)$_2$NR'R'', or S(O)$_2$OH;
R$^3$ is H, halogen, CN, NO$_2$, C$_1$-C$_6$ alkyl, C(O)R', NR'R'', NR'C(O)R'', OR, OC(O)R', OC(O)NR'R'', OS(O)$_2$OH, SR, S(O)R', S(O)$_2$R', S(O)$_2$NR'R'', or S(O)$_2$OH;
R$^4$ is H, halogen, CN, NO$_2$, C$_1$-C$_6$ alkyl, C(O)R', NR'R'', NR'C(O)R'', OR, OC(O)R', OC(O)NR'R'', OS(O)$_2$OH, SR, S(O)R', S(O)$_2$R', S(O)$_2$NR'R'', or S(O)$_2$OH;

each R' is independently H, $C_1$-$C_6$ alkyl, C(O)R, $N(R)_2$, or OR;

each R" is independently H, $C_1$-$C_6$ alkyl, C(O)R, $N(R)_2$, or OR;

each R is independently H or $C_1$-$C_6$ alkyl;

each $R_5$ is independently H or $C_1$-$C_4$ alkyl;

$R_6$ is $OC_1$-$C_6$ alkyl;

$W_1$ is —$(CH_2)_{n1}$—;

$W_2$ is —$(CH_2)_{n2}$—;

X is absent;

Y is H;

n1 is 1;

n2 is 0; and n3 is 0.

2. The compound of claim 1, wherein the compound is represented by formula (IA-1):

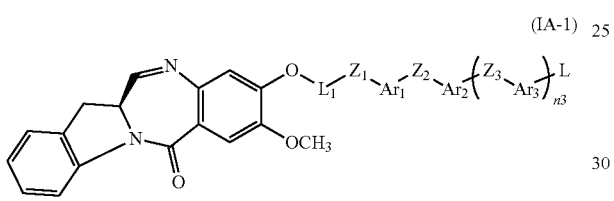

(IA-1)

or a pharmaceutically acceptable salt thereof.

3. The compound of claim 1, wherein:

m1 is 3, 4, or 5; and each $R_5$ is independently H or $CH_3$.

4. The compound of claim 1, wherein the compound is represented by formula (IA-1a):

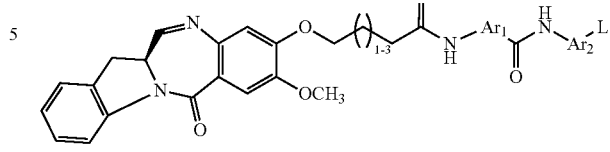

(IA-1a)

or a pharmaceutically acceptable salt thereof.

5. The compound of claim 4, wherein $Ar_2$ is:

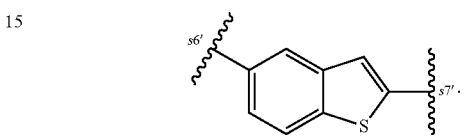

6. The compound of claim 1, wherein $Ar_2$ is:

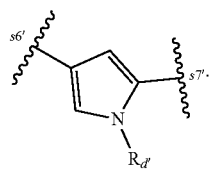

7. The compound of claim 1, wherein $Ar_2$ is:

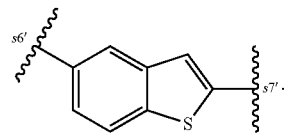 [SMILES: *c1ccc2sc(*)cc2c1]

8. The compound of claim 1, wherein the compound is represented by formula (IA-1b):

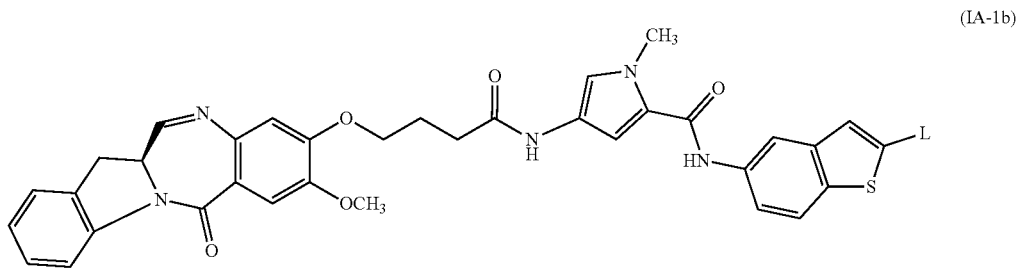

(IA-1b)

or a pharmaceutically acceptable salt thereof.

9. The compound of claim 1, wherein L is:
(i) C(O)R$_a$; and
(a) R$_a$ is OH or OC$_1$-C$_6$ alkyl; or
(b) R$_a$ is

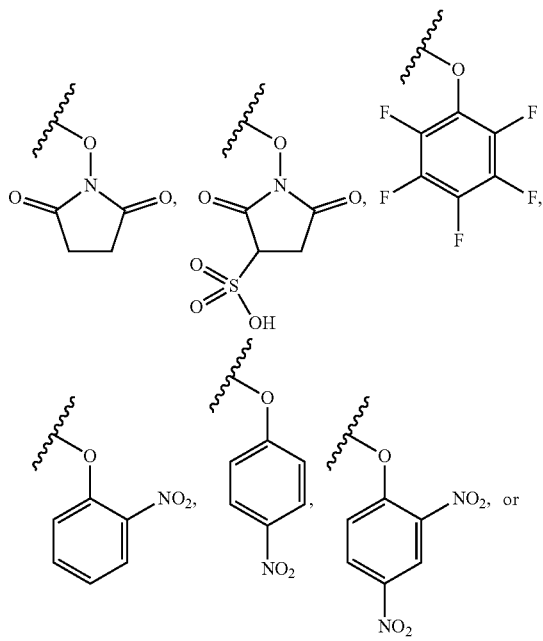

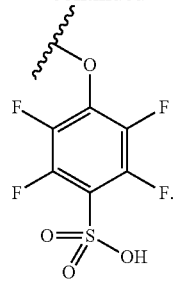

10. The compound of claim 1, wherein L is:
(ii) formula (L3a) or formula (L3c):

$$C(O)NR_{5a}\text{—}R^{x1}\text{—}SZ^s \qquad (L3a); or$$

$$C(O)NR_{5a}\text{—}R^{x3}\text{-}J \qquad (L3c); or$$

(iii) formula (L4a) or formula (L4c):

$$C(O)NR_{5a}\text{—}R^{x1}\text{—}SZ^{c1} \qquad (L4a); or$$

$$C(O)NR_{5a}\text{—}R^{x3}C(O)\text{—}Z^{c2} \qquad (L4c); or$$

(iv) formula (L5a) or formula (L5c):

$$C(O)NR_{5a}\text{—}R^{x1}\text{—}SZ^{s1}\text{-}J^s \qquad (L5a); or$$

$$C(O)NR_5\text{—}R^{x3}Z_{a2}\text{—}R^{x3}\text{-}J^s \qquad (L5c).$$

11. The compound of claim 1, wherein the compound is represented by any one of the following formulas:

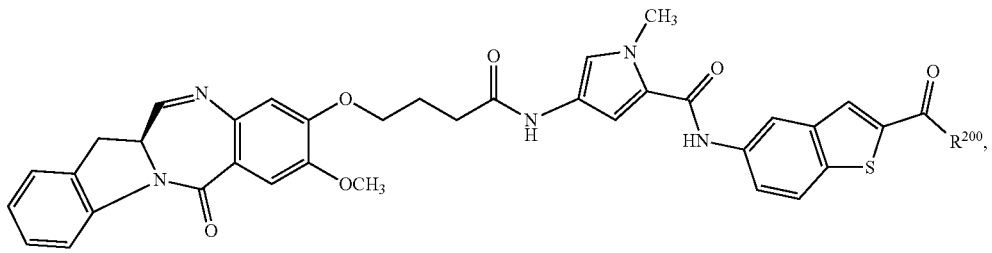

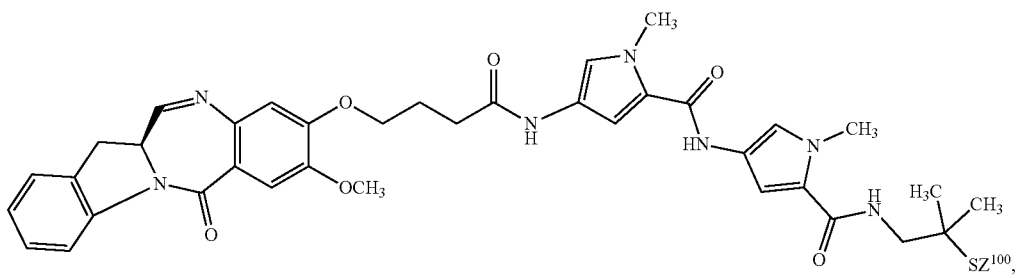

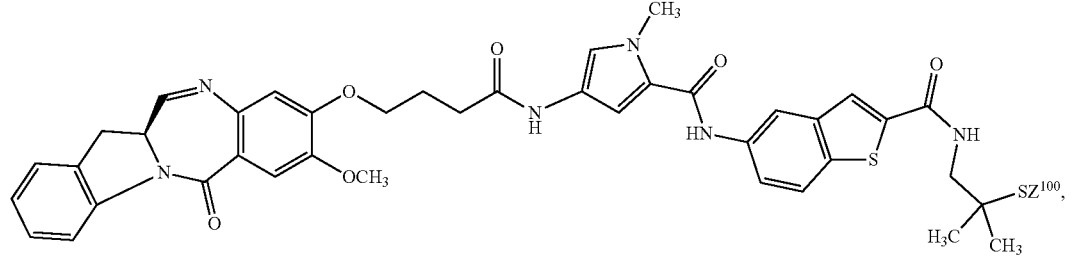
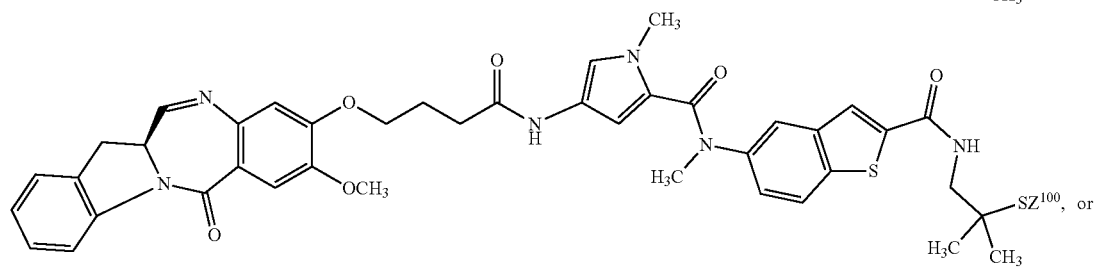
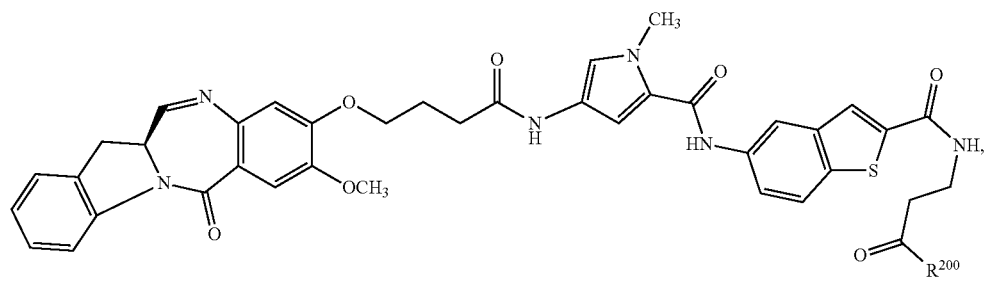
or a pharmaceutically acceptable salt thereof, wherein:
(a) $R^{200}$ is OH or $OC_1$-$C_3$ alkyl; or
(b) $R^{200}$ is
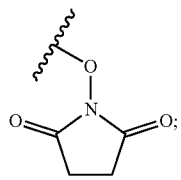 [SMILES: *ON1C(=O)CCC1=O]
and
$Z^{100}$ is H or $SR^e$.
12. The compound of claim 1, wherein the compound is selected from the group consisting of:
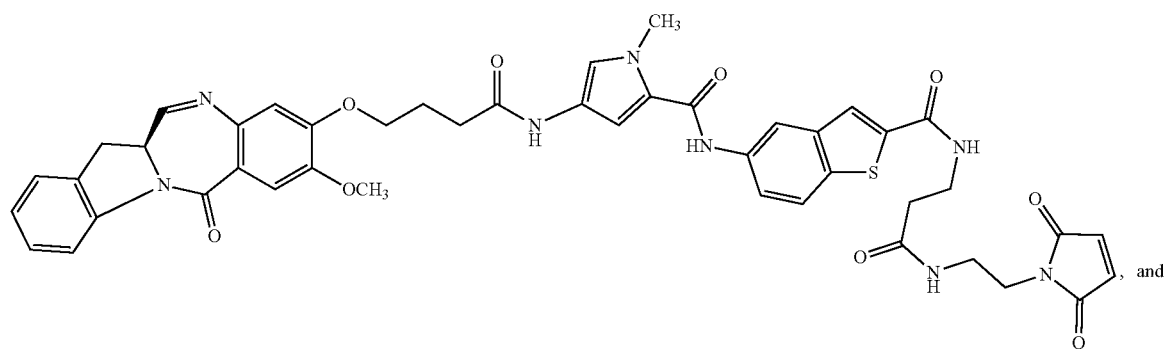
, and -continued
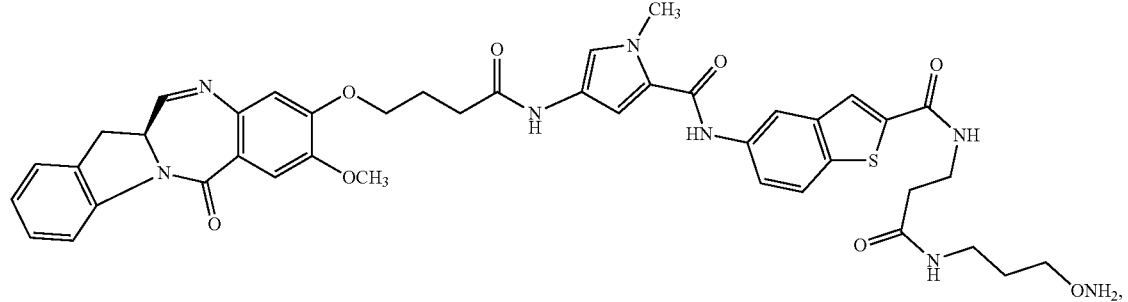
or a pharmaceutically acceptable salt thereof.

UNITED STATES PATENT AND TRADEMARK OFFICE
CERTIFICATE OF CORRECTION

PATENT NO. : 11,793,885 B2
APPLICATION NO. : 16/954878
DATED : October 24, 2023
INVENTOR(S) : Michael Louis Miller et al.

Page 1 of 2

It is certified that error appears in the above-identified patent and that said Letters Patent is hereby corrected as shown below:

In the Claims

At Column 389, Claim number 1, Line number 40, please replace formula L4b1:

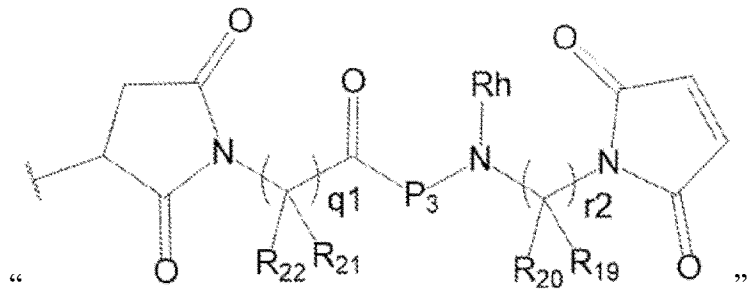

With the following formula:

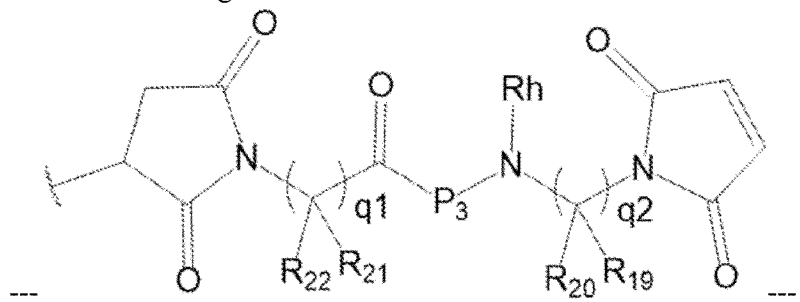

At Column 391, Claim number 1, Line number 5, please replace:
"each R is independently H or $C_1$-$C_6$ alkyl;"
With:
---each R is independently H or $C_1$-$C_4$ alkyl;---

At Column 395, Claim number 11, Line number 36, please replace:
"(a) $R^{200}$ is OH or $OC_1$-$C_3$ alkyl; or"

Signed and Sealed this
First Day of October, 2024

Katherine Kelly Vidal
*Director of the United States Patent and Trademark Office*

CERTIFICATE OF CORRECTION (continued)
U.S. Pat. No. 11,793,885 B2

With:
---(a) $R^{200}$ is OH or $O(C_1-C_3)$alkyl; or---

SEQUENCE LISTING

<160> NUMBER OF SEQ ID NOS: 33

<210> SEQ ID NO 1
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ala Leu Ala Leu
1

<210> SEQ ID NO 2
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Beta-Ala

<400> SEQUENCE: 2

Ala Leu Ala Leu
1

<210> SEQ ID NO 3
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Phe Leu Gly
1

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Tyr Phe Met Asn
1               5

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (14)..(14)
<223> OTHER INFORMATION: /replace="Gln" or "His" or "Arg"

```
<220> FEATURE:
<221> NAME/KEY: MOD_RES
<222> LOCATION: (16)..(16)
<223> OTHER INFORMATION: /replace="His" or "Asn" or "Arg"
<220> FEATURE:
<221> NAME/KEY: MOD_RES
<222> LOCATION: (17)..(17)
<223> OTHER INFORMATION: /replace="Glu" or "Thr" or "Ser" or "Ala" or
      "Val"
<220> FEATURE:
<221> NAME/KEY: MISC_FEATURE
<222> LOCATION: (1)..(17)
<223> OTHER INFORMATION: /note="Variant residues given in the sequence
      have no preference with respect to those in the annotations
      for variant positions"

<400> SEQUENCE: 5

Arg Ile His Pro Tyr Asp Gly Asp Thr Phe Tyr Asn Gln Lys Phe Gln
1               5                   10                  15

Gly

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Tyr Asp Gly Ser Arg Ala Met Asp Tyr
1               5

<210> SEQ ID NO 7
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Lys Ala Ser Gln Ser Val Ser Phe Ala Gly Thr Ser Leu Met His
1               5                   10                  15

<210> SEQ ID NO 8
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Arg Ala Ser Asn Leu Glu Ala
1               5

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9
```

```
Gln Gln Ser Arg Glu Tyr Pro Tyr Thr
1               5

<210> SEQ ID NO 10
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Arg Ile His Pro Tyr Asp Gly Asp Thr Phe Tyr Asn Gln Lys Phe Gln
1               5                   10                  15

Gly

<210> SEQ ID NO 11
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
```

```
                    245                 250                 255
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 12
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160
```

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 13
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

```
Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 14
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
        50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
            115

<210> SEQ ID NO 15
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
                20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp
        50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 16
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
                20                  25                  30

Gly Thr Ser Leu Met His Trp Tyr His Gln Lys Pro Gly Gln Gln Pro
            35                  40                  45

Arg Leu Leu Ile Tyr Arg Ala Ser Asn Leu Glu Ala Gly Val Pro Asp

```
                    50                  55                  60
Arg Phe Ser Gly Ser Gly Ser Lys Thr Asp Phe Thr Leu Thr Ile Ser
 65                  70                  75                  80

Pro Val Glu Ala Glu Asp Ala Ala Thr Tyr Tyr Cys Gln Gln Ser Arg
                    85                  90                  95

Glu Tyr Pro Tyr Thr Phe Gly Gly Gly Thr Lys Leu Glu Ile Lys Arg
                100                 105                 110

<210> SEQ ID NO 17
<211> LENGTH: 445
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gln Val Gln Leu Gln Glu Ser Gly Pro Gly Leu Val Lys Pro Ser Glu
  1               5                  10                  15

Thr Leu Ser Leu Thr Cys Thr Val Ser Gly Leu Ser Leu Ala Ser Asn
                 20                  25                  30

Ser Val Ser Trp Ile Arg Gln Pro Pro Gly Lys Gly Leu Glu Trp Met
             35                  40                  45

Gly Val Ile Trp Asn His Gly Gly Thr Asp Tyr Asn Pro Ser Ile Lys
 50                  55                  60

Ser Arg Leu Ser Ile Ser Arg Asp Thr Ser Lys Ser Gln Val Phe Leu
 65                  70                  75                  80

Lys Met Asn Ser Leu Thr Ala Ala Asp Thr Ala Met Tyr Phe Cys Val
                 85                  90                  95

Arg Lys Gly Gly Ile Tyr Phe Asp Tyr Trp Gly Gln Gly Val Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
                435                 440                 445

<210> SEQ ID NO 18
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Asp Thr Val Leu Thr Gln Ser Pro Ser Leu Ala Val Ser Pro Gly Glu
1               5                   10                  15

Arg Ala Thr Ile Ser Cys Arg Ala Ser Glu Ser Val Ser Thr Leu Met
                20                  25                  30

His Trp Tyr Gln Gln Lys Pro Gly Gln Gln Pro Lys Leu Leu Ile Tyr
            35                  40                  45

Leu Ala Ser His Arg Glu Ser Gly Val Pro Ala Arg Phe Ser Gly Ser
    50                  55                  60

Gly Ser Gly Thr Asp Phe Thr Leu Thr Ile Asp Pro Met Glu Ala Glu
65                  70                  75                  80

Asp Thr Ala Thr Tyr Tyr Cys Gln Gln Ser Arg Asn Asp Pro Trp Thr
                85                  90                  95

Phe Gly Gln Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210

<210> SEQ ID NO 19
<211> LENGTH: 448
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Thr Tyr Thr Gln Lys Phe
    50                  55                  60

Gln Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr

```
                    340                 345                 350
Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 20
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Tyr Gln His Lys Pro Gly Lys Gly Pro Lys Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Ser Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 21
<211> LENGTH: 214
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Asn Tyr
            20                  25                  30

Leu Ala Trp Tyr Gln His Lys Pro Gly Lys Pro Lys Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Ser Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 22
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gln Val Gln Leu Val Gln Pro Gly Ala Glu Val Val Lys Pro Gly Ala
1               5                   10                  15

Ser Val Lys Leu Ser Cys Lys Thr Ser Gly Tyr Thr Phe Thr Ser Asn
            20                  25                  30

Trp Met His Trp Val Lys Gln Ala Pro Gly Gln Gly Leu Glu Trp Ile
        35                  40                  45

Gly Glu Ile Asp Pro Ser Asp Ser Tyr Thr Asn Tyr Asn Gln Asn Phe
    50                  55                  60

Gln Gly Lys Ala Lys Leu Thr Val Asp Lys Ser Thr Ser Thr Ala Tyr
65                  70                  75                  80

Met Glu Val Ser Ser Leu Arg Ser Asp Asp Thr Ala Val Tyr Tyr Cys
                85                  90                  95
```

Ala Arg Gly Ser Asn Pro Tyr Tyr Tyr Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 23
<211> LENGTH: 211
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

```
<400> SEQUENCE: 23

Glu Ile Val Leu Thr Gln Ser Pro Ala Ile Met Ser Ala Ser Pro Gly
1               5                   10                  15

Glu Arg Val Thr Met Thr Cys Ser Ala Ser Ser Gly Val Asn Tyr Met
            20                  25                  30

His Trp Tyr Gln Gln Lys Pro Gly Thr Ser Pro Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Asp Tyr Ser Leu Thr Ile Ser Ser Met Glu Pro Glu
65              70                  75                  80

Asp Ala Ala Thr Tyr Tyr Cys His Gln Arg Gly Ser Tyr Thr Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
        210

<210> SEQ ID NO 24
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Gln Ala Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Tyr Ile Tyr Pro Gly Asn Gly Ala Thr Asn Tyr Asn Gln Lys Phe
    50                  55                  60

Gln Gly Lys Ala Thr Leu Thr Ala Asp Thr Ser Ser Ser Thr Ala Tyr
65              70                  75                  80

Met Gln Ile Ser Ser Leu Thr Ser Glu Asp Ser Ala Val Tyr Phe Cys
                85                  90                  95

Ala Arg Gly Asp Ser Val Pro Phe Ala Tyr Trp Gly Gln Gly Thr Leu
            100                 105                 110

Val Thr Val Ser Ala Ala Ser Thr Lys Gly Pro Ser Val Phe Pro Leu
        115                 120                 125
```

```
Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 25
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Ile Val Leu Thr Gln Ser Pro Ala Thr Met Ser Ala Ser Pro Gly
1               5                   10                  15

Glu Arg Val Thr Ile Thr Cys Ser Ala His Ser Ser Val Ser Phe Met
            20                  25                  30
```

```
His Trp Phe Gln Gln Lys Pro Gly Thr Ser Pro Lys Leu Trp Ile Tyr
         35                  40                  45

Ser Thr Ser Ser Leu Ala Ser Gly Val Pro Ala Arg Phe Gly Gly Ser
 50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Arg Ser Ser Phe Pro Leu Thr
                 85                  90                  95

Phe Gly Ala Gly Thr Lys Leu Glu Leu Lys Arg Thr Val Ala Ala Pro
                100                 105                 110

Ser Val Phe Ile Phe Pro Pro Ser Asp Glu Gln Leu Lys Ser Gly Thr
             115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 26
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gln Val Gln Leu Gln Gln Pro Gly Ala Glu Val Val Lys Pro Gly Ala
1               5                   10                  15

Ser Val Lys Met Ser Cys Lys Ala Ser Gly Tyr Thr Phe Thr Ser Tyr
             20                  25                  30

Tyr Ile His Trp Ile Lys Gln Thr Pro Gly Gln Gly Leu Glu Trp Val
         35                  40                  45

Gly Val Ile Tyr Pro Gly Asn Asp Asp Ile Ser Tyr Asn Gln Lys Phe
 50                  55                  60

Gln Gly Lys Ala Thr Leu Thr Ala Asp Lys Ser Ser Thr Thr Ala Tyr
 65                  70                  75                  80

Met Gln Leu Ser Ser Leu Thr Ser Glu Asp Ser Ala Val Tyr Tyr Cys
                 85                  90                  95

Ala Arg Glu Val Arg Leu Arg Tyr Phe Asp Val Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
```

```
                    165                 170                 175
Ser Ser Gly Leu Tyr Ser Leu Ser Ser Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 27
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Glu Ile Val Leu Thr Gln Ser Pro Gly Ser Leu Ala Val Ser Pro Gly
1               5                   10                  15

Glu Arg Val Thr Met Ser Cys Lys Ser Ser Gln Ser Val Phe Phe Ser
            20                  25                  30

Ser Ser Gln Lys Asn Tyr Leu Ala Trp Tyr Gln Gln Ile Pro Gly Gln
        35                  40                  45

Ser Pro Arg Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80
```

```
Ile Ser Ser Val Gln Pro Glu Asp Leu Ala Ile Tyr Tyr Cys His Gln
                85                  90                  95

Tyr Leu Ser Ser Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 28
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

```
Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
                210

<210> SEQ ID NO 29
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser

```
                340             345             350
Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
        435                 440

<210> SEQ ID NO 30
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255
```

```
Val Thr Cys Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly
        435                 440

<210> SEQ ID NO 31
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Asn Leu Pro Tyr Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 32
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Gln Val Gln Leu Gln Glu Ser Gly Pro Gly Leu Leu Lys Pro Ser Gln
 1               5                  10                  15

Ser Leu Ser Leu Thr Cys Thr Val Ser Gly Tyr Ser Ile Thr Ser Gly
            20                  25                  30

Phe Ala Trp His Trp Ile Arg Gln His Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
```

```
                290                 295                 300
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 33
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      KDEL sequence"

<400> SEQUENCE: 33

Lys Asp Glu Leu
1
```